United States Patent
Walker et al.

(10) Patent No.: US 9,115,358 B2
(45) Date of Patent: Aug. 25, 2015

(54) MOENOMYCIN BIOSYNTHESIS-RELATED COMPOSITIONS AND METHODS OF USE THEREOF

(75) Inventors: Suzanne Walker, Brookline, MA (US); Bohdan Omelyanovich Ostash, L'viv (UA)

(73) Assignee: President and Fellows of Harvard College, Cambridge, MA (US)

( * ) Notice: Subject to any disclaimer, the term of this patent is extended or adjusted under 35 U.S.C. 154(b) by 1460 days.

(21) Appl. No.: 12/377,117

(22) PCT Filed: Aug. 13, 2007

(86) PCT No.: PCT/US2007/017999
§ 371 (c)(1),
(2), (4) Date: May 18, 2010

(87) PCT Pub. No.: WO2008/021367
PCT Pub. Date: Feb. 21, 2008

(65) Prior Publication Data
US 2010/0279980 A1    Nov. 4, 2010

Related U.S. Application Data

(60) Provisional application No. 60/837,047, filed on Aug. 11, 2006.

(51) Int. Cl.
C07K 14/00 (2006.01)
C12N 15/52 (2006.01)

(52) U.S. Cl.
CPC .................................... *C12N 15/52* (2013.01)

(58) Field of Classification Search
None
See application file for complete search history.

(56) References Cited

U.S. PATENT DOCUMENTS

| | | |
|---|---|---|
| 3,949,070 A | 4/1976 | Arai et al. |
| 3,992,263 A | 11/1976 | Dietrich et al. |
| 4,270,537 A | 6/1981 | Romaine |
| 4,522,811 A | 6/1985 | Eppstein et al. |
| 4,596,556 A | 6/1986 | Morrow et al. |
| 4,684,626 A | 8/1987 | Welzel et al. |
| 4,790,824 A | 12/1988 | Morrow et al. |
| 4,842,857 A | 6/1989 | Meyers et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,206,405 A | 4/1993 | Aretz et al. |
| 5,260,051 A | 11/1993 | Cho |
| 5,260,206 A | 11/1993 | Aretz et al. |
| 5,312,335 A | 5/1994 | McKinnon et al. |
| 5,315,038 A | 5/1994 | Aretz et al. |
| 5,316,929 A | 5/1994 | Aretz et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,454,971 A | 10/1995 | Sakai et al. |
| 5,466,220 A | 11/1995 | Brenneman |
| 5,480,381 A | 1/1996 | Weston |
| 5,503,627 A | 4/1996 | McKinnon et al. |
| 5,506,140 A | 4/1996 | Aretz et al. |
| 5,520,639 A | 5/1996 | Peterson et al. |

(Continued)

FOREIGN PATENT DOCUMENTS

| | | |
|---|---|---|
| EP | 0 652 205 A2 | 5/1995 |
| EP | 1 069 130 A1 | 1/2001 |

(Continued)

OTHER PUBLICATIONS

PCT International Search Report—(PCT/US2007/017999) Date of mailing Sep. 30, 2008.
Xiang, et al., "The Crystal Structure of *Escherichia coli* MoeA and Its Relationship to the Multifunctional Protein Gephyrin", Structure, Apr. 2001, vol. 9, pp. 299-310.
U.S. Appl. No. 61/621,161, filed Apr. 6, 2012, Kahne et al.
U.S. Appl. No. 61/621,229, filed Apr. 6, 2012, Kahne et al.
U.S. Appl. No. 61/621,186, filed Apr. 6, 2012, Kahne et al.
International Search Report and Written Opinion for PCT/US2008/078771, mailed Mar. 10, 2009.
International Preliminary Report on Patentability for PCT/US2008/078771, mailed Apr. 15, 2010.
International Search Report and Written Opinion for PCT/US2007/017999, mailed Sep. 30, 2008.

(Continued)

*Primary Examiner* — Michele K Joike
(74) *Attorney, Agent, or Firm* — Wolf, Greenfield & Sacks, P.C.

(57) ABSTRACT

The methods and compositions described herein relate to the identification, isolation, and characterization of genes which encode proteins useful for the biosynthesis of transglycosylase inhibitors such as moes. The methods and compositions also relate to the production of such proteins, and their use in the synthesis of moes, the expression of moes, and the production of modified moes.

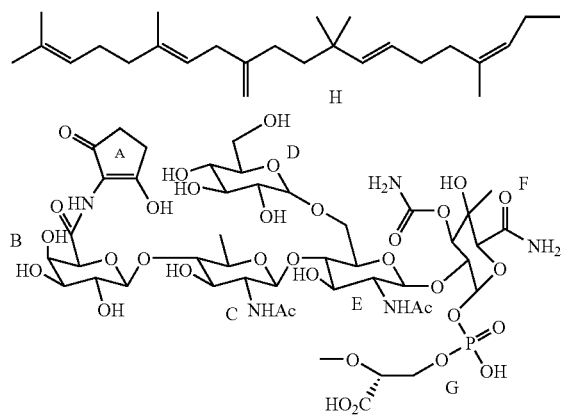

12 Claims, 21 Drawing Sheets

(56) References Cited

U.S. PATENT DOCUMENTS

| | | | |
|---|---|---|---|
| 5,527,288 | A | 6/1996 | Gross et al. |
| 5,569,189 | A | 10/1996 | Parsons |
| 5,599,302 | A | 2/1997 | Lilley et al. |
| 5,649,912 | A | 7/1997 | Peterson |
| 5,704,911 | A | 1/1998 | Parsons |
| 5,736,533 | A | 4/1998 | Simon et al. |
| 5,888,721 | A | 3/1999 | Rothstein et al. |
| 5,893,397 | A | 4/1999 | Peterson et al. |
| 5,986,089 | A | 11/1999 | Vertesy et al. |
| 5,993,412 | A | 11/1999 | Deily et al. |
| 6,077,830 | A | 6/2000 | Vertesy et al. |
| 6,114,309 | A | 9/2000 | Allanson et al. |
| 6,153,381 | A | 11/2000 | Rothstein |
| 6,207,820 | B1 | 3/2001 | Allanson et al. |
| 6,242,424 | B1 * | 6/2001 | Riess et al. .......... 514/25 |
| 6,274,716 | B1 | 8/2001 | Allanson et al. |
| 6,461,829 | B1 | 10/2002 | Kahne |
| 6,534,278 | B1 | 3/2003 | Rothstein |
| 6,911,318 | B2 | 6/2005 | Kahne |
| 6,913,895 | B1 | 7/2005 | Goldman et al. |
| 7,129,229 | B2 | 10/2006 | Raddatz et al. |
| 7,186,813 | B1 | 3/2007 | Schweitzer et al. |
| 8,604,004 | B2 | 12/2013 | Kahne et al. |
| 2003/0108969 | A1 | 6/2003 | DeSousa et al. |
| 2003/0129683 | A1 | 7/2003 | Kahne |
| 2003/0158093 | A1 | 8/2003 | Sun et al. |
| 2004/0018582 | A1 | 1/2004 | Eggert et al. |
| 2004/0042981 | A1 | 3/2004 | Vertesy et al. |
| 2004/0127403 | A1 | 7/2004 | Parenti et al. |
| 2004/0147441 | A1 | 7/2004 | Leach et al. |
| 2005/0026214 | A1 | 2/2005 | Biton et al. |
| 2005/0106555 | A1 | 5/2005 | Desousa |
| 2005/0186653 | A1 | 8/2005 | Helmann et al. |
| 2005/0287181 | A1 | 12/2005 | Murthy |
| 2005/0287198 | A1 | 12/2005 | Murthy |
| 2005/0287200 | A1 | 12/2005 | Murthy |
| 2005/0287219 | A1 | 12/2005 | Murthy |
| 2005/0287220 | A1 | 12/2005 | Murthy |
| 2006/0040891 | A1 | 2/2006 | Jiang et al. |
| 2006/0093632 | A1 | 5/2006 | Murthy |
| 2006/0094669 | A1 | 5/2006 | Murthy |
| 2006/0142217 | A1 | 6/2006 | Meutermans et al. |
| 2007/0060506 | A1 | 3/2007 | Walsh et al. |
| 2011/0136759 | A1 | 6/2011 | Kahne et al. |

FOREIGN PATENT DOCUMENTS

| | | |
|---|---|---|
| WO | WO 97/13537 A1 | 4/1997 |
| WO | WO 97/37705 A1 | 10/1997 |
| WO | WO 99/26956 A1 | 6/1999 |
| WO | WO 99/34850 A1 | 7/1999 |
| WO | WO 00/52035 A1 | 9/2000 |
| WO | WO 00/64915 A1 | 11/2000 |
| WO | WO 03/020962 A2 | 3/2003 |
| WO | WO 2008/021367 A2 | 2/2008 |
| WO | WO 2009/046314 A2 | 4/2009 |
| WO | WO 2013/151697 A1 | 10/2013 |
| WO | WO 2013/152277 A2 | 10/2013 |
| WO | WO 2013/152279 A1 | 10/2013 |

OTHER PUBLICATIONS

International Preliminary Report on Patentability for PCT/US2007/017999, mailed Feb. 26, 2009.
GenBank Submission; NIH/NCBI, Accession No. AAF24002; Belanger et al.; Jan. 12, 2000.
GenBank Submission; NIH/NCBI, Accession No. AAG34163; Yoo et al.; Mar. 6, 2001.
GenBank Submission; NIH/NCBI, Accession No. AAO06921; Rascher et al.; Feb. 21, 2003.
GenBank Submission; NIH/NCBI, Accession No. AAU93096; Ward et al.; Nov. 21, 2011.
GenBank Submission; NIH/NCBI, Accession No. AAX98210; McAlpine et al.; Apr. 25, 2005.
GenBank Submission; NIH/NCBI, Accession No. AY240962; Petricek et al.; Jul. 5, 2006.
GenBank Submission; NIH/NCBI, Accession No. BAC68501; Omura et al.; Dec. 21, 2007.
GenBank Submission; NIH/NCBI, Accession No. BAC68502; Omura et al.; Dec. 21, 2007.
GenBank Submission; NIH/NCBI, Accession No. BAC70368; Omura et al.; Dec. 21, 2007.
GenBank Submission; NIH/NCBI, Accession No. CAA22758; Bentley et al.; Oct. 23, 2008.
GenBank Submission; NIH/NCBI, Accession No. CAC01594; Bentley et al.; Oct. 23, 2008.
GenBank Submission; NIH/NCBI, Accession No. CAC37544; Bentley et al.; Oct. 23, 2008.
GenBank Submission; NIH/NCBI, Accession No. CAC37545; Bentley et al.; Oct. 23, 2008.
GenBank Submission; NIH/NCBI, Accession No. CAI08539; Rabus et al.; Sep. 11, 2009.
GenBank Submission; NIH/NCBI, Accession No. EAM38951; Jun. 15, 2005.
GenBank Submission; NIH/NCBI, Accession No. EAO07657; Jul. 26, 2005.
GenBank Submission; NIH/NCBI, Accession No. EAS11435; Apr. 9, 2007.
GenBank Submission; NIH/NCBI, Accession No. EAS23724; Mar. 22, 2006.
GenBank Submission; NIH/NCBI, Accession No. EAS99725; Apr. 18, 2006.
GenBank Submission; NIH/NCBI, Accession No. JC7965; Nemoto et al.; Mar. 15, 2004.
GenBank Submission; NIH/NCBI, Accession No. NP_142754; Kawarabayasi et al.; Jan. 19, 2012.
GenBank Submission; NIH/NCBI, Accession No. NP_220145; Griffiths et al.; Sep. 15, 2011.
GenBank Submission; NIH/NCBI, Accession No. NP_630535; Hsiao et al.; Jan. 19, 2012.
GenBank Submission; NIH/NCBI, Accession No. YP_074610; Ueda et al.; Jan. 23, 2012.
GenBank Submission; NIH/NCBI, Accession No. YP_075255; Ueda et al.; Jan. 23, 2012.
GenBank Submission; NIH/NCBI, Accession No. YP_075256; Ueda et al.; Jan. 23, 2012.
GenBank Submission; NIH/NCBI, Accession No. ZP_00616987; Heuts et al.; Jun. 28, 2007.
Adachi et al., Degradation and reconstruction of moenomycin A and derivatives: dissecting the function of the isoprenoid chain. J Am Chem Soc. Nov. 1, 2006;128(43):14012-3.
Arai et al., Pholipomycin, a new member of phosphoglycolipid antibiotics. I. Taxonomy of producing organism and fermentation and isolation of pholipomycin. J Antibiot (Tokyo). Dec. 1977;30(12):1049-54.
Bardone et al., Teichomycins, new antibiotics from *Actinoplanes teichomyceticus* nov. sp. II. Extraction and chemical characterization. J Antibiot (Tokyo). Mar. 1978;31(3):170-7.
Barrett et al., Kinetic characterization of the glycosyltransferase module of *Staphylococcus aureus* PBP2. J Bacteriol. Mar. 2005;187(6):2215-7.
Belanger et al., Functional analysis of genes responsible for the synthesis of the B-band O antigen of *Pseudomonas aeruginosa* serotype O6 lipopolysaccharide. Microbiology. Dec. 1999;145 (Pt 12):3505-21.
Bentley et al., Complete genome sequence of the model actinomycete *Streptomyces coelicolor* A3(2). Nature. May 9, 2002;417(6885):141-7.
Berge et al., Pharmaceutical salts. J Pharm Sci. Jan. 1977;66(1):1-19.
Bibb, Regulation of secondary metabolism in streptomycetes. Curr Opin Microbiol. Apr. 2005;8(2):208-15.
Bierman et al., Plasmid cloning vectors for the conjugal transfer of DNA from *Escherichia coli* to *Streptomyces* spp. Gene. Jul. 1, 1992;116(1):43-9.
Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.

(56) References Cited

OTHER PUBLICATIONS

Blondelet-Rouault et al., Antibiotic resistance gene cassettes derived from the omega interposon for use in *E. coli* and *Streptomyces*. Gene. May 6, 1997;190(2):315-7.
Castro-Palomino et al., N-Tetrachlorophthaloyl-Protected Trichloroacetimidate of Glucosamine as Glycosyl Donor in Oligosaccharide Synthesis. Tetrahedron Lett. 1995;36:5343-46.
Chaffin et al., CpsK of *Streptococcus agalactiae* exhibits alpha2,3-sialyltransferase activity in *Haemophilus ducreyi*. Mol Microbiol. Jul. 2002;45(1):109-22.
Chang, Multidrug resistance ABC transporters. FEBS Lett. Nov. 27, 2003;555(1):102-5.
Chater, *Streptomyces* inside-out: a new perspective on the bacteria that provide us with antibiotics. Philos Trans R Soc Lond B Biol Sci. May 29, 2006;361(1469):761-8.
Chen et al., Vancomycin analogues active against vanA-resistant strains inhibit bacterial transglycosylase without binding substrate. Proc Natl Acad Sci U S A. May 13, 2003;100(10):5658-63. Epub Apr. 24, 2003.
Cheng et al., Domain requirement of moenomycin binding to bifunctional transglycosylases and development of high-throughput discovery of antibiotics. Proc Natl Acad Sci U S A. Jan. 15, 2008;105(2):431-6. Epub Jan. 8, 2008.
Coates et al., Stereoselective Synthesis of Moenocinol and Assignment of Its Carbon-13 Nuclear Magnetic Resonance Spectrum. J Org Chem. 1980;45:2685-97.
Crich et at, Are Glycosyl Triflates Intermediates in the Sulfoxide Glycosylation Method? A Chemical and 1H, 13C, and 19F NMR Spectroscopic Investigation. J Am Chem Soc. 1997;119:11217-23.
Crich et al., Chapter 2. Gylcosylation with Sulfoxides and Sulfinates as Donors or Promoters. Org React. 2004;64:115-251.
Crich et al., Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxy-glucosamine derivatives in glycosylation. 2-Picolinyl ethers as reactivity-enhancing replacements for benzyl ethers. J Am Chem Soc. Jul. 18, 2001;123(28):6819-25.
Dairi, Studies on biosynthetic genes and enzymes of isoprenoids produced by actinomycetes. J Antibiot (Tokyo). Apr. 2005;58(4):227-43.
Datsenko et al., One-step inactivation of chromosomal genes in *Escherichia coli* K-12 using PCR products. Proc Natl Acad Sci USA. Jun. 6, 2000;97(12):6640-5.
Debenham et al., Two New Orthogonal Amine-Protecting Groups That Can Be Cleaved under Mild or Neutral Conditions. J Am Chem Soc. 1995;117:3302-03.
Decker et al., A general approach for cloning and characterizing dNDP-glucose dehydratase genes from actinomycetes. FEMS Microbiol Lett. Aug. 1, 1996;141(2-3):195-201.
Dirksen et al., Rapid oxime and hydrazone ligations with aromatic aldehydes for biomolecular labeling. Bioconjug Chem. Dec. 2008;19(12):2543-8.
Du et al., Identification and functional analysis of dTDP-glucose-4,6-dehydratase gene and its linked gene cluster in an aminoglycoside antibiotics producer of *Streptomyces tenebrarius* H6. Curr Microbiol. Aug. 2004;49(2):99-107.
Durr et al., Biosynthesis of the terpene phenalinolactone in *Streptomyces* sp. Tü6071: analysis of the gene cluster and generation of derivatives. Chem Biol. Apr. 2006;13(4):365-77.
Ebenezer, Colabomycin Co-Metabolites. Synthesis of 2880-II, A Metabolite Related to Ferulic Acid. J Synth Commun. 1991;21:351-58.
Eichhorn et al., Characterization of moenomycin antibiotics from medicated chicken feed by ion-trap mass spectrometry with electrospray ionization. Rapid Commun Mass Spectrom. 2005;19(15):2179-86.
El-Abadla et al., Moenomycin A: The Role of the Methyl Group in the Moenuronamide Unit and a General Discussion of Structure-Activity Relationships. Tetrahedron. 1999;55(3):699-722.

Ellervik et al., A High Yielding Chemical Synthesis of Sialyl Lewis x Tetrasaccharide and Lewis X Trisaccharide; Examples of Regio-and Stereodifferentiated Glycosylations. J Org Chem. 1998;63:9314-22.
Fehlhaber et al., Moenomycin A: A Structural Revision and New Structure-Activity Relations. Tetrahedron. 1990;46(5):1557-68.
Feng et al., Structure of the *Shigella dysenteriae* 7 O antigen gene cluster and identification of its antigen specific genes. Microb Pathog. Feb. 2004;36(2):109-15.
Flett et al., High efficiency intergeneric conjugal transfer of plasmid DNA from *Escherichia coli* to methyl DNA-restricting streptomycetes. FEMS Microbiol Lett. Oct. 15, 1997;155(2):223-9.
Fuse et al., Functional and Structural Analysis of a Key Region of the Cell Wall Inhibitor Moenomycin. ACS Chem Biol. 2010;5(7):701-711.
Garegg et al., Formation of Internucleotidic Bonds via Phosphonate Intermediates. Chem Scr. 1985;25:280-82.
Gildersleeve et al., Scavenging Byproducts in the Sulfoxide Glycosylation Reaction: Application to the Synthesis of Ciclamycin 0. J Am Chem Soc. 1999;121:6176-82.
Gildersleeve et al., Sulfenate Intermediates in the Sulfoxide Glycosylation Reaction. J Am Chem Soc. 1998;120:5961-69.
Goldman et al., Differential antibacterial activity of moenomycin analogues on gram-positive bacteria. Bioorg Med Chem Lett. Oct. 16, 2000;10(20):2251-4.
Goldman et al., Inhibition of transglycosylation involved in bacterial peptidoglycan synthesis. Curr Med Chem. Aug. 2000;7(8):801-20.
Gromyko et al., Generation of *Streptomyces globisporus* SMY622 strain with increased landomycin E production and it's initial characterization. J Antibiot (Tokyo). Jun. 2004;57(6):383-9.
Gust et al., PCR-targeted *Streptomyces* gene replacement identifies a protein domain needed for biosynthesis of the sesquiterpene soil odor geosmin. Proc Natl Acad Sci U S A. Feb. 18, 2003;100(4):1541-6. Epub Jan. 31, 2003.
Halliday et al., Targeting the forgotten transglycosylases. Biochem Pharmacol. Mar. 30, 2006;71(7):957-67. Epub Nov. 18, 2005.
Hang et al., Probing Glycosyltransferase Activities with the Staudinger Ligation. J Am Chem Soc. 2004;126(1):6-7.
Hang et al., Small molecule inhibitors of mucin-type O-linked glycosylation from a uridine-based library. Chem Biol. Mar. 2004;11(3):337-45.
Hang et al., The chemistry and biology of mucin-type O-linked glycosylation. Bioorg Med Chem. Sep. 1, 2005;13(17):5021-34.
He et al., Isolation and structural elucidation of AC326-alpha, a new member of the moenomycin group. J Antibiot (Tokyo). Feb. 2000;53(2):191-5.
Hebler-Klintz et al., The First Moenomycin Antibiotic Without the Methyl-Branched Uronic Acid Constituent.-Unexpected Structure Activity Relations. Tetrahedron. 1993;35:7667-78.
Hernández-Torres et al., Temperature-controlled regioselectivity in the reductive cleavage of p-methoxybenzylidene acetals. J Org Chem. Oct. 15, 2004;69(21):7206-11.
Hodgson, Primary metabolism and its control in streptomycetes: a most unusual group of bacteria. Adv Microb Physiol. 2000;42:47-238.
Hong et al., A signal transduction system in *Streptomyces coelicolor* that activates the expression of a putative cell wall glycan operon in response to vancomycin and other cell wall-specific antibiotics. Mol Microbiol. Jun. 2002;44(5):1199-121 1.
Hong et al., Inactivation of the carbamoyltransferase gene refines post-polyketide synthase modification steps in the biosynthesis of the antitumor agent geldanamycin. J Am Chem Soc. Sep. 15, 2004;126(36):11142-3.
Hopwood, Soil to genomics: the *Streptomyces* chromosome. Annu Rev Genet. 2006;40:1-23.
Ishikawa et al., FramePlot: a new implementation of the frame analysis for predicting protein-coding regions in bacterial DNA with a high G + C content. FEMS Microbiol Lett. May 15, 1999;174(2):251-3.
Iyobe et al., Sex pili mutants isolated by macarbomycin treatment. Antimicrob Agents Chemother. May 1973;3(5):614-20.
Jabbouri et al., Involvement of nodS in N-methylation and nodU in 6-O-carbamoylation of *Rhizobium* sp. NGR234 nod factors. J Biol Chem. Sep. 29, 1995;270(39):22968-73.

(56) References Cited

OTHER PUBLICATIONS

Jansson et al., 2-(Trimethylsilyl)ethyl Glycosides. Synthesis, Anomeric Deblocking, and Transformation into 1,2-Trans 1-O-Acyl Sugars. J Org Chem. 1988;53:5629-47.

Kahne et al., Glycosylation of Unreactive Substrates. J Am Chem Soc. 1989;111:6881-82.

Kaplan et al., Genes involved in the synthesis and degradation of matrix polysaccharide in *Actinobacillus actinomycetemcomitans* and *Actinobacillus pleuropneumoniae* biofilms. J Bacteriol. Dec. 2004;186(24):8213-20.

Kartha et al., Iodine: A Versatile Reagent in Carboyhydrate Chemistry III. Efficient Activation of Glycosyl Halides in Combination with DDQI . Tetrahedron Lett. 1996;37:8807-10.

Kaur, Expression and characterization of DrrA and DrrB proteins of *Streptomyces peucetius* in *Escherichia coli*: DrrA is an ATP binding protein. J Bacteriol. Feb. 1997;179(3):569-75.

Kawasaki et al., Biosynthesis of a natural polyketide-isoprenoid hybrid compound, furaquinocin A: identification and heterologous expression of the gene cluster. J Bacteriol. Feb. 2006;188(4):1236-44.

Kawasaki et al., Interconversion of the product specificity of type I eubacterial farnesyl diphosphate synthase and geranylgeranyl diphosphate synthase through one amino acid substitution. J Biochem. Jan. 2003;133(1):83-91.

Khidekel et al., A chemoenzymatic approach toward the rapid and sensitive detection of O-GlcNAc posttranslational modifications. J Am Chem Soc. Dec. 31, 2003;125(52):16162-3.

Knirel et al., Somatic antigens of *Shigella*: structure of the O-specific polysaccharide chain of the *Shigella dysenteriae* type 7 lipopolysaccharide. Carbohydr Res. Aug. 15, 1988;179:51-60.

Kudo et al., A new family of glucose-1-phosphate/glucosamine-1-phosphate nucleotidylyltransferase in the biosynthetic pathways for antibiotics. J Am Chem Soc. Feb. 16, 2005;127(6):1711-8.

Kuiper et al., A Selective and Mild Synthetic Route to Dialkyl Phosphates. Synthesis. 2003;5:695-98.

Lay et al., Synthesis of N-acetylglucosamine containing Lewis A and Lewis X building blocks based on N-tetrachlorophthaloyl protection—synthesis of Lewis X pentasaccharide. Carbohydr Res. Aug. 1998;310(3):157-71.

Lehtovaara et al., A new method for random mutagenesis of complete genes: enzymatic generation of mutant libraries in vitro. Protein Eng. Apr. 1988;2(1):63-8.

Leimkuhler et al., Differential inhibition of *Staphylococcus aureus* PBP2 by lycopeptides antibiotics. J Am Chem Soc. Mar 16, 2005;127(10):3250-1.

Leskiw et al., Accumulation of bldA-specified tRNA is temporally regulated in *Streptomyces coelicolor* A3(2). J Bacteriol. Apr. 1993;175(7):1995-2005.

Leskiw et al., TTA codons in some genes prevent their expression in a class of developmental, antibiotic-negative, *Streptomyces* mutants. Proc Natl Acad Sci U S A. Mar. 15, 1991;88(6):2461-5.

Lin et al., Sequence analysis and molecular characterization of genes required for the biosynthesis of type 1 capsular polysaccharide in *Staphylococcus aureus*. J Bacteriol. Nov. 1994;176(22):7005-16.

Linnett et al., Additional antibiotic inhibitors of peptidoglycan synthesis. Antimicrob Agents Chemother. Sep. 1973;4(3):231-6.

Liu et al., Acceptor specificity and inhibition of the bacterial cell-wall glycosyltransferase MurG. Chembiochem. Jul. 7, 2003;4(7):603-9.

Lombo et al., The mithramycin gene cluster of *Streptomyces argillaceus* contains a positive regulatory gene and two repeated DNA sequences that are located at both ends of the cluster. J Bacteriol. Jan. 1999;181(2):642-7.

Lovering et al., Structural insight into the transglycosylation step of bacterial cell-wall biosynthesis. Science. Mar 9, 2007;315(5817):1402-5.

Luzhetskii et al., [Interspecies conjugation of *Escherichia coli*-*Streptomyces globisporus* 1912 using integrative plasmid pSET152 and its derivatives]. Genetika. Oct. 2001;37(10):1340-7. Russian.

Luzhetskyy et al., Iteratively acting glycosyltransferases involved in the hexasaccharide biosynthesis of landomycin A. Chem Biol. Jul. 2005;12(7):725-9.

Marzian et al., Moenomycin A: Reactions at the Lipid Part. New Structure-Activity Relations. Tetrahedron. 1994;50:5299-308.

McAlpine et al., Microbial genomics as a guide to drug discovery and structural elucidation: ECO-02301, a novel antifungal agent, as an example. J Nat Prod. Apr. 2005;68(4):493-6.

McKeegan et al., The structure and function of drug pumps: an update. Trends Microbiol. Jan. 2003;11(1):21-9.

Men et al., Substrate Synthesis and Activity Assay for MurG. J. Am. Chem. Soc. Feb. 1998;120(10):2484-2485.

Mendez et al., The role of ABC transporters in antibiotic-producing organisms: drug secretion and resistance mechanisms. Res Microbiol. Apr.-May 2001;152(3-4):341-50.

Metten et al., The First Enzymatic Degradation Products of the Antibiotic Moenomycin A. Tetrahedron. 1992;48:8401-18.

Meyers et al., The Diumycins. New Members of an Antibiotic Family Having Prolonged In Vivo Activity. J Antibiot. 1969;22:490-93.

Müller et al., Utility of Glycosyl Phosphites as Glycosyl Donors-Fructofuranosyl and 2-Deoxyhexopyranosyl Phosphites in Glycoside Bond Formation. Tetrahedron Lett. 1994;35:4763-66.

Murrell et al., Biochemical characterization of the SgcA1 alpha-D-glucopyranosyl-1-phosphate thymidylyltransferase from the enediyne antitumor antibiotic C-1027 biosynthetic pathway and overexpression of sgcA1 in *Streptomyces globisporus* to improve C-1027 production. J Nat Prod. Feb. 2004;67(2):206-13.

Muth et al., A vector sytem with temperature-sensitive replication for gene disruption and mutational cloning in streptomycetes. Mol Gen Genet. 1989;219:341-48.

Nakagawa et al., Biosynthesis of asukamycin. Formation of the 2-amino-3-hydroxycyclopent-2-enone-moiety. J Chem Soc Chem Commun. 1985:519-21.

Nemoto et al., Purification and characterization of geranylgeranylglyceryl phosphate synthase from a thermoacidophilic archaeon, Thermoplasma acidophilum. J Biochem. May 2003;133(5):651-7.

Oh et al., Denaturation of circular or linear DNA facilitates targeted integrative transformation of *Streptomyces coelicolor* A3(2): possible relevance to other organisms. J Bacteriol. Jan. 1997;179(1):122-7.

Ostash et al., A streamlined metabolic pathway for the biosynthesis of moenomycin A. Chem Biol. Mar. 2007;14(3):257-67.

Ostash et al., Bacterial transglycosylase inhibitors. Curr Opin Chem Biol. Oct. 2005;9(5):459-66.

Ostash et al., Complete characterization of the seventeen step moenomycin biosynthetic pathway. Biochemistry. Sep. 22, 2009;48(37):8830-41.

Pacholec et al., Characterization of the aminocoumarin ligase SimL from the simocyclinone pathway and tandem incubation with NovM,P,N from the novobiocin pathway. Biochemistry. Mar. 29, 2005;44(12):4949-56.

Paton et al., Molecular characterization of the locus encoding biosynthesis of the lipopolysaccharide O antigen of *Escherichia coli* serotype O113. Infect Immun. Nov. 1999;67(11):5930-7.

Paulsen, Advances in Selective Chemical Syntheses of Complex Oligosaccharides. Angew Chem Int Ed Engl. 1982;21:155-73.

Petricek et al., Occurrence of two 5-aminolevulinate biosynthetic pathways in *Streptomyces nodosus* subsp. *asukaensis* is linked with the production of asukamycin. J Bacteriol. Jul. 2006;188(14):5113-23.

Pfaller, Flavophospholipol use in animals: positive implications for antimicrobial resistance based on its microbiologic properties. Diagn Microbiol Infect Dis. Oct. 2006;56(2):115-21. Epub May 15, 2006.

Ramakrishnan et al., alpha-Lactalbumin (LA) stimulates milk beta-1,4-galactosyltransferase I (beta 4Gal-T1) to transfer glucose from UDP-glucose to N-acetylglucosamine. Crystal structure of beta 4Gal-T1 x LA complex with UDP-Glc. J Biol Chem. Oct. 5, 2001;276(40):37665-71. Epub Aug. 2, 2001.

Ramakrishnan et al., Structure-based design of beta 1,4-galactosyltransferase I (beta 4Gal-T1) with equally efficient N-acetylgalactosaminyltransferase activity: point mutation broadens

(56) References Cited

OTHER PUBLICATIONS beta 4Gal-T1 donor specificity. J Biol Chem. Jun. 7, 2002;277(23):20833-9. Epub Mar. 26, 2002.
Rascher et al., Cloning and characterization of a gene cluster for geldanamycin production in *Streptomyces hygroscopicus* NRRL 3602. FEMS Microbiol Lett. Jan. 28, 2003;218(2):223-30.
Rebets et al., Expression of the regulatory protein LndI for landomycin E production in *Streptomyces globisporus* 1912 is controlled by the availability of tRNA for the rare UUA codon. FEMS Microbiol Lett. Mar. 2006;256(1):30-7.
Redenbach et al., The *Streptomyces lividans* 66 chromosome contains a 1 MB deletogenic region flanked by two amplifiable regions. Mol Gen Genet. Nov. 1993;241(3-4):255-62.
Riedl et al., Impact of flavophospholipol and vancomycin on conjugational transfer of vancomycin resistance plasmids. Antimicrob Agents Chemother. Nov. 2000;44(11):3189-92.
Ritzeler et al., Search for new moenomycin structure-activity relationships Synthesis of a trisaccharide precursor of a moenomycin analogue. Tetrahedron. 1997;53:1665-74.
Rose et al., Consensus-degenerate hybrid oligonucleotide primers for amplification of distantly related sequences. Nucleic Acids Res. Apr. 1, 1998;26(7):1628-35.
Schmidt et al., Nitriles as Solvents in Glycosylation Reactions: Highly Selective β-Glycoside Synthesis. Synlett. 1990;11:694-96.
Schuricht et al., Studies on the Biosynthesis of the Antibiotic Moenomycin A. J Prakt Chem. 2000;342(8):761-72.
Sekurova et al., In vivo analysis of the regulatory genes in the nystatin biosynthetic gene cluster of *Streptomyces noursei* ATCC 11455 reveals their differential control over antibiotic biosynthesis. J Bacteriol. Mar. 2004;186(5):1345-54.
Shin et al., Total synthesis and structure of the ramoplanin A1 and A3 aglycons: two minor components of the ramoplanin complex. Proc Natl Acad Sci U S A. Aug. 17, 2004;101(33):11977-9. Epub Jun. 2, 2004.
Sletten et al., A bioorthogonal quadricyclane ligation. J Am Chem Soc. Nov. 9, 2011;133(44):17570-3. Epub Oct. 17, 2011.
Slusarchyk et al., The Structure of a Novel Lipid from the Antibiotic Diumycin. J Am Chem Soc. 1970;92:4486-88.
Slusarchyk et al., The structure of the lipid portion of the antibiotic prasinomycin. Tetrahedron Lett. Feb. 1969;8:659-62.
Smith et al., The cps genes of *Streptococcus suis* serotypes 1, 2, and 9: development of rapid serotype-specific PCR assays. J Clin Microbiol. Oct. 1999;37(10):3146-52.
Soderberg et al., Geranylgeranylglyceryl phosphate synthase. Characterization of the recombinant enzyme from *Methanobacterium thermoautotrophicum*. Biochemistry. Dec. 11, 2011;40(49):14847-54.
Sosio et al., The gene cluster for the biosynthesis of the glycopeptide antibiotic A40926 by nonomuraea species. Chem Biol. Jun. 2003;10(6):541-9.
Srivastava et al., Combined chemical-enzymic synthesis of deoxygenated oligosaccharide analogs: transfer of deoxygenated D-GlcpNAc residues from their UDP-GlcpNAc derivatives using N-acetylglucosaminyltransferase I. Carbohydr Res. Oct. 25, 1990;207(2):259-76.
Stawinski, Chapter 8. Some Aspects of H-Phosphonate Chemistry. In: Handbook of Organophosphorus Chemistry. R. Engel ed. Marcel Dekker, New York. 1992:377-434.
Stumpp et al., Synthesis of Moenocinol. Tetrahedron. 1986;42:5941-48.
Subramaniam-Niehaus et al., Isolation and analysis of moenomycin and its biosynthetic intermediates from *Streptomyces ghanaensis* (ATCC 14672) wildtype and selected mutants. Z Naturforsch C. Mar.-Apr. 1997;52(3-4):217-26.
Tachibana et al., Novel prenyltransferase gene encoding farnesylgeranyl diphosphate synthase from a hyperthermophilic archaeon, *Aeropyrum pernix*. Molecular evolution with alteration in product specificity. Eur J Biochem. Jan. 2000;267(2):321-8.

Tahlan et al., Three unlinked gene clusters are involved in clavam metabolite biosynthesis in *Streptomyces clavuligerus*. Can J Microbiol. Oct. 2004;50(10):803-10.
Tai et al., Parallel identification of O-GlcNAc-modified proteins from cell lysates. J Am Chem Soc. Sep. 1, 2004;126(34):10500-1.
Takahashi et al., A two-stage one-pot enzymatic synthesis of TDP-L-mycarose from thymidine and glucose-l-phosphate. J Am Chem Soc. Feb. 8, 2006;128(5):1432-3.
Takahashi et al., Macarbomycin, a new antibiotic containing phosphorus. J Antibiot (Tokyo). Jan. 1970;23(1):48-50.
Thuy et al., Functional characterizations of novWUS involved in novobiocin biosynthesis from *Streptomyces spheroides*. Arch Biochem Biophys. Apr. 1, 2005;436(1):161-7.
Tirado et al., Stereochemistry of the Iodocarbonation of cis- and trans-3-Methyl-4-pentene-1,2-diols: The Unusual Formation of Several Anti Iodo Carbonates. J Org Chem. 1993;58:5666-73.
Trepanier et al., The positive activator of cephamycin C and clavulanic acid production in *Streptomyces clavuligerus* is mistranslated in a bldA mutant. Microbiology. Mar. 2002;148(Pt 3):643-56.
Van Heijenoort, Formation of the glycan chains in the synthesis of bacterial peptidoglycan. Glycobiology. Mar. 2001;11(3):25R-36R.
Vocadlo et al., A chemical approach for identifying O-GlcNAc-modified proteins in cells. Proc Natl Acad Sci U S A. Aug. 5, 2003;100(16):9116-21. Epub Jul. 21, 2003.
Vocadlo et al., A strategy for functional proteomic analysis of glycosidase activity from cell lysates. Angew Chem Int Ed Engl. Oct. 11, 2004;43(40):5338-42.
Vogel et al., Moenomycin analogues with modified lipid side chains from indium-mediated Barbier-type reaction. Tetrahedron. 2001;57:4139-46.
Vogel et al., Some selective reactions of moenomycin A. Bioorg Med Chem Lett. Sep. 4, 2000;10(17):1963-5.
Volke et al., Characterisation of antibiotic moenomycin A interaction with phospholipid model membranes. Chem Phys Lipids. Feb. 28, 1997;85(2):115-23.
Wallhausser et al., Moenomycin, a new antibiotic. I. Fermentation and isolation. Antimicrob Agents Chemother (Bethesda). 1965;5:734-6.
Wang et al., The pgaABCD locus of *Escherichia coli* promotes the synthesis of a polysaccharide adhesin required for biofilm formation. J Bacteriol. May 2004;186(9):2724-34.
Weber et al., Exploiting the genetic potential of polyketide producing streptomycetes. J Biotechnol. Dec. 19, 2003;106(2-3):221-32.
Weisenborn et al., The prasinomycins: antibiotics containing phosphorus. Nature. Mar. 18, 1967;213(5081):1092-4.
Welzel et al., [Moenomycin A: Spaltung Des Antibiotikums Mit Trifluoressigsaure/2-Propanol Und Bestimmung Der Verknupfung Von D-Glucose Und 2-Acetamido-2-Desoxy-D-Glucose.] Tetrahedron. 1981;37:97-104. German.
Welzel, Transglycosylase Inhibition. In: Antibiotics and antiviral compounds- chemical synthesis and modification. Krohn et al., eds. Weinheim, Germany. 1993:373-78.
Westerduin et al., Synthesis of the Fragment GlcNAc-α(1-P-6)-GlcNac of the Cell Wall Polymer of *Staphylococcus lactis* Having Repeating N-Acetyl-D-Glucosamine Phosphate Units. Tetrahedron Lett. 1986;27:6271-74.
Westrich et al., Cloning and characterization of a gene cluster from *Streptomyces cyanogenus* S136 probably involved in landomycin biosynthesis. FEMS Microbiol Lett. Jan. 15, 1999;170(2):381-7.
White et al., New oligomeric catalyst for the hydrolytic kinetic resolution of terminal epoxides under solvent-free conditions. Tetrahedron Asymm. 2003;14:3633-38.
Wilen et al., Strategies in Optical Resolutions. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Wilson et al., Molecular analysis of tlrB, an antibiotic-resistance gene from tylosin-producing *Streptomyces fradiae*, and discovery of a novel resistance mechanism. J Antibiot (Tokyo). Mar. 1999;52(3):288-96.

(56) References Cited

OTHER PUBLICATIONS

Ye et al., Better substrates for bacterial transglycosylases. J Am Chem Soc. Apr. 4, 2001;123(13):3155-6.

Yu et al., The biosynthetic gene cluster of the maytansinoid antitumor agent ansamitocin from *Actinosynnema pretiosum*. Proc Natl Acad Sci U S A. Jun. 11, 2002;99(12):7968-73.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zalkin et al., Enzymes utilizing glutamine as an amide donor. Adv Enzymol Relat Areas Mol Biol. 1998;72:87-144.

Zehl et al., Characterization of moenomycin antibiotic complex by multistage MALDI-IT/RTOF-MS and ESI-IT-MS. J Am Soc Mass Spectrom. Aug. 2006;17(8):1081-90. Epub May 30, 2006.

Zhang et al., A Simple Statistical Parameter for Use in Evaluation and Validation of High Throughput Screening Assays. J Biomol Screen. 1999;4(2):67-73.

Zhang et al., Molecular and chemical characterization of the lipopolysaccharide O-antigen and its role in the virulence of *Yersinia enterocolitica* serotype O:8. Mol Microbiol. Jan. 1997;23(1):63-76.

Zhu et al., Identification of the function of gene IndM2 encoding a bifunctional oxygenase-reductase involved in the biosynthesis of the antitumor antibiotic landomycin E by *Streptomyces globisporus* 1912 supports the originally assigned structure for landomycinone. J Org Chem. Jan. 21, 2005;70(2):631-8.

Baizman, et al., "Antibacterial Activity of Synthetic Analogues Based on Disaccharide Structure of Moe, an Inhibitor of Bacterial Transglycosylase", Microbiology, 2000, vol. 146, pp. 3129-3140.

Garneau, et al., "Synthesis of Mono- and Disaccharide Analogs of Moe and Lipid II for Inhibition of Transglycosylase Activity of Penicillin-Binding Protein 1b", Bioorg Med Chem, 2004, vol. 12, pp. 6473-6494.

Neundorfi, et al., "Evidence for the Combined Participation of a C10 and a C15 Precursor in the Biosynthesis of Moenocinol, the Lipid Part of the Moe Antibiotics", ChemBioChem., 2003, vol. 4, pp. 1201-1205.

Schuricht, et al., "The Biosynthesis of Moenocinol, the Lipid Part of the Moe Antibiotics", Tetrahedron Lett., 2001, vol. 42, pp. 3835-3837.

Taylor, et al., "The Total Synthesis of Moenomycin A", J. Am. Chem. Soc., 2006, vol. 128, pp. 15084-15085.

Welzel, "Synthesis around the Transglycosylation Step in Peptidoglycan Biosynthesis", Chem Rev., 2005, vol. 105, pp. 4610-4660.

Welzel, et al., "Moe A: Minimum Structural Requirements for Biological Activity", Tetrahedron, 1987, vol. 43, pp. 585-598.

Invitation to Pay Additional Fees for PCT/US2013/035416, mailed Jun. 10, 2012.

International Search Report and Written Opinion for PCT/US2013/030800, mailed Jun. 18, 2013.

International Search Report and Written Opinion for PCT/US2013/035427, mailed Jun. 28, 2013.

Office Communication, mailed Jan. 16, 2013 for U.S. Appl. No. 12/681,052.

Daghish et al., Tetrafunctional photoaffinity labels based on Nakanishi's m-nitroalkoxy-substituted phenyltrifluoromethyldiazirine. Angew Chem Int Ed Engl. Jul. 2, 2002;41(13):2293-7.

Gampe et al., Tuning the moenomycin pharmacophore to enable discovery of bacterial cell wall synthesis inhibitors. J Am Chem Soc. Mar. 13, 2013;135(10):3776-9. doi: 10.1021/ja4000933. Epub Mar. 4, 2013.

Luning et al., Moenomycin-Type Transglycosylase Inhibitors: Inhibiting Activity vs. Topology around the Phosphoric Acid Diester Group. Tetrahedron Lett. 1994;35(12):1859-62.

Riedel et al., Synthesis and Transglycosylase-Inhibiting Properties of a Disaccharide Analogue of Moenomycin A Lacking Substitution at C-4 of Unit f. Tetrahedron. 1999;55(7):1921-36.

Rühl et al., A trifunctional reagent for photoaffinity labeling. Tetrahedron Lett. 2000;41(23):4555-58.

Schurer et al., Fluorescence correlation spectroscopy as a new method for the investigation of aptamer/target interactions. Biol Chem. Mar. 2001;382(3):479-81.

Volke et al., On Penicillin-Binding Protein 1b Affinity-Labeling Reagents. Helvetica Chimica Acta. 2003;86(12):4214-32.

Extended European Search Report for EP 08834841.2, mailed Jul. 2, 2013.

International Search Report and Written Opinion for PCT/US2013/035416, mailed Oct. 15, 2013.

International Preliminary Report on Patentability for PCT/US2013/035416, mailed Oct. 16, 2014.

International Preliminary Report on Patentability for PCT/US2013/030800, mailed Oct. 16, 2014.

International Preliminary Report on Patentability for PCT/US2013/035427, mailed Oct. 16, 2014.

\* cited by examiner

FIG. 8
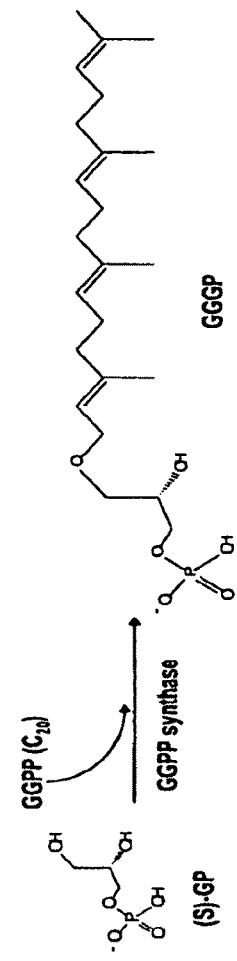
A
Biosynthesis of intermediate of archaeal membrane lipid
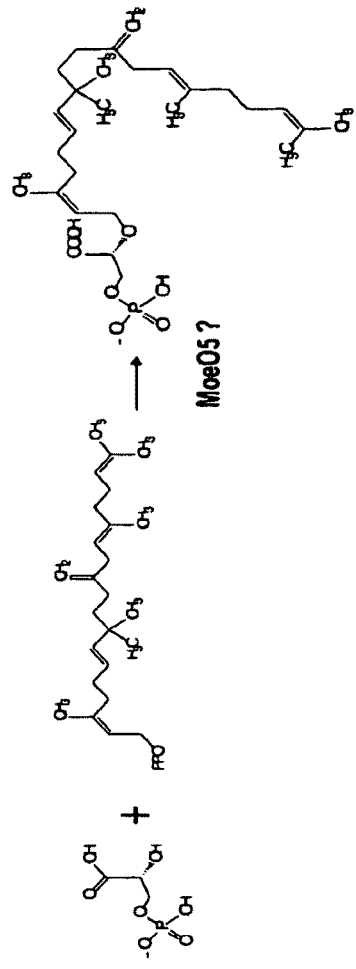
B
Proposed scheme of phosphoglyceric acid incorporation into moenomycin

SEQUENCE LISTING

```
<160> NUMBER OF SEQ ID NOS: 152

<210> SEQ ID NO 1
<211> LENGTH: 35000
<212> TYPE: DNA
<213> ORGANISM: Streptomyces ghanaensis

<400> SEQUENCE: 1
cgcgcccctc cggaggctgt ccggaagggc gcggcacggg tggggcggg  tcggccgggt      60 tccgccggcc gggtcgggtc agccgacgac ggccggctgt gcgggcgcct cccgcgggcc     120
gccgctgatc ggcaggacct cggcgtccga ggtccgcacg aagcggggac cgtccggccc     180
gtacaccccg cgcggctccg ggaacagggt gagcaggacg aggtagagca ccgccgccag     240
```

```
ggccaggccg accggcagcg agacgtccat gccgtcggcc aggtcgccga gcggtccgac     300
gaactgaccg ggcaggttgg tgaagagcag ggccacggcg gcggagacca gccaggtggc     360
caggccgcgc cagttccacc cgtgggcgaa ccagtagcgg ccgccggtgc ggcgctggtt     420
gaagacctgg agcgcctccg ggtcgtacca gccccggcgg gtgacgtagc cgaggatcat     480
cacgaccatc cacggcgcgg tgcaggtgat gatcagggtg gcgaaggtgg agatcgactg     540
cgtgaggttc agccagaagc ggccggcgaa gatgaacacg atggacagca cgccgatgaa     600
gatcgtcgcc tgaacgcggc tgaagcgggt gaagacgctg cagaagtcca gtccggtgcc     660
gtacagcgcg gtcgtgccgg tggacaggcc gccgatcagc gcgatgaggc agagcggcag     720
gaagtaccag ccgggcgcga tcgcgagcag gccgccgacg tagttgggcg cgtcggggtc     780
gaggtacgcc ccggcccggg tggcgatgat cgacgcggtg gccaggccga agacgaacgg     840
cagcagcgtg gcgatctggg ccaggaacgc cgcgcccatc acccggcggc gggggtcgc     900 ggccgggatg tagcgggacc agtcgccgag gaacgcgccg aaggagaccg ggttggagag     960
cacgatcagt gcggacccga tgaaggacgg ccagaagagc gggtccgcgg tcgaggcgaa    1020
ggtgcccgcg taaccggggt cgaagtcgcc ggcgaaggcg aaggcgccca gcacgaacag    1080
ggccgaggcc gccaccacgg cgatcttgtt gaccagcagc atgaagcgga agccgtagat    1140
gcagaccacc agcacgagac cggcgaagac cgcgtaggcc agggcgtacg tcaccgtcga    1200
ctcggggact cccagcaacc ggtgcgcgcc gccgaccagg cgtccccg aggaccacac    1260 cgagatcgag aagaaggcga tcgcggtgag cagcgcgagg aaggagccga cgaccttcc    1320 gtgcaccccc aggtgggcgg aggaggagac ggagttgctg gtgccgttcg tgggcccgaa    1380
gagcgccatg ggcgcgagca gcagcgcgcc cgcgaccagg ccgagcagcg tcgccgcgag    1440
cccctgccag aaggagaggc cgaacaggat gggggaaggtg cccagcacac aggtggcgaa    1500
ggtgttggcg ccgccgaagg cgaggcggaa cagatcgagc ggacgggccg tgcggtcctc    1560
gtccggaatc tgctcgacac cgtatgtctc gatgtcggtg accgcggtct tcacgggatc    1620
tcctccttct gttcacgccc cggggatgg ccccacagtc tgaatccccc cactgacctg    1680
cgacaactgt gtcaatcaca gagaggtagc ctgctttatg tggccaccaa caaactgacc    1740
gtcgaggatc tgctctcctt ccccgccctc cagctgacgc tgcgggcggg gaagagtgga    1800
ctctcacgct ccgtttcctg ggcccacacc agcgagttgg ccgatccgac ccctggctg    1860 ctgggggccg aggtgatcat gacgacgggg ctcgcgatcc cccgcaccgc gaccgggcag    1920
cgccgctatc tggagcggct ggacgacgcc ggggtctccg cgctgcccct gtcggcgcag    1980
ctgcacatgc cgccgctgca cgacgcgttc ttcaaggcgg ccgaggaacg gggcttcccc    2040
gtcctggagt gccgctcgc cgttccgttc atcgcggtct cccaggaggt cgccgccgcg    2100
gtgcaggagg acgcccggca ccggctgggc gcgcagctgc aggtcttcgg ctcgctgcgc    2160
tggatggtcg ccgaggacct cgacaccccc accctcctgc gccgcctcga gcgcctgtcc    2220
gggtacaacg tcttcctctg cacccccag ggccgcccgc tgctgcccgg ggtgcccacc    2280
cccgacccgg gcgtgctgcc cgcctcggtg gacgccccgc cgaccgtccc cggcggtttc    2340
gtcctgcccg tgccggcacc gggcggtccg gccggtttcc tggtggcgta cgagaggcag    2400
ggcgcccagc ccgccgggct cgcggtcgtc cagcacatcg ccacggtggc ggcgctgcgg    2460
ctggcgatgg tgcgcaacga acgcgagacg ctgccgccgcg agggcgccga gaccctcgcc    2520
gaactgctcc gggaggtgct cgacccggac gccgcccgcc gccggctcgc ccggcacgcg    2580
atcgagggcg agaccgtgct gctcgtggtc cggaacacca ccgacgaggc actgctgcac    2640
```

```
tgcctggagg accgccccca cctgctgctc acccggggcg acgaccggta cgtgctcggg    2700
gccccggagc tggccccggc gatcggcgaa ctgcccgggg tggcggccgg gatgagccgc    2760
gcccttccgc cgggcgcggc cctgaaggtc gccgagcgcg aggccctgtg ggcgctgagc    2820
aaggcggtcg agtcgggccg ccccctggtc cgctacggcg acgacgcgac gggccgctgg    2880
ctgccggagg accccgcggt gctgagcgcg ctggtcgagc acgtcctcgg cgaggtgctg    2940
cgctacgacc tggcccacgg ctcccagctc ctggtctccg tgcgcacctg gctgagcgc     3000
gaccgccgta cggagaccgc cgcggccgcc ctccacatcc accccaacac gctcgcctac    3060
cggctgcgcc gcttcggcgc cctctcccgg cgcgacctgt cctcgaccgg cgcgctggcg    3120
gaggtctggc tggcgatcca ggcggccggg acgctggggc tcaccgactg agcgcgccgg    3180
acaccggccc cgggcgggga cacgaccgg gcggcgcgca ccgcctccga ggcgttcgtc     3240
cgggccgggc cgccccgcc ggcggggaac cggccgggc cgtcaccct cggccgggcc       3300
gcccccgcct cgtcggacga ccggagccgg acggccggct cccccttgag gaccttgccg    3360
ccgggtccca ggggaagccg gtcggggagg accacccgcc gcggacgccg gtacgccgcg    3420
atgtgccgct caccccacgc cacgacggaa tccgccagtg ccccgtccgg tgtcgggccg    3480
tcccgtggca ccaccaccgc gcacacctcc tggccgtaca ccgggtcggg gagccccacc    3540
accgcgaccc gggcgaccgc cggatggcgg agcagcgctt cctcgacctc acggggatgg    3600
acgtcgtacc cgccccgcag gatcacgtcc ttctcgcggt cgacggcggt ggggtacccc    3660
tcctcgtcca gcagccctag atcgccggtg cggaaccagc cgtccacgaa cgcggcggcc    3720
gtggcgcggg gggcgtcgac gtacccggcc atcaggttgt gcccgcggac gacgatctcg    3780
cccacctcgc cggagggagc ggcccgacgg cgtcctccgc ctcggaccgg ggctgtcgcg    3840
acctccacgc cccagaggtg atccgctcgg cgcccgcgac caccgcggtg cgctccggcc    3900
accggcccgc ggagtccgag aggatcgtgg ccgccgagag ggtcgccccc gggcccgccc    3960
acgtgttccc gccgtcggtg acggctccgg aatccgtcgt gaacggccct gccggaggtt    4020
ttcgtacgcg ctcgtcgcga ctccgcctcg cttgccggta atcggcttcc atcggccgga    4080
cgacagcatg agacgtcttc tgtgcaagac ccgcggtgga tcccaggatg agaccggccc    4140
gaagggtagc gaaaggagcg gaccttggac atctcctcgt ccatggactt cttcgtgcga    4200
ctcgcccgcg aaaccggtga ccggaagagg gagtttctcg aactcggccg caaggcgggt    4260
cggttccccg cggcgagcac ctcgaatggc gagatttcca tctggtgcag caacgactac    4320
ctgggtatgg ggcagcaccc ggacgtcctc gacgccatga agcgctccgt ggacgaatac    4380
ggcggaggat ccgggggttc gcggaacaca ggcggaacca accacttcca tgtggctctg    4440
gagcgggagc cggccgagcc gcacggaaag gaggacgccg ttctcttcac ctcggggtat    4500
tccgccaatg agggatccct gtcggttctg gccggggccg tcgacgactg ccaggtcttc    4560
tcggattcgg cgaaccacgc gtccatcatc gacggtttac ggcacagcgg cgcccgcaag    4620
cacgtattcc ggcacaagga cgggcggcat ctggaggagt tgctggccgc ggccgaccgg    4680
gacaagccga agttcatcgc cctggagtcc gtgcattcga tgcgggggcga catcgcgctc    4740
ctggccgaga tcgccggcct ggccaagcgg tacgagcgg tcaccttcct cgacgaggtg     4800
cacgcggtcg gcatgtacgg cccgggcgga gcgggcatcg cggcccggga cggcgtgcac    4860
tgcgagttca cggtggtgat ggggacccctc gccaaggcct tcggcatgac cggcggctac    4920
gtggcgggac cggccgtgct catggacgcg gtgcgcgccc gggcccgttc cttcgtcttc    4980
```

```
accacggcgc tgccgccggc ggtcgcggcg ggcgcgctcg ccgcggtgcg gcacctgcgc    5040
ggctcggacg aggagcggcg gcggccggcg gagaacgcgc ggctgacgca cggcctgctc    5100
cgcgagcggg acatccccgt gctgtcggac cggtccccca tcgtcccggt gctggtcggc    5160
gaggaccgga tgtgcaagcg catgtcggcc ctgccgctgg agcggcacgg cgcgtacgtc    5220
caggccatcg acgcgcccag cgtcccggcc ggcgaggaga tcctgcggat cgcgccctcg    5280
gcggtgcacg agaccgagga gatccaccgg ttcgtggacg ccctggacgg catctggtcc    5340
gaactggggg ccgcccggcg cgtctgacgc cccgcagtgt caccccgcgg gagggctctg    5400
cggagcgggc ccggcgtccc cgcccccggg acccgcaccc gtccagatcc ggcccatctc    5460
ggcggagacc gccatgacct cctcgaaggt gcccgaggcc tccacccgcc cgccctcgag    5520
caccaccacg cggtcggccg cgcgcagcag agcgggccgg tgggagaccg cgagcacggt    5580
ccgcgtcccg tccagcagcc tctcccacag caggtgctcg gtctccgggt ccagggcact    5640
ggagacgtcg tccagcacca cgagttcggg gtcgccgacc agcatgcggg cgatcgcgac    5700
ccgctggatc tgcccgcccg agaggcgcag gccccgcggg cccaccacgg tgtccgggcc    5760
gtcctgcatc gccgccaggt cgggctccgc cacggcgagg cgcacggcct cgtcgaaggc    5820
cgcgccgtcc cggcccagca ggacgttctc ccgcaccgtc ccgctgaaca gacacgggac    5880
ctgcggggtg tacccgcagc gcggcgccac caggaacgac gcggggtcgg cgatcggttc    5940
gccgttccac agcacggtgc ccgctcgtg cgggagcagt ccgaggacgg cccggaccag    6000
ggtgctcttg ccggaaccga cccggccggt gaccacggtg acggtgtgcc gctccaccac    6060
caggtccacg tcctctatgc cgtgcccgc cccggggtgg cgggccgtca gcccgcgcac    6120
ggccagttcc cgcaggggcg gggcgggctc cggcccggcg tccggggcgg cggccccctc    6180
gccggtccct cccggcgcgt cggacgcgat cggcggactg gcccgctcca gggaccgccg    6240
cagccggcag ccgaggttgt tggtgatccg gccgagcgcc accgagaccc gctgcaaccg    6300
cacgacagca tgccgatcg accccagggc ctcggtcagg atctgcaggt agaaggcgaa    6360
cagggcgaga tcgccgacgc tgaaggtccc ctcgtccatc cgccccgcga ccagcagcag    6420
caccacgccg accccgatcg gggccgggtt gccgatcacc gtgcgctgga cgacggcgta    6480
cagctcctcc cgcaccgcgg cttcggcacg ggcgccgttc agcccggcga cgtgcgcggc    6540
gacctgcggg tcggcggcgg cggcctgcac cgcgcccacc gcgcccacca tctcccgcag    6600
ggctcccgcc acctccccgg acgcggcccg ggtggcccgc cggtgccgca ggaaccggct    6660
gtgggccagc gcggtgacca gcgtcagcag gacgaggagg cgcggagggg cgccggtgac    6720
cacggcgtcg atccgcatca tcaccgtgac cgacgcggcg acgaacagcc agtgggcgag    6780
gttcgtcggc gcccaggcga cgaagaaccc cgtctcgtcg acgtcctcgc ccaccgttcg    6840
cagggactcg ccggggctgg tgcgggccgt cacctccgac ccgcgcaggg ccgatcccag    6900
cagggcgtgc cgcagccgcg ccgtggtgcc gtactggacc cgcggctcca gcctgttgat    6960
catcacgccg aactggagga acagccgtcc cgcctcgatc gcggccacca acgcgatgat    7020
cagccacacg ccccgcccg cgccagcgc gtcgaacagc cgctggaaca gcaggcccac    7080
caccagggtt cccgcccgca gcaggaccca cagaccggtg agggtccagt aggtgcgggc    7140
cgagccgcgc agcacgtccg cgagccgtcc caggacggac tgccgcccg ctccgtcgtc    7200 cgcccgcctc gctctcccct ctgcccgctc cgctccgtcg tccgcccgcc tcgtctcccc    7260
ccctgcccgc tccgctccgt cgtccgcccg ctccactcct ggcaccccgc tccccctccc    7320
gtccccgttc ctcaccgggt ggctccggcc gtgcggagga gtgcgtggaa gcgcgacccg    7380
```

```
ggatcggcgg cgaggaccct ccgctccccc tcctcggcga ccttcccctc ctccagcacc   7440
aggatccggt cgacgttccg gagcaggtgc gggcggtgct ccaccacgac ggcggtgcgg   7500
ccctcgagca gccgctccag cgcgggcatc aggagccgct cgctgtacgg atccagccgg   7560
gccgtcggct cgtccatcag gaccagcccc ggatcgcgca ggaacaccct ggccagcgcg   7620
agctgctgct cctcgcccgc ggacatgccg cgggccccgg cgccgagcgg cgtgtccaga   7680
ccgtcgggca gggtgcgcag ccaggggccg agcccggcct cgccgagagc ggcgcgcagc   7740
cggtcgtcgg ggacggagcg gtcgaagaag gtgaggttgt cccgcagcga ggcgtggaag   7800
acgtgcacct cctgggtgac cagcgcgacc cggctgcgca gcgcccgggg atcgatctcc   7860
gtcaggtcca ggccgcctgc cgacaccgag cccgcccccg ggtggtggag cccgaacagc   7920
agccggacca cggtggactt gccgctgccg gtgcgtccca cgacgccgag gcgttcgccg   7980
gggcgcaggg tgaaggagac gtcccgcagc accggctcgt cgggctcgta gccgaaggag   8040
accccgtcga gcggactcc gggcagtccg gccggcagcg tcccgcgtcc cgtgcggggc   8100
gccgccgtcc cgtggcccag caggtccctc agccgctggg cgctcgcggc ggcgtcctcg   8160
agttcgcgga gcgggtggt gaccgcgagc aggggcggc gcagcagcat cgcgtaggac   8220
agggaggcga aggccgtccc cgtggagagc tgtccgcggg cgtgcagcca ggcgctgacc   8280
gccagggcca ggacgacgct gacggcggac aggccctgca ccgtggcggg ccagcggacc   8340
gaggcccgcg ccgcgtcgcg ggccttccgg tacaggtcgt cctgccggtc gccgagttcc   8400
cgcagggtgt accgcgaggc cccgttgacg cggaggtcct ccgccgccgc gaggcgctcc   8460
tcgaggaagc cctgcaggtc cgccgcgacc cgctgccgcg cggtgacgaa gggcatggcg   8520
cggcccacca gggtccgcag cagcaggagg gtgcctgccg cgaacggggc gaccaccagg   8580
gccagccgcc attccagccg gaacagggcg acgaggatgc cgacgatcag cagtgcctgc   8640
gccagcagtt ccagcagcag cgtcgacatc accgcggcga gccgggtgac gtcgccgtcc   8700
atccgctcga cgagttcgcc gggcggatgc ttgcggtaga agcccggcgg ccggctcagg   8760
cagtgctcga ccaggtccgc gcgcaaccgg ttggtgctgc gccaggcgac ccgtgaggac   8820
agcgcctcgg tgcccgcggt gaccacgagc gtccgacgg cggccgccag gaccaggcg   8880 gcgaggtcca gcagcgtctt ccgggagtcg ccggagagcg ccccgtcgat gaatccgcgc   8940
agcaggtagg gcgccaccag ctggagcccc atccccgcgg ggaccaggag ggcgagcagc   9000
gccacggcgg tccgttcacc gcgcaggtag cggacaaacg tggagagatg ccgcaacgga   9060
ctgtctgcca acgcgcccct ccccgttcg cccggcggcg agcggccagc ataaagtcct   9120
gtgcgcctcc ttgtgaatga cgcctcgtca acggcggccg gagcacgccc tttctgcggg   9180
aatgccgata gcggacgccg ctccggggag gggcgaagca caccattgct cgtgattgac   9240
gcatgctgtt agactcccca cgtctcttgg tccggacatg cgtttctcaa cgccgaaagc   9300
ctggtcaacc gcactttcgg caccgcacag tcccacggcg tccagcggt cgcgcgagtc   9360 ggcccggtcg agcagagggc agccacacga acgtgcaccg caatgcaccg ccttgatcag   9420
ccagttgtga gcgaaacaag ggggattcgt gtcgagcgat acacacggaa cggacttagc   9480
ggacggcgac gttttggtca ccggtgcggc cggcttcatc gggtcgcacc tggtgacgga   9540
actgaggaat tccggcagaa acgttgtggc ggtggaccgg agacccttc cggacgactt   9600 ggagagtacg tccccgccct ttaccggttc gctccgggag atacgcggtg acctcaactc   9660
attgaatctg gtggactgcc tgaaaaacat ctcgacggtc ttccacttgg ccgcgttacc   9720
```

```
cggagtccgc ccgtcctgga cccaattccc cgagtacctc cggtgcaatg tactggcgac   9780
ccagcgcctg atggaggcct gtgtgcaggc cggcgtggaa cgcgtggtgg tcgcctcgtc   9840
ctccagcgtc tacggcggcg cggacggcgt gatgagcgag gacgacctgc cccgtccgct   9900 ctcccctac ggggtcacca aactcgccgc ggagcggctg gccctggcct tcgcggcccg   9960
cggcgacgcc gagctctcgg tcggcgccct gaggttcttc accgtctacg ccccggcca  10020 gcgcccggac atgttcatct cccggctgat ccgggcgacg ctccggggcg aaccgtcga  10080 gatctacggc gacgggaccc agctccgcga cttcacccat gtgtccgacg tggtgcgggc  10140
gctgatgctg accgcgtcgg tgcgggaccg gggcagcgcg gtgctgaaca tcggcaccgg  10200
gagcgccgtc tcggtcaacg aagtggtctc catgaccgcg gagctgaccg gtctgcgccc  10260
gtgcaccgcg tacggttccg cccgcatcgg cgacgtccgc tcgaccaccg ccgacgtgcg  10320
gcaggcccag agcgtcctgg gcttcacggc ccggacgggt ctgcgggaag gtctcgccac  10380
ccagatcgag tggaccccgg ggtcactgtc cggcgccgag caggacaccg tcccggtcgg  10440
cggctcctcg gtgtccgtgc cgcggctgta ggcggcatgt gcggcttcgt cggattcagt  10500
gacgccggcg ccgggcagga ggacgcccgt gtcacggccg agcgcatgct cgccgccgtg  10560
gcgcaccgcg gccccgacgg ctcggactgg tgccaccacc ggggcgtcac cctcgcgcac  10620
tgcgccctga ccttcaccga tccggaccac ggcgcgcagc cgttcgtctc cgcgtcggga  10680
gccaccgccg tggtgttcaa cggcgagctc tacaaccacg ccgtgctggg cgacggggcg  10740
ttgccctgcg cacccggagg cgacacagaa gttcctggtg gaactctacg agttgctggg  10800
catgcggatg ctcgaccggc tgcggggcat gttcgccttc gcgctgcagg acgcccgcac  10860
cggcaccacg gtgctggccg cgaccgatgg ggaagagccc ctctactaac acccgcgtgc  10920
gagacggaca tcgctttcgc gtcggaactc acgtctctgc tgcggcaccc cgccgcgccg  10980
cgcacaccgg aggtgcgggc gctcgccgac tacctggtgc tccaggcgtt ctgcgccccc  11040
gcctcggccg tgtcggggt gtgcaaggtg cgccccggca gctacgtgac ccaccggcac  11100
ggcgcgttgg acgagaccga gttctggcgg ccccgcctga ccccgaccg ggggcgggc  11160 cgcggccccg gacggcggga ggccgcgcgg cggttcgagg agctcttccg cgccgcggtc  11220
gcccgccgga tgaccagcac cgaccgccgc ctcggcgtac tgctcagcgg cggcctggac  11280 tccagcgcg tcgccgcggt ggcccagcag ctcctgccgg gacggccggt gcccaccttc  11340
agcgcggggt tcgcggaccc ggacttcgac gagagcgacc acgcacgggc ggtggcgcgc  11400
cacctcggca ccgagcacca tgtggtgcgg atcggcgggg ccgacctcgc cggtgtggtg  11460
gagtccgaac tcgccgtggc cgacgagccg ttggccgatc cctccctgct gcccacacgt  11520
ctggtctgcc gggcggcgcg cgagcacgtc cgcggcgtgc tcaccggtga cggcgcggac  11580
gaactgctcc tgggctaccg ctacttccag gccgagcggg cgatcgagct gctgctgcgc  11640
gtgctgccgg ccccccggct ggaggccctc gtccggctgc tggtgcgccg gctgccggcc  11700
cgttccggca acctccccgt gacccacgcc ctcggtctgc tggccaaggg cctgcgcgcg  11760
gcaccggagc accggttcta cctctcgacg gcgcccttcg gcccgggcga gctgccacgg  11820
ctgctcaccc ccgaggccgg ggccgaactg accgggcacg accgttcac cgaggtgtcg  11880 cgcctcctgc ggggacagcc gggcctgacc ggtgtccagc gcagccagct cgccgtggtg  11940
acccacttcc tgcgggacgt gatcctcacc aagacggacc ggggcggcat gcgcagctcc  12000
ctcgagctgc gttcccccctt tctcgacctg gacctggtcg agtacggcaa ctccctgccc  12060
accggcctga agctgcaccg gttcaccggc aagtacctgc tgcggcaggt cgccgccggc  12120
```

```
tggctgcccc cttccgtcgt ccagcggacg aagctgggtt tccgcgcgcc ggtggcggcc   12180
ctgctccgcg gcgagctgcg gccctgctc ctggacaccc tctccccgtc gtccctgcgc    12240
cgcggcggcc tgttcgacac cggggcggtg cgcctgctga tcgacgacca cctcggcggc   12300
cggcgcgaca cctcccgcaa gctgtgggcg ctgctggtct accagctctg gttcgagagc   12360
ctgacggccg accccgcgc cctcgagtcc cccgcgtacc cggccctctc ctaggagacc    12420
catggctgcc cccgaccgac cgctcgtcca ggtgctctcc ccccggacct ggggcgagtt   12480
cggcaactac ctcgccgcga cgcgcttctc ccgcgcgctc cggagcgtga tcgacgcgga   12540
agtgaccctg ctggaggcgg agccgatcct cccgtggatc ggcgaggccg gggcgcagat   12600
ccggaccatc tccctggaga gccccgacgc cgtcgtccgc aaccagcggt acatggccct   12660 catgaccgc ctccaggcac gcttcccgga ggggttcgag gcggacccca ccgccgccca    12720
gcgggcggac ctggaaccgc tcacccggca cctgcgggag agcgcccccg acgtggtggt   12780
cggcacgaag gggttcgtgg cgaggctgtg cgtggccgcc gtccggctcg ccgggacgtc   12840
caccagggtc gtcagccacg tgaccaaccc cgggctgctg cagctgccgc tgcaccgcag   12900
ccggtacccg gacctgacac tcgtcggctt ccccgggcg aaggagcacc tgctggccac    12960
ggccggcggc gacccggagc gcgtccaggt ggtgggcccg ctcgtcgccc agcacgacct   13020
gcgggacttc atgaccagtg agacggccgt ctccgaggcg gggccctggg gcggcgactc   13080
gggcccggac cggccacggg tgatcatctt ctccaaccgc ggcggggaca cctaccccga   13140
gctggtgcgg cgcctcgccg accgccaccc cggcatcgac ctcgtcttcg tcggctacgg   13200
cgacccggag ctcgcccgcc gcaccgctgc ggtcgggcgg ccccactggc ggttccacag   13260
cgtcctcggc cagagcgagt acttcgacta catccggcgt gcctcccggt ccaggtacgg   13320
gctcctcgtc tcgaaggcgg ggcccaacac caccctggag gcggcctact cggcataccc   13380
ggtcctgatg ctcgagtcgg ggctgcccat ggagcggtgg gtgccgggac tgatccacga   13440
ggaggggctg ggccacgcct gcgccacccc cgaggagctg ttccgcacgg cggacgactg   13500
gctgacccgc ccgtcggtga tcgaggtgca caagaaggcc gcggtctcct tcgccgcttc   13560
cgtactggac caggacgcgg tgacggccag gatcaaggcc gccctccagc ccctgctgga   13620
cgcccgatga cggtccgccg cccggccgcg tccgccccc gcgtcctcct gaccgcgggc    13680
cccgacgggg tgcgcgtgga gggcgacggg gaggcgcgcc tcgggcaccc cctcaccggt   13740
gaccacctgg acccgggccc gccggccgaa ggcgtcttcg ccgggtggag gtgggacggc   13800
gagcgcctgg tggcccgcaa cgaccgctac ggcgtctgcc ccctcttcta ccgggccggc   13860
ggcggctcac tcgcgctctc ccccgacccg ctcgccctgc tgccggagga cgggcccgtc   13920
gagctggacc acgacgcgct cgccgtcttc ctgcggacgg ggttcttcct cgccgaggac   13980
acggccttcg cacaggtccg cgcactgccc ccggcggcca cgctcacctg gacaccggc    14040 gggctgcggg tgcggtccga cgggccgccg cgccccgggg ccgccgcgat gaccgaggcg   14100
caggcggtcg acggcttcgt cgacctgttc cgcgcctcgg tggcccgccg gctgccggc    14160 gaaccgtacg acctgccgct cagcggcggc cggactcgc ggcacatcct gctcgagctg    14220
tgccgccgcg gcgcaccgcc gcggcggtgc gtcagcggcg ccaagttccc tcccgacccg   14280
ggggccgacg cgcgcgtggc ggccgccctg gcgggccggc tcggtctgcc gcacacggtg   14340
gtgccgcgcc cccgttcgca gttccgcgcg gagctcgccg ccctgccggc ccagggcatg   14400
accaccctgg acggcgcgtg gacccagccg gtcctggccc acctgcgccg ccacagccgc   14460
```

```
atctcgtacg acggtctcgg cggcggggag ctcgtccaga acccgagcgt ggagttcatc   14520
cgggccaacc cctacgaccc cgcggacctg cccggcctgg cggaccggtt gctggccgcg   14580
agccggaccg gcccccacgt ggagcacctg ctgagccccc ggacgaacgc cctgtggagc   14640
aggcaggcgg cgcggcggcg cctcgtcacc gagctggccc ggcacgccga cagcgccagc   14700
ccgctcagtt ccttcttctt ctggaaccgg accggcgct ccatctccgc ggctccgttc   14760
gccctggggg acggacgggt cctgacgcac acccccctacc tcgaccacgc cctcttcgac   14820
cacctcgcct cggtgccgca ccgcttcctg gtcgacggga cgttccacga ccgggcgctg   14880
caccgggcct tccccgagca cgcggacctg gggttcgcct cgtcggtgcc ccagcggcac   14940
ggacccgtgc tggtcgcgca ccgactggcg tacctgctcc ggttcctcgc ccacgcgacg   15000
gtcgtggaac cgggctggtg gcgcggcccc gaccgcttcc tgcaacggct gctggccgcc   15060
ggccgggggc ccggggcccc gcagcgcgtc agcaggctgc agccctggc gctctacctg   15120 ctgcagttgg aggacctcgc cgtccgaagg gccgccgcc ggccgtagcg gggccggacc   15180
gccgcagacc cccacttcac gagacatcag ccgcagggcc cagaaggagc acatcgcatg   15240
cggaagacat tgcccgtgat cagcacaggt cccgccgcgg gagcgacgtc gggcggatgc   15300
tccgccccgg ccgagacccc ggccggtcg ggaataccgc tgtggcgcaa cgcaaactg   15360 cggatcgccc tggtgcgcca tcacgacctg tgcctgaaca cccgtcagat cgcgcgggtc   15420
cagaagcggg ccggcgtgct gccgcacctc ggggctgggt tacatccaca ccgcgctcaa   15480
gtcggccggg ttccaccacg tcatccaggt cgacaccccc gccctgggcc tcgacagcga   15540
ggggctgcgc aagctgctcg cggacttcga gccggacctg gtcggggtga gcaccacgac   15600
acccggtctg cccggcgcca tcgaggcgtg cgaggcggcc aagagcaccg gggcgaaggt   15660
gatcctgggc gggccgcaca cggaggtgta cgcgcacgag aacctggtcc acgagtccat   15720
cgactacgtg ggcgtcggcg aaggcgtcac gatcatgccg gaactggcgg aggcgatgga   15780
gcggggcgag gagccggagg gcatccgcgc cctggtgacc cgcaagcacg acggcggtgc   15840
cgcgccgatg gtgaacctgg aggaggtcgg ctggcccgaa cgcgccgggc tcccgatgga   15900
ccgctactac tcgatcatgg ctccgcggcc gttcgcgacg atgatctcca gccgcggctg   15960 cccccttcaag tgcagcttct gcttcaagca ggccgtggac aagaagtcca tgtaccgcag   16020
tcccgaggac gtcgtcggtg agatgacgga gctcaaggag cggtgggggg tgaaggagat   16080
catgttctac gacgacgtgt tcaccctgca ccgcggccgg gtgcgggaga tctgcgggct   16140
catcggggag accggcctca aggtccgctg ggaggcgccc accgcgtcg acctggtgcc   16200 cgagccgctg ctggaggcga tggccggggc cgggtgcgtg cgcctgcggt tcggcatcga   16260
gcacggtgac agcgagatcc tcgagcggat gcgcaaggag agcgacatcc agaagatcga   16320
gaaggccgtc acctccgccc acgaggccgg gatcaagggc ttcgggtact tcatcgtcgg   16380
ctggctcggg gagacccggg agcagttccg caggaccgtc gacctcgcct gccgcctccc   16440
gctggactac gccagcttct acaccgcgac gcccctgccg gcacccccc tgcacacgga   16500 gtccgtggcc gccggccaga tcccgcccga ctactgggac cgcttttcgt gcggggcgag   16560
ttcgacgcgc ggatcgggta cctggtgccg gacgcgcagg agcgcgccca gtgggcgtac   16620
cgctccttct tcatgcgccg ctccatggtc aagccgctgc tgtcgcacat ggcggtgacc   16680
ggccagtggc gcaacacgct ggacggcctg cacagcctgt accggtcgac ctccaacacc   16740
gaccgtgact tctgagcccg ccgccccggc cgtcccgcac ccgccggtgc gtccggggcc   16800
gccggtccgt ctcaaccggc cgctggcgcg gcgcaggcgg cggccggccg gggaggggtt   16860
```

-continued

```
cgtgacgcac cacctgcgga gcaccatggc ccgcgggttc cgcccccgg agtcctggga    16920
ggtccccgtc cggcacgtcc tgcccggtct gccggccgac gggactccgc gcgccgagga    16980
ggccgctcag gcgctgcgca cgcccgccgg gcggccgggc atcgccctcg tcgtgccgac    17040
ctacgtctcc cgggtgagcc tggcgcggca gcgggagtgg ttcgacgcgc tgctggacca    17100
ggcggccgcg gtgacgcggg accacccct ggtgcccctg gtgctgttcg tcggcatgca    17160
gtggtcgtcg gccgaggagg agcgggaggc gctgcgcgc ctgcgtgtgc tgctggacga    17220
cgcccgcacc cggctgcccg gactgcggat ctgcggtctc gcgctgcccg ggccgggcaa    17280
accccgcacc ctcaacgggg cgatcgccgt cgccgagctc ctcggctgtg cgggcgtcgg    17340
gtggaccgac gacgacgtga ccctggagga ggactgcctg tcccggctgg tgcgggactt    17400
cctggcggcg ggctgccgcg gggcggtggg cgcgaccaag gttgcgcaca cccatgagta    17460
cgccacctcc cggctgctgt cccgggccaa ggcgatcgcc gccccggcca cgaactaccc    17520
gcacggctgc tgcatcctgg tggccaccga cgtggtggcc ggtggtctgc cgggacgcta    17580
cgtatccgac gacggctacg tgtgcttccg cctcctcgac cccgcgctgc ccgacccgct    17640
ggcccggctg cggctggttc cggacgcccg gtgccactac tacgtggcgg ggccggccgg    17700
cgagacccgc cgcaggatcc gcaggctgct gctcaaccac ctcgtcgacc tcgccgactg    17760
gcccctgccg gtggtccgtc actacttccg ccacgtcctg ttcggcggca tgtgccgct    17820
gaccggcttc gactcctccc gcggtgcccg ccgcggtgtg cagaaggcgc tcatcaagtg    17880
gctctacttc gcctggttcg cgggcatcgg gggcgaactc tacgtgcgcg ggctgtccgg    17940
caggccactg cgccgcatcg agtgggctcc ctactcggac atccgcaggc tcactccgtc    18000
gtcctcaccc acgcgtcagg agagctgatg aaggtactgt cgctccactc cgccggccac    18060
gacaccggcg tcgcctactt cgaggacggg cggctggtct tcgcggtcga gaccgaacgg    18120
ctcacccggg tcaagcacga ccaccgctcc gacgtcgccc tgcggcacgt gctcgagcag    18180
gagtgcgtgg acaccgacgg gatcgacctg gtggccgtca gcaccccggt ccgcagcggg    18240
ctgctgcgca tacccgacct ggaccgggcc atggagcgga tcgggcgggg cgccctccac    18300
caccggaccg tctgcgagat gctggggcgg cgggtggagt gcgtcgtggt cacccacgag    18360
gtctcccacg cggcgctggc cgcccactac gcggactggg aggaaggcac cgtcgtcctc    18420
gtcaacgagg gccgcggcca gctcacccgc agctccctgt ccgggtgac cggcggggcc    18480
ctggagtggg tcgacaagga cccgctgccc tggtacggca acggcttcgg gtggacggcg    18540
atcgggtacc tcctcggctt cggcccgagc cccagcgtgg cgggcaaggt gatggccatg    18600
ggcggctacg ggcagccgga cccgcgcatc cgcgaacagc tgctgtcggt ggatccggag    18660
gtgatgaacg accgggaact cgccgagcgg gtgcgcgcgg acctggccgg ccggcccgag    18720
ttcgcccccg ggttcgagac ggcgtcgcag gtggtggcga cgttccagga gatgttcacc    18780
gaggccgtcc gggcggtgct cgaccggcat gtgacgcgca cggacgccgg ggtgggcccg    18840
atcgccctgg gcggcgggtg cgccctgaac atcgtggcca actcggcgct gcgggaggag    18900
tacgggcggg acgtcgccat cccgccccgcc tgcggggacg cgggtcacct gacgggcgcc    18960
ggcctctacg ccctcgcgca ggtggccggg gtgaagccgg agccgttcag cgtgtaccgc    19020
aacggcgggg gcgaggcccg ggccgccgtc ctggaggcgg tgagggcgc ggggttgcgg    19080
gccgttccct acgaccggtc cgcggtcgcc ggggtgctgg ccggggcgg ggtggtggcc    19140
ctgacgcagg gagcggcgga actggggccg cgggcgctgg ggcaccggtc gctgctgggc    19200
```

```
agtcccgcgg tgccgggcat gcgcgagcgg atgagcgaga agctcaagcg gcgcgagtgg   19260
ttccggccgc tgggcgccgt gatgcgcgac gagcgcttcg ccgggctgta cccggggcgg   19320
gcgccgtcgc cgtacatgct cttcgagtac cggctgccgg acgggatcgc gcccgaggcc   19380
cggcacgtca acggcacctg ccggatccag accctgggcc ccgaggagga ccggctgtac   19440
ggtctgctcg ccgagttcga ggagctgagc ggtgtgccgg cgctgatcaa cacgtcgctc   19500
aacggcccgg gcaagcccat cgcgcacacc gcccgggacg tgctcgacga cttcgcgcgc   19560
accgacgtcg acctcttcgt gttcgacgac ctgatggtgc ggggcgccgc cgcgcggtag   19620
cccccggggt ggggcgggac ggccggccgg agacgctccg gccggccgtc ggtcactccc   19680
ccaggtgccg gggaagcagc cgtaccagca cgtcgtccgt gtagaggtgg acgaccggca   19740
ccagaccggg cgcgccgggc ggtgccgcca ccgcggcgag ggcccgcccg cgcagctcct   19800
ccagcaggtc cacgacgtcc tggccggcca cggccccggt ccgcatcaga tgggcgaggt   19860
tgccgtcccg ctcgccgttg cggtcgtagt cggtcaggtc gtccgccatg gtgatggtca   19920
tggcgaaagc ctctgcgaac tcccttacgg agtccgccgg ttggccttcc cccccgcagg   19980
cggccgcgag tgccccgtag cggcccagga aggtggagcc gtaggtgctc gcatgggcgc   20040
gccactcccg gaggttcgtc gcccgagagc gtttggtgcg tatctggccg ccgcagaggt   20100
ggacggcgtc ctgctccagg atgtccgtca ccgccttggg gtcccgggcg agggattcca   20160
gttcgtgcag cgcccgcagg tggaggcgga ggcagacaca ggcgagttcg acccggtcga   20220
gtccggtgtc gtcgtccatc aggtcgtcga ggagcttcat ggagacgatg tcgagggcca   20280
gcgcgcggga caccgcggcc cgccggtccg ggtcggtcgt ccactcggtg aggaagtggg   20340
gcaccctcag gtacaggcgc agggcggcgg tgtgcgccac caggtccggc gacccaccgg   20400
tctgcgcgac gcaccgcgtg acatggtcgc ggttggcggc ctcggcggcg agcatggtct   20460
ccgtgtagtc cgccggcagg gccgtggccg gggcggccgt caccgccgc tccccggacg   20520 ggccggggcg gcgggccgcc tcccggcgat ctcggcgagg gcggaccgcc agtccggctg   20580
ttccagggct ccggcgaacc ccacgtagtc cgccccgctg tcgaggtact cggtgacctg   20640
ccgcccggag cggacgttgc cgctcacgaa gagcacctgg tcgggccga gccccttgcg   20700 gaagtggcgt acgacctcgg gcggcacgtg ctcgttgcgc gagtacaggt acaccatgtg   20760
gaaaccgaag gcacgggcga cgtggaggta ccggtcgatc tcctcggtgg aggccgtgct   20820
caccggcacg gtgccgagca ggtccccggt gcggggtcc tcgccgaagg tgagggcgac   20880
ggtgaggagc agctcgggcc actcctcgcg gggtattcgg ccggggaagg cggccagcgt   20940
ctcgaggaag ctcttccaga cgaagtagtc gtcgcccgag cccagcagcg cgggcagcag   21000
gagcgcgtcc gcgccgcgga ccaccgggaa gccggccccc gggcggggcg ggaagtgcag   21060
gacgaccggt aacggggtgg ccgccttcac cgccgccacg tacggctcca tgtgcgactc   21120
gaacgactcg tagtcggtgc tggccagaag gacggcggcg aagcccagcc gcgtgagctc   21180
cgccgccttc tcgaccgctt ccgtcaccgg gaccttgaag gggtcgatga tgtggacggg   21240
gcccggttgg tgctcgcgca gccgggcgag cacgcgtccc ggccgccaga gcggtggtgc   21300
ggcgtggagt tccgtgtggt ggtccagttg cggtgaggcg ttcaccagcg tcttccccct   21360
tgtcgtccgg ctcgtcgtcc ggcttgtcgt ccggtcgggt cacgcgacgg ggtgccggcc   21420
gcgtcgcacg tgcggatcgc gtccggatga ggtgtcgcgc gttcggatgg aggtgcgggg   21480
cgccctggtc gccgaggccg ttccggccg ccgggagtg ttcctcccgg tgtgccgcgc   21540
cggcgcgaaa gccgtggtcc ggcgccgtcg cgcggttttcc ttcagacccg ccgggggaac   21600
```

```
tgcgtgaccg ttccggcaca cgccgcggtc gagggagtgc ggaagtgctc ggaaatcctt    21660
cggcgggccc gtccggcgga ttcaccggcg gacggacgaa aagcgtcgtt cacgtactcc    21720
ccttccactg gagagacgaa cagcgggtcc accgggccgc ctcgaggaca gggtgcggca    21780
gggcggttgc cgatactaca cgcgttcgtt tccgtggggt agggagactt tgtgcggcgg    21840
ttatgcattc ctgccggacg gaagaaggca cgccccgacg gtttcgcgcc gtgcggggcg    21900
ttctcggcgg tgtccggcgt atttcacgcg aattgcagat ggcgccggcg cgcaatcgg    21960 cccgccgtca cgcaaccgct caccgcgacc agcagcagcg tcactccgac ggcgtgggcc    22020
accccggagt cgaacgaccc gctgtccgcg ccgtcgaccg cgtaggtgat gatctcccgg    22080
gtcgaccaga agggaagcac cttggccgaa tccttggccg gatccatcac catctgggcg    22140
ccgatgacgg agatcagcag cagggcgccc tccatgtccc gtggcacggc cgccccgagc    22200
agcagtccca gcggcaccgc caccagtgtg gtcagcgcca gttccaccgc gacggcccgc    22260
gggtgcgcca cgtcctgccc gaccaggatg atcacggcgt agagggcgga cacgcccatg    22320
ccggcggtga ggagggccag caggcggccc aggaagagct ggagcgggcg aacccggag    22380 agggccagga gcggttcgat ctcccggccg ccgaccgcgg agaagagggc gcggcgctg    22440 accgcgaagc ccaccccgag gctggcgaac cggaccgcct ggccggtctg gtcgtaacgc    22500
ccgaggtaga agacgagcgg gaccaggagc agcaggccca gcacgccccg ccggcgcagc    22560
agttcgcgga aggtcatctc cgccatccgc agggtggccg tcatcggttg ccccttcctt    22620
tgccgggggt gaggtccagc acctggtcca cccggtcgag ctggttgagc atgtgcgtca    22680
ccacgacgac ggccttgccc gcctcgcgcc actcccagac gctctgccag aagtccacgt    22740
aggagccgtg gtcgaagccc tggtagggct cgtcgagcag cagcaggtcc gggtctccca    22800
gggccgacag gacgacgttc agcttctggc gggttcctcc cgacaggtcc ttggcaagga    22860
cgccctccgc gggggcccag tcgagctctc ccgcgagtct ccggccgcgg cggtcggact    22920
cccggcggct caggccccgg ccggtgccga agagggtgaa gtgctcccgg ggggtcagga    22980
agcccatgac ccccgcgttc tgcgggcagt agccgaggtg gccggagacg gtgacccgtc    23040 cttttgtcggg ggagagcaga ccggcgcaga tcttgagcag ggtggacttg cccgtcccgt    23100
tgctgccgac gatcgcggcg acctcgcccg cgtgcacgac aagatcgacc ccggtcagga    23160
cgcggcggcg cttgtagcgt ttcacgacgc cgcgcgcctg caggagaatc ttgcggtcgg    23220
cgggctcgga catgccgtgg taccctctc gggcaccgac ggaatggccc atgactgcca    23280
cctttctgcc gaccgcgacg aagggcacgc attgtcggcc tcaatggtca ggatgcgtga    23340
tccggtcggg ttcatcgccc cggccgcacg cgcacggctc agcctgccac acggcctgcc    23400
ccacatagcg cgtatcggtc gggccccac ttccccgaaa gtccgggccc ccggccggtg    23460
ttccggggat cctacggggc gaccgggcga aggactgaag ccgggcatcc gcgtttcggc    23520
catctctcgc cgatacccgg ggcgcccttg taggccggcc cggggctggt tagcgtaccg    23580
accgaccgca attcaccgct cactcgtgcg tcgcccgcac cagcttttcc cttcttccgg    23640
agtccgccgc cggggcggga gcggcgggac ccgcacccccg ttcaggcaag agggaaatcc    23700
gctcggaatc gacgaagggg acgtgcatgc gcgggggac cgtggaccgt cgtgtctggt    23760
ggcaacgggc cgtggcccgc ggtttcgcgc ccaccgccgg cgcggcccac cccgttcgtc    23820
ctggtgggac ccgagggacc ggactcggac gtccgggcga ggtgcgcgcg gacggcgtga    23880
tcggcgcgcg gccgggcggg gcggcgttcc gctgcgtccg gcgggctcgg ggtgctgctg    23940
```

```
ccactacgtc ggcagtgcga cgcgagcgca cgagcagacg tcgtcatgtg ctgcgccgtc   24000
tggccgaggt gcgggaagcg cacccgtccc tgccgctgac cgtctgggtg ggcatgcagt   24060
acggccccgg ggaggacgag gaggcgctgc gcaggctgcg ccggctgtgc gccccggtgc   24120
ccggggcccc ggccctcacc gtggtcggcc tggccctgcc cgggccgggc aagctccgca   24180
cggtgagcac ggtcctgcgg ctctccgagg acctcggcta cgccggctgg ctctggacgg   24240
acgacgacat cgagatcgcc ccccactgcc tcgccctgct ggtctcccgt ttccgggagc   24300
gggggagcg gggcgcggtc ggggcgcatt cggtcgcgct ggccagggag acggtcacct   24360
cacaggccat ggaccgggtc tccggggtca ccgccccgcc gaaggcctgc ccggcggcgg   24420
cctgcctggt cgtcgcgacg gacgtgctgg gcaccggcat tccggtcagg cgcctgaccg   24480
acgacgggta cgtggtgttc gaactgctcg acgccggggc gcccgatccg ctgcacgacc   24540
tggaggtgct gcccgaggcc cggatcagct tctaccgcgt cagccgcacc cacgacacgt   24600
tccagcgcct cgcgccgctcc ctctacagcc atgtgacctg cgtcgccgac tatccctggc   24660
ccaccgcgcg ggtctacctc acccgggtcc tcttccacgg tctgtggccg ctcgcggcgt   24720
gggacgcag ccggggccg gtgcacgggc tgcagcgctg gctggtcaag ggcctgcact   24780
tcacctggtt ctgcggggtg gccggctcgc tggcggtccg gggcgcggtg ggacggcccc   24840
ttcgccgggt ggcgtggggc gacgaggggg acttccgcag ccccaccgtc gaggagcccg   24900
ccgcgggagc ggccgccggg cgctgacaca cgaggtcacc ccgaggggcg ccccggaagg   24960
agacgcgatg gtgacagcgg ggccggccgg ggcggcggtg accgtcgtcc tgcctcacta   25020
cgactgcgcg gcgtacctgg gtgcggccgt cggatcggtg ctctcccagg accgcccgga   25080
cctgcgcctg acggtggtgg acgaatgctc gcccgaagag aagtgggccc gcgcactcca   25140
cccgtacgcc ggcgaccccc ggctgaccgt ggtccgcacc tcccgcaacg tcggccacct   25200
gcggatcaag aacaaggtcc tggaatcggt ggacaccccc tacgtggcct tccaggacgc   25260
cgacgacatc agcctgccgg gccggctgcg ccaccagctg gccctcctgg agagcggcgg   25320
cgccgatctg gtcggctgcg cctactccta catcgacgag gcgggccgta cgacgggaca   25380
ccggcggatg ccccgcaacg gcaacctctg gatgcggctg gggcggacga ccgtgctcct   25440
gcacccgtcc tcggtggtgc ggcgctcggt gctcgagagg ctcggcggct tcgacggcac   25500
cgcgcgcctg ggggccgaca ccgacttcca cctgcgggcc gcccgcctgt accggctgcg   25560
cagtgtgcgc aaggtgctct accggtaccg gatctggccc aagtcgctca cccaggcgcc   25620
ggacaccggg ttcgggtccg cggagcgccg ggcctacacc gaggcgatga ccgcgcagga   25680
ggagcggcgg cgacgggcgc ggacccgtga ggagctgctg ccgctgctgg tcgccccgcc   25740
caacgacgtc gacttcaccc tgacccgggt cgacctcgac tagccgacgg aggggggaacg   25800
gcgtggacgg cacctcggcg aggaccgcgg acgaggcgtt gcccggggtc gcggtggtgg   25860
tggtcgatcc ggacggcgac gggcggcgcg ccgtgcgcgg cctcctcgcc cagacggtgc   25920
gtcccgtctc gatcaccctg gtgacggcgg ccggcccgac ggccggcggc acccggtccc   25980
ccgggccggc cgtgcccttc gacgacccgg cggtgaaagc ccgtacgggt cgtccggtgc   26040
gctcgcgggg acctcggccc ggctttgcgt cgacgcggcc aggaacgcgg gggcgccgta   26100
cgtggccgtc ctccgcggtg acgacgaggc gctcccccac tggctgtggc acctggcgcg   26160
ggcggtctgg tacggcggcg gggacggcac cgggccggtc ggcctggtgc agtgcgcgcg   26220
cctgcggctg agggacgacg gcctggtgga cgggttcgcc ctgccgcccg cgtccccgcg   26280
gacccggccc tcccccctcgg acctcctcga gggcgcctac gcggtgcggc gcgaactgct   26340
```

```
ggacgcggac ggcggtacgg cgccctgggt cgccctgccc atgccgctgg tccgccgccg    26400
gtccggcggc gccggggacc cggccgcggt cctggccccc gggacgcgcg tcgcgcgacg    26460
cacccgcctg gtccggcacg ggtaccggcc gcccgccgcg aggccgcgga acgggagcac    26520
tccccggctg gtgtcggtgg tcgtcccggt gcgcaacggc gcccgcacgc tcgccgccca    26580
gctgaccgcc ctggcccggc agaccggagc cgtcgcctac gaggtgctgg tcgtcgacaa    26640
cggctcgacg gacaccaccc gcgaggtcgc cgaacgggcc cgcgccgagc tgccggacct    26700
gcggatcgtg gacgcgtccg accgtgccgg tgagagctgt gcccgcaacc ggggaatcgc    26760
cgcggcgcgc ggcgacttcg tcgcgttctg cgacgcggac gacgtcgccg acaccggctg    26820
gctggccgcg atggcccagg cggccaagga ggccgatctg gtgggaggcg gactggagac    26880
ctccgtgctc agtcccggcc gcgtcgacga gcagcccctg ccgatggacg cccagaccga    26940
tttcctgccg ttcgcccggg gggcgaactg cggtgcctgg aaggacgtcc tgaccgcgct    27000
gggcggctgg gacgagcgct accggggcgg cggggaggac atggacctct cctggcgcgc    27060
ccagctctgc ggttacctcg tccgctacgc ggacgacgcc cggatgcact accggttgcg    27120
ggacggactg ccgcgctgg cacggcagaa gtggaactac ggccgttccg ggcccagtt     27180
```

(Note: some lines may be slightly imperfect due to image quality)

```
gtacgccgcg taccggcgcg ccgggttcga acggcgcgac ggccgggtgg tcgtcaggaa    27240
ctggtgctgg ctgctgctgc acgttccgaa cctggtccgg tccaccggac cctgcggcca    27300
cgctgagtcc gctacgcgcc cggctggccg gtttcctggt ttgtgaacgt gcggcagggc    27360
gtcaggtcct tgttggtggg cgggcgtccg gcgcccgcgg gacgccgggc cggcaccgcg    27420
gtggcccggc gcgccgctcc cgggttcaga ccagccggtg gccggggtcc tgcgccaccg    27480
ggtcgtcgcc cgccatggcg aggcaggtgg cgcgcagggc ggcgacgacg gcctggtcct    27540
cgccccaggc gtcgagttcc gggccgtccc ccgccttcag ggccggcacc ggcacttcca    27600
tgatcttcgg atgcccgtgc cggaccgggg actcggaagg ggccaccagc gcctcggtga    27660
gcttctcccc cggccgcagc ccgacgtagc ggaccgggag ctccgcaccg gcgtgcgcga    27720
tgagccttct ggcgatgtcg aggatccgga cctgttcccc catgtccagg accagggcgt    27780
ggccgacgct gcccagcgcg accgactgga tgaccagttc cacggcctcc tggacggtca    27840
tcagatagcg cgtcacctcg gggtgggtga ccgtcaccgg tctgccggcc gcgatctgcc    27900
gggcgaagac gtcgaggaag gacccctggc aaccgagcac gttgccgaag cgcacgctca    27960
cgtacggtct gcccgcctgg atcgcggccg ccgcggtgag tccttcggct atgcgtttcg    28020
agtatccgag caccccgacc ggatcgaccg ccttgtcggt cgagatgttc accaggaacg    28080
cgacgtccgc ggccagggcc gcctcgagca ccgctcgggt gccgaagaca ttcgtcttga    28140
cggcttcccc ggggaacttc tccaggatgg gcacccattt gagggccgcc gcgtggaaga    28200
cggtgtccgg ccggcactgc tggaacagcc gggcgagccc tctggagtcc ctgatgtccg    28260
cgaggaggat ggaggtccgc accgacgggg agacgttccc gatgctggtg gccgccaggt    28320
ggagggccgt ctcgttccgg tcgagcatca tgaggctctc gggttcccac cggctgagct    28380
gccggcacag ttccgatccg atgtagccgc cggctccggt gaccaggatc cgtcggccgc    28440
gcagtaatcc ggcgctgctc tcgagaccgg tccttattcg ttggcggccg ataatcctct    28500
cgaggtccaa ggtgagaggt ccaccggccg gaaagttcgc gtcgtacccc acggaattat    28560
cgccaaacat gcagtcacac ttccttttg acaagagtca tgactgacgt gccgaccac     28620 acgacgaacg ggaccgacgt atcgtcttgg tgctttcctc accggcacca ccgcgttccc    28680
```

```
ccaccggtgc ctgcgcacgg ggatcacatt ccggcggccg ggtcgccacc cgctgcgccg   28740
gctccgccga cgtcggacgt gtcctcttcc gacaccccag gacgaccgcg aaaatcactt   28800
tatcgaggcg cggcgcggtg cgggcgggtt ttctcaacgg acgcccgcg tcaccggaac    28860 gccggggccg aggaattcgc gcgcgccccg caaccgggtc cggagccggg cccgcgtggc   28920
atcggtgacg agacggatgt cgaggttccc cggcggggcc acctcgctcc gcagaccggc   28980
cggcagccgg gccgggtcca gtccgtcccg ccgggctatg aggacaccca ggtcgtgacg   29040
gttcatcgcg tccggtcccg ccacgtggaa caccccggac ccgtccgacg ccgcgatctc   29100
caaaagcgcg gaggccagat cgtcgacgtg gaccggacag cggacgtcgt ccgtgaacag   29160
gacgccggcg cgccggccgg ccgccagggc gtgcaccgcc tcctcgtggg cggaccggtt   29220 gtgcccacg atgagcgagg tgcgcaccac ggcggcctcg ggcacggcca ccctgacggc    29280
cgtctccgcc gcggccttgg ccgcgccgta cggggagacg gggtcgggga gggcctcctc   29340
cgggtagtgg acgtcggctc cggagaacac ggcgtcggag gagacgtgga ctagtcggca   29400
gccggcgcgc gccgcctcca gggcgaggcg ggccgcgccg tcggccgtga ccgcccagtc   29460
ggcgtgtccg ctcgacgcgt tgatcaccgc ggcggccgg gtccgggcca gcacctctcc    29520
catccgcccc gggtcacgga ggtcggcccg gtaccaggtg accggcggca gttcctcggg   29580
gcgggtccgg taggtcgcgg ccacgtccca cccggcggcc acggcccggc ggagcacctc   29640
gtacccgagg aagccgctcc cgccgacgac aagaactctc acgcaccgcc ccctgacgt    29700 ccggcccgcc cccgatcgcg cccagaagt acggggacga cggcctgtgc ggccgtgtcg    29760
agccgtggtt cctgtgggcc cgatgctact gaaggccacc gagcggcggg gagagtgagt   29820
gctttccgtc ttcggtccga accggccggg gaggctccgc aacggctccc gcgggcagga   29880
gggcggcggc cccgagcggc cttgcgcacg gcggacgcc gggcccgcgg tccgaggcgt    29940
tcccccgggg cgcgcagccg gtgccaccgg cggggcggcg acggcccgtc ccgctcctgg   30000
tcccggggcg ggcggcgtgt gacccgcccg ccccggccga gcgggtgcgt ccccgtcagg   30060
cacggcgggg tgcgccccgt caggtacgac agggagccgg gttctccggc cgggcgggga   30120
tccccgcccg cacacgggcg agcagggcgg ccgggtccgg gtccgcctgc agggaccgca   30180
gcaccagcgt ccaccactgc tccagtcgct ccctccagtc cagcccgccc ggcatctcgt   30240
cggtcagggt gcagagtccg aagaacgcg agacgagcgt cacggccgcg ccgacggct     30300 cgaccccttc cgcgagttcg ccccggcgc gggcctcggc gaggagccgg gtggcagccg    30360
ccgcccaggc gtcgaacggc gggggcacgg cggcctcgat ggtgtggcgc tccgcccaca   30420
gccgggcacc ggcacgtgcc acgacgtcct cgctgaggga ctgcgcgacc cggaagctga   30480
ggccgaccag cttctccagc ggaggaacgc cgggcgtggt gtaggcggcg gcgagttgcg   30540
gccaggtggc gaactgctcg cggaccacgg ccaatgccag cttctccttg ctggagtaat   30600
ggaaatagat cgccccgctg gttcttcccg agtgatcgct tatgtcattg acgtcgttc    30660 cggcatatcc ctgttcaacg aacagatgtg ccgctgtttc cagcagcact ttgcgggttg   30720
cacgcgccct gtcctgcact tctgctccac cttcgctcac acacgccgac gccacgacgg   30780
aaaagtccag gcgcccccgg aggcagggtc gcagcgcgcg aagatcttat tattcttcgg   30840
ccgtgtgcgc cgcagggggcg acttcacaca acacgcccct ctgtccggcc gaatcgattc   30900
gggcgggcgc gggaactccg ccccgatcaa tgccgcggca ccccggagga gcctcccacc   30960
aggcccgttg gccgcgttcc gggcgctgcg gcccctcctc ccgttccgtg tgcgggagtc   31020
ggccgccttc ggccgcgggca tgcacataca cccgaatcgg tgattgtgga aatcgaagaa   31080
```

```
gcgaaattaa cataacgggc acgatgtttt tcggcgtggt cgaaagcgac gacccgcgcc  31140
cgccatgacg cgcccacggc gcgctcagcc gtgtccacgt ggccgcaaac ggccgtgcga  31200
catcacccgt ttccgctcat ttccgcgagt ggaccacccg catccctgca cccgcctgcg  31260
cccgtgcacc gaaccggtcg acgcagcctc ccagaacggc agtcacatga cagctcaccg  31320
catcctttcc tggtccccct ccgccatcgt cttcgactgc gacggaaccc tgatggacac  31380
ggaacgacac tggcaggagg cccggaacct caccttccgg gcgttcggcc tgaaaccgcc  31440
ggccgggttc gccgaccgcg ccaagggcat gcactacacc gagtgcggag cgctcatggc  31500
cgaagagacc gggaaaccgg gcctcgtcgg ggagttgacc gacacgctcc tcggcacctt  31560
caccaccctg gtcgaccagg accccgtcac catgccgggg gccgcctcgc tggtccggct  31620
ggcctctcgc caccgccctc tcgcggtggc gagcaactgc ccccgggagg tggtggaatc  31680
atgcctctac cgggccgggc tcctcgactg cttcggccac gtcgtggtcg ccggcgggga  31740
ggtacggccg aagccggaac ccgacgtcta cgcggtggcc gcccgcctct gcggcgtccc  31800
tcccgaggag gctctggccg tggaggactc gctcaccggt atggagtcgg cccgccgggc  31860
gggccttcgc gtcatcggca tcggaccgtg cccaccgggg ccggaggcgg agaaggccga  31920
tctgtgggtc gcgagcctcg ccgacggcga gctgctgtcg tgggcccgca cccggatcgg  31980
cgagtaggac acccggggcc ccgtcgcacg ggcccgggc gggaggggcg gaccgcggtt  32040
ccgtcagcgg agccgggcgg cgaacgccgc gtacgcctgc tcgtcgaaga ggacgaaccg  32100
gatctcctcc accgcggttt cggcgtcgcg caccgtctgc accgcgatgc gcgcggcgtc  32160
ctccatcggc cagccgtaga caccggtgga gacgccggga aacgcgacgg tgcgcgcgcc  32220
gagtccgtcg gcgacccgca gcgactcccg gtagcaggag gccagcagcg ccgagcggtc  32280
ctcctcgcgg ctgaacaccg gccgacggt gtggatcacc cagcgggcgt ccaggtcgcc  32340
ggcggtggtg gcgacggccc ggccggtggg caggccctcg ccgtaccgag aagcgcgcag  32400
gcggcggcac tcctccagga tcgccgggcc gccccggcgg tggatcgcgc cgtcgacgcc  32460
gcctccgccg agcagggacg agttcgccgc gttgacgatc gcgtcggcgc tctggcgggt  32520
gatgtcgccc cggacgaggg tgagggtggc gctcatgtct gccgcagcct cctccagacg  32580
gccttcgccg cgttgtgtcc cgacatgccg tgcaccccgg ggccgggcgg ggtggccgag  32640
gagcagatga agaccgcggg gtgcgggtt gcgtacggga acaggacgg tctgggcgc  32700
agcaggagct ggagtccgga ggccgcgccg gtgccgatgt cgccgccgac gtagttggcg  32760
ttgcgggcg cgagttcggg cgggccggcg gtggcgcggg ccaggacgcg gtcgcggaag  32820
cccggtgcgt agcgctccag ctggcgctcg atggcgtcgg tgaggtctcc ggtccagccg  32880
tgcgggacgt ggccgtaggc ccagaagacg tgctggcccg ccgtgcccg ggtgggtcg  32940
gcgacgccgg gctgcacggt gatgaggaac ggcgcgtcgg gggcccggcc ctcccgggag  33000
gcggcgcgca gggcggcgcc gatctcccg ctgtccgcgc cgatctgcac ggtcccggcg  33060
acgcgggcct cgggcgcggt ccacggcacc gggccgtcca gcgcgtagtc gatcttgaag  33120
acgccggggc cgtaccggta gttcgcgtag gtgccgccga agccggcgat gcgggccagg  33180
gcggtgggcg aggtgtcgaa gacgtaggcg cgggcggcg gcaggtcgtc gaggcgcttg  33240
acctcgtagt cggtgtggac gctgccgccg aggtccttca ggtacgcggc gagggcgtcg  33300
gagagcgcat ggaccgccg cggccacggc cagccgcggg cgtgcgcggc gagggcgaag  33360
acgaggccga cggcgccggt ggcgagacca ccgagggggg ccatcacatg ggcgacgagc  33420
```

```
cccgcgaaca gggtcctggc ccgctcgtcg cggaagcggc gcatgagcca ggtcgagggg    33480
ggcaggccga ccaggccgaa gcgggcgagg gtgaccgggt cgcggggcag cgcggtcagc    33540
ggcagggaca tgaagtcgcg gaccagggtg tcccacctgg acaggaaggg tgcgacgagc    33600
cgtcggtacg ggccggcgtc gcgcgggccg aaggaggcgg ccgtctcgcc gaccgaccgg    33660
gacagcacgg ccgcggtgcc gtccgggaag gggtgcgcca tggggagccg ggggtgcatc    33720
cactccagcc cgtagcgctc cagcgggagg gcgcggaagg cgggcgagtt gatgccgagg    33780
gggtgcgcgg cggagcacgg gtcgtgccgg aagccgggca gggtgagctc ctcggtgcgg    33840
gcgccgccgc ccacggtgtc cctggcctcg aacagggcca ccgagaagcc gcgccgggcc    33900
agctccacgg cagcggtcag cccgttcggc cccgcaccca ccacgaccgc gtcgagcatc    33960
gacggcacct tcggactcct tcgtcagccg acgccactg gcatcaggat atgccggggc    34020
gccggtaccg ggagatcagg ctccttccga cagcagcccc accacccgct gtgccgtggc    34080
cgcgtcgcgg gccgcggtga aggggagggt gttgccgccg gtgatgcgga agggctcgcc    34140
cgcgcgggtc agatgggtgc cgcccgcctc ctcgaccagg agcagaccgg ccgcgtggtc    34200
ccaggcggct tcccaggaga aggcggtggc gtcggactcg ccgcggggcga cggccaggta    34260 ctccaggccg gccgagccgc agggacgggg tgccacgccc tcggtccgca gggcgagcag    34320
ggaccgcttc tgttcgtccg tggtgaagtc cgggtgggag gtggccacgc gcaggtcgcg    34380
gccgggttcc ggggagcccg cgcggagccg ttcgccgtcg aggtgggcgc ccttgccccg    34440
tacggccgtg gcgaattggt ggcgggccgg ggcgaaggtc caggaggcgt acaggactcc    34500
gcgccgggca agggcgacca gggtgcagaa accggtgtct ccgtgcacga actgccgggt    34560
gccgtcgacg gggtcgacta tccagaccgg cgcctcgccc cgaaccgcct cgtacgacgt    34620
cgggttggcg tgcacggcct cctcgcccac cacgaccgag ccgggcagca gggcggtgag    34680
cgcctccgtg aggtacagct ccgccttgcg gtcggcgtcg gtcacgaggt cgtgcgggcc    34740
gctcttcagg tccacctcgt gttcggcgag ccggcgccag cgcggcatga tctcctgcgc    34800
ggcggccttg cggacggctt cctccacgtc gacggcgtgc cggtcgagaa actcttcgat    34860
ggtttcgttg tccttgatca tgcctccatg agaccacgcc cggccgacgt tccccaccgt    34920
cccggtgcac tgcgggggga atcggcatga atatggggtg ccggaccacg ggcgggtggg    34980
ctcagcggcc caccgcgtag                                                 35000
```

<210> SEQ ID NO 2
<211> LENGTH: 7600
<212> TYPE: DNA
<213> ORGANISM: Streptomyces ghanaensis

<400> SEQUENCE: 2

```
gacgagaacg gagtgcgctg tttcggacgg gcgcgtccgt cagcgcgacg gaatggacgg        60
atcacgtgac cgacttgctg gagccgaggc aacactgggt taggcggtta cacccttcac       120
cggacagcga tgtcacggtg gtctgcttcc cgcacgcggg tggatcggcc agctacttcc       180
acccgttgtc cgctcggctg acgccccgtg ccgaggtgct ggcgctgcag tatccgggcc       240
gccaggaccg ccggttcgag cctgcgctca ccagtatcga cgagctggtg gagggaatca       300
ccgaggcgct gcgcgagcac gtcgaccggc ccctcgtgtt cttcgggcac agcatgggcg       360
ggacgctcgc cttcgagacc gcggcgcgca tggagccgga gctcgacggg cggttgctgg       420
ggctggtcgt gtcggggcgc aggtcgcccg gcagcgtgcg ccggacgacg gtgcatctgc       480
gggacgacgc ggggctcatc gcggaaatac gcgaactgca ggggaccgcc tcgacgttgc       540
```

```
tggacgacga agacgtggtg cggatgatcc tgccgtccct ccgcgccgac tacaccgcgg    600
tggagcggta cgtgtaccgg ccgggaccgg cactgagttg cccctgtac gtctacaccg     660 gtgacgccga tccccaggtg aacgaggagg aggcggcggg atgggcggag cacacccgcg    720
cggacttccg gatccgcact ttcagcggcg gtcacttcta cctcgccgag cagagcgagc    780
aggtgatcgc ggcactgcgt gaggacgtga cgggcttcca ggagcgttcc cggaccggcg    840
ccgagcgctg atccgggccc gggaagggtg cacgcaccgg acgtgaggcc gtgcagttca    900
gccaccgccg gcgaagcggg cggcgagttc gcgtttcagt accttgccgc tcggcccgag    960
ggggaagtcc tcgacgaact ccacccggcg cgggtacttg tacgcggcga ttcgctgcct   1020
gctccaggac acgatgtgcg cggccagcgc cgcgtccgga tccgtgcccg ccgcgtccg    1080 caccacggcg cacacctcct cgccgtactt gtcgtcgggg acaccgatga cggcaacctg   1140
ggcgacggcc gggtgacgca tcagcacctc ctccacctcg cgtggataga cgttgtagcc   1200
accgcgcagc accatgtcct tcttgcggtc gacgatggtc agatagccgt cggcgtcctt   1260
catccccagg tcgcccgagc ggaaccagcc gtcgaccagc acggctgcgg tggcttccgg   1320
ccggttgagg tagccggcca tgacgttgtg gccgcgtacg acgatctccc cgatctcccc   1380
ggccggcagc agctcgatac ggtcctccac gtcggcggcg gcgatctccg cctccacgcc   1440
ccagatgggg cgcccacgg tgccgggcct gcgcggccac gccttctggt tgtacgccac    1500
caccggcgag gtctccgtga ggccgtaccc ctcgtagatc gggcagccgt agacctcctg   1560
gaactcctcg agcaccttga ccggtagcgc cgaaccgccg gagaaggcgc ggtcgagcac   1620
ggggcggcgg gcgtcgtgag cggcggcgtc gaggagggcc aggtacatgg tcgggacgcc   1680
catgaacacc gtgcagccct cggtgaccat gaggtcgagc gcgccggggc cgtcgaagcg   1740
gttcatgagc accagggtgc cgccggccag gaaacaggcg ctcatgccgc aggtctggcc   1800
gaaggtgtgg aacagcggca gacagcccag cagcacgtcc tcgggccgga ggtcgaacgg   1860
cgagcgcatc gtggtgctga cgttcatcac caggttgagg tgggtgatca tcgcgccctt   1920
gggccggccg gtggtgcccg aggtgtacag caccaaggcc aagtcgtcgg gcgcgcgcgg   1980
caccagaccg tccaggggct ccgcccgttc ggcgagcacg tcgaggcgtg ccgggccgtc   2040
gtcgtcctcg ccgttctcga ccatgacggt gagcagcgga accccggccg tcccggccgc   2100
cttggcgccc tcggtcagca tcggggccgc gcacaccatg gccttcgcct cggagtcgcc   2160
cagcacgtgg acgatctcgt cggcacgcag caggccgtgc accgggacca ccacggcacc   2220
gagcgccagc acgccgtagt acaccatcgg gaagtgcggt gtgttcggca gcagcaggc    2280 gatccggtcg cccgggcgca caccgcggtc cctcagcacc gccgcgtacc ggcgggttgc   2340
gagccagagc tcggcgtagg tgatgcgttc ggagccgaag acgagcgcgg ggtggtcggg   2400
gcgtcgcccg gcggactcgg ccagtacgga cgcggcggtc agggtcatgc cgcaccgttg   2460
tgccgtgcgg ccagccgcgg cttgtccggt tttccggcac gggtgagggg cagcgcgtcg   2520
tggaacgtca ccacggccgg tacgtgcttc ggagacagct cggcggcgac gtggccgatc   2580
agcgtcccgg agtcggcggt gccgccggc cgtaccacga cggcggcgtg gatgtgctcc    2640
acgcggtcct cgtcgaccac gcagtacaca gcggcctggt tgacctccgg atgggtcagc   2700
agcgcgttct ccacatcggt gggatggacc ttgatgccgt tggtcttcat cacctcgccc   2760
atgcggccgt gcaggcgcag aaagccgttc tcgtcgaggg aaccgaggtc gccggtgtgc   2820
acccagccgt cgcggatgat cgcggcggtc agctccggtt cgcccagta gccgagcatg   2880
```

```
gtggacgggc tctgcacgca cacctcgccg atctcgccgg cggcaggtc gcggtcgtcg   2940
tccacgtcgc ggatgcgtat ctccgtggtc ggacgtccga cggtccggcg cagttccggg   3000
tcgaagtggt cctgcggcat cagcatgctg atgccgttga cttccgtggt cccgtagagc   3060
tggagcaaca ccgggccgaa cacctcgacc gcctcggcca gtcggcgggg ggccgcgggg   3120
gaaccgaggt aggtgatgag cctgatgctc gaacggtcgg tggtggcggt gtcggggtgg   3180
tcgatcagca tgtacagctg cggcggggtg atggtcagcg tggagacgcg gtgctgttcc   3240
acggcccgca gcacttcgcc cgcctcgaac ccgtcgtgca ggacgaccgt tccgccggag   3300
gcgagcgcga cgtcgacggc ggagccgctg gagttgctca ccggcagggt cgacaggtac   3360
acgatgggtt cggggggactg gagggccact tggaggttgg cacggcgaag gcggtacggc   3420
tgcgtgacac ccttgggacg tccgctggta ccgctggtgt agatcaccac ggccggctgt   3480
tcggggtcgg cctcgacggc gtcgtggccg aaggcgtccg gtcgcccga cgagaggtcc   3540
aggacatcgg ggccgagggc accgagagcg cgagacgcg gtggctcggg cagccggtcg   3600
cacagctctc gggccgcgtc gaggttctcc ttgtcgacgg cgaggaaggt cgccccggtc   3660
ttgctgagaa tgtccagccg ggcggcggcg gccagctggt cggtggggtc caccgcgttc   3720
gtggagtgca ggtggaccag ggtggccccg gccaggttgg ccgcgtagcg gaggatgatg   3780
gtcgccgggc tgttggtgac ggtcagcacc gccacaaccg gggccttgcc ttccgcactc   3840
gggtctcgat gttccgtgaa gtgccggagc agaagttccg ctgccgtgag aaccgccctg   3900
gagacctggc ccgcggtgat ttcttcacca tccgcccaca gggcaatccg gtcggggtcg   3960
gaggccagcg cctcaagcac ccggcggacg taattctcgt tcgaggacat cgttcccca   4020
ccatgctggt tcgtttatcg gtcagtgcag acttacatga tcgcgcgaaa gcgcgacaac   4080
ccgctctcgg taaccattgg gcgtgcggcc ggtgagcacg gctgccgtcg gccagttctc   4140
aacacccggc agccttgggc gagttgaatg cctgccggag tcgatgatat acagacgtta   4200
ccttcatgcc cttcccctgt gttgcgaatg gtgaggccgc tcccgcgcga tttcgccagt   4260
gacacgttcg caccggcgcc ggggacaagc agaatccagt catggccgtg cgatttcagc   4320
cagttatgcg cggttgcccg tagttgcatg tagcctcaga cggcctggaa cgaagcgagt   4380
agacgtgacg acccaatatc tggatctctt tgcacgcctc acagaaaact ccgacggggg   4440
aaagagggag ttcctggaga tcggacggct cgccggggagc ttccccgcgg ccagcgtccg   4500
cagcagtgga cccgtgaccg gccgggacag catcagcgtc tggtgcagca acgactacct   4560
cggcatgggc cagcatcccg cagtgctcaa agccatgaag gacgcgatcg acgagtacgg   4620
cgccggcgcc ggcggctcac gcaacatcgg cggcaccaac cactaccacg tgctgctgga   4680
gagagagctc gccgcgctcc acggcaagga cgaggccctg ctgttcacct ccggttacac   4740
cgccaacgac ggtgcgctgt ccgtcatcgc cggccgcatg gagaagtgtg tcgtcttctc   4800
cgacgcactc aaccacgcgt ccatcatcga cggcctgcgc cacagccgcg cccagaagca   4860
gatcttccgc cacaacgacc ccgctcacct ggaagaactg atagcggcgg ccgacccga   4920
cgtccccaag ctcatcgtcg ccgagtccgt gtactcgatg aacggcgaca tcgccccgct   4980
gtccgaaatc gccgacatcg ccaagcgcca cggggcgatg acgtacctcg acgaggtgca   5040
cgcggtgggc atgtacggcc cggagggtgc cggcatcgcg gccgggagg gcatcgccga   5100
cgacttcacc gtcatcatgg gcaccttggc caagggtttc ggcaccaccg gcggctacat   5160
cgcagggccc gccgaaaatca tcgaggcggt gcgcatgttc tcccgctcct tcgtcttcac   5220
caccgcgctg gcgccggccg tggccgccgg cgccctggca gccgtacacc atctgcggtc   5280
```

```
ctccgaggtc gagcgggaac agctctggtc gaacgcgcag ttgatgcacc ggctgctgaa    5340
cgagcgtggc atcccttca tttcggacca gacgcacatc gtgtccgtca tggtggggga    5400
cgaggccgtg tgcaagcgga tgtccgcgct gctgctcgac cggcacggaa tctacgtgca    5460
ggcgatcaac gcgccgagcg tgcgggtcgg tgaggagatc ctgcgggtcg ccccggagc    5520
cgtgcacacc gccgacgacg tacgcgaatt cgtcgacgct ctgagccagg tctgggagga    5580
agtgggctcc gcccgcgtgc cggcgacccc ggccgctctc tgatccgtcc acgtcaagat    5640
gtgcgggcca cggctacgcc ggccagatgt gcggactccg gttctcgggg agggcggtgt    5700
gtctttgacg tgtcacgcac gtacggcgga aacgaacggc gctttcctca cggaccatgg    5760
acagggaccc tgccccacgg tcaggacacg gacaatgtcg aaaggctgcc ggaaggctcg    5820
caggacatgc gcctcggccg aagacaagtc cggccggtcc ctcatactcg acccacaggt    5880
cccggaaccc cgcgcatccg gagaacgggc cggacacccg tggagtgccc ggcccgtcac    5940
ggtgccgcgt acctacgtgt ctgctcggag aacgccgtct acctcgccat ggccgtgctc    6000
ctggtgcgtc gcctcacgag accagtccgc tgagaggctt ttcagacgcc ctctagggtg    6060
cgggctccca gatcctgacc gcaccgcaac cgcacgactg gaccgagatc ggcggccggg    6120
tgctcctgga gtgctgagcc tgcgctcagc ccatctcctc caacgtcctg cccttggtct    6180
ccggcaccca cttgaggatg aacgggaccc ccagcgtggc gaagatcgcg tagatcacgt    6240
acgaaccgga caggttccac tccgccatgc tcgggaacgt cgcggtgacc agccagttgg    6300
cgacccactg cgcgcaggcg gcgacgccga gcgcggccgc gcggatgcgg ctggggaaca    6360
tctcgcccag cagcacccag gccgccacgc ccagcgacat ggcgaagaag aggacgaagg    6420
cgtgggcggc gaccagcgcg acggtggcct gggtgtcggg cagcgagatg tcgtcacccg    6480
ttccggtctt gtaggagaag gcccaggcga cggcggcgag ggagaccgcc ataccggcgg    6540
aaccggtcgc ggccagcggc ttgcggccga cccggtcgat gagcaccatc gcgatcaccg    6600
tgcccacgat gttgatgacc gaggtggtga acgagtagaa gaacgagctc gacgggtcga    6660
tgcccaccga ctgccacagc gaggagctgt agtagaagat cacgttgata ccgacgaact    6720
gctggaagac cgacaggccg acaccgaccc agacgatcgg cagcaggccg aaacggccgc    6780
ggaggtcctt gaaccgcggt gccttgtcgc tgcgcgcggc gtgctcgatc tcggccaccc    6840
gggcatcgag atcgacctgc gcgccttcga gggtgcgcag cacctccttg gcctcgccgg    6900
tcctgccgac tgagaccagg tagcgcggcg actccgggat gcgcaacgcc agcagaccgt    6960
agaccagggc gggaacggcc gcgatgccga gcatgacctg ccacgcctcc agtccgagca    7020
ggctgccgcg ctggtccccg tcggcgaggg agagcaccat ccagttgacc aactgggaga    7080
cggcgatgcc cagcacgacg gcggcctgct ggaaggagac gagccggccg cggtactcgg    7140
tgggcgcgac ctcggcgatg tacgtggggc cgatcacgga ggccatgccg atggccacgc    7200
cgcccacgat gcgccagaag gacaggtccc acgccgtgaa cggcagcatc gagccgatac    7260
tgctggccag gaagagcagg gcggccaact gcatcacccg gaggcggccg acgcggtcgg    7320
cgagccgtcc cgcgagcatg gcgcggcgg ccgcgccgag cagggcgatg gcgatgacgg    7380
ctccgagcgt ggcggcgccg acgtcgaacc gtccctgat gccctcgacg gcgccgttga    7440
tcacggcgct gtcgtagccg aagaggaagc gcccatggc ggcggacgcc gcgatgaaga    7500
cgacgtgacg cagctggttc ggccgggccg cgaggccccc ggcggcgggt tgttgtgctg    7560
tgctcgtcac ctaaggactc ctgtggtgat gtgtgtcgtt                          7600
```

<210> SEQ ID NO 3
<211> LENGTH: 1185
<212> TYPE: DNA
<213> ORGANISM: Streptomyces ghanaensis

<400> SEQUENCE: 3

| | | | | | |
|---|---|---|---|---|---|
| atggacttct | tcgtgcgact | cgcccgcgaa | accggtgacc | ggaagaggga | gtttctcgaa | 60 |
| ctcggccgca | aggcgggtcg | gttccccgcg | gcgagcacct | cgaatggcga | gatttccatc | 120 |
| tggtgcagca | acgactacct | gggtatgggg | cagcacccgg | acgtcctcga | cgccatgaag | 180 |
| cgctccgtgg | acgaatacgg | cggaggatcc | gggggttcgc | ggaacacagg | cggaaccaac | 240 |
| cacttccatg | tggctctgga | gcgggagccg | gccgagccgc | acggaaagga | ggacgccgtt | 300 |
| ctcttcacct | cggggtattc | cgccaatgag | ggatccctgt | cggttctggc | cggggccgtc | 360 |
| gacgactgcc | aggtcttctc | ggattcggcg | aaccacgcgt | ccatcatcga | cggtttacgg | 420 |
| cacagcggcg | cccgcaagca | cgtattccgg | cacaaggacg | ggcggcatct | ggaggagttg | 480 |
| ctggccgcgc | ccgaccggga | caagccgaag | ttcatcgccc | tggagtccgt | gcattcgatg | 540 |
| cggggcgaca | tcgcgctcct | ggccgagatc | gccggcctgg | ccaagcggta | cggagcggtc | 600 |
| accttcctcg | acgaggtgca | cgcggtcggc | atgtacggcc | cgggcggagc | gggcatcgcg | 660 |
| gcccgggacg | gcgtgcactg | cgagttcacg | gtggtgatgg | ggaccctcgc | caaggccttc | 720 |
| ggcatgaccg | gcgctacgt | ggcgggaccg | gccgtgctca | tggacgcggt | gcgcgcccgg | 780 |
| gcccgttcct | tcgtcttcac | cacggcgctg | ccgccggcgg | tcgcggcggg | cgcgctcgcc | 840 |
| gcggtgcggc | acctgcgcgg | ctcggacgag | gagcggcggc | ggccggcgga | gaacgcgcg | 900 |
| ctgacgcacg | gcctgctccg | cgagcgggac | atccccgtgc | tgtcggaccg | gtcccccatc | 960 |
| gtcccggtgc | tggtcggcga | ggaccggatg | tgcaagcgca | tgtcggccct | gccgctggag | 1020 |
| cggcacggcg | cgtacgtcca | ggccatcgac | gcgcccagcg | tcccggccgg | cgaggagatc | 1080 |
| ctgcggatcg | cgccctcggc | ggtgcacgag | accgaggaga | tccaccggtt | cgtggacgcc | 1140 |
| ctggacggca | tctggtccga | actgggggcc | gcccggcgcg | tctga | | 1185 |

<210> SEQ ID NO 4
<211> LENGTH: 906
<212> TYPE: DNA
<213> ORGANISM: Streptomyces ghanaensis

<400> SEQUENCE: 4

| | | | | | |
|---|---|---|---|---|---|
| gtgggcgggc | ccgggggcga | ccctctcggc | ggccacgatc | ctctcggact | ccgcgggccg | 60 |
| gtggccggag | cgcaccgcgg | tggtcgcggg | cgccgagcgg | atcacctctg | ggcgtggag | 120 |
| gtcgcgacag | ccccggtccg | aggcggagga | cgccgtcggg | ccgctccctc | cggcgaggtg | 180 |
| ggcgagatcg | tcgtccgcgg | gcacaacctg | atggccgggt | acgtcgacgc | ccccgcgcc | 240 |
| acggccgccg | cgttcgtgga | cggctggttc | cgcaccggcg | atctagggct | gctggacgag | 300 |
| gagggtacc | ccaccgccgt | cgaccgcgag | aaggacgtga | tcctgcgggg | cgggtacgac | 360 |
| gtccatcccc | gtgaggtcga | ggaagcgctg | ctccgccatc | cggcggtcgc | ccgggtcgcg | 420 |
| gtggtggggc | tccccgaccc | ggtgtacggc | caggaggtgt | gcgcggtggt | ggtgccacgg | 480 |
| gacggcccga | caccggacgg | ggcactggcg | gattccgtcg | tggcgtgggg | tgagcggcac | 540 |
| atcgcggcgt | accggcgtcc | gcggcgggtg | gtcctccccg | accggcttcc | cctgggaccc | 600 |
| ggcggcaagg | tcctcaaggg | ggagccggcc | gtccggctcc | ggtcgtccga | cgaggcgggg | 660 |
| gcggcccggc | cgaggggtga | cggccccggc | cggttccccg | ccgcggggg | cggcccggcc | 720 |

| | |
|---|---:|
| cggacgaacg cctcggaggc ggtgcgcgcc gcccggtccg tgtccccgcc cggggccggt | 780 |
| gtccggcgcg ctcagtcggt gagccccagc gtccggccg cctggatcgc cagccagacc | 840 |
| tccgccagcg cgccggtcga ggacaggtcg cgccgggaga gggcgccgaa gcggcgcagc | 900 |
| cggtag | 906 |

```
<210> SEQ ID NO 5
<211> LENGTH: 1239
<212> TYPE: DNA
<213> ORGANISM: Streptomyces ghanaensis

<400> SEQUENCE: 5
```

| | |
|---|---:|
| gtgacgaccc aatatctgga tctctttgca cgcctcacag aaaactccga cggggggaaag | 60 |
| agggagttcc tggagatcgg acggctcgcc gggagcttcc ccgcggccag cgtccgcagc | 120 |
| agtggacccg tgaccggccg ggacagcatc agcgtctggt gcagcaacga ctacctcggc | 180 |
| atgggccagc atcccgcagt gctcaaagcc atgaaggacg cgatcgacga gtacggcgcc | 240 |
| ggcgccggcg gctcacgcaa catcggcggc accaaccact accacgtgct gctggagaga | 300 |
| gagctcgccg cgctccacgg caaggacgag gccctgctgt tcacctccgg ttacaccgcc | 360 |
| aacgacggtg cgctgtccgt catcgccggc cgcatggaga agtgtgtcgt cttctccgac | 420 |
| gcactcaacc acgcgtccat catcgacggc ctgcgccaca gccgcgccca gaagcagatc | 480 |
| ttccgccaca acgaccccgc tcacctggaa gaactgatag cggcggccga ccccgacgtc | 540 |
| cccaagctca tcgtcgccga gtccgtgtac tcgatgaacg cgacatcgc cccgctgtcc | 600 |
| gaaatcgccg acatcgccaa cgccacgggg cgatgacgt acctcgacga ggtgcacgcg | 660 |
| gtgggcatgt acggcccgga gggtgccggc atcgcggccc ggagggcat cgccgacgac | 720 |
| ttcaccgtca tcatgggcac cttggccaag ggtttcggca ccaccggcgg ctacatcgca | 780 |
| gggcccgccg aaatcatcga ggcggtgcgc atgttctccc gctccttcgt cttcaccacc | 840 |
| gcgctggcgc cggccgtggc cgccggcgcc ctggcagccg tacaccatct gcggtcctcc | 900 |
| gaggtcgagc gggaacagct ctggtcgaac gcgcagttga tgcaccggct gctgaacgag | 960 |
| cgtggcatcc ccttcatttc ggaccagacg cacatcgtgt ccgtcatggt gggggacgag | 1020 |
| gccgtgtgca gcggatgtc cgcgctgctg ctcgaccggc acggaatcta cgtgcaggcg | 1080 |
| atcaacgcgc cgagcgtgcg ggtcggtgag gagatcctgc gggtcgcccc cggagccgtg | 1140 |
| cacaccgccg acgacgtacg cgaattcgtc gacgctctga ccaggtctg ggaggaagtg | 1200 |
| ggctccgccc gcgtgccggc gaccccggcc gctctctga | 1239 |

```
<210> SEQ ID NO 6
<211> LENGTH: 1551
<212> TYPE: DNA
<213> ORGANISM: Streptomyces ghanaensis

<400> SEQUENCE: 6
```

| | |
|---|---:|
| atgaccctga ccgccgcgtc cgtactggcc gagtccgccg ggcgacgccc cgaccacccc | 60 |
| gcgctcgtct tcggctccga acgcatcacc tacgccgagc tctggctcgc aaccgccgg | 120 |
| tacgcggcgg tgctgaggga ccgcggtgtg cgcccgggcg accggatcgc cctgctgctg | 180 |
| ccgaacacac cgcacttccc gatggtgtac tacggcgtgc tggcgctcgg tgccgtggtg | 240 |
| gtccggtgc acggcctgct gcgtgccgac gagatcgtcc acgtgctggg cgactccgag | 300 |
| gcgaaggcca tggtgtgcgc ggccccgatg ctgaccgagg gcgccaaggc ggccgggacg | 360 |

```
gccggggttc cgctgctcac cgtcatggtc gagaacggcg aggacgacga cggcccggca    420
cgcctcgacg tgctcgccga acgggcggag ccctggacg  tgctggtgcc gcgcgcgccc    480
gacgacttgg ccttggtgct gtacacctcg ggcaccacg  gccggcccaa gggcgcgatg    540
atcacccacc tcaacctggt gatgaacgtc agcaccacga tgcgctcgcc gttcgacctc    600
ggccccgagg acgtgctgct gggctgtctg ccgctgttcc acaccttcgg ccagacctgc    660
ggcatgagcg cctgtttcct ggccggcggc accctggtgc tcatgaaccg cttcgacggc    720
cccggcgcgc tcgacctcat ggtcaccgag ggctgcacgg tgttcatggg cgtcccgacc    780
atgtacctgg ccctcctcga cgccgccgct cacgacgccc gccgcccgt  gctcgaccgc    840
gccttctccg gcggttcggc gctaccggtc aaggtgctcg aggagttcca ggaggtctac    900
ggctgcccga tctacgaggg gtacggcctc acggagacct cgccggtggt ggcgtacaac    960
cagaaggcgt ggccgcgcag gcccggcacc gtggggcgcc ccatctgggg cgtggaggcg   1020
gagatcgccg ccgccgacgt ggaggaccgt atcgagctgc tgccggccgg ggagatcggg   1080
gagatcgtcg tacgcggcca caacgtcatg gccggctacc tcaaccggcc ggaagccacc   1140
gcagccgtgc tggtcgacgg ctggttccgc tcgggcgacc tggggatgaa ggacgccgac   1200
ggctatctga ccatcgtcga ccgcaagaag gacatggtgc tgcgcggtgg ctacaacgtc   1260
tatccacgcg aggtggagga ggtgctgatg cgtcacccgg ccgtcgccca ggttgccgtc   1320
atcggtgtcc ccgacgacaa gtacggcgag gaggtgtgcg ccgtggtgcg gacgcggccg   1380
ggcacggatc cggacgcggc gctggccgcg cacatcgtgt cctggagcag gcagcgaatc   1440
gccgcgtaca gtacccgcg  ccgggtggag ttcgtcgagg acttccccct cgggccgagc   1500
ggcaaggtac tgaaacgcga actcgccgcc cgcttcgccg gcggtggctg a            1551
```

<210> SEQ ID NO 7
<211> LENGTH: 1566
<212> TYPE: DNA
<213> ORGANISM: Streptomyces ghanaensis

<400> SEQUENCE: 7

```
atgtcctcga acgagaatta cgtccgccgg gtgcttgagg cgctggcctc cgaccccgac     60
cggattgccc tgtgggcgga tggtgaagaa atcaccgcgg gccaggtctc cagggcggtt    120
ctcacggcag cggaacttct gctccggcac ttcacggaac atcgagaccc gagtgcggaa    180
ggcaaggccc cggttgtggc ggtgctgacc gtcaccaaca gcccggcgac catcatcctc    240
cgctacgcgg ccaacctggc cggggccacc ctggtccacc tgcactccac gaacgcggtg    300
gaccccaccg accagctggc cgccgccgcc cggctggaca ttctcagcaa gaccggggcg    360
accttcctcg ccgtcgacaa ggagaacctc gacgcggccc gagagctgtg cgaccggctg    420
cccgagccac cgcgtctcgc cgctctcggt gccctcggcc ccgatgtcct ggacctctcg    480
tcgggcgacc cggacgcctt cggccacgac gccgtcgagg ccgaccccga acagccggcc    540
gtggtgatct acaccagcgg taccagcgga cgtcccaagg gtgtcacgca gccgtaccgc    600
cttcgccgtg ccaacctcca gtggccctc  cagtccccg  aacccatcgt gtacctgtcg    660
accctgccgg tgagcaactc cagcggctcc gccgtcgacg tcgcgctcgc ctccggcgga    720
acggtcgtcc tgcacgacgg gttcgaggcg ggcgaagtgc tgcgggccgt ggaacagcac    780
cgcgtctcca cgctgaccat cacccgcgcc agctgtaca  tgctgatcga ccaccccgac    840
accgccacca ccgaccgttc gagcatcagg ctcatcacct acctcggttc ccccgcggcc    900
cccgcccgac tggccgaggc ggtcgaggtg ttcggcccgg tgttgctcca gctctacggg    960
```

| | |
|---|---:|
| accacggaag tcaacggcat cagcatgctg atgccgcagg accacttcga cccggaactg | 1020 |
| cgccggaccg tcggacgtcc gaccacggag atacgcatcc gcgacgtgga cgacgaccgc | 1080 |
| gacctgccgc ccggcgagat cggcgaggtg tgcgtgcaga gcccgtccac catgctcggc | 1140 |
| tactggggcg aaccggagct gaccgccgcg atcatccgcg acggctgggt gcacaccggc | 1200 |
| gacctcggtt ccctcgacga gaacggcttt ctgcgcctgc acggccgcat gggcgaggtg | 1260 |
| atgaagacca acggcatcaa ggtccatccc accgatgtgg agaacgcgct gctgacccat | 1320 |
| ccggaggtca cccaggccgc tgtgtactgc gtggtcgacg aggaccgcgt ggagcacatc | 1380 |
| cacgccgccg tcgtggtacg gccgggcggc accgccgact ccgggacgct gatcggccac | 1440 |
| gtcgccgccg agctgtctcc gaagcacgta ccggccgtgg tgacgttcca cgacgcgctg | 1500 |
| cccctcaccc gtgccggaaa accggacaag ccggcgctgg ccgcacggca caacggtgcg | 1560 |
| gcatga | 1566 |

<210> SEQ ID NO 8
<211> LENGTH: 1209
<212> TYPE: DNA
<213> ORGANISM: Streptomyces ghanaensis

<400> SEQUENCE: 8

| | |
|---|---:|
| atggctgccc ccgaccgacc gctcgtccag gtgctctccc cccggacctg gggcgagttc | 60 |
| ggcaactacc tcgccgcgac gcgcttctcc cgcgcgctcc ggagcgtgat cgacgcggaa | 120 |
| gtgacccctgc tggaggcgga gccgatcctc ccgtggatcg gcgaggccgg ggcgcagatc | 180 |
| cggaccatct ccctggagag ccccgacgcc gtcgtccgca accagcggta catggccctc | 240 |
| atggaccgcc tccaggcacg cttcccggag gggttcgagg cggaccccac cgccgcccag | 300 |
| cgggcggacc tggaaccgct caccggcac ctgcgggaga gcgcccccga cgtggtggtc | 360 |
| ggcacgaagg ggttcgtggc gaggctgtgc gtggccgccg tccggctcgc cgggacgtcc | 420 |
| accagggtcg tcagccacgt gaccaacccc gggctgctgc agctgccgct gcaccgcagc | 480 |
| cggtacccgg acctgacact cgtcggcttc ccccggggcga aggagcacct gctggccacg | 540 |
| gccggcggcg acccggagcg cgtccaggtg gtgggccccg tcgtcgccca gcacgacctg | 600 |
| cgggacttca tgaccagtga gacggccgtc tccgaggcgg ggccctgggg cggcgactcg | 660 |
| ggcccggacc ggccacgggt gatcatcttc tccaaccgcg gcggggacac ctaccccgag | 720 |
| ctggtgcggc gcctcgccga ccgccacccc ggcatcgacc tcgtcttcgt cggctacggc | 780 |
| gacccggagc tcgcccgccg caccgctgcg gtcgggcggc cccactggcg gttccacagc | 840 |
| gtcctcggcc agagcgagta cttcgactac atccggcgtg cctccggtc caggtacggg | 900 |
| ctcctcgtct cgaaggcggg gcccaacacc accctggagg cggcctactt cggcataccg | 960 |
| gtcctgatgc tcgagtcggg gctgcccatg gagcggtggg tgccgggact gatccacgag | 1020 |
| gaggggctgg gccacgcctg cgccaccccc gaggagctgt tccgcacggc ggacgactgg | 1080 |
| ctgacccgcc cgtcggtgat cgaggtgcac aagaaggccg cggtctcctt cgccgcttcc | 1140 |
| gtactggacc aggacgcggt gacggccagg atcaaggccg ccctccagcc cctgctggac | 1200 |
| gcccgatga | 1209 |

<210> SEQ ID NO 9
<211> LENGTH: 861
<212> TYPE: DNA
<213> ORGANISM: Streptomyces ghanaensis

```
<400> SEQUENCE: 9
ctgacacacg aggtcacccc gaggggcggc ccggaaggag acgcgatggt gacagcgggg      60
ccggccgggg cggcggtgac cgtcgtcctg cctcactacg actgcgcggc gtacctgggt     120
gcggccgtcg gatcggtgct ctcccaggac cgcccggacc tgcgcctgac ggtggtggac     180
gaatgctcgc ccgaagagaa gtgggcccgc gcactccacc cgtacgccgg cgaccccgg      240 ctgaccgtgg tccgcacctc ccgcaacgtc ggccacctgc ggatcaagaa caaggtcctg     300
gaatcggtgg acaccccca cgtggccttc caggacgccg acgacatcag cctgccgggc     360
cggctgcgcc accagctggc cctcctggag agcggcggcg ccgatctggt cggctgcgcc     420
tactcctaca tcgacgaggc gggccgtacg acgggacacc ggcggatgcc ccgcaacggc     480
aacctctgga tgcggctggg gcggacgacc gtgctcctgc acccgtcctc ggtggtgcgg     540
cgctcggtgc tcgagaggct cggcggcttc gacggcaccg cgcgcctggg ggccgacacc     600
gacttccacc tgcgggccgc ccgcctgtac cggctgcgca gtgtgcgcaa ggtgctctac     660
cggtaccgga tctggcccaa gtcgctcacc caggcgccgg acaccgggtt cgggtccgcg     720
gagcgccggg cctacaccga ggcgatgacc cgcaggagg agcggcggcg acgggcgcgg     780
acccgtgagg agctgctgcc gctgctggtc gccccgccca cgacgtcga cttcaccctg      840 acccgggtcg acctcgacta g                                               861

<210> SEQ ID NO 10
<211> LENGTH: 1245
<212> TYPE: DNA
<213> ORGANISM: Streptomyces ghanaensis

<400> SEQUENCE: 10
gtggccgtcc tccgcggtga cgacgaggcg ctcccccact ggctgtggca cctggcgcgg      60
gcggtctggt acggcggcgg ggacggcacc gggccggtcg gcctggtgca gtgcggcgcc     120
ctgcggctga gggacgacgg cctggtggac gggttcgccc tgccgccgcg gtccccgcgg     180
acccggccct ccccctcgga cctcctcgag ggcgcctacg cggtgcggcg cgaactgctg     240
gacgcggacg gcgtacggc gccctgggtc gccctgccca tgccgctggt ccgccgccgg     300
tccggcggcg ccggggaccc ggccgcggtc ctggcccccg ggacgcgcgt cgcgcgacgc     360
acccgcctgg tccggcacgg gtaccggccg ccgccgcga ggccgcggaa cgggagcact      420
ccccggctgg tgtcggtggt cgtcccggtg cgcaacggcg cccgcacgct cgccgcccag     480
ctgaccgccc tggccggca gaccggagcc gtcgcctacg aggtgctggt cgtcgacaac      540
ggctcgacgg acaccacccg cgaggtcgcc gaacgggccc gcgccgagct gccggacctg     600
cggatcgtgg acgcgtccga ccgtgccggt gagagctgtg cccgcaaccg gggaatcgcc     660
gcggcgcgcg gcgacttcgt cgcgttctgc gacgcggacg acgtcgccga caccggctgg     720
ctggccgcga tggcccaggc ggccaaggag gccgatctgg tgggaggcgg actggagacc     780
tccgtgctca gtcccggccg cgtcgacgag cagcccctgc cgatggacgc ccagaccgat     840
ttcctgccgt tcgcccgggg ggcgaactgc ggtgcctgga aggacgtcct gaccgcgctg     900
ggcggctggg acgagcgcta ccggggcggc ggggaggaca tggacctctc ctggcgcgcc     960
cagctctgcg gttacctcgt ccgctacgcg gacgacgccc ggatgcacta ccggttgcgg    1020
gacggactgc cggcgctggc acggcagaag tggaactacg ccgttccggg ggcccagttg    1080
tacgccgcgt accggcgcgc cggggttcgaa cggcgcgacg gccgggtggt cgtcaggaac    1140
tggtgctggc tgctgctgca cgttccgaac ctggtccggt ccaccggacc ctgcggccac    1200
```

```
gctgagtccg ctacgcgccc ggctggccgg tttcctggtt tgtga            1245
```

<210> SEQ ID NO 11
<211> LENGTH: 1284
<212> TYPE: DNA
<213> ORGANISM: Streptomyces ghanaensis

<400> SEQUENCE: 11

```
gtgacttctg agcccgccgc cccggccgtc ccgcacccgc cggtgcgtcc ggggccgccg    60
gtccgtctca accggccgct ggcgcggcgc aggcggcggc cggccgggga ggggttcgtg   120
acgcaccacc tgcggagcac catggcccgc gggttccgcc cccggagtc ctggaggtc    180
cccgtccggc acgtcctgcc cggtctgccg gccgacggga ctccgcgcgc cgaggaggcc   240
gctcaggcgc tgcgcacgcc cgccgggcgg ccgggcatcg ccctcgtcgt gccgacctac   300
gtctcccggg tgagcctggc gcggcagcgg gagtggttcg acgcgctgct ggaccaggcg   360
gccgcggtga cgcgggacca cccctggtg cccctggtgc tgttcgtcgg catgcagtgg   420
tcgtcggccg aggaggagcg ggaggcgctg cggcgcctgc gtgtgctgct ggacgacgcc   480
cgcacccggc tgcccggact gcggatctgc ggtctcgcgc tgcccgggcc gggcaaaccc   540
cgcaccctca acggggcgat cgccgtcgcc gagctcctcg gctgtgcggg cgtcgggtgg   600
accgacgacg acgtgaccct ggaggaggac tgcctgtccc ggctggtgcg ggacttcctg   660
gcggcgggct gccgcggggc ggtgggcgcg accaaggttg cgcacaccca tgagtacgcc   720
acctcccggc tgctgtcccg ggccaaggcg atcgccgccc cggccacgaa ctacccgcac   780
ggctgctgca tcctggtggc caccgacgtg gtggccggtg gtctgccggg acgctacgta   840
tccgacgacg gctacgtgtg cttccgcctc ctcgaccccg cgctgcccga cccgctggcc   900
cggctgcggc tggttccgga cgcccggtgc cactactacg tggcggggcc ggccggcgag   960
acccgccgca ggatccgcag gctgctgctc aaccacctcg tcgacctcgc cgactggccc  1020
ctgccggtgg tccgtcacta cttccgccac gtcctgttcg gcggcatgtg gccgctgacc  1080
ggcttcgact cctcccgcgg tgcccgccgc ggtgtgcaga aggcgctcat caagtggctc  1140
tacttcgcct ggttcgcggg catcggggc gaactctacg tgcgcgggct gtccggcagg  1200
ccactgcgcc gcatcgagtg ggctccctac tcggacatcc gcaggctcac tccgtcgtcc  1260
tcacccacgc gtcaggagag ctga                                          1284
```

<210> SEQ ID NO 12
<211> LENGTH: 939
<212> TYPE: DNA
<213> ORGANISM: Streptomyces ghanaensis

<400> SEQUENCE: 12

```
gtgctgcgcc gtctggccga ggtgcgggaa gcgcacccgt ccctgccgct gaccgtctgg    60
gtgggcatgc agtacggccc cggggaggac gaggaggcgc tgcgcaggct gcgccggctg   120
tgcgccccgg tgcccggggg cccggccctc accgtggtcg gcctggccct gccgggcgcg   180
ggcaagctcc gcacggtgag cacggtcctg cggctctccg aggacctcgg ctacgccggc   240
tggctctgga cggacgacga catcgagatc gcccccact gcctcgccct gctggtctcc   300
cgtttccggg agcgggggga gcggggcgcg gtcggggcgc attcggtcgc gctggccagg   360
gagacggtca cctcacaggc catgaccggg tctccgggg tcaccgcccc gccgaaggcc   420
tgcccggcgg cggcctgcct ggtcgtcgcg acggacgtgc tgggcaccgg cattccggtc   480
```

```
aggcgcctga ccgacgacgg gtacgtggtg ttcgaactgc tcgacgccgg ggcgcccgat        540
ccgctgcacg acctggaggt gctgcccgag gcccggatca gcttctaccg cgtcagccgc        600
acccacgaca cgttccagcg cctgcgccgc tccctctaca gccatgtgac ctgcgtcgcc        660
gactatccct ggcccaccgc gcgggtctac ctcacccggg tcctcttcca cggtctgtgg        720
ccgctcgcgg cgtgggacgg cagccggggg ccggtgcacg ggctgcagcg ctggctggtc        780
aagggcctgc acttcacctg gttctgcggg gtggccggct cgctggcggt ccggggcgcg        840
gtgggacggc cccttcgccg ggtggcgtgg ggcgacgagg gggacttccg cagccccacc        900
gtcgaggagc ccgccgcggg agcggccgcc gggcgctga                              939
```

\<210\> SEQ ID NO 13
\<211\> LENGTH: 1938
\<212\> TYPE: DNA
\<213\> ORGANISM: Streptomyces ghanaensis

\<400\> SEQUENCE: 13

```
atgtgcggct tcgtcggatt cagtgacgcc ggcgccgggc aggaggacgc ccgtgtcacg         60
gccgagcgca tgctcgccgc cgtggcgcac cgcggccccg acggctcgga ctggtgccac        120
caccggggcg tcaccctcgc gcactgcgcc ctgaccttca ccgatccgga ccacggcgcg        180
cagccgttcg tctccgcgtc gggagccacc gccgtggtgt tcaacggcga gctctacaac        240
cacgccgtgc tgggcgacgg ggcgttgccc tgcgcacccg aggcgacaca gaagttcct         300 ggtggaactc tacgagttgc tgggcatgcg gatgctcgac cggctgcggg gcatgttcgc        360
cttcgcgctg caggacgccc gcaccggcac cacggtgctg ccgcgaccg atggggaaga        420 gccctctac taacacccgc gtgcgagacg gacatcgctt tcgcgtcgga actcacgtct         480
ctgctgcggc accccgccgc gccgcgcaca ccggaggtgc gggcgctcgc cgactacctg        540
gtgctccagg cgttctgcgc cccgcctcg gccgtgtcgg gggtgtgcaa ggtgcgcccc         600
ggcagctacg tgacccaccg gcacggcgcg ttggacgaga ccgagttctg gcggccccgc        660
ctgacccccg accgggggggc gggccgcggc cccggacggc gggaggccgc gcggcggttc        720
gaggagctct tccgcgccgc ggtcgcccgc cggatgacca gcaccgaccg ccgcctcggc        780
gtactgctca gcggcggcct ggactccagc gcggtcgccg cggtggccca gcagctcctg        840
ccgggacggc cggtgcccac cttcagcgcg gggttcgcgg acccggactt cgacgagagc        900
gaccacgcac gggcggtggc gcgccacctc ggcaccgagc accatgtggt gcggatcggc        960
ggggccgacc tcgccggtgt ggtggagtcc gaactcgccg tggccgacga ccgttggcc        1020 gatccctccc tgctgcccac acgtctggtc tgccgggcgg cgcgcgagca cgtccgcggc       1080
gtgctcaccg gtgacggcgc ggacgaactg ctcctgggct accgctactt ccaggccgag       1140
cgggcgatcg agctgctgct gcgcgtgctg ccggcccccc ggctggaggc cctcgtccgg       1200
ctgctggtgc ccggctgcc ggccgttcc ggcaacctcc ccgtgaccca cgccctcggt        1260
ctgctggcca agggcctgcg cgcggcaccg gagcaccggt tctacctctc gacggcgccc       1320
ttcggcccgg gcgagctgcc acggctgctc accccgagg ccgggccga actgaccggg        1380 cacgacccgt tcaccgaggt gtcgcgcctc ctgcggggac agccgggcct gaccggtgtc       1440
cagcgcagcc agctcgccgt ggtgacccac ttcctgcggg acgtgatcct caccaagacg      1500
gaccggggcg gcatgcgcag ctccctcgag ctgcgttccc cctttctcga cctggacctg      1560
gtcgagtacg gcaactccct gcccaccggc ctgaagctgc accggttcac cggcaagtac      1620
ctgctgcggc aggtcgccgc cggctggctg cccccttccg tcgtccagcg gacgaagctg      1680
```

```
ggtttccgcg cgccggtggc ggccctgctc cgcggcgagc tgcggcccct gctcctggac    1740
accctctccc cgtcgtccct gcgccgcggc ggcctgttcg acaccggggc ggtgcgcctg    1800
ctgatcgacg accacctcgg cggccggcgc gacacctccc gcaagctgtg ggcgctgctg    1860
gtctaccagc tctggttcga gagcctgacg gccggacccc gcgccctcga gtccccgcg     1920 tacccggccc tctcctag                                                  1938

<210> SEQ ID NO 14
<211> LENGTH: 1542
<212> TYPE: DNA
<213> ORGANISM: Streptomyces ghanaensis

<400> SEQUENCE: 14
atgacggtcc gccgcccggc cgcgtccgcc ccccgcgtcc tcctgaccgc ggggccccgac     60 ggggtgcgcg tggagggcga cggggaggcg cgcctcgggc accccctcac cggtgaccac    120
ctggacccgg gccgccggc cgaaggcgtc ttcgccgggt ggaggtggga cggcgagcgc     180
ctggtggccc gcaacgaccg ctacggcgtc tgcccctct ctaccgggc cggcggcggc      240 tcactcgcgc tctcccccga cccgctcgcc ctgctgccgg aggacggggcc cgtcgagctg    300 gaccacgacg cgctcgccgt cttcctgcgg acggggttct tcctcgccga ggacacggcc    360
ttcgcacagg tccgcgcact gccccggcg gccacgctca cctgggacac cggcgggctg     420
cggctgcggt ccgacgggcc gccgcgcccc ggggccgccg cgatgaccga ggcgcaggcg    480
gtcgacggct tcgtcgacct gttccgcgcc tcggtggccc gccggctgcc cggcgaaccg    540
tacgacctgc cgctcagcgg cggccgggac tcgcggcaca tcctgctcga gctgtgccgc    600
cgcggcgcac cgccgcggcg gtgcgtcagc ggcgccaagt tccctcccga cccgggggcc    660
gacgcgcgcg tggcggccgc cctggcgggc cggctcggtc tgccgcacac ggtggtgccg    720 cgccccgtt cgcagttccg cgcggagctc gccgccctgc cggcccaggg catgaccacc     780
ctggacggcg cgtggaccca gccggtcctg gcccacctgc cgccacag ccgcatctcg      840 tacgacggtc tcggcggcgg ggagctcgtc cagaacccga gcgtggagtt catccgggcc    900
aacccctacg accccgcgga cctgcccggc ctggcggacc ggttgctggc cgcgagccgg    960
accggccccc acgtggagca cctgctgagc ccccggacga cgccctgtg gagcaggcag    1020 gcggcgcggc ggcgcctcgt caccgagctg gcccggcacg ccgacagcgc cagcccgctc    1080
agttccttct tcttctggaa ccggacccgg cgctccatct ccgcggctcc gttcgccctg    1140
ggggacggac gggtcctgac gcacaccccc tacctcgacc acgccctctt cgaccacctc    1200
gcctcggtgc cgcaccgctt cctggtcgac gggacgttcc acgaccgggc gctgcaccgg    1260
gccttccccg agcacgcgga cctggggttc gcctcgtcgg tgccccagcg gcacggaccc    1320
gtgctggtcg cgcaccgact ggcgtacctg ctccggttcc tcgcccacgc gacggtcgtg    1380
gaaccgggct ggtggcgcgg ccccgaccgc ttcctgcaac ggctgctggc cgccggccgg    1440
gggcccgggg ccccgcagcg cgtcagcagg ctgcagcccc tggcgctcta cctgctgcag    1500
ttggaggacc tcgccgtccg aagggcccgc cgccggccgt ag                      1542

<210> SEQ ID NO 15
<211> LENGTH: 1224
<212> TYPE: DNA
<213> ORGANISM: Streptomyces ghanaensis

<400> SEQUENCE: 15
```

| | |
|---|---|
| ctgggttaca tccacaccgc gctcaagtcg gccgggttcc accacgtcat ccaggtcgac | 60 |
| accccccgccc tgggcctcga cagcgagggg ctgcgcaagc tgctcgcgga cttcgagccg | 120 |
| gacctggtcg gggtgagcac cacgacaccc ggtctgcccg gcgccatcga ggcgtgcgag | 180 |
| gcggccaaga gcaccggggc gaaggtgatc ctgggcgggc cgcacacgga ggtgtacgcg | 240 |
| cacgagaacc tggtccacga gtccatcgac tacgtgggcg tcggcgaagg cgtcacgatc | 300 |
| atgccggaac tggcggaggc gatggagcgg ggcgaggagc cggagggcat ccgcggcctg | 360 |
| gtgacccgca agcacgacgg cggtgccgcg ccgatggtga acctggagga ggtcggctgg | 420 |
| cccgaacgcg ccgggctccc gatgaccgc tactactcga tcatggctcc gcggccgttc | 480 |
| gcgacgatga tctccagccg cggctgcccc ttcaagtgca gcttctgctt caagcaggcc | 540 |
| gtggacaaga agtccatgta ccgcagtccc gaggacgtcg tcggtgagat gacggagctc | 600 |
| aaggagcggt gggggggtgaa ggagatcatg ttctacgacg acgtgttcac cctgcaccgc | 660 |
| ggccgggtgc gggagatctg cgggctcatc ggggagaccg gcctcaaggt ccgctgggag | 720 |
| gcgcccaccc gcgtcgacct ggtgcccgag ccgctgctgg aggcgatggc cggggccggg | 780 |
| tgcgtgcgcc tgcggttcgg catcgagcac ggtgacagcg agatcctcga gcggatgcgc | 840 |
| aaggagagcg acatccagaa gatcgagaag gccgtcacct ccgcccacga ggccgggatc | 900 |
| aagggcttcg ggtacttcat cgtcggctgg ctcggggaga cccgggagca gttccgcagg | 960 |
| accgtcgacc tcgcctgccg cctcccgctg gactacgcca gcttctacac cgcgacgccc | 1020 |
| ctgccgggca ccccctgca cacggagtcc gtggccgccg ccagatcccc gcccgactac | 1080 |
| tgggaccgct tttcgtgcgg ggcgagttcg acgcgcggat cgggtacctg gtgccggacg | 1140 |
| cgcaggagcg cgcccagtgg gcgtaccgct ccttcttcat gcgccgctcc atggtcaagc | 1200 |
| cgctgctgtc gcacatggcg gtga | 1224 |

<210> SEQ ID NO 16
<211> LENGTH: 1593
<212> TYPE: DNA
<213> ORGANISM: Streptomyces ghanaensis

<400> SEQUENCE: 16

| | |
|---|---|
| atgaaggtac tgtcgctcca ctccgccggc cacgacaccg gcgtcgccta cttcgaggac | 60 |
| gggcggctgg tcttcgcggt cgagaccgaa cggctcaccc gggtcaagca cgaccaccgc | 120 |
| tccgacgtcg ccctgcggca cgtgctcgag caggagtgcg tggacaccga cgggatcgac | 180 |
| ctggtggccg tcagcacccc ggtccgcagc gggctgctgc gcataccga cctgaccgg | 240 |
| gccatggagc ggatcggggc gggcgccctc caccaccgga ccgtctgcga gatgctgggg | 300 |
| cggcgggtgg agtgcgtcgt ggtcacccac gaggtctccc acgcggcgct ggccgcccac | 360 |
| tacgcggact gggaggaagg caccgtcgtc ctcgtcaacg agggccgcgg ccagctcacc | 420 |
| cgcagctccc tgttccgggt gaccggcggg ccctggagt gggtcgacaa ggacccgctg | 480 |
| ccctggtacg gcaacggctt cgggtggacg gcgatcgggt acctcctcgg cttcggcccg | 540 |
| agccccagcg tggcgggcaa ggtgatggcc atgggcggct acgggcagcc ggacccgcgc | 600 |
| atccgcgaac agctgctgtc ggtggatccg gaggtgatga cgaccgggga actcgccgag | 660 |
| cgggtgcgcg cggacctggc cggccggccc gagttcgccc ccgggttcga cggcgtcg | 720 |
| caggtggtgg cgacgttcca ggagatgttc accgaggccg tccgggcggt gctcgaccgg | 780 |
| catgtgacgc gcacggacgc cggggtgggc ccgatcgccc tggcggcgg gtgcgccctg | 840 |
| aacatcgtgg ccaactcggc gctgcgggag gagtacgggc gggacgtcgc catcccgccc | 900 |

```
gcctgcgggg acgcgggtca cctgacgggc gccggcctct acgccctcgc gcaggtggcc      960
ggggtgaagc cggagccgtt cagcgtgtac cgcaacggcg ggggcgaggc ccgggccgcc     1020
gtcctggagg cggtggaggg cgcggggttg cgggccgttc cctacgaccg gtccgcggtc     1080
gccggggtgc tggccggggg cggggtggtg cgcgctgacg cagggagcgg cggaactgggg    1140 ccgcgggcgc tggggcaccg gtcgctgctg ggcagtcccg cggtgccggg catgcgcgag     1200
cggatgagcg agaagctcaa gcggcgcgag tggttccggc cgctgggcgc cgtgatgcgc     1260
gacgagcgct tcgccgggct gtacccgggg cgggcgccgt cgccgtacat gctcttcgag     1320
taccggctgc cggacgggat cgcgcccgag gcccggcacg tcaacggcac ctgccggatc     1380
cagaccctgg gccccgagga ggaccggctg tacggtctgc tcgccgagtt cgaggagctg     1440
agcggtgtgc cggcgctgat caacacgtcg ctcaacggcc cgggcaagcc catcgcgcac     1500
accgcccggg acgtgctcga cgacttcgcg cgcaccgacg tcgacctctt cgtgttcgac     1560
gacctgatgg tgcggggcgc cgccgcgcgg tag                                  1593
```

<210> SEQ ID NO 17
<211> LENGTH: 1125
<212> TYPE: DNA
<213> ORGANISM: Streptomyces ghanaensis

<400> SEQUENCE: 17

```
atgtttggcg ataattccgt ggggtacgac gcgaactttc cggccggtgg acctctcacc       60
ttggacctcg agaggattat cggccgccaa cgaataagga ccggtctcga gagcagcgcc      120
ggattactgc gcggccgacg gatcctggtc accggagccg gcggctacat cggatcggaa      180
ctgtgccggc agctcagccg gtgggaaccc gagagcctca tgatgctcga ccggaacgag      240
acggccctcc acctggcggc caccagcatc gggaacgtct ccccgtcggt gcggacctcc      300
atcctcctcg cggacatcag ggactccaga gggctcgccc ggctgttcca gcagtgccgg      360
ccggacaccg tcttccacgc ggcggccctc aaatgggtgc ccatcctgga agttccccc     420 ggggaagccg tcaagacgaa tgtcttcggc acccgagcgg tgctcgaggc ggccctggcc     480
gcggacgtcg cgttcctggt gaacatctcg accgacaagg cggtcgatcc ggtcggggtg      540
ctcggatact cgaaacgcat agccgaagga ctcaccgcgg cggccgcgat ccaggcgggc      600
agaccgtacg tgagcgtgcg cttcggcaac gtgctcggtt gccagggggtc cttcctcgac     660 gtcttcgccc ggcagatcgc ggccggcaga ccggtgacgg tcacccaccc cgaggtgacg      720
cgctatctga tgaccgtcca ggaggccgtg gaactggtca tccagtcggt cgcgctgggc      780
agcgtcggcc acgccctggt cctggacatg ggggaacagg tccggatcct cgacatcgcc      840
agaaggctca tcgcgcacgc cggtgcggag ctcccggtcc gctacgtcgg gctgcggccg     900
ggggagaagc tcaccgaggc gctggtggcc ccttccgagt cccccggtccg gcacgggcat     960 ccgaagatca tggaagtgcc ggtgccggcc ctgaaggcgg gggacggccc ggaactcgac    1020
gcctggggcg aggaccaggc cgtcgtcgcc gccctgcgcg ccacctgcct cgccatggcg    1080
ggcgacgacc cggtggcgca ggaccccggc caccggctgg tctga                     1125
```

<210> SEQ ID NO 18
<211> LENGTH: 849
<212> TYPE: DNA
<213> ORGANISM: Streptomyces ghanaensis

<400> SEQUENCE: 18

| | |
|---|---|
| gtgagagttc ttgtcgtcgg cgggagcggc ttcctcgggt acgaggtgct ccgccgggcc | 60 |
| gtggccgccg ggtgggacgt ggccgcgacc taccggaccc gccccgagga actgccgccg | 120 |
| gtcacctggt accgggccga cctccgtgac ccggggcgga tgggagaggt gctggcccgg | 180 |
| acccggccgg ccgcggtgat caacgcgtcg agcggacacg ccgactgggc ggtcacggcc | 240 |
| gacggcgcgg cccgcctcgc cctggaggcg gcgcgcgccg gctgccgact agtccacgtc | 300 |
| tcctccgacg ccgtgttctc cggagccgac gtccactacc cggaggaggc cctccccgac | 360 |
| cccgtctccc cgtacggcgc ggccaaggcc gcggcggaga cggccgtcag ggtggccgtg | 420 |
| cccgaggccg ccgtggtgcg cacctcgctc atcgtgggc acaaccggtc cgcccacgag | 480 |
| gaggcggtgc acgccctggc ggccggccgg cgcgccggcg tcctgttcac ggacgacgtc | 540 |
| cgctgtccgg tccacgtcga cgatctggcc tccgcgcttt tggagatcgc ggcgtcggac | 600 |
| gggtccgggg tgttccacgt ggcgggaccg gacgcgatga accgtcacga cctgggtgtc | 660 |
| ctcatagccc ggcgggacgg actgaccccg gcccggctgc cggccggtct gcggagcgag | 720 |
| gtggccccgc cggggaacct cgacatccgt ctcgtcaccg atgccacgcg ggcccggctc | 780 |
| cggacccggt tgcggggcgc gcgcgaattc ctcggccccg gcgttccggt gacgcggggc | 840 |
| gtccgttga | 849 |

<210> SEQ ID NO 19
<211> LENGTH: 1023
<212> TYPE: DNA
<213> ORGANISM: Streptomyces ghanaensis

<400> SEQUENCE: 19

| | |
|---|---|
| gtgtcgagcg atacacacgg aacggactta gcggacggcg acgttttggt caccggtgcg | 60 |
| gccggcttca tcgggtcgca cctggtgacg gaactgagga attccggcag aaacgttgtg | 120 |
| gcggtggacc ggagacccct tccggacgac ttggagagta cgtccccgcc ctttaccggt | 180 |
| tcgctccggg agatacgcgg tgacctcaac tcattgaatc tggtggactg cctgaaaaac | 240 |
| atctcgacgg tcttccactt ggccgcgtta cccggagtcc gcccgtcctg gacccaattc | 300 |
| cccgagtacc tccggtgcaa tgtactggcg acccagcgcc tgatggaggc ctgtgtgcag | 360 |
| gccggcgtgg aacgcgtggt ggtcgcctcg tcctccagcg tctacggcgg cgcggacggc | 420 |
| gtgatgagcg aggacgacct gccccgtccg ctctcccct acgggtcac caaactcgcc | 480 |
| gcggagcggc tggccctggc cttcgcggcc cgcggcgacg ccgagctctc ggtcggcgcc | 540 |
| ctgaggttct tcaccgtcta cggccccggc cagcgcccgg acatgttcat ctcccggctg | 600 |
| atccgggcga cgctccgggg cgaacccgtc gagatctacg gcgacgggac ccagctccgc | 660 |
| gacttcaccc atgtgtccga cgtggtgcgg gcgctgatgc tgaccgcgtc ggtgcgggac | 720 |
| cggggcagcg cggtgctgaa catcggcacc gggagcgccg tctcggtcaa cgaagtggtc | 780 |
| tccatgaccg cggagctgac cggtctcgcg ccgtgcaccg cgtacggttc cgcccgcatc | 840 |
| ggcgacgtcc gctcgaccac cgccgacgtg cggcaggccc agagcgtcct gggcttcacg | 900 |
| gccccggacgg gtctgcggga aggtctcgcc acccagatcg agtggacccg gcggtcactg | 960 |
| tccgcgccg agcaggacac cgtcccggtc ggcggctcct cggtgtccgt gccgcggctg | 1020 |
| tag | 1023 |

<210> SEQ ID NO 20
<211> LENGTH: 783
<212> TYPE: DNA
<213> ORGANISM: Streptomyces ghanaensis

```
<400> SEQUENCE: 20
atgctcgccg ccgaggccgc caaccgcgac catgtcacgc ggtgcgtcgc gcagaccggt    60
gggtcgccgg acctggtggc gcacaccgcc gccctgcgcc tgtacctgag ggtgccccac   120
ttcctcaccg agtggacgac cgacccggac cggcggccg cggtgtcccg cgcgctggcc    180
ctcgacatcg tctccatgaa gctcctcgac gacctgatgg acgacgacac cggactcgac   240
cgggtcgaac tcgcctgtgt ctgcctccgc ctccacctgc gggcgctgca cgaactggaa   300
tccctcgccc gggaccccaa ggcggtgacg gacatcctgg agcaggacgc cgtccacctc   360
tgcggcggcc agatacgcac caaacgctct cgggcgacga acctccggga gtggcgcgcc   420
catgcgagca cctacggctc caccttcctg ggccgctacg ggcactcgc ggccgcctgc    480 gggggggaag gccaaccggc ggactccgta agggagttcg cagaggcttt cgccatgacc   540
atcaccatgg cggacgacct gaccgactac gaccgcaacg gcgagcggga cggcaacctc   600
gcccatctga tgcggaccgg ggccgtggcc ggccaggacg tcgtggacct gctggaggag   660
ctgcgcgggc gggccctcgc cgcggtggcg gcaccgcccg gcgcgcccgg tctggtgccg   720
gtcgtccacc tctacacgga cgacgtgctg gtacggctgc ttccccggca cctggggggag  780 tga                                                                  783

<210> SEQ ID NO 21
<211> LENGTH: 846
<212> TYPE: DNA
<213> ORGANISM: Streptomyces ghanaensis

<400> SEQUENCE: 21
gtgaacgcct caccgcaact ggaccaccac acggaactcc acgccgcacc accgctctgg    60
cggccgggac gcgtgctcgc ccggctgcgc gagcaccaac cgggcccccgt ccacatcatc   120 gaccccttca aggtcccggt gacggaagcg gtcgagaagg cggcggagct cacgcggctg   180
ggcttcgccg ccgtccttct ggccagcacc gactacgagt cgttcgagtc gcacatggag   240
ccgtacgtgg cggcggtgaa ggcggccacc ccgttaccgg tcgtcctgca cttcccgccc   300
cgcccggggg ccggcttccc ggtggtccgc ggcgcggacg cgctcctgct gcccgcgctg   360
ctgggctcgg gcgacgacta cttcgtctgg aagagcttcc tcgagacgct ggccgccttc   420 cccgccgaa taccccgcga ggagtggccc gagctgctcc tcaccgtcgc cctcaccttc   480
ggcgaggacc cccgcaccgg ggacctgctc ggcaccgtgc cggtgagcac ggcctccacc   540
gaggagatcg accggtacct ccacgtcgcc cgtgccttcg gtttccacat ggtgtacctg   600
tactcgcgca acgagcacgt gccgcccgag gtcgtacgcc acttccgcaa ggggctcggc   660
cccgaccagg tgctcttcgt gagcggcaac gtccgctccg gcggcaggt caccgagtac   720 ctcgacagcg gggcggacta cgtggggttc gccggagccc tggaacagcc ggactggcgg   780
tccgccctcg ccgagatcgc cgggaggcgg cccgccgccc cggcccgtcc ggggagcggg    840
cggtga                                                              846

<210> SEQ ID NO 22
<211> LENGTH: 672
<212> TYPE: DNA
<213> ORGANISM: Streptomyces ghanaensis

<400> SEQUENCE: 22
atgggccatt ccgtcggtgc ccgagagggg taccacggca tgtccgagcc cgccgaccgc    60
```

| | |
|---|---|
| aagattctcc tgcaggcgcg cggcgtcgtg aaacgctaca agcgccgccg cgtcctgacc | 120 |
| ggggtcgatc ttgtcgtgca cgcgggcgag gtcgccgcga tcgtcggcag caacgggacg | 180 |
| ggcaagtcca ccctgctcaa gatctgcgcc ggtctgctct cccccgacaa aggacgggtc | 240 |
| accgtctccg gccacctcgg ctactgcccg cagaacgcgg gggtcatggg cttcctgacc | 300 |
| ccccggggagc acttcaccct cttcggcacc ggccggggcc tgagccgccg ggagtccgac | 360 |
| cgccgcggcc ggagactcgc gggagagctc gactgggccc ccgcggaggg cgtccttgcc | 420 |
| aaggacctgt cgggaggaac ccgccagaag ctgaacgtcg tcctgtcggc cctgggagac | 480 |
| ccggacctgc tgctgctcga cgagccctac cagggcttcg accacggctc ctacgtggac | 540 |
| ttctggcaga gcgtctggga gtggcgcgag gcgggcaagg ccgtcgtcgt ggtgacgcac | 600 |
| atgctcaacc agctcgaccg ggtggaccag gtgctggacc tcaccccggg caaaggaagg | 660 |
| ggcaaccgat ga | 672 |

<210> SEQ ID NO 23
<211> LENGTH: 681
<212> TYPE: DNA
<213> ORGANISM: Streptomyces ghanaensis

<400> SEQUENCE: 23

| | |
|---|---|
| atgacggcca ccctgcggat ggcggagatg accttccgcg aactgctgcg ccggcggggc | 60 |
| gtgctgggcc tgctgctcct ggtcccgctc gtcttctacc tcgggcgtta cgaccagacc | 120 |
| ggccaggcgg tccggttcgc cagcctcggg gtgggcttcg cggtcagcgc cgcggccctc | 180 |
| ttctccgcgg tcgcggaccg ggagatcgaa ccgctcctgg ccctctccgg gttccgcccg | 240 |
| ctccagctct tcctgggccg cctgctggcc ctcctcaccg ccggcatggg cgtgtccgcc | 300 |
| ctctacgccg tgatcatcct ggtcgggcag gacgtggcgc accgcgggc cgtcgcggtg | 360 |
| gaactggcgc tgaccacact ggtggcggtg ccgctgggac tgctgctcgg ggcggccgtg | 420 |
| ccacgggaca tggagggcgc cctgctgctg atctccgtca tcggcgccca gatggtgatg | 480 |
| gatccggcca aggattcggc caaggtgctt cccttctggt cgacccggga gatcatcacc | 540 |
| tacgcggtcg acggcgcgga cagcgggtcg ttcgactccg gggtggccca cgccgtcgga | 600 |
| gtgacgctgc tgctggtcgc ggtgagcggt tgcgtgacgg cgggccgatt cgccgccgg | 660 |
| cgccatctgc aattcgcgtg a | 681 |

<210> SEQ ID NO 24
<211> LENGTH: 1775
<212> TYPE: DNA
<213> ORGANISM: Streptomyces ghanaensis

<400> SEQUENCE: 24

| | |
|---|---|
| gtgctgcgcg gctcggcccg cacctactgg accctcaccg gtctgtgggt cctgctgcgg | 60 |
| gcgggaaccc tggtggtggg cctgctgttc cagcggctgt tcgacgcgct gggcgcgggc | 120 |
| gggggcgtgt ggctgatcat cgcgttggtg gccgcgatcg aggcgggacg gctgttcctc | 180 |
| cagttcggcg tgatgatcaa caggctggag ccgcgggtcc agtacggcac cacggcgcgg | 240 |
| ctgcggcacg ccctgctggg atcgccctg cgcgggtcgg aggtgacggc ccgcaccagc | 300 |
| cccggcgagt ccctgcgaac ggtgggcgag gacgtcgacg agacggggtt cttcgtcgcc | 360 |
| tgggcgccga cgaacctcgc ccactggctg ttcgtcgccg cgtcggtcac ggtgatgatg | 420 |
| cggatcgacg ccgtggtcac cggcgccctc ctcgccctcc tcgtcctgct gacgctggtc | 480 |
| accgcgctgg cccacagccg gttcctgcgg caccggcggg ccacccgggc cgcgtccggg | 540 |

```
gaggtggcgg gagccctgcg ggagatggtg ggcgcggtgg gcgcggtgca ggccgccgcc      600
gccgagccgc aggtcgccgc gcacgtcgcc gggctgaacg gcgcccgtgc cgaagccgcg      660
gtgcgggagg agctgtacgc cgtcgtccag cgcacggtga tcggcaaccc ggccccgatc      720
ggggtcggcg tggtgctgct gctggtcgcg gggcggatgg acgaggggac cttcagcgtc      780
ggcgatctcg ccctgttcgc cttctacctg cagatcctga ccgaggccct ggggtcgatc      840
ggcatgctgt ccgtgcggtt gcagcgggtc tcggtggcgc tcggccggat caccaacaac      900
ctcggctgcc ggctgcggcg gtccctggag cgggccagtc cgccgatcgc gtccgacgcg      960
ccgggaggga ccggcgaggg ggccgccgcc ccggacgccg ggccggagcc cgccccgccc     1020
ctgcgggaac tggccgtgcg cgggctgacg gcccgccacc ccggggcggg gcacggcata     1080
gaggacgtgg acctggtggt ggagcggcac accgtcaccg tggtcaccgg ccgggtcggt     1140
tccggcaaga gcaccctggt ccgggccgtc ctcggactgc tcccgcacga gcggggcacc     1200
gtgctgtgga acgcgaacc gatcgccgac cccgcgtcgt tcctggtggc gccgcgctgc     1260
gggtacaccc cgcaggtccc cgtgtctgttc agcgggacgg tgcgggagaa cgtcctgctg     1320
ggccggacgg cgcggccttc gacgaggccg tgcgcctcgc cgtggcggag cccgacctgg     1380
cggcgatgca ggacggcccg gacaccgtgg tgggcccgcg gggcctgcgc ctctcgggcg     1440
ggcagatcca gcgggtcgcg atcgcccgca tgctggtcgg cgaccccgaa ctcgtggtgc     1500
tggacgacgt ctccagtgcc ctggacccgg agaccgagca cctgctgtgg gagaggctgc     1560
tggacgggac gcggaccgtg ctcgcggtct cccaccggcc cgctctgctg cgcgcggccg     1620
accgcgtggt ggtgctcgag ggcgggcggg tggaggcctc gggcaccttc gaggaggtca     1680
tggcggtctc cgccgagatg ggccggatct ggacgggtgc gggtccgggg ggcggggacg     1740
ccgggcccgc tccgcagagc cctcccgcgg ggtga                                 1775

<210> SEQ ID NO 25
<211> LENGTH: 1695
<212> TYPE: DNA
<213> ORGANISM: Streptomyces ghanaensis

<400> SEQUENCE: 25
ctgcgcggtg aacggaccgc cgtggcgctg ctcgccctcc tggtccccgc ggggatgggg       60
ctccagctgg tggcgcccta cctgctgcgc ggattcatcg acggggcgct ctccggcgac      120
tcccggaaga cgctgctgga cctgccgcc tggtccctgg cggccgccgt cgggacgctc      180
gtggtcaccg cgggcaccga ggcgctgtcc tcacgggtcg cctggcgcag caccaaccgg      240
ttgcgcgcgg acctggtcga gcactgcctg agccggccgc cgggcttcta ccgcaagcat      300
ccgcccggcg aactcgtcga gcggatggac ggcgacgtca cccggctcgc cgcggtgatg      360
tcgacgctgc tgctggaact gctggcgcag gcactgctga tcgtcggcat cctcgtcgcc      420
ctgttccggc tggaatggcg gctggccctg gtggtcgccc cgttcgcggc aggcaccctc      480
ctgctgctgc ggaccctggt gggccgcgcc atgcccttcg tcaccgcgcg gcagcgggtc      540
gcggcggacc tgcagggctt cctcgaggag cgcctcgcgg cggcggagga cctccgcgtc      600
aacggggcct cgcggtacac cctgcgggaa ctcggcgacc ggcaggacga cctgtaccgg      660
aaggccgcg acgcggcgcg ggcctcggtc cgctggcccg ccacggtgca gggcctgtcc      720
gccgtcagcg tcgtcctggc cctggcggtc agcgcctggc tgcacgcccg cggacagctc      780
tccacgggga cggccttcgc ctcccgtgcc tacgcgatgc tgctgcgccg ccccctgctc      840
```

```
gcggtcacca cccgcttccg cgaactcgag gacgccgccg cgagcgccca gcggctgagg    900
gacctgctgg ccacgggac ggcggcgccc cgcacgggac gcgggacgct gccggccgga    960
ctgcccggag tccgcttcga cggggtctcc ttcggctacg agcccgacga gccggtgctg   1020
cgggacgtct ccttcaccct gcgccccggc gaacgcctcg gcgtcgtggg acgcaccggc   1080
agcggcaagt ccaccgtggt ccggctgctg ttcgggctcc accacccggg ggcgggctcg   1140
gtgtcggcag gcggcctgga cctgacggag atcgatcccc gggcgctgcg cagcggggtc   1200
gcgctggtca cccaggaggt gcacgtcttc cacgcctcgc tgcgggacaa cctcaccttc   1260
ttcgaccgct ccgtccccga cgaccggctg cgcgccgctc tcggcgaggc cgggctcggc   1320
ccctggctgc gcaccctgcc cgacggtctg gacacgccgc tcggcgccgg ggcccgcggc   1380
atgtccgcgg gcgaggagca gcagctcgcg ctggccaggg tgttcctgcg cgatccgggg   1440
ctggtcctga tggacgagcc gacggcccgg ctggatccgt acagcgagcg gctcctgatg   1500
cccgcgctgg agcggctgct cgagggccgc accgccgtcg tggtggagca ccgcccgcac   1560
ctgctccgga acgtcgaccg gatcctggtg ctggaggagg ggaaggtcgc cgaggagggg   1620
gagcggaggg tcctcgccgc cgatcccggg tcgcgcttcc acgcactcct ccgcacggcc   1680
ggagccaccc ggtga                                                    1695
```

<210> SEQ ID NO 26
<211> LENGTH: 394
<212> TYPE: PRT
<213> ORGANISM: Streptomyces ghanaensis

<400> SEQUENCE: 26

```
Met Asp Phe Phe Val Arg Leu Ala Arg Glu Thr Gly Asp Arg Lys Arg
1               5                   10                  15

Glu Phe Leu Glu Leu Gly Arg Lys Ala Gly Arg Phe Pro Ala Ala Ser
            20                  25                  30

Thr Ser Asn Gly Glu Ile Ser Ile Trp Cys Ser Asn Asp Tyr Leu Gly
        35                  40                  45

Met Gly Gln His Pro Asp Val Leu Asp Ala Met Lys Arg Ser Val Asp
    50                  55                  60

Glu Tyr Gly Gly Gly Ser Gly Gly Ser Arg Asn Thr Gly Gly Thr Asn
65                  70                  75                  80

His Phe His Val Ala Leu Glu Arg Glu Pro Ala Glu Pro His Gly Lys
                85                  90                  95

Glu Asp Ala Val Leu Phe Thr Ser Gly Tyr Ser Ala Asn Glu Gly Ser
            100                 105                 110

Leu Ser Val Leu Ala Gly Ala Val Asp Asp Cys Gln Val Phe Ser Asp
        115                 120                 125

Ser Ala Asn His Ala Ser Ile Ile Asp Gly Leu Arg His Ser Gly Ala
    130                 135                 140

Arg Lys His Val Phe Arg His Lys Asp Gly Arg His Leu Glu Glu Leu
145                 150                 155                 160

Leu Ala Ala Ala Asp Arg Asp Lys Pro Lys Phe Ile Ala Leu Glu Ser
                165                 170                 175

Val His Ser Met Arg Gly Asp Ile Ala Leu Leu Ala Glu Ile Ala Gly
            180                 185                 190

Leu Ala Lys Arg Tyr Gly Ala Val Thr Phe Leu Asp Glu Val His Ala
        195                 200                 205

Val Gly Met Tyr Gly Pro Gly Gly Ala Gly Ile Ala Ala Arg Asp Gly
    210                 215                 220
```

```
Val His Cys Glu Phe Thr Val Met Gly Thr Leu Ala Lys Ala Phe
225                 230                 235                 240

Gly Met Thr Gly Gly Tyr Val Ala Gly Pro Ala Val Leu Met Asp Ala
                245                 250                 255

Val Arg Ala Arg Ala Arg Ser Phe Val Phe Thr Thr Ala Leu Pro Pro
            260                 265                 270

Ala Val Ala Ala Gly Ala Leu Ala Ala Val Arg His Leu Arg Gly Ser
            275                 280                 285

Asp Glu Glu Arg Arg Pro Ala Glu Asn Ala Arg Leu Thr His Gly
290                 295                 300

Leu Leu Arg Glu Arg Asp Ile Pro Val Leu Ser Asp Arg Ser Pro Ile
305                 310                 315                 320

Val Pro Val Leu Val Gly Glu Asp Arg Met Cys Lys Arg Met Ser Ala
                325                 330                 335

Leu Pro Leu Glu Arg His Gly Ala Tyr Val Gln Ala Ile Asp Ala Pro
                340                 345                 350

Ser Val Pro Ala Gly Glu Glu Ile Leu Arg Ile Ala Pro Ser Ala Val
                355                 360                 365

His Glu Thr Glu Glu Ile His Arg Phe Val Asp Ala Leu Asp Gly Ile
370                 375                 380

Trp Ser Glu Leu Gly Ala Ala Arg Arg Val
385                 390

<210> SEQ ID NO 27
<211> LENGTH: 301
<212> TYPE: PRT
<213> ORGANISM: Streptomyces ghanaensis

<400> SEQUENCE: 27

Val Gly Gly Pro Gly Gly Asp Pro Leu Gly Gly His Asp Pro Leu Gly
1               5                   10                  15

Leu Arg Gly Pro Val Ala Gly Ala His Arg Gly Arg Gly Arg Arg
            20                  25                  30

Ala Asp His Leu Trp Gly Val Glu Val Ala Thr Ala Pro Val Arg Gly
            35                  40                  45

Gly Gly Arg Arg Arg Ala Ala Pro Ser Gly Glu Val Gly Glu Ile Val
        50                  55                  60

Val Arg Gly His Asn Leu Met Ala Gly Tyr Val Asp Ala Pro Arg Ala
65                  70                  75                  80

Thr Ala Ala Ala Phe Val Asp Gly Trp Phe Arg Thr Gly Asp Leu Gly
                85                  90                  95

Leu Leu Asp Glu Glu Gly Tyr Pro Thr Ala Val Asp Arg Glu Lys Asp
                100                 105                 110

Val Ile Leu Arg Gly Gly Tyr Asp Val His Pro Arg Glu Val Glu Glu
            115                 120                 125

Ala Leu Leu Arg His Pro Ala Val Ala Arg Val Ala Val Val Gly Leu
130                 135                 140

Pro Asp Pro Val Tyr Gly Gln Glu Val Cys Ala Val Val Val Pro Arg
145                 150                 155                 160

Asp Gly Pro Thr Pro Asp Gly Ala Leu Ala Asp Ser Val Val Ala Trp
                165                 170                 175

Gly Glu Arg His Ile Ala Ala Tyr Arg Arg Pro Arg Val Val Leu
            180                 185                 190

Pro Asp Arg Leu Pro Leu Gly Pro Gly Gly Lys Val Leu Lys Gly Glu
```

```
              195                 200                 205
Pro Ala Val Arg Leu Arg Ser Ser Asp Glu Ala Gly Ala Ala Arg Pro
    210                 215                 220

Arg Gly Asp Gly Pro Gly Arg Phe Pro Ala Gly Gly Gly Pro Ala
225                 230                 235                 240

Arg Thr Asn Ala Ser Glu Ala Val Arg Ala Ala Arg Ser Val Ser Pro
                245                 250                 255

Pro Gly Ala Gly Val Arg Arg Ala Gln Ser Val Ser Pro Ser Val Pro
                260                 265                 270

Ala Ala Trp Ile Ala Ser Gln Thr Ser Ala Ser Ala Pro Val Glu Asp
                275                 280                 285

Arg Ser Arg Arg Glu Arg Ala Pro Lys Arg Arg Ser Arg
    290                 295                 300
```

<210> SEQ ID NO 28
<211> LENGTH: 412
<212> TYPE: PRT
<213> ORGANISM: Streptomyces ghanaensis

<400> SEQUENCE: 28

```
Val Thr Thr Gln Tyr Leu Asp Leu Phe Ala Arg Leu Thr Glu Asn Ser
1               5                   10                  15

Asp Gly Gly Lys Arg Glu Phe Leu Glu Ile Gly Arg Leu Ala Gly Ser
                20                  25                  30

Phe Pro Ala Ala Ser Val Arg Ser Ser Gly Pro Val Thr Gly Arg Asp
                35                  40                  45

Ser Ile Ser Val Trp Cys Ser Asn Asp Tyr Leu Gly Met Gly Gln His
    50                  55                  60

Pro Ala Val Leu Lys Ala Met Lys Asp Ala Ile Asp Glu Tyr Gly Ala
65              70                  75                  80

Gly Ala Gly Gly Ser Arg Asn Ile Gly Gly Thr Asn His Tyr His Val
                85                  90                  95

Leu Leu Glu Arg Glu Leu Ala Ala Leu His Gly Lys Asp Glu Ala Leu
                100                 105                 110

Leu Phe Thr Ser Gly Tyr Thr Ala Asn Asp Gly Ala Leu Ser Val Ile
                115                 120                 125

Ala Gly Arg Met Glu Lys Cys Val Val Phe Ser Asp Ala Leu Asn His
                130                 135                 140

Ala Ser Ile Ile Asp Gly Leu Arg His Ser Arg Ala Gln Lys Gln Ile
145                 150                 155                 160

Phe Arg His Asn Asp Pro Ala His Leu Glu Glu Leu Ile Ala Ala Ala
                165                 170                 175

Asp Pro Asp Val Pro Lys Leu Ile Val Ala Glu Ser Val Tyr Ser Met
                180                 185                 190

Asn Gly Asp Ile Ala Pro Leu Ser Glu Ile Ala Asp Ile Ala Lys Arg
                195                 200                 205

His Gly Ala Met Thr Tyr Leu Asp Glu Val His Ala Val Gly Met Tyr
    210                 215                 220

Gly Pro Glu Gly Ala Gly Ile Ala Ala Arg Glu Gly Ile Ala Asp Asp
225                 230                 235                 240

Phe Thr Val Ile Met Gly Thr Leu Ala Lys Gly Phe Gly Thr Thr Gly
                245                 250                 255

Gly Tyr Ile Ala Gly Pro Ala Glu Ile Ile Glu Ala Val Arg Met Phe
                260                 265                 270
```

```
Ser Arg Ser Phe Val Phe Thr Thr Ala Leu Ala Pro Ala Val Ala Ala
        275                 280                 285

Gly Ala Leu Ala Ala Val His His Leu Arg Ser Ser Glu Val Glu Arg
    290                 295                 300

Glu Gln Leu Trp Ser Asn Ala Gln Leu Met His Arg Leu Leu Asn Glu
305                 310                 315                 320

Arg Gly Ile Pro Phe Ile Ser Asp Gln Thr His Ile Val Ser Val Met
                325                 330                 335

Val Gly Asp Glu Ala Val Cys Lys Arg Met Ser Ala Leu Leu Leu Asp
            340                 345                 350

Arg His Gly Ile Tyr Val Gln Ala Ile Asn Ala Pro Ser Val Arg Val
        355                 360                 365

Gly Glu Glu Ile Leu Arg Val Ala Pro Gly Ala Val His Thr Ala Asp
    370                 375                 380

Asp Val Arg Glu Phe Val Asp Ala Leu Ser Gln Val Trp Glu Glu Val
385                 390                 395                 400

Gly Ser Ala Arg Val Pro Ala Thr Pro Ala Ala Leu
                405                 410

<210> SEQ ID NO 29
<211> LENGTH: 516
<212> TYPE: PRT
<213> ORGANISM: Streptomyces ghanaensis

<400> SEQUENCE: 29

Met Thr Leu Thr Ala Ala Ser Val Leu Ala Glu Ser Ala Gly Arg Arg
1               5                   10                  15

Pro Asp His Pro Ala Leu Val Phe Gly Ser Glu Arg Ile Thr Tyr Ala
            20                  25                  30

Glu Leu Trp Leu Ala Thr Arg Arg Tyr Ala Ala Val Leu Arg Asp Arg
        35                  40                  45

Gly Val Arg Pro Gly Asp Arg Ile Ala Leu Leu Leu Pro Asn Thr Pro
    50                  55                  60

His Phe Pro Met Val Tyr Tyr Gly Val Leu Ala Leu Gly Ala Val Val
65                  70                  75                  80

Val Pro Val His Gly Leu Leu Arg Ala Asp Glu Ile Val His Val Leu
                85                  90                  95

Gly Asp Ser Glu Ala Lys Ala Met Val Cys Ala Ala Pro Met Leu Thr
            100                 105                 110

Glu Gly Ala Lys Ala Ala Gly Thr Ala Gly Val Pro Leu Leu Thr Val
        115                 120                 125

Met Val Glu Asn Gly Glu Asp Asp Gly Pro Ala Arg Leu Asp Val
    130                 135                 140

Leu Ala Glu Arg Ala Glu Pro Leu Asp Gly Leu Val Pro Arg Ala Pro
145                 150                 155                 160

Asp Asp Leu Ala Leu Val Leu Tyr Thr Ser Gly Thr Thr Gly Arg Pro
                165                 170                 175

Lys Gly Ala Met Ile Thr His Leu Asn Leu Val Met Asn Val Ser Thr
            180                 185                 190

Thr Met Arg Ser Pro Phe Asp Leu Gly Pro Glu Asp Val Leu Leu Gly
        195                 200                 205

Cys Leu Pro Leu Phe His Thr Phe Gly Gln Thr Cys Gly Met Ser Ala
    210                 215                 220

Cys Phe Leu Ala Gly Gly Thr Leu Val Leu Met Asn Arg Phe Asp Gly
225                 230                 235                 240
```

Pro Gly Ala Leu Asp Leu Met Val Thr Glu Gly Cys Thr Val Phe Met
                245                 250                 255

Gly Val Pro Thr Met Tyr Leu Ala Leu Asp Ala Ala His Asp
            260                 265                 270

Ala Arg Arg Pro Val Leu Asp Arg Ala Phe Ser Gly Ser Ala Leu
        275                 280                 285

Pro Val Lys Val Leu Glu Glu Phe Gln Glu Val Tyr Gly Cys Pro Ile
    290                 295                 300

Tyr Glu Gly Tyr Gly Leu Thr Glu Thr Ser Pro Val Val Ala Tyr Asn
305                 310                 315                 320

Gln Lys Ala Trp Pro Arg Arg Pro Gly Thr Val Gly Arg Pro Ile Trp
                325                 330                 335

Gly Val Glu Ala Glu Ile Ala Ala Asp Val Glu Asp Arg Ile Glu
            340                 345                 350

Leu Leu Pro Ala Gly Glu Ile Gly Glu Ile Val Val Arg Gly His Asn
        355                 360                 365

Val Met Ala Gly Tyr Leu Asn Arg Pro Glu Ala Thr Ala Ala Val Leu
    370                 375                 380

Val Asp Gly Trp Phe Arg Ser Gly Asp Leu Gly Met Lys Asp Ala Asp
385                 390                 395                 400

Gly Tyr Leu Thr Ile Val Asp Arg Lys Lys Asp Met Val Leu Arg Gly
                405                 410                 415

Gly Tyr Asn Val Tyr Pro Arg Glu Val Glu Val Leu Met Arg His
            420                 425                 430

Pro Ala Val Ala Gln Val Ala Val Ile Gly Val Pro Asp Asp Lys Tyr
        435                 440                 445

Gly Glu Glu Val Cys Ala Val Val Arg Thr Arg Pro Gly Thr Asp Pro
450                 455                 460

Asp Ala Ala Leu Ala Ala His Ile Val Ser Trp Ser Arg Gln Arg Ile
465                 470                 475                 480

Ala Ala Tyr Lys Tyr Pro Arg Arg Val Glu Phe Val Glu Asp Phe Pro
                485                 490                 495

Leu Gly Pro Ser Gly Lys Val Leu Lys Arg Glu Leu Ala Ala Arg Phe
            500                 505                 510

Ala Gly Gly Gly
        515

<210> SEQ ID NO 30
<211> LENGTH: 521
<212> TYPE: PRT
<213> ORGANISM: Streptomyces ghanaensis

<400> SEQUENCE: 30

Met Ser Ser Asn Glu Asn Tyr Val Arg Arg Val Leu Glu Ala Leu Ala
1               5                   10                  15

Ser Asp Pro Asp Arg Ile Ala Leu Trp Ala Asp Gly Glu Glu Ile Thr
            20                  25                  30

Ala Gly Gln Val Ser Arg Ala Val Leu Thr Ala Ala Glu Leu Leu Leu
        35                  40                  45

Arg His Phe Thr Glu His Arg Asp Pro Ser Ala Glu Gly Lys Ala Pro
    50                  55                  60

Val Val Ala Val Leu Thr Val Thr Asn Ser Pro Ala Thr Ile Ile Leu
65                  70                  75                  80

Arg Tyr Ala Ala Asn Leu Ala Gly Ala Thr Leu Val His Leu His Ser

-continued

```
                85                  90                  95
Thr Asn Ala Val Asp Pro Thr Asp Gln Leu Ala Ala Ala Arg Leu
                100                 105                 110

Asp Ile Leu Ser Lys Thr Gly Ala Thr Phe Leu Ala Val Asp Lys Glu
                115                 120                 125

Asn Leu Asp Ala Ala Arg Glu Leu Cys Asp Arg Leu Pro Glu Pro Pro
                130                 135                 140

Arg Leu Ala Ala Leu Gly Ala Leu Gly Pro Asp Val Leu Asp Leu Ser
145                 150                 155                 160

Ser Gly Asp Pro Asp Ala Phe Gly His Asp Ala Val Glu Ala Asp Pro
                165                 170                 175

Glu Gln Pro Ala Val Val Ile Tyr Thr Ser Gly Thr Ser Gly Arg Pro
                180                 185                 190

Lys Gly Val Thr Gln Pro Tyr Arg Leu Arg Arg Ala Asn Leu Gln Val
                195                 200                 205

Ala Leu Gln Ser Pro Glu Pro Ile Val Tyr Leu Ser Thr Leu Pro Val
                210                 215                 220

Ser Asn Ser Ser Gly Ser Ala Val Asp Val Ala Leu Ala Ser Gly Gly
225                 230                 235                 240

Thr Val Val Leu His Asp Gly Phe Glu Ala Gly Glu Val Leu Arg Ala
                245                 250                 255

Val Glu Gln His Arg Val Ser Thr Leu Thr Ile Thr Pro Pro Gln Leu
                260                 265                 270

Tyr Met Leu Ile Asp His Pro Asp Thr Ala Thr Thr Asp Arg Ser Ser
                275                 280                 285

Ile Arg Leu Ile Thr Tyr Leu Gly Ser Pro Ala Ala Pro Ala Arg Leu
                290                 295                 300

Ala Glu Ala Val Glu Val Phe Gly Pro Val Leu Leu Gln Leu Tyr Gly
305                 310                 315                 320

Thr Thr Glu Val Asn Gly Ile Ser Met Leu Met Pro Gln Asp His Phe
                325                 330                 335

Asp Pro Glu Leu Arg Arg Thr Val Gly Arg Pro Thr Thr Glu Ile Arg
                340                 345                 350

Ile Arg Asp Val Asp Asp Arg Asp Leu Pro Pro Gly Glu Ile Gly
                355                 360                 365

Glu Val Cys Val Gln Ser Pro Ser Thr Met Leu Gly Tyr Trp Gly Glu
                370                 375                 380

Pro Glu Leu Thr Ala Ala Ile Ile Arg Asp Gly Trp Val His Thr Gly
385                 390                 395                 400

Asp Leu Gly Ser Leu Asp Glu Asn Gly Phe Leu Arg Leu His Gly Arg
                405                 410                 415

Met Gly Glu Val Met Lys Thr Asn Gly Ile Lys Val His Pro Thr Asp
                420                 425                 430

Val Glu Asn Ala Leu Leu Thr His Pro Glu Val Thr Gln Ala Ala Val
                435                 440                 445

Tyr Cys Val Val Asp Glu Asp Arg Val Glu His Ile His Ala Ala Val
                450                 455                 460

Val Val Arg Pro Gly Gly Thr Ala Asp Ser Gly Thr Leu Ile Gly His
465                 470                 475                 480

Val Ala Ala Glu Leu Ser Pro Lys His Val Pro Ala Val Val Thr Phe
                485                 490                 495

His Asp Ala Leu Pro Leu Thr Arg Ala Gly Lys Pro Asp Lys Pro Ala
                500                 505                 510
```

Leu Ala Ala Arg His Asn Gly Ala Ala
            515                 520

<210> SEQ ID NO 31
<211> LENGTH: 402
<212> TYPE: PRT
<213> ORGANISM: Streptomyces ghanaensis

<400> SEQUENCE: 31

Met Ala Ala Pro Asp Arg Pro Leu Val Gln Val Leu Ser Pro Arg Thr
1               5                   10                  15

Trp Gly Glu Phe Gly Asn Tyr Leu Ala Ala Thr Arg Phe Ser Arg Ala
            20                  25                  30

Leu Arg Ser Val Ile Asp Ala Glu Val Thr Leu Leu Glu Ala Glu Pro
        35                  40                  45

Ile Leu Pro Trp Ile Gly Glu Ala Gly Ala Gln Ile Arg Thr Ile Ser
    50                  55                  60

Leu Glu Ser Pro Asp Ala Val Val Arg Asn Gln Arg Tyr Met Ala Leu
65                  70                  75                  80

Met Asp Arg Leu Gln Ala Arg Phe Pro Glu Gly Phe Glu Ala Asp Pro
                85                  90                  95

Thr Ala Ala Gln Arg Ala Asp Leu Glu Pro Leu Thr Arg His Leu Arg
            100                 105                 110

Glu Ser Ala Pro Asp Val Val Gly Thr Lys Gly Phe Val Ala Arg
        115                 120                 125

Leu Cys Val Ala Ala Val Arg Leu Ala Gly Thr Ser Thr Arg Val Val
130                 135                 140

Ser His Val Thr Asn Pro Gly Leu Leu Gln Leu Pro Leu His Arg Ser
145                 150                 155                 160

Arg Tyr Pro Asp Leu Thr Leu Val Gly Phe Pro Arg Ala Lys Glu His
                165                 170                 175

Leu Leu Ala Thr Ala Gly Gly Asp Pro Glu Arg Val Gln Val Val Gly
            180                 185                 190

Pro Leu Val Ala Gln His Asp Leu Arg Asp Phe Met Thr Ser Glu Thr
        195                 200                 205

Ala Val Ser Glu Ala Gly Pro Trp Gly Gly Asp Ser Gly Pro Asp Arg
    210                 215                 220

Pro Arg Val Ile Ile Phe Ser Asn Arg Gly Gly Asp Thr Tyr Pro Glu
225                 230                 235                 240

Leu Val Arg Arg Leu Ala Asp Arg His Pro Gly Ile Asp Leu Val Phe
                245                 250                 255

Val Gly Tyr Gly Asp Pro Glu Leu Ala Arg Arg Thr Ala Ala Val Gly
            260                 265                 270

Arg Pro His Trp Arg Phe His Ser Val Leu Gly Gln Ser Glu Tyr Phe
        275                 280                 285

Asp Tyr Ile Arg Arg Ala Ser Arg Ser Arg Tyr Gly Leu Leu Val Ser
    290                 295                 300

Lys Ala Gly Pro Asn Thr Thr Leu Glu Ala Ala Tyr Phe Gly Ile Pro
305                 310                 315                 320

Val Leu Met Leu Glu Ser Gly Leu Pro Met Glu Arg Trp Val Pro Gly
                325                 330                 335

Leu Ile His Glu Glu Gly Leu Gly His Ala Cys Ala Thr Pro Glu Glu
            340                 345                 350

Leu Phe Arg Thr Ala Asp Asp Trp Leu Thr Arg Pro Ser Val Ile Glu

```
                 355                 360                 365
Val His Lys Lys Ala Ala Val Ser Phe Ala Ala Ser Val Leu Asp Gln
            370                 375                 380

Asp Ala Val Thr Ala Arg Ile Lys Ala Ala Leu Gln Pro Leu Leu Asp
385                 390                 395                 400

Ala Arg

<210> SEQ ID NO 32
<211> LENGTH: 286
<212> TYPE: PRT
<213> ORGANISM: Streptomyces ghanaensis

<400> SEQUENCE: 32

Leu Thr His Glu Val Thr Pro Arg Gly Gly Pro Glu Gly Asp Ala Met
1               5                   10                  15

Val Thr Ala Gly Pro Ala Gly Ala Ala Val Thr Val Leu Pro His
            20                  25                  30

Tyr Asp Cys Ala Ala Tyr Leu Gly Ala Ala Val Gly Ser Val Leu Ser
            35                  40                  45

Gln Asp Arg Pro Asp Leu Arg Leu Thr Val Val Asp Glu Cys Ser Pro
50                  55                  60

Glu Glu Lys Trp Ala Arg Ala Leu His Pro Tyr Ala Gly Asp Pro Arg
65                  70                  75                  80

Leu Thr Val Val Arg Thr Ser Arg Asn Val Gly His Leu Arg Ile Lys
                85                  90                  95

Asn Lys Val Leu Glu Ser Val Asp Thr Pro Tyr Val Ala Phe Gln Asp
            100                 105                 110

Ala Asp Asp Ile Ser Leu Pro Gly Arg Leu Arg His Gln Leu Ala Leu
        115                 120                 125

Leu Glu Ser Gly Gly Ala Asp Leu Val Gly Cys Ala Tyr Ser Tyr Ile
130                 135                 140

Asp Glu Ala Gly Arg Thr Thr Gly His Arg Arg Met Pro Arg Asn Gly
145                 150                 155                 160

Asn Leu Trp Met Arg Leu Gly Arg Thr Thr Val Leu Leu His Pro Ser
                165                 170                 175

Ser Val Val Arg Arg Ser Val Leu Glu Arg Leu Gly Gly Phe Asp Gly
            180                 185                 190

Thr Ala Arg Leu Gly Ala Asp Thr Asp Phe His Leu Arg Ala Ala Arg
        195                 200                 205

Leu Tyr Arg Leu Arg Ser Val Arg Lys Val Leu Tyr Arg Tyr Arg Ile
210                 215                 220

Trp Pro Lys Ser Leu Thr Gln Ala Pro Asp Thr Gly Phe Gly Ser Ala
225                 230                 235                 240

Glu Arg Arg Ala Tyr Thr Glu Ala Met Thr Ala Gln Glu Glu Arg Arg
                245                 250                 255

Arg Arg Ala Arg Thr Arg Glu Glu Leu Leu Pro Leu Leu Val Ala Pro
            260                 265                 270

Pro Asn Asp Val Asp Phe Thr Leu Thr Arg Val Asp Leu Asp
        275                 280                 285

<210> SEQ ID NO 33
<211> LENGTH: 414
<212> TYPE: PRT
<213> ORGANISM: Streptomyces ghanaensis

<400> SEQUENCE: 33
```

-continued

```
Val Ala Val Leu Arg Gly Asp Asp Glu Ala Leu Pro His Trp Leu Trp
  1               5                  10                 15

His Leu Ala Arg Ala Val Trp Tyr Gly Gly Asp Gly Thr Gly Pro
             20                  25                 30

Val Gly Leu Val Gln Cys Gly Ala Leu Arg Leu Arg Asp Asp Gly Leu
             35                  40                 45

Val Asp Gly Phe Ala Leu Pro Pro Ala Ser Pro Arg Thr Arg Pro Ser
 50                  55                  60

Pro Ser Asp Leu Leu Glu Gly Ala Tyr Ala Val Arg Arg Glu Leu Leu
 65                  70                  75                 80

Asp Ala Asp Gly Gly Thr Ala Pro Trp Val Ala Leu Pro Met Pro Leu
             85                  90                 95

Val Arg Arg Arg Ser Gly Gly Ala Gly Asp Pro Ala Ala Val Leu Ala
            100                 105                110

Pro Gly Thr Arg Val Ala Arg Arg Thr Arg Leu Val Arg His Gly Tyr
            115                 120                 125

Arg Pro Pro Ala Ala Arg Pro Arg Asn Gly Ser Thr Pro Arg Leu Val
            130                 135                140

Ser Val Val Pro Val Arg Asn Gly Ala Arg Thr Leu Ala Ala Gln
145                 150                 155                160

Leu Thr Ala Leu Ala Arg Gln Thr Gly Ala Val Ala Tyr Glu Val Leu
                165                 170                 175

Val Val Asp Asn Gly Ser Thr Asp Thr Thr Arg Glu Val Ala Glu Arg
                180                 185                 190

Ala Arg Ala Glu Leu Pro Asp Leu Arg Ile Val Asp Ala Ser Asp Arg
            195                 200                 205

Ala Gly Glu Ser Cys Ala Arg Asn Arg Gly Ile Ala Ala Ala Arg Gly
            210                 215                 220

Asp Phe Val Ala Phe Cys Asp Ala Asp Val Ala Asp Thr Gly Trp
225                 230                 235                240

Leu Ala Ala Met Ala Gln Ala Ala Lys Glu Ala Asp Leu Val Gly Gly
                245                 250                 255

Gly Leu Glu Thr Ser Val Leu Ser Pro Gly Arg Val Asp Glu Gln Pro
            260                 265                 270

Leu Pro Met Asp Ala Gln Thr Asp Phe Leu Pro Phe Ala Arg Gly Ala
            275                 280                 285

Asn Cys Gly Ala Trp Lys Asp Val Leu Thr Ala Leu Gly Gly Trp Asp
            290                 295                 300

Glu Arg Tyr Arg Gly Gly Glu Asp Met Asp Leu Ser Trp Arg Ala
305                 310                 315                 320

Gln Leu Cys Gly Tyr Leu Val Arg Tyr Ala Asp Asp Ala Arg Met His
                325                 330                 335

Tyr Arg Leu Arg Asp Gly Leu Pro Ala Leu Ala Arg Gln Lys Trp Asn
            340                 345                 350

Tyr Gly Arg Ser Gly Ala Gln Leu Tyr Ala Ala Tyr Arg Arg Ala Gly
            355                 360                 365

Phe Glu Arg Arg Asp Gly Arg Val Val Val Arg Asn Trp Cys Trp Leu
            370                 375                 380

Leu Leu His Val Pro Asn Leu Val Arg Ser Thr Gly Pro Cys Gly His
385                 390                 395                 400

Ala Glu Ser Ala Thr Arg Pro Ala Gly Arg Phe Pro Gly Leu
                405                 410
```

```
<210> SEQ ID NO 34
<211> LENGTH: 427
<212> TYPE: PRT
<213> ORGANISM: Streptomyces ghanaensis

<400> SEQUENCE: 34

Val Thr Ser Glu Pro Ala Ala Pro Ala Val Pro His Pro Pro Val Arg
1               5                   10                  15

Pro Gly Pro Pro Val Arg Leu Asn Arg Pro Leu Ala Arg Arg Arg Arg
            20                  25                  30

Arg Pro Ala Gly Glu Gly Phe Val Thr His His Leu Arg Ser Thr Met
        35                  40                  45

Ala Arg Gly Phe Arg Pro Pro Glu Ser Trp Glu Val Pro Val Arg His
50                  55                  60

Val Leu Pro Gly Leu Pro Ala Asp Gly Thr Pro Arg Ala Glu Glu Ala
65                  70                  75                  80

Ala Gln Ala Leu Arg Thr Pro Ala Gly Arg Pro Gly Ile Ala Leu Val
                85                  90                  95

Val Pro Thr Tyr Val Ser Arg Val Ser Leu Ala Arg Gln Arg Glu Trp
            100                 105                 110

Phe Asp Ala Leu Leu Asp Gln Ala Ala Val Thr Arg Asp His Pro
        115                 120                 125

Leu Val Pro Leu Val Leu Phe Val Gly Met Gln Trp Ser Ser Ala Glu
130                 135                 140

Glu Glu Arg Glu Ala Leu Arg Arg Leu Arg Val Leu Leu Asp Asp Ala
145                 150                 155                 160

Arg Thr Arg Leu Pro Gly Leu Arg Ile Cys Gly Leu Ala Leu Pro Gly
                165                 170                 175

Pro Gly Lys Pro Arg Thr Leu Asn Gly Ala Ile Ala Val Ala Glu Leu
            180                 185                 190

Leu Gly Cys Ala Gly Val Gly Trp Thr Asp Asp Val Thr Leu Glu
        195                 200                 205

Glu Asp Cys Leu Ser Arg Leu Val Arg Asp Phe Leu Ala Ala Gly Cys
210                 215                 220

Arg Gly Ala Val Gly Ala Thr Lys Val Ala His Thr His Glu Tyr Ala
225                 230                 235                 240

Thr Ser Arg Leu Leu Ser Arg Ala Lys Ala Ile Ala Ala Pro Ala Thr
                245                 250                 255

Asn Tyr Pro His Gly Cys Cys Ile Leu Val Ala Thr Asp Val Val Ala
            260                 265                 270

Gly Gly Leu Pro Gly Arg Tyr Val Ser Asp Asp Gly Tyr Val Cys Phe
        275                 280                 285

Arg Leu Leu Asp Pro Ala Leu Pro Asp Pro Leu Ala Arg Leu Arg Leu
290                 295                 300

Val Pro Asp Ala Arg Cys His Tyr Tyr Val Ala Gly Pro Ala Gly Glu
305                 310                 315                 320

Thr Arg Arg Arg Ile Arg Arg Leu Leu Leu Asn His Leu Val Asp Leu
                325                 330                 335

Ala Asp Trp Pro Leu Pro Val Val Arg His Tyr Phe Arg His Val Leu
            340                 345                 350

Phe Gly Gly Met Trp Pro Leu Thr Gly Phe Asp Ser Ser Arg Gly Ala
        355                 360                 365

Arg Arg Gly Val Gln Lys Ala Leu Ile Lys Trp Leu Tyr Phe Ala Trp
370                 375                 380
```

```
Phe Ala Gly Ile Gly Gly Glu Leu Tyr Val Arg Gly Leu Ser Gly Arg
385                 390                 395                 400

Pro Leu Arg Arg Ile Glu Trp Ala Pro Tyr Ser Asp Ile Arg Arg Leu
            405                 410                 415

Thr Pro Ser Ser Ser Pro Thr Arg Gln Glu Ser
            420                 425
```

<210> SEQ ID NO 35
<211> LENGTH: 312
<212> TYPE: PRT
<213> ORGANISM: Streptomyces ghanaensis

<400> SEQUENCE: 35

```
Val Leu Arg Arg Leu Ala Glu Val Arg Glu Ala His Pro Ser Leu Pro
1               5                   10                  15

Leu Thr Val Trp Val Gly Met Gln Tyr Gly Pro Gly Glu Asp Glu Glu
            20                  25                  30

Ala Leu Arg Arg Leu Arg Arg Leu Cys Ala Pro Val Pro Gly Gly Pro
        35                  40                  45

Ala Leu Thr Val Val Gly Leu Ala Leu Pro Gly Pro Gly Lys Leu Arg
    50                  55                  60

Thr Val Ser Thr Val Leu Arg Leu Ser Glu Asp Leu Gly Tyr Ala Gly
65                  70                  75                  80

Trp Leu Trp Thr Asp Asp Ile Glu Ile Ala Pro His Cys Leu Ala
                85                  90                  95

Leu Leu Val Ser Arg Phe Arg Glu Arg Gly Glu Arg Gly Ala Val Gly
                100                 105                 110

Ala His Ser Val Ala Leu Ala Arg Glu Thr Val Thr Ser Gln Ala Met
        115                 120                 125

Asp Arg Val Ser Gly Val Thr Ala Pro Pro Lys Ala Cys Pro Ala Ala
130                 135                 140

Ala Cys Leu Val Val Ala Thr Asp Val Leu Gly Thr Gly Ile Pro Val
145                 150                 155                 160

Arg Arg Leu Thr Asp Asp Gly Tyr Val Val Phe Glu Leu Leu Asp Ala
                165                 170                 175

Gly Ala Pro Asp Pro Leu His Asp Leu Glu Val Leu Pro Glu Ala Arg
            180                 185                 190

Ile Ser Phe Tyr Arg Val Ser Arg Thr His Asp Thr Phe Gln Arg Leu
        195                 200                 205

Arg Arg Ser Leu Tyr Ser His Val Thr Cys Val Ala Asp Tyr Pro Trp
210                 215                 220

Pro Thr Ala Arg Val Tyr Leu Thr Arg Val Leu Phe His Gly Leu Trp
225                 230                 235                 240

Pro Leu Ala Ala Trp Asp Gly Ser Arg Gly Pro Val His Gly Leu Gln
                245                 250                 255

Arg Trp Leu Val Lys Gly Leu His Phe Thr Trp Phe Cys Gly Val Ala
            260                 265                 270

Gly Ser Leu Ala Val Arg Gly Ala Val Gly Arg Pro Leu Arg Arg Val
        275                 280                 285

Ala Trp Gly Asp Glu Gly Asp Phe Arg Ser Pro Thr Val Glu Glu Pro
    290                 295                 300

Ala Ala Gly Ala Ala Ala Gly Arg
305                 310
```

<210> SEQ ID NO 36
<211> LENGTH: 645
<212> TYPE: PRT
<213> ORGANISM: Streptomyces ghanaensis

<400> SEQUENCE: 36

```
Met Cys Gly Phe Val Gly Phe Ser Asp Ala Gly Ala Gly Gln Glu Asp
1               5                   10                  15

Ala Arg Val Thr Ala Glu Arg Met Leu Ala Ala Val Ala His Arg Gly
            20                  25                  30

Pro Asp Gly Ser Asp Trp Cys His His Arg Gly Val Thr Leu Ala His
        35                  40                  45

Cys Ala Leu Thr Phe Thr Asp Pro Asp His Gly Ala Gln Pro Phe Val
    50                  55                  60

Ser Ala Ser Gly Ala Thr Ala Val Val Phe Asn Gly Glu Leu Tyr Asn
65                  70                  75                  80

His Ala Val Leu Gly Asp Gly Ala Leu Pro Cys Ala Pro Gly Gly Asp
                85                  90                  95

Thr Glu Val Pro Gly Gly Thr Leu Arg Val Ala Gly His Ala Asp Ala
            100                 105                 110

Arg Pro Ala Ala Gly His Val Arg Leu Arg Ala Ala Gly Arg Pro His
        115                 120                 125

Arg His His Gly Ala Gly Arg Asp Arg Trp Gly Arg Ala Pro Leu Leu
    130                 135                 140

Thr Pro Ala Cys Glu Thr Asp Ile Ala Phe Ala Ser Glu Leu Thr Ser
145                 150                 155                 160

Leu Leu Arg His Pro Ala Ala Pro Arg Thr Pro Glu Val Arg Ala Leu
                165                 170                 175

Ala Asp Tyr Leu Val Leu Gln Ala Phe Cys Ala Pro Ala Ser Ala Val
            180                 185                 190

Ser Gly Val Cys Lys Val Arg Pro Gly Ser Tyr Val Thr His Arg His
        195                 200                 205

Gly Ala Leu Asp Glu Thr Glu Phe Trp Arg Pro Arg Leu Thr Pro Asp
    210                 215                 220

Arg Gly Ala Gly Arg Gly Pro Gly Arg Arg Glu Ala Ala Arg Arg Phe
225                 230                 235                 240

Glu Glu Leu Phe Arg Ala Ala Val Ala Arg Arg Met Thr Ser Thr Asp
                245                 250                 255

Arg Arg Leu Gly Val Leu Leu Ser Gly Gly Leu Asp Ser Ser Ala Val
            260                 265                 270

Ala Ala Val Ala Gln Gln Leu Leu Pro Gly Arg Pro Val Pro Thr Phe
        275                 280                 285

Ser Ala Gly Phe Ala Asp Pro Asp Phe Asp Glu Ser Asp His Ala Arg
    290                 295                 300

Ala Val Ala Arg His Leu Gly Thr Glu His Val Val Arg Ile Gly
305                 310                 315                 320

Gly Ala Asp Leu Ala Gly Val Val Glu Ser Leu Ala Val Ala Asp
                325                 330                 335

Glu Pro Leu Ala Asp Pro Ser Leu Leu Pro Thr Arg Leu Val Cys Arg
            340                 345                 350

Ala Ala Arg Glu His Val Arg Gly Val Leu Thr Gly Asp Gly Ala Asp
        355                 360                 365

Glu Leu Leu Leu Gly Tyr Arg Tyr Phe Gln Ala Glu Arg Ala Ile Glu
    370                 375                 380
```

```
Leu Leu Leu Arg Val Leu Pro Ala Pro Arg Leu Glu Ala Leu Val Arg
385                 390                 395                 400

Leu Leu Val Arg Arg Leu Pro Ala Arg Ser Gly Asn Leu Pro Val Thr
            405                 410                 415

His Ala Leu Gly Leu Leu Ala Lys Gly Leu Arg Ala Ala Pro Glu His
        420                 425                 430

Arg Phe Tyr Leu Ser Thr Ala Pro Phe Gly Pro Gly Glu Leu Pro Arg
    435                 440                 445

Leu Leu Thr Pro Glu Ala Gly Ala Glu Leu Thr Gly His Asp Pro Phe
    450                 455                 460

Thr Glu Val Ser Arg Leu Leu Arg Gly Gln Pro Gly Leu Thr Gly Val
465                 470                 475                 480

Gln Arg Ser Gln Leu Ala Val Val Thr His Phe Leu Arg Asp Val Ile
            485                 490                 495

Leu Thr Lys Thr Asp Arg Gly Gly Met Arg Ser Ser Leu Glu Leu Arg
        500                 505                 510

Ser Pro Phe Leu Asp Leu Asp Leu Val Glu Tyr Gly Asn Ser Leu Pro
    515                 520                 525

Thr Gly Leu Lys Leu His Arg Phe Thr Gly Lys Tyr Leu Leu Arg Gln
    530                 535                 540

Val Ala Ala Gly Trp Leu Pro Pro Ser Val Val Gln Arg Thr Lys Leu
545                 550                 555                 560

Gly Phe Arg Ala Pro Val Ala Ala Leu Leu Arg Gly Glu Leu Arg Pro
            565                 570                 575

Leu Leu Leu Asp Thr Leu Ser Pro Ser Ser Leu Arg Arg Gly Gly Leu
        580                 585                 590

Phe Asp Thr Gly Ala Val Arg Leu Leu Ile Asp Asp His Leu Gly Gly
    595                 600                 605

Arg Arg Asp Thr Ser Arg Lys Leu Trp Ala Leu Leu Val Tyr Gln Leu
    610                 615                 620

Trp Phe Glu Ser Leu Thr Ala Gly Pro Arg Ala Leu Glu Ser Pro Ala
625                 630                 635                 640

Tyr Pro Ala Leu Ser
            645

<210> SEQ ID NO 37
<211> LENGTH: 513
<212> TYPE: PRT
<213> ORGANISM: Streptomyces ghanaensis

<400> SEQUENCE: 37

Met Thr Val Arg Arg Pro Ala Ala Ser Ala Pro Arg Val Leu Leu Thr
1               5                   10                  15

Ala Gly Pro Asp Gly Val Arg Val Glu Gly Asp Gly Glu Ala Arg Leu
            20                  25                  30

Gly His Pro Leu Thr Gly Asp His Leu Asp Pro Gly Pro Pro Ala Glu
        35                  40                  45

Gly Val Phe Ala Gly Trp Arg Trp Asp Gly Glu Arg Leu Val Ala Arg
    50                  55                  60

Asn Asp Arg Tyr Gly Val Cys Pro Leu Phe Tyr Arg Ala Gly Gly Gly
65                  70                  75                  80

Ser Leu Ala Leu Ser Pro Asp Pro Leu Ala Leu Leu Pro Glu Asp Gly
                85                  90                  95

Pro Val Glu Leu Asp His Asp Ala Leu Ala Val Phe Leu Arg Thr Gly
            100                 105                 110
```

-continued

```
Phe Phe Leu Ala Glu Asp Thr Ala Phe Ala Gln Val Arg Ala Leu Pro
            115                 120                 125
Pro Ala Ala Thr Leu Thr Trp Asp Thr Gly Gly Leu Arg Leu Arg Ser
130                 135                 140
Asp Gly Pro Pro Arg Pro Gly Ala Ala Ala Met Thr Glu Ala Gln Ala
145                 150                 155                 160
Val Asp Gly Phe Val Asp Leu Phe Arg Ala Ser Val Ala Arg Arg Leu
                165                 170                 175
Pro Gly Glu Pro Tyr Asp Leu Pro Leu Ser Gly Gly Arg Asp Ser Arg
            180                 185                 190
His Ile Leu Leu Glu Leu Cys Arg Arg Gly Ala Pro Pro Arg Arg Cys
            195                 200                 205
Val Ser Gly Ala Lys Phe Pro Pro Asp Pro Gly Ala Asp Ala Arg Val
        210                 215                 220
Ala Ala Ala Leu Ala Gly Arg Leu Gly Leu Pro His Thr Val Val Pro
225                 230                 235                 240
Arg Pro Arg Ser Gln Phe Arg Ala Glu Leu Ala Ala Leu Pro Ala Gln
                245                 250                 255
Gly Met Thr Thr Leu Asp Gly Ala Trp Thr Gln Pro Val Leu Ala His
            260                 265                 270
Leu Arg Arg His Ser Arg Ile Ser Tyr Asp Gly Leu Gly Gly Gly Glu
        275                 280                 285
Leu Val Gln Asn Pro Ser Val Glu Phe Ile Arg Ala Asn Pro Tyr Asp
    290                 295                 300
Pro Ala Asp Leu Pro Gly Leu Ala Asp Arg Leu Leu Ala Ala Ser Arg
305                 310                 315                 320
Thr Gly Pro His Val Glu His Leu Leu Ser Pro Arg Thr Asn Ala Leu
                325                 330                 335
Trp Ser Arg Gln Ala Ala Arg Arg Leu Val Thr Glu Leu Ala Arg
            340                 345                 350
His Ala Asp Ser Ala Ser Pro Leu Ser Ser Phe Phe Phe Trp Asn Arg
        355                 360                 365
Thr Arg Arg Ser Ile Ser Ala Ala Pro Phe Ala Leu Gly Asp Gly Arg
    370                 375                 380
Val Leu Thr His Thr Pro Tyr Leu Asp His Ala Leu Phe Asp His Leu
385                 390                 395                 400
Ala Ser Val Pro His Arg Phe Leu Val Asp Gly Thr Phe His Asp Arg
                405                 410                 415
Ala Leu His Arg Ala Phe Pro Glu His Ala Asp Leu Gly Phe Ala Ser
            420                 425                 430
Ser Val Pro Gln Arg His Gly Pro Val Leu Val Ala His Arg Leu Ala
        435                 440                 445
Tyr Leu Leu Arg Phe Leu Ala His Ala Thr Val Val Glu Pro Gly Trp
    450                 455                 460
Trp Arg Gly Pro Asp Arg Phe Leu Gln Arg Leu Leu Ala Ala Gly Arg
465                 470                 475                 480
Gly Pro Gly Ala Pro Gln Arg Val Ser Arg Leu Gln Pro Leu Ala Leu
                485                 490                 495
Tyr Leu Leu Gln Leu Glu Asp Leu Ala Val Arg Arg Ala Arg Arg Arg
            500                 505                 510
Pro
```

<210> SEQ ID NO 38
<211> LENGTH: 407
<212> TYPE: PRT
<213> ORGANISM: Streptomyces ghanaensis

<400> SEQUENCE: 38

```
Leu Gly Tyr Ile His Thr Ala Leu Lys Ser Ala Gly Phe His His Val
1               5                   10                  15

Ile Gln Val Asp Thr Pro Ala Leu Gly Leu Asp Ser Glu Gly Leu Arg
            20                  25                  30

Lys Leu Leu Ala Asp Phe Glu Pro Asp Leu Val Gly Val Ser Thr Thr
        35                  40                  45

Thr Pro Gly Leu Pro Gly Ala Ile Glu Ala Cys Glu Ala Ala Lys Ser
50                  55                  60

Thr Gly Ala Lys Val Ile Leu Gly Gly Pro His Thr Glu Val Tyr Ala
65                  70                  75                  80

His Glu Asn Leu Val His Glu Ser Ile Asp Tyr Val Gly Val Gly Glu
                85                  90                  95

Gly Val Thr Ile Met Pro Glu Leu Ala Glu Ala Met Glu Arg Gly Glu
            100                 105                 110

Glu Pro Glu Gly Ile Arg Gly Leu Val Thr Arg Lys His Asp Gly Gly
        115                 120                 125

Ala Ala Pro Met Val Asn Leu Glu Glu Val Gly Trp Pro Glu Arg Ala
130                 135                 140

Gly Leu Pro Met Asp Arg Tyr Tyr Ser Ile Met Ala Pro Arg Pro Phe
145                 150                 155                 160

Ala Thr Met Ile Ser Ser Arg Gly Cys Pro Phe Lys Cys Ser Phe Cys
                165                 170                 175

Phe Lys Gln Ala Val Asp Lys Lys Ser Met Tyr Arg Ser Pro Glu Asp
            180                 185                 190

Val Val Gly Glu Met Thr Glu Leu Lys Glu Arg Trp Gly Val Lys Glu
        195                 200                 205

Ile Met Phe Tyr Asp Asp Val Phe Thr Leu His Arg Gly Arg Val Arg
210                 215                 220

Glu Ile Cys Gly Leu Ile Gly Glu Thr Gly Leu Lys Val Arg Trp Glu
225                 230                 235                 240

Ala Pro Thr Arg Val Asp Leu Val Pro Glu Pro Leu Leu Glu Ala Met
                245                 250                 255

Ala Gly Ala Gly Cys Val Arg Leu Arg Phe Gly Ile Glu His Gly Asp
            260                 265                 270

Ser Glu Ile Leu Glu Arg Met Arg Lys Glu Ser Asp Ile Gln Lys Ile
        275                 280                 285

Glu Lys Ala Val Thr Ser Ala His Glu Ala Gly Ile Lys Gly Phe Gly
290                 295                 300

Tyr Phe Ile Val Gly Trp Leu Gly Glu Thr Arg Glu Gln Phe Arg Arg
305                 310                 315                 320

Thr Val Asp Leu Ala Cys Arg Leu Pro Leu Asp Tyr Ala Ser Phe Tyr
                325                 330                 335

Thr Ala Thr Pro Leu Pro Gly Thr Pro Leu His Thr Glu Ser Val Ala
            340                 345                 350

Ala Gly Gln Ile Pro Pro Asp Tyr Trp Asp Arg Phe Ser Cys Gly Ala
        355                 360                 365

Ser Ser Thr Arg Gly Ser Gly Thr Trp Cys Arg Thr Arg Arg Ser Ala
370                 375                 380
```

```
Pro Ser Gly Arg Thr Ala Pro Ser Ser Cys Ala Ala Pro Trp Ser Ser
385                 390                 395                 400

Arg Cys Cys Arg Thr Trp Arg
                405
```

<210> SEQ ID NO 39
<211> LENGTH: 530
<212> TYPE: PRT
<213> ORGANISM: Streptomyces ghanaensis

<400> SEQUENCE: 39

```
Met Lys Val Leu Ser Leu His Ser Ala Gly His Asp Thr Gly Val Ala
1               5                   10                  15

Tyr Phe Glu Asp Gly Arg Leu Val Phe Ala Val Glu Thr Glu Arg Leu
                20                  25                  30

Thr Arg Val Lys His Asp His Arg Ser Asp Val Ala Leu Arg His Val
            35                  40                  45

Leu Glu Gln Glu Cys Val Asp Thr Asp Gly Ile Asp Leu Val Ala Val
50                  55                  60

Ser Thr Pro Val Arg Ser Gly Leu Leu Arg Ile Pro Asp Leu Asp Arg
65                  70                  75                  80

Ala Met Glu Arg Ile Gly Ala Gly Ala Leu His His Arg Thr Val Cys
                85                  90                  95

Glu Met Leu Gly Arg Arg Val Cys Val Val Thr His Glu Val
            100                 105                 110

Ser His Ala Ala Leu Ala Ala His Tyr Ala Asp Trp Glu Glu Gly Thr
            115                 120                 125

Val Val Leu Val Asn Glu Gly Arg Gly Gln Leu Thr Arg Ser Ser Leu
130                 135                 140

Phe Arg Val Thr Gly Gly Ala Leu Glu Trp Val Asp Lys Asp Pro Leu
145                 150                 155                 160

Pro Trp Tyr Gly Asn Gly Phe Gly Trp Thr Ala Ile Gly Tyr Leu Leu
                165                 170                 175

Gly Phe Gly Pro Ser Pro Ser Val Ala Gly Lys Val Met Ala Met Gly
            180                 185                 190

Gly Tyr Gly Gln Pro Asp Pro Arg Ile Arg Glu Gln Leu Leu Ser Val
            195                 200                 205

Asp Pro Glu Val Met Asn Asp Arg Glu Leu Ala Glu Arg Val Arg Ala
210                 215                 220

Asp Leu Ala Gly Arg Pro Glu Phe Ala Pro Gly Phe Glu Thr Ala Ser
225                 230                 235                 240

Gln Val Val Ala Thr Phe Gln Glu Met Phe Thr Glu Ala Val Arg Ala
                245                 250                 255

Val Leu Asp Arg His Val Thr Arg Thr Asp Ala Gly Val Gly Pro Ile
            260                 265                 270

Ala Leu Gly Gly Gly Cys Ala Leu Asn Ile Val Ala Asn Ser Ala Leu
            275                 280                 285

Arg Glu Glu Tyr Gly Arg Asp Val Ala Ile Pro Pro Ala Cys Gly Asp
290                 295                 300

Ala Gly His Leu Thr Gly Ala Gly Leu Tyr Ala Leu Ala Gln Val Ala
305                 310                 315                 320

Gly Val Lys Pro Glu Pro Phe Ser Val Tyr Arg Asn Gly Gly Glu
                325                 330                 335

Ala Arg Ala Ala Val Leu Glu Ala Val Glu Gly Ala Gly Leu Arg Ala
            340                 345                 350
```

```
Val Pro Tyr Asp Arg Ser Ala Val Ala Gly Val Leu Ala Gly Gly Gly
            355                 360                 365

Val Val Ala Leu Thr Gln Gly Ala Ala Glu Leu Gly Pro Arg Ala Leu
    370                 375                 380

Gly His Arg Ser Leu Leu Gly Ser Pro Ala Val Pro Gly Met Arg Glu
385                 390                 395                 400

Arg Met Ser Glu Lys Leu Lys Arg Arg Glu Trp Phe Arg Pro Leu Gly
                405                 410                 415

Ala Val Met Arg Asp Glu Arg Phe Ala Gly Leu Tyr Pro Gly Arg Ala
            420                 425                 430

Pro Ser Pro Tyr Met Leu Phe Glu Tyr Arg Leu Pro Asp Gly Ile Ala
            435                 440                 445

Pro Glu Ala Arg His Val Asn Gly Thr Cys Arg Ile Gln Thr Leu Gly
        450                 455                 460

Pro Glu Glu Asp Arg Leu Tyr Gly Leu Leu Ala Glu Phe Glu Glu Leu
465                 470                 475                 480

Ser Gly Val Pro Ala Leu Ile Asn Thr Ser Leu Asn Gly Pro Gly Lys
                485                 490                 495

Pro Ile Ala His Thr Ala Arg Asp Val Leu Asp Phe Ala Arg Thr
            500                 505                 510

Asp Val Asp Leu Phe Val Phe Asp Asp Leu Met Val Arg Gly Ala Ala
            515                 520                 525

Ala Arg
    530

<210> SEQ ID NO 40
<211> LENGTH: 374
<212> TYPE: PRT
<213> ORGANISM: Streptomyces ghanaensis

<400> SEQUENCE: 40

Met Phe Gly Asp Asn Ser Val Gly Tyr Asp Ala Asn Phe Pro Ala Gly
1               5                   10                  15

Gly Pro Leu Thr Leu Asp Leu Glu Arg Ile Ile Gly Arg Gln Arg Ile
            20                  25                  30

Arg Thr Gly Leu Glu Ser Ser Ala Gly Leu Leu Arg Gly Arg Arg Ile
        35                  40                  45

Leu Val Thr Gly Ala Gly Gly Tyr Ile Gly Ser Glu Leu Cys Arg Gln
    50                  55                  60

Leu Ser Arg Trp Glu Pro Glu Ser Leu Met Met Leu Asp Arg Asn Glu
65                  70                  75                  80

Thr Ala Leu His Leu Ala Ala Thr Ser Ile Gly Asn Val Ser Pro Ser
                85                  90                  95

Val Arg Thr Ser Ile Leu Leu Ala Asp Ile Arg Asp Ser Arg Gly Leu
            100                 105                 110

Ala Arg Leu Phe Gln Gln Cys Arg Pro Asp Thr Val Phe His Ala Ala
        115                 120                 125

Ala Leu Lys Trp Val Pro Ile Leu Glu Lys Phe Pro Gly Glu Ala Val
    130                 135                 140

Lys Thr Asn Val Phe Gly Thr Arg Ala Val Leu Glu Ala Ala Leu Ala
145                 150                 155                 160

Ala Asp Val Ala Phe Leu Val Asn Ile Ser Thr Asp Lys Ala Val Asp
                165                 170                 175

Pro Val Gly Val Leu Gly Tyr Ser Lys Arg Ile Ala Glu Gly Leu Thr
```

```
                    180                 185                 190
Ala Ala Ala Ala Ile Gln Ala Gly Arg Pro Tyr Val Ser Val Arg Phe
            195                 200                 205

Gly Asn Val Leu Gly Cys Gln Gly Ser Phe Leu Asp Val Phe Ala Arg
        210                 215                 220

Gln Ile Ala Ala Gly Arg Pro Val Thr Val Thr His Pro Glu Val Thr
225                 230                 235                 240

Arg Tyr Leu Met Thr Val Gln Glu Ala Val Glu Leu Val Ile Gln Ser
                245                 250                 255

Val Ala Leu Gly Ser Val Gly His Ala Leu Val Leu Asp Met Gly Glu
            260                 265                 270

Gln Val Arg Ile Leu Asp Ile Ala Arg Arg Leu Ile Ala His Ala Gly
        275                 280                 285

Ala Glu Leu Pro Val Arg Tyr Val Gly Leu Arg Pro Gly Glu Lys Leu
    290                 295                 300

Thr Glu Ala Leu Val Ala Pro Ser Glu Ser Pro Val Arg His Gly His
305                 310                 315                 320

Pro Lys Ile Met Glu Val Pro Val Pro Ala Leu Lys Ala Gly Asp Gly
                325                 330                 335

Pro Glu Leu Asp Ala Trp Gly Glu Asp Gln Ala Val Val Ala Ala Leu
            340                 345                 350

Arg Ala Thr Cys Leu Ala Met Ala Gly Asp Asp Pro Val Ala Gln Asp
        355                 360                 365

Pro Gly His Arg Leu Val
    370

<210> SEQ ID NO 41
<211> LENGTH: 282
<212> TYPE: PRT
<213> ORGANISM: Streptomyces ghanaensis

<400> SEQUENCE: 41

Val Arg Val Leu Val Val Gly Gly Ser Gly Phe Leu Gly Tyr Glu Val
1               5                   10                  15

Leu Arg Arg Ala Val Ala Ala Gly Trp Asp Val Ala Ala Thr Tyr Arg
            20                  25                  30

Thr Arg Pro Glu Glu Leu Pro Pro Val Thr Trp Tyr Arg Ala Asp Leu
        35                  40                  45

Arg Asp Pro Gly Arg Met Gly Glu Val Leu Ala Arg Thr Arg Pro Ala
    50                  55                  60

Ala Val Ile Asn Ala Ser Ser Gly His Ala Asp Trp Ala Val Thr Ala
65                  70                  75                  80

Asp Gly Ala Ala Arg Leu Ala Leu Glu Ala Ala Arg Ala Gly Cys Arg
                85                  90                  95

Leu Val His Val Ser Ser Asp Ala Val Phe Ser Gly Ala Asp Val His
            100                 105                 110

Tyr Pro Glu Glu Ala Leu Pro Asp Pro Val Ser Pro Tyr Gly Ala Ala
        115                 120                 125

Lys Ala Ala Ala Glu Thr Ala Val Arg Val Ala Val Pro Glu Ala Ala
    130                 135                 140

Val Val Arg Thr Ser Leu Ile Val Gly His Asn Arg Ser Ala His Glu
145                 150                 155                 160

Glu Ala Val His Ala Leu Ala Ala Gly Arg Arg Ala Gly Val Leu Phe
                165                 170                 175
```

```
Thr Asp Asp Val Arg Cys Pro Val His Val Asp Asp Leu Ala Ser Ala
            180                 185                 190

Leu Leu Glu Ile Ala Ala Ser Asp Gly Ser Gly Val Phe His Val Ala
        195                 200                 205

Gly Pro Asp Ala Met Asn Arg His Asp Leu Gly Val Leu Ile Ala Arg
    210                 215                 220

Arg Asp Gly Leu Asp Pro Ala Arg Leu Pro Ala Gly Leu Arg Ser Glu
225                 230                 235                 240

Val Ala Pro Pro Gly Asn Leu Asp Ile Arg Leu Val Thr Asp Ala Thr
                245                 250                 255

Arg Ala Arg Leu Arg Thr Arg Leu Arg Gly Ala Arg Glu Phe Leu Gly
            260                 265                 270

Pro Gly Val Pro Val Thr Arg Gly Val Arg
        275                 280

<210> SEQ ID NO 42
<211> LENGTH: 340
<212> TYPE: PRT
<213> ORGANISM: Streptomyces ghanaensis

<400> SEQUENCE: 42

Val Ser Ser Asp Thr His Gly Thr Asp Leu Ala Asp Gly Asp Val Leu
1               5                   10                  15

Val Thr Gly Ala Ala Gly Phe Ile Gly Ser His Leu Val Thr Glu Leu
            20                  25                  30

Arg Asn Ser Gly Arg Asn Val Val Ala Val Asp Arg Arg Pro Leu Pro
        35                  40                  45

Asp Asp Leu Glu Ser Thr Ser Pro Pro Phe Thr Gly Ser Leu Arg Glu
    50                  55                  60

Ile Arg Gly Asp Leu Asn Ser Leu Asn Leu Val Asp Cys Leu Lys Asn
65                  70                  75                  80

Ile Ser Thr Val Phe His Leu Ala Ala Leu Pro Gly Val Arg Pro Ser
                85                  90                  95

Trp Thr Gln Phe Pro Glu Tyr Leu Arg Cys Asn Val Leu Ala Thr Gln
            100                 105                 110

Arg Leu Met Glu Ala Cys Val Gln Ala Gly Val Glu Arg Val Val Val
        115                 120                 125

Ala Ser Ser Ser Val Tyr Gly Gly Ala Asp Gly Val Met Ser Glu
    130                 135                 140

Asp Asp Leu Pro Arg Pro Leu Ser Pro Tyr Gly Val Thr Lys Leu Ala
145                 150                 155                 160

Ala Glu Arg Leu Ala Leu Ala Phe Ala Ala Arg Gly Asp Ala Glu Leu
                165                 170                 175

Ser Val Gly Ala Leu Arg Phe Phe Thr Val Tyr Gly Pro Gly Gln Arg
            180                 185                 190

Pro Asp Met Phe Ile Ser Arg Leu Ile Arg Ala Thr Leu Arg Gly Glu
        195                 200                 205

Pro Val Glu Ile Tyr Gly Asp Gly Thr Gln Leu Arg Asp Phe Thr His
    210                 215                 220

Val Ser Asp Val Val Arg Ala Leu Met Leu Thr Ala Ser Val Arg Asp
225                 230                 235                 240

Arg Gly Ser Ala Val Leu Asn Ile Gly Thr Gly Ser Ala Val Ser Val
                245                 250                 255

Asn Glu Val Val Ser Met Thr Ala Glu Leu Thr Gly Leu Arg Pro Cys
            260                 265                 270
```

```
Thr Ala Tyr Gly Ser Ala Arg Ile Gly Asp Val Arg Ser Thr Thr Ala
            275                 280                 285

Asp Val Arg Gln Ala Gln Ser Val Leu Gly Phe Thr Ala Arg Thr Gly
290                 295                 300

Leu Arg Glu Gly Leu Ala Thr Gln Ile Glu Trp Thr Arg Arg Ser Leu
305                 310                 315                 320

Ser Gly Ala Glu Gln Asp Thr Val Pro Val Gly Gly Ser Ser Val Ser
            325                 330                 335

Val Pro Arg Leu
            340

<210> SEQ ID NO 43
<211> LENGTH: 260
<212> TYPE: PRT
<213> ORGANISM: Streptomyces ghanaensis

<400> SEQUENCE: 43

Met Leu Ala Ala Glu Ala Ala Asn Arg Asp His Val Thr Arg Cys Val
1               5                   10                  15

Ala Gln Thr Gly Gly Ser Pro Asp Leu Val Ala His Thr Ala Ala Leu
            20                  25                  30

Arg Leu Tyr Leu Arg Val Pro His Phe Leu Thr Glu Trp Thr Thr Asp
        35                  40                  45

Pro Asp Arg Arg Ala Ala Val Ser Arg Ala Leu Ala Leu Asp Ile Val
50                  55                  60

Ser Met Lys Leu Leu Asp Asp Leu Met Asp Asp Thr Gly Leu Asp
65                  70                  75                  80

Arg Val Glu Leu Ala Cys Val Cys Leu Arg Leu His Leu Arg Ala Leu
                85                  90                  95

His Glu Leu Glu Ser Leu Ala Arg Asp Pro Lys Ala Val Thr Asp Ile
            100                 105                 110

Leu Glu Gln Asp Ala Val His Leu Cys Gly Gly Gln Ile Arg Thr Lys
        115                 120                 125

Arg Ser Arg Ala Thr Asn Leu Arg Glu Trp Arg Ala His Ala Ser Thr
130                 135                 140

Tyr Gly Ser Thr Phe Leu Gly Arg Tyr Gly Ala Leu Ala Ala Ala Cys
145                 150                 155                 160

Gly Gly Glu Gly Gln Pro Ala Asp Ser Val Arg Glu Phe Ala Glu Ala
                165                 170                 175

Phe Ala Met Thr Ile Thr Met Ala Asp Asp Leu Thr Asp Tyr Asp Arg
            180                 185                 190

Asn Gly Glu Arg Asp Gly Asn Leu Ala His Leu Met Arg Thr Gly Ala
        195                 200                 205

Val Ala Gly Gln Asp Val Val Asp Leu Leu Glu Glu Leu Arg Gly Arg
210                 215                 220

Ala Leu Ala Ala Val Ala Ala Pro Pro Gly Ala Pro Gly Leu Val Pro
225                 230                 235                 240

Val Val His Leu Tyr Thr Asp Asp Val Leu Val Arg Leu Leu Pro Arg
                245                 250                 255

His Leu Gly Glu
            260

<210> SEQ ID NO 44
<211> LENGTH: 281
<212> TYPE: PRT
```

<213> ORGANISM: Streptomyces ghanaensis

<400> SEQUENCE: 44

| | | | | | | | | | | | | | | | |
|---|---|---|---|---|---|---|---|---|---|---|---|---|---|---|---|
|Val|Asn|Ala|Ser|Pro|Gln|Leu|Asp|His|His|Thr|Glu|Leu|His|Ala|Ala|
|1| | | |5| | | | |10| | | | |15| |
|Pro|Pro|Leu|Trp|Arg|Pro|Gly|Arg|Val|Leu|Ala|Arg|Leu|Arg|Glu|His|
| | | | |20| | | | |25| | | | |30| |
|Gln|Pro|Gly|Pro|Val|His|Ile|Ile|Asp|Pro|Phe|Lys|Val|Pro|Val|Thr|
| | | |35| | | | |40| | | | |45| | |
|Glu|Ala|Val|Glu|Lys|Ala|Ala|Glu|Leu|Thr|Arg|Leu|Gly|Phe|Ala|Ala|
| |50| | | | |55| | | | |60| | | | |
|Val|Leu|Leu|Ala|Ser|Thr|Asp|Tyr|Glu|Ser|Phe|Glu|Ser|His|Met|Glu|
|65| | | | |70| | | | |75| | | | |80|
|Pro|Tyr|Val|Ala|Ala|Val|Lys|Ala|Ala|Thr|Pro|Leu|Pro|Val|Val|Leu|
| | | | |85| | | | |90| | | | |95| |
|His|Phe|Pro|Pro|Arg|Pro|Gly|Ala|Gly|Phe|Pro|Val|Val|Arg|Gly|Ala|
| | | |100| | | | |105| | | | |110| | |
|Asp|Ala|Leu|Leu|Leu|Pro|Ala|Leu|Leu|Gly|Ser|Gly|Asp|Asp|Tyr|Phe|
| | |115| | | | |120| | | | |125| | | |
|Val|Trp|Lys|Ser|Phe|Leu|Glu|Thr|Leu|Ala|Ala|Phe|Pro|Gly|Arg|Ile|
| |130| | | | |135| | | | |140| | | | |
|Pro|Arg|Glu|Glu|Trp|Pro|Glu|Leu|Leu|Leu|Thr|Val|Ala|Leu|Thr|Phe|
|145| | | | |150| | | | |155| | | | |160|
|Gly|Glu|Asp|Pro|Arg|Thr|Gly|Asp|Leu|Leu|Gly|Thr|Val|Pro|Val|Ser|
| | | | |165| | | | |170| | | | |175| |
|Thr|Ala|Ser|Thr|Glu|Glu|Ile|Asp|Arg|Tyr|Leu|His|Val|Ala|Arg|Ala|
| | | |180| | | | |185| | | | |190| | |
|Phe|Gly|Phe|His|Met|Val|Tyr|Leu|Tyr|Ser|Arg|Asn|Glu|His|Val|Pro|
| | |195| | | | |200| | | | |205| | | |
|Pro|Glu|Val|Val|Arg|His|Phe|Arg|Lys|Gly|Leu|Gly|Pro|Asp|Gln|Val|
| |210| | | | |215| | | | |220| | | | |
|Leu|Phe|Val|Ser|Gly|Asn|Val|Arg|Ser|Gly|Arg|Gln|Val|Thr|Glu|Tyr|
|225| | | | |230| | | | |235| | | | |240|
|Leu|Asp|Ser|Gly|Ala|Asp|Tyr|Val|Gly|Phe|Ala|Gly|Ala|Leu|Glu|Gln|
| | | | |245| | | | |250| | | | |255| |
|Pro|Asp|Trp|Arg|Ser|Ala|Leu|Ala|Glu|Ile|Ala|Gly|Arg|Pro|Ala|
| | | |260| | | | |265| | | | |270| | |
|Ala|Pro|Ala|Arg|Pro|Gly|Ser|Gly|Arg| | | | | | | |
| | |275| | | | |280| | | | | | | | |

<210> SEQ ID NO 45
<211> LENGTH: 223
<212> TYPE: PRT
<213> ORGANISM: Streptomyces ghanaensis

<400> SEQUENCE: 45

| | | | | | | | | | | | | | | | |
|---|---|---|---|---|---|---|---|---|---|---|---|---|---|---|---|
|Met|Gly|His|Ser|Val|Gly|Ala|Arg|Glu|Gly|Tyr|His|Gly|Met|Ser|Glu|
|1| | | |5| | | | |10| | | | |15| |
|Pro|Ala|Asp|Arg|Lys|Ile|Leu|Leu|Gln|Ala|Arg|Gly|Val|Val|Lys|Arg|
| | | |20| | | | |25| | | | |30| | |
|Tyr|Lys|Arg|Arg|Arg|Val|Leu|Thr|Gly|Val|Asp|Leu|Val|His|Ala|
| | | |35| | | | |40| | | | |45| | |
|Gly|Glu|Val|Ala|Ala|Ile|Val|Gly|Ser|Asn|Gly|Thr|Gly|Lys|Ser|Thr|
| |50| | | | |55| | | | |60| | | | |
|Leu|Leu|Lys|Ile|Cys|Ala|Gly|Leu|Leu|Ser|Pro|Asp|Lys|Gly|Arg|Val|

```
                65                  70                  75                  80
Thr Val Ser Gly His Leu Gly Tyr Cys Pro Gln Asn Ala Gly Val Met
                    85                  90                  95
Gly Phe Leu Thr Pro Arg Glu His Phe Thr Leu Phe Gly Thr Gly Arg
                100                 105                 110
Gly Leu Ser Arg Arg Glu Ser Asp Arg Gly Arg Arg Leu Ala Gly
            115                 120                 125
Glu Leu Asp Trp Ala Pro Ala Glu Gly Val Leu Ala Lys Asp Leu Ser
            130                 135                 140
Gly Gly Thr Arg Gln Lys Leu Asn Val Val Leu Ser Ala Leu Gly Asp
145                 150                 155                 160
Pro Asp Leu Leu Leu Leu Asp Glu Pro Tyr Gln Gly Phe Asp His Gly
                165                 170                 175
Ser Tyr Val Asp Phe Trp Gln Ser Val Trp Glu Trp Arg Glu Ala Gly
                180                 185                 190
Lys Ala Val Val Val Val Thr His Met Leu Asn Gln Leu Asp Arg Val
            195                 200                 205
Asp Gln Val Leu Asp Leu Thr Pro Gly Lys Gly Arg Gly Asn Arg
    210                 215                 220

<210> SEQ ID NO 46
<211> LENGTH: 226
<212> TYPE: PRT
<213> ORGANISM: Streptomyces ghanaensis

<400> SEQUENCE: 46

Met Thr Ala Thr Leu Arg Met Ala Glu Met Thr Phe Arg Glu Leu Leu
1               5                   10                  15
Arg Arg Arg Gly Val Leu Gly Leu Leu Leu Val Pro Leu Val Phe
                20                  25                  30
Tyr Leu Gly Arg Tyr Asp Gln Thr Gly Gln Ala Val Arg Phe Ala Ser
                35                  40                  45
Leu Gly Val Gly Phe Ala Val Ser Ala Ala Ala Leu Phe Ser Ala Val
        50                  55                  60
Gly Gly Arg Glu Ile Glu Pro Leu Leu Ala Leu Ser Gly Phe Arg Pro
65                  70                  75                  80
Leu Gln Leu Phe Leu Gly Arg Leu Leu Ala Leu Thr Ala Gly Met
                85                  90                  95
Gly Val Ser Ala Leu Tyr Ala Val Ile Ile Leu Val Gly Gln Asp Val
                100                 105                 110
Ala His Pro Arg Ala Val Ala Val Glu Leu Ala Leu Thr Leu Val
            115                 120                 125
Ala Val Pro Leu Gly Leu Leu Leu Gly Ala Ala Val Pro Arg Asp Met
            130                 135                 140
Glu Gly Ala Leu Leu Leu Ile Ser Val Ile Gly Ala Gln Met Val Met
145                 150                 155                 160
Asp Pro Ala Lys Asp Ser Ala Lys Val Leu Pro Phe Trp Ser Thr Arg
                165                 170                 175
Glu Ile Ile Thr Tyr Ala Val Asp Gly Ala Asp Ser Gly Ser Phe Asp
                180                 185                 190
Ser Gly Val Ala His Ala Val Gly Val Thr Leu Leu Leu Val Ala Val
            195                 200                 205
Ser Gly Cys Val Thr Ala Gly Arg Leu Arg Arg Arg His Leu Gln
    210                 215                 220
```

-continued

Phe Ala
225

<210> SEQ ID NO 47
<211> LENGTH: 591
<212> TYPE: PRT
<213> ORGANISM: Streptomyces ghanaensis

<400> SEQUENCE: 47

Val Leu Arg Gly Ser Ala Arg Thr Tyr Trp Thr Leu Thr Gly Leu Trp
1               5                   10                  15

Val Leu Leu Arg Ala Gly Thr Leu Val Val Gly Leu Leu Phe Gln Arg
                20                  25                  30

Leu Phe Asp Ala Leu Gly Ala Gly Gly Val Trp Leu Ile Ile Ala
            35                  40                  45

Leu Val Ala Ala Ile Glu Ala Gly Arg Leu Phe Leu Gln Phe Gly Val
    50                  55                  60

Met Ile Asn Arg Leu Glu Pro Arg Val Gln Tyr Gly Thr Thr Ala Arg
65                  70                  75                  80

Leu Arg His Ala Leu Leu Gly Ser Ala Leu Arg Gly Ser Glu Val Thr
                85                  90                  95

Ala Arg Thr Ser Pro Gly Glu Ser Leu Arg Thr Val Gly Glu Asp Val
                100                 105                 110

Asp Glu Thr Gly Phe Phe Val Ala Trp Ala Pro Thr Asn Leu Ala His
            115                 120                 125

Trp Leu Phe Val Ala Ala Ser Val Thr Val Met Met Arg Ile Asp Ala
    130                 135                 140

Val Val Thr Gly Ala Leu Leu Ala Leu Leu Val Leu Leu Thr Leu Val
145                 150                 155                 160

Thr Ala Leu Ala His Ser Arg Phe Leu Arg His Arg Arg Ala Thr Arg
                165                 170                 175

Ala Ala Ser Gly Glu Val Ala Gly Ala Leu Arg Glu Met Val Gly Ala
                180                 185                 190

Val Gly Ala Val Gln Ala Ala Ala Ala Glu Pro Gln Val Ala Ala His
            195                 200                 205

Val Ala Gly Leu Asn Gly Ala Arg Ala Glu Ala Ala Val Arg Glu Glu
    210                 215                 220

Leu Tyr Ala Val Val Gln Arg Thr Val Ile Gly Asn Pro Ala Pro Ile
225                 230                 235                 240

Gly Val Gly Val Val Leu Leu Leu Val Ala Gly Arg Met Asp Glu Gly
                245                 250                 255

Thr Phe Ser Val Gly Asp Leu Ala Leu Phe Ala Phe Tyr Leu Gln Ile
            260                 265                 270

Leu Thr Glu Ala Leu Gly Ser Ile Gly Met Leu Ser Val Arg Leu Gln
    275                 280                 285

Arg Val Ser Val Ala Leu Gly Arg Ile Thr Asn Asn Leu Gly Cys Arg
290                 295                 300

Leu Arg Arg Ser Leu Glu Arg Ala Ser Pro Ile Ala Ser Asp Ala
305                 310                 315                 320

Pro Gly Gly Thr Gly Glu Gly Ala Ala Pro Asp Ala Gly Pro Glu
                325                 330                 335

Pro Ala Pro Pro Leu Arg Glu Leu Ala Val Arg Gly Leu Thr Ala Arg
            340                 345                 350

His Pro Gly Ala Gly His Gly Ile Glu Asp Val Asp Leu Val Val Glu
    355                 360                 365

Arg His Thr Val Thr Val Thr Gly Arg Val Gly Ser Gly Lys Ser
    370             375             380

Thr Leu Val Arg Ala Val Leu Gly Leu Leu Pro His Glu Arg Gly Thr
385             390             395             400

Val Leu Trp Asn Gly Glu Pro Ile Ala Asp Pro Ala Ser Phe Leu Val
            405             410             415

Ala Pro Arg Cys Gly Tyr Thr Pro Gln Val Pro Cys Leu Phe Ser Gly
            420             425             430

Thr Val Arg Glu Asn Val Leu Leu Gly Arg Asp Gly Ala Ala Phe Asp
            435             440             445

Glu Ala Val Arg Leu Ala Val Ala Glu Pro Asp Leu Ala Ala Met Gln
450             455             460

Asp Gly Pro Asp Thr Val Val Gly Pro Arg Gly Leu Arg Leu Ser Gly
465             470             475             480

Gly Gln Ile Gln Arg Val Ala Ile Ala Arg Met Leu Val Gly Asp Pro
            485             490             495

Glu Leu Val Val Leu Asp Asp Val Ser Ser Ala Leu Asp Pro Glu Thr
            500             505             510

Glu His Leu Leu Trp Glu Arg Leu Leu Asp Gly Thr Arg Thr Val Leu
            515             520             525

Ala Val Ser His Arg Pro Ala Leu Leu Arg Ala Ala Asp Arg Val Val
            530             535             540

Val Leu Glu Gly Gly Arg Val Glu Ala Ser Gly Thr Phe Glu Glu Val
545             550             555             560

Met Ala Val Ser Ala Glu Met Gly Arg Ile Trp Thr Gly Ala Gly Pro
            565             570             575

Gly Gly Gly Asp Ala Gly Pro Ala Pro Gln Ser Pro Ala Gly
            580             585             590

<210> SEQ ID NO 48
<211> LENGTH: 564
<212> TYPE: PRT
<213> ORGANISM: Streptomyces ghanaensis

<400> SEQUENCE: 48

Leu Arg Gly Glu Arg Thr Ala Val Ala Leu Leu Ala Leu Leu Val Pro
1               5               10              15

Ala Gly Met Gly Leu Gln Leu Val Ala Pro Tyr Leu Leu Arg Gly Phe
            20              25              30

Ile Asp Gly Ala Leu Ser Gly Asp Ser Arg Lys Thr Leu Leu Asp Leu
            35              40              45

Ala Ala Trp Ser Leu Ala Ala Val Gly Thr Leu Val Val Thr Ala
50              55              60

Gly Thr Glu Ala Leu Ser Ser Arg Val Ala Trp Arg Ser Thr Asn Arg
65              70              75              80

Leu Arg Ala Asp Leu Val Glu His Cys Leu Ser Arg Pro Pro Gly Phe
            85              90              95

Tyr Arg Lys His Pro Pro Gly Glu Leu Val Glu Arg Met Asp Gly Asp
            100             105             110

Val Thr Arg Leu Ala Ala Val Met Ser Thr Leu Leu Glu Leu Leu
            115             120             125

Ala Gln Ala Leu Leu Ile Val Gly Ile Leu Val Ala Leu Phe Arg Leu
130             135             140

Glu Trp Arg Leu Ala Leu Val Val Ala Pro Phe Ala Ala Gly Thr Leu

```
            145                 150                 155                 160
Leu Leu Leu Arg Thr Leu Val Gly Arg Ala Met Pro Phe Val Thr Ala
                165                 170                 175
Arg Gln Arg Val Ala Ala Asp Leu Gln Gly Phe Leu Glu Glu Arg Leu
                180                 185                 190
Ala Ala Ala Glu Asp Leu Arg Val Asn Gly Ala Ser Arg Tyr Thr Leu
                195                 200                 205
Arg Glu Leu Gly Asp Arg Gln Asp Asp Leu Tyr Arg Lys Ala Arg Asp
        210                 215                 220
Ala Ala Arg Ala Ser Val Arg Trp Pro Ala Thr Val Gln Gly Leu Ser
225                 230                 235                 240
Ala Val Ser Val Val Leu Ala Leu Ala Val Ser Ala Trp Leu His Ala
                245                 250                 255
Arg Gly Gln Leu Ser Thr Gly Thr Ala Phe Ala Ser Leu Ser Tyr Ala
                260                 265                 270
Met Leu Leu Arg Arg Pro Leu Leu Ala Val Thr Thr Arg Phe Arg Glu
                275                 280                 285
Leu Glu Asp Ala Ala Ala Ser Ala Gln Arg Leu Arg Asp Leu Leu Gly
        290                 295                 300
His Gly Thr Ala Ala Pro Arg Thr Gly Arg Gly Thr Leu Pro Ala Gly
305                 310                 315                 320
Leu Pro Gly Val Arg Phe Asp Gly Val Ser Phe Gly Tyr Glu Pro Asp
                325                 330                 335
Glu Pro Val Leu Arg Asp Val Ser Phe Thr Leu Arg Pro Gly Glu Arg
                340                 345                 350
Leu Gly Val Val Gly Arg Thr Gly Ser Gly Lys Ser Thr Val Val Arg
                355                 360                 365
Leu Leu Phe Gly Leu His His Pro Gly Ala Gly Ser Val Ser Ala Gly
        370                 375                 380
Gly Leu Asp Leu Thr Glu Ile Asp Pro Arg Ala Leu Arg Ser Arg Val
385                 390                 395                 400
Ala Leu Val Thr Gln Glu Val His Val Phe His Ala Ser Leu Arg Asp
                405                 410                 415
Asn Leu Thr Phe Phe Asp Arg Ser Val Pro Asp Asp Arg Leu Arg Ala
                420                 425                 430
Ala Leu Gly Glu Ala Gly Leu Gly Pro Trp Leu Arg Thr Leu Pro Asp
                435                 440                 445
Gly Leu Asp Thr Pro Leu Gly Ala Gly Ala Arg Gly Met Ser Ala Gly
        450                 455                 460
Glu Gln Gln Gln Leu Ala Leu Ala Arg Val Phe Leu Arg Asp Pro Gly
465                 470                 475                 480
Leu Val Leu Met Asp Glu Pro Thr Ala Arg Leu Asp Pro Tyr Ser Glu
                485                 490                 495
Arg Leu Leu Met Pro Ala Leu Glu Arg Leu Leu Glu Gly Arg Thr Ala
                500                 505                 510
Val Val Val Glu His Arg Pro His Leu Leu Arg Asn Val Asp Arg Ile
                515                 520                 525
Leu Val Leu Glu Glu Gly Lys Val Ala Glu Gly Glu Arg Arg Val
        530                 535                 540
Leu Ala Ala Asp Pro Gly Ser Arg Phe His Ala Leu Leu Arg Thr Ala
545                 550                 555                 560
Gly Ala Thr Arg
```

```
<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaaaagcttg acgacttggc cttggtgctg t                                  31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaagaattcc gtttcagtac cttgccgctc g                                  31

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aaaaagcttg accgggaact cgccgag                                       27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaagaattcg tcgtagggaa cggcccg                                       27

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aaaaagcttg acctgacact cgtcggcttc                                    30

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaagaattct cgagacgagg agcccgtac                                     29
```

-continued

```
<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaaaagcttg ttctgcgacg cggacgac                                        28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aaagaattca ggttcggaac gtgcagca                                        28

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aagaattcta gatcgagtgg gctccctact c                                    31

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaagaattca cctgggggag tgaccgac                                        28

<210> SEQ ID NO 59
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcagtgcgac gcgagcgcac gagcagacgt cgtcatgtgt aggctggagc tgcttc        56

<210> SEQ ID NO 60
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcggggtgac ctcgtgtgtc agcgcccggc ggccgctcca tatgaatatc ctccttag      58

<210> SEQ ID NO 61
```

```
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgaggagccc gccgcgggag cggccgccgg gcgctgacag tgtaggctgg agctgcttc      59

<210> SEQ ID NO 62
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gccgaggtgc cgtccacgcc gttcccctc cgtcggctac atatgaatat cctccttag      59

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgaggggga cttccgcag                                                  19

<210> SEQ ID NO 64
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgtgcgcagc gcggtcttcg gcttcgacgg ggtacggatg aatatcctcc ttagttc       57

<210> SEQ ID NO 65
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agacgcgccg ggcggccccc agttcggacc agatgccgta ggctggagct gcttcg        56

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
catatgaata tcctccttag ttc                                             23

<210> SEQ ID NO 67
<211> LENGTH: 27
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aaatctagat caagagcggc cggggtc                                           27

<210> SEQ ID NO 68
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggctcctcg gtgtccgtgc cgcggctgta ggcggcatgt aggctggagc tgcttc          56

<210> SEQ ID NO 69
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tggacgagcg gtcggtcggg ggcagccatg ggtctcctac atatgaatct ccttagttc       59

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtctcggtca acgaagtggt c                                                 21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctctccaggg agatggtccg                                                   20

<210> SEQ ID NO 72
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgcacagcct gtaccggtcg acctccaaca ccgaccgtgt aggctggagc tgctt           55

<210> SEQ ID NO 73
<211> LENGTH: 59
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 73
tcagctctcc tgacgcgtgg gtgaggacga cggagtgagc atatgaatct ccttagttc    59

<210> SEQ ID NO 74
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tccagaagcg ggccggcgtg ctgccgcacc tcggggctgt aggctggagc tgcttcg      57

<210> SEQ ID NO 75
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgtgcaggcc gtccagcgtg ttgcgccact ggccggtcat atgaatatcc tccttag      57

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aaaaagcttg ttctgcgacg cggacgac                                      28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aaagaattca ggttcggaac gtgcagca                                      28

<210> SEQ ID NO 78
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aggccgccct ccagcccctg ctggacgccc gatgacggtg taggctggag ctgcttc      57

<210> SEQ ID NO 79
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tctcgtgaag tggggggtctg cggcggtccg gccccgctac atatgaatat cctccttag    59

<210> SEQ ID NO 80
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccggccacgg ccctgccggc ggactacacg gagaccatgt aggctggagc tgcttcg      57

<210> SEQ ID NO 81
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggacggccgg ccggagacgc tccggccggc cgtcggtcat atgaatatcc tccttag      57

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aaacaattgt tctgcgacgc ggacgac                                       27

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aaatctagag gactctgcac cctgac                                        26

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aaatctagac gcgatgaacc gtcacg                                        26

<210> SEQ ID NO 85
<211> LENGTH: 28
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 85
aaatctagac gtgcccttcg acgacccg                                            28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aaagaattcc cacgccctgg tcctggac                                            28

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aaatctagac aggtcaccga gtacctcga                                           29

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
aaagaattcc gctgatcaac acgtcgctc                                           29

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aaatctagac acccagatcg agtggacc                                            28

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
aaagaattca tgggtctcct aggagag                                             27

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 91
aaatctagag taccgctcct tcttcatgc                                                      29

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aaagaattca gtggagcgac agtaccttc                                                      29

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aaatctagac tggaccagga cgcggtg                                                        27

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aaagaattcg ctgatgtctc gtgaagtgg                                                  29

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aaatctagag ggaccggact cggacgt                                                    27

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aaagaattcg gtgacctcgt gtgtcagc                                              28

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 97
aaatctagaa gggcctgcac ttcacct                                              27

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aaagaattcg ccgtccggat cgacca                                               26

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
aaatctagat ccagcgtgtt gcgc                                                 24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aaagaattca cgagacatca gccg                                                 24

<210> SEQ ID NO 101
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aaaaagcttc ggggcgtgcc ttcttc                                               26

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aaatctagac cgcccgctcc ccggac                                               26

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 103
aaaaagcttg acgtgaggcc gtgcagttc                                            29

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
aaacaattgg cacatcttga cgtggacgg                                            29

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aaaaagcttc cgcccgctcc ccggac                                               26

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
aaacatatgc tcgcccggct gcgc                                                 24

<210> SEQ ID NO 107
<211> LENGTH: 392
<212> TYPE: PRT
<213> ORGANISM: Streptomyces ghanaensis

<400> SEQUENCE: 107

Ile Ser Ser Ser Met Asp Phe Phe Val Arg Leu Ala Arg Glu Thr Gly
1               5                   10                  15

Asp Arg Lys Arg Glu Phe Leu Glu Leu Gly Arg Lys Ala Gly Arg Phe
            20                  25                  30

Pro Ala Ala Ser Thr Ser Asn Gly Glu Ile Ser Ile Trp Cys Ser Asn
        35                  40                  45

Asp Tyr Leu Gly Met Gly Gln His Pro Asp Val Leu Asp Ala Met Lys
    50                  55                  60

Arg Ser Val Asp Glu Tyr Gly Gly Gly Ser Gly Ser Arg Asn Thr
65                  70                  75                  80

Gly Gly Thr Asn His Phe His Val Ala Leu Glu Arg Glu Pro Ala Glu
                85                  90                  95

Pro His Gly Lys Glu Asp Ala Val Leu Phe Thr Ser Gly Tyr Ser Ala
            100                 105                 110

Asn Glu Gly Ser Leu Ser Val Leu Ala Gly Ala Val Asp Asp Cys Gln
        115                 120                 125

Val Phe Ser Asp Ser Ala Asn His Ala Ser Ile Ile Asp Gly Leu Arg
    130                 135                 140

His Ser Gly Ala Arg Lys His Val Phe Arg His Lys Asp Gly Arg His

```
                145                 150                 155                 160
Leu Glu Glu Leu Leu Ala Ala Asp Arg Asp Lys Pro Lys Phe Ile
                165                 170                 175

Ala Leu Glu Ser Val His Ser Met Arg Gly Asp Ile Ala Leu Leu Ala
            180                 185                 190

Glu Ile Ala Gly Leu Ala Lys Arg Tyr Gly Ala Val Thr Phe Leu Asp
            195                 200                 205

Glu Val His Ala Val Gly Met Tyr Gly Pro Gly Gly Ala Gly Ile Ala
        210                 215                 220

Ala Arg Asp Gly Val His Cys Glu Phe Thr Val Val Met Gly Thr Leu
225                 230                 235                 240

Ala Lys Ala Phe Gly Met Thr Gly Gly Tyr Val Ala Gly Pro Ala Val
                245                 250                 255

Leu Met Asp Ala Val Arg Ala Arg Ala Arg Ser Phe Val Phe Thr Thr
            260                 265                 270

Ala Leu Pro Pro Ala Val Ala Ala Gly Ala Leu Ala Ala Val Arg His
        275                 280                 285

Leu Arg Gly Ser Asp Glu Glu Arg Arg Pro Ala Glu Asn Ala Arg
    290                 295                 300

Leu Thr His Gly Leu Leu Arg Glu Arg Asp Ile Pro Val Leu Ser Asp
305                 310                 315                 320

Arg Ser Pro Ile Val Pro Val Leu Val Gly Glu Asp Arg Met Cys Lys
                325                 330                 335

Arg Met Ser Ala Leu Pro Leu Glu Arg His Gly Ala Tyr Val Gln Ala
            340                 345                 350

Ile Asp Ala Pro Ser Val Pro Ala Gly Glu Glu Ile Leu Arg Ile Ala
        355                 360                 365

Pro Ser Ala Val His Glu Thr Glu Glu Ile His Arg Phe Val Asp Ala
    370                 375                 380

Leu Asp Gly Ile Trp Ser Glu Leu
385                 390

<210> SEQ ID NO 108
<211> LENGTH: 398
<212> TYPE: PRT
<213> ORGANISM: Streptomyces nodosus

<400> SEQUENCE: 108

Met Asn Lys His Leu Asp Phe Phe Ala Arg Glu Met Glu Glu Phe Gly
1               5                   10                  15

Ala Arg Arg Arg Glu Phe Leu Glu Ile Gly Arg Arg Ala Gly Arg Phe
            20                  25                  30

Pro Ser Ala Val Ala Arg Gln Gly Gln Asp Gly Thr Asp Val Glu Ile
        35                  40                  45

Ser Val Trp Cys Ser Asn Asp Tyr Leu Gly Met Gly Gln Asn Pro Phe
    50                  55                  60

Val Leu Glu Ala Val Lys Asn Ala Val Asp Ala Phe Gly Ala Gly Ser
65                  70                  75                  80

Gly Gly Ser Arg Asn Ile Gly Gly Thr Asn His Tyr His Val Leu Leu
                85                  90                  95

Glu Asn Glu Leu Ala Ala Leu His Gly Lys Glu Glu Ala Leu Ile Phe
            100                 105                 110

Pro Ser Gly Phe Thr Ala Asn Asp Gly Ala Leu Thr Val Leu Ala Gly
        115                 120                 125
```

Arg Ala Pro Gly Thr Leu Val Phe Ser Asp Glu Leu Asn His Ala Ser
            130                 135                 140

Ile Ile Asp Gly Leu Arg His Ser Gly Ala Glu Lys Arg Ile Phe Arg
145                 150                 155                 160

His Asn Asp Met Ala His Leu Glu Glu Leu Leu Ala Ala Ala Asp Pro
                165                 170                 175

Glu Arg Pro Lys Leu Ile Val Leu Glu Ser Val Tyr Ser Met Ser Gly
            180                 185                 190

Asp Ile Ala Pro Leu Ala Glu Thr Ala Ala Leu Ala Arg Arg His Gly
            195                 200                 205

Ala Thr Thr Phe Ile Asp Glu Val His Ala Val Gly Met Tyr Gly Pro
210                 215                 220

Gln Gly Ala Gly Ile Ala Ala Arg Glu Gly Ile Ala Asp Glu Phe Thr
225                 230                 235                 240

Val Val Met Gly Thr Leu Ala Lys Gly Phe Gly Thr Ala Gly Gly Tyr
                245                 250                 255

Ile Ala Gly Pro Ala Ala Leu Ile Asp Ala Val Arg Asn Phe Ser Arg
            260                 265                 270

Gly Phe Ile Phe Thr Thr Ser Ile Pro Pro Ala Thr Ala Ala Gly Ala
            275                 280                 285

Leu Ala Ala Val Gln His Leu Arg Ala Ser Glu Gly Glu Arg Thr Arg
290                 295                 300

Leu Ala Ala Asn Ala Gly Leu Leu His Arg Leu Leu Lys Glu Arg Asp
305                 310                 315                 320

Ile Pro Phe Val Ser Asp Gln Ser His Ile Val Ser Val Phe Val Gly
                325                 330                 335

Asp Asp Gly Leu Cys Arg Gln Ala Ser Ala Leu Leu Leu Glu Arg His
            340                 345                 350

Gly Ile Tyr Val Gln Pro Ile Asn Ala Pro Ser Val Arg Ala Gly Glu
            355                 360                 365

Glu Ile Leu Arg Val Ala Pro Ser Ala Thr His Thr Thr Gly Asp Val
370                 375                 380

Glu Lys Phe Ala Glu Ala Val Glu Gly Ile Trp Arg Asp Leu
385                 390                 395

<210> SEQ ID NO 109
<211> LENGTH: 175
<212> TYPE: PRT
<213> ORGANISM: Streptomyces ghanaensis

<400> SEQUENCE: 109

Gly Val Glu Val Ala Thr Ala Pro Val Arg Gly Gly Arg Arg
1               5                   10                  15

Ala Ala Pro Ser Gly Glu Val Gly Glu Ile Val Arg Gly His Asn
            20                  25                  30

Leu Met Ala Gly Tyr Val Asp Ala Pro Arg Ala Thr Ala Ala Phe
                35                  40                  45

Val Asp Gly Trp Phe Arg Thr Gly Asp Leu Gly Leu Leu Asp Glu Glu
50                  55                  60

Gly Tyr Pro Thr Ala Val Asp Arg Glu Lys Asp Val Ile Leu Arg Gly
65                  70                  75                  80

Gly Tyr Asp Val His Pro Arg Glu Val Glu Ala Leu Leu Arg His
                85                  90                  95

Pro Ala Val Ala Arg Val Ala Val Val Gly Leu Pro Asp Pro Val Tyr
            100                 105                 110

Gly Gln Glu Val Cys Ala Val Val Pro Arg Asp Gly Pro Thr Pro
            115                 120                 125

Asp Gly Ala Leu Ala Asp Ser Val Val Ala Trp Gly Glu Arg His Ile
130                 135                 140

Ala Ala Tyr Arg Arg Pro Arg Arg Val Val Leu Pro Asp Arg Leu Pro
145                 150                 155                 160

Leu Gly Pro Gly Gly Lys Val Leu Lys Gly Glu Pro Ala Val Arg
                165                 170                 175

<210> SEQ ID NO 110
<211> LENGTH: 175
<212> TYPE: PRT
<213> ORGANISM: Streptomyces aizunensis

<400> SEQUENCE: 110

Gly Val Arg Val Ala Ile Ala Asp Ala Glu Leu Glu Gly Arg Ile Arg
1               5                   10                  15

Leu Leu Lys Gln Gly Asp Ile Gly Glu Ile Val Val Ser Gly His Asn
            20                  25                  30

Val Met Ala Gly Tyr Leu Gly Arg Pro Gln Glu Thr Ala Glu Val Leu
        35                  40                  45

Val Asp Gly Trp Phe Arg Thr Gly Asp Met Gly Val Gln Asp Glu Asp
50                  55                  60

Gly Tyr Leu Ser Ile Val Asp Arg Lys Lys Asp Met Ile Val Arg Gly
65                  70                  75                  80

Gly Tyr Asn Val Tyr Pro Arg Glu Val Glu Asp Val Leu Leu Arg His
                85                  90                  95

Pro Ala Val Asp Gly Ala Cys Val Val Gly Val Pro Ser Val Lys His
            100                 105                 110

Gly Glu Glu Val Cys Ala Val Val Arg Val Lys Pro Gly Gln Arg Ala
            115                 120                 125

Ser Gly Leu Leu Ala Glu Glu Ile Val Ala Trp Ser Arg Val His Met
130                 135                 140

Ala Ala Tyr Lys Tyr Pro Arg Arg Val Glu Phe Val Glu Thr Phe Pro
145                 150                 155                 160

Leu Gly Ser Ser Gly Lys Val Leu Lys Arg Glu Leu Ala His Arg
                165                 170                 175

<210> SEQ ID NO 111
<211> LENGTH: 401
<212> TYPE: PRT
<213> ORGANISM: Streptomyces ghanaensis

<400> SEQUENCE: 111

Gln Tyr Leu Asp Leu Phe Ala Arg Leu Thr Glu Asn Ser Asp Gly Gly
1               5                   10                  15

Lys Arg Glu Phe Leu Glu Ile Gly Arg Leu Ala Gly Ser Phe Pro Ala
            20                  25                  30

Ala Ser Val Arg Ser Ser Gly Pro Val Thr Gly Arg Asp Ser Ile Ser
        35                  40                  45

Val Trp Cys Ser Asn Asp Tyr Leu Gly Met Gly Gln His Pro Ala Val
50                  55                  60

Leu Lys Ala Met Lys Asp Ala Ile Asp Glu Tyr Gly Ala Gly Ala Gly
65                  70                  75                  80

Gly Ser Arg Asn Ile Gly Gly Thr Asn His Tyr His Val Leu Leu Glu
                85                  90                  95

Arg Glu Leu Ala Ala Leu His Gly Lys Asp Glu Ala Leu Leu Phe Thr
            100                 105                 110

Ser Gly Tyr Thr Ala Asn Asp Gly Ala Leu Ser Val Ile Ala Gly Arg
            115                 120                 125

Met Glu Lys Cys Val Val Phe Ser Asp Ala Leu Asn His Ala Ser Ile
130                 135                 140

Ile Asp Gly Leu Arg His Ser Arg Ala Gln Lys Gln Ile Phe Arg His
145                 150                 155                 160

Asn Asp Pro Ala His Leu Glu Glu Leu Ile Ala Ala Asp Pro Asp
                165                 170                 175

Val Pro Lys Leu Ile Val Ala Glu Ser Val Tyr Ser Met Asn Gly Asp
            180                 185                 190

Ile Ala Pro Leu Ser Glu Ile Ala Asp Ile Ala Lys Arg His Gly Ala
            195                 200                 205

Met Thr Tyr Leu Asp Glu Val His Ala Val Gly Met Tyr Gly Pro Glu
210                 215                 220

Gly Ala Gly Ile Ala Ala Arg Glu Gly Ile Ala Asp Asp Phe Thr Val
225                 230                 235                 240

Ile Met Gly Thr Leu Ala Lys Gly Phe Gly Thr Thr Gly Gly Tyr Ile
            245                 250                 255

Ala Gly Pro Ala Glu Ile Ile Glu Ala Val Arg Met Phe Ser Arg Ser
            260                 265                 270

Phe Val Phe Thr Thr Ala Leu Ala Pro Ala Val Ala Ala Gly Ala Leu
            275                 280                 285

Ala Ala Val His His Leu Arg Ser Ser Glu Val Glu Arg Glu Gln Leu
            290                 295                 300

Trp Ser Asn Ala Gln Leu Met His Arg Leu Leu Asn Glu Arg Gly Ile
305                 310                 315                 320

Pro Phe Ile Ser Asp Gln Thr His Ile Val Ser Val Met Val Gly Asp
            325                 330                 335

Glu Ala Val Cys Lys Arg Met Ser Ala Leu Leu Leu Asp Arg His Gly
            340                 345                 350

Ile Tyr Val Gln Ala Ile Asn Ala Pro Ser Val Arg Val Gly Glu Glu
            355                 360                 365

Ile Leu Arg Val Ala Pro Gly Ala Val His Thr Ala Asp Asp Val Arg
370                 375                 380

Glu Phe Val Asp Ala Leu Ser Gln Val Trp Glu Val Gly Ser Ala
385                 390                 395                 400

Arg

<210> SEQ ID NO 112
<211> LENGTH: 400
<212> TYPE: PRT
<213> ORGANISM: Streptomyces nodosus

<400> SEQUENCE: 112

Lys His Leu Asp Phe Phe Ala Arg Glu Met Glu Glu Phe Gly Ala Arg
1               5                   10                  15

Arg Arg Glu Phe Leu Glu Ile Gly Arg Arg Ala Gly Arg Phe Pro Ser
            20                  25                  30

Ala Val Ala Arg Gln Gly Gln Asp Gly Thr Asp Val Glu Ile Ser Val
            35                  40                  45

Trp Cys Ser Asn Asp Tyr Leu Gly Met Gly Gln Asn Pro Phe Val Leu
50                  55                  60

Glu Ala Val Lys Asn Ala Val Asp Ala Phe Gly Ala Gly Ser Gly Gly
65                  70                  75                  80

Ser Arg Asn Ile Gly Gly Thr Asn His Tyr His Val Leu Leu Glu Asn
                85                  90                  95

Glu Leu Ala Ala Leu His Gly Lys Glu Ala Leu Ile Phe Pro Ser
            100                 105                 110

Gly Phe Thr Ala Asn Asp Gly Ala Leu Thr Val Leu Ala Gly Arg Ala
            115                 120                 125

Pro Gly Thr Leu Val Phe Ser Asp Glu Leu Asn His Ala Ser Ile Ile
            130                 135                 140

Asp Gly Leu Arg His Ser Gly Ala Glu Lys Arg Ile Phe Arg His Asn
145                 150                 155                 160

Asp Met Ala His Leu Glu Glu Leu Leu Ala Ala Asp Pro Glu Arg
                165                 170                 175

Pro Lys Leu Ile Val Leu Glu Ser Val Tyr Ser Met Ser Gly Asp Ile
            180                 185                 190

Ala Pro Leu Ala Glu Thr Ala Ala Leu Ala Arg Arg His Gly Ala Thr
            195                 200                 205

Thr Phe Ile Asp Glu Val His Ala Val Gly Met Tyr Gly Pro Gln Gly
            210                 215                 220

Ala Gly Ile Ala Ala Arg Glu Gly Ile Ala Asp Glu Phe Thr Val Val
225                 230                 235                 240

Met Gly Thr Leu Ala Lys Gly Phe Gly Thr Ala Gly Gly Tyr Ile Ala
            245                 250                 255

Gly Pro Ala Ala Leu Ile Asp Ala Val Arg Asn Phe Ser Arg Gly Phe
            260                 265                 270

Ile Phe Thr Thr Ser Ile Pro Pro Ala Thr Ala Gly Ala Leu Ala
            275                 280                 285

Ala Val Gln His Leu Arg Ala Ser Glu Gly Glu Arg Thr Arg Leu Ala
            290                 295                 300

Ala Asn Ala Gly Leu Leu His Arg Leu Leu Lys Glu Arg Asp Ile Pro
305                 310                 315                 320

Phe Val Ser Asp Gln Ser His Ile Val Ser Val Phe Val Gly Asp Asp
                325                 330                 335

Gly Leu Cys Arg Gln Ala Ser Ala Leu Leu Leu Glu Arg His Gly Ile
            340                 345                 350

Tyr Val Gln Pro Ile Asn Ala Pro Ser Val Arg Ala Gly Glu Glu Ile
            355                 360                 365

Leu Arg Val Ala Pro Ser Ala Thr His Thr Thr Gly Asp Val Glu Lys
            370                 375                 380

Phe Ala Glu Ala Val Glu Gly Ile Trp Arg Asp Leu Gly Ile Pro Arg
385                 390                 395                 400

<210> SEQ ID NO 113
<211> LENGTH: 513
<212> TYPE: PRT
<213> ORGANISM: Streptomyces ghanaensis

<400> SEQUENCE: 113

Met Thr Leu Thr Ala Ala Ser Val Leu Ala Glu Ser Ala Gly Arg Arg
1               5                   10                  15

Pro Asp His Pro Ala Leu Val Phe Gly Ser Glu Arg Ile Thr Tyr Ala
            20                  25                  30

Glu Leu Trp Leu Ala Thr Arg Arg Tyr Ala Ala Val Leu Arg Asp Arg

```
                35                  40                  45
Gly Val Arg Pro Gly Asp Arg Ile Ala Leu Leu Pro Asn Thr Pro
 50                  55                  60
His Phe Pro Met Val Tyr Tyr Gly Val Leu Ala Leu Gly Ala Val Val
 65                      70                  75                  80
Val Pro Val His Gly Leu Leu Arg Ala Asp Glu Ile Val His Val Leu
                 85                  90                  95
Gly Asp Ser Glu Ala Lys Ala Met Val Cys Ala Ala Pro Met Leu Thr
                100                 105                 110
Glu Gly Ala Lys Ala Ala Gly Thr Ala Gly Val Pro Leu Leu Thr Val
                115                 120                 125
Met Val Glu Asn Gly Glu Asp Asp Gly Pro Ala Arg Leu Asp Val
130                 135                 140
Leu Ala Glu Arg Ala Glu Pro Leu Asp Gly Leu Val Pro Arg Ala Pro
145                 150                 155                 160
Asp Asp Leu Ala Leu Val Leu Tyr Thr Ser Gly Thr Thr Gly Arg Pro
                165                 170                 175
Lys Gly Ala Met Ile Thr His Leu Asn Leu Val Met Asn Val Ser Thr
                180                 185                 190
Thr Met Arg Ser Pro Phe Asp Leu Gly Pro Glu Asp Val Leu Leu Gly
                195                 200                 205
Cys Leu Pro Leu Phe His Thr Phe Gly Gln Thr Cys Gly Met Ser Ala
                210                 215                 220
Cys Phe Leu Ala Gly Gly Thr Leu Val Leu Met Asn Arg Phe Asp Gly
225                 230                 235                 240
Pro Gly Ala Leu Asp Leu Met Val Thr Glu Gly Cys Thr Val Phe Met
                245                 250                 255
Gly Val Pro Thr Met Tyr Leu Ala Leu Leu Asp Ala Ala His Asp
                260                 265                 270
Ala Arg Arg Pro Val Leu Asp Arg Ala Phe Ser Gly Gly Ser Ala Leu
                275                 280                 285
Pro Val Lys Val Leu Glu Glu Phe Gln Glu Val Tyr Gly Cys Pro Ile
                290                 295                 300
Tyr Glu Gly Tyr Gly Leu Thr Glu Thr Ser Pro Val Val Ala Tyr Asn
305                 310                 315                 320
Gln Lys Ala Trp Pro Arg Arg Pro Gly Thr Val Gly Arg Pro Ile Trp
                325                 330                 335
Gly Val Glu Ala Glu Ile Ala Ala Ala Asp Val Glu Asp Arg Ile Glu
                340                 345                 350
Leu Leu Pro Ala Gly Glu Ile Gly Glu Ile Val Val Arg Gly His Asn
                355                 360                 365
Val Met Ala Gly Tyr Leu Asn Arg Pro Glu Ala Thr Ala Ala Val Leu
                370                 375                 380
Val Asp Gly Trp Phe Arg Ser Gly Asp Leu Gly Met Lys Asp Ala Asp
385                 390                 395                 400
Gly Tyr Leu Thr Ile Val Asp Arg Lys Lys Asp Met Val Leu Arg Gly
                    405                 410                 415
Gly Tyr Asn Val Tyr Pro Arg Glu Val Glu Val Leu Met Arg His
                420                 425                 430
Pro Ala Val Ala Gln Val Ala Val Ile Gly Val Pro Asp Asp Lys Tyr
                435                 440                 445
Gly Glu Glu Val Cys Ala Val Val Arg Thr Arg Pro Gly Thr Asp Pro
450                 455                 460
```

-continued

Asp Ala Ala Leu Ala Ala His Ile Val Ser Trp Ser Arg Gln Arg Ile
465                 470                 475                 480

Ala Ala Tyr Lys Tyr Pro Arg Arg Val Glu Phe Val Glu Asp Phe Pro
            485                 490                 495

Leu Gly Pro Ser Gly Lys Val Leu Lys Arg Glu Leu Ala Ala Arg Phe
        500                 505                 510

Ala

<210> SEQ ID NO 114
<211> LENGTH: 506
<212> TYPE: PRT
<213> ORGANISM: Streptomyces aizunensis

<400> SEQUENCE: 114

Met Thr Arg Ser Val Ala Val Leu Ala Glu Ser Ala Gly Arg Trp
1               5                   10                  15

Pro Ser Arg Thr Ala Leu Val Cys Gly Ala Glu Arg Ile Ser Tyr Ala
            20                  25                  30

Arg Leu Trp Asp Arg Ala Arg Arg Tyr Ala Ala Leu Arg Gly Gln
        35                  40                  45

Gly Ile Gly Pro Asp Asp Lys Val Ala Leu Leu Met Pro Asn Thr Pro
    50                  55                  60

Glu Phe Ala Ala Val Tyr Phe Ala Val Leu Ala Leu Gly Ala Val Val
65                  70                  75                  80

Val Pro Val His Thr Leu Leu Lys Pro Ala Glu Val Ser His Leu Leu
                85                  90                  95

Arg Asp Ser Gly Ala Arg Ala Leu Val Trp Ala Gly Thr Leu Pro Gln
            100                 105                 110

Glu Thr Ala Arg Asp Ala Gly Glu Thr Gly Val Leu Leu Leu Thr Val
        115                 120                 125

Gly Glu Ala Leu His Gly Ser Val Leu Leu Asp Asp Gly Val Glu Pro
    130                 135                 140

Ile Asp Thr Tyr Val Glu Arg Gly Ala Asp Asp Leu Ala Leu Val Leu
145                 150                 155                 160

Tyr Thr Ser Gly Thr Thr Gly Arg Pro Lys Gly Ala Met Leu Thr His
                165                 170                 175

Gly Asn Val Ala Thr Asn Ile Ala Val Thr Ala Val Ser Pro Phe Ala
            180                 185                 190

Phe Gly Glu Asp Asp Val Leu Leu Gly Ala Leu Pro Leu Ser His Thr
        195                 200                 205

Phe Gly Gln Ile Cys Gly Met Ala Val Thr Phe His Ala Gly Ala Thr
    210                 215                 220

Leu Val Val Met Glu Arg Phe Glu Ala His Asp Ala Leu Arg Leu Met
225                 230                 235                 240

Arg Glu His Gly Cys Thr Val Phe Met Gly Val Pro Thr Met Tyr His
                245                 250                 255

Ala Leu Leu Glu Ala Val Ala Ala Gly Ala Pro Ala Pro Arg Leu Thr
            260                 265                 270

Arg Val Tyr Ser Gly Gly Ser Ala Leu Pro Val Pro Val Leu Asp Arg
        275                 280                 285

Val Arg Ala Ala Phe Gly Cys Glu Val Tyr Glu Gly Tyr Gly Leu Thr
    290                 295                 300

Glu Thr Ser Pro Cys Val Ala Tyr Asn Gln Pro Gly Ile Pro Cys Lys
305                 310                 315                 320

```
Pro Gly Thr Val Gly Leu Pro Ile Asp Gly Val Arg Val Ala Ile Ala
                325                 330                 335

Asp Ala Glu Leu Gly Arg Ile Arg Leu Leu Lys Gln Gly Asp Ile
            340                 345                 350

Gly Glu Ile Val Ser Gly His Asn Val Met Ala Gly Tyr Leu Gly
            355                 360                 365

Arg Pro Gln Glu Thr Ala Glu Val Leu Val Asp Gly Trp Phe Arg Thr
370                 375                 380

Gly Asp Met Gly Val Gln Asp Glu Asp Gly Tyr Leu Ser Ile Val Asp
385                 390                 395                 400

Arg Lys Lys Asp Met Ile Val Arg Gly Gly Tyr Asn Val Tyr Pro Arg
                405                 410                 415

Glu Val Glu Asp Val Leu Leu Arg His Pro Ala Val Asp Gly Ala Cys
            420                 425                 430

Val Val Gly Val Pro Ser Val Lys His Gly Glu Glu Val Cys Ala Val
            435                 440                 445

Val Arg Val Lys Pro Gly Gln Arg Ala Ser Gly Leu Leu Ala Glu Glu
    450                 455                 460

Ile Val Ala Trp Ser Arg Val His Met Ala Ala Tyr Lys Tyr Pro Arg
465                 470                 475                 480

Arg Val Glu Phe Val Glu Thr Phe Pro Leu Gly Ser Ser Gly Lys Val
                485                 490                 495

Leu Lys Arg Glu Leu Ala His Arg Tyr Ala
                500                 505

<210> SEQ ID NO 115
<211> LENGTH: 515
<212> TYPE: PRT
<213> ORGANISM: Streptomyces ghanaensis

<400> SEQUENCE: 115

Met Ser Ser Asn Glu Asn Tyr Val Arg Arg Val Leu Glu Ala Leu Ala
1               5                   10                  15

Ser Asp Pro Asp Arg Ile Ala Leu Trp Ala Asp Gly Glu Glu Ile Thr
            20                  25                  30

Ala Gly Gln Val Ser Arg Ala Val Leu Thr Ala Ala Glu Leu Leu Leu
        35                  40                  45

Arg His Phe Thr Glu His Arg Asp Pro Ser Ala Glu Gly Lys Ala Pro
    50                  55                  60

Val Val Ala Val Leu Thr Val Thr Asn Ser Pro Ala Thr Ile Ile Leu
65                  70                  75                  80

Arg Tyr Ala Ala Asn Leu Ala Gly Ala Thr Leu Val His Leu His Ser
                85                  90                  95

Thr Asn Ala Val Asp Pro Thr Asp Gln Leu Ala Ala Ala Ala Arg Leu
            100                 105                 110

Asp Ile Leu Ser Lys Thr Gly Thr Phe Leu Ala Val Asp Lys Glu
        115                 120                 125

Asn Leu Asp Ala Ala Arg Glu Leu Cys Asp Arg Leu Pro Glu Pro Pro
    130                 135                 140

Arg Leu Ala Ala Leu Gly Ala Leu Gly Pro Asp Val Leu Asp Leu Ser
145                 150                 155                 160

Ser Gly Asp Pro Asp Ala Phe Gly His Asp Ala Val Glu Ala Asp Pro
                165                 170                 175

Glu Gln Pro Ala Val Val Ile Tyr Thr Ser Gly Thr Ser Gly Arg Pro
```

```
            180                 185                 190
Lys Gly Val Thr Gln Pro Tyr Arg Leu Arg Arg Ala Asn Leu Gln Val
        195                 200                 205

Ala Leu Gln Ser Pro Glu Pro Ile Val Tyr Leu Ser Thr Leu Pro Val
        210                 215                 220

Ser Asn Ser Ser Gly Ser Ala Val Asp Val Ala Leu Ala Ser Gly Gly
225                 230                 235                 240

Thr Val Val Leu His Asp Gly Phe Glu Ala Gly Glu Val Leu Arg Ala
                245                 250                 255

Val Glu Gln His Arg Val Ser Thr Leu Thr Ile Thr Pro Pro Gln Leu
                260                 265                 270

Tyr Met Leu Ile Asp His Pro Asp Thr Ala Thr Thr Asp Arg Ser Ser
            275                 280                 285

Ile Arg Leu Ile Thr Tyr Leu Gly Ser Pro Ala Ala Pro Ala Arg Leu
            290                 295                 300

Ala Glu Ala Val Glu Val Phe Gly Pro Val Leu Leu Gln Leu Tyr Gly
305                 310                 315                 320

Thr Thr Glu Val Asn Gly Ile Ser Met Leu Met Pro Gln Asp His Phe
                325                 330                 335

Asp Pro Glu Leu Arg Arg Thr Val Gly Arg Pro Thr Thr Glu Ile Arg
            340                 345                 350

Ile Arg Asp Val Asp Asp Arg Asp Leu Pro Pro Gly Glu Ile Gly
            355                 360                 365

Glu Val Cys Val Gln Ser Pro Ser Thr Met Leu Gly Tyr Trp Gly Glu
        370                 375                 380

Pro Glu Leu Thr Ala Ala Ile Ile Arg Asp Gly Trp Val His Thr Gly
385                 390                 395                 400

Asp Leu Gly Ser Leu Asp Glu Asn Gly Phe Leu Arg Leu His Gly Arg
                405                 410                 415

Met Gly Glu Val Met Lys Thr Asn Gly Ile Lys Val His Pro Thr Asp
                420                 425                 430

Val Glu Asn Ala Leu Leu Thr His Pro Glu Val Thr Gln Ala Ala Val
            435                 440                 445

Tyr Cys Val Val Asp Glu Asp Arg Val Glu His Ile His Ala Ala Val
        450                 455                 460

Val Val Arg Pro Gly Gly Thr Ala Asp Ser Gly Thr Leu Ile Gly His
465                 470                 475                 480

Val Ala Ala Glu Leu Ser Pro Lys His Val Pro Ala Val Val Thr Phe
                485                 490                 495

His Asp Ala Leu Pro Leu Thr Arg Ala Gly Lys Pro Asp Lys Pro Ala
                500                 505                 510

Leu Ala Ala
        515

<210> SEQ ID NO 116
<211> LENGTH: 507
<212> TYPE: PRT
<213> ORGANISM: Streptomyces antibioticus

<400> SEQUENCE: 116

Met Glu Gly Asn Glu His Tyr Val Arg Gln Ile Leu Asn Thr Leu Arg
1               5                   10                  15

Ala Asp Pro Ser Gly Val Ala Leu Val His Arg Asp Thr Pro Val Ile
            20                  25                  30
```

```
Ala Gly Asp Leu Ala Asp Ser Ile Thr Ser Ala Ala Glu Ala Met Arg
         35                  40                  45

Gly Ser Gly Val Gly Val Gly Ser Val Val Gly Ile Leu Thr Asp Pro
 50                  55                  60

Asn Thr Pro Ala Thr Leu Val Ala Arg Tyr Ala Ala Asn Leu Leu Gly
 65                  70                  75                  80

Ala Thr Val Val His Leu Phe Gly Val Asn Ala Ala Asn Pro Ser Asp
                 85                  90                  95

Leu Leu Ser Ala Glu Ala Gln Gly Gly Ile Val Ala Glu Ala Leu Pro
            100                 105                 110

Ala Met Val Val Asp Ala Ala Asn Leu Glu Arg Ala Arg Ala Ile
            115                 120                 125

Arg Glu Val Pro Ser Val Arg Pro Val Leu Ser Gly Leu Gly Glu Leu
130                 135                 140

Gly His Asp Val Ile Asp Leu Thr Asp Ser Pro Ala Gly Ala Phe Arg
145                 150                 155                 160

Pro Asp Ala Ala Arg Asp Gly Asp Thr Ala Val Val Thr Phe Ser Ser
            165                 170                 175

Gly Ser Thr Gly Arg Pro Lys Gly Thr Ala Trp Ser Phe Arg Val Lys
            180                 185                 190

Ala Asp Met Val Ala Ala Ser Ala Arg Arg Ala Gln Lys Ala Thr Ala
            195                 200                 205

Leu Val Thr Ala Pro Leu Thr His Ser Asn Gly Phe Val Ala Asp Asp
210                 215                 220

Val Leu Val Ser Gly Gly Thr Val Val Leu Pro Gly Phe Asp Glu
225                 230                 235                 240

Thr Glu Val Leu Arg Ser Val Ala Arg Tyr Gln Val Asn Arg Leu Ala
                245                 250                 255

Val Ser Ala Pro Gln Leu Tyr Ala Leu Ala Asp His Pro Glu Thr Thr
            260                 265                 270

Arg Thr Asp Leu Ser Ser Val Arg Asp Leu Phe Tyr Thr Gly Val Ala
            275                 280                 285

Ala Ser Pro Glu Arg Val Ala Val Ala Glu Lys Val Phe Gly Ser Val
            290                 295                 300

Leu Met Gln Val Tyr Gly Thr Ser Glu Thr Asn Ile Ile Ser Trp Leu
305                 310                 315                 320

Ile Ala Gly Glu His Thr Asp Ala Gly Leu Arg Ala Thr Val Gly Arg
                325                 330                 335

Pro Leu Glu Trp Leu Arg Val Thr Ile Arg Asp Pro Gln Asp Glu Arg
            340                 345                 350

Val Leu Pro Thr Gly Glu Thr Gly Glu Val Trp Val Asn Ser Pro Trp
            355                 360                 365

Arg Met Asp His Tyr Trp Asn Asp Pro Glu Gln Thr Ala Arg Thr Val
370                 375                 380

Arg Asp Gly Trp Ile Arg Thr Gly Asp Val Gly His Leu Asp Asp Ala
385                 390                 395                 400

Gly Tyr Leu His Leu His Gly Arg Leu Ala Gly Val Ile Lys Thr Asn
                405                 410                 415

Gly Ile Lys Val Tyr Pro Val Ala Val Glu Arg Ser Leu Leu Asp His
            420                 425                 430

Pro Asp Val Ala Glu Ala Val Phe Gly Val Glu Asn Ser Asp Arg
            435                 440                 445

Val Glu Arg Ile His Ala Val Val Val Leu Arg Glu Gly Ala Gly Ala
```

```
                        450                 455                 460
Gly Pro Glu Asp Leu Arg Gln His Val Ser Ser His Leu Ser Pro Asn
465                 470                 475                 480

His Ala Pro Ala Asp Ile Glu Leu Arg Ser Ser Leu Pro Leu Ile Gly
                485                 490                 495

Phe Gly Lys Pro Asp Lys Leu Arg Leu Arg Ala
                500                 505
```

<210> SEQ ID NO 117
<211> LENGTH: 242
<212> TYPE: PRT
<213> ORGANISM: Streptomyces ghanaensis

<400> SEQUENCE: 117

```
Ser Arg Tyr Pro Asp Leu Thr Leu Val Gly Phe Pro Arg Ala Lys Glu
1               5                   10                  15

His Leu Leu Ala Thr Ala Gly Gly Asp Pro Glu Arg Val Gln Val Val
                20                  25                  30

Gly Pro Leu Val Ala Gln His Asp Leu Arg Asp Phe Met Thr Ser Glu
            35                  40                  45

Thr Ala Val Ser Glu Ala Gly Pro Trp Gly Gly Asp Ser Gly Pro Asp
    50                  55                  60

Arg Pro Arg Val Ile Ile Phe Ser Asn Arg Gly Gly Asp Thr Tyr Pro
65                  70                  75                  80

Glu Leu Val Arg Arg Leu Ala Asp Arg His Pro Gly Ile Asp Leu Val
                85                  90                  95

Phe Val Gly Tyr Gly Asp Pro Glu Leu Ala Arg Arg Thr Ala Ala Val
            100                 105                 110

Gly Arg Pro His Trp Arg Phe His Ser Val Leu Gly Gln Ser Glu Tyr
        115                 120                 125

Phe Asp Tyr Ile Arg Arg Ala Ser Arg Ser Arg Tyr Gly Leu Leu Val
    130                 135                 140

Ser Lys Ala Gly Pro Asn Thr Thr Leu Glu Ala Ala Tyr Phe Gly Ile
145                 150                 155                 160

Pro Val Leu Met Leu Glu Ser Gly Leu Pro Met Glu Arg Trp Val Pro
                165                 170                 175

Gly Leu Ile His Glu Glu Gly Leu Gly His Ala Cys Ala Thr Pro Glu
            180                 185                 190

Glu Leu Phe Arg Thr Ala Asp Asp Trp Leu Thr Arg Pro Ser Val Ile
        195                 200                 205

Glu Val His Lys Lys Ala Ala Val Ser Phe Ala Ala Ser Val Leu Asp
    210                 215                 220

Gln Asp Ala Val Thr Ala Arg Ile Lys Ala Ala Leu Gln Pro Leu Leu
225                 230                 235                 240

Asp Ala
```

<210> SEQ ID NO 118
<211> LENGTH: 233
<212> TYPE: PRT
<213> ORGANISM: Polaromonas naphthalenivorans

<400> SEQUENCE: 118

```
Ser Lys Arg Ile Asp Arg Thr Phe Leu Ala His Thr Asp Leu Glu Ser
1               5                   10                  15

Arg Trp Leu Ala Ala Gly Val Pro Pro Asp Lys Val Thr Ser Gly
                20                  25                  30
```

-continued

```
Met Pro Val Arg Ala Pro Ala Ala Asp Gly Ala Thr Arg Glu Thr Ala
            35                  40                  45

Leu Thr Ala Leu Gly Leu Ala Pro Asp Ala Pro Val Leu Ile Thr
 50                  55                  60

Ser Gly Lys Glu Gly Val Gly Asp Tyr Ala Leu Val Val Glu Ser Leu
 65                  70                  75                  80

Ala Arg His His Pro Gly Pro Leu Gln Ile Ile Ala Val Cys Gly Ala
                85                  90                  95

Asn Ala Arg Gln Gln Ala Leu Leu Thr Ala Leu Gln Lys Arg Leu Pro
                100                 105                 110

Glu Pro Val Ala Leu Lys Val Cys Gly Leu Val Pro His Ala Asp Leu
                115                 120                 125

Leu Ala Trp Met Arg Ala Ala Asp Leu Leu Ile Thr Lys Ala Gly Gly
        130                 135                 140

Met Thr Pro Ala Glu Ala Phe Ala Val Gly Thr Pro Thr Ile Leu Leu
145                 150                 155                 160

Asp Val Val Ser Gly His Glu Arg Glu Asn Ala Ala Leu Phe Val Arg
                165                 170                 175

Leu Gly Val Ala Asp Leu Ala Asp Thr Leu Ala Gln Ala Gly Glu Leu
                180                 185                 190

Ala Ala Ala Val Leu Ala Ser Pro Gln Arg Gln Thr Ala Met Arg Arg
                195                 200                 205

Ala Gln Leu Ala Phe His Asp Arg Ala Gly Leu Gly Arg Ile Ala Arg
        210                 215                 220

Phe Ala Leu Asp Pro Ala Leu Pro Ala
225                 230

<210> SEQ ID NO 119
<211> LENGTH: 224
<212> TYPE: PRT
<213> ORGANISM: Streptomyces ghanaensis

<400> SEQUENCE: 119

Pro Arg Gly Gly Pro Glu Gly Asp Ala Met Val Thr Ala Gly Pro Ala
 1               5                  10                  15

Gly Ala Ala Val Thr Val Val Leu Pro His Tyr Asp Cys Ala Ala Tyr
                20                  25                  30

Leu Gly Ala Ala Val Gly Ser Val Leu Ser Gln Asp Arg Pro Asp Leu
            35                  40                  45

Arg Leu Thr Val Val Asp Glu Cys Ser Pro Glu Glu Lys Trp Ala Arg
 50                  55                  60

Ala Leu His Pro Tyr Ala Gly Asp Pro Arg Leu Thr Val Val Arg Thr
 65                  70                  75                  80

Ser Arg Asn Val Gly His Leu Arg Ile Lys Asn Lys Val Leu Glu Ser
                85                  90                  95

Val Asp Thr Pro Tyr Val Ala Phe Gln Asp Ala Asp Asp Ile Ser Leu
                100                 105                 110

Pro Gly Arg Leu Arg His Gln Leu Ala Leu Leu Glu Ser Gly Gly Ala
                115                 120                 125

Asp Leu Val Gly Cys Ala Tyr Ser Tyr Ile Asp Glu Ala Gly Arg Thr
        130                 135                 140

Thr Gly His Arg Arg Met Pro Arg Asn Gly Asn Leu Trp Met Arg Leu
145                 150                 155                 160

Gly Arg Thr Thr Val Leu Leu His Pro Ser Ser Val Val Arg Arg Ser
```

```
                165                 170                 175
Val Leu Glu Arg Leu Gly Gly Phe Asp Gly Thr Ala Arg Leu Gly Ala
            180                 185                 190

Asp Thr Asp Phe His Leu Arg Ala Ala Arg Leu Tyr Arg Leu Arg Ser
            195                 200                 205

Val Arg Lys Val Leu Tyr Arg Tyr Arg Ile Trp Pro Lys Ser Leu Thr
210                 215                 220

<210> SEQ ID NO 120
<211> LENGTH: 225
<212> TYPE: PRT
<213> ORGANISM: Methylococcus capsulatus

<400> SEQUENCE: 120

Pro His His Val Pro His Arg Asp Met Thr His His Ser Arg Pro Pro
1               5                   10                  15

Gly His Ala Pro Arg Val Thr Ile Leu Met Pro Val Tyr Asn Gly Glu
            20                  25                  30

Lys Tyr Leu Ala Ala Ala Met Glu Ser Ile Leu Asp Gln Thr Phe Arg
        35                  40                  45

Asp Phe Ile Leu Leu Ile Ile Asp Asp Gly Ser Ser Asp Ser Ser Leu
    50                  55                  60

Ala Ile Ala Arg Ser Phe Gly Asp Pro Arg Val Gln Val Glu Arg Asn
65                  70                  75                  80

Pro Lys Asn Leu Gly Leu Val Lys Thr Leu Asn Arg Gly Leu Asp Leu
                85                  90                  95

Val Gln Thr Glu Phe Val Ala Arg Met Asp Cys Asp Asp Ile Ala Leu
            100                 105                 110

Pro Asp Arg Leu Glu Lys Gln Ile Ala Phe Leu Asp Glu Asn Pro Asp
        115                 120                 125

Ile Gly Met Cys Gly Thr Ala Tyr Glu Leu Phe His Glu Ser Leu Arg
    130                 135                 140

Gln Thr Ile Arg Pro Pro Cys Arg His Glu Glu Ile Val Tyr Gly Leu
145                 150                 155                 160

Leu Asp Asp Asn Val Phe Leu His Ser Ser Val Ile Val Arg Met Glu
                165                 170                 175

Val Leu Asn Arg His Gly Leu Arg Tyr Arg Glu Asp Tyr Arg Leu Ala
            180                 185                 190

Glu Asp Tyr Glu Leu Trp Ala Arg Leu Ala Arg Tyr Thr His Ile Gly
        195                 200                 205

Asn Leu Pro Gln Val Leu Arg Tyr Arg Ser His Pro Glu Asn Val
    210                 215                 220

Ser
225

<210> SEQ ID NO 121
<211> LENGTH: 270
<212> TYPE: PRT
<213> ORGANISM: Streptomyces ghanaensis

<400> SEQUENCE: 121

Val Ser Val Val Val Pro Val Arg Asn Gly Ala Arg Thr Leu Ala Ala
1               5                   10                  15

Gln Leu Thr Ala Leu Ala Arg Gln Thr Gly Ala Val Ala Tyr Glu Val
            20                  25                  30

Leu Val Val Asp Asn Gly Ser Thr Asp Thr Thr Arg Glu Val Ala Glu
```

```
            35                  40                  45
Arg Ala Arg Ala Glu Leu Pro Asp Leu Arg Ile Val Asp Ala Ser Asp
 50                  55                  60

Arg Ala Gly Glu Ser Cys Ala Arg Asn Arg Gly Ile Ala Ala Ala Arg
 65                  70                  75                  80

Gly Asp Phe Val Ala Phe Cys Asp Ala Asp Val Ala Asp Thr Gly
                 85                  90                  95

Trp Leu Ala Ala Met Ala Gln Ala Ala Lys Glu Ala Asp Leu Val Gly
                100                 105                 110

Gly Gly Leu Glu Thr Ser Val Leu Ser Pro Gly Arg Val Asp Glu Gln
            115                 120                 125

Pro Leu Pro Met Asp Ala Gln Thr Asp Phe Leu Pro Phe Ala Arg Gly
        130                 135                 140

Ala Asn Cys Gly Ala Trp Lys Asp Val Leu Thr Ala Leu Gly Gly Trp
145                 150                 155                 160

Asp Glu Arg Tyr Arg Gly Gly Gly Glu Asp Met Asp Leu Ser Trp Arg
                165                 170                 175

Ala Gln Leu Cys Gly Tyr Leu Val Arg Tyr Ala Asp Asp Ala Arg Met
            180                 185                 190

His Tyr Arg Leu Arg Asp Gly Leu Pro Ala Leu Ala Arg Gln Lys Trp
        195                 200                 205

Asn Tyr Gly Arg Ser Gly Ala Gln Leu Tyr Ala Ala Tyr Arg Arg Ala
210                 215                 220

Gly Phe Glu Arg Arg Asp Gly Arg Val Val Arg Asn Trp Cys Trp
225                 230                 235                 240

Leu Leu Leu His Val Pro Asn Leu Val Arg Ser Thr Gly Pro Cys Gly
                245                 250                 255

His Ala Glu Ser Ala Thr Arg Pro Ala Gly Arg Phe Pro Gly
            260                 265                 270

<210> SEQ ID NO 122
<211> LENGTH: 276
<212> TYPE: PRT
<213> ORGANISM: Kineococcus radiotolerans

<400> SEQUENCE: 122

Val Ser Val Val Ile Pro Cys Phe Asn Ala Thr Arg Asp Leu Pro Ala
 1                   5                  10                  15

Gln Leu Glu Ala Leu Ala Gly Gln Ser Thr Val Cys Thr Phe Glu Val
                20                  25                  30

Val Val Ser Asp Asn Gly Ser Thr Asp Gly Leu Ala Glu Phe Val Glu
            35                  40                  45

Glu Trp Ser Arg Arg Val Pro Phe Met Leu Arg Arg Val Asp Ala Ser
 50                  55                  60

Ala Arg Arg Gly Val Ala His Ala Arg Asn Ala Gly Cys Arg Ala Ala
 65                  70                  75                  80

Leu Ala Asp Val Ile Leu Val Cys Asp Ala Asp Val Val Gly Val
                85                  90                  95

Gly Trp Val Asp Ala Met Ala Arg Ala Leu Glu Gln Ala Asp Leu Val
                100                 105                 110

Gly Gly Thr Leu Val His Gly His Leu Asn Thr Ala Leu Val Gln Gln
            115                 120                 125

Trp Arg Pro Thr Ser Pro Pro Gly Val Leu Pro Thr Lys Leu Ser His
        130                 135                 140
```

```
Leu Pro Tyr Ala Val Gly Ala Asn Val Gly Leu Arg Arg Glu Val Phe
145                 150                 155                 160

Asp Ala Leu Gly Gly Trp Asp Glu Gly Phe Val Ala Gly Gly Asp Asp
                165                 170                 175

Val Glu Phe Ser Trp Arg Ala Gln His Ala Gly Phe Cys Leu Arg Ser
            180                 185                 190

Ala Pro Asp Ala Val Ile Ala Tyr Arg Met Arg Thr Thr Leu Ser Ala
        195                 200                 205

Asn Val Lys Gln Ser Tyr Phe Tyr Ala Arg Ser Asp Ala Leu Leu Met
    210                 215                 220

Arg Thr Phe Arg Ser Ala Gly Val Pro Arg Arg Gly Leu Arg Pro Leu
225                 230                 235                 240

Ile Thr Glu Ser Lys Trp Leu Val Arg Asn Val Pro Arg Thr Arg Glu
                245                 250                 255

Pro Gly Phe Arg Gly Gln Trp Leu Arg Arg Ala Ala Met Leu Ala Gly
            260                 265                 270

Arg Phe Val Gly
            275

<210> SEQ ID NO 123
<211> LENGTH: 181
<212> TYPE: PRT
<213> ORGANISM: Streptomyces ghanaensis

<400> SEQUENCE: 123

His His Leu Arg Ser Thr Met Ala Arg Gly Phe Arg Pro Pro Glu Ser
1               5                   10                  15

Trp Glu Val Pro Val Arg His Val Leu Pro Gly Leu Pro Ala Asp Gly
            20                  25                  30

Thr Pro Arg Ala Glu Glu Ala Ala Gln Ala Leu Arg Thr Pro Ala Gly
        35                  40                  45

Arg Pro Gly Ile Ala Leu Val Val Pro Thr Tyr Val Ser Arg Val Ser
    50                  55                  60

Leu Ala Arg Gln Arg Glu Trp Phe Asp Ala Leu Leu Asp Gln Ala Ala
65                  70                  75                  80

Ala Val Thr Arg Asp His Pro Leu Val Pro Leu Val Leu Phe Val Gly
                85                  90                  95

Met Gln Trp Ser Ser Ala Glu Glu Arg Glu Ala Leu Arg Arg Leu
            100                 105                 110

Arg Val Leu Leu Asp Asp Ala Arg Thr Arg Leu Pro Gly Leu Arg Ile
        115                 120                 125

Cys Gly Leu Ala Leu Pro Gly Pro Gly Lys Pro Arg Thr Leu Asn Gly
    130                 135                 140

Ala Ile Ala Val Ala Glu Leu Leu Gly Cys Ala Gly Val Gly Trp Thr
145                 150                 155                 160

Asp Asp Asp Val Thr Leu Glu Glu Asp Cys Leu Ser Arg Leu Val Arg
                165                 170                 175

Asp Phe Leu Ala Ala
            180

<210> SEQ ID NO 124
<211> LENGTH: 152
<212> TYPE: PRT
<213> ORGANISM: Mycobacterium vanbaalenii

<400> SEQUENCE: 124
```

-continued

```
His His Ala Arg Val Leu Val Arg His Gln Gly Gln Pro Val Ala Phe
1               5                   10                  15

Val Glu Val Pro Val Arg Asp Ala Leu Ile Arg Leu Pro Ala Cys Pro
            20                  25                  30

Leu Pro Glu Asp Leu Asp Ala Gly Gln Pro Ala Arg Leu Met Pro Ile
        35                  40                  45

Ser Val Val Leu Cys Thr Arg Asp Arg Pro Asp Gln Leu Ala Asp Ala
50                  55                  60

Leu Lys Ser Ile Leu Ser Leu Asp Tyr Pro Glu Phe Glu Val Val Val
65                  70                  75                  80

Val Asp Asn Ala Ala Arg Thr Asp Ala Thr Ala Gly Val Val Ala Gln
                85                  90                  95

Leu Gly Asp Ala Arg Val Arg Arg Val Ala Glu Pro Ile Pro Gly Leu
            100                 105                 110

Ser Thr Ala Arg Asn Thr Gly Leu Arg His Ala Ala His Pro Val Val
        115                 120                 125

Ala Phe Thr Asp Asp Val Val Val Asp Arg Gln Trp Leu Arg Gly
    130                 135                 140

Leu Ala Arg Gly Phe Ala Arg Ala
145                 150
```

<210> SEQ ID NO 125
<211> LENGTH: 628
<212> TYPE: PRT
<213> ORGANISM: Streptomyces ghanaensis

<400> SEQUENCE: 125

```
Met Cys Gly Phe Val Gly Phe Ser Asp Ala Gly Ala Gly Gln Glu Asp
1               5                   10                  15

Ala Arg Val Thr Ala Glu Arg Met Leu Ala Ala Val Ala His Arg Gly
            20                  25                  30

Pro Asp Gly Ser Asp Trp Cys His His Arg Gly Val Thr Leu Ala His
        35                  40                  45

Cys Ala Leu Thr Phe Thr Asp Pro Asp His Gly Ala Gln Pro Phe Val
50                  55                  60

Ser Ala Ser Gly Ala Thr Ala Val Val Phe Asn Gly Glu Leu Tyr Asn
65                  70                  75                  80

His Ala Val Leu Gly Asp Gly Ala Leu Pro Cys Ala Pro Gly Gly Asp
                85                  90                  95

Thr Glu Val Pro Gly Gly Thr Leu Arg Val Ala Gly His Ala Asp Ala
            100                 105                 110

Arg Pro Ala Ala Gly His Val Arg Leu Arg Ala Ala Gly Arg Pro His
        115                 120                 125

Arg His His Gly Ala Gly Arg Asp Arg Trp Gly Arg Ala Pro Leu Leu
    130                 135                 140

Thr Pro Ala Cys Glu Thr Asp Ile Ala Phe Ala Ser Glu Leu Thr Ser
145                 150                 155                 160

Leu Leu Arg His Pro Ala Ala Pro Arg Thr Pro Glu Val Arg Ala Leu
                165                 170                 175

Ala Asp Tyr Leu Val Leu Gln Ala Phe Cys Ala Pro Ala Ser Ala Val
            180                 185                 190

Ser Gly Val Cys Lys Val Arg Pro Gly Ser Tyr Val Thr His Arg His
        195                 200                 205

Gly Ala Leu Asp Glu Thr Glu Phe Trp Arg Pro Arg Leu Thr Pro Asp
    210                 215                 220
```

```
Arg Gly Ala Gly Arg Gly Pro Gly Arg Arg Glu Ala Ala Arg Arg Phe
225                 230                 235                 240

Glu Glu Leu Phe Arg Ala Ala Val Ala Arg Arg Met Thr Ser Thr Asp
            245                 250                 255

Arg Arg Leu Gly Val Leu Leu Ser Gly Gly Leu Asp Ser Ser Ala Val
            260                 265                 270

Ala Ala Val Ala Gln Gln Leu Leu Pro Gly Arg Pro Val Pro Thr Phe
            275                 280                 285

Ser Ala Gly Phe Ala Asp Pro Asp Phe Asp Glu Ser Asp His Ala Arg
            290                 295                 300

Ala Val Ala Arg His Leu Gly Thr Glu His His Val Val Arg Ile Gly
305                 310                 315                 320

Gly Ala Asp Leu Ala Gly Val Val Glu Ser Glu Leu Ala Val Ala Asp
                325                 330                 335

Glu Pro Leu Ala Asp Pro Ser Leu Leu Pro Thr Arg Leu Val Cys Arg
                340                 345                 350

Ala Ala Arg Glu His Val Arg Gly Val Leu Thr Gly Asp Gly Ala Asp
                355                 360                 365

Glu Leu Leu Leu Gly Tyr Arg Tyr Phe Gln Ala Glu Arg Ala Ile Glu
370                 375                 380

Leu Leu Leu Arg Val Leu Pro Ala Pro Arg Leu Glu Ala Leu Val Arg
385                 390                 395                 400

Leu Leu Val Arg Arg Leu Pro Ala Arg Ser Gly Asn Leu Pro Val Thr
                405                 410                 415

His Ala Leu Gly Leu Leu Ala Lys Gly Leu Arg Ala Ala Pro Glu His
                420                 425                 430

Arg Phe Tyr Leu Ser Thr Ala Pro Phe Gly Pro Gly Glu Leu Pro Arg
                435                 440                 445

Leu Leu Thr Pro Glu Ala Gly Ala Glu Leu Thr Gly His Asp Pro Phe
450                 455                 460

Thr Glu Val Ser Arg Leu Leu Arg Gly Gln Pro Gly Leu Thr Gly Val
465                 470                 475                 480

Gln Arg Ser Gln Leu Ala Val Val Thr His Phe Leu Arg Asp Val Ile
                485                 490                 495

Leu Thr Lys Thr Asp Arg Gly Gly Met Arg Ser Ser Leu Glu Leu Arg
                500                 505                 510

Ser Pro Phe Leu Asp Leu Asp Leu Val Glu Tyr Gly Asn Ser Leu Pro
                515                 520                 525

Thr Gly Leu Lys Leu His Arg Phe Thr Gly Lys Tyr Leu Leu Arg Gln
                530                 535                 540

Val Ala Ala Gly Trp Leu Pro Pro Ser Val Val Gln Arg Thr Lys Leu
545                 550                 555                 560

Gly Phe Arg Ala Pro Val Ala Ala Leu Leu Arg Gly Glu Leu Arg Pro
                565                 570                 575

Leu Leu Leu Asp Thr Leu Ser Pro Ser Ser Leu Arg Arg Gly Gly Leu
                580                 585                 590

Phe Asp Thr Gly Ala Val Arg Leu Leu Ile Asp Asp His Leu Gly Gly
                595                 600                 605

Arg Arg Asp Thr Ser Arg Lys Leu Trp Ala Leu Leu Val Tyr Gln Leu
                610                 615                 620

Trp Phe Glu Ser
625
```

```
<210> SEQ ID NO 126
<211> LENGTH: 627
<212> TYPE: PRT
<213> ORGANISM: Pseudomonas aeruginosa

<400> SEQUENCE: 126

Met Cys Gly Ile Ala Gly Phe Trp Asn Ile Thr Gly Thr Leu Leu Gly
1               5                   10                  15

Asp Asn Ala Arg Val Ala Arg Gln Met Ala Ala Ile His His Arg
            20                  25                  30

Gly Pro Asp Glu Ser Gly Ile Trp Tyr Glu Ala Pro Arg Ala Pro Ile
        35                  40                  45

Leu Val His Ala Arg Leu Ala Val Leu Glu Leu Ser Pro Ala Gly Ser
    50                  55                  60

Gln Pro Met His Ser Asp Cys Gly Arg Tyr Val Leu Ile Tyr Asn Gly
65                  70                  75                  80

Glu Ile Tyr Asn His Leu Ala Leu Arg Ala Arg Leu Ser Glu Ala Gly
                85                  90                  95

Val Thr His Ser Trp Arg Gly Gly Ser Asp Thr Glu Thr Leu Leu Ala
            100                 105                 110

Cys Phe Ala Gln Trp Gly Val Glu Ser Thr Leu Lys Leu Thr Val Gly
        115                 120                 125

Met Phe Ala Leu Ala Leu Trp Asp Arg Gln Glu Lys Thr Ile Thr Leu
    130                 135                 140

Ala Arg Asp Arg Met Gly Glu Lys Pro Leu Tyr Trp Gly Trp Gln Asn
145                 150                 155                 160

Gly Val Leu Phe Phe Ala Ser Glu Leu Lys Ala Leu Lys Glu His Pro
                165                 170                 175

Leu Phe Arg Gly Asp Ile Asp Arg Asp Ala Leu Ala Leu Phe Leu Arg
            180                 185                 190

Tyr Gly Tyr Val Pro Ala Pro Tyr Ser Ile Tyr Lys Gly Ile Gly Lys
        195                 200                 205

Leu Arg Ala Gly Ser Tyr Leu Val Leu Ser Glu Arg Ser Leu Asn Glu
    210                 215                 220

Thr Cys Glu Pro Ala Ala Tyr Trp Ser Ala Asn Ala Ala Ile Glu Glu
225                 230                 235                 240

Ala Leu Ser Asn Pro Phe Gln Gly Thr Asp Ala Glu Ala Val Asp Leu
                245                 250                 255

Leu Glu Ser Gln Leu Arg Thr Ser Ile Ser Asp Gln Met Val Ser Asp
            260                 265                 270

Val Pro Leu Gly Ala Phe Leu Ser Gly Gly Val Asp Ser Ser Thr Val
        275                 280                 285

Val Ala Leu Met Gln Gln Ser Ser Arg Pro Ile Arg Thr Phe Ser
    290                 295                 300

Ile Gly Phe Asp Glu Pro Gly Tyr Asp Glu Ala Val Tyr Ala Lys Ala
305                 310                 315                 320

Val Ala Glu His Ile Gly Thr Asp His Thr Glu Leu Tyr Val Asn Ser
                325                 330                 335

Lys Asp Ala Leu Asp Val Ile Pro Ser Leu Pro Lys Ile Tyr Cys Glu
            340                 345                 350

Pro Phe Gly Asp Ser Ser Gln Ile Pro Thr Leu Ile Val Ser Gly Leu
        355                 360                 365

Ala Arg Gln Gln Val Thr Val Ala Leu Ser Gly Asp Gly Gly Asp Glu
    370                 375                 380
```

Leu Phe Gly Gly Tyr Asn Pro Tyr Gln Phe Thr Pro Arg Val Trp Arg
385                 390                 395                 400

Met Leu Glu Arg Phe Pro His Ser Met Arg Arg Phe Ala Ser Ala Phe
            405                 410                 415

Ala Gln Asp Leu Pro Leu Pro Glu Lys Leu Gly Lys Leu Arg Asp Val
            420                 425                 430

Phe Ala Ser Arg Thr Ala Glu Glu Leu Phe Tyr Arg Leu Asn Ser His
            435                 440                 445

Trp Arg Asn His Glu Tyr Pro Val Ile Gly Ala Gln Gly His Thr Ala
            450                 455                 460

Leu Leu Asp Thr Pro Glu Arg Trp Pro Arg Val Asp Ser Phe Gln His
465                 470                 475                 480

Trp Met Met Ala Met Asp Val Gln Gly Tyr Met Pro Asp Asp Ile Leu
            485                 490                 495

Val Lys Val Asp Arg Ala Ala Met Ala Asn Ser Leu Glu Thr Arg Val
            500                 505                 510

Pro Leu Ile Asp His Arg Val Phe Glu Leu Ala Trp Arg Met Pro Leu
            515                 520                 525

His Met Lys Ile Arg Asn Gly Lys Gly Lys Trp Leu Leu Arg Glu Val
            530                 535                 540

Leu Tyr Arg His Val Ser Arg Glu Leu Ile Glu Arg Pro Lys Lys Gly
545                 550                 555                 560

Phe Ser Val Pro Val Ser Asp Trp Leu Arg Gly Pro Leu Lys Glu Trp
            565                 570                 575

Ala Glu Ser Leu Leu Asp Glu Arg Leu Gln Gln Glu Gly Tyr Leu
            580                 585                 590

Asp Ser Arg Leu Ile Arg Arg Ile Trp Asn Asp His Leu Ala Gly Arg
            595                 600                 605

Arg Asp His Ser Arg Arg Leu Trp Ser Val Leu Met Phe Gln Ala Trp
            610                 615                 620

Leu Glu Ser
625

<210> SEQ ID NO 127
<211> LENGTH: 160
<212> TYPE: PRT
<213> ORGANISM: Streptomyces ghanaensis

<400> SEQUENCE: 127

Glu Gly Val Phe Ala Gly Trp Arg Trp Asp Gly Glu Arg Leu Val Ala
1               5                   10                  15

Arg Asn Asp Arg Tyr Gly Val Cys Pro Leu Phe Tyr Arg Ala Gly Gly
            20                  25                  30

Gly Ser Leu Ala Leu Ser Pro Asp Pro Leu Ala Leu Leu Pro Glu Asp
            35                  40                  45

Gly Pro Val Glu Leu Asp His Asp Ala Leu Ala Val Phe Leu Arg Thr
        50                  55                  60

Gly Phe Phe Leu Ala Glu Asp Thr Ala Phe Ala Gln Val Arg Ala Leu
65                  70                  75                  80

Pro Pro Ala Ala Thr Leu Thr Trp Asp Thr Gly Gly Leu Arg Leu Arg
                85                  90                  95

Ser Asp Gly Pro Pro Arg Pro Gly Ala Ala Ala Met Thr Glu Ala Gln
            100                 105                 110

Ala Val Asp Gly Phe Val Asp Leu Phe Arg Ala Ser Val Ala Arg Arg

```
                115                 120                 125
Leu Pro Gly Glu Pro Tyr Asp Leu Pro Leu Ser Gly Gly Arg Asp Ser
        130                 135                 140

Arg His Ile Leu Leu Glu Leu Cys Arg Arg Gly Ala Pro Pro Arg Arg
145                 150                 155                 160

<210> SEQ ID NO 128
<211> LENGTH: 165
<212> TYPE: PRT
<213> ORGANISM: Azoarcus sp.

<400> SEQUENCE: 128

Asp Gly Met Phe Asn Phe Ala Leu Trp Asp Ala Arg Arg Lys Arg Leu
1               5                   10                  15

Leu Ile Gly Arg Asp Pro Leu Gly Val Lys Pro Leu Tyr Val His Arg
            20                  25                  30

Ser Ala Ser Met Leu Ala Phe Ala Thr Glu Ala Lys Ala Leu Leu Glu
        35                  40                  45

Leu Pro Gly Val Thr Arg Glu Leu Asp His Asp Val Val Ala Asp Tyr
    50                  55                  60

Leu His Leu Gly Tyr Val Ala Ala Pro His Ser Met Phe Arg Asp Ile
65                  70                  75                  80

Arg Lys Leu Pro Pro Ala Thr Leu Leu Ser Val Glu Asn Gly Glu Val
                85                  90                  95

Arg Gln Trp Arg Tyr Trp Arg Leu Pro Ser Ser Val Ala Arg Tyr Val
            100                 105                 110

Thr Glu Ala Glu Trp Ile Gly Arg Ile Arg Asp Gly Met Glu Arg Ala
        115                 120                 125

Val His Arg Gln Met Val Ser Asp Val Pro Ile Gly Ala Phe Leu Ser
    130                 135                 140

Gly Gly Val Asp Ser Ser Ala Val Val Ala Phe Met Ala Lys His Ser
145                 150                 155                 160

Ala His Pro Ile Arg
                165

<210> SEQ ID NO 129
<211> LENGTH: 365
<212> TYPE: PRT
<213> ORGANISM: Streptomyces ghanaensis

<400> SEQUENCE: 129

Leu Gly Tyr Ile His Thr Ala Leu Lys Ser Ala Gly Phe His His Val
1               5                   10                  15

Ile Gln Val Asp Thr Pro Ala Leu Gly Leu Asp Ser Glu Gly Leu Arg
            20                  25                  30

Lys Leu Leu Ala Asp Phe Glu Pro Asp Leu Val Gly Val Ser Thr Thr
        35                  40                  45

Thr Pro Gly Leu Pro Gly Ala Ile Glu Ala Cys Glu Ala Ala Lys Ser
    50                  55                  60

Thr Gly Ala Lys Val Ile Leu Gly Gly Pro His Thr Glu Val Tyr Ala
65                  70                  75                  80

His Glu Asn Leu Val His Glu Ser Ile Asp Tyr Val Gly Val Gly Glu
                85                  90                  95

Gly Val Thr Ile Met Pro Glu Leu Ala Glu Ala Met Glu Arg Gly Glu
            100                 105                 110

Glu Pro Glu Gly Ile Arg Gly Leu Val Thr Arg Lys His Asp Gly Gly
```

115                 120                 125
Ala Ala Pro Met Val Asn Leu Glu Glu Val Gly Trp Pro Glu Arg Ala
    130                 135                 140

Gly Leu Pro Met Asp Arg Tyr Tyr Ser Ile Met Ala Pro Arg Pro Phe
145                 150                 155                 160

Ala Thr Met Ile Ser Ser Arg Gly Cys Pro Phe Lys Cys Ser Phe Cys
                    165                 170                 175

Phe Lys Gln Ala Val Asp Lys Lys Ser Met Tyr Arg Ser Pro Glu Asp
                180                 185                 190

Val Val Gly Glu Met Thr Glu Leu Lys Glu Arg Trp Gly Val Lys Glu
            195                 200                 205

Ile Met Phe Tyr Asp Asp Val Phe Thr Leu His Arg Gly Arg Val Arg
        210                 215                 220

Glu Ile Cys Gly Leu Ile Gly Glu Thr Gly Leu Lys Val Arg Trp Glu
225                 230                 235                 240

Ala Pro Thr Arg Val Asp Leu Val Pro Glu Pro Leu Leu Glu Ala Met
                    245                 250                 255

Ala Gly Ala Gly Cys Val Arg Leu Arg Phe Gly Ile Glu His Gly Asp
                260                 265                 270

Ser Glu Ile Leu Glu Arg Met Arg Lys Glu Ser Asp Ile Gln Lys Ile
            275                 280                 285

Glu Lys Ala Val Thr Ser Ala His Glu Ala Gly Ile Lys Gly Phe Gly
        290                 295                 300

Tyr Phe Ile Val Gly Trp Leu Gly Glu Thr Arg Glu Gln Phe Arg Arg
305                 310                 315                 320

Thr Val Asp Leu Ala Cys Arg Leu Pro Leu Asp Tyr Ala Ser Phe Tyr
                    325                 330                 335

Thr Ala Thr Pro Leu Pro Gly Thr Pro Leu His Thr Glu Ser Val Ala
                340                 345                 350

Ala Gly Gln Ile Pro Pro Asp Tyr Trp Asp Arg Phe Ser
            355                 360                 365

<210> SEQ ID NO 130
<211> LENGTH: 372
<212> TYPE: PRT
<213> ORGANISM: Pyrococcus horikoshii

<400> SEQUENCE: 130

Leu Gly Leu Ala Tyr Leu Ala Ser Met Val Arg Glu Glu His Asp Val
1               5                   10                  15

Lys Ile Ile Asp Gly Leu Ala Glu Asp Leu Thr Phe Ser Asp Ile Ala
                20                  25                  30

Lys Ile Ile Lys Lys Phe Asp Pro Asp Ile Val Gly Ile Thr Ala Thr
            35                  40                  45

Thr Ser Ala Met Tyr Asp Ala Tyr Thr Val Ala Lys Ile Ala Lys Asn
        50                  55                  60

Ile Asn Glu Asn Val Phe Val Met Gly Gly Pro His Val Thr Phe
65                  70                  75                  80

Thr Pro Glu Leu Thr Met Arg Glu Cys Pro Cys Ile Asp Ala Val Val
                    85                  90                  95

Arg Gly Glu Gly Glu Leu Thr Phe Lys Glu Leu Val Asp Ala Leu Ser
                100                 105                 110

Lys Gly Arg Glu Leu Lys Gly Ile Leu Gly Leu Ser Tyr Lys Glu Asn
            115                 120                 125

Gly Lys Val Arg Asn Glu Pro Pro Arg Pro Leu Ile Gln Asn Val Asp
130                 135                 140

Glu Ile Pro Ile Pro Ser Tyr Asp Leu Leu Pro Met Asp Lys Tyr Lys
145                 150                 155                 160

Ala Asp Gly Val Pro Phe Gly Val Val Met Thr Ser Arg Gly Cys Pro
                165                 170                 175

Phe Asn Cys Val Phe Cys Ser Ser Leu Gln Phe Gly Lys Arg Trp
            180                 185                 190

Arg Gly His Ser Val Glu Arg Val Ile Glu Leu Ser Ile Leu His
                195                 200                 205

Tyr Glu Tyr Gly Ile Lys Glu Ile Glu Phe Leu Asp Asp Thr Phe Thr
210                 215                 220

Leu Asn Lys Lys Arg Ala Ile Asp Ile Ser Leu Arg Ile Lys Gln Glu
225                 230                 235                 240

Gly Leu Asp Ile Ser Trp Thr Ala Ser Ser Arg Val Asn Thr Phe Asn
                245                 250                 255

Glu Lys Val Ala Lys Ala Met Lys Glu Gly Gly Cys His Thr Val Tyr
                260                 265                 270

Phe Gly Ile Glu Ser Ala Ser Pro Arg Ile Leu Glu Phe Ile Gly Lys
            275                 280                 285

Gly Ile Thr Pro Gln Gln Ser Ile Asp Ala Val Lys Thr Ala Lys Lys
290                 295                 300

Phe Gly Leu His Ala Leu Gly Ser Phe Ile Ile Gly Phe Pro Asp Glu
305                 310                 315                 320

Thr Arg Glu Glu Val Glu Ala Thr Ile Lys Phe Ala Lys Lys Leu Asp
                325                 330                 335

Ile Asp Tyr Ala Gln Phe Thr Ile Ala Thr Pro Tyr Pro Gly Thr Arg
                340                 345                 350

Leu Trp Glu Tyr Ala Ile Ala Asn Asn Leu Leu Leu Thr Met Asn Trp
            355                 360                 365

Arg Lys Tyr Thr
        370

<210> SEQ ID NO 131
<211> LENGTH: 519
<212> TYPE: PRT
<213> ORGANISM: Streptomyces ghanaensis

<400> SEQUENCE: 131

His Asp Thr Gly Val Ala Tyr Phe Glu Asp Gly Arg Leu Val Phe Ala
1               5                   10                  15

Val Glu Thr Glu Arg Leu Thr Arg Val Lys His Asp His Arg Ser Asp
                20                  25                  30

Val Ala Leu Arg His Val Leu Gln Glu Cys Val Asp Thr Asp Gly
            35                  40                  45

Ile Asp Leu Val Ala Val Ser Thr Pro Val Arg Ser Gly Leu Leu Arg
        50                  55                  60

Ile Pro Asp Leu Asp Arg Ala Met Glu Arg Ile Gly Ala Gly Ala Leu
65                  70                  75                  80

His His Arg Thr Val Cys Glu Met Leu Gly Arg Arg Val Glu Cys Val
                85                  90                  95

Val Val Thr His Glu Val Ser His Ala Ala Leu Ala Ala His Tyr Ala
            100                 105                 110

Asp Trp Glu Glu Gly Thr Val Val Leu Val Asn Glu Gly Arg Gly Gln
        115                 120                 125

```
Leu Thr Arg Ser Ser Leu Phe Arg Val Thr Gly Gly Ala Leu Glu Trp
        130                 135                 140

Val Asp Lys Asp Pro Leu Pro Trp Tyr Gly Asn Gly Phe Gly Trp Thr
145                 150                 155                 160

Ala Ile Gly Tyr Leu Leu Gly Phe Gly Pro Ser Pro Ser Val Ala Gly
                165                 170                 175

Lys Val Met Ala Met Gly Gly Tyr Gly Gln Pro Asp Pro Arg Ile Arg
                180                 185                 190

Glu Gln Leu Leu Ser Val Asp Pro Glu Val Met Asn Asp Arg Glu Leu
                195                 200                 205

Ala Glu Arg Val Arg Ala Asp Leu Ala Gly Arg Pro Glu Phe Ala Pro
210                 215                 220

Gly Phe Glu Thr Ala Ser Gln Val Val Ala Thr Phe Gln Glu Met Phe
225                 230                 235                 240

Thr Glu Ala Val Arg Ala Val Leu Asp Arg His Val Thr Arg Thr Asp
                245                 250                 255

Ala Gly Val Gly Pro Ile Ala Leu Gly Gly Cys Ala Leu Asn Ile
                260                 265                 270

Val Ala Asn Ser Ala Leu Arg Glu Glu Tyr Gly Arg Asp Val Ala Ile
                275                 280                 285

Pro Pro Ala Cys Gly Asp Ala Gly His Leu Thr Gly Ala Gly Leu Tyr
290                 295                 300

Ala Leu Ala Gln Val Ala Gly Val Lys Pro Glu Pro Phe Ser Val Tyr
305                 310                 315                 320

Arg Asn Gly Gly Gly Glu Ala Arg Ala Ala Val Leu Glu Ala Val Glu
                325                 330                 335

Gly Ala Gly Leu Arg Ala Val Pro Tyr Asp Arg Ser Ala Val Ala Gly
                340                 345                 350

Val Leu Ala Gly Gly Gly Val Val Ala Leu Thr Gln Gly Ala Ala Glu
                355                 360                 365

Leu Gly Pro Arg Ala Leu Gly His Arg Ser Leu Leu Gly Ser Pro Ala
370                 375                 380

Val Pro Gly Met Arg Glu Arg Met Ser Glu Lys Leu Lys Arg Arg Glu
385                 390                 395                 400

Trp Phe Arg Pro Leu Gly Ala Val Met Arg Asp Glu Arg Phe Ala Gly
                405                 410                 415

Leu Tyr Pro Gly Arg Ala Pro Ser Pro Tyr Met Leu Phe Glu Tyr Arg
                420                 425                 430

Leu Pro Asp Gly Ile Ala Pro Glu Ala Arg His Val Asn Gly Thr Cys
                435                 440                 445

Arg Ile Gln Thr Leu Gly Pro Glu Glu Asp Arg Leu Tyr Gly Leu Leu
450                 455                 460

Ala Glu Phe Glu Glu Leu Ser Gly Val Pro Ala Leu Ile Asn Thr Ser
465                 470                 475                 480

Leu Asn Gly Pro Gly Lys Pro Ile Ala His Thr Ala Arg Asp Val Leu
                485                 490                 495

Asp Asp Phe Ala Arg Thr Asp Val Asp Leu Phe Val Phe Asp Asp Leu
                500                 505                 510

Met Val Arg Gly Ala Ala Ala
                515

<210> SEQ ID NO 132
<211> LENGTH: 546
```

<212> TYPE: PRT
<213> ORGANISM: Streptomyces hygroscopicus

<400> SEQUENCE: 132

```
His Asp Ser Ala Ala Ser Leu Ile Arg Asp Gly Glu Leu Val Ala Ala
1               5                   10                  15

Val Glu Glu Arg Leu Asn Arg Ile Lys Lys Thr Thr Lys Phe Pro
            20                  25                  30

Leu Asn Ala Val Arg Glu Cys Leu Ala Leu Ala Gly Ala Arg Pro Glu
            35                  40                  45

Asp Val Asp Ala Val Gly Tyr Tyr Phe Pro Glu Asn His Ile Asp Thr
        50                  55                  60

Val Leu Asn His Leu Tyr Thr Glu Tyr Pro Arg Ala Pro Leu Arg Tyr
65                  70                  75                  80

Ser Arg Glu Leu Ile Arg Gln Arg Leu Lys Gly Leu Gly Trp Asp
                85                  90                  95

Leu Pro Asp Glu Lys Leu Val Tyr Val Pro His His Glu Ala His Ala
            100                 105                 110

Tyr Ser Ser Tyr Leu His Ser Gly Met Asp Ser Ala Leu Val Leu Val
            115                 120                 125

Leu Asp Gly Arg Gly Glu Leu His Ser Gly Thr Val Tyr Arg Ala Glu
130                 135                 140

Gly Thr Arg Leu Glu Lys Leu Ala Asp Tyr Pro Val Pro Lys Ser Leu
145                 150                 155                 160

Gly Gly Leu Tyr Leu Asn Ala Thr Tyr Leu Leu Gly Tyr Gly Phe Gly
                165                 170                 175

Asp Glu Tyr Lys Val Met Gly Leu Ala Pro Trp Gly Asn Pro Glu Thr
            180                 185                 190

Tyr Arg Asp Thr Phe Ala Lys Leu Tyr Thr Leu Gln Asp Asn Gly Glu
            195                 200                 205

Tyr Glu Leu His Gly Asn Ile Met Val Pro Asn Leu Val Ser Pro Leu
210                 215                 220

Phe Tyr Ala Glu Gly Phe Arg Pro Arg Arg Lys Gly Glu Pro Phe Thr
225                 230                 235                 240

Gln Ala His Arg Asp Phe Ala Ala Leu Gln Glu Thr Val Glu Lys
                245                 250                 255

Ile Val Leu His Ile Leu Glu Tyr Trp Ala Lys Thr Ser Gly His Ser
            260                 265                 270

Arg Leu Cys Phe Gly Gly Val Ala His Asn Ser Ser Leu Asn Gly
            275                 280                 285

Leu Ile Leu Lys Ser Gly Leu Phe Asp Glu Val Phe Val His Pro Ala
290                 295                 300

Ser His Asp Ala Gly Ala Gly Glu Gly Ala Tyr Ala Ala Ala Ala
305                 310                 315                 320

Ser Leu Gly Thr Leu Glu Arg Pro Gly Lys Arg Leu Leu Ser Ala Ser
                325                 330                 335

Leu Gly Pro Ala Leu Gly Gly Arg Glu Gln Ile Arg Ala Arg Leu Ala
            340                 345                 350

Asp Trp Ala Pro Leu Ile Asp Val Glu Phe Pro Asp Asp Ala Val Glu
            355                 360                 365

Thr Ala Ala Gly Leu Leu Ala Glu Gly Gln Val Leu Gly Trp Ala Tyr
        370                 375                 380

Gly Arg Ser Glu Phe Gly Pro Arg Ala Leu Gly His Arg Ser Ile Val
385                 390                 395                 400
```

```
Ala Asp Ala Arg Pro Glu Glu Asn Arg Thr Arg Ile Asn Ala Met Val
                405                 410                 415

Lys Lys Arg Glu Gly Phe Arg Pro Phe Ala Pro Val Val Thr Ala Glu
            420                 425                 430

Ala Ala Arg Asp Tyr Phe Asp Leu Ser Gly Ala Asp Gly Asn His Glu
        435                 440                 445

Phe Met Ser Phe Val Val Pro Val Leu Pro Glu Arg Arg Thr Glu Leu
    450                 455                 460

Gly Ala Val Thr His Val Asp Gly Thr Ala Arg Val Gln Val Val Ser
465                 470                 475                 480

Ala Glu Ser Gly Glu Arg Phe His Arg Leu Val Arg Arg Phe Gly Glu
                485                 490                 495

Leu Thr Gly Thr Pro Val Leu Leu Asn Thr Ser Phe Asn Asn Asn Ala
            500                 505                 510

Glu Pro Ile Val Gln Ser Leu Asp Asp Val Val Thr Ser Phe Leu Thr
        515                 520                 525

Thr Asp Leu Asp Val Leu Val Val Glu Asp Cys Leu Val Arg Gly Lys
    530                 535                 540

Ala Ser
545

<210> SEQ ID NO 133
<211> LENGTH: 344
<212> TYPE: PRT
<213> ORGANISM: Streptomyces ghanaensis

<400> SEQUENCE: 133

Leu Asp Leu Glu Arg Ile Ile Gly Arg Gln Arg Ile Arg Thr Gly Leu
1               5                   10                  15

Glu Ser Ser Ala Gly Leu Leu Arg Gly Arg Arg Ile Leu Val Thr Gly
            20                  25                  30

Ala Gly Gly Tyr Ile Gly Ser Glu Leu Cys Arg Gln Leu Ser Arg Trp
        35                  40                  45

Glu Pro Glu Ser Leu Met Met Leu Asp Arg Asn Glu Thr Ala Leu His
    50                  55                  60

Leu Ala Ala Thr Ser Ile Gly Asn Val Ser Pro Ser Val Arg Thr Ser
65                  70                  75                  80

Ile Leu Leu Ala Asp Ile Arg Asp Ser Arg Gly Leu Ala Arg Leu Phe
                85                  90                  95

Gln Gln Cys Arg Pro Asp Thr Val Phe His Ala Ala Leu Lys Trp
            100                 105                 110

Val Pro Ile Leu Glu Lys Phe Pro Gly Glu Ala Val Lys Thr Asn Val
        115                 120                 125

Phe Gly Thr Arg Ala Val Leu Glu Ala Ala Leu Ala Ala Asp Val Ala
    130                 135                 140

Phe Leu Val Asn Ile Ser Thr Asp Lys Ala Val Asp Pro Val Gly Val
145                 150                 155                 160

Leu Gly Tyr Ser Lys Arg Ile Ala Glu Gly Leu Thr Ala Ala Ala Ala
                165                 170                 175

Ile Gln Ala Gly Arg Pro Tyr Val Ser Val Arg Phe Gly Asn Val Leu
            180                 185                 190

Gly Cys Gln Gly Ser Phe Leu Asp Val Phe Ala Arg Gln Ile Ala Ala
        195                 200                 205

Gly Arg Pro Val Thr Val Thr His Pro Glu Val Thr Arg Tyr Leu Met
```

```
                210                 215                 220
Thr Val Gln Glu Ala Val Glu Leu Val Ile Gln Ser Val Ala Leu Gly
225                 230                 235                 240

Ser Val Gly His Ala Leu Val Leu Asp Met Gly Glu Gln Val Arg Ile
                245                 250                 255

Leu Asp Ile Ala Arg Arg Leu Ile Ala His Ala Gly Ala Glu Leu Pro
                260                 265                 270

Val Arg Tyr Val Gly Leu Arg Pro Gly Glu Lys Leu Thr Glu Ala Leu
                275                 280                 285

Val Ala Pro Ser Glu Ser Pro Val Arg His Gly His Pro Lys Ile Met
290                 295                 300

Glu Val Pro Val Pro Ala Leu Lys Ala Gly Asp Gly Pro Glu Leu Asp
305                 310                 315                 320

Ala Trp Gly Glu Asp Gln Ala Val Val Ala Ala Leu Arg Ala Thr Cys
                325                 330                 335

Leu Ala Met Ala Gly Asp Asp Pro
                340
```

<210> SEQ ID NO 134
<211> LENGTH: 346
<212> TYPE: PRT
<213> ORGANISM: Nocardioides sp.

<400> SEQUENCE: 134

```
Ile Asn Ile Thr Asp Val Leu Gly Arg Asn Gln Leu Asp Thr Asp Val
1               5                   10                  15

Ala Ser Ile Ala Gly Tyr Leu Ala Gly Arg Lys Val Leu Val Thr Gly
                20                  25                  30

Ala Gly Gly Ser Ile Gly Ser Glu Leu Cys Arg Gln Ile Tyr Arg Tyr
            35                  40                  45

Gln Pro Ala Glu Leu Met Met Leu Asp Arg Asp Glu Ser Ala Leu His
        50                  55                  60

Ser Val Gln Leu Ser Ile His Gly Arg Ala Leu Leu Asp Ser Asp Asp
65                  70                  75                  80

Val Ile Leu Cys Asp Ile Arg Asp Glu Lys Ala Val Arg Thr Ile Phe
                85                  90                  95

Ala Asn Arg Arg Pro Asp Val Val Phe His Ala Ala Leu Lys His
            100                 105                 110

Leu Pro Met Leu Glu Gln Tyr Pro Ala Glu Ala Val Lys Thr Asn Val
        115                 120                 125

Ile Gly Thr Arg Thr Val Leu Asp Ala Ala Asp Leu Val Gly Val Asp
130                 135                 140

Arg Phe Val Asn Ile Ser Thr Asp Lys Ala Ala Asn Pro Ser Ser Val
145                 150                 155                 160

Leu Gly Tyr Ser Lys Arg Val Ala Glu Arg Ile Thr Ala Ala Gln Ala
                165                 170                 175

Arg Glu Ala Ser Gly Thr Tyr Leu Ser Val Arg Phe Gly Asn Val Leu
            180                 185                 190

Gly Ser Arg Gly Ser Val Leu Ala Ala Phe Ala Arg Gln Ile Ala Ala
        195                 200                 205

Gly Gly Pro Ile Thr Val Thr His Pro Asp Val Ser Arg Phe Phe Met
    210                 215                 220

Thr Ile Glu Glu Ala Cys Gln Leu Val Ile Gln Ala Ala Ala Ile Gly
225                 230                 235                 240
```

-continued

```
Gly Pro Gly Glu Ala Leu Val Leu Asp Met Gly Glu Pro Val Lys Ile
            245                 250                 255

Val Asp Val Ala Glu Gln Leu Ile Glu Gln Ala Gly Thr Pro Val Pro
        260                 265                 270

Ile Glu Tyr Thr Gly Leu Arg Glu Gly Glu Lys Leu His Glu Glu Leu
            275                 280                 285

Phe Gly Glu Gly Glu Pro Cys Asp Val Arg Pro Arg His Pro Leu Val
        290                 295                 300

Ser His Val Pro Val Pro Ile Thr Asp Gly Glu Val Leu Gly Leu
305                 310                 315                 320

Thr Leu Val Gly Glu Pro Asp Asp Val Arg Gln Ala Leu His Asp Ala
            325                 330                 335

Cys Leu Val Ser Ile Glu Ala Asp Asp Pro
            340                 345

<210> SEQ ID NO 135
<211> LENGTH: 269
<212> TYPE: PRT
<213> ORGANISM: Streptomyces ghanaensis
<220> FEATURE:
<221> NAME/KEY: MOD_RES
<222> LOCATION: (53)..(53)
<223> OTHER INFORMATION: Any amino acid

<400> SEQUENCE: 135

Val Leu Val Val Gly Gly Ser Gly Phe Leu Gly Tyr Glu Val Leu Arg
1               5                   10                  15

Arg Ala Val Ala Ala Gly Trp Asp Val Ala Thr Tyr Arg Thr Arg
            20                  25                  30

Pro Glu Glu Leu Pro Pro Val Thr Trp Tyr Arg Ala Asp Leu Arg Asp
        35                  40                  45

Pro Gly Arg Met Xaa Glu Val Leu Ala Arg Thr Arg Pro Ala Ala Val
    50                  55                  60

Ile Asn Ala Ser Ser Gly His Ala Asp Trp Ala Val Thr Ala Asp Gly
65                  70                  75                  80

Ala Ala Arg Leu Ala Leu Glu Ala Ala Arg Ala Gly Cys Arg Leu Val
                85                  90                  95

His Val Ser Ser Asp Ala Val Phe Ser Gly Ala Asp Val His Tyr Pro
            100                 105                 110

Glu Glu Ala Leu Pro Asp Pro Val Ser Pro Tyr Gly Ala Ala Lys Ala
        115                 120                 125

Ala Ala Glu Thr Ala Val Arg Val Ala Val Pro Glu Ala Ala Val Val
    130                 135                 140

Arg Thr Ser Leu Ile Val Gly His Asn Arg Ser Ala His Glu Glu Ala
145                 150                 155                 160

Val His Ala Leu Ala Ala Gly Arg Arg Ala Gly Val Leu Phe Thr Asp
                165                 170                 175

Asp Val Arg Cys Pro Val His Val Asp Asp Leu Ala Ser Ala Leu Leu
            180                 185                 190

Glu Ile Ala Ala Ser Asp Gly Ser Gly Val Phe His Val Ala Gly Pro
        195                 200                 205

Asp Ala Met Asn Arg His Asp Leu Gly Val Leu Ile Ala Arg Arg Asp
    210                 215                 220

Gly Leu Asp Pro Ala Arg Leu Pro Ala Gly Leu Arg Ser Glu Val Ala
225                 230                 235                 240

Pro Pro Gly Asn Leu Asp Ile Arg Leu Val Thr Asp Ala Thr Arg Ala
```

245                 250                 255
Arg Leu Arg Thr Arg Leu Arg Gly Ala Arg Glu Phe Leu
            260                 265

<210> SEQ ID NO 136
<211> LENGTH: 269
<212> TYPE: PRT
<213> ORGANISM: Streptomyces coelicolor

<400> SEQUENCE: 136

Val Leu Val Val Gly Gly Ser Gly Phe Leu Gly Thr Glu Leu Val Arg
1               5                   10                  15

Gln Ala Ser Ala Ala Gly His Arg Val Ala Ala Thr Phe Ala Thr Arg
            20                  25                  30

Pro Cys Asp Gly Pro Glu Ala Thr Trp His Glu Val Asp Leu Arg Asp
        35                  40                  45

Gly Ala Arg Val Glu Glu Val Val Ala Ser Leu Ala Pro Cys Val Val
    50                  55                  60

Ile Asn Ala Ser Ser Gly Ser Ala Asp Trp Ala Val Thr Ala Glu Gly
65                  70                  75                  80

Ser Val Arg Leu Ala Met Thr Ala Val Lys Tyr Asp Cys Arg Leu Val
                85                  90                  95

His Val Ser Ser Asp Ala Val Phe Ser Gly Ser Arg Val His Tyr Asp
            100                 105                 110

Glu Ser Cys Leu Pro Asp Pro Val Thr Pro Tyr Gly Ala Ala Lys Ala
        115                 120                 125

Ala Ala Glu Thr Gly Ile Arg Leu Leu Ala Pro Ala Val Ile Ala
    130                 135                 140

Arg Thr Ser Leu Ile Ile Gly Gly Ile Gln Ser Glu His Val Arg Leu
145                 150                 155                 160

Val His Asp Leu Ala Thr Gly Ser Arg Thr Gly Ala Leu Phe Thr Asp
                165                 170                 175

Asp Val Arg Cys Pro Val His Val Glu Asp Leu Ala Ala Ala Leu Leu
            180                 185                 190

Glu Leu Ala Phe Thr Gly Ala Cys Gly Val His His Leu Ala Gly Lys
        195                 200                 205

Asp Ala Val Ser Arg His Gly Leu Gly Val Leu Ile Ala Gln Arg Asp
    210                 215                 220

Gly Leu Asp Ala Ser Arg Leu Pro Glu Gly Leu Arg Ala Gly Thr Ser
225                 230                 235                 240

Leu Ser Gly Ala Leu Asp Val Arg Leu Asp Ser Arg Ala Thr Arg Ala
                245                 250                 255

Lys Leu Arg Thr Arg Val Arg Gly Val His Glu Phe Leu
            260                 265

<210> SEQ ID NO 137
<211> LENGTH: 300
<212> TYPE: PRT
<213> ORGANISM: Streptomyces ghanaensis

<400> SEQUENCE: 137

Leu Val Thr Gly Ala Ala Gly Phe Ile Gly Ser His Leu Val Thr Glu
1               5                   10                  15

Leu Arg Asn Ser Gly Arg Asn Val Val Ala Val Asp Arg Arg Pro Leu
            20                  25                  30

Pro Asp Asp Leu Glu Ser Thr Ser Pro Pro Phe Thr Gly Ser Leu Arg

```
                35                  40                  45
Glu Ile Arg Gly Asp Leu Asn Ser Leu Asn Leu Val Asp Cys Leu Lys
 50                  55                  60

Asn Ile Ser Thr Val Phe His Leu Ala Ala Leu Pro Gly Val Arg Pro
 65                  70                  75                  80

Ser Trp Thr Gln Phe Pro Glu Tyr Leu Arg Cys Asn Val Leu Ala Thr
                 85                  90                  95

Gln Arg Leu Met Glu Ala Cys Val Gln Ala Gly Val Glu Arg Val Val
                100                 105                 110

Val Ala Ser Ser Ser Val Tyr Gly Gly Ala Asp Gly Val Met Ser
            115                 120                 125

Glu Asp Asp Leu Pro Arg Pro Leu Ser Pro Tyr Gly Val Thr Lys Leu
130                 135                 140

Ala Ala Glu Arg Leu Ala Leu Ala Phe Ala Ala Arg Gly Asp Ala Glu
145                 150                 155                 160

Leu Ser Val Gly Ala Leu Arg Phe Phe Thr Val Tyr Gly Pro Gly Gln
                165                 170                 175

Arg Pro Asp Met Phe Ile Ser Arg Leu Ile Arg Ala Thr Leu Arg Gly
                180                 185                 190

Glu Pro Val Glu Ile Tyr Gly Asp Gly Thr Gln Leu Arg Asp Phe Thr
            195                 200                 205

His Val Ser Asp Val Val Arg Ala Leu Met Leu Thr Ala Ser Val Arg
210                 215                 220

Asp Arg Gly Ser Ala Val Leu Asn Ile Gly Thr Gly Ser Ala Val Ser
225                 230                 235                 240

Val Asn Glu Val Val Ser Met Thr Ala Glu Leu Thr Gly Leu Arg Pro
                245                 250                 255

Cys Thr Ala Tyr Gly Ser Ala Arg Ile Gly Asp Val Arg Ser Thr Thr
                260                 265                 270

Ala Asp Val Arg Gln Ala Gln Ser Val Leu Gly Phe Thr Ala Arg Thr
            275                 280                 285

Gly Leu Arg Glu Gly Leu Ala Thr Gln Ile Glu Trp
290                 295                 300

<210> SEQ ID NO 138
<211> LENGTH: 282
<212> TYPE: PRT
<213> ORGANISM: Symbiobacterium thermophilum

<400> SEQUENCE: 138

Leu Val Thr Gly Ala Ala Gly Phe Ile Gly Ser His Leu Val Glu Ala
 1               5                  10                  15

Leu Arg Ala Ala Gly His Asp Val Gly Val Asp Arg Arg Pro Gly
            20                  25                  30

Ala Asp Val Val Gly Asp Leu Leu Thr Leu Asp Leu Ala Pro Leu Leu
            35                  40                  45

Asp Gly Val Glu Tyr Val Val His Leu Ala Gly Gln Pro Gly Val Arg
        50                  55                  60

Glu Ser Trp Ser Gln Phe Pro Ala Tyr Leu Ala Gly Asn Leu Gln Thr
 65                  70                  75                  80

Thr Gln Arg Leu Leu Glu Ser Leu Arg Asp Arg Pro Leu Lys Lys Phe
                85                  90                  95

Val Leu Ala Ser Thr Ser Ser Val Tyr Gly Glu Val Pro Met Pro Ala
            100                 105                 110
```

Arg Glu Asp Gly Pro Ala Met Pro Val Ser Pro Tyr Gly Leu Thr Lys
            115                 120                 125

Leu Ala Ala Glu Lys Leu Cys Asp Leu Tyr Gly Arg Thr Ala Gly Ile
        130                 135                 140

Pro Trp Val Ala Leu Arg Tyr Phe Thr Val Tyr Gly Pro Arg Gln Arg
145                 150                 155                 160

Pro Asp Met Ala Phe Ser Arg Trp Phe Asn Ala Ala Leu Asp Gly Glu
                165                 170                 175

Pro Ile Gln Ile Tyr Gly Asp Gly Ser Gln Leu Arg Asp Phe Thr Tyr
            180                 185                 190

Val Ala Asp Ala Val Thr Ala Thr Gln Arg Ala Ala Leu Asn Pro Val
        195                 200                 205

Val Gly Val Pro Ile Asn Val Gly Gly Ser Ala Val Thr Val Arg
210                 215                 220

Glu Ala Ile Arg Leu Ile Ala Ala Ile Thr Gly Arg Pro Ile Arg Ile
225                 230                 235                 240

Arg Gln Leu Pro Pro Ala Pro Gly Asp Met Arg Glu Thr Arg Ala Asp
                245                 250                 255

Thr Glu Arg Leu Trp Arg Glu Val Gly Phe Arg Pro Ser Thr Pro Leu
            260                 265                 270

Glu Glu Gly Leu Trp Gln Gln Tyr Arg Trp
        275                 280

<210> SEQ ID NO 139
<211> LENGTH: 115
<212> TYPE: PRT
<213> ORGANISM: Streptomyces ghanaensis

<400> SEQUENCE: 139

His Ala Ser Thr Tyr Gly Ser Thr Phe Leu Gly Arg Tyr Gly Ala Leu
1               5                   10                  15

Ala Ala Ala Cys Gly Gly Glu Gly Gln Pro Ala Asp Ser Val Arg Glu
            20                  25                  30

Phe Ala Glu Ala Phe Ala Met Thr Ile Thr Met Ala Asp Asp Leu Thr
        35                  40                  45

Asp Tyr Asp Arg Asn Gly Glu Arg Asp Gly Asn Leu Ala His Leu Met
    50                  55                  60

Arg Thr Gly Ala Val Ala Gly Gln Asp Val Val Asp Leu Leu Glu Glu
65                  70                  75                  80

Leu Arg Gly Arg Ala Leu Ala Ala Val Ala Pro Pro Gly Ala Pro
                85                  90                  95

Gly Leu Val Pro Val Val His Leu Tyr Thr Asp Asp Val Leu Val Arg
            100                 105                 110

Leu Leu Pro
        115

<210> SEQ ID NO 140
<211> LENGTH: 115
<212> TYPE: PRT
<213> ORGANISM: Loktanella vestfoldensis

<400> SEQUENCE: 140

His Gln Ala Lys Thr Gly Ala Leu Phe Ile Ala Ala Thr Gln Met Gly
1               5                   10                  15

Ala Val Ala Ala Gly Gln Glu Ala Glu Pro Trp Ala Glu Leu Gly Ala
            20                  25                  30

```
Arg Ile Gly Glu Ala Phe Gln Val Ala Asp Asp Leu Arg Asp Ala Leu
            35                  40                  45

Cys Asp Asp Ala Thr Leu Gly Lys Pro Ala Gly Gln Asp Asp Leu His
 50                  55                  60

Gly Arg Pro Asn Ala Val Ala Ala Tyr Gly Val Gln Gly Ala Val Lys
 65                  70                  75                  80

Arg Phe Asp Asp Ile Leu Gly Gly Ala Ile Ser Ser Ile Pro Ala Cys
                 85                  90                  95

Pro Gly Glu Ala Ala Leu Ala Gln Met Val Arg Ala Tyr Ala Asp Arg
            100                 105                 110

Leu Val Pro
        115

<210> SEQ ID NO 141
<211> LENGTH: 234
<212> TYPE: PRT
<213> ORGANISM: Streptomyces ghanaensis

<400> SEQUENCE: 141

Val Leu Ala Arg Leu Arg Glu His Gln Pro Gly Pro Val His Ile Ile
 1               5                  10                  15

Asp Pro Phe Lys Val Pro Val Thr Glu Ala Val Glu Lys Ala Ala Glu
                20                  25                  30

Leu Thr Arg Leu Gly Phe Ala Ala Val Leu Leu Ala Ser Thr Asp Tyr
            35                  40                  45

Glu Ser Phe Glu Ser His Met Glu Pro Tyr Val Ala Ala Val Lys Ala
 50                  55                  60

Ala Thr Pro Leu Pro Val Val Leu His Phe Pro Pro Arg Pro Gly Ala
 65                  70                  75                  80

Gly Phe Pro Val Val Arg Gly Ala Asp Ala Leu Leu Leu Pro Ala Leu
                 85                  90                  95

Leu Gly Ser Gly Asp Asp Tyr Phe Val Trp Lys Ser Phe Leu Glu Thr
            100                 105                 110

Leu Ala Ala Phe Pro Gly Arg Ile Pro Arg Glu Glu Trp Pro Glu Leu
        115                 120                 125

Leu Leu Thr Val Ala Leu Thr Phe Gly Glu Asp Pro Arg Thr Gly Asp
    130                 135                 140

Leu Leu Gly Thr Val Pro Val Ser Thr Ala Ser Thr Glu Glu Ile Asp
145                 150                 155                 160

Arg Tyr Leu His Val Ala Arg Ala Phe Gly Phe His Met Val Tyr Leu
                165                 170                 175

Tyr Ser Arg Asn Glu His Val Pro Pro Glu Val Val Arg His Phe Arg
            180                 185                 190

Lys Gly Leu Gly Pro Asp Gln Val Leu Phe Val Ser Gly Asn Val Arg
        195                 200                 205

Ser Gly Arg Gln Val Thr Glu Tyr Leu Asp Ser Gly Ala Asp Tyr Val
    210                 215                 220

Gly Phe Ala Gly Ala Leu Glu Gln Pro Asp
225                 230

<210> SEQ ID NO 142
<211> LENGTH: 224
<212> TYPE: PRT
<213> ORGANISM: Thermofilum pendens

<400> SEQUENCE: 142
```

Ile Leu Glu Lys Ile Arg Glu His Gly Ala Ile His Met Thr Leu Ile
1               5                   10                  15

Asp Pro Glu Lys Thr Thr Pro Glu Val Ala Ala Arg Ile Ala Arg Glu
            20                  25                  30

Val Ala Glu Ala Gly Thr Ser Ala Ile Met Val Gly Gly Ser Ile Gly
        35                  40                  45

Val Ser Glu Ala Met Thr Asp Glu Val Val Leu Ala Ile Lys Arg Ser
    50                  55                  60

Thr Glu Val Pro Val Ile Leu Phe Pro Gly Ser Pro Thr Ala Leu Ser
65                  70                  75                  80

Arg His Ala Asp Ala Val Trp Phe Leu Ser Val Leu Asn Ser Gln Asn
                85                  90                  95

Pro Tyr Phe Ile Thr Gly Ala Gln Met Gln Gly Ala Pro Ile Val Lys
            100                 105                 110

Arg Tyr Gly Leu Glu Val Leu Pro Leu Gly Tyr Ile Ile Val Gly Glu
        115                 120                 125

Gly Gly Ala Val Ser Ile Val Ser Tyr Thr Arg Pro Leu Pro Phe Ala
    130                 135                 140

Lys Pro Glu Val Val Ala Ala Tyr Ala Leu Ala Ala Glu Tyr Met Gly
145                 150                 155                 160

Phe Gln Phe Val Tyr Leu Glu Gly Ser Gly Glu Pro Val Pro
                165                 170                 175

Pro Lys Ile Val Lys Met Val Lys Gly Val Thr Thr Leu Pro Leu Ile
            180                 185                 190

Val Gly Gly Gly Ile Arg Ser Pro Glu Val Ala Lys Glu Leu Ala Lys
        195                 200                 205

Ala Gly Ala Asp Ile Ile Val Thr Gly Thr Ile Val Glu Glu Ser Glu
    210                 215                 220

<210> SEQ ID NO 143
<211> LENGTH: 180
<212> TYPE: PRT
<213> ORGANISM: Streptomyces ghanaensis

<400> SEQUENCE: 143

Leu Thr Gly Val Asp Leu Val Val His Ala Gly Glu Val Ala Ala Ile
1               5                   10                  15

Val Gly Ser Asn Gly Thr Gly Lys Ser Thr Leu Leu Lys Ile Cys Ala
            20                  25                  30

Gly Leu Leu Ser Pro Asp Lys Gly Arg Val Thr Val Ser Gly His Leu
        35                  40                  45

Gly Tyr Cys Pro Gln Asn Ala Gly Val Met Gly Phe Leu Thr Pro Arg
    50                  55                  60

Glu His Phe Thr Leu Phe Gly Thr Gly Arg Gly Leu Ser Arg Arg Glu
65                  70                  75                  80

Ser Asp Arg Arg Gly Arg Arg Leu Ala Gly Glu Leu Asp Trp Ala Pro
                85                  90                  95

Ala Glu Gly Val Leu Ala Lys Asp Leu Ser Gly Gly Thr Arg Gln Lys
            100                 105                 110

Leu Asn Val Val Leu Ser Ala Leu Gly Asp Pro Asp Leu Leu Leu Leu
        115                 120                 125

Asp Glu Pro Tyr Gln Gly Phe Asp His Gly Ser Tyr Val Asp Phe Trp
    130                 135                 140

Gln Ser Val Trp Glu Trp Arg Glu Ala Gly Lys Ala Val Val Val Val
145                 150                 155                 160

```
Thr His Met Leu Asn Gln Leu Asp Arg Val Asp Gln Val Leu Asp Leu
                165                 170                 175

Thr Pro Gly Lys
            180

<210> SEQ ID NO 144
<211> LENGTH: 180
<212> TYPE: PRT
<213> ORGANISM: Mycobacterium flavescens

<400> SEQUENCE: 144

Leu Arg Gly Val Asp Leu Thr Leu Gln Pro Gly Glu Val Val Gly Leu
1               5                   10                  15

Val Gly Glu Asn Gly Ser Gly Lys Ser Thr Ile Met Lys Ile Leu Val
                20                  25                  30

Gly Glu Leu Ala Pro Asp Ala Gly Thr Val Val Arg Ser Gly Val Leu
            35                  40                  45

Gly Tyr Cys Pro Gln Gln Pro Val Val Tyr Glu Arg Leu Thr Cys Asp
    50                  55                  60

Glu His Ile Glu Leu Phe Ala Arg Ala Tyr Arg Met Thr His Glu Gly
65                  70                  75                  80

Glu Arg Arg Ala Arg Arg Asp Leu Tyr Glu Ala Leu Gly Phe Glu Arg
                85                  90                  95

Tyr Ala Gly Thr Arg Ala Asp Arg Leu Ser Gly Gly Thr Leu Ala Lys
            100                 105                 110

Leu Asn Leu Thr Leu Ala Met Leu Ala Asp Pro Gln Val Leu Leu Leu
        115                 120                 125

Asp Glu Pro Tyr Ala Gly Phe Asp Trp Asp Thr Tyr Leu Lys Phe Trp
130                 135                 140

Asp Leu Val Ala Arg Arg Asp Asp Gly Arg Ser Val Leu Ile Ile
145                 150                 155                 160

Ser His Phe Val Ala Asp Glu His Arg Phe Asp Arg Ile Val Lys Leu
                165                 170                 175

Cys Asp Gly Arg
            180

<210> SEQ ID NO 145
<211> LENGTH: 218
<212> TYPE: PRT
<213> ORGANISM: Streptomyces ghanaensis

<400> SEQUENCE: 145

Thr Leu Arg Met Ala Glu Met Thr Phe Arg Glu Leu Leu Arg Arg Arg
1               5                   10                  15

Gly Val Leu Gly Leu Leu Leu Val Pro Leu Val Phe Tyr Leu Gly
                20                  25                  30

Arg Tyr Asp Gln Thr Gly Gln Ala Val Arg Phe Ala Ser Leu Gly Val
            35                  40                  45

Gly Phe Ala Val Ser Ala Ala Ala Leu Phe Ser Ala Val Gly Gly Arg
    50                  55                  60

Glu Ile Glu Pro Leu Leu Ala Leu Ser Gly Phe Arg Pro Leu Gln Leu
65                  70                  75                  80

Phe Leu Gly Arg Leu Leu Ala Leu Leu Thr Ala Gly Met Gly Val Ser
                85                  90                  95

Ala Leu Tyr Ala Val Ile Ile Leu Val Gly Gln Asp Val Ala His Pro
            100                 105                 110
```

```
Arg Ala Val Ala Val Glu Leu Ala Leu Thr Thr Leu Val Ala Val Pro
            115                 120                 125

Leu Gly Leu Leu Leu Gly Ala Ala Val Pro Arg Asp Met Glu Gly Ala
        130                 135                 140

Leu Leu Leu Ile Ser Val Ile Gly Ala Gln Met Val Met Asp Pro Ala
145                 150                 155                 160

Lys Asp Ser Ala Lys Val Leu Pro Phe Trp Ser Thr Arg Glu Ile Ile
                165                 170                 175

Thr Tyr Ala Val Asp Gly Ala Asp Ser Gly Ser Phe Asp Ser Gly Val
            180                 185                 190

Ala His Ala Val Gly Val Thr Leu Leu Val Ala Val Ser Gly Cys
        195                 200                 205

Val Thr Ala Gly Arg Leu Arg Arg Arg
    210                 215

<210> SEQ ID NO 146
<211> LENGTH: 236
<212> TYPE: PRT
<213> ORGANISM: Mycobacterium sp.

<400> SEQUENCE: 146

Thr Leu Leu Leu Thr Arg Ser Phe Ile Thr Asp Tyr Val Arg Asn Pro
1               5                   10                  15

Val Asn Leu Ile Met Leu Ile Leu Val Pro Leu Val Phe Val Leu Val
                20                  25                  30

Ala Ala Gly Ser Ile Ala Asp Ala Met Glu Leu Leu Gln Gly Arg Thr
            35                  40                  45

Gly Ala Ala Thr Gln Thr Ala Thr Ser Gly Trp Ala Ala Gly Phe Leu
        50                  55                  60

Ser Gly Leu Ala Met Tyr Phe Gln Ile Arg Ser Ala Arg Arg Ala Asp
65                  70                  75                  80

Lys Arg Leu Gln Leu Ala Gly Leu Pro Ala Ala Arg Leu Leu Ala Ala
                85                  90                  95

Arg Ala Gly Thr Gly Leu Leu Met Ala Gly Leu Val Ser Ala Val Ala
            100                 105                 110

Leu Ala Ala Leu Ala Ala Arg Thr Gly Ile Asp Asn Pro Ala Arg Val
        115                 120                 125

Ile Val Gly Thr Leu Met Phe Ala Leu Ile Tyr Leu Ala Ile Gly Ala
    130                 135                 140

Leu Val Gly Ala Val Ile Ala Asp Pro Val Asn Gly Ala Val Ile Ile
145                 150                 155                 160

Leu Leu Ile Trp Met Ile Asp Val Phe Val Gly Pro Ala Gly Ser Gly
                165                 170                 175

Gly Asp Tyr Val Ala Thr Arg Trp Phe Pro Thr His Phe Val Thr Leu
            180                 185                 190

Trp Met Val Gly Thr Pro Ser His His Ala Gly Arg Leu Gly Asp Leu
        195                 200                 205

Gly Val Ala Ser Val Trp Met Val Gly Ala Leu Ala Val Ala Gly Thr
    210                 215                 220

Val Val Ser Ala Gly Ser Arg Thr Gly Arg Arg Arg
225                 230                 235

<210> SEQ ID NO 147
<211> LENGTH: 548
<212> TYPE: PRT
```

-continued

<213> ORGANISM: Streptomyces ghanaensis

<400> SEQUENCE: 147

```
Leu Val Val Gly Leu Phe Gln Arg Leu Phe Asp Ala Leu Gly Ala
1               5                   10                  15

Gly Gly Gly Val Trp Leu Ile Ile Ala Leu Val Ala Ile Glu Ala
            20                  25                  30

Gly Arg Leu Phe Leu Gln Phe Gly Val Met Ile Asn Arg Leu Glu Pro
        35                  40                  45

Arg Val Gln Tyr Gly Thr Thr Ala Arg Leu Arg His Ala Leu Leu Gly
    50                  55                  60

Ser Ala Leu Arg Gly Ser Glu Val Thr Ala Arg Thr Ser Pro Gly Glu
65                  70                  75                  80

Ser Leu Arg Thr Val Gly Glu Asp Val Asp Glu Thr Gly Phe Phe Val
                85                  90                  95

Ala Trp Ala Pro Thr Asn Leu Ala His Trp Leu Phe Val Ala Ala Ser
            100                 105                 110

Val Thr Val Met Met Arg Ile Asp Ala Val Thr Gly Ala Leu Leu
        115                 120                 125

Ala Leu Leu Val Leu Leu Thr Leu Val Thr Ala Leu Ala His Ser Arg
    130                 135                 140

Phe Leu Arg His Arg Arg Ala Thr Arg Ala Ala Ser Gly Glu Val Ala
145                 150                 155                 160

Gly Ala Leu Arg Glu Met Val Gly Ala Val Gly Ala Val Gln Ala Ala
                165                 170                 175

Ala Ala Glu Pro Gln Val Ala Ala His Val Ala Gly Leu Asn Gly Ala
            180                 185                 190

Arg Ala Glu Ala Ala Val Arg Glu Glu Leu Tyr Ala Val Val Gln Arg
        195                 200                 205

Thr Val Ile Gly Asn Pro Ala Pro Ile Gly Val Gly Val Val Leu Leu
    210                 215                 220

Leu Val Ala Gly Arg Met Asp Glu Gly Thr Phe Ser Val Gly Asp Leu
225                 230                 235                 240

Ala Leu Phe Ala Phe Tyr Leu Gln Ile Leu Thr Glu Ala Leu Gly Ser
                245                 250                 255

Ile Gly Met Leu Ser Val Arg Leu Gln Arg Val Ser Val Ala Leu Gly
            260                 265                 270

Arg Ile Thr Asn Asn Leu Gly Cys Arg Leu Arg Arg Ser Leu Glu Arg
        275                 280                 285

Ala Ser Pro Pro Ile Ala Ser Asp Ala Pro Gly Gly Thr Gly Glu Gly
    290                 295                 300

Ala Ala Ala Pro Asp Ala Gly Pro Glu Pro Ala Pro Leu Arg Glu
305                 310                 315                 320

Leu Ala Val Arg Gly Leu Thr Ala Arg His Pro Gly Ala Gly His Gly
                325                 330                 335

Ile Glu Asp Val Asp Leu Val Val Glu Arg His Thr Val Thr Val Val
            340                 345                 350

Thr Gly Arg Val Gly Ser Gly Lys Ser Thr Leu Val Arg Ala Val Leu
        355                 360                 365

Gly Leu Leu Pro His Glu Arg Gly Thr Val Leu Trp Asn Gly Glu Pro
    370                 375                 380

Ile Ala Asp Pro Ala Ser Phe Leu Val Ala Pro Arg Cys Gly Tyr Thr
385                 390                 395                 400
```

```
Pro Gln Val Pro Cys Leu Phe Ser Gly Thr Val Arg Glu Asn Val Leu
                405                 410                 415

Leu Gly Arg Asp Gly Ala Ala Phe Asp Glu Ala Val Arg Leu Ala Val
            420                 425                 430

Ala Glu Pro Asp Leu Ala Ala Met Gln Asp Gly Pro Asp Thr Val Val
            435                 440                 445

Gly Pro Arg Gly Leu Arg Leu Ser Gly Gly Gln Ile Gln Arg Val Ala
            450                 455                 460

Ile Ala Arg Met Leu Val Gly Asp Pro Glu Leu Val Val Leu Asp Asp
465                 470                 475                 480

Val Ser Ser Ala Leu Asp Pro Glu Thr Glu His Leu Leu Trp Glu Arg
                485                 490                 495

Leu Leu Asp Gly Thr Arg Thr Val Leu Ala Val Ser His Arg Pro Ala
                500                 505                 510

Leu Leu Arg Ala Ala Asp Arg Val Val Leu Glu Gly Gly Arg Val
                515                 520                 525

Glu Ala Ser Gly Thr Phe Glu Glu Val Met Ala Val Ser Ala Glu Met
            530                 535                 540

Gly Arg Ile Trp
545

<210> SEQ ID NO 148
<211> LENGTH: 548
<212> TYPE: PRT
<213> ORGANISM: Symbiobacterium thermophilum

<400> SEQUENCE: 148

Val Val Pro Gly Leu Leu Thr Gln Ala Phe Asp Arg Leu Thr Gly
1               5                   10                  15

Ala Ala Pro Val Ala Leu Asp Pro Trp Ala Ile Ile Ala Leu Leu Met
                20                  25                  30

Ala Ala Ala Val Ala Arg Val Ala Ala Leu Ala Ala Gly Phe Phe Ala
            35                  40                  45

Ser Ala Thr Gly Arg Glu Ser Met Ala Asn Leu Leu Arg Arg Asn Val
50                  55                  60

Leu Glu Arg Ile Leu Glu Met Pro Gly Ala Ala Ala Leu Pro Glu Ser
65                  70                  75                  80

Pro Gly Glu Ala Leu Asn Arg Leu Arg Asp Asp Val Leu His Ala Glu
                85                  90                  95

Glu Thr Ala Asp Phe Met Leu Asp Val Val Gly Gln Thr Thr Phe Ala
            100                 105                 110

Ala Val Ala Leu Ser Met Leu Leu Arg Ile Asp Ala Arg Leu Thr Val
            115                 120                 125

Leu Val Phe Leu Pro Leu Ala Leu Val Leu Val Thr Arg Ala Val
            130                 135                 140

Gly Arg Arg Ile Leu Gln Asn Arg Arg Trp Ser Arg Glu Ala Thr Ala
145                 150                 155                 160

Arg Val Thr Ala Leu Ile Ala Glu Leu Phe Ala Ser Val Gln Ala Val
                165                 170                 175

Gln Val Ala Gly Ala Glu Ser Arg Val Val Ala His Leu Arg Arg Leu
            180                 185                 190

Asn Asp Glu Arg Arg Arg Ala Met Val Ala Asp Arg Leu Leu Thr Gln
            195                 200                 205

Val Leu Glu Ser Ile Ala Leu Asn Ala Ser Ser Val Gly Thr Gly Leu
            210                 215                 220
```

Ile Leu Leu Leu Gly Ala Arg Thr Met Ala Thr Gly Gln Phe Thr Val
225                 230                 235                 240

Gly Glu Phe Ala Leu Phe Val Tyr Tyr Leu Gly Tyr Val Ala Asp Phe
            245                 250                 255

Thr His Phe Ala Gly Arg Trp Leu Ala Leu Tyr Arg Gln Ala Gly Val
        260                 265                 270

Ala Lys Asp Arg Leu Leu Ala Leu Leu Gln Gly Ala Pro Pro Thr Arg
    275                 280                 285

Leu Leu Arg Arg Thr Glu Ile Pro Leu Arg Gly Pro Val Pro Val Pro
290                 295                 300

Pro Glu Pro Pro Pro Pro Ala Glu Pro Leu Arg Glu Leu Arg Thr
305                 310                 315                 320

Glu Gly Leu Thr Tyr Arg Tyr Pro Asp Ser Gly Arg Gly Ile Glu Gly
                325                 330                 335

Val Ser Leu Thr Ile Pro Arg Gly Ser Phe Thr Val Ile Ala Gly Arg
            340                 345                 350

Val Gly Ser Gly Lys Thr Thr Leu Leu Arg Val Leu Met Gly Leu Leu
        355                 360                 365

Pro Ala Gln Ala Gly Thr Val Tyr Trp Asn Gly Glu Pro Val Ala Asp
    370                 375                 380

Pro Gly Ser Phe Met Val Pro Pro Arg Cys Ala Ala Thr Pro Gln Val
385                 390                 395                 400

Pro Ile Leu Phe Ser Gly Thr Leu Ala Glu Asn Ile Arg Met Gly Leu
                405                 410                 415

Asp Ala Thr Glu Ala Glu Val Ala Ala Val Tyr Asp Ala Val Leu
            420                 425                 430

Glu Arg Asp Leu Ala Gly Met Glu Asp Gly Leu Glu Thr Gln Val Gly
        435                 440                 445

Ala Arg Gly Val Arg Leu Ser Gly Gly Gln Val Gln Arg Thr Ala Ala
    450                 455                 460

Ala Arg Met Phe Leu Arg Arg Pro Glu Leu Leu Ile Met Asp Asp Leu
465                 470                 475                 480

Ser Ser Ala Leu Asp Val Glu Thr Glu Gln Ile Leu Trp Glu Arg Leu
                485                 490                 495

Phe Arg Gln Arg Asp Val Thr Cys Leu Val Val Ser His Arg Glu Ala
            500                 505                 510

Ala Leu Arg Arg Ala Asp Gln Ile Ile Leu Leu Lys Asp Gly Arg Val
        515                 520                 525

Val Asp Arg Gly Thr Leu Asp Glu Leu Leu Ala Arg Ser Ala Glu Met
    530                 535                 540

Arg Ala Leu Trp
545

<210> SEQ ID NO 149
<211> LENGTH: 541
<212> TYPE: PRT
<213> ORGANISM: Streptomyces ghanaensis

<400> SEQUENCE: 149

Met Gly Leu Gln Leu Val Ala Pro Tyr Leu Leu Arg Gly Phe Ile Asp
1               5                   10                  15

Gly Ala Leu Ser Gly Asp Ser Arg Lys Thr Leu Leu Asp Leu Ala Ala
            20                  25                  30

Trp Ser Leu Ala Ala Ala Val Gly Thr Leu Val Val Thr Ala Gly Thr

-continued

```
            35                  40                  45
Glu Ala Leu Ser Ser Arg Val Ala Trp Arg Ser Thr Asn Arg Leu Arg
 50                  55                  60
Ala Asp Leu Val Glu His Cys Leu Ser Arg Pro Pro Gly Phe Tyr Arg
 65                  70                  75                  80
Lys His Pro Pro Gly Glu Leu Val Glu Arg Met Asp Gly Asp Val Thr
                 85                  90                  95
Arg Leu Ala Ala Val Met Ser Thr Leu Leu Glu Leu Leu Ala Gln
            100                 105                 110
Ala Leu Leu Ile Val Gly Ile Leu Val Ala Leu Phe Arg Leu Glu Trp
            115                 120                 125
Arg Leu Ala Leu Val Val Ala Pro Phe Ala Ala Gly Thr Leu Leu Leu
            130                 135                 140
Leu Arg Thr Leu Val Gly Arg Ala Met Pro Phe Val Thr Ala Arg Gln
145                 150                 155                 160
Arg Val Ala Ala Asp Leu Gln Gly Phe Leu Glu Glu Arg Leu Ala Ala
                165                 170                 175
Ala Glu Asp Leu Arg Val Asn Gly Ala Ser Arg Tyr Thr Leu Arg Glu
            180                 185                 190
Leu Gly Asp Arg Gln Asp Asp Leu Tyr Arg Lys Ala Arg Asp Ala Ala
            195                 200                 205
Arg Ala Ser Val Arg Trp Pro Ala Thr Val Gln Gly Leu Ser Ala Val
210                 215                 220
Ser Val Val Leu Ala Leu Ala Val Ser Ala Trp Leu His Ala Arg Gly
225                 230                 235                 240
Gln Leu Ser Thr Gly Thr Ala Phe Ala Ser Leu Ser Tyr Ala Met Leu
                245                 250                 255
Leu Arg Arg Pro Leu Leu Ala Val Thr Thr Arg Phe Arg Glu Leu Glu
            260                 265                 270
Asp Ala Ala Ala Ser Ala Gln Arg Leu Arg Asp Leu Leu Gly His Gly
            275                 280                 285
Thr Ala Ala Pro Arg Thr Gly Arg Thr Leu Pro Ala Gly Leu Pro Gly
            290                 295                 300
Val Arg Phe Asp Gly Val Ser Phe Gly Tyr Glu Pro Asp Glu Pro Val
305                 310                 315                 320
Leu Arg Asp Val Ser Phe Thr Leu Arg Pro Gly Glu Arg Leu Gly Val
                325                 330                 335
Val Gly Arg Thr Gly Ser Gly Lys Ser Thr Val Val Arg Leu Leu Phe
            340                 345                 350
Gly Leu His His Pro Gly Ala Gly Ser Val Ser Ala Gly Gly Leu Asp
            355                 360                 365
Leu Thr Glu Ile Asp Pro Arg Ala Leu Arg Ser Arg Val Ala Leu Val
            370                 375                 380
Thr Gln Glu Val His Val Phe His Ala Ser Leu Arg Asp Asn Leu Thr
385                 390                 395                 400
Phe Phe Asp Arg Ser Val Pro Asp Asp Arg Leu Arg Ala Ala Leu Gly
                405                 410                 415
Glu Ala Gly Leu Gly Pro Trp Leu Arg Thr Leu Pro Gly Leu Asp
            420                 425                 430
Thr Pro Leu Gly Ala Gly Ala Arg Gly Met Ser Ala Gly Glu Glu Gln
            435                 440                 445
Gln Leu Ala Leu Ala Arg Val Phe Leu Arg Asp Pro Gly Leu Val Leu
            450                 455                 460
```

```
Met Asp Glu Pro Thr Ala Arg Leu Asp Pro Tyr Ser Glu Arg Leu Leu
465                 470                 475                 480

Met Pro Ala Leu Glu Arg Leu Leu Glu Gly Arg Thr Ala Val Val Val
                485                 490                 495

Glu His Arg Pro His Leu Leu Arg Asn Val Asp Arg Ile Leu Val Leu
            500                 505                 510

Glu Glu Gly Lys Val Ala Glu Gly Glu Arg Val Leu Ala Ala
            515                 520                 525

Asp Pro Gly Ser Arg Phe His Ala Leu Leu Arg Thr Ala
            530                 535                 540

<210> SEQ ID NO 150
<211> LENGTH: 543
<212> TYPE: PRT
<213> ORGANISM: Symbiobacterium thermophilum

<400> SEQUENCE: 150

Ile Gly Leu Gln Leu Ile Asn Pro Gln Ile Leu Arg Arg Phe Leu Asp
1               5                   10                  15

Thr Ala Ala Gly Glu Val Ser Gly Gly Pro Ser Leu Val Thr Leu Ala
                20                  25                  30

Leu Ala Phe Ile Gly Val Ala Phe Ala Val Gln Ala Val Thr Val Leu
            35                  40                  45

Ala Arg Tyr Leu Ser Glu Ser Val Ser Trp Arg Ala Thr Asn Glu Leu
        50                  55                  60

Arg Ala Asp Leu Ala Glu His Cys Leu Arg Leu Asp Leu Gly Phe His
65                  70                  75                  80

Lys Arg Arg Thr Pro Gly Glu Met Val Glu Arg Ile Asp Gly Asp Val
                85                  90                  95

Thr Ala Leu Ser Gln Phe Phe Ser Gln Leu Phe Ile Gly Val Leu Ala
            100                 105                 110

Asn Leu Val Leu Met Leu Gly Ile Leu Val Leu Leu Phe Arg Glu Asp
            115                 120                 125

Trp Arg Ala Gly Val Ala Met Thr Leu Phe Ala Ala Phe Thr Leu Trp
130                 135                 140

Val Leu Gly Arg Ile His Glu Leu Ser Val Pro Val Trp Thr Arg Gln
145                 150                 155                 160

Arg Gln Ala Ser Ala Glu Phe Tyr Gly Tyr Leu Gly Glu Val Leu Ser
                165                 170                 175

Gly Thr Glu Ala Ile Arg Ala Gly Gly Ala Arg Gly Trp Ala Leu His
            180                 185                 190

Arg Phe Leu Arg Asn Val Gln Asp Phe Tyr Arg Gln Asn Leu Ala Ala
            195                 200                 205

Ser Met Met Phe Trp Leu Thr Trp Ser Thr Ser Ile Val Thr Phe Ala
210                 215                 220

Val Gly Ala Ala Leu Ser Leu Gly Val Gly Ala Trp Leu Tyr Ala Arg
225                 230                 235                 240

Gly Gly Val Thr Val Gly Thr Val Tyr Leu Leu Phe His Tyr Thr Glu
                245                 250                 255

Leu Leu Arg Arg Pro Ile Glu Gln Ile Arg Thr His Leu Gln Glu Leu
            260                 265                 270

Gln Arg Ala Gly Ala Ala Val Glu Arg Val Glu Glu Leu Phe Ala Gln
            275                 280                 285

Arg Thr Arg Val Pro Asp Gly Pro Gly Arg Ala Leu Pro Pro Gly Pro
```

```
                    290                 295                 300

Leu Ser Val Glu Leu Val Gly Val Ser Phe Ala Tyr Glu Pro Gly Ala
305                 310                 315                 320

Pro Val Leu Arg Asp Val Asp Val Arg Ile Glu Pro Gly Glu Val Val
                325                 330                 335

Gly Leu Leu Gly Arg Thr Gly Ser Gly Lys Ser Thr Leu Ala Arg Leu
            340                 345                 350

Leu Leu Arg Phe Tyr Asp Pro Asp Ala Gly Ile Val Arg Leu Gly Gly
        355                 360                 365

Val Asp Leu Arg Glu Ala Thr Val Ala Gly Val Arg Ala Arg Val Gly
    370                 375                 380

Phe Val Thr Gln Asp Val Gln Leu Phe Ala Gly Thr Val Arg Asp Asn
385                 390                 395                 400

Leu Thr Phe Phe Ser Pro Glu Val Ser Asp Gly Arg Leu Leu Ala Val
                405                 410                 415

Leu Glu Glu Leu Gly Leu Gly Pro Trp Leu Gln Ser Leu Pro Gln Gly
            420                 425                 430

Leu Asp Thr Pro Leu Glu Ser Gly Gly Gly Leu Ser Ala Gly Glu
        435                 440                 445

Ala Gln Leu Leu Ala Leu Ala Arg Val Phe Leu Ala Asp Pro Gly Leu
    450                 455                 460

Val Ile Leu Asp Glu Ala Ser Ser Arg Leu Asp Pro Ala Thr Glu Ser
465                 470                 475                 480

Leu Val Glu Arg Ala Val Asp Arg Leu Leu Glu Gly Arg Thr Gly Ile
                485                 490                 495

Ile Ile Ala His Arg Leu Ala Thr Val Glu Arg Ala Asp Thr Ile Leu
            500                 505                 510

Ile Leu Glu Asp Gly Arg Val Val Glu Tyr Gly Pro Arg Ala Glu Leu
        515                 520                 525

Ala Ala Asp Pro Ala Ser Arg Phe Phe Arg Met Leu Arg Ala Gly
    530                 535                 540

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Asp Ala Leu Leu Leu
1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ala Asp Tyr Val Gly
1               5
```

MOENOMYCIN BIOSYNTHESIS-RELATED COMPOSITIONS AND METHODS OF USE THEREOF

CROSS-REFERENCE TO RELATED APPLICATIONS

This application claims priority as a national stage application of International Patent Application serial number PCT/US2007/017999 (filed Aug. 13, 2007), which claims the benefit of priority to U.S. Provisional Application No. 60/837,047 (filed Aug. 11, 2006), which are incorporated by reference in their entireties.

FIELD OF THE INVENTION

The invention provides polynucleotides and polypeptides related to moe biosynthesis and methods of use thereof. The invention also relates to derivatives of moe A having antibacterial activity.

BACKGROUND

The following discussion of the background of the invention is merely provided to aid the reader in understanding the invention and is not admitted to describe or constitute prior art to the invention.

The bacterial genus *Streptomyces* is an important natural source of many antibiotics, which include streptomycin, tetracycline, chloramphenicol, macrolides (e.g., erythromycin, carbomycin) and moenomycins ("moes").

Moes are complex mixtures of phosphoglycolipid compounds produced by many *Streptomyces* strains as well as other *Actinomycets*. *Streptomyces ederensis*, *Streptomyces geysiriensis*, and *Streptomyces bambergiensis* (exemplary American Type Culture Collection deposits include ATCC15304, ATCC15303, ATCC13879, respectively) have all been shown to produce moes. See Wallhausser et al., 1965; Lindner et al., 1961. There have also been reports of an unidentified *Actinomyces* strain which produces compound AC326-alpha, a close relative of one of the moes in the mixture, moe A (He et at, 2000). Additionally, there are reports of *Streptomyces* strains producing compounds similar to moe A, however the exact chemical structure of these compounds has not yet been established (Weisenborn et al., 1967; Slusarchyk et at, 1969; Takahashi et al., 1970; Meyers et al., 1969).

Although the mixture of moes (e.g., the mixture produced by the strain *Streptomyces ghanaensis*) has not been thoroughly analyzed, it has been found to contain moe A (FIG. 1) and several other moes, including $A_{12}$, $C_1$, $C_3$ and $C_4$. Moes $A_{12}$, $C_1$, $C_3$ and $C_4$ have been shown to represent either shunt products or intermediates of common biosynthetic pathway operating in the producer strain. Additionally, compounds which are thought to be novel moes (Eichhorn, P. et al., 2005; Liu et al., 2003) have also been discovered.

The chemical structure for some moes (e.g., pholipomycin and AC326α) has been established, while the chemical nature of other members of the mixture (e.g., prasinomycins, macarbomycin, teichomycin A1, 11837RP, 8036RP (quebemycin), 19402RP, ensanchomycin, prenomycin) remains to be determined.

Moe A, a major component of the moe mixture, belongs to a unique family of phosphorus-containing secondary metabolites. Moe A is a pentasaccharide decorated with a $C_{25}$ isoprene chain on one end and a chromophore on the other. The structure of moe A is shown below in Formula I:

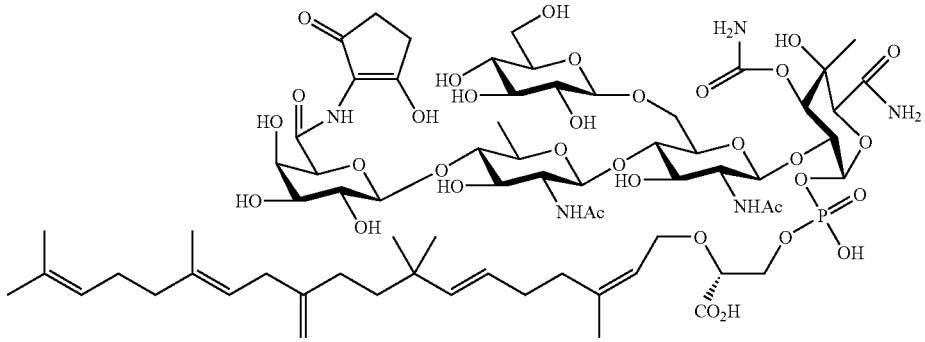

Moe A is active against many bacterial strains and is the only antibiotic known to bind directly to and inhibit bacterial transglycosylase ("TG"), enzymes involved in peptidoglycan biosynthesis (FIG. 2). Because peptidoglycan biosynthesis is essential for bacterial survival, the inhibition of transglycosylase is an attractive and as-yet unexploited drug target. Moe A has potent antibiotic activity, with minimum inhibitory concentrations against many Gram positive organisms ("MICs") in the range of 0.01 to 0.1 µg/mL (Chen L et al., 2003) or greater than 0.1 µg/mL. For example, moe A is an effective inhibitor of cell wall biosynthesis in Gram-positive cocci, including glycopeptide-resistant strains (Goldman, 2000).

It is assumed that the outer membrane of Gram-negative bacteria prevents moe A from reaching the enzymatic target; however, there are several studies showing selective toxicity of moe A and macarbomycin to Gram-negative bacteria carrying conjugative R-plasmids (Iyobe 1973; Ridel 2000). Additionally, some moe A producing *Streptomyces* strains and various strains not known to produce moe A (or structurally related compounds) are resistant to high concentrations of moe A. Therefore, some general and widely distributed resistance mechanism may exist which is not necessarily associated with moe A biosynthesis. Perhaps some *Streptomyces* transglycosylases are intrinsically resistant to moe A, or an unusually thick cell wall prevents moe A from reaching its target, or both. Additionally, or alternatively, by analogy to vancomycin resistance genes in *S. coelicolor* (Hong 2002), there could be a specific, as-yet unidentified moe A resistance gene or gene cluster in Streptomycetes.

The structure-activity relationships of moe A and its derivatives have been studied by Welzel and coworkers. For example, various domains involved in bioactivity and target interactions (Welzel, 1992) have been identified (labeled A through H) (FIG. 1). It has been shown that the C-E-F trisaccharide portion of moe retains inhibitory activity both in vitro and in vivo, while the E-F disaccharide shows activity only in vitro. The phospholipid moiety appears essential for in vivo activity, but the lipid chain can be manipulated to some extent (e.g., hydrogenation of the double bonds does not significantly alter activity). The lipid may be responsible either for anchoring moe to the cell membrane and/or interacting with hydrophobic regions of TGs. Moe analogs containing neryl chains have enzyme inhibitory activity but no biological activity. The carbamoyl group at C3', the hydroxyl group at C4', and the carboxamide entity at C5' of the F ring, as well as the acetyl group at C2' of the E ring, are all thought to define the moe pharmacophore (Ostash 2005). Unlike many other natural product antibiotics, moe does not contain structural elements of polyketide or non-ribosomal polypeptide origin. However, moes do contain a phosphoglycerate lipid moiety, a structural element not found in any other secondary metabolites. Moe A has been used as a growth promoter in animal feed under the trademark Flavomycin®.

SUMMARY OF THE INVENTION

The present invention provides polynucleotide and/or polypeptide compositions involved in moe biosynthesis and methods of use. For example, polypeptides encoded by nucleic acid sequences such as SEQ ID NOs: 3-25, or fragments, or natural or an artificial variants thereof are contemplated, as are the polypeptides of SEQ ID NOS. 26-48. Compositions including one or more nucleic acid sequences, such as SEQ ID NOs: 3-25, or fragments, or natural or artificial variants thereof are also contemplated. In other embodiments, the nucleic acid sequences or fragments may include an open reading frame. In some embodiments, these nucleic acid compositions may be inserted into expression vectors, and expressed, for example in mammalian, insect, yeast or bacterial cells. Composition comprising one or more polypeptides such as SEQ ID NOs: 26-48, natural or artificial variants, or fragments thereof are also provided.

The methods and compositions also relate to one or more proteins that participate in or are activated for moe biosynthesis. By way of example, but not by way of limitation, these polypeptides may include a composition comprising one or more of the polypeptides selected from the group consisting of: moe A4, moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, moeGT5, fragments thereof, or a natural or artificial variant thereof. In one embodiment, the invention provides a composition comprising a one or more of the genes encoding the polypeptides recited above.

The methods and compositions also relate to moe A molecule, derivative or intermediate produced by an organism, such as a bacterial, insect, yeast or mammalian cell, wherein the organism carries one or more mutant or inactivated genes. In some embodiments, the mutant or inactivated gene may be one or more of moe A4, moeB4, moeC4, moeB5, moe A5, moeD5, moeJ5, moeE5, moeF5, moeH5. moeK5, moeM5, moeN5, moeO5, moeX5, moeP5, moeR5, moeS5, moeGT1, moeGT2, moeGT3, moeGT4, and moeGT5. In some embodiments, bacteria may be a *Streptomyces* strain, such as for example, *S. ghanaensis*. In other embodiments, the bacteria may be *S. ghanaensis* ATCC14627, *S. lividans* TK24, *S. albus* J1074.

The methods and compositions also relate to enzymatic methods of synthesizing moe, a moe derivative, or a moe intermediate wholly or partially in vitro. In some embodiments, the method includes reacting a one or more moenomycin precursor, derivative and/or moenomycin intermediate with a one or more polypeptide selected from the group consisting of: moeA4, moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5, under conditions wherein the moenomycin, the moenomycin derivative, or the intermediate is wholly or partially synthesized. In some embodiments of the method, the method further comprises reacting the moenomycin, moenomycin derivative and/or moenomycin intermediate with a one or more reactants selected from the group consisting of: UDP-sugars, prenyl-pyrophosphates, phosphoglycerate, amino acids, carbamoyl phosphate, ATP and biological cofactors.

The methods and compositions also enzymatic of modifying a moenomycin wholly or partially in vitro. In some embodiments, the method includes reacting a moenomycin, a moenomycin derivative or a moe intermediate with a one or more polypeptide selected from the group consisting of: moeA4, moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5, under conditions wherein the moenomycin, the moenomycin derivative, or the intermediate is modified. In some embodiments, the method further comprises reacting the moenomycin, moenomycin derivatives and/or moenomycin intermediates with a one or more reactants selected from the group consisting of: UDP-sugars, prenyl-pyrophosphates, phosphoglycerate, amino acids, carbamoyl phosphate, ATP and biological cofactors.

The methods and compositions described herein also relate to pharmaceutically acceptable compositions of moes, and the treatment of mammals, such as humans, by administering such compositions in a therapeutically effective amount. In some embodiments, the pharmaceutical composition may include a moe synthesized or modified by the methods of the present disclosure.

In another embodiment, the present invention provides an isolated *Streptomyces* strain selected from the group consisting of: *Streptomyces ghanaensis*, *Streptomyces ederensis*, *Streptomyces geysiriensis*, and *Streptomyces bambergiensis* strain which carries a one or more mutant or inactivated genes, wherein the mutant or inactivated genes are selected from the group consisting of: moeA4, moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5. For example, the *Streptomyces ghanaensis* strain may be *Streptomyces ghanaensis* ATCC14627.

In another embodiment, the present invention relates to an isolated recombinant cell expressing one or more polypeptides or fragments, or natural or artificial variants thereof selected from the group consisting of moeA4, moeB4, moeC4, moeB5, moeA5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5. In some embodiments, the cell is selected from the group consisting of: *Streptomyces lividans* TK24, *E. coli*, mammalian cells, yeast and insect cells.

In another embodiment, the compositions described herein further relate to a moenomycin A molecule derivative or intermediate produced by an isolated recombinant cell expressing one or more polypeptides or fragments, or natural or artificial variants thereof selected from the group consisting of: moeA4 moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5.

In one embodiment, the present invention provides a moenomycin derivative having the structure:

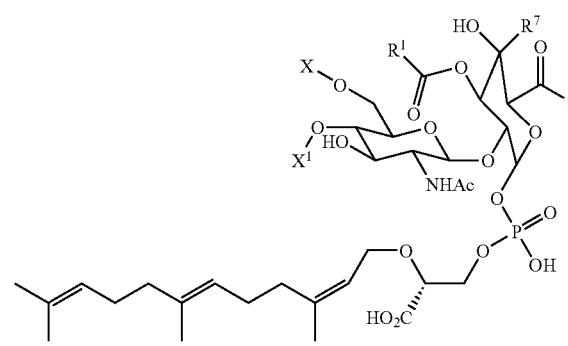

wherein Ac refers to acetyl;

R and R¹ independently are selected from the group consisting of hydroxyl and —NHR² where R² is selected from the group consisting of hydrogen, alkyl, cycloalkyl, and substituted cycloalkyl;

X is hydrogen, or

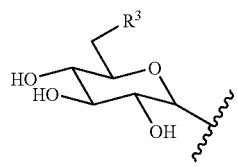

where R³ is selected from the group consisting of hydrogen and hydroxyl; and

X¹ is hydrogen,

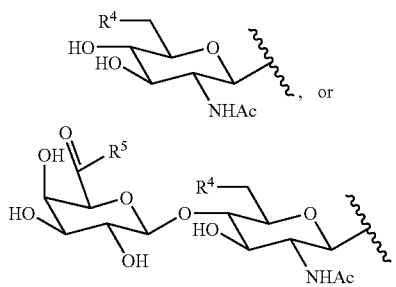

where R⁴ is selected from the group consisting of hydrogen and hydroxyl;

R⁵ is selected from the group consisting of hydroxyl and —NHR⁶ where R⁶ is hydrogen, alkyl, cycloalkyl, or substituted cycloalkyl, and R⁷ is hydrogen or methyl, or a pharmaceutically acceptable salt, tautomer, and/or ester thereof.

In some embodiments, R and R¹ independently are —NH₂. In some embodiments, X is hydrogen. In other embodiments, X is

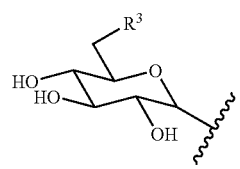

where R³ is selected from the group consisting of hydrogen and hydroxyl.

In some embodiments, X¹ is hydrogen. In other embodiments, X¹ is

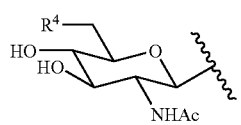

In still other embodiments, X¹ is

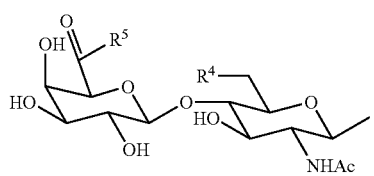

where R⁴ is selected from the group consisting of hydrogen and hydroxyl and R⁵ is selected from the group consisting of hydroxyl and —NH₂.

In some embodiments, the structure of the moenomycin derivative is:

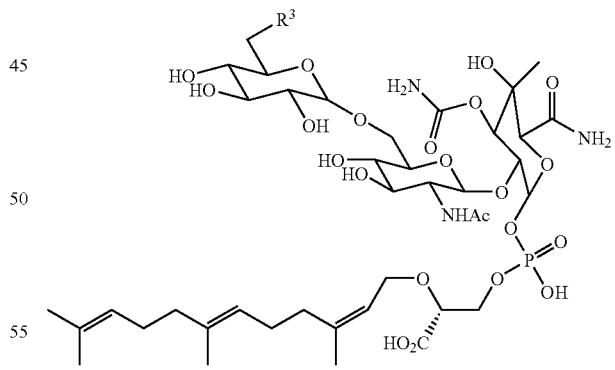

where R³ is selected from the group consisting of hydrogen and hydroxyl, or a pharmaceutically acceptable salt, tautomer, and/or ester thereof.

In some embodiments, R³ is hydrogen. In other embodiments, R³ is hydroxyl.

In some embodiments, the structure of the moenomycin derivative is:

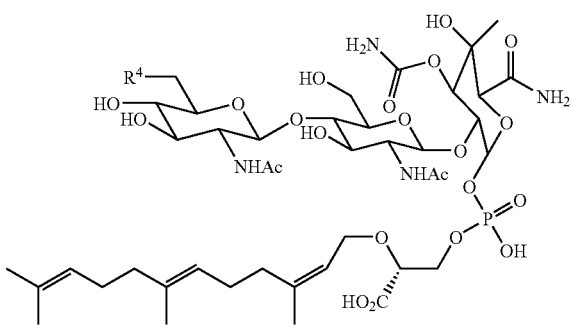

where R⁴ is selected from the group consisting of hydrogen and hydroxyl, or a pharmaceutically acceptable salt, tautomer, and/or ester thereof.

In some embodiments, $R^4$ is hydrogen. In other embodiments, $R^4$ is hydroxyl.

In some embodiments, the structure of the moenomycin derivative is:

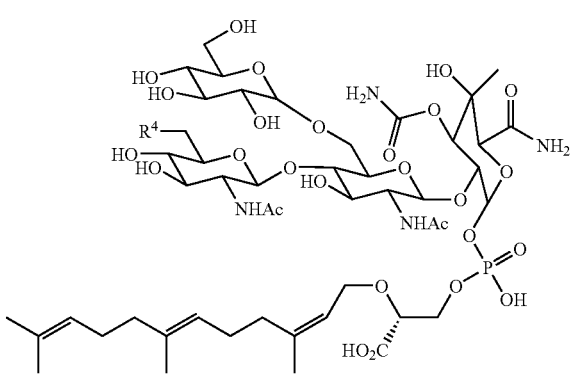

where R⁴ is selected from the group consisting of hydrogen and hydroxyl, or a pharmaceutically acceptable salt, tautomer, and/or ester thereof.

In some embodiments, $R^4$ is hydrogen. In other embodiments, $R^4$ is hydroxyl.

In some embodiments, the structure of the moenomycin derivative is:

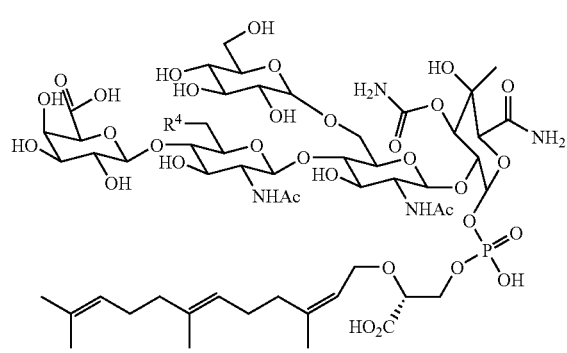

where R⁴ is selected from the group consisting of hydrogen and hydroxyl, or a pharmaceutically acceptable salt, tautomer, and/or ester thereof.

In some embodiments, $R^4$ is hydrogen. In other embodiments, $R^4$ is hydroxyl.

In some embodiments, the structure of the moenomycin derivative is:

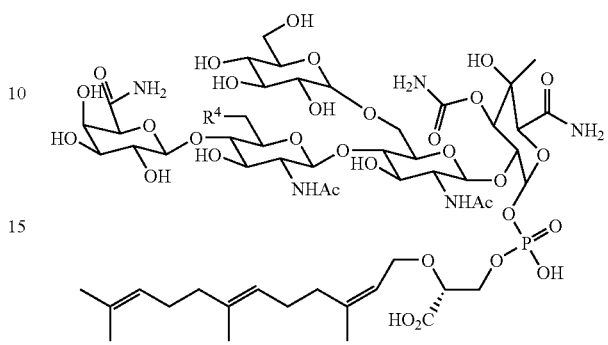

where R⁴ is selected from the group consisting of hydrogen and hydroxyl, or a pharmaceutically acceptable salt, tautomer, and/or ester thereof.

In some embodiments $R^4$ is hydrogen. In other embodiments, $R^4$ is hydroxyl.

In some embodiments, the structure of the moenomycin derivative is:

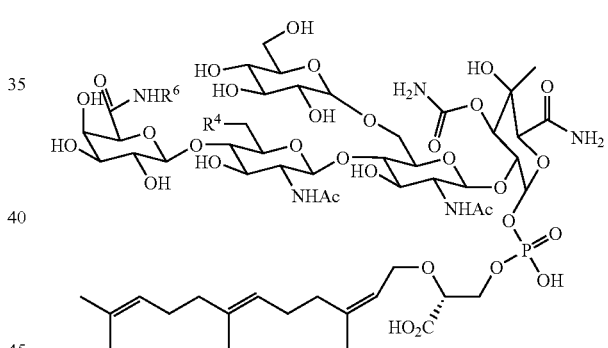

wherein $R^4$ is hydrogen or hydroxyl and $R^6$ is selected from the group consisting of hydrogen, alkyl, cycloalkyl, and substituted cycloalkyl, or a pharmaceutically acceptable salt, tautomer, and/or ester thereof.

In some embodiments, $R^4$ is hydrogen. In other embodiments, $R^4$ is hydroxyl.

In some embodiments, $R^6$ is hydrogen or substituted cycloalkyl. In some preferred embodiments; substituted cycloalkyl is

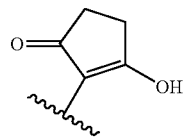 [SMILES: *C1=C(O)CCC1=O]

In some embodiments, $R^4$ is hydroxyl and $R^6$ is

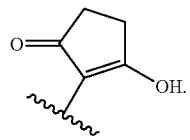

In some embodiments, the invention provides a pharmaceutical composition comprising the moenomycin derivative as defined above and a pharmaceutically acceptable carrier.

In another embodiment, the present invention provides a moenomycin derivative having the structure:

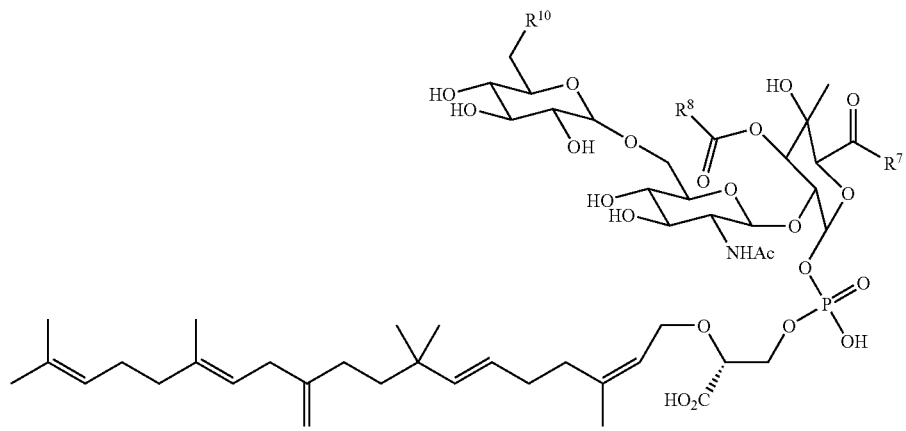

wherein $R^7$ and $R^8$ independently are selected from the group consisting of hydroxyl and —$NHR^9$ where $R^9$ is hydrogen, alkyl, cycloalkyl, or substituted cycloalkyl; and $R^{10}$ is hydrogen or hydroxyl;

or a pharmaceutically acceptable salt, tautomer, and/or ester thereof.

In some embodiments, $R^7$ and $R^8$ independently are —$NH_2$. In some embodiments, $R^{10}$ is hydroxyl.

In some embodiments, the structure of the moenomycin derivative is:

or a pharmaceutically acceptable salt, tautomer, and/or ester thereof.

In some embodiments, invention provides a pharmaceutical composition comprising the moenomycin derivative as defined above and a pharmaceutically acceptable carrier.

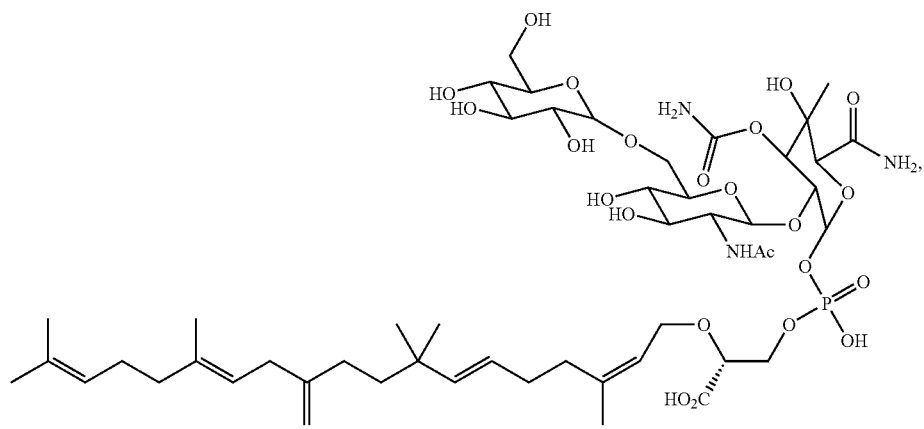

Figure 7:
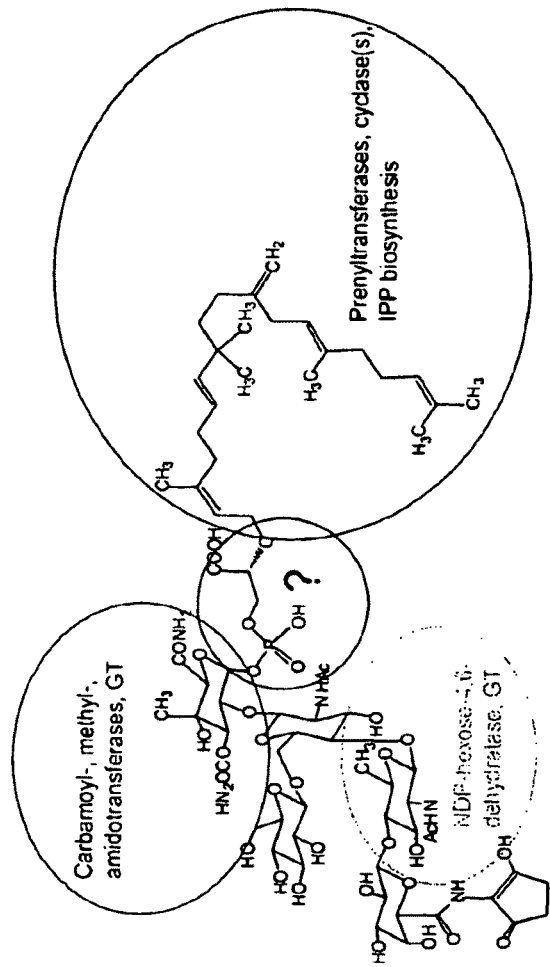

FIG. 7 shows a schematic describing an approach for in silico screening involving classes of enzymes directed to producing different domains of moes.

FIG. 8 shows a schematic for the possible role of the moeO5 protein in moe biosynthesis. FIG. 8A shows biosynthesis of intermediate of archael membrane lipid. FIG. 8B shows biosynthesis of phosphoglyceric acid incorporation into moenomycin.

Figure 9:
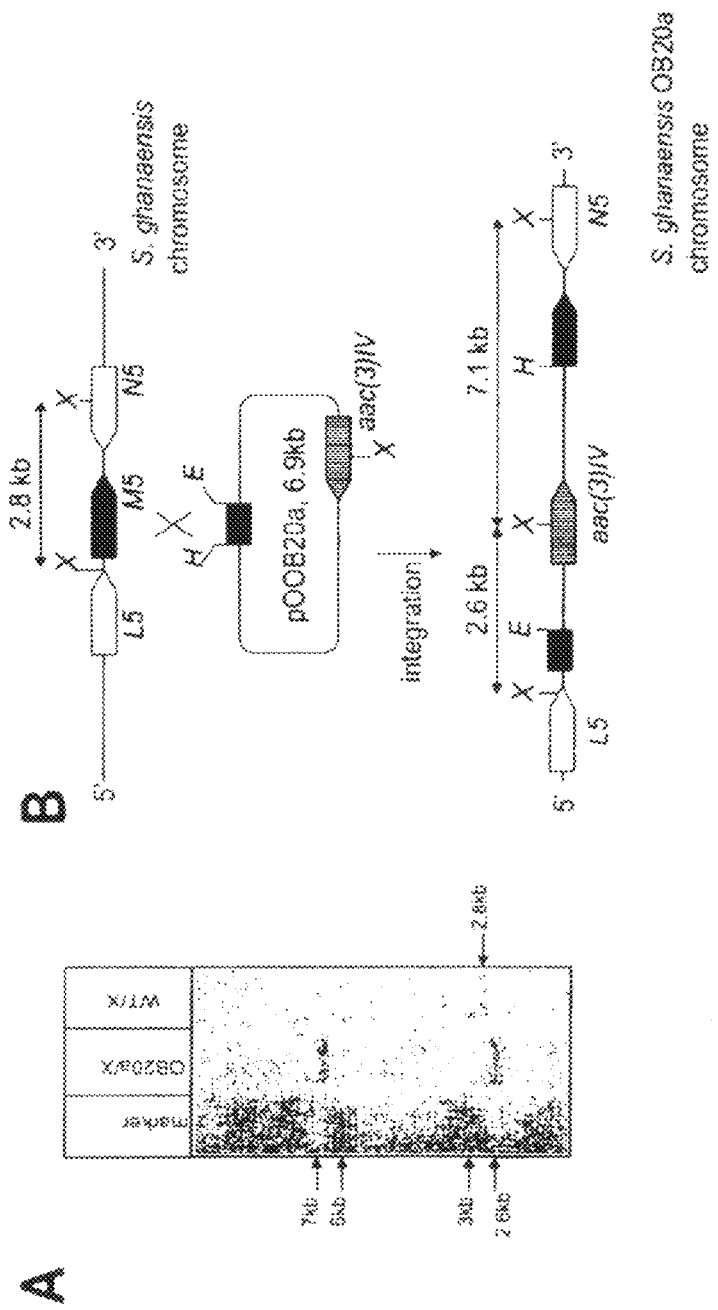

FIG. 9 shows a schematic for the insertional inactivation of the moeM5 gene (FIG. 9B) and confirmation of specific integration of the disruption sequences by Southern analysis (FIG. 9A).

Figure 10:
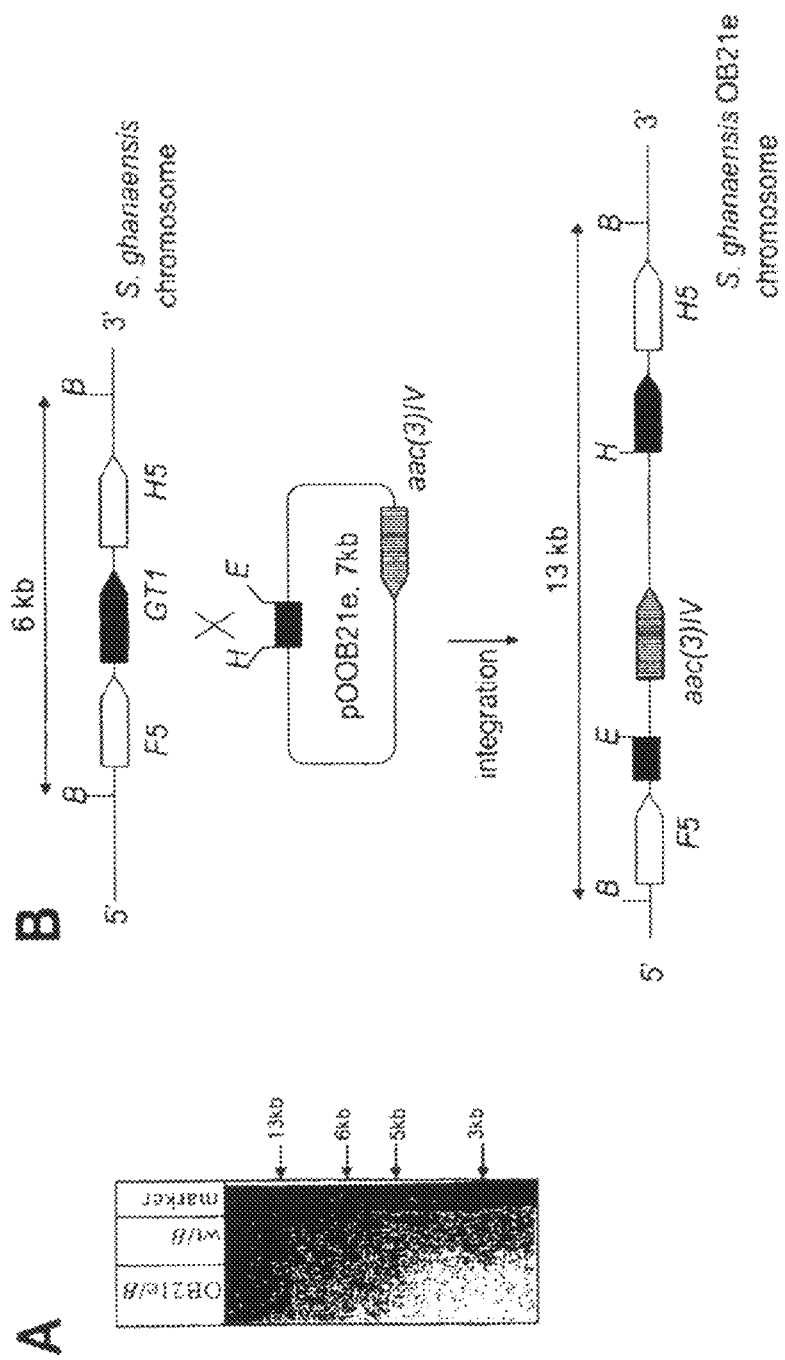

FIG. 10 shows a schematic of the insertional inactivation of the moeGT1 gene (FIG. 10B) and confirmation of specific integration of the disruption sequences by Southern analysis (FIG. 10A).

Figure 11:
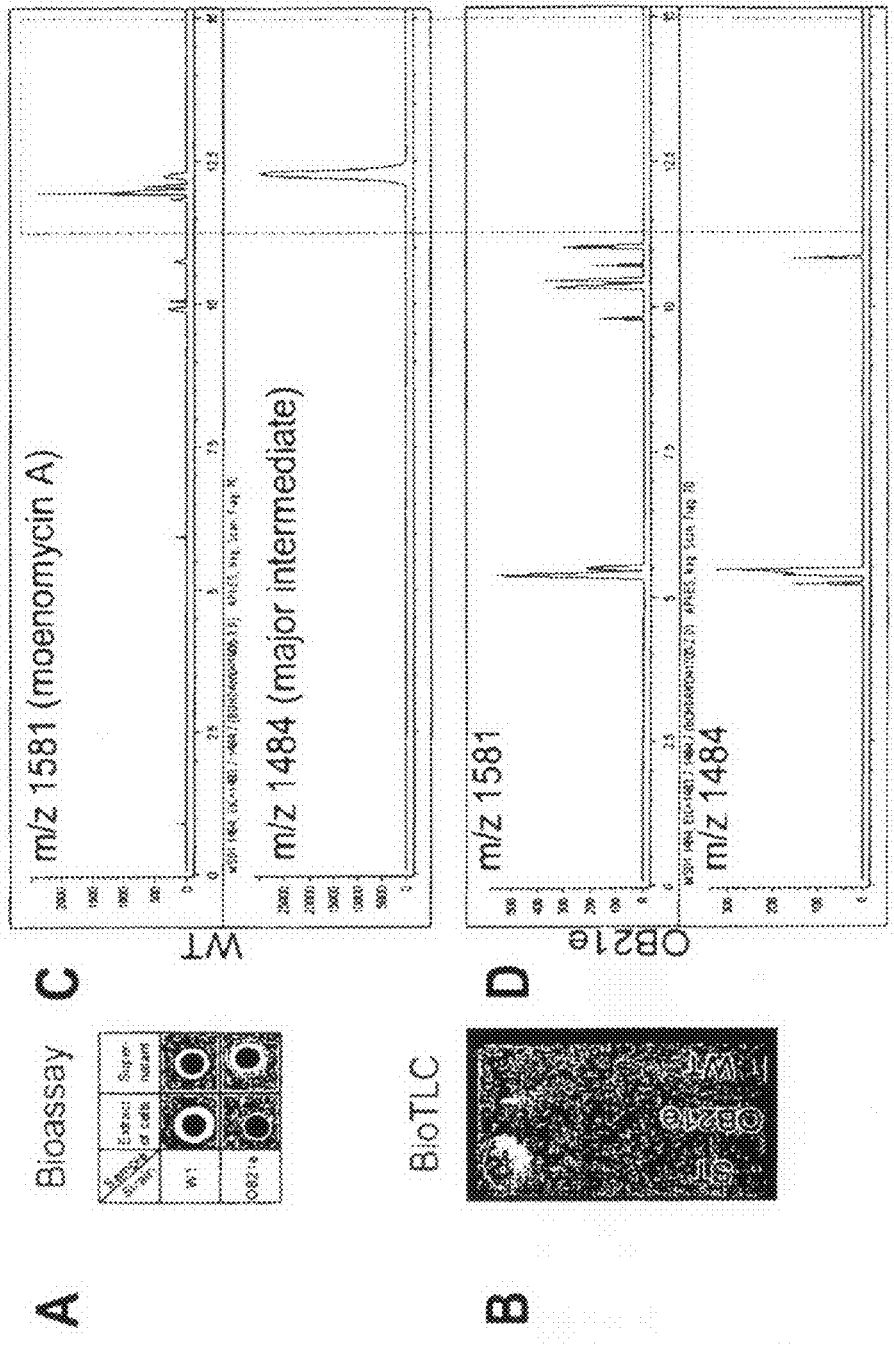

FIG. 11 shows bioassay (FIG. 11A), BioTLC (FIG. 11B) and liquid chromatography and mass spectrometry ("LC-MS") data (FIG. 11C and FIG. 11D) indicating that in the moeGT1 mutant, moe A production appears to be reduced or abolished.

Figures 12A, 12B:
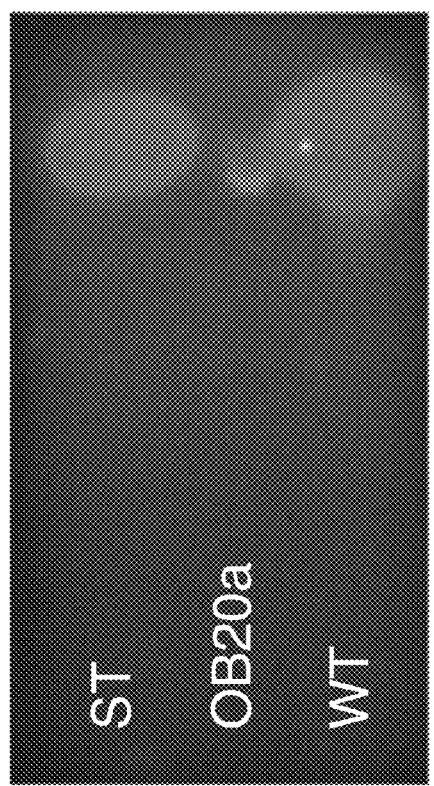
Figure 12C:
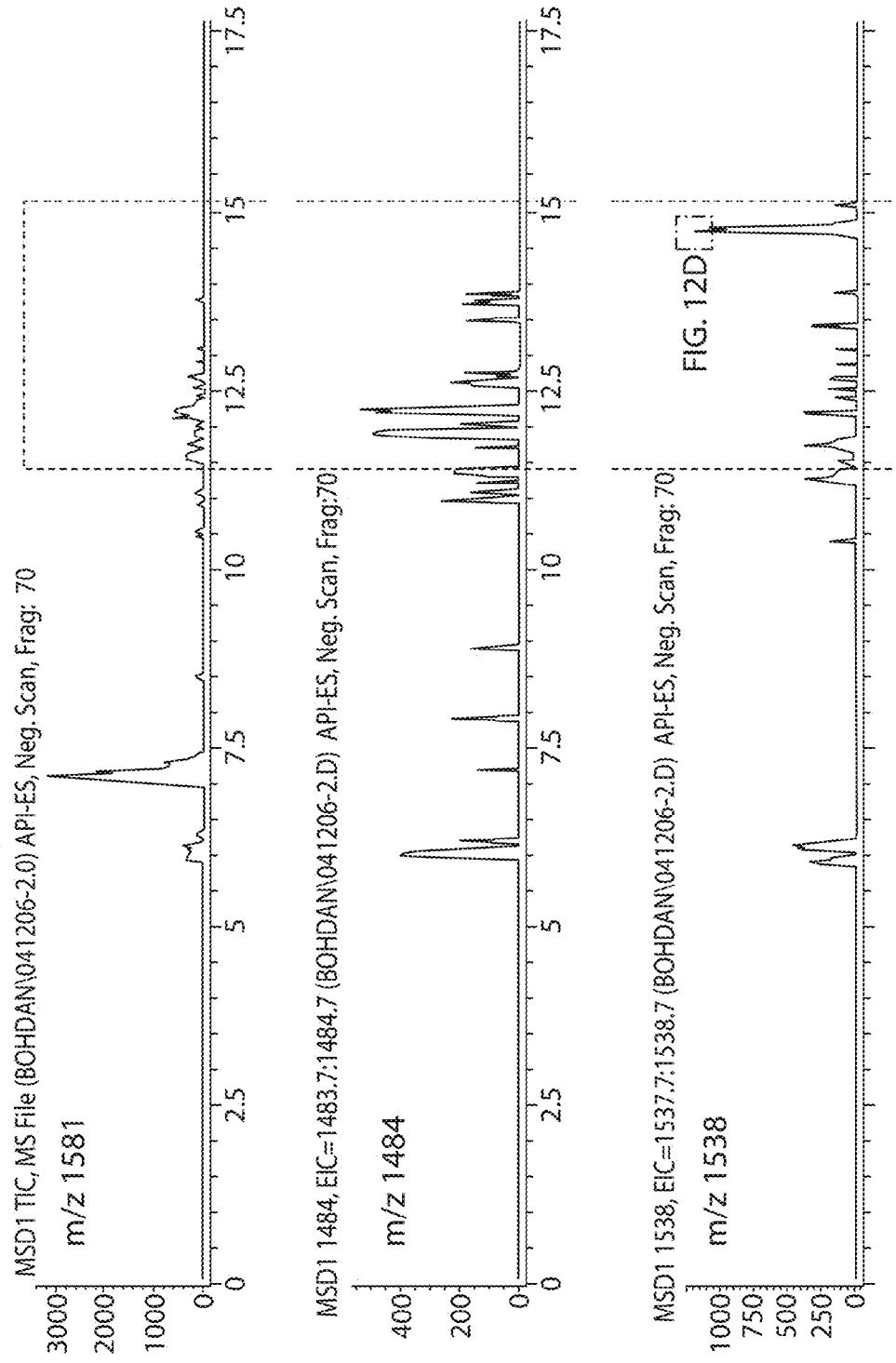
Figure 12D:
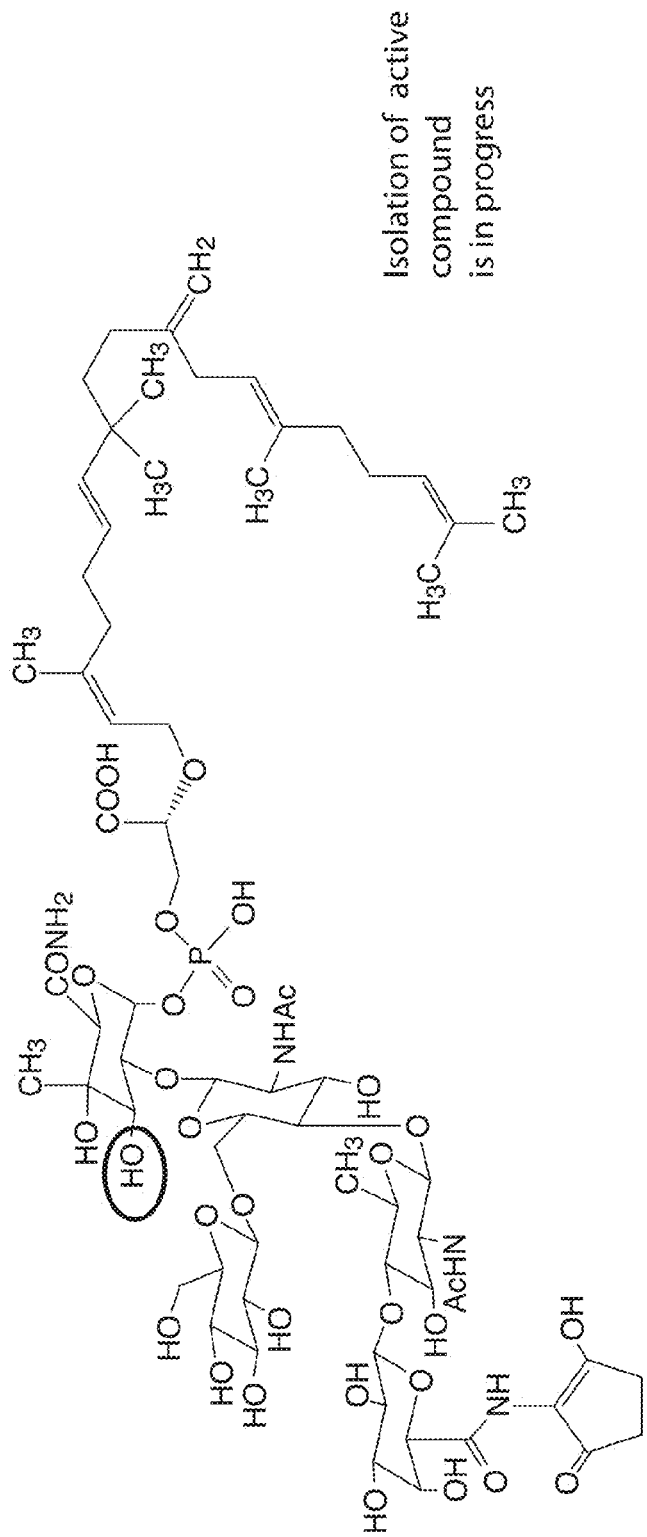

FIG. 12 shows a bioassay (FIG. 12A), BioTLC (FIG. 12B) and LC-MS data (FIG. 12C and FIG. 12D) of the moe A analog in the moeM5 mutant.

Figure 13:
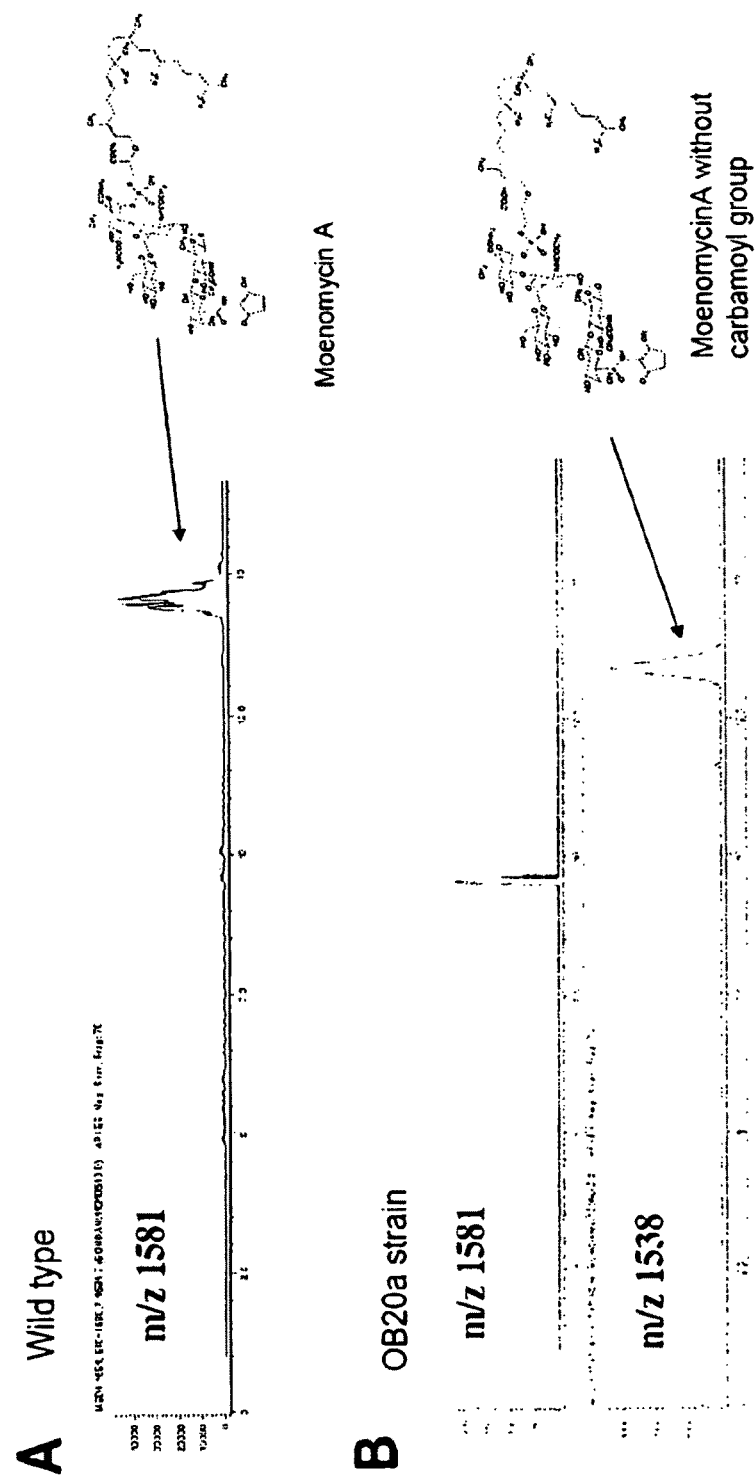

FIG. 13 shows graphs of LC-MS analysis of moe extracts from wild-type (FIG. 13A) and moeM5 deficient strain OB20a (FIG. 13B).

Figure 14:
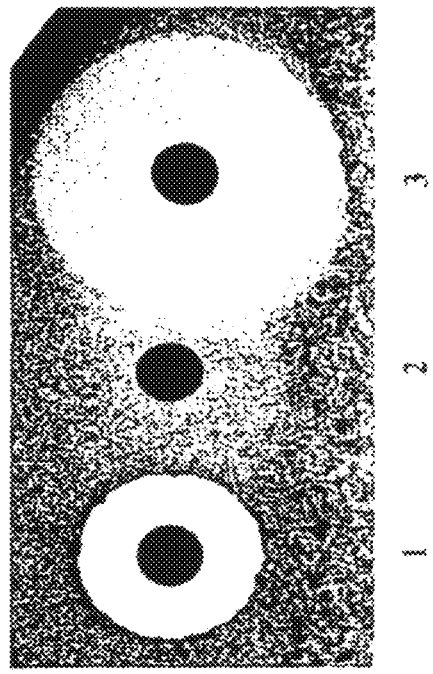

FIG. 14 shows a bioassay of methanol extracts from 2 g of mycelia of strains S. lividans J1725 38-1$^+$ (2) and S. lividans J1725 38-1$^+$ pIJ584$^+$ (3). (1)—standard (moe A, 4 mcg).

Figure 15:
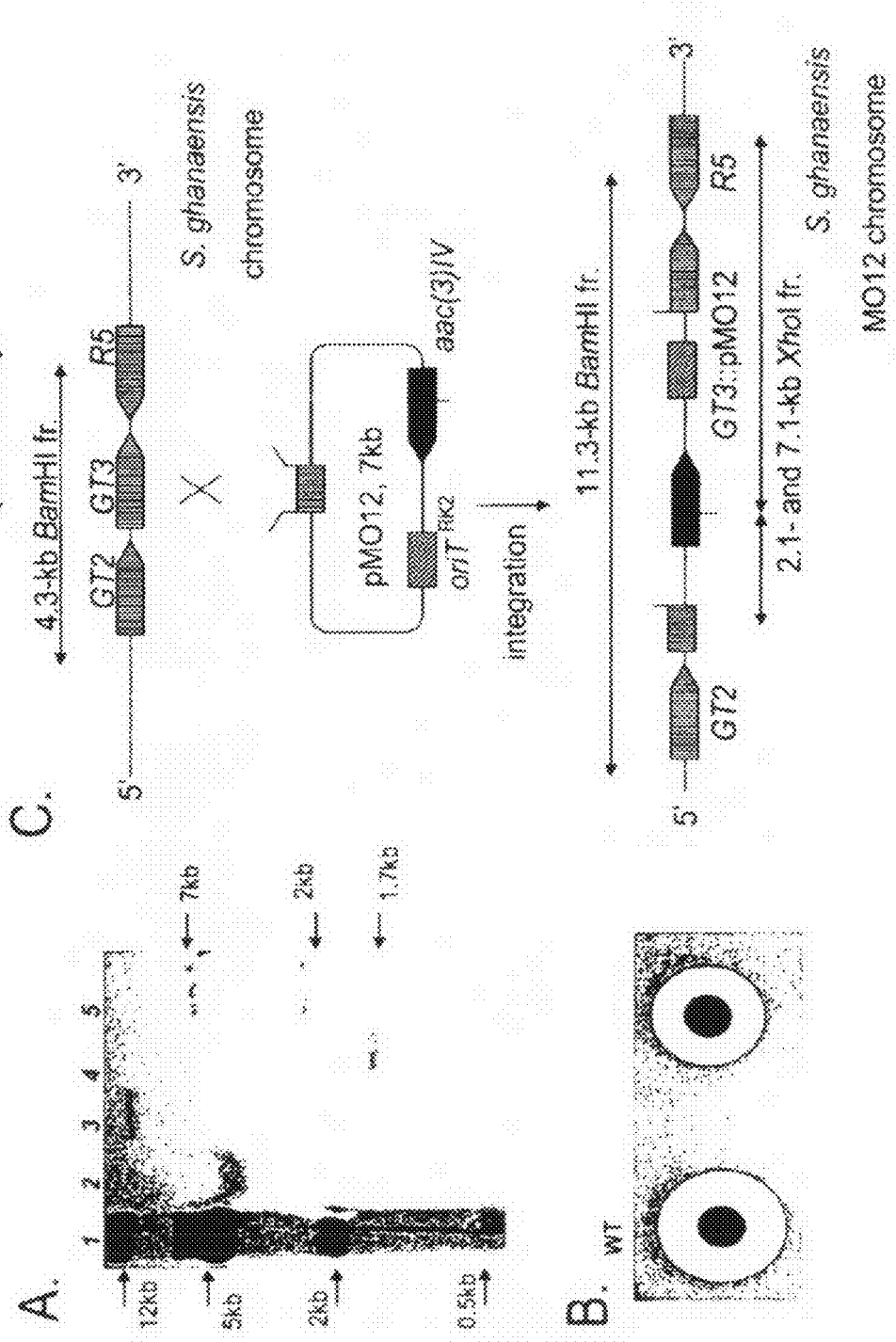

FIG. 15A shows a Southern analysis of BamHI and XhoI digests of total DNA of wild type S. ghanaensis (lanes 2 and 4, respectively) and MO12 strain with disrupted moeGT3 (lanes 3 and 5). Lane 1—mixture of plasmids pMO12, pMO14 and pOOB58 underdigested with PstI. FIG. 15B shows the results of a bioassay of semipurified extracts from 1 g (wet weight) of mycelia of wild type strain (WT) and MO12. FIG. 15C presents a scheme of moeGT3 disruption in the S. ghanaensis genome. X, H, E mark XhoI, HindIII, EcoRI sites, respectively.

Figure 16:
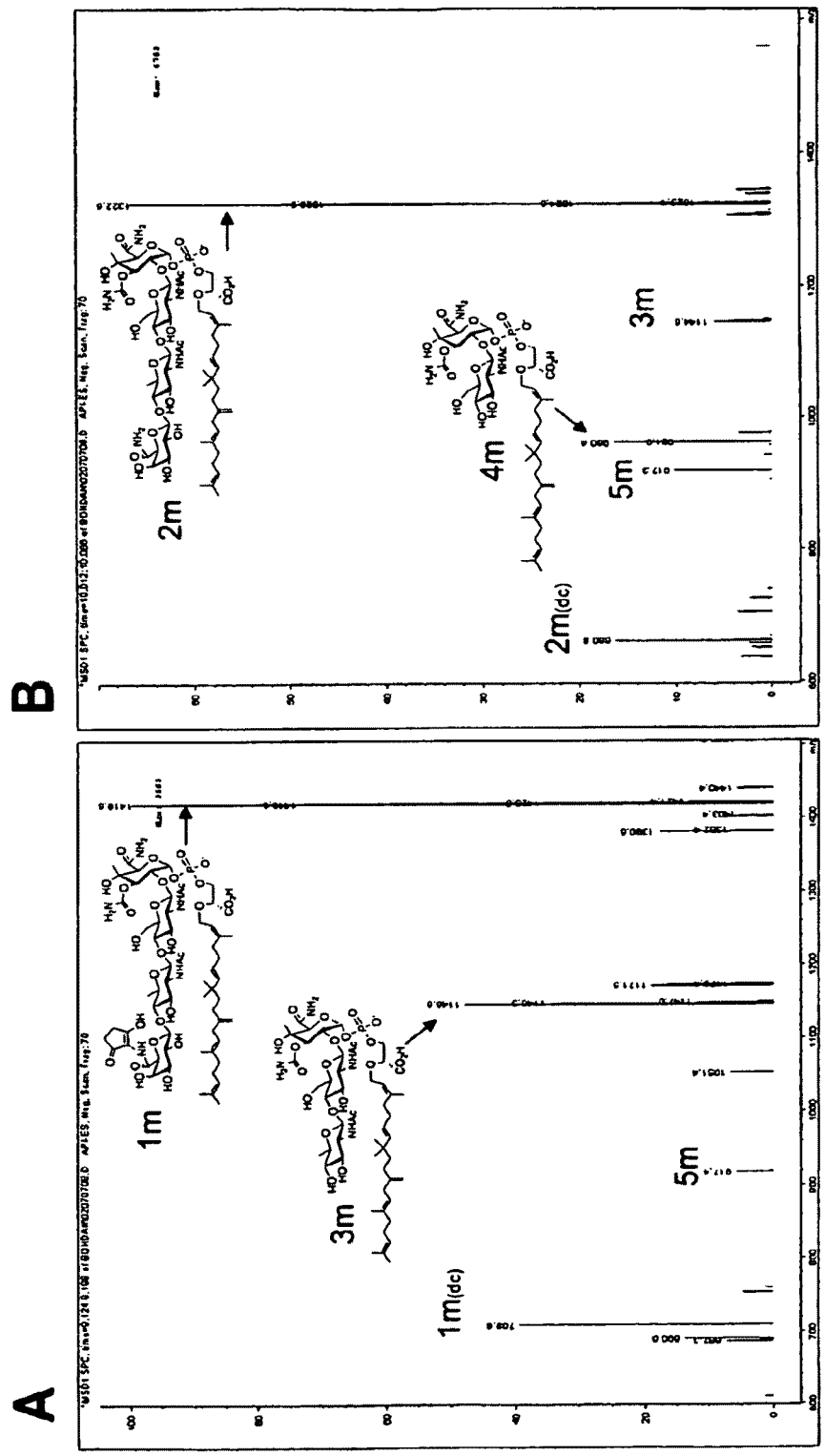

FIG. 16 shows graphs of LC-MS analysis of moenomycin metabolites accumulated by S. ghanaensis MO12 strain. The final product is moenomycin C4 (1m) having Rt 9.2 min (FIG. 16A). The strain also accumulates its precursor lacking chromophore unit (2m; Rt 10.0 min) (FIG. 16B). Peaks corresponding to trisaccharide and disaccharide precursors of moenomycin C4 (3m and 4m, respectively) are observed. 5m is decarbamoylated derivative of 4m. 2m(dc) and 1m(dc) are doubly charged ions of 2m and 1m, respectively.

Figure 17:
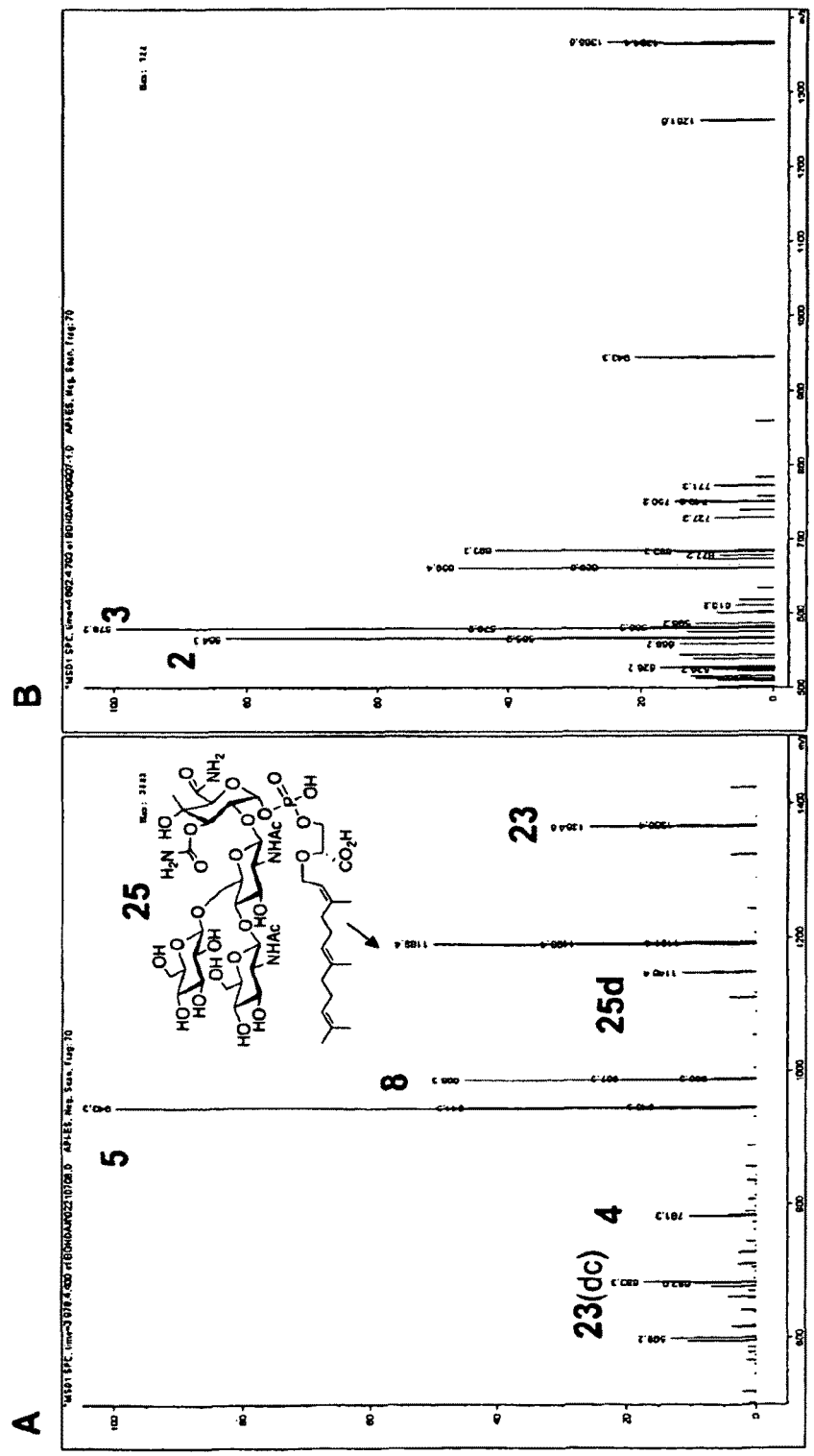

FIG. 17 shows a graph of LC-MS analysis of moenomycin metabolites accumulated by S. lividans TK24 ΔmoeN5 strain (FIG. 17A). The final product is compound 23 having Rt 4.2 min (FIG. 17B). The strain also accumulates its monosaccharide precursors 2 and 3 (Rt 4.7-4.8 min). Structures of compounds 2, 3, 4, 8 and 23 are shown on FIG. 4. Compounds 5 and 25d are decarbamoylated derivatives of 8 and 25, respectively. 23(dc) is doubly charged ion of 23.

Figure 18:
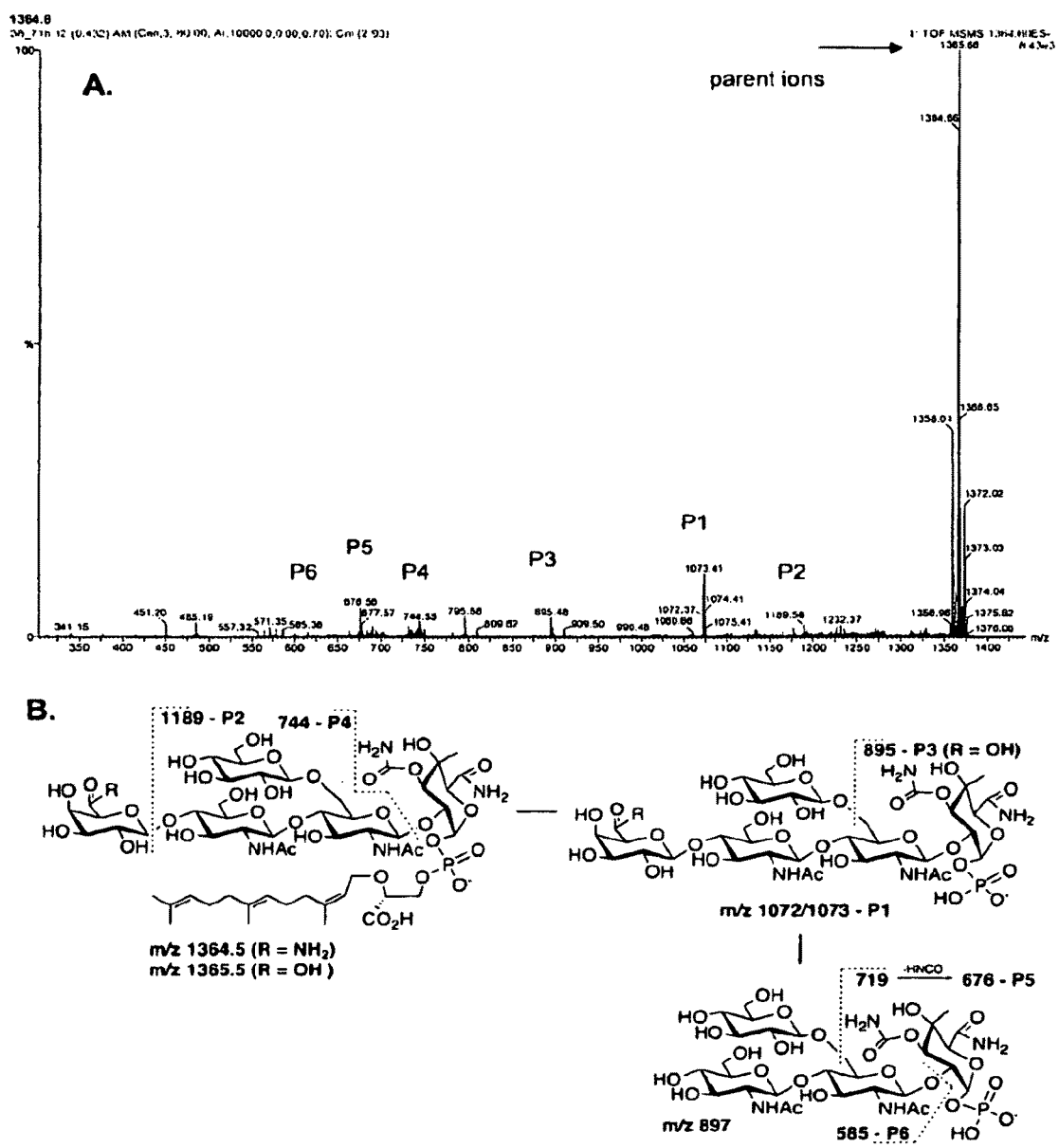

FIG. 18 shows a LC-MS spectrum of (A) Mixed (−)-ESI-MS2 spectrum of compounds 22 and 23 produced by the S. lividans ΔmoeN5 strain (FIGS. 18A) and (B) the proposed fragmentation pathway of the compounds (FIG. 18B).

Figure 19:
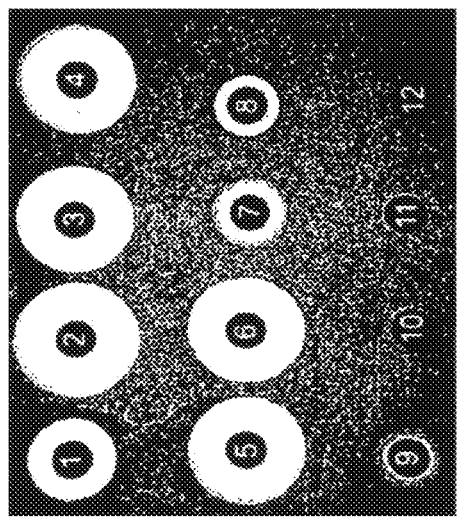

FIG. 19 shows the results of a disc diffusion assay of antibacterial activity of moe a intermediates against B. cereus. Spots 1 and 2—moe A (100 and 10 nM per disc, respectively); 3—compound 15 (100 nM); 4—compound 16 (100 nM), 5—compound 17 (100 nM), 6—compound 24 (100 nM), 7—mixture of compounds 22 and 23 (200 nM), 8—compound 11 (100 nM), 9—mixture of compounds 22 and 23 (50 nM), 10—mixture of compounds 2 and 3 (200 nM), 11—compound 1 (200 nM), 12—extract from 5 g S. lividans TK24 mycelial cake.

DETAILED DESCRIPTION

Definitions

The definitions of certain terms as used in this specification are provided below.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "alkyl" refers to monovalent saturated aliphatic hydrocarbyl groups having from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH$_2$—), t-butyl (($CH_3$)$_3$C—), n-pentyl ($CH_3CH_2CH_2CH_2CH_2$—), and neopentyl (($CH_3$)$_3$CCH$_2$—).

As used herein, the term "amino" refers to the group —$NH_2$.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, "cycloalkyl" refers to a saturated or partially saturated cyclic group of 5 carbon atoms and no ring heteroatoms. The term "cycloalkyl" includes cycloalkenyl groups. Example of cycloalkyl group includes, for instance, cyclopentyl or cyclopentenyl.

As used herein, "substituted cycloalkyl" refers to a cycloalkyl group, as defined herein, having from 1 to 3 substituents selected from the group consisting of oxo and hydroxy, wherein said substituents are as defined herein. The term "substituted cycloalkyl" includes substituted cycloalkenyl groups.

As used herein, the term "ester" include formate, acetate, propionate, butyrate, acrylate, and ethylsuccinate derivatives of the compounds of the invention.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" includes an amino acid (e.g., peptide or polypeptide) generated when a gene is transcribed and translated.

As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

As used herein, "hydroxy" or "hydroxyl" refers to the group —OH.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding a moeA biosynthetic polypeptide of the invention as described herein or amino acid sequence of an moeA biosynthetic polypeptide described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An "isolated" or "purified" polypeptide or biologically-active portion thereof is substantially free of cellular material or other contaminating polypeptide or non-moeA-related agents from the cell from which the is derived, or substantially free from chemical precursors or other chemicals when chemically synthesized.

As used herein, the term "nucleotide pair" means the two nucleotides bound to each other between the two nucleotide strands.

As used herein, the term "oxo" refers to the atom (=O).

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polynucleotide" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences from a moeA biosynthetic gene of the invention.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from a polypeptide encoded by a moeA biosynthetic gene of the invention.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "small molecule" means a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substitution" is one of mutations that is generally used in the art. Those substitution variants have at least one amino acid residue in the polypeptides encoded by the moeA biosynthetic genes of the invention replaced by a different residue. The sites of greatest interest for substitutional mutagenesis include the active sites or regulatory regions of the polypeptides encoded by the moeA biosynthetic genes of the invention. "Conservative substitutions" are shown in the Table below under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ile ala; phe | |

TABLE 1-continued

Amino Acid Substitutions

| Original Residue | Exemplary Substitutions | Preferred Substitutions |
|---|---|---|
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Once such variants are generated, the panel of variants is subjected to screening as described herein and variants with similar or superior properties in one or more relevant assays may be selected for further development.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease or condition that is being treated, e.g., the conditions associated with a bacterial infection. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. For example, a "therapeutically effective amount" of moe A derivatives is meant levels in which effects of bacterial infection are, at a minimum, ameliorated.

As used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

As used herein, the term "tautomer" refers to alternate forms of a compound that differ in the position of a proton, such as enol-keto and imine-enamine tautomers.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder characterized by bacterial infection if, after receiving a therapeutic amount of a moe A derivative according to the methods of the present invention, the subject shows observable and/or measurable reduction in or absence of one or more signs and symptoms of a particular disease or condition. For example, for infection, inhibition (i.e., slow to some extent and preferably stop) of bacterial growth; and/or relief to some extent, of one or more of the symptoms associated with the specific infection; reduced morbidity and mortality, and improvement in quality of life issues.

General

The methods and compositions described herein relate to the identification, isolation, and characterization of genes which encode proteins useful for the biosynthesis of TG inhibitors such as moes, and their homologues. The methods and compositions also relate to the production of such proteins, and their use in the synthesis of moes, the production of modified moes, and the altered expression (e.g., overexpression) of moes. In one embodiment, the moe is moe A.

The methods and compositions also relate to the mutation, disruption, and expression of genes involved in the moe biosynthetic pathway. The present disclosure describes the isolation of gene clusters for moe biosynthesis from S. ghanaensis ATCC14672 (a.k.a., "moe biosynthesis-related genes") as well as the insertional inactivation of certain moe biosynthetic genes as evidence of (i) cloning of moe biosynthesis gene clusters and (ii) the potential for generating bioactive moe derivatives through mutagenesis. The present disclosure also describes manipulations of regulatory genes to improve moe production in S. ghanaensis ATCC 14672. The present disclosure also describes the heterologous expression of moe biosynthesis related genes in S. lividans TK24.

The moe biosynthesis-related genes of the present invention are useful for the chemoenzymatic generation of clinically valuable moe derivatives. For example, the moe biosynthesis-related genes of the invention are useful for the development of analogs suitable for use in humans. They are valuable tools for the chemoenzymatic synthesis of novel bioactive molecules and chemical probes. Additionally, manipulation of the moe biosynthesis-related genes of the present invention in cellular expression systems is useful for the generation of moe production and enrichment. In one embodiment, the moe biosynthesis-related genes of the invention are manipulated for overexpression of moes in a prokaryote.

The moe biosynthesis-related genes of the present invention may be selected from the group consisting of moeA4 moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5. Exemplary polynucleotide sequences of moe biosynthesis-related genes include SEQ ID NOS: 3-25. Exemplary polypeptide sequences of moe biosynthesis-related genes include SEQ ID NOS: 26-48.

In one embodiment, the moe biosynthesis-related genes encode polypeptide fragments or variants of a natural moe biosynthesis-related polypeptide, wherein the variants comprise one or more conservative or non-conservative amino acid substitutions, additions or deletions compared to the natural moe biosynthesis-related polypeptide. A moe polypeptide (a.k.a., moe biosynthesis-related polypeptide") in its native state is related to the biosynthesis of moes (e.g., moenomycin A), intermediates, derivatives or homologues, thereof. Variant polypeptides can be prepared by altering the sequence of polynucleotides that encode the natural moe biosynthesis-related polypeptide sequence. This is accomplished by methods of recombinant DNA technology well know to those skilled in the art. For example, site directed mutagenesis can be performed on recombinant polynucleotides encoding the moe biosynthesis-related polypeptide sequence to introduce changes in the polynucleotide sequence so that the altered polynucleotide encodes the peptides of the invention.

In some embodiments, the variants are at least about 85% identical, at least about 90% identical, or at least about 95% identical to the corresponding natural moe biosynthesis-related polypeptide. Typically, the variant moe biosynthesis-related polypeptides retain at least about 25%, at least about 50%, at least about 75%, at least about 80%, at least about 90%, or at least about 95% of the the biological activity of the natural polypeptide. The biological activity of the variant polypeptides and the natural polypeptide may be assayed according to the methods described herein, e.g. the type and/or quantity of moes or moe derivatives/intermediates produced by a heterologous host expressing the variant sequence may be compared to the type and/or quantity of moes or moe derivatives/intermediates produced by the same organism expressing the natural polypeptide.

As used herein the term "moe intermediate" or "moenomycin intermediate" encompasses moe-related biosynthesis precursor molecules and/or metabolites of moe biosynthesis. Alternatively, the variant polypeptides may possess a biological activity different from the natural polypeptide. For example, variations in the primary amino acid sequence may affect the binding of a moe biosynthesis-related polypeptide to one or more substrates, thereby providing moe derivatives different from those produced by the the natural polypeptide. Assessing whether variant polypeptides have activity different from the natural polypeptide may also be performed according to the methods described herein. For instance, the variant polypeptide may be expressed in a heterologous host and the appearance of a new moes or moe derivatives may be observed using LC-MS analysis.

Although some portions of the discussion and examples focus on S. ghanaensis ATCC14672 or S. lividans TK24, it is understood that any bacterial strain or mammalian cell line which produces moe, moe-like compounds, or which includes homologues of the genes identified for moe biosynthesis, may also be used. Thus, using the teachings described herein, moe biosynthesis related genes may be expressed in heterologous systems including, but not limited to bacterial (e.g., Streptomyces sp., E. coli), mammalian (e.g., mouse, human, rat, hamster, etc., such as NIH-3T3, HeLa, HEK 293, etc.), yeast (e.g., Saccharomyces cerevisiae, Pichia pastoris) and insect cells (e.g., Drosophila melanogaster Schneider cells to generate moes and moe derivatives.

In preparing the recombinant expression constructs to express moe biosynthesis-related genes in heterologous hosts, the various polynucleotides of the present invention may be inserted or substituted into a bacterial plasmid-vector. Any convenient plasmid may be employed, which will be characterized by having a bacterial replication system, a marker which allows for selection in a bacterium and generally one or more unique, conveniently located cloning sites. Numerous plasmids, also referred to as vectors, are available for transformation. Suitable vectors include, but are not limited to, the following: viral vectors, such as lambda vector system gt11, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/- or KS+/- (Stratagene, La Jolla, Calif.), and any derivatives thereof. Also suitable are yeast expression vectors, which may be highly useful for cloning and expression. Exemplary yeast plasmids include, without limitation, pPICZ, and pFLD. (Invitrogen, Carlsbad, Calif.). The selection of a vector will depend on the preferred transformation technique and target host cells.

The nucleic acid molecules encoding moe biosynthesis-related genes are inserted into a vector in the 5' to 3' direction, such that the open reading frame is properly oriented for the expression of the encoded protein under the control of a promoter of choice. In this way, the moe biosynthesis structural gene is said to be "operably linked" to the promoter. Single or multiple nucleic acids may be inserted into an appropriate vector in this way, each under the control of suitable promoters, to prepare a nucleic acid construct of the present invention.

Certain regulatory sequences may also be incorporated into the expression constructs of the present invention. These include non-transcribed regions of the vector, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used.

A constitutive promoter is a promoter that directs constant expression of a gene in a cell. Examples of some constitutive promoters that are widely used for inducing expression of heterologous polynucleotides include the ADH1 promoter for expression in yeast, those derived from any of the several actin genes, which are known to be expressed in most eukaryotic cell types, and the ubiquitin promoter, which is the promoter of a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter.

Also suitable as a promoter in the plasmids of the present invention is a promoter that allows for external control over the regulation of gene expression. One way to regulate the amount and the timing of gene expression is to use an inducible promoter. Unlike a constitutive promoter, an inducible promoter is not always optimally active. An inducible promoter is capable of directly or indirectly activating transcription of one or more DNA sequences or genes in response to an inducing agent (or inducer). Some inducible promoters are activated by physical means, such as the heat shock promoter (HSP), which is activated at certain temperatures. Other promoters are activated by a chemical means, for example, IPTG. Other examples of inducible promoters include the metallothionine promoter, which is activated by heavy metal ions, and hormone-responsive promoters, which are activated by treatment of certain hormones. In the absence of an inducer, the nucleic acid sequences or genes under the control of the inducible promoter will not be transcribed or will only be minimally transcribed. Promoters of the nucleic acid construct of the present invention may be either homologous (derived from the same species as the host cell) or heterologous (derived from a different species than the host cell).

Once the nucleic acid construct of the present invention has been prepared, it may be incorporated into a host cell. This is carried out by transforming or transfecting a host or cell with a plasmid construct of the present invention, using standard procedures known in the art, such as described by Sambrook et al., *Molecular Cloning: A Laboratory Manual, Third Edition*, Cold Spring Harbor: Cold Spring Harbor Laboratory Press, New York (2001). Suitable hosts and cells for the present invention include, without limitation, bacterial cells, virus, yeast cells, insect cells, plant cells, and mammalian cells, including human cells, as well as any other cell system that is suitable for producing a recombinant protein. Exemplary bacterial cells include, without limitation, *E. coli* and *Mycobacterium* sp. Exemplary yeast hosts include without limitation, *Pischia pastoris, Saccharomyces cerevisiae*, and *Schizosaccharomyces pombe*. Methods of transformation or transfection may result in transient or stable expression of the genes of interest contained in the plasmids. After transformation, the transformed host cells can be selected and expanded in suitable culture. Transformed cells are first identified using a selection marker simultaneously introduced into the host cells along with the nucleic acid construct of the present invention. Suitable markers include markers encoding for antibiotic resistance, such as resistance to kanamycin, gentamycin, ampicillin, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Additionally, or in the alternative, reporter genes, including, but not limited to, β-galactosidase, β-glucuronidase, luciferase, green fluorescent protein (GFP) or enhanced green fluorescent protein (EGFP), may be used for selection of transformed cells. The selection marker employed will depend on the target species.

Expression is induced if the coding sequences is under the control of an inducible promoter. To isolate the protein, the host cell carrying an expression vector is propagated, homogenized, and the homogenate is centrifuged to remove bacterial debris. The supernatant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by HPLC. Alternative methods of protein purification may be used as suitable. See J. E. Coligan et al., eds., *Current Protocols in Protein Science* (John Wiley & Sons, 2003). Upon obtaining the substantially purified recombinant protein, the protein may be administered to a subject as described herein.

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art. Standard techniques are used for nucleic acid and peptide synthesis. Standard techniques, or modifications thereof, are used for chemical syntheses and chemical analyses.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

All references, patents, and/or applications cited in the specification are incorporated by reference in their entireties, including any tables and FIGS., to the same extent as if each reference had been incorporated by reference in its entirety individually.

Moe Biosynthesis-Related Genes of the Invention

The candidate *S. ghanaensis* moe biosynthetic genes were identified by in silica scanning of shotgun sequenced fragments of the *S. ghanaensis* genome. As a result of genome scanning, 4 neighboring contigs were identified. Two of the identified genes, moeD5 and moeGT3, were used as a hybridization probes to retrieve additional overlapping cosmids from a genomic library of *S. ghanaensis* that cover one of the moe gene clusters. Physical mapping and partial sequencing of the cosmids confirmed that the in silico assembly of contigs coincided with their localization on the chromosome. A detailed discussion of the methods and procedures outlined above is provided in the Experimental Examples, Sections II and III.

Two gene clusters (e.g., gene cluster 1 and gene cluster 2) were identified which contain the moe biosynthesis-related genes of the invention. Sequence data indicated at least 1.3 Mbp separate gene cluster 1 from cluster 2. The polynucleotide sequence of gene cluster 1 (SEQ ID NO: 1) is shown in Table 2. The polynucleotide sequence of gene cluster 2 (SEQ ID NO: 2) is shown in Table 3.

TABLE 2

Complete DNA sequence of *S. ghanaensis* ATCC14672 moe (moe) biosynthesis gene cluster 1.

CGCGCCCCTCCGGAGGCTGTCCGGAAGGGCGCGGCACGGGTGGGGCGGGTCGGCCGGGTTCCGCCGGCCGGGTCGGGTC

AGCCGACGACGGCCGGCTGTGCGGGCGCCTCCCGCGGGCCGCCGCTGATCGGCAGGACCTCGGCGTCCGAGGTCCGCACG

AAGCGGGGACCGTCCGGCCCGTACACCCCGCGCGGCTCCGGGAACAGGGTGAGCAGGACGAGGTAGAGCACCGCCGCCAG

GGCCAGGCCGACCGGCAGCGAGACGTCCATGCCGTCGGCCAGGTCGCCGAGCGGTCCGACGAACTGACCGGGCAGGTTGG

TGAAGAGCAGGGCCACGGCGGCGGAGACCAGCCAGGTGGCCAGGCCGCGCCAGTTCCACCCGTGGGCGAACCAGTAGCGG

CCGCCGGTGCGGCGCTGGTTGAAGACCTGGAGCGCCTCCGGGTCGTACCAGCCCCGGCGGGTGACGTAGCCGAGGATCAT

CACGACCATCCACGGCGCGGTGCAGGTGATGATCAGGGTGGCGAAGGTGGAGATCGACTGCGTGAGGTTCAGCCAGAAGC

GGCCGGCGAAGATGAACACGATGGACAGCACGCCGATGAAGATCGTCGCCTGAACGCGGCTGAAGCGGGTGAAGACGCTG

CAGAAGTCCAGTCCGGTGCCGTACAGCGCGGTCGTGCCGGTGGACAGGCCGCCGATCAGCGCGATGAGGCAGAGCGGCAG

GAAGTACCAGCCGGGCGCGATCGCGAGCAGGCCGCCGACGTAGTTGGGCGCGTCGGGGTCGAGGTACGCCCCGGCCCGGG

TGGCGATGATCGACGCGGTGGCCAGGCCGAAGACGAACGGCAGCAGCGTGGCGATCTGGGCCAGGAACGCCGCGCCCATC

ACCCGGCGGCGGGGGGTCGCGGCCGGGATGTAGCGGGACCAGTCGCCGAGGAACGCGCCGAAGGAGACCGGGTTGGAGAG

CACGATCAGTGCGGACCCGATGAAGGACGGCCAGAAGAGCGGGTCCGCGGTCGAGGCGAAGGTGCCCGCGTAACCGGGGT

CGAAGTCGCCGGCGAAGGCGAAGGCGCCCAGCACGAACAGGGCCGAGGCCGCCACCACGGCGATCTTGTTGACCAGCAGC

ATGAAGCGGAAGCCGTAGATGCAGACCACCAGCACGAGACCGGCGAAGACCGCGTAGGCCAGGGCGTACGTCACCGTCGA

CTCGGGGACTCCCAGCAACCGGTGCGCGCCGCCGACCAGGGCGTCCCCGAGGACCACACCGAGATCGAGAAGAAGGCGA

TCGCGGTGAGCAGCGCGAGGAAGGAGCCGACGACCCTTCCGTGCACCCCCAGGTGGGCGGAGGAGGAGACGGAGTTGCTG

GTGCCGTTCGTGGGCCCGAAGAGCGCCATGGGCGCGAGCAGCAGCGCGCCCGCGACCAGGCCGAGCAGCGTCGCCGCGAG

CCCCTGCCAGAAGGAGAGGCCGAACAGGATGGGGAAGGTGCCCAGCACACAGGTGGCGAAGGTGTTGGCGCCGCCGAAGG

CGAGGCGGAACAGATCGAGCGGACGGGCCGTGCGGTCCTCGTCCGGAATCTGCTCGACACCGTATGTCTCGATGTCGGTG

ACCGCGGTCTTCACGGGATCTCCTCCTTCTGTTCACGCCCCGGGGATGGCCCCACAGTCTGAATCCCCCACTGACCTG

CGACAACTGTGTCAATCACAGAGAGGTAGCCTGCTTTATGTGGCCACCAACAAACTGACCGTCGAGGATCTGCTCTCCTT

CCCCGCCCTCCAGCTGACGCTGCGGGCGGGGAAGAGTGGACTCTCACGCTCCGTTTCCTGGGCCCACACCAGCGAGTTGG

CCGATCCGACCCCCTGGCTGCTGGGGGCCGAGGTGATCATGACGACGGGGCTCGCGATCCCCCGCACCGCGACCGGGCAG

TABLE 2-continued

Complete DNA sequence of *S. ghanaensis* ATCC14672 moe (moe) biosynthesis gene cluster 1.

CGCCGCTATCTGGAGCGGCTGGACGACGCCGGGGTCTCCGCGCTGGCCCTGTCGGCGCAGCTGCACATGCCGCCGCTGCA

CGACGCGTTCTTCAAGGCGGCCGAGGAACGGGGCTTCCCCGTCCTGGAGGTGCCGCTCGCCGTTCCGTTCATCGCGGTCT

CCCAGGAGGTCGCCGCCGCGGTGCAGGAGGACGCCCGGCACCGGCTGGGCGCGCAGCTGCAGGTCTTCGGCTCGCTGCGC

TGGATGGTCGCCGAGGACCTCGACACCCCGACCCTCCTGCGCCGCCTCGAGCGCCTGTCCGGGTACAACGTCTTCCTCTG

CACCCCGCAGGGCCGCCCGCTGCTGCCCGGGGTGCCCACCCCCGACCCGGGCGTGCTGCCCGCCTCGGTGGACGCCCCGC

CGACCGTCCCCGGCGGTTTCGTCCTGCCCGTGCCGGCACCGGGCGGTCCGGCCGGTTTCCTGGTGGCGTACGAGAGGCAG

GGCGCCCAGCCCGCCGGGCTCGCGGTCGTCCAGCACATCGCCACGGTGGCGGCGCTGCGGCTGGCGATGGTGCGCAACGA

ACGCGAGACGCTGCGCCGCGAGGGCGCCGAGACCCTCGCCGAACTGCTCCGGGAGGTGCTCGACCCGGACGCCGCCCGCC

GCCGGCTCGCCCGGCACGCGATCGAGGGCGAGACCGTGCTGCTCGTGGTCCGGAACACCACCGACGAGGCACTGCTGCAC

TGCCTGGAGGACCGCCCCCACCTGCTGCTCACCCGGGGCGACGACCGGTACGTGCTCGGGGCCCGGAGCTGGCCCCGGC

GATCGGCGAACTGCCCGGGGTGGCGGCCGGGATGAGCCGCGCCCTTCCGCCGGGCGCGGCCCTGAAGGTCGCCGAGCGCG

AGGCCCTGTGGGCGCTGAGCAAGGCGGTCGAGTCGGGCCGCCCCCTGGTCCGCTACGGCGACGACGCGACGGGCCGCTGG

CTGCCGGAGGACCCCGCGGTGCTGAGCGCGCTGGTCGAGCACGTCCTCGGCGAGGTGCTGCGCTACGACCTGGCCCACGG

CTCCCAGCTCCTGGTCTCCGTGCGCACCTGGCTGGAGCGCGACCGCCGTACGGAGACCGCCGCGGCCGCCCTCCACATCC

ACCCCAACACGCTCGCCTACCGGCTGCGCCGCTTCGGCGCCCTCTCCCGGCGCGACCTGTCCTCGACCGGCGCGCTGGCG

GAGGTCTGGCTGGCGATCCAGGCGGCCGGGACGCTGGGGCTCACCGACTGAGCGCGCCGGACACCGGCCCCGGGCGGGGA

CACGGACCGGGCGGCGCGCACCGCCTCCGAGGCGTTCGTCCGGGCCGGGCCGCCCCGCCGGCGGGGAACCGGCCGGGGC

CGTCACCCCTCGGCCGGGCCGCCCCGCCTCGTCGGACGACCGGAGCCGGACGGCCGGCTCCCCCTTGAGGACCTTGCCG

CCGGGTCCCAGGGGAAGCCGGTCGGGGAGGACCACCCGCCGCGGACGCCGGTACGCCGCGATGTGCCGCTCACCCCACGC

CACGACGGAATCCGCCAGTGCCCCGTCCGGTGTCGGGCCGTCCCGTGGCACCACCACCGCGCACACCTCCTGGCCGTACA

CCGGGTCGGGGAGCCCCACCACCGCGACCCGGGCGACCGCCGGATGGCGGAGCAGCGCTTCCTCGACCTCACGGGGATGG

ACGTCGTACCCGCCCCGCAGGATCACGTCCTTCTCGCGGTCGACGGCGGTGGGGTACCCCTCCTCGTCCAGCAGCCCTAG

ATCGCCGGTGCGGAACCAGCCGTCCACGAACGCGGCGGCCGTGGCGCGGGGGGCGTCGACGTACCCGGCCATCAGGTTGT

GCCCGCGGACGACGATCTCGCCCACCTCGCCGGAGGGAGCGGCCCGACGGCGTCCTCCGCCTCGGACCGGGGCTGTCGCG

ACCTCCACGCCCCAGAGGTGATCCGCTCGGCGCCCGCGACCACCGCGGTGCGCTCCGGCCACCGGCCGCGGAGTCCGAG

AGGATCGTGGCCGCCGAGAGGGTCGCCCCCGGGCCCGCCCACGTGTTCCCGCCGTCGGTGACGGCTCCGGAATCCGTCGT

GAACGGCCCTGCCGGAGGTTTTCGTACGCGCTCGTCGCGACTCCGCCTCGCTTGCCGGTAATCGGCTTCCATCGGCCGGA

CGACAGCATGAGACGTCTTCTGTGCAAGACCCGCGGTGGATCCCAGGATGAGACCGGCCCGAAGGGTAGCGAAAGGAGCG

GACCTTGGACATCTCCTCGTCCATGGACTTCTTCGTGCGACTCGCCCGCGAAACCGGTGACCGGAAGAGGGAGTTTCTCG

AACTCGGCCGCAAGGCGGGTCGGTTCCCCGCGGCGAGCACCTCGAATGGCGAGATTTCCATCTGGTGCAGCAACGACTAC

CTGGGTATGGGGCAGCACCCGGACGTCCTCGACGCCATGAAGCGCTCCGTGGACGAATACGGCGGAGGATCCGGGGGTTC

GCGGAACACAGGCGGAACCAACCACTTCCATGTGGCTCTGGAGCGGGAGCCGGCCGAGCCGCACGGAAAGGAGGACGCCG

TTCTCTTCACCTCGGGGTATTCCGCCAATGAGGGATCCCTGTCGGTTCTGGCCGGGGCCGTCGACGACTGCCAGGTCTTC

TCGGATTCGGCGAACCACGCGTCCATCATCGACGGTTTACGGCACAGCGGCGCCCGCAAGCACGTATTCGGCACAAGGA

CGGGCGGCATCTGGAGGAGTTGCTGGCCGCGGCCGACCGGGACAAGCCGAAGTTCATCGCCCTGGAGTCCGTGCATTCGA

TGCGGGGCGACATCGCGCTCCTGGCCGAGATCGCCGGCCTGGCCAAGCGGTACGGAGCGGTCACCTTCCTCGACGAGGTG

CACGCGGTCGGCATGTACGGCCCGGGCGGAGCGGGCATCGCGGCCCGGGACGGCGTGCACTGCGAGTTCACGGTGGTGAT

GGGGACCCTCGCCAAGGCCTTCGGCATGACCGGCGGCTACGTGGCGGGACCGGCCGTGCTCATGGACGCGGTGCGCGCCC

TABLE 2-continued

Complete DNA sequence of *S. ghanaensis* ATCC14672 moe (moe) biosynthesis gene cluster 1.

```
GGGCCCGTTCCTTCGTCTTCACCACGGCGCTGCCGCCGGCGGTCGCGGCGGGCGCGCTCGCCGCGGTGCGGCACCTGCGC
GGCTCGGACGAGGAGCGGCGGCGGCCGGCGGAGAACGCGCGGCTGACGCACGGCCTGCTCCGCGAGCGGGACATCCCCGT
GCTGTCGGACCGGTCCCCCATCGTCCCGGTGCTGGTCGGCGAGGACCGGATGTGCAAGCGCATGTCGGCCCTGCCGCTGG
AGCGGCACGGCGCGTACGTCCAGGCCATCGACGCGCCCAGCGTCCCGGCCGGCGAGGAGATCCTGCGGATCGCGCCCTCG
GCGGTGCACGAGACCGAGGAGATCCACCGGTTCGTGGACGCCCTGGACGGCATCTGGTCCGAACTGGGGGCCGCCCGGCG
CGTCTGACGCCCCGCAGTGTCACCCCGCGGGAGGGCTCTGCGGAGCGGGCCCGGCGTCCCCGCCCCCGGACCCGCACCC
GTCCAGATCCGGCCCATCTCGGCGGAGACCGCCATGACCTCCTCGAAGGTGCCCGAGGCCTCCACCCGCCCGCCCTCGAG
CACCACCACGCGGTCGGCCGCGCGCAGCAGAGCGGGCCGGTGGGAGACCGCGAGCACGGTCCGCGTCCCGTCCAGCAGCC
TCTCCCACAGCAGGTGCTCGGTCTCCGGGTCCAGGGCACTGGAGACGTCGTCCAGCACCACGAGTTCGGGGTCGCCGACC
AGCATGCGGGCGATCGCGACCCGCTGGATCTGCCCGCCCGAGAGGCGCAGGCCCCGGGGCCCACCACGGTGTCCGGGCC
GTCCTGCATCGCCGCCAGGTCGGGCTCCGCCACGGCGAGGCGCACGGCCTCGTCGAAGGCGCGCCGTCCCGGCCCAGCA
GGACGTTCTCCCGCACCGTCCCGCTGAACAGACACGGGACCTGCGGGGTGTACCCGCAGCGCGGCGCCACCAGGAACGAC
GCGGGGTCGGCGATCGGTTCGCCGTTCCACAGCACGGTGCCCCGCTCGTGCGGGAGCAGTCCGAGGACGGCCCGGACCAG
GGTGCTCTTGCCGGAACCGACCCGGCCGGTGACCACGGTGACGGTGTGCCGCTCCACCACCAGGTCCACGTCCTCTATGC
CGTGCCCCGCCCCGGGGTGGCGGGCCGTCAGCCCGCGCACGGCCAGTTCCCGCAGGGGCGGGCGGGCTCCGGCCCGGCG
TCCGGGCGGCGGCCCCCTCGCCGGTCCCTCCCGGCGCGTCGGACGCGATCGGCGGACTGGCCCGCTCCAGGGACCGCCG
CAGCCGGCAGCCGAGGTTGTTGGTGATCCGGCCGAGCGCCACCGAGACCCGCTGCAACCGCACGGACAGCATGCCGATCG
ACCCCAGGGCCTCGGTCAGGATCTGCAGGTAGAAGGCGAACAGGGCGAGATCGCCGACGCTGAAGGTCCCCTCGTCCATC
CGCCCCGCGACCAGCAGCAGCACCACGCCGACCCCGATCGGGGCCGGGTTGCCGATCACCGTGCGCTGGACGACGGCGTA
CAGCTCCTCCCGCACCGCGGCTTCGGCACGGGCGCCGTTCAGCCCGGCGACGTGCGCGGCGACCTGCGGCTCGGCGGCGG
CGGCCTGCACCGCGCCCACCGCGCCCACCATCTCCCGCAGGGCTCCCGCCACCTCCCCGGACGCGGCCCGGGTGGCCCGC
CGGTGCCGCAGGAACCGGCTGTGGGCCAGCGCGGTGACCAGCGTCAGCAGGACGAGGAGGGCGAGGAGGGCGCCGGTGAC
CACGGCGTCGATCCGCATCATCACCGTGACCGACGCGGCGACGAACAGCCAGTGGGCGAGGTTCGTCGGCGCCCAGGCGA
CGAAGAACCCCGTCTCGTCGACGTCCTCGCCCACCGTTCGCAGGGACTCGCCGGGGCTGGTGCGGGCCGTCACCTCCGAC
CCGCGCAGGGCCGATCCCAGCAGGGCGTGCCGCAGCCGCGCCGTGGTGCCGTACTGGACCCGCGGCTCCAGCCTGTTGAT
CATCACGCCGAACTGGAGGAACAGCCGTCCCGCCTCGATCGCGGCCACCAACGCGATGATCAGCCACACGCCCCCGCCCG
CGCCCAGCGCGTCGAACAGCCGCTGGAACAGCAGGCCCACCACCAGGGTTCCCGCCCGCAGCAGGACCCACAGACCGGTG
AGGGTCCAGTAGGTGCGGGCCGAGCCGCGCAGCACGTCCGCGAGCCGTCCCAGGACGGACTGCCGCCCCGCTCCGTCGTC
CGCCCGCCTCGCTCTCCCTCCTGCCCGCTCCGCTCCGTCGTCCGCCCGCCTCGCTCTCCCCCCTGCCCGCTCCGCTCCGT
CGTCCGCCCGCTCCACTCCTGGCACCCCGCTCCCCCTCCCGTCCCCGTTCCTCACCGGGTGGCTCCGGCCGTGCGGAGGA
GTGCGTGGAAGCGCGACCCGGGATCGGCGGCGAGGACCCTCCGCTCCCCCTCCTCGGCGACCTTCCCCTCCTCCAGCACC
AGGATCCGGTCGACGTTCCGGAGCAGGTGCGGGCGGTGCTCCACCACGACGGCGGTGCGGCCCTCGAGCAGCCGCTCCAG
CGCGGGCATCAGGAGCCGCTCGCTGTACGGATCCAGCCGGGCCGTCGGCTCGTCCATCAGGACCAGCCCCGGATCGCGCA
GGAACACCCTGGCCAGCGCGAGCTGCTGCTCCTCGCCCGCGGACATGCCGCGGGCCCCGGCGCCGAGCGGCGTGTCCAGA
CCGTCGGGCAGGGTGCGCAGCCAGGGGCCGAGCCCGGCCTCGCCGAGAGCGGCGCGCAGCCGGTCGTCGGGGACGGAGCG
GTCGAAGAAGGTGAGGTTGTCCCGCAGCGAGGCGTGGAAGACGTGCACCTCCTGGGTGACCAGCGCGACCCGGCTGCGCA
GCGCCCGGGGATCGATCTCCGTCAGGTCCAGGCCGCCTGCCGACACCGAGCCCGCCCCCGGGTGGTGGAGCCCGAACAGC
AGCCGGACCACGGTGGACTTGCCGCTGCCGGTGCGTCCCACGACGCCGAGGCGTTCGCCGGGGCGCAGGGTGAAGGAGAC
GTCCCGCAGCACCGGCTCGTCGGGCTCGTAGCCGAAGGAGACCCCGTCGAAGCGGACTCCGGGCAGTCCGGCCGGCAGCG
```

TABLE 2-continued

Complete DNA sequence of *S. ghanaensis* ATCC14672 moe (moe) biosynthesis gene cluster 1.

```
TCCCGCGTCCCGTGCGGGGCGCCGCCGTCCCGTGGCCCAGCAGGTCCCTCAGCCGCTGGGCGCTCGCGGCGGCGTCCTCG
AGTTCGCGGAAGCGGGTGGTGACCGCGAGCAGGGGGCGGCGCAGCAGCATCGCGTAGGACAGGGAGGCGAAGGCCGTCCC
CGTGGAGAGCTGTCCGCGGGCGTGCAGCCAGGCGCTGACCGCCAGGGCCAGGACGACGCTGACGGCGGACAGGCCCTGCA
CCGTGGCGGGCCAGCGGACCGAGGCCCGCGCCGCGTCGCGGGCCTTCCGGTACAGGTCGTCCTGCCGGTCGCCGAGTTCC
CGCAGGGTGTACCGCGAGGCCCCGTTGACGCGGAGGTCCTCCGCCGCCGCGAGGCGCTCCTCGAGGAAGCCCTGCAGGTC
CGCCGCGACCCGCTGCCGCGCGGTGACGAAGGGCATGGCGCGGCCCACCAGGGTCCGCAGCAGCAGGAGGGTGCCTGCCG
CGAACGGGGCGACCACCAGGGCCAGCCGCCATTCCAGCCGGAACAGGGCGACGAGGATGCCGACGATCAGCAGTGCCTGC
GCCAGCAGTTCCAGCAGCAGCGTCGACATCACCGCGGCGAGCCGGGTGACGTCGCCGTCCATCCGCTCGACGAGTTCGCC
GGGCGGATGCTTGCGGTAGAAGCCCGGCGGCCGGCTCAGGCAGTGCTCGACCAGGTCCGCGCGCAACCGGTTGGTGCTGC
GCCAGGCGACCCGTGAGGACAGCGCCTCGGTGCCCGCGGTGACCACGAGCGTCCCGACGGCGGCCGCCAGGGACCAGGCG
GCGAGGTCCAGCAGCGTCTTCCGGGAGTCGCCGGAGAGCGCCCCGTCGATGAATCCGCGCAGCAGGTAGGGCGCCACCAG
CTGGAGCCCCATCCCCGCGGGGACCAGGAGGGCGAGCAGCGCCACGGCGGTCCGTTCACCGCGCAGGTAGCGGACAAACG
TGGAGAGATGCCGCAACGGACTGTCTGCCAACGCGCCCTCCCCCGTTCGCCCGGCGGCGAGCGGCCAGCATAAAGTCCT
GTGCGCCTCCTTGTGAATGACGCCTCGTCAACGGCGGCCGGAGCACGCCCTTTCTGCGGGAATGCCGATAGCGGACGCCG
CTCCGGGAGGGGGCGAAGCACACCATTGCTCGTGATTGACGCATGCTGTTAGACTCCCCACGTCTCTTGGTCCGGACATG
CGTTTCTCAACGCCGAAAGCCTGGTCAACCGCACTTTCGGCACCGCACAGTCCCACGGCGTCCGAGCGGTCGCGCGAGTC
GGCCCGGTCGAGCCAGAGGCAGCCACACGAACGTGCACCGCAATGCACCGCCTTGATCAGCCAGTTGTGAGCGAAACAAG
GGGGATTCGTGTCGAGCGATACACACGGAACGGACTTAGCGGACGGCGACGTTTTGGTCACCGGTGCGGCCGGCTTCATC
GGGTCGCACCTGGTGACGGAACTGAGGAATTCCGGCAGAAACGTTGTGGCGGTGGACCGGAGACCCCTTCCGGACGACTT
GGAGAGTACGTCCCCGCCCTTTACCGGTTCGCTCCGGGAGATACGCGGTGACCTCAACTCATTGAATCTGGTGGACTGCC
TGAAAAACATCTCGACGGTCTTCCACTTGGCCGCGTTACCCGGAGTCCGCCCGTCCTGGACCCAATTCCCCGAGTACCTC
CGGTGCAATGTACTGGCGACCCAGCGCCTGATGGAGGCCTGTGTGCAGGCCGGCGTGGAACGCGTGGTGGTCGCCTCGTC
CTCCAGCGTCTACGGCGGCGCGGACGGCGTGATGAGCGAGGACGACCTGCCCCGTCCGCTCTCCCCCTACGGGGTCACCA
AACTCGCCGCGGAGCGGCTGGCCCTGGCCTTCGCGGCCCGCGGCGACGCCGAGCTCTCGGTCGGCGCCCTGAGGTTCTTC
ACCGTCTACGGCCCCGGCCAGCGCCCGGACATGTTCATCTCCCGGCTGATCCGGGCGACGCTCCGGGGCGAACCCGTCGA
GATCTACGGCGACGGGACCCAGCTCCGCGACTTCACCCATGTGTCCGACGTGGTGCGGGCGCTGATGCTGACCGCGTCGG
TGCGGGACCGGGGCAGCGCGGTGCTGAACATCGGCACCGGGAGCGCCGTCTCGGTCAACGAAGTGGTCTCCATGACCGCG
GAGCTGACCGGTCTGCGCCCGTGCACCGCGTACGGTTCCGCCCGCATCGGCGACGTCCGCTCGACCACCGCCGACGTGCG
GCAGGCCCAGAGCGTCCTGGGCTTCACGGCCCGGACGGGTCTGCGGGAAGGTCTCGCCACCCAGATCGAGTGGACCCGGC
GGTCACTGTCCGGCGCCGAGCAGGACACCGTCCCGGTCGGCGGCTCCTCGGTGTCCGTGCCGCGGCTGTAGGCGGCATGT
GCGGCTTCGTCGGATTCAGTGACGCCGGCGCCGGGCAGGAGGACGCCCGTGTCACGGCCGAGCGCATGCTCGCCGCCGTG
GCGCACCGCGGCCCCGACGGCTCGGACTGGTGCCACCACCGGGGCGTCACCCTCGCGCACTGCGCCCTGACCTTCACCGA
TCCGGACCACGGCGCGCAGCCGTTCGTCTCCGCGTCGGGAGCCACCGCCGTGGTGTTCAACGGCGAGCTCTACAACCACG
CCGTGCTGGGCGACGGGCGTTGCCCTGCGCACCCGGAGGCGACACAGAAGTTCCTGGTGGAACTCTACGAGTTGCTGGG
CATGCGGATGCTCGACCGGCTGCGGGGCATGTTCGCCTTCGCGCTGCAGGACGCCCGCACCGGCACCACGGTGCTGGCCG
CGACCGATGGGAAGAGCCCCTCTACTAACACCCGCGTGCGAGACGGACATCGCTTTCGCGTCGGAACTCACGTCTCTGC
TGCGGCACCCCGCCGCGCCGCGCACACCGGAGGTGCGGGCGCTCGCCGACTACCTGGTGCTCCAGGCGTTCTGCGCCCCC
GCCTCGGCCGTGTCGGGGGTGTGCAAGGTGCGCCCCGGCAGCTACGTGACCCACCGGCACGGCGCGTTGGACGAGACCGA
```

TABLE 2-continued

Complete DNA sequence of *S. ghanaensis* ATCC14672 moe (moe) biosynthesis gene cluster 1.

```
GTTCTGGCGGCCCCGCCTGACCCCCGACCGGGGGCGGGCCGCGGCCCCGGACGGCGGGAGGCCGCGCGGCGGTTCGAGG
AGCTCTTCCGCGCCGCGGTCGCCGCCGGATGACCAGCACCGACCGCCGCCTCGGCGTACTGCTCAGCGGCGGCCTGGAC
TCCAGCGCGGTCGCCGCGGTGGCCCAGCAGCTCCTGCCGGGACGGCCGGTGCCCACCTTCAGCGCGGGGTTCGCGGACCC
GGACTTCGACGAGAGCGACCACGCACGGGCGGTGGCGCGCCACCTCGGCACCGAGCACCATGTGGTGCGGATCGGCGGGG
CCGACCTCGCCGGTGTGGTGGAGTCCGAACTCGCCGTGGCCGACGAGCCGTTGGCCGATCCCTCCCTGCTGCCCACACGT
CTGGTCTGCCGGGCGGCGCGCGAGCACGTCCGCGGCGTGCTCACCGGTGACGGCGCGGACGAACTGCTCCTGGGCTACCG
CTACTTCCAGGCCGAGCGGGCGATCGAGCTGCTGCTGCGCGTGCTGCCGGCCCCCGGCTGGAGGCCCTCGTCCGGCTGC
TGGTGCGCCGGCTGCCGGCCCGTTCCGGCAACCTCCCCGTGACCCACGCCCTCGGTCTGCTGGCCAAGGGCCTGCGCGCG
GCACCGGAGCACCGGTTCTACCTCTCGACGGCGCCCTTCGGCCCGGGCGAGCTGCCACGGCTGCTCACCCCCGAGGCCGG
GGCCGAACTGACCGGGCACGACCCGTTCACCGAGGTGTCGCGCCTCCTGCGGGGACAGCCGGGCCTGACCGGTGTCCAGC
GCAGCCAGCTCGCCGTGGTGACCCACTTCCTGCGGGACGTGATCCTCACCAAGACGGACCGGGGCGGCATGCGCAGCTCC
CTCGAGCTGCGTTCCCCCTTTCTCGACCTGGACCTGGTCGAGTACGGCAACTCCCTGCCCACCGGCCTGAAGCTGCACCG
GTTCACCGGCAAGTACCTGCTGCGGCAGGTCGCCGCCGGCTGGCTGCCCCCTTCCGTCGTCCAGCGGACGAAGCTGGGTT
TCCGCGCGCCGGTGGCGGCCCTGCTCCGCGGCGAGCTGCGGCCCCTGCTCCTGGACACCCTCTCCCCGTCGTCCCTGCGC
CGCGGCGGCCTGTTCGACACCGGGGCGGTGCGCCTGCTGATCGACGACCACCTCGGCGGCCGGCGCGACACCTCCCGCAA
GCTGTGGGCGCTGCTGGTCTACCAGCTCTGGTTCGAGAGCCTGACGGCCGGACCCCGCGCCCTCGAGTCCCCCGCGTACC
CGGCCCTCTCCTAGGAGACCCATGGCTGCCCCCGACCGACCGCTCGTCCAGGTGCTCTCCCCCGGACCTGGGGCGAGTT
CGGCAACTACCTCGCCGCGACGCGCTTCTCCCGCGCGCTCCGGAGCGTGATCGACGCGGAAGTGACCCTGCTGGAGGCGG
AGCCGATCCTCCCGTGGATCGGCGAGGCCGGGGCGCAGATCCGGACCATCTCCCTGGAGAGCCCCGACGCCGTCGTCCGC
AACCAGCGGTACATGGCCCTCATGGACCGCCTCCAGGCACGCTTCCCGGAGGGGTTCGAGGCGGACCCCACCGCCGCCCA
GCGGGCGGACCTGGAACCGCTCACCCGGCACCTGCGGGAGAGCGCCCCCGACGTGGTGGTCGGCACGAAGGGGTTCGTGG
CGAGGCTGTGCGTGGCCGCCGTCCGGCTCGCCGGGACGTCCACCAGGGTCGTCAGCCACGTGACCAACCCCGGGCTGCTG
CAGCTGCCGCTGCACCGCAGCCGGTACCCGGACCTGACACTCGTCGGCTTCCCCCGGGCGAAGGAGCACCTGCTGGCCAC
GGCCGGCGGCGACCCGGAGCGCGTCCAGGTGGTGGGCCCGCTCGTCGCCCAGCACGACCTGCGGGACTTCATGACCAGTG
AGACGGCCGTCTCCGAGGCGGGGCCCTGGGGCGGCGACTCGGGCCCGGACCGGCCACGGGTGATCATCTTCTCCAACCGC
GGCGGGGACACCTACCCCGAGCTGGTGCGGCGCCTCGCCGACCGCCACCCCGGCATCGACCTCGTCTTCGTCGGCTACGG
CGACCCGGAGCTCGCCCGCCGCACCGCTGCGGTCGGGCGGCCCCACTGGCGGTTCCACAGCGTCCTCGGCCAGAGCGAGT
ACTTCGACTACATCCGGCGTGCCTCCCGGTCCAGGTACGGGCTCCTCGTCTCGAAGGCGGGGCCCAACACCACCCTGGAG
GCGGCCTACTTCGGCATACCGGTCCTGATGCTCGAGTCGGGGCTGCCCATGGAGCGGTGGGTGCCGGGACTGATCCACGA
GGAGGGGCTGGGCCACGCCTGCGCCACCCCCGAGGAGCTGTTCCGCACGGCGGACGACTGGCTGACCCGCCCGTCGGTGA
TCGAGGTGCACAAGAAGGCCGCGGTCTCCTTCGCCGCTTCCGTACTGGACCAGGACGCGGTGACGGCCAGGATCAAGGCC
GCCCTCCAGCCCCTGCTGGACGCCCGATGACGGTCCGCCGCCCGGCCGCGTCCGCCCCCGCGTCCTCCTGACCGCGGGC
CCCGACGGGGTGCGCGTGGAGGGCGACGGGAGGCGCGCCTCGGGCACCCCCTCACCGGTGACCACCTGGACCCGGGCCC
GCCGGCCGAAGGCGTCTTCGCCGGGTGGAGGTGGGACGGCGAGCGCCTGGTGGCCCGCAACGACCGCTACGGCGTCTGCC
CCCTCTTCTACCGGGCCGGCGGCGGCTCACTCGCGCTCTCCCCCGACCCGCTCGCCCTGCTGCCGGAGGACGGGCCCGTC
GAGCTGGACCACGACGCGCTCGCCGTCTTCCTGCGGACGGGGTTCTTCCTCGCCGAGGACACGGCCTTCGCACAGGTCCG
CGCACTGCCCCGGCGCCACGCTCACCTGGGACACCGGCGGGCTGCGGCTGCGGTCCGACGGGCCGCCGCGCCCCGGGG
CCGCCGCGATGACCGAGGCGCAGGCGGTCGACGGCTTCGTCGACCTGTTCCGCGCCTCGGTGGCCCGCCGGCTGCCCGGC
GAACCGTACGACCTGCCGCTCAGCGGCGGCCGGGACTCGCGGCACATCCTGCTCGAGCTGTGCCGCCGCGGCGCACCGCC
```

TABLE 2-continued

Complete DNA sequence of *S. ghanaensis* ATCC14672 moe (moe) biosynthesis gene cluster 1.

GCGGCGGTGCGTCAGCGGCGCCAAGTTCCCTCCCGACCCGGGGGCCGACGCGCGCGTGGCGGCCGCCCTGGCGGGCCGGC

TCGGTCTGCCGCACACGGTGGTGCCGCGCCCCGTTCGCAGTTCCGCGCGGAGCTCGCCGCCCTGCCGGCCCAGGGCATG

ACCACCCTGGACGGCGCGTGGACCCAGCCGGTCCTGGCCCACCTGCGCCGCCACAGCCGCATCTCGTACGACGGTCTCGG

CGGCGGGGAGCTCGTCCAGAACCCGAGCGTGGAGTTCATCCGGGCCAACCCCTACGACCCCGCGGACCTGCCCGGCCTGG

CGGACCGGTTGCTGGCCGCGAGCCGGACCGGCCCCACGTGGAGCACCTGCTGAGCCCCCGGACGAACGCCCTGTGGAGC

AGGCAGGCGGCGCGGCGGCGCCTCGTCACCGAGCTGGCCCGGCACGCCGACAGCGCCAGCCCGCTCAGTTCCTTCTTCTT

CTGGAACCGGACCCGGCGCTCCATCTCCGCGGCTCCGTTCGCCCTGGGGGACGGACGGGTCCTGACGCACACCCCCTACC

TCGACCACGCCCTCTTCGACCACCTCGCCTCGGTGCCGCACCGCTTCCTGGTCGACGGGACGTTCCACGACCGGGCGCTG

CACCGGGCCTTCCCCGAGCACGCGGACCTGGGGTTCGCCTCGTCGGTGCCCCAGCGGCACGGACCCGTGCTGGTCGCGCA

CCGACTGGCGTACCTGCTCCGGTTCCTCGCCCACGCGACGGTCGTGGAACCGGGCTGGTGGCGCGGCCCCGACCGCTTCC

TGCAACGGCTGCTGGCCGCCGGCCGGGGGCCCGGGGCCCCGCAGCGCGTCAGCAGGCTGCAGCCCCTGGCGCTCTACCTG

CTGCAGTTGGAGGACCTCGCCGTCCGAAGGGCCCGCCGCCGGCCGTAGCGGGGCCGGACCGCCGCAGACCCCCACTTCAC

GAGACATCAGCCGCAGGGCCCAGAAGGAGCACATCGCATGCGGAAGACATTGCCCGTGATCAGCACAGGTCCCGCCGCGG

GAGCGACGTCGGGCGGATGCTCCGCCCCGGCCGAGACCCCGGCCCGGTCGGGAATACCGCTGTGGCGCAAGCGCAAACTG

CGGATCGCCCTGGTGCGCCATCACGACCTGTGCCTGAACACCCGTCAGATAGCGCGGGTCCAGAAGCGGGCCGGCGTGCT

GCCGCACCTCGGGGCTGGGTTACATCCACACCGCGCTCAAGTCGGCCGGGTTCCACCACGTCATCCAGGTCGACACCCCC

GCCCTGGGCCTCGACAGCGAGGGGCTGCGCAAGCTGCTCGCGGACTTCGAGCCGGACCTGGTCGGGGTGAGCACCACGAC

ACCCGGTCTGCCCGGCGCCATCGAGGCGTGCGAGGCGGCCAAGAGCACCGGGGCGAAGGTGATCCTGGGCGGGCCGCACA

CGGAGGTGTACGCGCACGAGAACCTGGTCCACGAGTCCATCGACTACGTGGGCGTCGGCGAAGGCGTCACGATCATGCCG

GAACTGGCGGAGGCGATGGAGCGGGCGAGGAGCCGGAGGGCATCCGCGGCCTGGTGACCCGCAAGCACGACGGCGGTGC

CGCGCCGATGGTGAACCTGGAGGAGGTCGGCTGGCCCGAACGCGCCGGGCTCCCGATGGACCGCTACTACTCGATCATGG

CTCCGCGGCCGTTCGCGACGATGATCTCCAGCCGCGGCTGCCCCTTCAAGTGCAGCTTCTGCTTCAAGCAGGCCGTGGAC

AAGAAGTCCATGTACCGCAGTCCCGAGGACGTCGTCGGTGAGATGACGGAGCTCAAGGAGCGGTGGGGGGTGAAGGAGAT

CATGTTCTACGACGACGTGTTCACCCTGCACCGCGGCCGGGTGCGGGAGATCTGCGGGCTCATCGGGGAGACCGGCCTCA

AGGTCCGCTGGGAGGCGCCCACCCGCGTCGACCTGGTGCCCGAGCGCTGCTGGAGGCGATGGCCGGGGCCGGGTGCGTG

CGCCTGCGGTTCGGCATCGAGCACGGTGACAGCGAGATCCTCGAGCGGATGCGCAAGGAGAGCGACATCCAGAAGATCGA

GAAGGCCGTCACCTCCGCCCACGAGGCCGGGATCAAGGGCTTCGGGTACTTCATCGTCGGCTGGCTCGGGGAGACCCGGG

AGCAGTTCCGCAGGACCGTCGACCTCGCCTGCCGCCTCCCGCTGGACTACGCCAGCTTCTACACCGCGACGCCCCTGCCG

GGCACCCCCTGCACACGGAGTCCGTGGCCGCCGGCCAGATCCCGCCCGACTACTGGGACCGCTTTTCGTGCGGGGCGAG

TTCGACGCGCGGATCGGGTACCTGGTGCCGGACGCGCAGGAGCGCGCCCAGTGGGCGTACCGCTCCTTCTTCATGCGCCG

CTCCATGGTCAAGCCGCTGCTGTCGCACATGGCGGTGACCGGCCAGTGGCGCAACACGCTGGACGGCCTGCACAGCCTGT

ACCGGTCGACCTCCAACACCGACCGTGACTTCTGAGCCCGCCGCCCCGGCCGTCCCGCACCCGCCGGTGCGTCCGGGCC

GCCGGTCCGTCTCAACCGGCCGCTGGCGCGGCGCAGGCGGCGGCCGGCCGGGAGGGGTTCGTGACGCACCACCTGCGGA

GCACCATGGCCCGCGGGTTCCGCCCCCGGAGTCCTGGGAGGTCCCCGTCCGGCACGTCCTGCCCGGTCTGCCGGCCGAC

GGGACTCCGCGCGCCGAGGAGGCCGCTCAGGCGCTGCGCACGCCCGCGGGCGGCCGGGCATCGCCCTCGTCGTGCCGAC

CTACGTCTCCCGGGTGAGCCTGGCGCGGCAGCGGGAGTGGTTCGACGCGCTGCTGGACCAGGCGGCCGCGGTGACGCGGG

ACCACCCCCTGGTGCCCCTGGTGCTGTTCGTCGGCATGCAGTGGTCGTCGGCCGAGGAGGAGCGGGAGGCGCTGCGCGC

CTGCGTGTGCTGCTGGACGACGCCCGCACCCGGCTGCCCGGACTGCGGATCTGCGGTCTCGCGCTGCCCGGGCCGGGCAA

TABLE 2-continued

Complete DNA sequence of *S. ghanaensis* ATCC14672 moe (moe) biosynthesis gene cluster 1.

ACCCCGCACCCTCAACGGGGCGATCGCCGTCGCCGAGCTCCTCGGCTGTGCGGGCGTCGGGTGGACCGACGACGACGTGA
CCCTGGAGGAGGACTGCCTGTCCCGGCTGGTGCGGGACTTCCTGGCGGCGGGCTGCCGCGGGGCGGTGGGCGCGACCAAG
GTTGCGCACACCCATGAGTACGCCACCTCCCGGCTGCTGTCCCGGGCCAAGGCGATCGCCGCCCCGGCCACGAACTACCC
GCACGGCTGCTGCATCCTGGTGGCCACCGACGTGGTGGCCGGTGGTCTGCCGGGACGCTACGTATCCGACGACGGCTACG
TGTGCTTCCGCCTCCTCGACCCCGCGCTGCCCGACCCGCTGGCCCGGCTGCGGCTGGTTCCGGACGCCCGGTGCCACTAC
TACGTGGCGGGGCCGGCCGGCGAGACCCGCCGCAGGATCCGCAGGCTGCTGCTCAACCACCTCGTCGACCTCGCCGACTG
GCCCCTGCCGGTGGTCCGTCACTACTTCCGCCACGTCCTGTTCGGCGGCATGTGGCCGCTGACCGGCTTCGACTCCTCCC
GCGGTGCCCGCCGCGGTGTGCAGAAGGCGCTCATCAAGTGGCTCTACTTCGCCTGGTTCGCGGGCATCGGGGGCGAACTC
TACGTGCGCGGGCTGTCCGGCAGGCCACTGCGCCGCATCGAGTGGGCTCCCTACTCGGACATCCGCAGGCTCACTCCGTC
GTCCTCACCCACGCGTCAGGAGAGCTGATGAAGGTACTGTCGCTCCACTCCGCCGGCCACGACACCGGCGTCGCCTACTT
CGAGGACGGGCGGCTGGTCTTCGCGGTCGAGACCGAACGGCTCACCCGGGTCAAGCACGACCACCGCTCCGACGTCGCCC
TGCGGCACGTGCTCGAGCAGGAGTGCGTGGACACCGACGGGATCGACCTGGTGGCCGTCAGCACCCCGGTCCGCAGCGGG
CTGCTGCGCATACCCGACCTGGACCGGGCCATGGAGCGGATCGGGGCGGGCGCCCTCCACCACCGGACCGTCTGCGAGAT
GCTGGGGCGGCGGGTGGAGTGCGTCGTGGTCACCCACGAGGTCTCCCACGCGGCGCTGGCCGCCCACTACGCGGACTGGG
AGGAAGGCACCGTCGTCCTCGTCAACGAGGGCCGCGGCCAGCTCACCCGCAGCTCCCTGTTCCGGGTGACCGGCGGGGCC
CTGGAGTGGGTCGACAAGGACCCGCTGCCCTGGTACGGCAACGGCTTCGGGTGGACGGCGATCGGGTACCTCCTCGGCTT
CGGCCCGAGCCCCAGCGTGGCGGGCAAGGTGATGGCCATGGGCGGCTACGGGCAGCCGGACCCGCGCATCCGCGAACAGC
TGCTGTCGGTGGATCCGGAGGTGATGAACGACCGGGAACTCGCCGAGCGGGTGCGCGCGGACCTGGCCGGCCGGCCCGAG
TTCGCCCCCGGGTTCGAGACGGCGTCGCAGGTGGTGGCGACGTTCCAGGAGATGTTCACCGAGGCCGTCCGGGCGGTGCT
CGACCGGCATGTGACGCGCACGGACGCCGGGGTGGGCCCGATCGCCCTGGGCGGCGGGTGCGCCCTGAACATCGTGGCCA
ACTCGGCGCTGCGGGAGGAGTACGGGCGGACGTCGCCATCCCGCCCGCCTGCGGGGACGCGGGTCACCTGACGGGCGCC
GGCCTCTACGCCCTCGCGCAGGTGGCCGGGGTGAAGCCGGAGCCGTTCAGCGTGTACCGCAACGGCGGGGCGAGGCCCG
GGCCGCCGTCCTGGAGGCGGTGGAGGGCGCGGGGTTGCGGGCCGTTCCCTACGACCGGTCCGCGGTCGCCGGGGTGCTGG
CCGGGGGCGGGGTGGTGGCGCTGACGCAGGGAGCGGCGGAACTGGGGCCGCGGGCGCTGGGGCACCGGTCGCTGCTGGGC
AGTCCCGCGGTGCCGGGCATGCGCGAGCGGATGAGCGAGAAGCTCAAGCGGCGCGAGTGGTTCCGGCCGCTGGGCGCCGT
GATGCGCGACGAGCGCTTCGCCGGGCTGTACCCGGGGCGGGCGCCGTCGCCGTACATGCTCTTCGAGTACCGGCTGCCGG
ACGGGATCGCGCCCGAGGCCCGGCACGTCAACGGCACCTGCCGGATCCAGACCCTGGGCCCCGAGGAGGACCGGCTGTAC
GGTCTGCTCGCCGAGTTCGAGGAGCTGAGCGGTGTGCCGGCGCTGATCAACACGTCGCTCAACGGCCCGGGCAAGCCCAT
CGCGCACACCGCCCGGGACGTGCTCGACGACTTCGCGCGCACCGACGTCGACCTCTTCGTGTTCGACGACCTGATGGTGC
GGGGCGCCGCCGCGCGGTAGCCCCCGGGGTGGGGCGGGACGGCCGGCCGGAGACGCTCCGGCCGGCCGTCGGTCACTCCC
CCAGGTGCCGGGGAAGCAGCCGTACCAGCACGTCGTCCGTGTAGAGGTGGACGACCGGCACCAGACCGGGCGCGCCGGGC
GGTGCCGCCACCGCGGCGAGGGCCCGCCCCGCGCAGCTCCTCCAGCAGGTCCACGACGTCCTGGCCGGCCACGGCCCCGGT
CCGCATCAGATGGGCGAGGTTGCCGTCCCGCTCGCCGTTGCGGTCGTAGTCGGTCAGGTCGTCCGCCATGGTGATGGTCA
TGGCGAAAGCCTCTGCGAACTCCCTTACGGAGTCCGCCGGTTGGCCTTCCCCCCCGCAGGCGGCCGCGAGTGCCCCGTAG
CGGCCCAGGAAGGTGGAGCCGTAGGTGCTCGCATGGGCGCGCCACTCCCGGAGGTTCGTCGCCCGAGAGCGTTTGGTGCG
TATCTGGCCGCCGCAGAGGTGGACGGCGTCCTGCTCCAGGATGTCCGTCACCGCCTTGGGGTCCCGGGCGAGGGATTCCA
GTTCGTGCAGCGCCCGCAGGTGGAGGCGGAGGCAGACACAGGCGAGTTCGACCCGGTCGAGTCCGGTGTCGTCGTCCATC
AGGTCGTCGAGGAGCTTCATGGAGACGATGTCGAGGGCCAGCGCGCGGGACACCGCGGCCCGCCGGTCCGGGTCGGTCGT
CCACTCGGTGAGGAAGTGGGGCACCCTCAGGTACAGGCGCAGGGCGGCGGTGTGCGCCACCAGGTCCGGCGACCCACCGG

TABLE 2-continued

Complete DNA sequence of *S. ghanaensis* ATCC14672 moe (moe) biosynthesis gene cluster 1.

```
TCTGCGCGACGCACCGCGTGACATGGTCGCGGTTGGCGGCCTCGGCGGCGAGCATGGTCTCCGTGTAGTCCGCCGGCAGG
GCCGTGGCCGGGGCGGCCGTCACCGCCCGCTCCCCGGACGGGCCGGGGCGGCGGGCCGCCTCCCGGCGATCTCGGCGAGG
GCGGACCGCCAGTCCGGCTGTTCCAGGGCTCCGGCGAACCCCACGTAGTCCGCCCCGCTGTCGAGGTACTCGGTGACCTG
CCGCCCGGAGCGGACGTTGCCGCTCACGAAGAGCACCTGGTCGGGGCCGAGCCCCTTGCGGAAGTGGCGTACGACCTCGG
GCGGCACGTGCTCGTTGCGCGAGTACAGGTACACCATGTGGAAACCGAAGGCACGGGCGACGTGGAGGTACCGGTCGATC
TCCTCGGTGGAGGCCGTGCTCACCGGCACGGTGCCGAGCAGGTCCCCGGTGCGGGGTCCTCGCCGAAGGTGAGGGCGAC
GGTGAGGAGCAGCTCGGGCCACTCCTCGCGGGGTATTCGGCCGGGAAGGCGGCCAGCGTCTCGAGGAAGCTCTTCCAGA
CGAAGTAGTCGTCGCCCGAGCCCAGCAGCGCGGGCAGCAGGAGCGCGTCCGCCGCGGACCACCGGGAAGCCGGCCCCC
GGGCGGGGCGGGAAGTGCAGGACGACCGGTAACGGGGTGGCCGCCTTCACCGCCGCCACGTACGGCTCCATGTGCGACTC
GAACGACTCGTAGTCGGTGCTGGCCAGAAGGACGGCGGCGAAGCCCAGCCGCGTGAGCTCCGCCGCCTTCTCGACCGCTT
CCGTCACCGGGACCTTGAAGGGGTCGATGATGTGGACGGGGCCCGGTTGGTGCTCGCGCAGCCGGGCGAGCACGCGTCCC
GGCCGCCAGAGCGGTGGTGCGCGTGGAGTTCCGTGTGGTGGTCCAGTTGCGGTGAGGCGTTCACCAGCGTCTTCCCCCT
TGTCGTCCGGCTCGTCGTCCGGCTTGTCGTCCGGTCGGGTCACGCGACGGGGTGCCGGCCGCGTCGCACGTGCGGATCGC
GTCCGGATGAGGTGTCGCGCGTTCGGATGGAGGTGCGGGGCGCCCTGGTCGCCGAGGCCGTTCCCGGCCGGCCGGGAGTG
TTCCTCCCGGTGTGCCGCGCCGGCGCGAAAGCCGTGGTCCGGCGCCGTCGCGCGGTTTCCTTCAGACCCGCCCGGGGAAC
TGCGTGACCGTTCCGGCACACGCCGCGGTCGAGGGAGTGCGGAAGTGCTCGGAAATCCTTCGGCGGGCCCGTCCGGCGGA
TTCACCGGCGGACGGACGAAAAGCGTCGTTCACGTACTCCCCTTCCACTGGAGAGACGAACAGCGGGTCCACCGGGCCGC
CTCGAGGACAGGGTGCGGCAGGGCGGTTGCCGATACTACACGCGTTCGTTTCCGTGGGGTAGGGAGACTTTGTGCGGCGG
TTATGCATTCCTGCCGGACGGAAGAAGGCACGCCCCGACGGTTTCGCGCCGTGCGGGGCGTTCTCGGCGGTGTCCGGCGT
ATTTCACGCGAATTGCAGATGGCGCCGGCGGCGCAATCGGCCCGCCGTCACGCAACCGCTCACCGCGACCAGCAGCAGCG
TCACTCCGACGGCGTGGGCCACCCCGGAGTCGAACGACCCGCTGTCCGCGCCGTCGACCGCGTAGGTGATGATCTCCCGG
GTCGACCAGAAGGGAAGCACCTTGGCCGAATCCTTGGCCGGATCCATCACCATCTGGGCGCCGATGACGGAGATCAGCAG
CAGGGCGCCCTCCATGTCCCGTGGCACGGCCGCCCCGAGCAGCAGTCCCAGCGGCACCGCCACCAGTGTGGTCAGCGCCA
GTTCCACCGCGACGGCCCGCGGGTGCGCCACGTCCTGCCCGACCAGGATGATCACGGCGTAGAGGGCGGACACGCCCATG
CCGGCGGTGAGGAGGGCCAGCAGGCGGCCCAGGAAGAGCTGGAGCGGGCGGAACCCGGAGAGGGCCAGGAGCGGTTCGAT
CTCCCGGCCGCCGACCGCGGAGAAGAGGGCCGCGGCGCTGACCGCGAAGCCCACCCCGAGGCTGGCGAACCGGACCGCCT
GGCCGGTCTGGTCGTAACGCCCGAGGTAGAAGACGAGCGGGACCAGGAGCAGCAGGCCCAGCACGCCCCGCCGGCGCAGC
AGTTCGCGGAAGGTCATCTCCGCCATCCGCAGGGTGGCCGTCATCGGTTGCCCCTTCCTTTGCCGGGGGTGAGGTCCAGC
ACCTGGTCCACCCGGTCGAGCTGGTTGAGCATGTGCGTCACCACGACGACGGCCTTGCCCGCCTCGCGCCACTCCCAGAC
GCTCTGCCAGAAGTCCACGTAGGAGCCGTGGTCGAAGCCCTGGTAGGGCTCGTCGAGCAGCAGCAGGTCCGGGTCTCCCA
GGGCCGACAGGACGACGTTCAGCTTCTGGCGGGTTCCTCCCGACAGGTCCTTGGCAAGGACGCCCTCCGCGGGGGCCCAG
TCGAGCTCTCCCGCGAGTCTCCGGCCGCGGCGGTCGGACTCCCGGCGGCTCAGGCCCCGGCCGGTGCCGAAGAGGGTGAA
GTGCTCCCGGGGGGTCAGGAAGCCCATGACCCCCGCGTTCTGCGGGCAGTAGCCGAGGTGGCCGGAGACGGTGACCCGTC
CTTTGTCGGGGGAGAGCAGACCGGCGCAGATCTTGAGCAGGGTGGACTTGCCCGTCCCGTTGCTGCCGACGATCGCGGCG
ACCTCGCCCGCGTGCACGACAAGATCGACCCCGGTCAGGACGCGGCGGCGCTTGTAGCGTTTCACGACGCCGCGCGCCTG
CAGGAGAATCTTGCGGTCGGCGGGCTCGGACATGCCGTGGTACCCCTCTCGGGCACCGACGGAATGGCCCATGACTGCCA
CCTTTCTGCCGACCGCGACGAAGGCACGCATTGTCGGCCTCAATGGTCAGGATGCGTGATCCGGTCGGGTTCATCGCCC
CGGCCGCACGCGCACGGCTCAGCCTGCCACACGGCCTGCCCCACATAGCGCGTATCGGTCGGGCCCCACTTCCCCGAAA
```

TABLE 2-continued

Complete DNA sequence of *S. ghanaensis* ATCC14672 moe (moe) biosynthesis gene cluster 1.

```
GTCCGGGCCCCCGGCCGGTGTTCCGGGGATCCTACGGGCGACCGGGCGAAGGACTGAAGCCGGGCATCCGCGTTTCGGC
CATCTCTCGCCGATACCCGGGGCGCCCTTGTAGGCCGGCCCGGGGCTGGTTAGCGTACCGACCGACCGCAATTCACCGCT
CACTCGTGCGTCGCCCGCACCAGCTTTTCCCTTCTTCCGGAGTCCGCCGCCGGGGCGGGAGCGGGCGGGACCGCACCCCG
TTCAGGCAAGAGGGAAATCCGCTCGGAATCGACGAAGGGGACGTGCATGCGCGGGGGGACCGTGGACCGTCGTGTCTGGT
GGCAACGGGCCGTGGCCCGCGGTTTCGCGCCCACCGCCGGCGCGGCCCACCCCGTTCGTCCTGGTGGGACCCGAGGGACC
GGACTCGGACGTCCGGGCGAGGTGCGCGCGGACGGCGTGATCGGCGCGCGGCCGGGCGGGGCGGCGTTCCGCTGCGTCCG
GCGGGCTCGGGGTGCTGCTGCCACTACGTCGGCAGTGCGACGCGAGCGCACGAGCAGACGTCGTCATGTGCTGCGCCGTC
TGGCCGAGGTGCGGGAAGCGCACCCGTCCCTGCCGCTGACCGTCTGGGTGGGCATGCAGTACGGCCCCGGGGAGGACGAG
GAGGCGCTGCGCAGGCTGCGCCGGCTGTGCGCCCCGGTGCCCGGGGGCCCGGCCCTCACCGTGGTCGGCCTGGCCCTGCC
CGGGCCGGGCAAGCTCCGCACGGTGAGCACGGTCCTGCGGCTCTCCGAGGACCTCGGCTACGCCGGCTGGCTCTGGACGG
ACGACGACATCGAGATCGCCCCCCACTGCCTCGCCCTGCTGGTCTCCCGTTTCCGGGAGCGGGGGGAGCGGGGCGCGGTC
GGGGCGCATTCGGTCGCGCTGGCCAGGGAGACGGTCACCTCACAGGCCATGGACCGGGTCTCCGGGGTCACCGCCCCGCC
GAAGGCCTGCCCGGCGGCGGCCTGCCTGGTCGTCGCGACGGACGTGCTGGGCACCGGCATTCCGGTCAGGCGCCTGACCG
ACGACGGGTACGTGGTGTTCGAACTGCTCGACGCCGGGGCGCCCGATCCGCTGCACGACCTGGAGGTGCTGCCCGAGGCC
CGGATCAGCTTCTACCGCGTCAGCCGCACCCACGACACGTTCCAGCGCCTGCGCCGCTCCCTCTACAGCCATGTGACCTG
CGTCGCCGACTATCCCTGGCCCACCGCGCGGGTCTACCTCACCCGGGTCCTCTTCCACGGTCTGTGGCCGCTCGCGGCGT
GGGACGGCAGCCGGGGCCGGTGCACGGGCTGCAGCGCTGGCTGGTCAAGGGCCTGCACTTCACCTGGTTCTGCGGGGTG
GCCGGCTCGCTGGCGGTCCGGGGCGCGGTGGGACGGCCCCTTCGCCGGGTGGCGTGGGCGACGAGGGGACTTCCGCAG
CCCCACCGTCGAGGAGCCCGCCGCGGGAGCGGCCGCCGGGCGCTGACACACGAGGTCACCCCGAGGGGCGGCCCGGAAGG
AGACGCGATGGTGACAGCGGGGCCGGCCGGGCGGCGGTGACCGTCGTCCTGCCTCACTACGACTGCGCGGCGTACCTGG
GTGCGGCCGTCGGATCGGTGCTCTCCCAGGACCGCCCGGACCTGCGCCTGACGGTGGTGGACGAATGCTCGCCCGAAGAG
AAGTGGGCCCGCGCACTCCACCCGTACGCCGGCGACCCCCGGCTGACCGTGGTCCGCACCTCCCGCAACGTCGGCCACCT
GCGGATCAAGAACAAGGTCCTGGAATCGGTGGACACCCCCTACGTGGCCTTCCAGGACGCCGACGACATCAGCCTGCCGG
GCCGGCTGCGCCACCAGCTGGCCCTCCTGGAGAGCGGCGGCGCCGATCTGGTCGGCTGCGCCTACTCCTACATCGACGAG
GCGGGCCGTACGACGGGACACCGGCGGATGCCCCGCAACGGCAACCTCTGGATGCGGCTGGGCGGACGACCGTGCTCCT
GCACCCGTCCTCGGTGGTGCGGCGCTCGGTGCTCGAGAGGCTCGGCGGCTTCGACGGCACCGCGCGCCTGGGGGCCGACA
CCGACTTCCACCTGCGGGCCGCCCGCCTGTACCGGCTGCGCAGTGTGCGCAAGGTGCTCTACCGGTACCGGATCTGGCCC
AAGTCGCTCACCCAGGCGCCGGACACCGGGTTCGGGTCCGCGGAGCGCCGGGCCTACACCGAGGCGATGACCGCGCAGGA
GGAGCGGCGGCGACGGGCGCGGACCCGTGAGGAGCTGCTGCCGCTGCTGGTCGCCCCGCCCAACGACGTCGACTTCACCC
TGACCCGGGTCGACCTCGACTAGCCGACGGAGGGGAACGGCGTGGACGGCACCTCGGCGAGGACCGCGGACGAGGCGTT
GCCCGGGGTCGCGGTGGTGGTGGTCGATCCGGACGGCGACGGGCGGCGCGCCGTGCGCGGCCTCCTCGCCCAGACGGTGC
GTCCCGTCTCGATCACCCTGGTGACGGCGGCCGGCCCGACGGCCGGCGGCACCCGGTCCCCGGGCCGGCCGTGCCCTTC
GACGACCCGGCGGTGAAAGCCCGTACGGGTCGTCCGGTGCGCTCGCGGGGACCTCGGGCGGCTTTGCGTCGACGCGGCC
AGGAACGCGGGGGCGCCGTACGTGGCCGTCCTCCGCGGTGACGACGAGGCGCTCCCCCACTGGCTGTGGCACCTGGCGCG
GGCGGTCTGGTACGGCGGCGGGACGGCACCGGGCCGGTCGGCCTGGTGCAGTGCGCGCCCTGCGGCTGAGGGACGACG
GCCTGGTGGACGGGTTCGCCCTGCCGCCCCGCGTCCCCGCGGACCCGGCCCTCCCCCTCGGACCTCCTCGAGGGCGCCTAC
GCGGTGCGGCGCGAACTGCTGGACGCGGACGGCGGTACGGCGCCCTGGGTCGCCCTGCCCATGCCGCTGGTCCGCCGCCG
GTCCGGCGGCGCCGGGGACCCGGCCGCGGTCCTGGCCCCCGGGACGCGCGTCGCGCGACGCACCCGCCTGGTCCGGCACG
GGTACCGGCCGCCCGCCGCGAGGCCGCGGAACGGGAGCACTCCCCGGCTGGTGTCGGTGGTCGTCCCGGTGCGCAACGGC
```

TABLE 2-continued

Complete DNA sequence of *S. ghanaensis* ATCC14672 moe (moe) biosynthesis gene cluster 1.

```
GCCCGCACGCTCGCCGCCCAGCTGACCGCCCTGGCCCGGCAGACCGGAGCCGTCGCCTACGAGGTGCTGGTCGTCGACAA

CGGCTCGACGGACACCACCCGCGAGGTCGCCGAACGGGCCCGCGCCGAGCTGCCGGACCTGCGGATCGTGGACGCGTCCG

ACCGTGCCGGTGAGAGCTGTGCCCGCAACCGGGGAATCGCCGCGGCGCGCGGCGACTTCGTCGCGTTCTGCGACGCGGAC

GACGTCGCCGACACCGGCTGGCTGGCCGCGATGGCCCAGGCGGCCAAGGAGGCCGATCTGGTGGGAGGCGGACTGGAGAC

CTCCGTGCTCAGTCCCGGCCGCGTCGACGAGCAGCCCCTGCCGATGGACGCCCAGACCGATTTCCTGCCGTTCGCCCGGG

GGGCGAACTGCGGTGCCTGGAAGGACGTCCTGACCGCGCTGGGCGGCTGGGACGAGCGCTACCGGGGCGGCGGGGAGGAC

ATGGACCTCTCCTGGCGCGCCCAGCTCTGCGGTTACCTCGTCCGCTACGCGGACGACGCCCGGATGCACTACCGGTTGCG

GGACGGACTGCCGGCGCTGGCACGGCAGAAGTGGAACTACGCCGTTCCGGGGCCCAGTTGTACGCCGCGTACCGGCGCG

CCGGGTTCGAACGGCGCGACGGCCGGGTGGTCGTCAGGAACTGGTGCTGGCTGCTGCTGCACGTTCCGAACCTGGTCCGG

TCCACCGGACCCTGCGGCCACGCTGAGTCCGCTACGCGCCCGGCTGGCCGGTTTCCTGGTTTGTGAACGTGCGGCAGGGC

GTCAGGTCCTTGTTGGTGGGCGGGCGTCCGGCGCCCGCGGGACGCCGGGCCGGCACCGCGGTGGCCCGGCGCGCCGCTCC

CGGGTTCAGACCAGCCGGTGGCCGGGGTCCTGCGCCACCGGGTCGTCGCCCGCCATGGCGAGGCAGGTGGCGCGCAGGGC

GGCGACGACGGCCTGGTCCTCGCCCCAGGCGTCGAGTTCCGGGCCGTCCCCCGCCTTCAGGGCCGGCACCGGCACTTCCA

TGATCTTCGGATGCCCGTGCCGGACCGGGGACTCGGAAGGGGCCACCAGCGCCTCGGTGAGCTTCTCCCCCGGCCGCAGC

CCGACGTAGCGGACCGGGAGCTCCGCACCGGCGTGCGCGATGAGCCTTCTGGCGATGTCGAGGATCCGGACCTGTTCCCC

CATGTCCAGGACCAGGGCGTGGCCGACGCTGCCCAGCGCGACCGACTGGATGACCAGTTCCACGGCCTCCTGGACGGTCA

TCAGATAGCGCGTCACCTCGGGGTGGGTGACCGTCACCGGTCTGCCGGCCGCGATCTGCCGGGCGAAGACGTCGAGGAAG

GACCCCTGGCAACCGAGCACGTTGCCGAAGCGCACGCTCACGTACGGTCTGCCCGCCTGGATCGCGGCCGCCGCGGTGAG

TCCTTCGGCTATGCGTTTCGAGTATCCGAGCACCCCGACCGGATCGACCGCCTTGTCGGTCGAGATGTTCACCAGGAACG

CGACGTCCGCGGCCAGGGCCGCCTCGAGCACCGCTCGGGTGCCGAAGACATTCGTCTTGACGGCTTCCCCGGGGAACTTC

TCCAGGATGGGCACCCATTTGAGGGCCGCCGCGTGGAAGACGGTGTCCGGCCGGCACTGCTGGAACAGCCGGGCGAGCCC

TCTGGAGTCCCTGATGTCCGCGAGGAGGATGGAGGTCCGCACCGACGGGGAGACGTTCCCGATGCTGGTGGCCGCCAGGT

GGAGGGCCGTCTCGTTCCGGTCGAGCATCATGAGGCTCTCGGGTTCCCACCGGCTGAGCTGCCGGCACAGTTCCGATCCG

ATGTAGCCGCCGGCTCCGGTGACCAGGATCCGTCGGCCGCGCAGTAATCCGGCGCTGCTCTCGAGACCGGTCCTTATTCG

TTGGCGGCCGATAATCCTCTCGAGGTCCAAgGTGAGAGGTCCACCGGCCGGAAAGTTCGCGTCGTACCCCACGGAATTAT

CGCCAAACATGCAGTCACACTTCCTTTTTGACAAGAGTCATGACTGACGTGCCGACCCACACGACGAACGGGACCGACGT

ATCGTCTTGGTGCTTTCCTCACCGGCACCACCGCGTTCCCCCACCGGTGCCTGCGCACGGGATCACATTCCGGCGGCCG

GGTCGCCACCCGCTGCGCCGGCTCCGCCGACGTCGGACGTGTCCTCTTCCGACACCCCAGGACGACCGCGAAAATCACTT

TATCGAGGCGCGGCGCGGTGCGGGCGGGTTTTCTCAACGGACGCCCCGCGTCACCGGAACGCCGGGGCCGAGGAATTCGC

GCGCGCCCCGCAACCGGGTCCGGAGCCGGGCCCGCGTGGCATCGGTGACGAGACGGATGTCGAGGTTCCCCGGCGGGGCC

ACCTCGCTCCGCAGACCGGCCGGCAGCCGGGCCGGGTCCAGTCCGTCCCGCCGGGCTATGAGGACACCCAGGTCGTGACG

GTTCATCGCGTCCGGTCCCGCCACGTGGAACACCCCGGACCCGTCCGACGCCGCGATCTCCAAAAGCGCGGAGGCCAGAT

CGTCGACGTGGACCGGACAGCGGACGTCGTCCGTGAACAGGACGCCGGCGCGCCGGCCGGCCGCCAGGGCGTGCACCGCC

TCCTCGTGGGCGGACCGGTTGTGCCCCACGATGAGCGAGGTGCGCACCACGGCGGCCTCGGGCACGGCCACCCTGACGGC

CGTCTCCGCCGCGGCCTTGGCCGCGCCGTACGGGGAGACGGGGTCGGGGAGGGCCTCCTCCGGGTAGTGGACGTCGGCTC

CGGAGAACACGGCGTCGGAGGAGACGTGGACTAGTCGGCAGCCGCCGCGCGCCGCCTCCAGGGCGAGGCGGGCCGCGCCG

TCGGCCGTGACCGCCCAGTCGGCGTGTCCGCTCGACGCGTTGATCACCGCGGCCGGCCGGGTCCGGGCCAGCACCTCTCC

CATCCGCCCCGGGTCACGGAGGTCGGCCCGGTACCAGGTGACCGGCGGCAGTTCCTCGGGGCGGGTCCGGTAGGTCGCGG
```

TABLE 2-continued

Complete DNA sequence of *S. ghanaensis* ATCC14672 moe (moe) biosynthesis gene cluster 1.

```
CCACGTCCCACCCGGCGGCCACGGCCCGGCGGAGCACCTCGTACCCGAGGAAGCCGCTCCCGCCGACGACAAGAACTCTC
ACGCACCGCCCCCTGACGTCCGGCCCGCCCCGATCGCGCCCCAGAAGTACGGGGACGACGGCCTGTGCGGCCGTGTCG
AGCCGTGGTTCCTGTGGGCCCGATGCTACTGAAGGCCACCGAGCGGCGGGGAGAGTGAGTGCTTTCCGTCTTCGGTCCGA
ACCGGCCGGGGAGGCTCCGCAACGGCTCCCGCGGGCAGGAGGGCGGCGGCCCCGAGCGGCCTTGCGCACGGCGGGACGCC
GGGCCCGCGGTCCGAGGCGTTCCCCGGGGCGCGCAGCCGGTGCCACCGGCGGGGCGGCGACGGCCCGTCCCGCTCCTGG
TCCCGGGGCGGGCGGCGTGTGACCCGCCCGCCCCGGCCGAGCGGGTGCGTCCCCGTCAGGCACGGCGGGGTGCGCCCCGT
CAGGTACGACAGGGAGCCGGGTTCTCCGGCCGGGCGGGGATCCCCGCCCGCACACGGGCGAGCAGGGCGGCCGGGTCCGG
GTCCGCCTGCAGGGACCGCAGCACCAGCGTCCACCACTGCTCCAGTCGCTCCCTCCAGTCCAGCCCGCCCGGCATCTCGT
CGGTCAGGGTGCAGAGTCCGAAGAACGCGCAGACGAGCGTCACGGCCGCGGCCGACGGCTCGACCCCTTCCGCGAGTTCG
CCCCCGGCGCGGGCCTCGGCGAGGAGCCGGGTGGCAGCCGCCGCCCAGGCGTCGAACGGCGGGGGCACGGCGGCCTCGAT
GGTGTGGCGCTCCGCCCACAGCCGGGCACCGGCACGTGCCACGACGTCCTCGCTGAGGGACTGCGCGACCCGGAAGCTGA
GGCCGACCAGCTTCTCCAGCGGAGGAACGCCGGGCGTGGTGTAGGCGGCGGCGAGTTGCGGCCAGGTGGCGAACTGCTCG
CGGACCACGGCCAATGCCAGCTTCTCCTTGCTGGAGTAATGGAAATAGATCGCCCCGCTGGTTCTTCCCGAGTGATCGCT
TATGTCATTGACGCTCGTTCCGGCATATCCCTGTTCAACGAACAGATGTGCCGCTGTTTCCAGCAGCACTTTGCGGGTTG
CACGCGCCCTGTCCTGCACTTCTGCTCCACCTTCGCTCACACACGCCGACGCCACGACGGAAAAGTCCAGGCGCCCCGG
AGGCAGGGTCGCAGCGCGCGAAGATCTTATTATTCTTCGGCCGTGTGCGCCGCAGGGGCGACTTCACACAACACGCCCCT
CTGTCCGGCCGAATCGATTCGGGCGGGCGCGGGAACTCCGCCCCGATCAATGCCGCGGCACCCCGGAGGAGCCTCCCACC
AGGCCCGTTGGCCGCGTTCCGGGCGCTGCGGCCCCTCCTCCCGTTCCGTGTGCGGGAGTCGGCCGCCTTCGGCCGCGGCA
TGCACATACACCCGAATCGGTGATTGTGGAAATCGAAGAAGCGAAATTAACATAACGGGCACGATGTTTTTCGGCGTGGT
CGAAAGCGACGACCCGCGCCCGCCATGACGCGCCCACGGCGCGCTCAGCCGTGTCCACGTGGCCGCAAACGGCCGTGCGA
CATCACCCGTTTCCGCTCATTTCCGCGAGTGGACCACCCGCATCCCTGCACCCGCCTGCGCCCGTGCACCGAACCGGTCG
ACGCAGCCTCCCAGAACGGCAGTCACATGACAGCTCACCGCATCCTTTCCTGGTCCCCCTCCGCCATCGTCTTCGACTGC
GACGGAACCCTGATGGACACGGAACGACACTGGCAGGAGGCCCGGAACCTCACCTTCCGGGCGTTCGGCCTGAAACCGCC
GGCCGGGTTCGCCGACCGCGCCAAGGGCATGCACTACACCGAGTGCGGAGCGCTCATGGCCGAAGAGACCGGGAAACCGG
GCCTCGTCGGGGAGTTGACCGACACGCTCCTCGGCACCTTCACCACCCTGGTCGACCAGGACCCCGTCACCATGCCGGGG
GCCGCCTCGCTGGTCCGGCTGGCCTCTCGCCACCGCCCTCTCGCGGTGGCGAGCAACTGCCCCCGGGAGGTGGTGGAATC
ATGCCTCTACCGGGCCGGGCTCCTCGACTGCTTCGGCCACGTCGTGGTCGCCGGCGGGGAGGTACGGCCGAAGCCGGAAC
CCGACGTCTACGCGGTGGCCGCCCGCCTCTGCGGCGTCCCTCCCGAGGAGGCTCTGGCCGTGGAGGACTCGCTCACCGGT
ATGGAGTCGGCCCGCCGGGCGGGCCTTCGCGTCATCGGCATCGGACCGTGCCCACCGGGGCCGGAGGCGGAGAAGGCCGA
TCTGTGGGTCGCGAGCCTCGCCGACGGCGAGCTGCTGTCGTGGGCCCGCACCCGGATCGGCGAGTAGGACACCCGGGGCC
CCGTCGCACGGGCCCGGGCGGGAGGGGCGGACCGCGGTTCCGTCAGCGGAGCCGGGCGGCGAACGCCGCGTACGCCTGC
TCGTCGAAGAGGACGAACCGGATCTCCTCCACCGCGGTTTCGGCGTCGCGCACCGTCTGCACCGCGATGCGCGCGGCGTC
CTCCATCGGCCAGCCGTAGACACCGGTGGAGACGGCCGGGAACGCGACGGTGCGCGCGCCGAGTCCGTCGGCGACCCGCA
GCGACTCCCGGTAGCAGGAGGCCAGCAGCGCCGAGCGGTCCTCCTCGCGGCTGAACACCGGGCCGACGGTGTGGATCACC
CAGCGGGCGTCCAGGTCGCCGGCGGTGGTGGCGACGCCCCGGCCGGTGGGCAGGCCCTCGCCGTACCGAGAAGCGCGCAG
GCGGCGGCACTCCTCCAGGATCGCCGGGCCGCCCGGCGGTGGATCGCGCCGTCGACGCCGCCTCCGCCGAGCAGGGACG
AGTTCGCCGCGTTGACGATCGCGTCGGCGCTCTGGCGGGTGATGTCGCCCCGGACGAGGGTGAGGGTGGCGCTCATGTCT
GCCGCAGCCTCCTCCAGACGGCCTTCGCCGCGTTGTGTCCCGACATGCCGTGCACCCCGGGGCCGGGCGGGGTGGCCGAG
GAGCAGATGAAGACCGCGGGGTGCGGGGTTGCGTACGGGAACAGGGACGGTCTGGGGCGCAGCAGGAGCTGGAGTCCGGA
```

TABLE 2-continued

Complete DNA sequence of *S. ghanaensis* ATCC14672 moe (moe) biosynthesis gene cluster 1.

GGCCGCGCCGGTGCCGATGTCGCCGCCGACGTAGTTGGCGTTGCGGGCGGCGAGTTCGGGCGGGCCGGCGGTGGCGCGGG

CCAGGACGCGGTCGCGGAAGCCCGGTGCGTAGCGCTCCAGCTGGCGCTCGATGGCGTCGGTGAGGTCTCCGGTCCAGCCG

TGCGGGACGTGGCCGTAGGCCCAGAAGACGTGCTGGCCCGCCGGTGCCCGGGTGGGGTCGGCGACGCCGGGCTGCACGGT

GATGAGGAACGGCGCGTCGGGGGCCCGGCCCTCCCGGGAGGCGGCGCGCAGGGCGGCGCCGATCTCCCCGCTGTCCGCGC

CGATCTGCACGGTCCCGGCGACGCGGGCCTCGGGCGCGGTCCACGGCACCGGGCCGTCCAGCGCGTAGTCGATCTTGAAG

ACGCCGGGGCCGTACCGGTAGTTCGCGTAGGTGCCGCCGAAGCCGGCGATGCGGGCCAGGGCGGTGGGCGAGGTGTCGAA

GACGTAGGCGCGGGCGGGCGGCAGGTCGTCGAGGCGCTTGACCTCGTAGTCGGTGTGGACGCTGCCGCCGAGGTCCTTCA

GGTACGCGGCGAGGGCGTCGGAGAGCGCATGGAGCCGCCGCGGCCACGGCCAGCCGGGGCGTGCGCGGCGAGGGCGAAG

ACGAGGCCGACGGCGCCGGTGGCGAGACCACCGAGGGGGGCCATCACATGGGCGACGAGCCCCGCGAACAGGGTCCTGGC

CCGCTCGTCGCGGAAGCGGCGCATGAGCCAGGTCGAGGGGGGCAGGCCGACCAGGCCGAAGCGGGCGAGGGTGACCGGGT

CGCGGGGCAGCGCGGTCAGCGGCAGGGACATGAAGTCGCGGACCAGGGTGTCCCACCTGGACAGGAAGGGTGCGACGAGC

CGTCGGTACGGGCCGGCGTCGCGCGGGCCGAAGGAGGCGGCCGTCTCGCCGACCGACCGGGACAGCACGGCCGCGGTGCC

GTCCGGGAAGGGGTGCGCCATGGGGAGCCGGGGGTGCATCCACTCCAGCCCGTAGCGCTCCAGCGGGAGGGCGCGGAAGG

CGGGCGAGTTGATGCCGAGGGGGTGCGCGGCGGAGCACGGGTCGTGCCGGAAGCCGGGCAGGGTGAGCTCCTCGGTGCGG

GCGCCGCCGCCCACGGTGTCCCTGGCCTCGAACAGGGCCACCGAGAAGCCGCGCCGGGCCAGCTCCACGGCAGCGGTCAG

CCCGTTCGGCCCCGCACCCACCACGACCGCGTCGAGCATCGACGGCACCTTCGGACTCCTTCGTCAGCCGACGGCCACTG

GCATCAGGATATGCCGGGGCGCCGGTACCGGGAGATCAGGCTCCTTCCGACAGCAGCCCCACCACCCGCTGTGCCGTGGC

CGCGTCGCGGGCCGCGGTGAAGGGGAGGGTGTTGCCGCCGGTGATGCGGAAGGGCTCGCCCGCGCGGGTCAGATGGGTGC

CGCCCGCCTCCTCGACCAGGAGCAGACCGGCCGCGTGGTCCCAGGCGGCTTCCCAGGAGAAGGCGGTGGCGTCGGACTCG

CCGCGGGCGACGGCCAGGTACTCCAGGCCGGCCGAGCCGCAGGGACGGGGTGCCACGCCCTCGGTCCGCAGGGCGAGCAG

GGACCGCTTCTGTTCGTCCGTGGTGAAGTCCGGGTGGGAGGTGGCCACGCGCAGGTCGCGGCCGGGTTCCGGGGAGCCCG

CGCGGAGCCGTTCGCCGTCGAGGTGGGCGCCCTTGCCCCGTACGGCCGTGGCGAATTGGTGGCGGGCCGGGGCGAAGGTC

CAGGAGGCGTACAGGACTCCGCGCCGGGCAAGGGCGACCAGGGTGCAGAAACCGGTGTCTCCGTGCACGAACTGCCGGGT

GCCGTCGACGGGGTCGACTATCCAGACCGGCGCCTCGCCCCGAACCGCCTCGTACGACGTCGGGTTGGCGTGCACGGCCT

CCTCGCCCACCACGACCGAGCCGGGCAGCAGGGCGGTGAGCGCCTCCGTGAGGTACAGCTCCGCCTTGCGGTCGGCGTCG

GTCACGAGGTCGTGCGGGCCGCTCTTCAGGTCCACCTCGTGTTCGGCGAGCCGGCGCCAGCGCGGCATGATCTCCTGCGC

GGCGGCCTTGCGGACGGCTTCCTCCACGTCGACGGCGTGCCGGTCGAGAAACTCTTCGATGGTTTCGTTGTCCTTGATCA

TGCCTCCATGAGACCACGCCCGGCCGACGTTCCCCACCGTCCCGGTGCACTGCGGGGGGAATCGGCATGAATATGGGGTG

CCGGACCACGGGCGGGTGGGCTCAGCGGCCCACCGCGTAG (SEQ ID NO: 1)

TABLE 3

Sequence of Moe Cluster 2

GACGAGAACGGAGTGCGCTGTTTCGGACGGGCGCGTCCGTCAGCGCGACGGAATGGACGGATCACGTGACCGACTTGCTG

GAGCCGAGGCAACACTGGGTTAGGCGGTTACACCCTTCACCGGACAGCGATGTCACGGTGGTCTGCTTCCCGCACGCGGG

TGGATCGGCCAGCTACTTCCACCCGTTGTCCGCTCGGCTGACGCCCCGTGCCGAGGTGCTGGCGCTGCAGTATCCGGGCC

GCCAGGACCGCCGGTTCGAGCCTGCGCTCACCAGTATCGACGAGCTGGTGGAGGGAATCACCGAGGCGCTGCGCGAGCAC

GTCGACCGGCCCCTCGTGTTCTTCGGGCACAGCATGGGCGGGACGCTCGCCTTCGAGACCGCGCGGCGCATGGAGCCGGA

GCTCGACGGGCGGTTGCTGGGGCTGGTCGTGTCGGGGCGCAGGTCGCCCGGCAGCGTGCGCCGGACGACGGTGCATCTGC

TABLE 3-continued

Sequence of Moe Cluster 2

GGGACGACGCGGGGCTCATCGCGGAAATACGCGAACTGCAGGGGACCGCCTCGACGTTGCTGGACGACGAAGACGTGGTG

CGGATGATCCTGCCGTCCCTCCGCGCCGACTACACCGCGGTGGAGCGGTACGTGTACCGGCCGGGACCGGCACTGAGTTG

CCCCCTGTACGTCTACACCGGTGACGCCGATCCCCAGGTGAACGAGGAGGAGGCGGCGGGATGGGCGGAGCACACCCGCG

CGGACTTCCGGATCCGCACTTTCAGCGGCGGTCACTTCTACCTCGCCGAGCAGAGCGAGCAGGTGATCGCGGCACTGCGT

GAGGACGTGACGGGCTTCCAGGAGCGTTCCCGGACCGGCGCCGAGCGCTGATCCGGGCCCGGGAAGGGTGCACGCACCGG

ACGTGAGGCCGTGCAGTTCAGCCACCGCCGGCGAAGCGGGCGGCGAGTTCGCGTTTCAGTACCTTGCCGCTCGGCCCGAG

GGGGAAGTCCTCGACGAACTCCACCCGGCGCGGGTACTTGTACGCGGCGATTCGCTGCCTGCTCCAGGACACGATGTGCG

CGGCCAGCGCCGCGTCCGGATCCGTGCCCGGCCGCGTCCGCACCACGGCGCACACCTCCTCGCCGTACTTGTCGTCGGGG

ACACCGATGACGGCAACCTGGGCGACGGCCGGGTGACGCATCAGCACCTCCTCCACCTCGCGTGGATAGACGTTGTAGCC

ACCGCGCAGCACCATGTCCTTCTTGCGGTCGACGATGGTCAGATAGCCGTCGGCGTCCTTCATCCCCAGGTCGCCCGAGC

GGAACCAGCCGTCGACCAGCACGGCTGCGGTGGCTTCCGGCCGGTTGAGGTAGCCGGCCATGACGTTGTGGCCGCGTACG

ACGATCTCCCCGATCTCCCCGGCCGGCAGCAGCTCGATACGGTCCTCCACGTCGGCGGCGGCGATCTCCGCCTCCACGCC

CCAGATGGGGCGCCCCACGGTGCCGGGCCTGCGCGGCCACGCCTTCTGGTTGTACGCCACCACCGGCGAGGTCTCCGTGA

GGCCGTACCCCTCGTAGATCGGGCAGCCGTAGACCTCCTGGAACTCCTCGAGCACCTTGACCGGTAGCGCCGAACCGCCG

GAGAAGGCGCGGTCGAGCACGGGGCGGCGGGCGTCGTGAGCGGCGGCGTCGAGGAGGGCCAGGTACATGGTCGGGACGCC

CATGAACACCGTGCAGCCCTCGGTGACCATGAGGTCGAGCGCGCCGGGGCCGTCGAAGCGGTTCATGAGCACCAGGGTGC

CGCCGGCCAGGAAACAGGCGCTCATGCCGCAGGTCTGGCCGAAGGTGTGGAACAGCGGCAGACAGCCCAGCAGCACGTCC

TCGGGGCCGAGGTCGAACGGCGAGCGCATCGTGGTGCTGACGTTCATCACCAGGTTGAGGTGGGTGATCATCGCGCCCTT

GGGCCGGCCGGTGGTGCCCGAGGTGTACAGCACCAAGGCCAAGTCGTCGGGCGCGCGCGGCACCAGACCGTCCAGGGGCT

CCGCCCGTTCGGCGAGCACGTCGAGGCGTGCCGGCCGTCGTCGTCCTCGCCGTTCTCGACCATGACGGTGAGCAGCGGA

ACCCCGGCCGTCCCGGCCGCCTTGGCGCCCTCGGTCAGCATCGGGGCCGCGCACACCATGGCCTTCGCCTCGGAGTCGCC

CAGCACGTGGACGATCTCGTCGGCACGCAGCAGGCCGTGCACCGGGACCACCACGGCACCGAGCGCCAGCACGCCGTAGT

ACACCATCGGGAAGTGCGGTGTGTTCGGCAGCAGCAGGGCGATCCGGTCGCCCGGGCGCACACCGCGGTCCCTCAGCACC

GCCGCGTACCGGCGGGTTGCGAGCCAGAGCTCGGCGTAGGTGATGCGTTCGGAGCCGAAGACGAGCGCGGGGTGGTCGGG

GCGTCGCCCGGCGGACTCGGCCAGTACGGACGCGGCGGTCAGGGTCATGCCGCACCGTTGTGCCGTGCGGCCAGCGCCGG

CTTGTCCGGTTTTCCGGCACGGGTGAGGGCAGCGCGTCGTGGAACGTCACCACGGCCGGTACGTGCTTCGGAGACAGCT

CGGCGGCGACGTGGCCGATCAGCGTCCCGGAGTCGGCGGTGCCGCCCGGCCGTACCACGACGGCGGCGTGGATGTGCTCC

ACGCGGTCCTCGTCGACCACGCAGTACACAGCGGCCTGGGTGACCTCCGGATGGGTCAGCAGCGCGTTCTCCACATCGGT

GGGATGGACCTTGATGCCGTTGGTCTTCATCACCTCGCCCATGCGGCCGTGCAGGCGCAGAAAGCCGTTCTCGTCGAGGG

AACCGAGGTCGCCGGTGTGCACCCAGCCGTCGCGGATGATCGCGGCGGTCAGCTCCGGTTCGCCCCAGTAGCCGAGCATG

GTGGACGGGCTCTGCACGCACACCTCGCCGATCTCGCCGGGCGGCAGGTCGCGGTCGTCGTCCACGTCGCGGATGCGTAT

CTCCGTGGTCGGACGTCCGACGGTCCGGCGCAGTTCCGGGTCGAAGTGGTCCTGCGGCATCAGCATGCTGATGCCGTTGA

CTTCCGTGGTCCCGTAGAGCTGGAGCAACACCGGGCCGAACACCTCGACCGCCTCGGCCAGTCGGGCGGGGCCGCGGGG

GAACCGAGGTAGGTGATGAGCCTGATGCTCGAACGGTCGGTGGTGGCGGTGTCGGGGTGGTCGATCAGCATGTACAGCTG

CGGCGGGGTGATGGTCAGCGTGGAGACGCGGTGCTGTTCCACGGCCCGCAGCACTTCGCCCGCCTCGAACCCGTCGTGCA

GGACGACCGTTCCGCCGGAGGCGAGCGCGACGTCGACGGCGGAGCCGCTGGAGTTGCTCACCGGCAGGGTCGACAGGTAC

ACGATGGGTTCGGGGGACTGGAGGGCCACTTGGAGGTTGGCACGGCGAAGGCGGTACGGCTGCGTGACACCCTTGGGACG

TCCGCTGGTACCGCTGGTGTAGATCACCACGCCGGCTGTTCGGGGTCGGCCTCGACGGCGTCGTGGCCGAAGGCGTCCG

GGTCGCCCGACGAGAGGTCCAGGACATCGGGGCCGAGGGCACCGAGAGCGGCGAGACGCGGTGGCTCGGGCAGCCGGTCG

TABLE 3-continued

Sequence of Moe Cluster 2

CACAGCTCTCGGGCCGCGTCGAGGTTCTCCTTGTCGACGGCGAGGAAGGTCGCCCCGGTCTTGCTGAGAATGTCCAGCCG
GGCGGCGGCGGCCAGCTGGTCGGTGGGGTCCACCGCGTTCGTGGAGTGCAGGTGGACCAGGGTGGCCCCGGCCAGGTTGG
CCGCGTAGCGGAGGATGATGGTCGCCGGGCTGTTGGTGACGGTCAGCACCGCCACAACCGGGGCCTTGCCTTCCGCACTC
GGGTCTCGATGTTCCGTGAAGTGCCGGAGCAGAAGTTCCGCTGCCGTGAGAACCGCCCTGGAGACCTGGCCCGCGGTGAT
TTCTTCACCATCCGCCCACAGGGCAATCCGGTCGGGGTCGGAGGCCAGCGCCTCAAGCACCCGGCGGACGTAATTCTCGT
TCGAGGACATCGTTCCCCCACCATGCTGGTTCGTTTATCGGTCAGTGCAGACTTACATGATCGCGCGAAAGCGCGACAAC
CCGCTCTCGGTAACCATTGGGCGTGCGGCCGGTGAGCACGGCTGCCGTCGGCCAGTTCTCAACACCCGGCAGCCTTGGGC
GAGTTGAATGCCTGCCGGAGTCGATGATATACAGACGTTACCTTCATGCCCTTCCCCTGTGTTGCGAATGGTGAGGCCGC
TCCCGCGCGATTTCGCCAGTGACACGTTCGCACCGGCGCGGGGACAAGCAGAATCCAGTCATGGCCGTGCGATTTCAGC
CAGTTATGCGCGGTTGCCCGTAGTTGCATGTAGCCTCAGACGGCCTGGAACGAAGCGAGTAGACGTGACGACCCAATATC
TGGATCTCTTTGCACGCCTCACAGAAAACTCCGACGGGGGAAAGAGGGAGTTCCTGGAGATCGGACGGCTCGCCGGGAGC
TTCCCCGCGGCCAGCGTCCGCAGCAGTGGACCCGTGACCGGCCGGGACAGCATCAGCGTCTGGTGCAGCAACGACTACCT
CGGCATGGGCCAGCATCCCGCAGTGCTCAAAGCCATGAAGGACGCGATCGACGAGTACGGCGCCGGCGCCGGCGGCTCAC
GCAACATCGGCGGCACCAACCACTACCACGTGCTGCTGGAGAGAGAGCTCGCCGCGCTCCACGGCAAGGACGAGGCCCTG
CTGTTCACCTCCGGTTACACCGCCAACGACGGTGCGCTGTCCGTCATCGCCGGCCGCATGGAGAAGTGTGTCGTCTTCTC
CGACGCACTCAACCACGCGTCCATCATCGACGGCCTGCGCCACAGCCGCGCCCAGAAGCAGATCTTCCGCCACAACGACC
CCGCTCACCTGGAAGAACTGATAGCGGCGGCCGACCCCGACGTCCCCAAGCTCATCGTCGCCGAGTCCGTGTACTCGATG
AACGGCGACATCGCCCCGCTGTCCGAAATCGCCGACATCGCCAAGCGCCACGGGGCGATGACGTACCTCGACGAGGTGCA
CGCGGTGGGCATGTACGGCCCCGGAGGGTGCCGGCATCGCGGCCCGGGAGGGCATCGCCGACGACTTCACCGTCATCATGG
GCACCTTGGCCAAGGGTTTCGGCACCACCGGCGGCTACATCGCAGGGCCCGCCGAAATCATCGAGGCGGTGCGCATGTTC
TCCCGCTCCTTCGTCTTCACCACCGCGCTGGCGCCGGCCGTGGCCGCCGGCGCCCTGGCAGCCGTACACCATCTGCGGTC
CTCCGAGGTCGAGCGGGAACAGCTCTGGTCGAACGCGCAGTTGATGCACCGGCTGCTGAACGAGCGTGGCATCCCCTTCA
TTTCGGACCAGACGCACATCGTGTCCGTCATGGTGGGGACGAGGCCGTGTGCAAGCGGATGTCCGCGCTGCTGCTCGAC
CGGCACGGAATCTACGTGCAGGCGATCAACGCGCCGAGCGTGCGGGTCGGTGAGGAGATCCTGCGGGTCGCCCCCGGAGC
CGTGCACACCGCCGACGACGTACGCGAATTCGTCGACGCTCTGAGCCAGGTCTGGGAGGAAGTGGGCTCCGCCCGCGTGC
CGGCGACCCCGGCCGCTCTCTGATCCGTCCACGTCAAGATGTGCGGGCCACGGCTACGCCGGCCAGATGTGCGGACTCCG
GTTCTCGGGGAGGGCGGTGTGTCTTTGACGTGTCACGCACGTACGGCGGAAACGAACGGCGCTTTCCTCACGGACCATGG
ACAGGGACCCTGCCCCACGGTCAGGACACGGACAATGTCGAAAGGCTGCCGGAAGGCTCGCAGGACATGCGCCTCGGCCG
AAGACAAGTCCGGCCGGTCCCTCATACTCGACCCACAGGTCCCGGAACCCCGCGCATCCGGAGAACGGGCCGGACACCCG
TGGAGTGCCCGGCCCGTCACGGTGCCGCGTACCTACGTGTCTGCTCGGAGAACGCCGTCTACCTCGCCATGGCCGTGCTC
CTGGTGCGTCGCCTCACGAGACCAGTCCGCTGAGAGGCTTTTCAGACGCCCTCTAGGGTGCGGGCTCCCAGATCCTGACC
GCACCGCAACCGCACGACTGGACCGAGATCGGCGGCCGGGTGCTCCTGGAGTGCTGAGCCTGCGCTCAGCCCATCTCCTC
CAACGTCCTGCCCTTGGTCTCCGGCACCCACTTGAGGATGAACGGGACCGCCAGCGTGGCGAAGATCGCGTAGATCACGT
ACGAACCGGACAGGTTCCACTCCGCCATGCTCGGGAACGTCGCGGTGACCAGCCAGTTGGCGACCCACTGCGCGCAGGCG
GCGACGCCAGCGCGGCCGCGCGGATGCGGCTGGGGAACATCTCGCCCAGCAGCACCCAGGCCGCCACGCCCAGCGACAT
GGCGAAGAAGAGGACGAAGGCGTGGGCGGCGACCAGCGCGACGGTGGCCTGGGTGTCGGGCAGCGAGATGTCGTCACCCG
TTCCGGTCTTGTAGGAGAAGGCCCAGGCGACGGCGGCGAGGGAGACCGCCATACCGGCGGAACCGGTCGCGGCCAGCGGC
TTGCGGCCGACCCGGTCGATGAGCACCATCGCGATCACCGTGCCCACGATGTTGATGACCGAGGTGGTGAACGAGTAGAA
GAACGAGCTCGACGGGTCGATGCCCACCGACTGCCACAGCGAGGAGCTGTAGTAGAAGATCACGTTGATACCGACGAACT

TABLE 3-continued

Sequence of Moe Cluster 2

GCTGGAAGACCGACAGGCCGACACCGACCCAGACGATCGGCAGCAGGCCGAAACGGCCGCGGAGGTCCTTGAACCGCGGT

GCCTTGTCGCTGCGCGCGGCGTGCTCGATCTCGGCCACCCGGGCATCGAGATCGACCTGCGCGCCTTCGAGGGTGCGCAG

CACCTCCTTGGCCTCGCCGGTCCTGCCGACTGAGACCAGGTAGCGCGGCGACTCCGGGATGCGCAACGCCAGCAGACCGT

AGACCAGGGCGGGAACGGCCGCGATGCCGAGCATGACCTGCCACGCCTCCAGTCCGAGCAGGCTGCCGCGCTGGTCCCCG

TCGGCGAGGGAGAGCACCATCCAGTTGACCAACTGGGAGACGGCGATGCCCAGCACGACGGCGGCCTGCTGGAAGGAGAC

GAGCCGGCCGCGGTACTCGGTGGGCGCGACCTCGGCGATGTACGTGGGGCCGATCACGGAGGCCATGCCGATGGCCACGC

CGCCCACGATGCGCCAGAAGGACAGGTCCCACGCCGTGAACGGCAGCATCGAGCCGATACTGCTGGCCAGGAAGAGCAGG

GCGGCCAACTGCATCACCCGGAGGCGGCCGACGCGGTCGGCGAGCCGTCCCGCGAGCATGGCGCCGGCGGCCGCGCCGAG

CAGGGCGATGGCGATGACGGCTCCGAGCGTGGCGGCGCCGACGTCGAACCGTCCCTGATGCCCTCGACGGCGCCGTTGA

TCACGGCGCTGTCGTAGCCGAAGAGGAAGCCGCCCATGGCGGCGGACGCCGCGATGAAGACGACGTGACGCAGCTGGTTC

GGCCGGGCCGCGAGGCCCCCGGCGGCGGGTTGTTGTGCTGTGCTCGTCACCTAAGGACTCCTGTGGTGATGTGTGTCGTT
(SEQ ID NO: 2)

Figure 3:
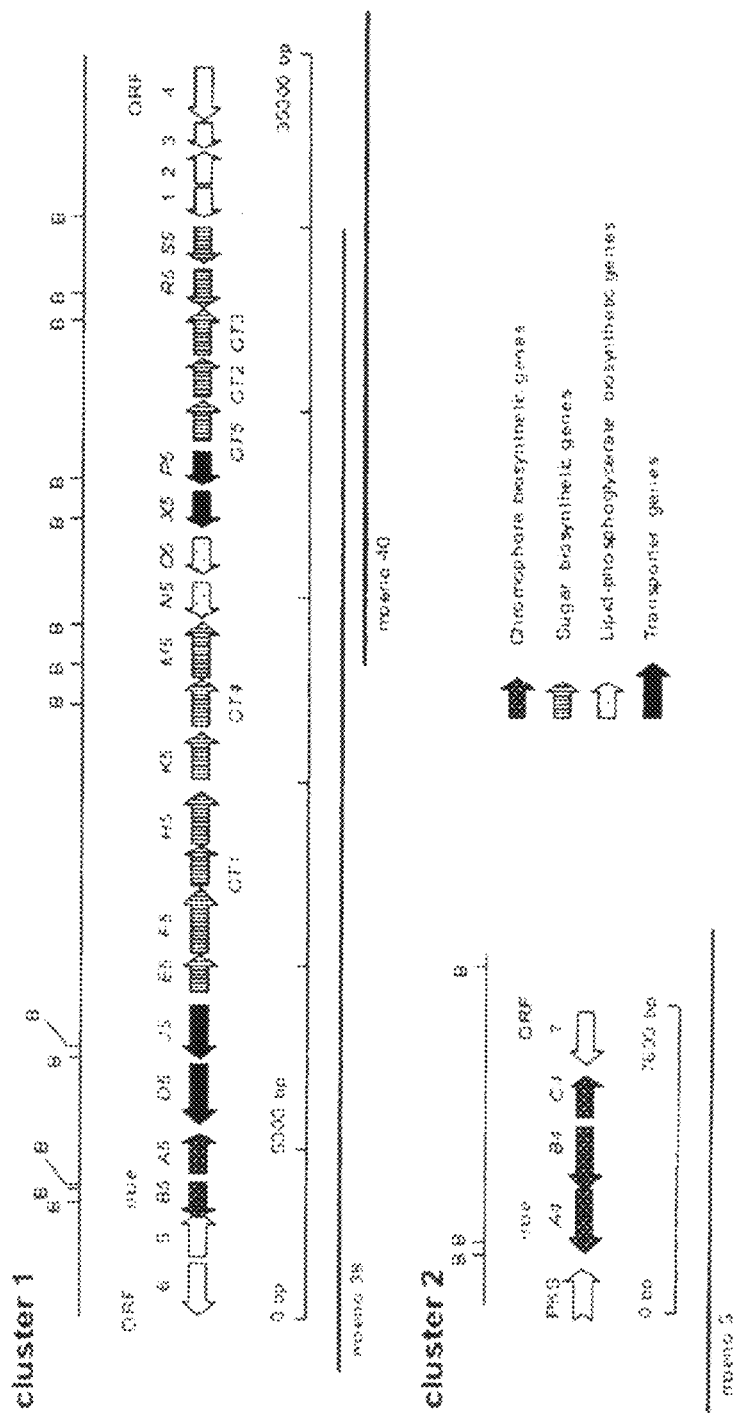
FIG. 3 shows a schematic of the moe gene clusters 1 (FIG. 3A) and 2 (FIG. 3B), and the relative positions of the identified ORFs and genes along the clusters.

The clusters, and relative positions of the genes are shown in FIG. 3. In general, the genes for chromophore biosynthesis appear to be in cluster 2; all other moe biosynthetic genes appear to be in cluster 1.

Constant rearrangements of chromosomal markers located in the ends of linear streptomycete chromosome is well documented (Redenbach 1993, Bentley 2002, Hopwood 2006). This may account for the duplication and divergence of the moe chromophore biosynthetic genes in *S. ghanaensis*, thus leading to the two-cluster organization. Such clusters are not unique. For example, the ansamitocin and clavam biosynthetic pathways from *Actinosynnema pretiosum* and *S. clavuligerus*, respectively, are also encoded by unlinked groups of genes (Yu 2002, Tahlan 2004). These findings suggest that a multi-clustered organization of secondary metabolism genes might be more common than it is anticipated.

A summary of the identified genes and their proposed function is presented below in Table 4. A detailed discussion of each gene and its function is presented in the Experimental Examples, Section III. In total, twenty-three open reading frames (ORFs) were found to be related to moe A biosynthesis (i.e. moe biosynthesis-related genes). The function of the encoded proteins was determined via bioinformatic and genetic analysis. The identified genes are sufficient for the biosynthesis of all four structurally different parts of moe; that is, the genes encoding the proteins necessary to form a structurally complete moe A molecule were identified.

TABLE 4

Deduced functions for genes in moe gene clusters 1 and 2

| Cluster | ORF | Amino Acids | Homologue | ID %/ SI % | Acc. No. of homologue | Proposed function |
|---|---|---|---|---|---|---|
| 1 | MoeB5* | 301 | Putative acyl CoA ligase (*S. aizunensis*) | 58/76 | AAX98210.1 | Nonfunctional acyl CoA ligase |
| 1 | Moe A5 | 394 | As in case of MoeC4 | 64/78 | AY240962 | Nonfunctional Aminolevulinate synthase |
| 1 | MoeD5 | 638 | Putative ABC transporter (*Symbiobacterium thermophilum*) | 41/55 | YP075256.1 | ABC transporter |
| 1 | MoeJ5 | 564 | As above | 45/61 | YP075255.1 | ABC transporter |
| 1 | MoeE5 | 340 | Putative UDP-glucose 4-epimerase (*Symbiobacterium thermophilum*) | 46/58 | YP074610.1 | NDP-hexose 4-epimerase |
| 1 | MoeF5 | 645 | WbpS (*Pseudomonas aeruginosa*) | 29/43 | AAF24002.1 | Unit F Amidotransferase |
| 1 | MoeGT1 | 402 | Putative glycosyltransferase (*Polaromonas sp*) | 28/40 | EAM38951.1 | Glycosyltransferase (transfers unit F) |
| 1 | MoeH5 | 513 | AsnB-like amidotransferase (*Azoarcus sp*) | 32/48 | CAI08539.1 | Unit B Amidotransferase |
| 1 | MoeK5 | 407 | Putative methyltransferase (*Pyrococcus horikoshii*) | 34/52 | NP142754.1 | Methyltransferase |
| 1 | MoeGT4 | 427 | Putative glycosyltransferase (*Mycobacterium vahbaalenii*) | 27/38 | EAS23724.1 | Glycosyltransferase (transfers unit E) |
| 1 | MoeM5 | 530 | GdmN (*Streptomyces hygroscopicus*) | 29/44 | AAO06921.1 | Carbamoyltransferase |

TABLE 4-continued

Deduced functions for genes in moe gene clusters 1 and 2

| Cluster | ORF | Amino Acids | Homologue | ID %/ SI % | Acc. No. of homologue | Proposed function |
|---|---|---|---|---|---|---|
| 1 | MoeN5 | 260 | Putative prenyltransferase (*Chlamydia trachomatis*) | 30/58 | NP220145 | Prenyltransferase |
| 1 | MoeO5 | 281 | GGGPS (*Thermoplasma acidophilum*) | 27/43 | JC7965 | Farnesyl-3-phosphoglycerate synthase |
| 1 | MoeX5 | 266 | Putative membrane protein (*Mycobacterium* sp) | 26/40 | EAS99725.1 | ABC transporter membrane protein |
| 1 | MoeP5 | 233 | ABC transporter ATPase (*Mycobacterium flavescens*) | 43/58 | EAS11435.1 | ABC transporter ATP-binding protein |
| 1 | MoeGT5 | 312 | MoeGT4 (see above) | 45/59 | | Glycosyltransferase (transfers unit C) |
| 1 | MoeGT2 | 286 | Putative glycosyltransferase (*Methylococcus capsulatus*) | 35/51 | AAU93096.1 | Glycosyltransferase (transfers unit B) |
| 1 | MoeGT3 | 414 | Putative glycosyltransferase (*Kineococcus radiotolerans*) | 44/56 | ZP_00616987.1 | Glycosyltransferase (transfers unit D) |
| 1 | MoeR5 | 374 | CapD (*Nocardioides* sp) | 53/68 | EAO07657.1 | Hexose-4,6-dehydratase |
| 1 | MoeS5 | 282 | SCO7194 (*Streptomyces coelicolor*) | 62/75 | CAC01594.1 | Hexose-4-ketoreductase |
| 2 | Moe A4 | 516 | Putative acyl CoA ligase (*Streptomyces aizunensis*) | 63/73 | AAX98210.1 | Acyl CoA ligase |
| 2 | MoeB4 | 521 | SimL (*Streptomyces antibioticus*) | 45/62 | AAG34163.1 | Amide synthetase |
| 2 | MoeC4 | 412 | HemA-AsuA (*Streptomyces asukaensis*) | 70/83 | AY240962 | Aminolevulinate synthase |

EXAMPLES

Genes involved in the synthesis of moe A were cloned and characterized from *S. ghanaensis* ATCC14672. This was followed by bioinformatic and genetic analysis of the identified moe sequences via a combination of gene disruption and heterologous expression approaches. Although not wishing to be bound by any theory, a likely moe A biosynthetic pathway has been elucidated (discussed below in section V). This pathway (see FIG. 4) appears to explain the mechanism of phosphoglycerate incorporation into bacterial secondary metabolites. Furthermore, the pathway provides a basis to generate and identify bioactive derivatives and intermediates of moe A, which may have clinical use as peptidoglycan glycosyltranferease inhibitors.

This section is divided into five main parts. Part I describes exemplary materials and methods used in many of the examples that follow. It will be clear to those skilled in the art that in some aspects of the experimental examples, other methods, reaction conditions, protocols, etc. may be used with comparable results. Part 11 describes the cloning of moe A genes from *S. ghanaensis* ATCC14672, and Part III describes the bioinformatic and genetic analysis of each gene identified in Part II. Part IV describes the characterization of several moe A intermediates. Part V describes a theoretical, overall assembly scheme for moe A based on the information from Parts II and III. Finally, Part VI includes additional experimental examples to show the diversity and utility of the methods and compositions disclosed herein. All experimental examples, whether actual or prophetic, are presented to be instructive and not limiting.

I. Materials and Methods

A. Bacterial Strains and Vector DNAs

Moes producers *S. ghanaensis* ATCC14672 and *S. bambergiensis* NRRL-B12101 were obtained from American Type Culture Collection ("ATCC") and the U.S. Department of Agriculture, respectively. *S. lividans* TK24, *S. coelicolor* M145 (Kieser 2000), *S. cyanogenus* S136 (Westrich 1999) were used in studies on moe A resistance in *Streptomyces*. *Bacillus cereus* ATCC19637 was used as a moe-sensitive test culture.

*Escherichia coli* NovaBlue (Novagen, San Diego, Calif.) was used as a general cloning host. *E. coli* XL1 Blue MR and cosmid SuperCos1 (Stratagene, La Jolla, Calif.) were used for generation of the *S. ghanaensis* genomic library. Methylation-deficient strain *E. coli* ET12567 carrying conjugative driver plasmid pUB307 (Flett 1997) was used for intergeneric *E. coli-Streptomyces* conjugations. *E. coli* BW25113 (pIJ790) was from John Innes Centre (Norwich, UK). *S. lividans* J1725 (bldA mutant) and pIJ584 plasmid harboring intact bldA gene were donated by B. Leskiw (University of Alberta, Canada). Strains *S. ghanaensis* MO12, LH1, OB20a, OB21e with disrupted moeGT3, moeA4, moeM5, moeGT1 genes and *S. lividans* strains expressing various subsets of moe genes were constructed as described below.

Conjugative shuttle vector pKC1139 with temperature-sensitive pSG5 replicon (Muth 1989, Bierman 1992) was used for gene disruption and expression in *S. ghanaensis*. Vector pMKI9 is a derivative of pKC1139 with the ermE promoter inserted into a polylinker (provided by I. Ostash, Dept. of Genetics, Ivan Franko National University, L'viv, Ukraine). Vectors pKC1139, pSET152, pMKI9, pOOB40 are described in Ostash 2007. Integrative vector pSOK804 (Sekurova 2004) was from S. Zotchev (Norwegian University of Science and Technology, Trondheim, Norway). Expression vector pAF1 (ori$^{pIJ101}$ bla tsr, PermE*, 6His tag) was provided by A. Bechthold (Freiburg University, Germany). Plasmids pKD4 and pCP20 (Datsenko 2000) were from J. Beckwith (Harvard Medical School, USA). Spectinomycin resistance cassette pHP45 was from J.-L. Pernodet (Université Paris-Sud, France). Apramycin resistance marker aac(3)IV in integrative conjugative vector pSET152 (Bierman 1992) was replaced with a spectinomycin resistance gene aadA to yield plasmid pOOB5. Plasmid pOOB40 carrying hygromycin resistance marker ("hyg") was generated in the same way.

B. Media and Culture Conditions

LB and LA media were used for cultivation of *E. coli* strains and *Bacillus cereus* ATCC19637. For moe A production, *S. ghanaensis* was grown on solid YMA medium (yeast extract: 4 g/L; malt extract: 10 g/L; glucose: 4 g/L; agar: 18 g/L; pH prior to autoclaving was adjusted to pH 7.5) or in liquid medium (LM) described in Subramaniam-Neihaus (1997) or in mTSB (tryptic soy broth supplemented with 0.5 g $MgCl_2$ and 2.5 mL of trace elements solution (Kieser 2000) per 1 L of medium). For abundant sporulation, *Streptomyces* strains were grown on OM agar (Gromyko 2004). *E. coli-S. ghanaensis* conjugative mixtures were plated onto either MS agar (Kieser 2000) or OM agar supplemented with 10 mM $MgCl_2$. For chromosomal DNA isolation *S. ghanaensis* was grown in TSB. *E. coli* strains were cultivated at 37° C. *B. cereus* and *Streptomyces* strains were grown at 30° C. for 2-3 days unless otherwise stated in a description of specific procedures.

C. DNA Manipulations

Table 5 summarizes the primers used for PCR. Plasmid preparation from *E. coli* was carried out using Qiagen nucleic acid isolation kits according to the manufacturer's instructions (Qiagen, Valencia, Calif.). Total DNA from *S. ghanaensis* was isolated using a salting out method (procedure B; Kieser 2000). For genome sequencing, chromosomal DNA of *S. ghanaensis* was isolated from a strain passed through three 4-day rounds of growth at 40° C. (to obtain a strain free of endogenous plasmid pSG5) and additionally purified using Qiagen Genomic-tip 500/G (Qiagen, Valencia, Calif.). Ultracentrifugation experiments and in silico genome analysis showed that the total DNA submitted to the Broad Institute (Cambridge, Mass.) for genome sequencing did not contain pSG5 or other small (e.g., 10-50 kb) plasmids.

For recovery of shuttle *E. coli-Streptomyces* plasmids from *S. ghanaensis*, *E. coli* was transformed with the total DNA of recombinant, plasmid-containing *S. ghanaensis* strains and then selected for appropriate resistance markers. Plasmid DNA from *E. coli* clones was then isolated and mapped with restriction endonucleases to confirm their identity.

Restriction enzymes and other molecular biology reagents were obtained from commercial sources and used according to the manufacturer's instructions. DNA treatment with endonucleases, Klenow fragment, T4-polymerase, phosphatase and T4-ligase was performed using standard methods (e.g., Sambrook 1989). Southern analysis, digoxigenin labeling of DNA probes, hybridization and detection were performed according to the manufacturer's protocols (Roche, Alameda, Calif.). PCR was performed using KOD Hot Start DNA polymerase (EMD Biosciences, San Diego, Calif.) with addition of DMSO to reaction mixture (10% of final volume).

TABLE 5

Oligonucleotide Primers for PCR Analysis

| Name | Primer Sequence (5' to 3') | SEQ ID NO. |
|---|---|---|
| ligup 1 HindIII | AAAAAGCTTGACGACTTGGCCTTGGTGCTGT | 49 |
| ligrp 1 EcoRI | AAAGAATTCCGTTTCAGTACCTTGCCGCTCG | 50 |
| CTcon73for | AAAAAGCTTGACCGGGAACTCGCCGAG | 51 |
| CTcon73rev | AAAGAATTCGTCGTAGGGAACGGCCCG | 52 |
| GTcon72for | AAAAAGCTTGACCTGACACTCGTCGGCTTC | 53 |
| GTcon72rev | AAAGAATTCTCGAGACGAGGAGCCCGTAC | 54 |
| GT2con73up | AAAAAGCTTGTTCTGCGACGCGGACGAC | 55 |
| GT2con73rp | AAAGAATTCAGGTTCGGAACGTGCAGCA | 56 |
| moeM5nEcoRXbaup | AAGAATTCTAGATCGAGTGGGCTCCCTACTC | 57 |
| moeM5nEcoRIrp | AAAGAATTCACCTGGGGGAGTGACCGAC' | 58 |
| moeGT5up_P1 | GCAGTGCGACGCGAGCGCACGAGCAGACGTCGTCATGT GTAGGCTGGAGCTGCTTC | 59 |
| moeGT5rp_P2 | TCGGGGTGACCTCGTGTGTCAGCGCCCGGCGGCCGCTCC ATATGAATATCCTCCTTAG | 60 |
| moeGT2up_P1 | CGAGGAGCCCGCCGCGGGAGCGGCCGCCGGGCGCTGAC AGTGTAGGCTGGAGCTGCTTC | 61 |
| moeGT2rp_P2 | GCCGAGGTGCCGTCCACGCCGTTCCCCCTCCGTCGGCTA CATATGAATATCCTCCTTAG | 62 |
| moeGT2up_check | ACGAGGGGGACTTCCGCAG | 63 |
| 38start_KD4 | CGTGCGCAGCGCGGTCTTCGGCTTCGACGGGGTACGGAT GAATATCCTCCTTAGTTC | 64 |
| moeA5_P3 | AGACGCGCCGGGCGGCCCCCAGTTCGGACCAGATGCCG TAGGCTGGAGCTGCTTCG | 65 |

TABLE 5-continued

Oligonucleotide Primers for PCR Analysis

| Name | Primer Sequence (5' to 3') | SEQ ID NO. |
|---|---|---|
| P2_KD4 | CATATGAATATCCTCCTTAGTTC | 66 |
| alsrev1 | AAATCTAGATCAAGAGCGGCCGGGGTC | 67 |
| moeF5up_P3 | CGGCTCCTCGGTGTCCGTGCCGCGGCTGTAGGCGGCATGTAGGCTGGAGCTGCTTC | 68 |
| moeF5rp_P2 | TGGACGAGCGGTCGGTCGGGGGCAGCCATGGGTCTCCTACATATGAATCTCCTTAGTTC | 69 |
| F5check_up | GTCTCGGTCAACGAAGTGGTC | 70 |
| F5_check_rp | CTCTCCAGGGAGATGGTCCG | 71 |
| moeGT4up_P3 | TGCACAGCCTGTACCGGTCGACCTCCAACACCGACCGTGTAGGCTGGAGCTGCTT | 72 |
| moeGT4rp_P2 | TCAGCTCTCCTGACGCGTGGGTGAGGACGACGGAGTGAGCATATGAATCTCCTTAGTTC | 73 |
| moeK5-P1 | TCCAGAAGCGGGCCGGCGTGCTGCCGCACCTCGGGGCTGTAGGCTGGAGCTGCTTCG | 74 |
| moeK5-P2 | TGTGCAGGCCGTCCAGCGTGTTGCGCCACTGGCCGGTCATATGAATATCCTCCTTAG | 75 |
| GT2con72up | AAAAAGCTTGTTCTGCGACGCGGACGAC | 76 |
| GT2con73rp | AAAGAATTCAGGTTCGGAACGTGCAGCA | 77 |
| moeH5up_P1 | AGGCCGCCCTCCAGCCCTGCTGGACGCCCGATGACGGTGTAGGCTGGAGCTGCTTC | 78 |
| moeH5rp_P2 | TCTCGTGAAGTGGGGGTCTGCGGCGGTCCGGCCCCGCTACATATGAATATCCTCCTTAG | 79 |
| moeN5up_P1 | CCGGCCACGCCCTGCCGGCGGACTACACGGAGACCATGTAGGCTGGAGCTGCTTCG | 80 |
| moeN5rp_P2 | GGACGGCCGGCCGGAGACGCTCCGGCCGGCCGTCGGTCATATGAATATCCTCCTTAG | 81 |
| moeGT3intMfeI | AAACAATTGTTCTGCGACGCGGACGAC | 82 |
| orflintXbaI | AAATCTAGAGGACTCTGCACCCTGAC | 83 |
| moeR5XbaIup | AAATCTAGAACGCGATGAACCGTCACG | 84 |
| moeGT3XbaIup | AAATCTAGACGTGCCCTTCGACGACCCG | 85 |
| moeGT3EcoRIrp | AAAGAATTCCCACGCCCTGGTCCTGGAC | 86 |
| moeN5XbaIup | AAATCTAGACAGGTCACCGAGTACCTCGA | 87 |
| moeN5EcoRIrp | AAAGAATTCCGCTGATCAACACGTCGCTC | 88 |
| moeF5XbaIup | AAATCTAGACACCCAGATCGAGTGGACC | 89 |
| moeF5EcoRIrp | AAAGAATTCATGGGTCTCCTAGGAGAG | 90 |
| moeGT4XbaIup | AAATCTAGAGTACCGCTCCTTCTTCATGC | 91 |
| moeGT4EcoRIrp | AAAGAATTCAGTGGAGCGACAGTACCTTC | 92 |
| moeH5XbaIup | AAATCTAGACTGGACCAGGACGCGGTG | 93 |
| moeH5EcoRIrp | AAAGAATTCGCTGATGTCTCGTGAAGTGG | 94 |
| moeGT5XbaIup | AAATCTAGAGGGACCGGACTCGGACGT | 95 |
| moeGT5EcoRIrp | AAAGAATTCGGTGACCTCGTGTGTCAGC | 96 |
| moeGT2XbaIup | AAATCTAGAAGGGCCTGCACTTCACCT | 97 |
| moeGT2EcoRIrp | AAAGAATTCGCCGTCCGGATCGACCA | 98 |

TABLE 5-continued

Oligonucleotide Primers for PCR Analysis

| Name | Primer Sequence (5' to 3') | SEQ ID NO. |
|---|---|---|
| moeK5XbaIup | AAATCTAGATCCAGCGTGTTGCGC | 99 |
| moeK5EcoRIrp | AAAGAATTCACGAGACATCAGCCG | 100 |
| moeO5HinDIIIup | AAAAAGCTTCGGGGCGTGCCTTCTTC | 101 |
| moeO5XbaIrp | AAATCTAGACCGCCCGCTCCCCGGAC | 102 |
| moe2HindIII-up | AAAAAGCTTGACGTGAGGCCGTGCAGTTC | 103 |
| moe2Mfel-rp | AAACAATTGGCACATCTTGACGTGGACGG | 104 |

The plasmid and cosmid libraries for *S. ghanaensis* ATCC14672 genome sequencing were created at Broad Institute (Cambridge, Mass.). The cosmid library used for the retrieval of moe clusters 1 and 2 was constructed using the SuperCos1 Vector system (Stratagene, La Jolla, Calif.) according to manufacturer's instructions. Sequencing of cosmids moeno5, 38, 40 and their subclones was done at Biopolymers Facility of Harvard Medical School using standard (M13, T4, T7, T3) and custom designed primers.

D. DNA and Protein Sequence Analysis

The generation, assembly and analysis of *S. ghanaensis* genomic sequences will be described separately. Briefly, the draft assembly yielded 1018 contigs containing 7.4 Mbp of *S. ghanaensis* genome (at 6.6× coverage) and about 1.2 Mbp are estimated to lie in the gap. BLAST search tools (on the server of the National Center for Biotechnology Information, Bethesda, Md.), FramePlot2.3.2 (Ishikawa 1999), CUPplot1.0 and Lasergene software package were used for *S. ghanaensis* sequences assembly, analysis and annotation. Homologues of moe gene translation products were found through BLASTP. Pair-wise amino acid sequence alignment was performed using the sequence analysis program on the server of European Bioinformatics Institute (Cambridge, UK). CDD search engine (BLAST server) and a set of programs (HHPred, Pfam, TMHHM) on ExPaSy proteomics server were utilized for identification of topology and conserved domains of the moe proteins.

E. Identification and Cloning of Moe Gene Clusters 1 and 2

Using BLASTX, all contigs provided by the Broad Institute were scanned in silico for the presence of clustered genes for glycosyltransferases, sugar tailoring genes and genes involved in isoprene metabolism. Seventy contigs containing at least some of the expected genes were then analyzed in more details using FramePlot and BLASTP programs. One stand-alone contig, contig 908, and three adjacent contigs 71, 72, 73 were identified as most likely carrying all or most of the genes involved in moe biosynthesis. On the basis of contig 908, sequence primers ligup1HindIII and ligrp1EcoRI were designed to amplify 1039 base-pair internal fragment of the moe A4 gene (which spans the moe A4 coding region from amino acid 160 to 506) from the *S. ghanaensis* ATCC14672 genome. Primers GTcon72for and GTcon72rev (designed base on the contig 72 sequence) were used to clone a 424 base-pair internal fragment of the moeGT1 gene (amino acids 164-305). A 489 base-pair fragment of the moeGT3 gene (amino acids 228-390) was amplified with primers GT2con73up and GT2con73rp (designed based on contig 73 sequence). DIG-labeled fragments of the moeA4, moeGT1, and moeGT3 genes were used to probe a *S. ghanaensis* cosmid library. Positive cosmids moeno38 and moeno40 were found to carry overlapping segments of *S. ghanaensis* genome that cover contigs 71, 72, 73. Cosmid moeno5 was found to cover contig 908. The aforementioned cosmids were used to finish sequencing moe clusters 1 and 2 (e.g., fill gaps of poor sequence resolution). One cosmid, moeno5, carried 3 moe biosynthetic genes, moe A4, moeB4, and moeC4 (moe cluster 2); the other two cosmids carried the rest of the identified moe genes (moe cluster 1). (See, e.g., FIG. 3).

F. DNA Introduction into *E. coli* and *Streptomyces* Strains

Figure 5:
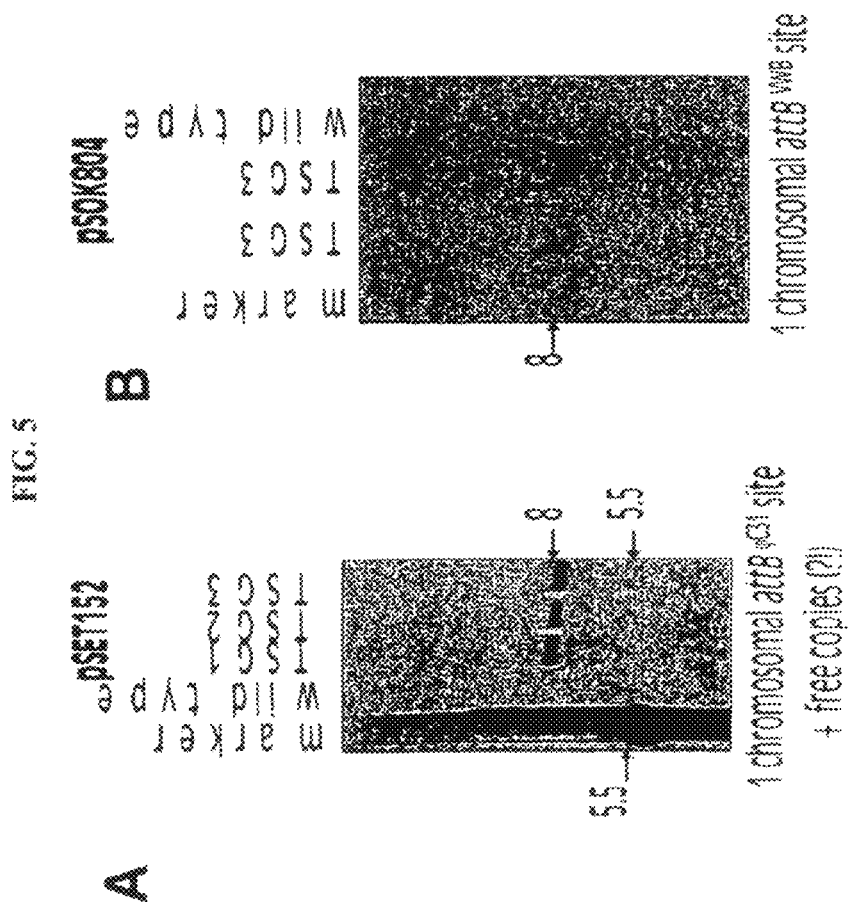
FIG. 5 shows a Southern blot demonstrating the integration of vectors pSET152 (FIG. 5A) and pSOK804 (FIG. 5B) in the S. ghanaensis genome.

Introduction of plasmids and cosmid library sequences into *E. coli* was done as described in Sambrook 1989. A slightly modified procedure of *Streptomyces-E. coli* conjugation (Kieser 2000) was employed to introduce plasmids into *S. ghanaensis* strains. Particularly, heat shocked ungerminated spores were used for matings, and conjugation mixtures were overlaid with selective antibiotics after 10 hours of growth. Conjugations with *S. ghanaensis* disruption mutants, aimed at obtaining complemented strains, were performed at 37° C. and overlaid after 7-8 hours of growth to avoid the excision of disruption plasmid from the mutated moe gene. The average frequency of appearance of *S. ghanaensis* pKC1139+ transconjugants was $6.6 \times 10^{-5}$. Plasmid pSET152 was transferred into *S. ghanaensis* ATCC14672 at frequency $1.0 \times 10^{-3}$. There was one attB$^{\phi C31}$ site in the *S. ghanaensis* chromosome (as judged from Southern analysis of the transconjugants, see e.g., FIG. 5). Also, free copies of pSET152 exist in *S. ghanaensis* cells as evident from Southern analysis and plasmid DNA analysis of Amr clones of *E. coli* obtained after transformation with total DNA of pSET152+ transconjugants. *S. ghanaensis* pSET152+ and pKC1139+ transconjugants did not differ from wild type in their ability to grow, sporulate and produce moe A. The introduction of plasmid and cosmid DNA into *S. lividans* was carried out according to published procedures described in Kieser 2000.

G. Construction of Plasmids for Moe Gene Disruptions and Expression

Internal fragments of moe A4 and moeGT1 genes used for screening the *S. ghanaensis* cosmid library were cloned as HindIII-EcoRI fragments into the HindIII and EcoRI sites of pKC1139 to yield pKC1139lig3 and pOOB21e, respectively.

An EcoRV fragment carrying hygromycin resistance cassette hyg (Kieser 2000) was excised from pHYG1 (Zhu 2005) and inserted into blunt-ended BamHI site of pKC1139lig3. In this way plasmid pLH1 was generated with internal moe A4 fragment being divided into two "arms" of 1 and 0.1 kb in length.

A 462 base pair internal fragment of moeM5 gene (corresponding to amino acid region 214-356 of the moeM5 protein) was amplified from cosmid moeno38 with primers CTcon73for and CTcon73rev. The PCR product was then digested with HindIII and EcoRI and cloned into the corresponding sites of conjugative *E. coli-Streptomyces* vector pKC1139 to yield plasmid pOOB20a. *E. coli* ET12567 (pUB307) was transformed with pOOB20a and the resulting strain was used as a donor in *E. coli* ET12567 (pUB307, pOOB20a)—*S. ghanaensis* ATCC14672 intergeneric conjugation. In this way, plasmid pOOB20a was transferred into *S. ghanaensis*. Under permissive conditions (growth at 30° C.) pKC1139-based plasmids replicate in *Streptomyces* hosts, but at temperatures higher then 34° C., these plasmids are either eliminated from the cells or forced to integrate into host's genome via homologous recombination (Muth 1989).

A 5 kb EcoRI fragment carrying 3'-truncated moeC4 gene and entire moeB4 genes was retrieved from cosmid moeno5 and cloned into EcoRI site of pOOB5 resulting in pKC11395-8 plasmid.

Gene moeGT1 along with its putative ribosome binding site ("RBS") was amplified from cosmid moeno38 with primers moeGT1XbaIup and moeGT1 EcoRIrp, treated with XbaI and EcoRI and cloned into XbaI-EcoRI digested pMKI9 in order to fuse moeGT1 with ermE promoter. From this intermediate construct (named pOOB32) PermE-moeGT1 was excised as a HindIII-EcoRI fragment, treated with T4 DNA polymerase and cloned into EcoRV site of pOOB40 to give pOOB41c.

Gene moeM5 along with its RBS was amplified from cosmid moeno38 with primers moeM5nEcoRXbaup and moeM5nEcoRIrp. The final pOOB40-based construct pOOB43a carrying PermE-moeM5 was generated in a two-step manner, similar to the construction of pOOB41c.

Genes moeD5 and J5 along with their putative promoter region were cloned from cosmid moeno38 with primers con71end and con72start, treated with XbaI and EcoRI and inserted into pMKI9 to yield pOOB38.

Additionally, gene moeM5 along with its ribosomal binding site was amplified from cosmid moeno38 with primers moeM5nEcoRXbaup and moeM5nEcoRIrp, treated with XbaI and EcoRI and cloned into XbaI-EcoRI digested pMKI9 (pKC1139 derivative with strong constitutive *Streptomyces* ermE promoter) in order to fuse moeM5 with ermE promoter. From this intermediate construct (named pOOB42) PermE-moeM5 was excised as a HindIII-EcoRI fragment, treated with T4 DNA polymerase and cloned into EcoRV site of pOOB40 (actinophage øC31-base integrative *E. coli-Streptomyces* vector) to give pOOB43a. This plasmid was introduced into *S. ghanaensis* OB20a strain for pOOB20a introduction into *S. ghanaensis* ATCC14672. The introduction of an intact copy of the moeM5 gene into *S. ghanaensis* OB20a strain was performed to demonstrate the restoration of moe A production in the mutant.

Genes moeF5, moeH5, moeGT4, moeGT5, moeGT2, moeGT3, moeN5, moeK5 were amplified via PCR using cosmid moeno38-1 as a template and respective primers listed in Table 4. Restriction sites for endonucleases XbaI and EcoRI were engineered into the primers to facilitate the cloning of the moe genes into XbaI-EcoRI digested vector pMKI9. The following plasmids were constructed: pOOB48a (moeF5), pOOB51 (moeH5), pOOB50 (moeGT4), pOOB52 (moeGT5), pOOB56c (moeGT2), pMO13 (moeGT3), pMO17 (moeN5), pKC1139EmoeK5 (moeK5). Genes moeO5moeN5 plus moeO5-moeX5 intergenic region were amplified using primers moeO5HindIII and moeN5EcoRI. The amplicon was digested with restriction endonucleases HindIII and EcoRI and cloned into respective sites of pSOK804 yielding pOOB63a. Gene moeO5 was amplified with primers moeO5HindIII and moeO5XbaIrp and cloned into HindIII-XbaI-digested vector pAF1 to give pMoeO5extra. Plasmids pOOB63a and pMoeO5extra were used for complementation of ΔmoeN5 strain. Genes moeA4moeB4moeC4 (moe cluster 2) were amplified with primers moe2HindIII and moe2MfeI. The resulting PCR product was treated with HindIII and MfeI and cloned into HindIII-EcoRI digested pSOK804 thus giving pOOB64b. A 1.5 kb HindIII-XbaI fragment containing moeGT3 fused to PermE was excised from pMO13, treated with Klenow enzyme and cloned into EcoRV site of pOOB40 (Hy') to give pMO14. This plasmid was used to complement moeGT3-deficient *S. ghanaensis* MO12 strain and to construct plasmid pOOB58 (see next chapter). Gene moeB4 has been subcloned from pOOB12 (Ostash 2007) as a XbaI-EcoRI fragment into respective sites of pMKI9, giving pOOB46e. This plasmid was coexpressed with various moeno38-1 derivatives to study the chromophore (unit A) biosynthesis. The fragment of moe cluster 1 containing moeR5moeS5 genes and putative moeS5 promoter (PmoeS5) was amplified with primers moeGT3intMfeI and orf1intXbaI, treated with MfeI and XbaI and cloned into XbaI-EcoRI digested pMKI9 to yield pOOB49f. PmoeS5-moeS5 fragment was retrieved from pOOB49f via XbaI-EcoRI digestion and cloned into pMKI9 to give pOOB55. Gene moeR5 was amplified from moeno38-1 with primers moeR5XbaIup and moeGT3intMfeI and cloned into XbaI-EcoRI digested pMKI9 to yield pOOB59. Plasmids pOOB49f, pOOB55, pOOB59 were coexpressed with the rest of moe cluster 1 to study the roles of moeR5 and moeS5 in moe A biosynthesis.

The internal fragment of moeGT3 was amplified with primers GT2con73up and GT2con73rp, digested with HindIII and EcoRI and cloned into respective sites of pKC1139. The resulting plasmid was named pMO12 and used to insertionally inactivate moeGT3 gene within *S. ghanaensis* ATCC14672 chromosome following the described protocol (Ostash 2007).

There is unique XhoI site in plasmid pMO14 located 205 by downstream of moeGT3 start codon. Plasmid pMO14 was digested with XhoI, treated with Klenow fragment and ligated to spectinomycin resistance gene aadA (retrieved as DraI fragment from pHP45). The resulting plasmid pOOB58 was used as a source of 3.3 kb XbaI-EcoRI linear moeGT3::aadA fragment to replace the intact moeGT3 in cosmid moeno38-91 (derivative of moeno38-1 with deleted moeGT5; see below) via λ-RED approach.

Figure 6:
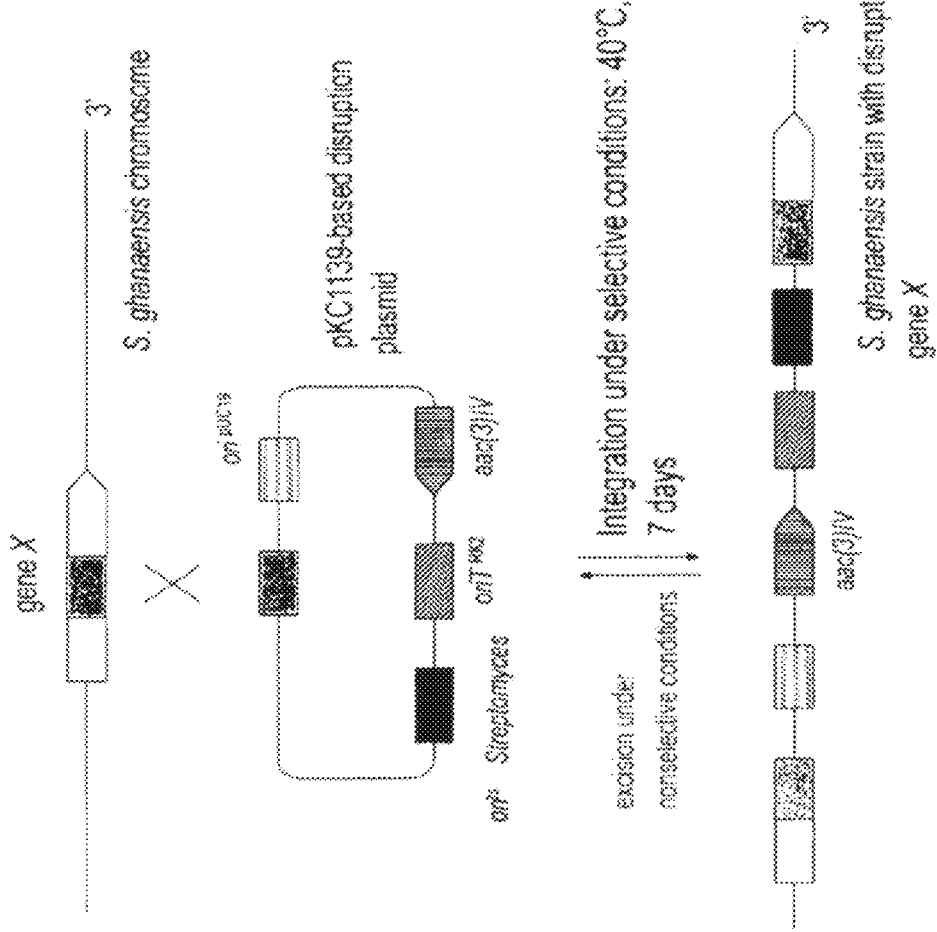
FIG. 6 shows a schematic for the generation of a conjugative plasmid that may be used for insertional gene inactivation.

H. Generation of *S. ghanaensis* and *S. lividans* Disruption Mutants and Their Analysis The same procedure was applied for all four gene knockouts described below in Section III (moeM5, moe A4, moeGT1 and moeGT3; see e.g., FIG. 6 for an exemplary schematic). Strains carrying pKC1139-based disruption plasmids in replicative form were grown for 3 days in TSB at 30° C. (e.g., strain *S. ghanaensis* carrying moeM5 disruption plasmid pOOB20a in replicative form). The biomass was then washed three times with water to remove apramycin used for plasmid selection, and approximately $10^5$ colony forming units ("cfu") were inoculated into fresh TSB (25 mL) without antibiotic. The culture was incubated for 6 days at 40° C. (to eliminate free plasmid), plated onto YMA supplemented with apramycin and grown for 4-5 days at 37° C.

In this way colonies with disruption plasmids integrated into genes of interest—via recombination between regions of homology in the chromosome (full copy of gene of interest) and on the plasmid (the internal fragment of the gene)—were obtained. This integration disrupted the coding region of the gene, leading to deficient strains of S. ghanaensis.

Ten independent colonies for each gene disruption experiment were assayed for moe A production, and in no case was the moe A+ phenotype detected due to possible non-specific integration of plasmid into S. ghanaensis genome. Additionally, the reversions to moe A+ phenotype was not detected when the strains were grown in presence of apramycin at 37° C. indicating that under the stated conditions the insertional inactivation mutants are stable. Passage of wild-type strains under cultivation conditions used to generate moe mutants did not negatively affect moe A production.

The site-specific integration of the disruption sequences was also confirmed by Southern analysis. For moeM5 confirmation, a moeM5 fragment (either radioactively or non-radioactively labeled) was used as a probe. A 2.8 kb XhoI fragment of wild-type digest hybridized with the moeM5 probe, whereas there were two different hybridizing bands in case of moeM5 mutant total DNA XhoI digest. This corresponded to integration of pOOB20a plasmid into the moeM5 gene and introduction of an additional XhoI site into this chromosomal region (See FIG. 9).

For moe A4 plasmid pLH1 in S. ghanaensis LH1 strain was confirmed by Southern analysis using DIG-labeled moe A internal fragment as a probe. In wild-type strains, the moe A4 gene resides in a 10 kb BamHI fragment, whereas in the LH1 strain, the corresponding hybridizing band is absent and a new 19 kb band was present. The latter corresponded to integration of 9 kb pLH1 plasmid into 10 kb BamHI moe A—containing fragment of S. ghanaensis chromosome.

Likewise the integration of the 7 kb moeGT1 disruption plasmid pOOB21e into 10 kb moeGT1-containing BamHI fragment of S. ghanaensis genome was demonstrated (See FIG. 10). For moeGT3 disruption, the plasmid pm012 was transferred into S. ghanaensis via conjugation and homologous integration. The integration was verified by Southern analysis.

Derivatives of moeno38-1 carrying the deletions of moe genes were generated via λ-RED approach. The following procedure was used for all λ-RED-assisted deletions of moe genes within cosmid moeno38-1 (except for moeGT3). Briefly, the entire open reading frame(s) was replaced with kanamycin resistance cassette (pKD4). Then the mutated cosmid was introduced into strain DH5α (pCP20) to evict kanR as described (Datsenko 2000). The presence of expected deletions within the cosmids was checked by PCR. λ-RED recombination was used to replace moeGT3 with disrupted allele moeGT3::aadA in ΔmoeGT5 derivative of moeno38-1.

For moeno38-5 (deletion of moeA5moeB5 genes), the kanamycin resistance gene from plasmid pKD4 was amplified with primers 38start-KD4 and moeA4-P3. The resulting amplicon was used to replace moeA4moeB5 gene pair as well as the entire nonessential "left arm" of moeno38-1 (FIG. 3). Our previous studies showed that deletion of this arm did not alter moe A production (data not shown). We did not evict kanR gene region from moeno38-5 because it did not exert any negative effects on moe A production. The replacement of moeA5moeB5 genes with kanR in moeno38-5 was confirmed via diagnostic PCR (primers P2-KD4 and alsrev1).

For moeno38-91 (deletion of moeGT5 gene), gene kanR was amplified with primers moeGT5up-P1 and moeGT5rp-P2. This amplicon was used to replace moeGT5 gene. The resulting cosmid moeno38-9 was introduced into E. coli DH5α (pCP20) to excise the kanR in FLP-mediated reaction (Datsenko 2000). The cosmid carrying 81 bp "scar" sequence instead of moeGT5 was named moeno38-91. Deletion of moeGT5 in moeno38-91 was confirmed via PCR (primers moeGT5XbaIup and moeGT5EcoRIrp).

For moeno38-31 (deletion of moeGT4), the cosmid moeno38-31 was constructed in the same way moeno38-91 was. The deletion of moeGT4 was checked by PCR (primers moeGT4XbaIup and moeGT4EcoRIrp).

For moeno38-81 (deletion of moeGT2), the cosmid moeno38-81 was constructed in the same way moeno38-91 was. Deletion of moeGT2 was confirmed via PCR (primers moeGT2XbaIup and moeGT2EcoRIrp).

For moeno38-911 (deletion of moeGT5 and disruption of moeGT3), a 3 kb XbaI-EcoRI fragment containing moeGT3:: aadA allele was retrieved from pOOB58 and used to replace moeGT3 in cosmid moeno38-91. The replacement of moeGT3 with moeGT3::aadA in moeno38-911 was verified by PCR (primers moeGT3XbaIup and moeGT3EcoRIrp).

For moeno38-41 (deletion of moeF5), the cosmid moeno38-41 was constructed in the same way moeno38-91 was. The deletion of moeF5 was checked by PCR (primers moeF5check-up and moeF5check-rp).

For moeno38-61 (deletion of moeH5), the cosmid moeno38-61 was constructed in the same way moeno38-91 was. The deletion of moeH5 was checked by PCR (primers moeH5XbaIup and moeH5EcoRIrp).

For moeno38-21 (deletion of moeK5), the cosmid moeno38-21 was constructed in the same way moeno38-91 was. The deletion of moeK5 was checked by PCR (primers moeK5XbaIup and moeK5EcoRIrp).

For moeno38-7 (deletion of moeN5), the gene moeN5 was replaced with the kanR cassette as described above for moeno38-5 construction. We did not excise the kanR cassette from moeno38-7 because it did not exert any polar effects on moe A production.

Gene moeGT3 was insertionally inactivated in S. ghanaensis genome according to established procedure (Ostash 2007). All constructs carrying moe genes were transferred into S. lividans via intergeneric conjugation. Plasmids pIJ584 and pMoeO5extra were introduced via protoplast transformation. Integration of moeno38-1 and its derivatives into S. lividans genome was checked as described in Ostash 2007.

I. Chemicals

Organic solvents, salts, sugars, ITPG, X-Gal and antibiotics were purchased from standard commercial suppliers. The purified samples of moe A have been kindly provided by J. Taylor and S. Fuse (Dept. of Chemistry and Chemical Biology, Harvard University). For recombinant strains selection following commercially available antibiotics were used (mg/mL): ampicillin (100), chloramphenicol (35), kanamycin (50), apramycin (50), hygromycin (100), spectinomycin (200), streptomycin (100), thiostrepton (50), nalidixic acid (50).

J. Moe Production and Resistance Analysis

1. Moe Production in S. ghanaensis

For all moe production analysis procedures, equal amounts of biomass (wet weight) and fermentation medium were used. For moes production, S. ghanaensis strains with disrupted moe genes were grown at 37° C. for 4-5 days in mTSB and for 10 days in LM. For antibiotic disc diffusion assays, fermentation medium and concentrated methanol extracts of moe A from mycelium of *S. ghanaensis* strains were applied to antibiotic assay discs (diem. 10 mm, Sigma, St. Louis, Mo.) and stacked onto LA plates overlaid with soft agar containing *B. cereus*. Semipurified samples of moe A and its derivatives were obtained by methanol extraction of mycelium of *S. ghanaensis* strains and further C18 solid phase extraction as described in (Eichhorn 2005) and then used for LC-MS analysis (Eichhorn 2005) and biochromatography. For the latter, dried silica gel aluminum TLC plate (mobile phase—methanol:acetonitrile:water 40:40:20) with separated moes were overlaid with soft agar containing *B. cereus*, incubated overnight at 30° C. and then visualized with UV light (254 nm).

For moeM5, *S. ghanaensis* OB20a was incubated in TSB medium supplemented with apramycin (to select for pOOB20a integration in moeM5) for 4 days at 37° C. and the moes were extracted from mycelium with methanol. The methanol extract was evaporated, and dry residue was dissolved in water and analyzed as noted above, by antibiotic disc diffusion assay, biochromatography and LC-MS.

2. Moe Production in *S. lividans*

Heterologous expression of moe biosynthetic genes in *S. lividans* TK24 leads to the production of moe derivatives and intermediates. Small-scale fermentation and purification of moenomycins was performed according to Ostash 2007. To obtain pure (>90 as judged by TLC) moenomycin intermediates from recombinant *S. lividans* strains, the following procedure was used. TSB medium (30 mL in 250 mL flask containing 70 glass beads (Ø 5 mm)) was inoculated with 100 µL (approx. $10^4$-$10^5$ cfu) of stock culture (kept in 10.3% sucrose at −20° C.). The flask was incubated on orbital shaker (240 rpm) for 2 days at 37° C. and then used as a preculture to start the fermentation. R5 medium (Kieser 2000) in a slightly modified form (sucrose: 6% instead of 10.3%; 1 mg/L $CoCl_2$ was added after autoclaving) was used as a fermentation medium. 8 4 L flasks (500 mL of medium per each one) containing beads were grown for 6 days at 37° C. The mycelium was harvested by centrifugation and extracted exhaustively with methanol-water (9:1) at 37° C. (when necessary, the pH of extraction mixture was adjusted to 7-7.5 with Tris-HCl). The extract was concentrated in rotovapor, reconstituted in water and extracted with dichloromethane. Aqueous phase was loaded on XAD-16 column (30×400 mm), washed with water (300 mL) and eluted with methanol (500 mL). Methanol fractions containing the desired compound were combined, concentrated and purified on Sep-Pak $C_{18}$ SPE cartridge (Waters) as described (Eihchorn 2005). Further silica gel flash chromatography or preparative TLC of the obtained extract according to (Adachi 2006) yielded pure compound 0.1-0.4 mg/4 L, depending on strain. Antibiotic disc diffusion assay, LC-MS, MS/MS and determination of accurate mass spectra of moenomycins were carried out as described in (Ostash 2007). $^1$H NMR spectra of compound 11 (FIG. 4) were recorded on a Varian Inova 500 (500 MHz) instrument in $D_2O$ (4.80 ppm). Chemical shifts are reported in parts per million (ppm) units.

100 µL (approx. $2\times10^6$ cfu) of 48 hour liquid cultures of *Streptomyces* strains were mixed with 4 mL of soft agar and spread on YMA plates. Then 5 mm antibiotic assay discs with different amounts of moe A were placed on top of soft agar. The moe A growth inhibition was monitored after 12, 24, 48, 72 and 96 hours of cultivation at 30° C.

II. Cloning of Moe Biosynthetic Genes from *S. ghanaensis* ATCC14672

"Reverse genetics" strategies (Weber 2003) became popular for identification of antibiotic biosynthesis gene clusters which share conserved motifs such as the polyketide synthase or nonribosomal peptide synthase genes. Moe A, too, contains structural elements for which dedicated biosynthetic enzyme activity may be ascribed (See e.g., FIG. 7). Using degenerate primers homologous to conserved regions of aforementioned genes (Decker 1996, Rascher 2003, Kawasaki 2003), a set of DNA fragments encoding candidate moe genes was amplified. However, disruption of these cloned genes in the *S. ghanaensis* genome showed that none of them is involved in moe production.

As PCR-based approaches did not lead to moe biosynthetic genes, an in silico, whole-genome scanning strategy was used. The genome of *S. ghanaensis* ATCC14672 (approximately 8.6 Mbp) was shot-gun sequenced to 6.6× coverage and partially assembled yielding 1018 contigs ranging from 1 to 95 Kbp in size. (this phase of the investigation was performed in collaboration with Broad Institute; see the trace sequences at "Traces" on the NCBI website). The structure of moe A suggests that clustered glycosyltransferase, sugar production and prenyltransferase genes as well as unknown genes for chromophore and phosphoglycerate unit incorporation would be identified (FIG. 7). Using BLASTX, all contigs provided by Broad Institute were scanned in silico for the presence of such genes and gene clusters. 70 contigs containing at least some of the expected genes were then analyzed in more detail using FramePlot and BLASTP programs. One stand-alone contig, 908, and three adjacent contigs, 71, 72 and 73 were identified as those most probably carrying all or most of the genes required for moe biosynthesis. These contigs were assigned to two different chromosomal locations or clusters (cluster 1 and cluster 2).

On the basis of the contig 908 sequence, primers ligup1HindIII and ligrp1EcoRI were designed to amplify 1039 bp internal fragment of the moe A4 gene (which spans moe A4 coding region from 160aa to 506aa) from *S. ghanaensis* ATCC14672 genome. Primers GTcon72for and GTcon72rev (designed on the basis of contig 72 sequence) were used to clone a 424 by internal fragment of moeGT1 gene (164-305aa). A 489 by fragment of moeGT3 gene (228-390aa) was amplified with primers GT2con73up and GT2con73rp (designed on basis of contig 73 sequence). For primer sequences, see Table 5. DIG-labeled fragments of moe A4, moeGT1, moeGT3 genes were used to probe a *S. ghanaensis* cosmid library. Positive cosmids moeno38 and moeno40 were found to carry overlapping segments of the *S. ghanaensis* genome that covered contigs 71, 72, 73; cosmid moeno5 was found to cover contig 908. One cosmid, moeno5, carried 3 moe biosynthetic genes, moe A4, moeB4, and moeC4 (moe cluster 2); the other two cosmids carried the rest of the moe genes (moe cluster 1), see FIG. 3.

In total, 43 Kb of the *S. ghanaensis* chromosome has been sequenced, and 30 open reading frames have been identified. The sequences of cluster 1 and cluster 2 are shown in Table 1 and Table 2, respectively. The open reading frames were found to contain the typical (for *Streptomyces*) GC bias in the third codon position of around 90%, and typical codon usage. On the basis of homology searches and functional analysis (see Bioinformatics and Genetic Analysis, Part III, below) 23 of the open reading frames were identified as likely to participate in moe biosynthesis (see Table 4 for predicted function).

III. Bioinformatics and Genetic Analysis

The function of each gene and the role it is likely to play in moe synthesis was determined based on both bioinformatics study and genetic analysis. An NCBI Database BLAST search of the protein sequence was performed. The closest homologue alignment, as determined by this search, is presented in the Tables associated with each open reading frame. In the alignment tables, "QUERY" indicates the moe protein sequence and "SUBJECT" indicates the homologue protein sequence. SeQ ID NOS corresponding to each contiguous stretch of amino acids are indicated in the table of above the respective sequence. The genes identified as likely to be material to moe biosyntheses are described below in seven groups (A-G) based on their function: (A) genes for 2-amino-3-hydroxycyclopent-2-enone moiety ($C_5N$ unit) biosynthesis and attachment to pentasaccharide moiety of Moe A; (B) glycosyltransferase genes; (C) sugar tailoring genes; (D) genes for phosphoglycerate-lipid moiety biosynthesis; (E) transport genes; (F) genes flanking moe clusters 1 and 2; (G) regulatory genes.

Figure 2:
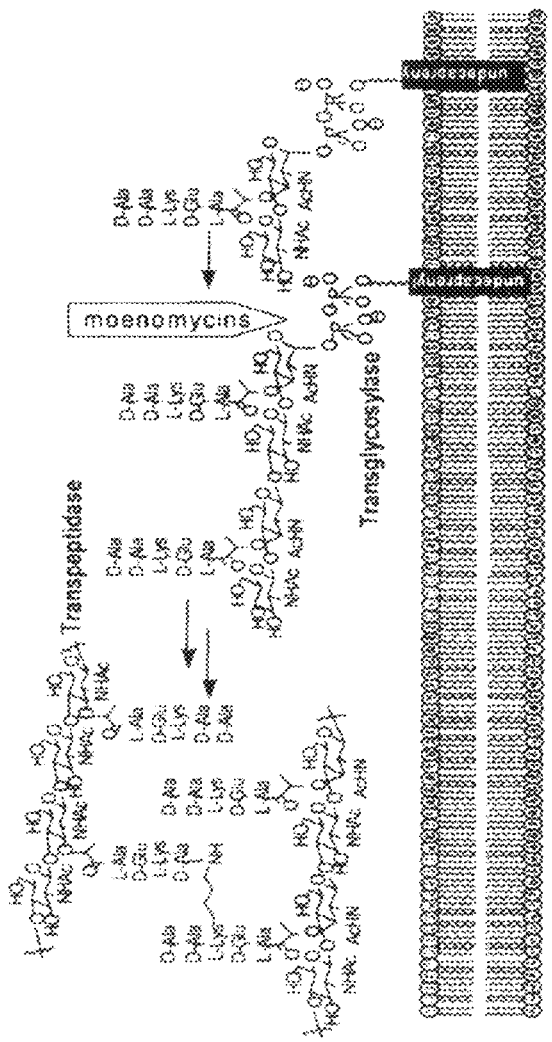
FIG. 2 shows interaction of moe A with the targets on the cell membrane.

We also used a genetic approach to decipher the moe A biosynthetic pathway. The major moe cluster 1 minus the moeR5moeS5 genes is located on the hygromycin resistant cosmid moeno38-1 (FIG. 3), which directs the production of precursor 19 in *S. lividans* TK24 (FIG. 4) (Ostash 2007). We also constructed a set of moeno38-1 derivatives carrying λ-Red-induced deletions (Datsenko 2000, Gust 2003) of individual moe genes; one double mutant cosmid (ΔmoeGT5ΔmoeGT3) was also created. Gene moeGT3 was disrupted in the moe A producer *S. ghanaensis* ATCC14672 (strain MO12) as well. Genes moeR5moeS5 are located within the pKC1139-based plasmid pOOB49f (FIG. 2). Plasmid pOOB64b (based on vector pSOK804 (Sekurova 2004) carries moe cluster 2, an apramycin resistance marker and an actinophage VWB attP-int fragment. Derivatives of moeno38-1 were integrated into the *S. lividans* attP$^{\Phi C31}$ site and then certain strains were further supplemented with either pOOB49f or pOOB64b, or their truncated versions. The mutations in individual moe genes were complemented with exact copies of the genes, thus ruling out any polar effects. All recombinant *S. lividans* strains were analyzed following purification by a set of spectroscopic methods and bioassays, which guided our prediction of the structures of moe A derivatives. We abbreviate the names of recombinant *S. lividans* strains. For example, *S. lividans* strain carrying moeno38-1 derivative with deleted moeF5 is referred to as ΔmoeF5; expression of moeR5 in ΔmoeH5 strain is marked as moeR5$^+$ΔmoeH5; strains carrying the parental cosmid moeno38-1 are marked as 38-1$^+$ strains.

A. Genes for 2-amino-3-hydroxycyclopent-2-enone Moiety ($C_5N$ Unit) Biosynthesis and Attachment to Pentasaccharide Moiety of Moe A Five different genes were identified that fit this functional category; two in cluster 1 (moe A5 and moeB5) and 3 in cluster 2 (moe A4, moeB4 and moeC4). Both moe clusters 1 and 2 carry a copy of putative aminolevulinate synthase gene (moeC4 and moeA5; FIG. 3), which is proposed to direct the production of 5-aminolevulinic acid, the putative precursor to the proposed aminocyclopentadione A ring (Ostash 2007).

1. Moe A5 (Cluster 1)

The biosynthetic studies led by Floss, Wetzel and Felsberg showed that 5-aminolevulinic acid (5-ALA) is a linear precursor of the $C_5N$ chromophore (Nakagawa 1985, Schuricht 2000, Petricek 2006). In moe cluster 1, the moeA5 gene, which displays end-to-end homology to known and putative 5-ALA synthases from various bacteria, was identified. The nucleotide and polypeptide sequences are shown in Tables 6 and 7, respectively.

TABLE 6

DNA Sequence of moeA5.

ATGGACTTCTTCGTGCGACTCGCCCGCGAAACCGGTGACCGGAAGAGGGA
GTTTCTCGAACTCGGCCGCAAGGCGGGTCGGTTCCCCGCGGCGAGCACCT
CGAATGGCGAGATTTCCATCTGGTGCAGCAACGACTACCTGGGTATGGGG
CAGCACCCGGACGTCCTCGACGCCATGAAGCGCTCCGTGGACGAATACGG
CGGAGGATCCGGGGGTTCGCGGAACACAGGCGGAACCAACCACTTCCATG
TGGCTCTGGAGCGGGAGCCGGCCGAGCCGCACGGAAAGGAGGACGCCGTT
CTCTTCACCTCGGGGTATTCCGCCAATGAGGGATCCCTGTCGGTTCTGGC
CGGGGCCGTCGACGACTGCCAGGTCTTCTCGGATTCGGCGAACCACGCGT
CCATCATCGACGGTTTACGGCACAGCGGCGCCCGCAAGCACGTATTCCGG
CACAAGGACGGGCGGCATCTGGAGGAGTTGCTGGCCGCGGCCGACCGGGA
CAAGCCGAAGTTCATCGCCCTGGAGTCCGTGCATTCGATGCGGGGCGACA
TCGCGCTCCTGGCCGAGATCGCCGGCCTGGCCAAGCGGTACGGAGCGGTC
ACCTTCCTCGACGAGGTGCACGCGGTCGGCATGTACGGCCCGGGCGGAGC
GGGCATCGCGGCCCGGGACGGCGTGCACTGCGAGTTCACGGTGGTGATGG
GGACCCTCGCCAAGGCCTTCGGCATGACCGGCGGCTACGTGGCGGGACCG
GCCGTGCTCATGGACGCGGTGCGCGCCCGGGCCCGTTCCTTCGTCTTCAC
CACGGCGCTGCCGCCGGCGGTCGCGGCGGGCGCGCTCGCCGCGGTGCGGC
ACCTGCGCGGCTCGGACGAGGAGCGGCGGCGCCGGCGGAGAACGCGCGG
CTGACGCACGGCCTGCTCCGCGAGCGGGACATCCCCGTGCTGTCGGACCG
GTCCCCCATCGTCCCGGTGCTGGTCGGCGAGGACCGGATGTGCAAGCGCA
TGTCGGCCCTGCCGCTGGAGCGGCACGGCGCGTACGTCCAGGCCATCGAC
GCGCCCAGCGTCCCGGCCGGCGAGGAGATCCTGCGGATCGCGCCCTCGGC
GGTGCACGAGACCGAGGAGATCCACCGGTTCGTGGACGCCCTGGACGGCA
TCTGGTCCGAACTGGGGGCCGCCCGGCGCGTCTGA (SEQ ID NO: 3)

TABLE 7

Amino Acid Sequence of moeA5

MDFFVRLARETGDRKREFLELGRKAGRFPAASTSNGEISIWCSNDYLGMG

QHPDVLDAMKRSVDEYGGGSGGSRNTGGTNHFHVALEREPAEPHGKEDAV

LFTSGYSANEGSLSVLAGAVDDCQVFSDSANHASIIDGLRHSGARKHVFR

HKDGRHLEELLAAADRDKPKFIALESVHSMRGDIALLAEIAGLAKRYGAV

TFLDEVHAVGMYGPGGAGIAARDGVHCEFTVVMGTLAKAFGMTGGYVAGP

AVLMDAVRARARSFVFTTALPPAVAAGALAAVRHLRGSDEERRRPAENAR

LTHGLLRERDIPVLSDRSPIVPVLVGEDRMCKRMSALPLERHGAYVQAID

APSVPAGEEILRIAPSAVHETEEIHRFVDALDGIWSELGAARRV (SEQ
ID NO: 26)

Two of the closest moe A5 homologues are found in streptomycetes-producers of the $C_5N$-containing antibiotics asukamycin and ECO-02301 (64% identity and 78% similarity) (Petricek 2006, McAlpine 2005). The sequence alignment is shown in Table 8. No moe A5-like genes were identified in the completely sequenced *S. coelicolor* and *S. avermitilis* genomes, suggesting that in *Streptomyces*, 5-ALA synthases control 5-ALA supply strictly for $C_5N$ anabolism.

coelicolor homologue SCO6968). However, due to a large deletion of the central portion of the moeB5 gene (relative to a full-length acyl-CoA ligase gene) it is unlikely that moeB5 encodes a functional ligase, even though all the features of open reading frame are present. The nucleotide and polypeptide sequences are shown in Tables 9 and 10, respectively. A sequence alignment between moeB5 and the closest homolog identified in the BLAST search is shown in Table 11.

TABLE 8

Sequence Homology of moeA5

```
gi|37932054|gb|AAO62615.1| aminolevulinate synthase (Streptomyces
nodosus subsp. asukaensis)
Length = 409
Score = 460 bits (1183), Expect = 3e-127
Identities = 258/398 (64%), Positives = 313/398 (78%), Gaps = 6/398 (1%)
Frame = +3

SEQ ID NO: 107                                  SEQ ID NO: 108
Query   375  ISSSMDFFVRLARETGDRKREFLELGRKAGRFPAASTSNG------EISIWCSNDYLGMG  536
             ++  +|||  |    |  |  |+|||||+|+|||||+|      |   |||+||||||||||
Sbjct     1  MNKHLDFFAREMEEFGARRREFLEIGRRAGRFPSAVARQGQDGTDVEISVWCSNDYLGMG   60
              SEQ ID NO: 109

Query   537  QHPDVLDAMKRSVDEYgggaggsrntggtnHFHVALEREPAEPHGKEDAVLFTSGYSANE  716
             |+|  ||+|+|  +||  +|   |||||||  |||||+|| ||| |  ||+|+|  ||++|+
Sbjct    61  QNPFVLEAVKNAVDAFGAGSGGSRNIGGTNHYHVLLENELAALHGKEEALIFPSGFTAND  120

Query   717  GSLSVLAGAVDDCQVFSDSANHASIIDGLRHSGARKHVFRHKDGRHLEELLAAADRDKPK  896
             |+|+||||      ||||  ||||||||||||||||||  +|||   |||||||||  ++||
Sbjct   121  GALTVLAGRAPGTLVFSDELNHASIIDGLRHSGAEKRIFRHNDMAHLEELLAAADPERPK  180

Query   897  FIALESVHSMRGDIALLAEIAGLAKRYGAVTFLDEVHAVGMYGPGGAGIAARDGVHCEFT 1076
             |  ||||+|| ||||  |||  | ||+|+||  |+|||||||||||||||||||  |+|+   |||
Sbjct   181  LIVLESVYSMSGDIAPLAETAALARRHGATTFIDEVHAVGMYGPQGAGIAAREGIADEFT  240

Query  1077  VVMGTLAKAFGMTGGYVAGPAVLMDAVRARARSFVFTTalppavaagalaavRHLRGSDE 1256
             ||||||||  ||   |||+||||  |+||||    +|  +||++++|||   ||||||||+|||   |+
Sbjct   241  VVMGTLAKGFGTAGGYIAGPAALIDAVRNFSRGFIFTTSIPPATAAGALAAVQHLRASEG  300

Query  1257  ERRRPAENARLTHGLLRERDIPVLSDRSPIVPVLVGEDRMCKRMSALPLERHGAYVQAID 1436
             ||   |||  |    |+|||||  +|+|  |  ||+  +++  |||  ||| ||  ||  |+
Sbjct   301  ERTRLAANAGLLHRLLKERDIPFVSDQSHIVSVFVGDDGLCRQASALLLERHGIYVQPIN  360

Query  1437  APSVPAGEEILRIAPSAVHETEEIHRFVDALDGIWSEL 1550
             ||||  ||||||+|||| |    |  ++ +|  +|++|||  +|
Sbjct   361  APSVRAGEEILRVAPSATHTTGDVEKFAEAVEGIWRDL  398
```

Figure 4:
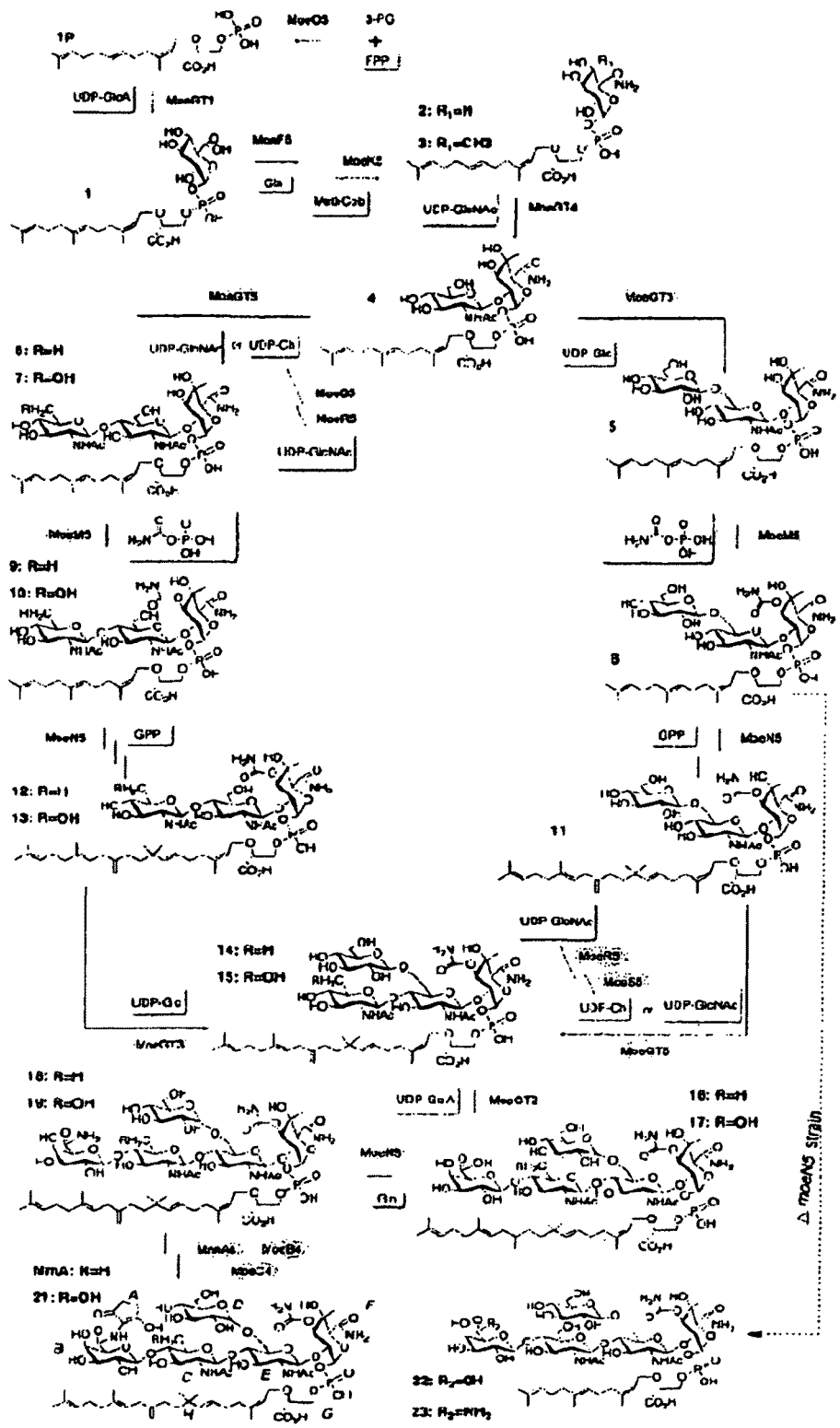
FIG. 4 is a schematic of the moe A biosynthetic pathway. Dotted arrow line represents multiple biosynthetic steps (omitted on the scheme) leading from compound 8 to 22/23

Coexpression of different truncated variants of moe clusters 1 and 2 has revealed that moeA5 is nonfunctional and that the moe cluster 2 genes are sufficient to convert the precursor 19 into pholipomycin 21 (FIG. 4). To probe whether unit A (FIG. 1) originates from 5-aminolevulinate produced by moeC4, as suggested, we fed 5-aminolevulinate to the moeB4+moeA4+ 38-1+ strain. Pholipomycin was not detected in cell extracts in our assay (data not shown). It was reported recently that similar supplementation of mutant asukamycin producers with aminolevulinate failed to yield unit A-tailored antibiotics (Petricek 2006). Perhaps 5-aminolevulinate is not the precursor for C5N units in secondary metabolites such as asukamycin and moenomycin. In any event, although the genes for unit A biogenesis have been identified, the biochemistry of synthesis and attachment remains obscure.

2. MoeB5 (Cluster 1)

The moeB5 gene is located near the moe A5 gene. MoeB5 appears to have homology to the C-terminal portion of an acyl-CoA ligase gene (56% identity and 71% similarity to *S.*

TABLE 9

DNA Sequence of moeB5.

```
GTGGGCGGGCCCGGGGGCGACCCTCTCGGCGGCCACGATCCTCTCGGACT
CCGCGGGCCGGTGGCCGGAGCGCACCGCGGTGGTCGCGGGCGCCGAGCGG
ATCACCTCTGGGGCGTGGAGGTCGCGACAGCCCCGGTCCGAGGCGGAGGA
CGCCGTCGGGCCGCTCCCTCCGGCGAGGTGGGCGAGATCGTCGTCCGCGG
GCACAACCTGATGGCCGGGTACGTCGACGCCCCCGCGCCACGGCCGCCG
CGTTCGTGGACGGCTGGTTCCGCACCGGCGATCTAGGGCTGCTGGACGAG
GAGGGGTACCCCACCGCCGTCGACCGCGAGAAGGACGTGATCCTGCGGGG
CGGGTACGACGTCCATCCCCGTGAGGTCGAGGAAGCGCTGCTCCGCCATC
CGGCGGTCGCCCGGGTCGCGGTGGTGGGGCTCCCCGACCCGGTGTACGGC
CAGGAGGTGTGCGCGGTGGTGGTGCCACGGGACGGCCCGACACCGGACGG
GGCACTGGCGGATTCCGTCGTGGCGTGGGGTGAGCGGCACATCGCGGCGT
ACCGGCGTCCGCGGCGGGTGGTCCTCCCCGACCGGCTTCCCCTGGGACCC
```

TABLE 9-continued
DNA Sequence of moeB5.

GGCGGCAAGGTCCTCAAGGGGGAGCCGGCCGTCCGGCTCCGGTCGTCCGA

CGAGGCGGGGCGGCCCGGCCGAGGGGTGACGGCCCCGGCCGGTTCCCCG

CCGGCGGGGCGGCCCGGCCCGGACGAACGCCTCGGAGGCGGTGCGCGCC

GCCCGGTCCGTGTCCCCGCCCGGGGCCGGTGTCCGGCGCGCTCAGTCGGT

GAGCCCCAGCGTCCCGGCCGCCTGGATCGCCAGCCAGACCTCCGCCAGCG

CGCCGGTCGAGGACAGGTCGCGCCGGGAGAGGGCGCCGAAGCGGCGCAGC

CGGTAG (SEQ ID NO: 4)

TABLE 10
Amino Acid Sequence of moeB5

VGGPGGDPLGGHDPLGLRGPVAGAHRGGRGRRADHLWGVEVATAPVRGGG

RRRAAPSGEVGEIVVRGHNLMAGYVDAPRATAAAFVDGWFRTGDLGLLDE

EGYPTAVDREKDVILRGGYDVHPREVEEALLRHPAVARVAVVGLPDPVYG

QEVCAVVVPRDGPTPDGALADSVVAWGERHIAAYRRPRRVVLPDRLPLGP

GGKVLKGEPAVRLRSSDEAGAARPRGDGPGRFPAGGGGPARTNASEAVRA

ARSVSPPGAGVRRAQSVSPSVPAAWIASQTSASAPVEDRSRRERAPKRRS

R (SEQ ID NO: 27)

TABLE 11
Sequence Homology of moeB5

```
gb|AAX98210.1| acyl CoA ligase [Streptomyces aizunensis]
Length = 506
Score = 197 bits (502), Expect = 3e-49
Identities = 98/175 (56%), Positives = 122/175 (69%), Gaps = 0/175 (0%)

SEQ ID NO: 110
Query    38  GVEVATAPVRGGGRRRAAPSGEVGEIVVRGHNLMAGYVDAPRATAAAFVDGWFRTGDLGL    97
             |  ||  |        ||  |    |++|||||  |||+||||+  |+  ||   ||||||||||+|+
Sbjct   330  GVRVAIADAELEGRIRLLKQGDIGEIVVSGHNVMAGYLGRPQETAEVLVDGWFRTGDMGV   389
              SEQ ID NO: 111

Query    98  LDEEGYPTAVDREKDVILRGGYDVHPREVEEALLRHPAVARVAVVGLPDPVYGQEVCAVV   157
             ||+||  +  |||+||+|+|+||||+|+|||||+  |||||||   |||+|   +|+||||||
Sbjct   390  QDEDGYLSIVDRKKDMIVRGGTNVYPREVEDVLLRHPAVDGACVVGVPSVKHGEEVCAVV   449

Query   158  VPRDGPTPDGALADSVVAWGERHIAAYRRPRRVVLPDRLPLGPGGKVLKGEPAVR       212
               + |    |  ||+ +|||    |+|||+ ||||      +     |||  |||||| |  |  |
Sbjct   450  RVKPGQRASGLLAEEIVAWSRVHMAAYKYPRRVEFVETFPLGSSGKVLKRELAHR       504
```

Like moe A5, moeB5 was shown to be nonfunctional in the course of heterologous expression of engineered moe cosmids. Thus, the likely lack of function of moeB5, along with the absence of dedicated amide synthase gene for $C_5N$ unit transfer to pentasaccharide moiety in moe cluster 1 led to additional in silico searches. In these additional searches, a three-gene operon (named moe cluster 2) similar to that found in genomes of asukamycin and ECO-02301 producers (McAlpine 2005, Petricek 2006) was identified.

3. MoeC4 (Cluster 2)

A second 5-ALA synthase encoding gene, moeC4, was identified in the moe cluster 2 (76.7% similarity between translation products of moe A5 and moeC4). The nucleotide and polypeptide sequences are shown in Tables 12 and 13, respectively. A sequence alignment between moeC4 and the closest homolog identified in the BLAST search is shown in Table 14. As described in Section III.A.1 above, moeC4 is involved in the production of 5-aminolevulinate.

TABLE 12
DNA Sequence of moeC4

GTGACGACCCAATATCTGGATCTCTTTGCACGCCTCACAGAAAACTCCGA

CGGGGGAAAGAGGGAGTTCCTGGAGATCGGACGGCTCGCCGGGAGCTTCC

CCGCGGCCAGCGTCCGCAGCAGTGGACCCGTGACCGGCCGGGACAGCATC

AGCGTCTGGTGCAGCAACGACTACCTCGGCATGGGCCAGCATCCCGCAGT

GCTCAAAGCCATGAAGGACGCGATCGACGAGTACGGCGCCGGCGCCGGCG

GCTCACGCAACATCGGCGGCACCAACCACTACCACGTGCTGCTGGAGAGA

GAGCTCGCCGCGCTCCACGGCAAGGACGAGGCCCTGCTGTTCACCTCCGG

TTACACCGCCAACGACGGTGCGCTGTCCGTCATCGCCGGCCGCATGGAGA

AGTGTGTCGTCTTCTCCGACGCACTCAACCACGCGTCCATCATCGACGGC

CTGCGCCACAGCCGCGCCCAGAAGCAGATCTTCCGCCACAACGACCCCGC

TCACCTGGAAGAACTGATAGCGGCGGCCGACCCCGACGTCCCCAAGCTCA

TCGTCGCCGAGTCCGTGTACTCGATGAACGGCGACATCGCCCCGCTGTCC

GAAATCGCCGACATCGCCAAGCGCCACGGGGCGATGACGTACCTCGACGA

GGTGCACGCGGTGGGCATGTACGCCCGGAGGGTGCCGGCATCGCGGCCC

TABLE 12-continued
DNA Sequence of moeC4

GGGAGGGCATCGCCGACGACTTCACCGTCATCATGGGCACCTTGGCCAAG

GGTTTCGGCACCACCGGCGGCTACATCGCAGGGCCCGCCGAAATCATCGA

GGCGGTGCGCATGTTCTCCCGCTCCTTCGTCTTCACCACCGCGCTGGCGC

CGGCCGTGGCCGCCGGCGCCCTGGCAGCCGTACACCATCTGCGGTCCTCC

GAGGTCGAGCGGGAACAGCTCTGGTCGAACGCGCAGTTGATGCACCGGCT

TABLE 12-continued

DNA Sequence of moeC4

GCTGAACGAGCGTGGCATCCCCTTCATTTCGGACCAGACGCACATCGTGT

CCGTCATGGTGGGGGACGAGGCCGTGTGCAAGCGGATGTCCGCGCTGCTG

CTCGACCGGCACGGAATCTACGTGCAGGCGATCAACGCGCCGAGCGTGCG

GGTCGGTGAGGAGATCCTGCGGGTCGCCCCCGGAGCCGTGCACACCGCCG

ACGACGTACGCGAATTCGTCGACGCTCTGAGCCAGGTCTGGGAGGAAGTG

GGCTCCGCCCGCGTGCCGGCGACCCCGGCCGCTCTCTGA (SEQ ID NO: 5)

TABLE 13

Amino Acid Sequence of moeC4

VTTQYLDLFARLTENSDGGKREFLEIGRLAGSFPAASVRSSGPVTGRDSI

SVWCSNDYLGMGQHPAVLKAMKDAIDEYGAGAGGSRNIGGTNHYHVLLER

ELAALHGKDEALLFTSGYTANDGALSVIAGRMEKCVVFSDALNHASIIDG

LRHSRAQKQIFRHNDPAHLEELIAAADPDVPKLIVAESVYSMNGDIAPLS

EIADIAKRHGAMTYLDEVHAVGMYGPEGAGIAAREGIADDFTVIMGTLAK

GFGTTGGYIAGPAEIIEAVRMFSRSFVFTTALAPAVAAGALAAVHHLRSS

EVEREQLWSNAQLMHRLLNERGIPFISDQTHIVSVMVGDEAVCKRMSALL

LDRHGIYVQAINAPSVRVGEEILRVAPGAVHTADDVREFVDALSQVWEEV

GSARVPATPAAL (SEQ ID NO: 28)

TABLE 14

Sequence Homology of moeC4

```
gb|AAO62615.1| aminolevulinate synthase; Streptomyces nodosus subsp.
asukaensis
Length = 409
Score = 570 bits (1470), Expect = 3e-161
Identities = 283/401 (70%), Positives = 336/401 (83%), Gaps = 1/401 (0%)

SEQ ID NO: 112
Query    4  QYLDLFARLTENSDGGKREFLEIGRLAGSFPAASVRSSGPVTGRDSISVWCSNDYLGMGQ   63
            ++|| ||| |     +|||||||| || ||+| |        | + ||||||||||||||
Sbjct    3  KHLDFFAREMEEFGARRREFLEIGRRAGRFPSAVARQGQDGTDVE-ISVWCSNDYLGMGQ   61
              SEQ ID NO: 113                              SEQ ID NO: 239

Query   64  HPAVLKAMKDAIDEYGAGAGGSRNIGGTNHYHVLLERELAALHGKDEALLFTSGYTANDG  123
            +|  ||+|+|+|+| +|||+|||||||||||||||||| ||||||+||+| ||+|||||
Sbjct   62  NPFVLEAVKNAVDAFGAGSGGSRNIGGTNHYHVLLENELAALHGKEEALIFPSGFTANDG  121

Query  124  ALSVIAGRMEKCVVFSDALNHASIIDGLRHSRAQKQIFRHNDPAHLEELIAAADPDVPKL  183
            ||+|+|||   +|||| ||||||||||||||||| |+|+|||||| |||||+||||+ |||
Sbjct  122  ALTVLAGRAPGTLVFSDELNHASIIDGLRHSGAEKRIFRHNDMAHLEELLAAADPERPKL  181

Query  184  IVAESVYSMNGDIAPLSEIADIAKRHGAMTYLDEVHAVGMYGPEGAGIAAREGIADDFTV  243
            || ||||||+||||||+| | +|+||| |++|||||||||||||+|||||||||||+|||
Sbjct  182  IVLESVYSMSGDIAPLAETAALARRHGATTFIDEVHAVGMYGPQGAGIAAREGIADEFTV  241

Query  244  IMGTLAKGFGTTGGYIAGPAEIIEAVRMFSRSFVFTTALAPAVAAGALAAVHHLRSSEVE  303
            +|||||||||| ||||||||| +|+||| ||| |+|||++ || |||||||||  |+|| |
Sbjct  242  VMGTLAKGFGTAGGYIAGPAALIDAVRNFSRGFIFTTSIPPATAAGALAAVQHLRASEGE  301

Query  304  REQLWSNAQLMHRLLNERGIPFISDQTHIVSVMVGDEAVCKRMSALLLDRHGIYVQAINA  363
              | +|  +|  |+|||| ||  ||+|||+|||| |||+ +|++  |||||+|||||||| |||
Sbjct  302  RTRLAANAGLLHRLLKERDIPFVSDQSHIVSVFVGDDGLCRQASALLLERHGIYVQPINA  361

Query  364  PSVRVGEEILRVAPGAVHTADDVREFVDALSQVWEEVGSAR  404
            |||| |||||||||| | || |+  +|+  +|  ++| |
Sbjct  362  PSVRAGEEILRVAPSATHTTGDVEKFAEAVEGIWRDLGIPR  402
```

Based on the studies of the present invention, it is propose that the polypeptide encoded by the moeC4 gene is an aminolevulinate synthase which participates in the conversion of Moe intermediate compound 18 or 19 in the course of moenomycin biosynthesis to yield a Moe compound MmA or 21, as shown in FIG. 4.

4. Moe A4 (Cluster 2)

Also identified in cluster 2 was the moe A4 gene, the translation product of which shows end-to-end homology to acy-CoA ligases (63% identity and 73% similarity to hypothetical acyl-CoA ligase from S. aizunensis). The nucleotide and polypeptide sequences are shown in Tables 15 and 16, respectively. A sequence alignment between moe A4 and the closest homolog identified in the BLAST search is shown in Table 17. The moe A4 protein may be involved in the formation of 5-ALA coenzyme A ester, a putative prerequisite for its intramolecular cyclization.

TABLE 15

DNA Sequence of moeA4

ATGACCCTGACCGCCGCGTCCGTACTGGCCGAGTCCGCCGGGCGACGCCC
CGACCACCCCGCGCTCGTCTTCGGCTCCGAACGCATCACCTACGCCGAGC
TCTGGCTCGCAACCCGCCGGTACGCGGCGGTGCTGAGGGACCGCGGTGTG
CGCCCGGGCGACCGGATCGCCCTGCTGCTGCCGAACACACCGCACTTCCC
GATGGTGTACTACGGCGTGCTGGCGCTCGGTGCCGTGGTGGTCCCGGTGC
ACGGCCTGCTGCGTGCCGACGAGATCGTCCACGTGCTGGGCGACTCCGAG
GCGAAGGCCATGGTGTGCGCGGCCCCGATGCTGACCGAGGGCGCCAAGGC
GGCCGGGACGGCCGGGGTTCCGCTGCTCACCGTCATGGTCGAGAACGGCG
AGGACGACGACGGCCCGGCACGCCTCGACGTGCTCGCCGAACGGGCGGAG
CCCCTGGACGGTCTGGTGCCGCGCGCGCCCGACGACTTGGCCTTGGTGCT
GTACACCTCGGGCACCACCGGCCGCCCAAGGGCGCGATGATCACCCACC
TCAACCTGGTGATGAACGTCAGCACCACGATGCGCTCGCCGTTCGACCTC
GGCCCCGAGGACGTGCTGCTGGGCTGTCTGCCGCTGTTCCACACCTTCGG
CCAGACCTGCGGCATGAGCGCCTGTTTCCTGGCCGGCGGCACCCTGGTGC
TCATGAACCGCTTCGACGGCCCCGGCGCGCTCGACCTCATGGTCACCGAG
GGCTGCACGGTGTTCATGGGCGTCCCGACCATGTACCTGGCCCTCCTCGA
CGCCGCCGCTCACCACGCCCGCCGCCCGTGCTCGACCGCGCCTTCTCCG
GCGGTTCGGCGCTACCGGTCAAGGTGCTCGAGGAGTTCCAGGAGGTCTAC
GGCTGCCCGATCTACGAGGGGTACGGCCTCACGGAGACCTCGCCGGTGGT
GGCGTACAACCAGAAGGCGTGGCCGCGCAGGCCCGGCACCGTGGGCGCC
CCATCTGGGGCGTGGAGGCGGAGATCGCCGCCGCCGACGTGGAGGACCGT
ATCGAGCTGCTGCCGGCCGGGGAGATCGGGGAGATCGTCGTACGCGGCCA
CAACGTCATGGCCGGCTACCTCAACCGGCCGGAAGCCACCGCAGCCGTGC
TGGTCGACGGCTGGTTCCGCTCGGGCGACCTGGGGATGAAGGACGCCGAC
GGCTATCTGACCATCGTCGACCGCAAGAAGGACATGGTGCTGCGCGGTGG
CTACAACGTCTATCCACGCGAGGTGGAGGAGGTGCTGATGCGTCACCCGG
CCGTCGCCCAGGTTGCCGTCATCGGTGTCCCCGACGACAAGTACGGCGAG
GAGGTGTGCGCCGTGGTGCGGACGCGGCCGGGCACGGATCCGGACGCGGC
GCTGGCCGCGCACATCGTGTCCTGGAGCAGGCAGCGAATCGCCGCGTACA
AGTACCCGCGCCGGGTGGAGTTCGTCGAGGACTTCCCCCTCGGGCCGAGC
GGCAAGGTACTGAAACGCGAACTCGCCGCCCGCTTCGCCGGCGGTGGCTG
A (SEQ ID NO: 6)

TABLE 16

Amino Acid Sequence of moeA4

MTLTAASVLAESAGRRPDHPALVFGSERITYAELWLATRRYAAVLRDRGV
RPGDRIALLLPNTPHFPMVYYGVLALGAVVVPVHGLLRADEIVHVLGDSE
AKAMVCAAPMLTEGAKAAGTAGVPLLTVMVENGEDDDGPARLDVLAERAE
PLDGLVPRAPDDLALVLYTSGTTGRPKGAMITHLNLVMNVSTTMRSPFDL
GPEDVLLGCLPLFHTFGQTCGMSACFLAGGTLVLMNRFDGPGALDLMVTE
GCTVFMGVPTMYLALLDAAAHDARRPVLDRAFSGGSALPVKVLEEFQEVY
GCPIYEGYGLTETSPVVAYNQKAWPRRPGTVGRPIWGVEAEIAAADVEDR
IELLPAGEIGEIVVRGHNVMAGYLNRPEATAAVLVDGWFRSGDLGMKDAD
GYLTIVDRKKDMVLRGGYNVYPREVEEVLMRHPAVAQVAVIGVPDDKYGE
EVCAVVRTRPGTDPDAALAAHIVSWSRQRIAAYKYPRRVEFVEDFPLGPS
GKVLKRELAARFAGGG (SEQ ID NO: 29)

TABLE 17

Sequence Homology of moeA4

```
gb|AAX98210.1| acyl CoA ligase [Streptomyces aizunensis]
Length = 506
Score = 624 bits (1610), Expect = 3e-177
Identities = 326/513 (63%), Positives = 379/513 (73%), Gaps = 7/513 (1%)

SEQ ID NO: 114
Query    1 MTLTAASVLAESAGRRPDHPALVFGSERITYAELWLATRRYAAVLRDRGVRPGDRIALLL   60
           || + |+|||||||| |   ||| |+|+|+|| ||   |||||| || +|+ | |++|||+
Sbjct    1 MTRSVAAVLAESAGRWPSRTALVCGAERISYARLWDRARRYAAALRGQGIGPDDKVALLM   60
           SEQ ID NO: 115

Query   61 PNTPHFPMVYYGVLALGAVVVPVHGLLRADEIVHVLGDSEAKAMVCAAPMLTEGAKAAGT  120
           |||| |   ||+ ||||||||||| ||+ |+ +|| ||+|+|  +  |  ||  |+ ||
Sbjct   61 PNTPEFAAVYFAVLALGAVVVPVHTLLKPAEVSHLLRDSGARALVWAGTLPQETARDAGE  120

Query  121 AGVPLLTVMVENGEDDDGPARLDVLAERAEPLDGLVPRAPDDLALVLYTSGTTGRPKGAM  180
           ||||||| ||       ||  |+|  |  | |||||||||||||||||||||
Sbjct  121 TGVLLLTV----GEALHGSVLLD---DGVEPIDTYVERGADDLALVLYTSGTTGRPKGAM  173
                       SEQ ID NO: 116   SEQ ID NO: 117

Query  181 ITHLNLVMNVSTTMRSPFDLGPEDVLLGCLPLFHTFGQTCGMSACFLAGGTLVLMNRFDG  240
           +|| |+ |++ |||  +|||| ||||| | | |||||| |||+ |  | ||+||+ |+
Sbjct  174 LTHGNVATNIAVTAVSPFAFGEDDVLLGALPLSHTFGQICGMAVTFHAGATLVVMERFEA  233
```

TABLE 17-continued

Sequence Homology of moeA4

```
Query  241 PGALDLMVTEGCTVFMGVPTMYLALLDAAAHDARRPVLDRAFSGGSALPVKVLEEFQEVY  300
               ||  |||||||||||  |||+|  |    |   | +|||||||||  ||+  +   +
Sbjct  234 HDALRLMREHGCTVFMGVPTMYHALLEAVAAGAPAPRLTRVYSGGSALPVPVLDRVRAAF  293

Query  301 GCPIYEGYGLTETSPVVAYNQKAWPRRPGTVGRPIWGVEAEIAAADVEDRIELLPAGEIG  360
           || +|||||||||||| |||||      | +|||||  || ||    || |++|  || ||  |+||
Sbjct  294 GCEVYEGYGLTETSPCVAYNQPGIPCKPGTVGLPIDGVRVAIADAELEGRIRLLKQGDIG  353

Query  361 EIVVRGHNVMAGYLNRPEATAAVLVDGWFRSGDLGMKDADGYLTIVDRKKDMVLRGGYNV  420
           ||||  |||||||||||  ||+  ||  |||||||||+||+|++|    ||||+||||||||||++|||||
Sbjct  354 EIVVSGHNVMAGYLGRPQETAEVLVDGWFRTGDMGVQDEDGYLSIVDRKKDMIVRGGYNV  413

Query  421 YPREVEEVLMRHPAVAQVAVIGVPDDKYGEEVCAVVRTRPGTDPDAALAAHIVSWSRQRI  480
           ||||||+||+|||||     |+|||   |+|||||||||||   +||       ||   ||  ||+|||   +
Sbjct  414 YPREVEDVLLRHPAVDGACVVGVPSVKHGEEVCAVVRVKPGQRASGLLAEEIVAWSRVHM  473

Query  481 AAYKYPRRVEFVEDFPLGPSGKVLKRELAARFA  513
           ||||||||||||||| ||||  ||||||||||||  |+|
Sbjct  474 AAYKYPRRVEFVETFPLGSSGKVLKRELQHRYA  506
```

To evaluate the function of moe A4 and to show that the genes in cluster 2 are used in moe biosynthesis, a moe A4 knockout strain of S. ghanaensis was generated. The mutant S. ghanaensis, termed LH1, did not produce moe A. Instead, it accumulated an antibacterially active moe intermediate. Testing via TLC, UV absorption and mass-spectrometry showed that the intermediate is identical to previously described moe A lacking the chromophore unit (Zehl 2006; see Materials & Methods).

The introduction of a functional copy of the moe A4 gene in trans into the LH1 mutant strain restored moe A production. Thus, the moe A4 knockout did not appear to alter the expression of other genes in the mutant. In sum, the data confirm that the moe A gene is used for $C_5N$ unit formation during moes biosynthesis.

Based on the studies of the present invention, it is propose that the polypeptide encoded by the moeA4 gene is an acyl CoA ligase which participates in the conversion of Moe intermediate compound 18 or 19 in the course of moenomycin biosynthesis to yield a Moe compound MmA or 21, as shown in FIG. 4.

5. MoeB4 (Cluster 2)

The moeB4 gene has been identified as a putative amide synthase gene, and is homologous to different AMP-dependent synthetases and ligases, particularly to aminocoumarin ligase SimL (45% identity and 62% similarity), The nucleotide and polypeptide sequences are shown in Tables 18 and 19, respectively. A sequence alignment between moeB4 and the closest homolog identified in the BLAST search is shown in Table 20. The stop codon of the moeB4 gene overlaps the start codon of moe A4 by one nucleotide, and these two genes are transcribed divergently with respect to the moeC4 transcriptional direction. It is probable that moeB4 can transfer a $C_5N$ unit onto the saccharide scaffold of moe A, similarly to the amide synthases involved in aminocoumarin antibiotics biosynthesis.

TABLE 18

DNA Sequence of moeB4

ATGTCCTCGAACGAGAATTACGTCCGCCGGGTGCTTGAGGCGCTGGCCTC

CGACCCCGACCGGATTGCCCTGTGGGCGGATGGTGAAGAAATCACCGCGG

TABLE 18-continued

DNA Sequence of moeB4

GCCAGGTCTCCAGGGCGGTTCTCACGGCAGCGGAACTTCTGCTCCGGCAC

TTCACGGAACATCGAGACCCGAGTGCGGAAGGCAAGGCCCCGGTTGTGGC

GGTGCTGACCGTCACCAACAGCCCGGCGACCATCATCCTCCGCTACGCGG

CCAACCTGGCCGGGGCCACCCTGGTCCACCTGCACTCCACGAACGCGGTG

GACCCCACCGACCAGCTGGCCGCCGCCGCCCGGCTGGACATTCTCAGCAA

GACCGGGGCGACCTTCCTCGCCGTCGACAAGGAGAACCTCGACGCGGCCC

GAGAGCTGTGCGACCGGCTGCCCGAGCCACCGCGTCTCGCCGCTCTCGGT

GCCCTCGGCCCCGATGTCCTGGACCTCTCGTCGGGCGACCCGGACGCCTT

CGGCCACGACGCCGTCGAGGCCGACCCCGAACAGCCGGCCGTGGTGATCT

ACACCAGCGGTACCAGCGGACGTCCCAAGGGTGTCACGCAGCCGTACCGC

CTTCGCCGTGCCAACCTCCAAGTGGCCCTCCAGTCCCCCGAACCCATCGT

GTACCTGTCGACCCTGCCGGTGAGCAACTCCAGCGGCTCCGCCGTCGACG

TCGCGCTCGCCTCCGGCGGAACGGTCGTCCTGCACGACGGGTTCGAGGCG

GGCGAAGTGCTGCGGGCCGTGGAACAGCACCGCGTCTCCACGCTGACCAT

CACCCCGCCGCAGCTGTACATGCTGATCGACCACCCCGACACCGCCACCA

CCGACCGTTCGAGCATCAGGCTCATCACCTACCTCGGTTCCCCCGCGGCC

CCCGCCCGACTGGCCGAGGCGGTCGAGGTGTTCGGCCCGGTGTTGCTCCA

GCTCTACGGGACCACGGAAGTCAACGGCATCAGCATGCTGATGCCGCAGG

ACCACTTCGACCCGGAACTGCGCCGGACCGTCGGACGTCCGACCACGGAG

ATACGCATCCGCGACGTGGACGACGACCGCGACCTGCCGCCCGGCGAGAT

CGGCGAGGTGTGCGTGCAGAGCCCGTCCACCATGCTCGGCTACTGGGGCG

AACCGGAGCTGACCGCCGCGATCATCCGCGACGGCTGGGTGCACACCGGC

GACCTCGGTTCCCTCGACGAGAACGGCTTTCTGCGCCTGCACGGCCGCAT

GGGCGAGGTGATGAAGACCAACGGCATCAAGGTCCATCCCACCGATGTGG

AGAACGCGCTGCTGACCCATCCGGAGGTCACCCAGGCCGCTGTGTACTGC

GTGGTCGACGAGGACCGCGTGGAGCACATCCACGCCGCCGTCGTGGTACG

TABLE 18-continued

DNA Sequence of moeB4

GCCGGGCGGCACCGCCGACTCCGGGACGCTGATCGGCCACGTCGCCGCCG

AGCTGTCTCCGAAGCACGTACCGGCCGTGGTGACGTTCCACGACGCGCTG

CCCCTCACCCGTGCCGGAAAACCGGACAAGCCGGCGCTGGCCGCACGGCA

CAACGGTGCGGCATGA (SEQ ID NO: 7)

TABLE 19

Amino Acid Sequence of moeB4

MSSNENYVRRVLEALASDPDRIALWADGEEITAGQVSRAVLTAAELLLRH

FTEHRDPSAEGKAPVVAVLTVTNSPATIILRYAANLAGATLVHLHSTNAV

TABLE 19-continued

Amino Acid Sequence of moeB4

DPTDQLAAAARLDILSKTGATFLAVDKENLDAARELCDRLPEPPRLAALG

ALGPDVLDLSSGDPDAFGHDAVEADPEQPAVVIYTSGTSGRPKGVTQPYR

LRRANLQVALQSPEPIVYLSTLPVSNSSGSAVDVALASGGTVVLHDGFEA

GEVLRAVEQHRVSTLTITPPQLYMLIDHPDTATTDRSSIRLITYLGSPAA

PARLAEAVEVFGPVLLQLYGTTEVNGISMLMPQDHFDPELRRTVGRPTTE

IRIRDVDDDRDLPPGEIGEVCVQSPSTMLGYWGEPELTAAIIRDGWVHTG

DLGSLDENGFLRLHGRMGEVMKTNGIKVHPTDVENALLTHPEVTQAAVYC

VVDEDRVEHIHAAVVVRPGGTADSGTLIGHVAAELSPKHVPAVVTFHDAL

PLTRAGKPDKPALAARHNGAA (SEQ ID NO: 30)

TABLE 20

Sequence Homology of moeB4 gb|AAK06803.1| putative aminocoumarin ligase SimD5 [Streptomyces antibioticus]
Length = 519
Score = 424 bits (1089), Expect = 7e-117
Identities = 236/517 (45%), Positives = 322/517 (62%), Gaps = 12/517 (2%)

```
              SEQ ID NO: 118
Query    1  MSSNENYVRRVLEALASDPDRIALWADGEEITAGQVSRAVLTAAELLLRHFTEHRDPSAE   60
            | ||+|||++|  |+||  +||     + || ++ ++ +||| +          |
Sbjct    1  MEGNEHYVRQILNTLRADPSGVALVHRDTPVIAGDLADSITSAAEAMRG--------SGV  52
              SEQ ID NO: 119

Query   61  GKAPVVAVLTVTNSPATIILRYAANLAGATLVHLHSTNAVDPTDQLAAAARLDILSKTGA  120
            |   || +||   |+|||++ |||||| |||+|||   || +|+ |+ |+  |+++
Sbjct   53  GVGSVVGILTDPNTPATLVARYAANLLGATVVHLFGVNAANPSDLLSAEAQGGIVAEALP  112
              SEQ ID NO: 120

Query  121  TFLAVDKENLDAARELCDRLPEPPRLAALGALGPDVLDLSSGDPDAFGHDAVEADPEQPA  180
             + ||  ||+ ||  + +     ||+ |||| ||+|+   ||   ||  | |   |
Sbjct  113  AMVVVDAANLERARAIREVPSVRPVLSGLGELGHDVIDLTDSPAGAFRPDA--ARDGDTA  170

Query  181  VVIYTSGTSGRPKGVTQPYRLRRANLQVALQSPEPIVYLSTLPVSNSSGSAVDVALASGG  240
            || ++||+||||||  +|++  |+  +  +    | |||+++||+||    |   | ||
Sbjct  171  VVTFSSGSTGRPKGTAWSFRVKADMVAASARRAQKATALVTAPLTHSNGFVADDVLVSGG  230
              SEQ ID NO: 121

Query  241  TVVLHDGFEAGEVLRAVEQHRVSTLTITPPQLYMLIDHPDTATTDRSSIRLITYLGSPAA  300
            ||||   ||+   |||| +  +||+ +++|++  ++   ||||    |++ |+ +  |+
Sbjct  171  TVVLLPGFDETEVLRSVARYQVNRLAVSAPQLYALADHPETTRTDLSSVRDLFYTGVAAS  290

Query  301  PARLAEAVEVFGPVLLQLYGTTEVNGISMLMPQDHFDPELRRTVGRPTTEIR--IRDVDD  358
             |+|  +||| ||+|+|+|+|+|  | |+  +| ||||  || ||+   +|    |||  |
Sbjct  291  PERVAEKVFGSVLMQVYGTSETNIISWLIAGEHTDAGLRATVGRPLEWLRVTIRDPQD   350

SEQ ID NO: 122
Query  359  DRDLPPGEIGEVCVQSPSTMLGYWGEPELTAAIIRDGWVHTGDLGSLDENGFLRLHGRMG  418
            +|  ||  ||| |   ||  | ||+|| +||+ ++|+ |+| |+ | +| +|+|||| +
Sbjct  351  ERVVPTGETGEVWVNSPWRMDHYWNDPEQTARTVRDGWIRTGDVGHLDDAGYLHLHGRLA  410

Query  419  EVMKTNGIKVHPTDVENALLTHPEVTQAAVYCVVDEDRVEHIHAAVVVRPGGTADSGTLI  478
            |+||||||+|   | ||  |+|| | +++|+| + |||| ||  |+|| +|          |
Sbjct  411  GVIKTNGIKVYPVAVERSLLDHPDVAEAAVFGVENSDRVERIHAVVVLREGAGAGPEDLR  470

Query  479  GHVAAELSPKHVPAVVTFHDALPLTRAGKPDKPALAA   515
            |+++ ||| ||+   +    +|||  |||||| +
Sbjct  471  QHVSSHLSPNHAPADIELRSSLPLIGFGKPDKLRLRA  507
```

Based on the studies of the present invention, it is propose that the polypeptide encoded by the moeB4 gene is an amide synthetase which participates in the conversion of Moe intermediate compound 18 or 19 in the course of moenomycin biosynthesis to yield a Moe compound MmA or 21, as shown in FIG. 4.

B. Glycosyltransferase Genes

Five putative glycosyltransferase (GT) genes were identified within moe cluster 1, moeGT1 through moeGT5. Five moe GT genes were proposed to govern the assembly of moe A pentasaccharide moiety, but the functions of these genes was not established. Based on sequence analysis, we have suggested that moeGT1 controls the attachment of the second sugar (unit E) during moe A production. However, we were unable to isolate any monosaccharide intermediates from the producing organism, S. ghanaensis, when moeGT1 was disrupted. However, we have found that a recombinant ΔmoeGT4 S. lividans TK24 strain accumulates two new compounds having LC characteristics and exact masses consistent with monosaccharide intermediates 2 and 3 (Table 21, FIG. 4), indicating that moeGT4 controls the attachment of the E ring. Notably, 2 and 3 contain C15 chains and we did not detect any monosaccharides having C25 chains. Strain ΔmoeGT5 was found to produce a trisaccharide, 11, which contained the complete C25 chain; the double mutant strain, ΔmoeGT5ΔmoeGT3, accumulated a disaccharide moe A intermediate 4 having a C15 chain (Table 21, FIG. 4).

TABLE 21

MoeA pathway products found in S. lividans TK24 strains carrying subsets of moe genes

| Mutation(s) in moeno38-1/ coexpression type | Mt. | Min[1] | Mass ((M − H)⁻) Calcd | Obsvd |
|---|---|---|---|---|
| ΔmoeN5 | 23 | 4.2 | 1364.5026 | 1364.5023 |
|  | 22 | 4.1 | 1365.4867 | 1365.4884 |
| ΔmoeGT4 | 2 | 4.7 | 564.2215 | 564.2210 |
|  | 3 | 4.8 | 578.2372 | 578.2374 |
| ΔmoeF5 | 1 | 3.9 | 565.2056 | 565.2054 |
| ΔmoeGT5GT3 | 4 | 4.8 | 781.3166 | 781.3143 |
| ΔmoeGT5 | 11 | 10.4 | 1122.5004 | 1122.5004 |
| ΔmoeGT2 | 15 | 10 | 1325.5797 | 1325.5789 |
| ΔmoeH5 | 17 | 9.3 | 1501.6118 | 1501.6115 |
| ΔmoeK5 | 24[2] | 9.6 | 1486.6122 | 1486.6116 |
| ΔmoeB5A5 | 19 | 9.9 | 1500.6278 | 1500.6273 |
| 5-1⁺ ΔmoeB5A5 | 21 | 9.3 | 1596.6490 | 1596.6492 |
| 5-1⁺ ΔmoeH5 | 17 | 9.7 | 1501.6118 | 1501.6122 |
| moeR5⁺ ΔmoeB5A5 | 18 | 10.0 | 1484.6329 | 1484.6326 |
| moeR5⁺ ΔmoeH5 | 16 | 9.4 | 1485.6169 | 1485.6195 |

[1]250 × 4.6 mm Agilent $C_{18}$ column, under LC conditions used for accurate mass determination (Ostash 2007)
[2]proposed structure of this compound is shown in SI The isolation of the farnesylated mono- and disaccharides 2, 3, and 4 and the moenocinylated trisaccharide 11 strongly suggests that MoeN5 converts C15-linked precursors into C25-linked intermediates after at least three glycosylation steps. Since moenomycins without the branching glucose unit D are naturally produced by S. ghanaensis (Welzel 2005), and accumulate when moeGT3 is disrupted in this strain, we propose that moe A biosynthesis can follow two branches from precursor 4, depicted on FIG. 4, which merge at the stage of tetrasaccharide 14/15. In one branch, MoeGT3 attaches the D ring glucose; in the other, MoeGT5 attaches the C ring, which can be either GlcNAc or chinovosamine (see below). Trisaccharides 8 and 9/10 from both branches of the biosynthetic pathway must be acceptor substrates for MoeN5-catalyzed lipid chain elongation. Strain ΔmoeGT2 accumulates the tetrasaccharide moe A precursor 15 (Table 21, FIG. 4), showing that moeGT2 controls the attachment of the B ring sugar. Thus, the gene disruption studies have allowed us to propose functions for all of the glycosyltransferases except MoeGT1 based on the identification of moe A intermediates. By a process of elimination, we propose that moeGT1 controls the first glycosylation to attach the F ring precursor to the farnesylated phosphoglycerate, which is consistent with our inability to detect any glycosylated moe A intermediates in the moeGT1-deficient S. ghanaensis mutant OB21e (Ostash 2007). Each of the moe glycosyltransferase (GT) genes will be discussed in further detail below.

1. MoeGT1

The closest homologues of the moeGT1 gene product are MurG-like UDP-N-acetylglucosamine: LPS-acetylglucosamine transferases from various bacteria (27% identity and 40% similarity to putative GT from Polaromonas sp JS666). Conserved domain database (CDD) search revealed presence of GT group 1 domain (pfam 00534) in C-terminal portion of moeGT1, as well as incomplete MurG and RfaG domains (COG0707 and COG0438, respectively). The nucleotide and polypeptide sequences are shown in Tables 22 and 23, respectively. A sequence alignment between moeGT1 and the closest homolog identified in the BLAST search is shown in Table 24. GTs having these domains have been shown to be involved in the synthesis of lipopolysaccharides. For example, in peptidoglycan biosynthesis, MurG transfers N-acetylglucosamine onto monoglycosylated carrier Lipid I, thus forming Lipid II (Men 1998, Heijenoort 2001).

TABLE 22

DNA Sequence of moeGT1.

ATGGCTGCCCCCGACCGACCGCTCGTCCAGGTGCTCTCCCCCCGGACCTG

GGGCGAGTTCGGCAACTACCTCGCCGCGACGCGCTTCTCCCGCGCGCTCC

GGAGCGTGATCGACGCGGAAGTGACCCTGCTGGAGGCGGAGCCGATCCTC

CCGTGGATCGGCGAGGCCGGGGCGCAGATCCGGACCATCTCCCTGGAGAG

CCCCGACGCCGTCGTCCGCAACCAGCGGTACATGGCCCTCATGGACCGCC

TCCAGGCACGCTTCCCGGAGGGGTTCGAGGCGGACCCCACCGCCGCCCAG

CGGGCGGACCTGGAACCGCTCACCCGGCACCTGCGGGAGAGCGCCCCCGA

CGTGGTGGTCGGCACGAAGGGGTTCGTGGCGAGGCTGTGCGTGGCCGCCG

TCCGGCTCGCCGGGACGTCCACCAGGGTCGTCAGCCACGTGACCAACCCC

GGGCTGCTGCAGCTGCCGCTGCACCGCAGCCGGTACCCGGACCTGACACT

CGTCGGCTTCCCCCGGGCGAAGGAGCACCTGCTGGCCACGGCCGGCGGCG

ACCCGGAGCGCGTCCAGGTGGTGGGCCCGCTCGTCGCCCAGCACGACCTG

CGGGACTTCATGACCAGTGAGACGGCCGTCTCCGAGGCGGGGCCCTGGGG

CGGCGACTCGGGCCCGGACCGGCCACGGGTGATCATCTTCTCCAACCGCG

GCGGGGACACCTACCCCGAGCTGGTGCGGCGCCTCGCCGACCGCCACCCC

GGCATCGACCTCGTCTTCGTCGGCTACGGCGACCCGGAGCTCGCCCGCCG

CACCGCTGCGGTCGGGCGGCCCCACTGGCGGTTCCACAGCGTCCTCGGCC

AGAGCGAGTACTTCGACTACATCCGGCGTGCCTCCCGGTCCAGGTACGGG

CTCCTCGTCTCGAAGGCGGGGCCCAACACCACCCTGGAGGCGGCCTACTT

TABLE 22-continued

DNA Sequence of moeGT1.

CGGCATACCGGTCCTGATGCTCGAGTCGGGGCTGCCCATGGAGCGGTGGG

TGCCGGGACTGATCCACGAGGAGGGGCTGGGCCACGCCTGCGCCACCCCC

GAGGAGCTGTTCCGCACGGCGGACGACTGGCTGACCCGCCCGTCGGTGAT

CGAGGTGCACAAGAAGGCCGCGGTCTCCTTCGCCGCTTCCGTACTGGACC

AGGACGCGGTGACGGCCAGGATCAAGGCCGCCCTCCAGCCCCTGCTGGAC

GCCCGATGA (SEQ ID NO: 8)

TABLE 23

Amino Acid Sequence of moeGTI

MAAPDRPLVQVLSPRTWGEFGNYLAATRFSRALRSVIDAEVTLLEAEPIL

PWIGEAGAQIRTISLESPDAVVRNQRYMALMDRLQARFPEGFEADPTAAQ

RADLEPLTRHLRESAPDVVVGTKGFVARLCVAAVRLAGTSTRVVSHVTNP

GLLQLPLHRSRYPDLTLVGFPRAKEHLLATAGGDPERVQVVGPLVAQHDL

RDFMTSETAVSEAGPWGGDSGPDRPRVIIFSNRGGDTYPELVRRLADRHP

GIDLVFVGYGDPELARRTAAVGRPHWRFHSVLGQSEYFDYIRRASRSRYG

LLVSKAGPNTTLEAAYFGIPVLMLESGLPMERWVPGLIHEEGLGHACATP

EELFRTADDWLTRPSVIEVHKKAAVSFAASVLDQDAVTARIKAALQPLLD

AR (SEQ ID NO: 31)

To evaluate the function of moeGT1 with respect to moe biosynthesis, a recombinant *S. ghanaensis* strain, termed OB21e, was generated (see Materials and Methods, see FIG. 10). OB21e included an insertionally inactivated moeGT1 gene. The moeGT1 deficient OB21e mutant did not produce moe A or any of its antibiotically active precursors as determined by bioassays and LC-MS analysis (see FIG. 11). To exclude the possibility of polar effects of the moeGT1 knockout on downstream genes expression, we introduced a functional copy of the moeGT1 gene under the control of the ermE promoter (plasmid pOOB41c) into OB21e strain. This complemented the moe A nonproducing phenotype of the OB21e mutant, yielding a full-size, functional moe A product. The trisaccharide degradation product of moe A (units C-E-F-G-H, FIG. 1) is known to display, in vivo, the full antibacterial activity of parent compound (Wetzel 1987). Based on the studies of the present invention, it is propose that the polypeptide encoded by moeGT1 gene is a glycosyl transferase that attaches the first sugar (e.g., glucuronic acid; GalA) to the phosphoglycerate-farnesyl moiety of Moe intermediate compound 1P in the course of moenomycin biosynthesis to yield a Moe intermediate compound 1, as shown in FIG. 4.

2. MoeGT2, Moe GT3, MoeGT4 and Moe GT5

The putative translation product of the moeGT2 gene shows homology to known GTs involved in lipopolysaccharide O-antigen biosynthesis in *Yersinia enterocolitica, Escherichia coli* and *Streptococcus agalactiae* (28% identity and 47% similarity) (Zhang 1997, Paton 1999, Chaffin 2002). The nucleotide and polypeptide sequences are shown in Tables 25 and 26, respectively. A sequence alignment between moeGT2 and the closest homolog identified in the BLAST search is shown in Table 27. MoeGT2 also contains a conserved GT domain (pfam00535) present in very diverse family-2 GTs, which transfer sugars to a range of substrates including cellulose, dolichol phosphate and teichoic acids.

TABLE 24

Sequence Homology of moeGT1

```
gi|84696063|gb|EAQ21850.1| similar to UDP-N-acetylglucosamine:LPS N-
acetylglucosamine-transferase [Polaromonas naphthalenivorans CJ2]
Length = 599
Score =  36.6 bits (83), Expect = 2.3, Method: Composition-based stats.
Identities = 68/246 (27%), Positives = 100/246 (40%), Gaps = 17/246 (6%)

SEQ ID NO: 123
Query  160  SRYPDLTLVGFPRAKEHLLATAGGDPERVQVVGPLVAQHDLRDFMTSETAVSEAGPWGGD  219
            |+  |  |+     +    ||  ||  |++|    |  +       |   | ||++   |
Sbjct  144  SKRIDRTFLAHTDLESRWLA-AGVPPDKVTTSG-MPVRAPAADGATRETALTALG-----  196
            SEQ ID NO: 124          SEQ ID NO: 240     SEQ ID NO: 241

SEQ ID NOS: 125  126        127
Query  220  SGPDRPRVIIFSNRGG-DTYPELVRRLADRHPG-IDLVFV-GYGDPELARRTAAVGR-PH  275
            ||  |  |+| | +    |   +|  ||  |||  +  ++  |     +   ||    ||
Sbjct  197  LAPDAPTVLITSGKEGVGDYALVVESLARHHPGPLQIIAVCGANARQQALLTALQKRLPE  256
            SEQ ID NO: 128

SEQ ID NOS: 129
Query  276  WRFHSVLGQSEYFDYIRRASRSRYGLLVSKAGPNTTLEAAYFGIPVLMLESGLPMERWVP  335
            |    |    + | +   |   •  ||++|||    |  ||    | |++|+       ||
Sbjct  257  PVALKVCGLVPHADLL--AWMRAADLLITKAGGMTPAEAFAVGTPTILLDVVSGHERENA  314
                               SEQ ID NO: 130

Query  336  GLIHEEGLGHACATPEELFRTADDWLTRPSVIEVHKKAAVSFAASVLDQDAVTARIKAAL  395
            |    |+     |   +    |  |  |     ++| ++|     |+ +    +  ||
Sbjct  315  ALFVRLGVADLADTLAQAGELAAAVLASPQRQTAMRRAQLAFH----DRAGLGRIARFAL  370
                                                        SEQ ID NO: 131

Query  396  QPLLDA  401
            |  |  |
Sbjct  371  DPALPA  376
```

TABLE 25

DNA Sequence of moeGT2

CTGACACACGAGGTCACCCCGAGGGGCGGCCCGGAAGGAGACGCGATGGT

GACAGCGGGGCCGGCCGGGCGGCGGTGACCGTCGTCCTGCCTCACTACG

ACTGCGCGGCGTACCTGGGTGCGGCCGTCGGATCGGTGCTCTCCCAGGAC

CGCCCGGACCTGCGCCTGACGGTGGTGGACGAATGCTCGCCCGAAGAGAA

GTGGGCCCGCGCACTCCACCCGTACGCCGGCGACCCCCGGCTGACCGTGG

TCCGCACCTCCCGCAACGTCGGCCACCTGCGGATCAAGAACAAGGTCCTG

GAATCGGTGGACACCCCCTACGTGGCCTTCCAGGACGCCGACGACATCAG

CCTGCCGGGCCGGCTGCGCCACCAGCTGGCCCTCCTGGAGAGCGGCGGCG

TABLE 26

Amino Acid Sequence of moeGT2

LTHEVTPRGGPEGDAMVTAGPAGAAVTVVLPHYDCAAYLGAAVGSVLSQD

RPDLRLTVVDECSPEEKWARALHPYAGDPRLTVVRTSRNVGHLRIKNKVL

ESVDTPYVAFQDADDISLPGRLRHQLALLESGGADLVGCAYSYIDEAGRT

TGHRRMPRNGNLWMRLGRTTVLLHPSSVVRRSVLERLGGFDGTARLGADT

DFHLRAARLYRLRSVRKVLYRYRIWPKSLTQAPDTGFGSAERRAYTEAMT

AQEERRRRARTREELLPLLVAPPNDVDFTLTRVDLD (SEQ ID NO: 32)

TABLE 27

Sequence Homology of moeGT2

```
gb|AAU93096.1| glycosyl transferase, group 2 family protein [Methylococcus
capsulatus str. Bath]
Length = 367
Score = 104 bits (260), Expect = 4e-21
Identities = 80/228 (35%), Positives = 117/228 (51%), Gaps = 7/228 (3%)

SEQ ID NO: 132         SEQ ID NO: 133
     Query   7 PRGGPEGDAMVTAGPAGAA--VTVVLPHYDCAAYLGAAVGSVLSQDRPDLRLTVVDECSP   64
               |   |   +  |  |     ||+++| |+   || | |+ |+|    |    ++|+ |
     Sbjct  11 PHHVPHRDMTHHSRPPGHAPRVTILMPVYNGEKYLAAAMESILDQTFRDFILLIIDDGSS   70
                                          SEQ ID NO: 242

Query  65 EEKWARALHPYAGDPRLTVVRTSRNVGHLRIKNKVLESVDTPYVAFQDADDISLPGRLRH  124
               +    | |        ||||+  |    +|+| ++  |+ |+ |   +||    |||+|| ||
     Sbjct  71 DSSLAIARS--FGDPRVQVERNPKNLGLVKTLNRGLDLVQTEFVARMDCDDIALPDRLEK  128
                                          SEQ ID NO: 134

SEQ ID NO: 135
     Query 125 QLALL-ESGGADLVGCAYSYIDEAGRTTGHRRMPRNGNLWMRLGRTTVLLHPSSVVRRSV  183
               |+|  |+    + | ||      |+ |  |    |+ +      | ||   +|| |
     Sbjct 129 QIAFLDENPDIGMCGTAYELFHESLRQT-IRPPCRHEEIVYGLLDDNVFLHSSVIVRMEV  187
                                          SEQ ID NO: 136

SEQ ID NO: 135
     Query 184 LERLG-GFDGTARLGADTDFHLRAARLYRLRSVRKVLYRYRIWPKSLT             230
               |  |   + | +   ||   |  ||      + ++ +||   |||   |++++
     Sbjct 188 LNRHGLRYREDYRLAEDYELWARLARYTHIGNLPQVLVRYRSHPENVS             235
```

TABLE 25-continued

DNA Sequence of moeGT2

CCGATCTGGTCGGCTGCGCCTACTCCTACATCGACGAGGCGGGCCGTACG

ACGGGACACCGGCGGATGCCCCGCAACGGCAACCTCTGGATGCGGCTGGG

GCGGACGACCGTGCTCCTGCACCCGTCCTCGGTGGTGCGGCGCTCGGTGC

TCGAGAGGCTCGGCGGCTTCGACGGCACCGCGCGCCTGGGGGCCGACACC

GACTTCCACCTGCGGGCCGCCCGCCTGTACCGGCTGCGCAGTGTGCGCAA

GGTGCTCTACCGGTACCGGATCTGGCCCAAGTCGCTCACCCAGGCGCCGG

ACACCGGGTTCGGGTCCGCGGAGCGCCGGGCCTACACCGAGGCGATGACC

GCGCAGGAGGAGCGGCGGCGACGGGCGCGGACCCGTGAGGAGCTGCTGCC

GCTGCTGGTCGCCCCGCCCAACGACGTCGACTTCACCCTGACCCGGGTCG

ACCTCGACTAG (SEQ ID NO: 9)

Based on the studies of the present invention, it is propose that the polypeptide encoded by the moeGT2 gene is a glycosyltransferase that attaches a sugar moiety (e.g., glucuronic acid (GalA)) to the Moe intermediate compound 14 or 15 in the course of moenomycin biosynthesis to yield a Moe intermediate compound 16 or 17, respectively, as shown in FIG. 4.

The product of the moeGT3 gene is similar to family-2 GTs involved in antibiotic production (32% identity and 45% similarity to AprG1 GT from *S. tenebrarius* apramycin gene biosynthetic cluster) (Du 2004), and biofilm and antigen biosynthesis (23% identity and 44% similarity) (Kaplan 2004, Wang 2004). It also has homology to putative GTs involved in cell wall biogenesis. The moeGT3 gene includes a putative conserved GT domain (COG1216) which is present in many GTs. The nucleotide and polypeptide sequences are shown in Tables 28 and 29, respectively. A sequence alignment between moeGT3 and the closest homolog identified in the BLAST search is shown in Table 30.

TABLE 28

DNA Sequence of moeGT3

GTGGCCGTCCTCCGCGGTGACGACGAGGCGCTCCCCCACTGGCTGTGGCA

CCTGGCGCGGGCGGTCTGGTACGGCGGCGGGGACGGCACCGGGCCGGTCG

GCCTGGTGCAGTGCGGCGCCCTGCGGCTGAGGGACGACGGCCTGGTGGAC

GGGTTCGCCCTGCCGCCCGCGTCCCCGCGGACCCGGCCCTCCCCCTCGGA

CCTCCTCGAGGGCGCCTACGCGGTGCGGCGCGAACTGCTGGACGCGGACG

GCGGTACGGCGCCCTGGGTCGCCCTGCCCATGCCGCTGGTCCGCCGCCGG

TCCGGCGGCGCCGGGGACCCGGCCGCGGTCCTGGCCCCCGGGACGCGCGT

CGCGCGACGCACCCGCCTGGTCCGGCACGGGTACCGGCCGCCCGCCGCGA

GGCCGCGGAACGGGAGCACTCCCCGGCTGGTGTCGGTGGTCGTCCCGGTG

CGCAACGGCGCCCGCACGCTCGCCGCCCAGCTGACCGCCCTGGCCCGGCA

GACCGGAGCCGTCGCCTACGAGGTGCTGGTCGTCGACAACGGCTCGACGG

ACACCACCCGCGAGGTCGCCGAACGGGCCCGCGCCGAGCTGCCGGACCTG

CGGATCGTGGACGCGTCCGACCGTGCCGGTGAGAGCTGTGCCCGCAACCG

GGGAATCGCCGCGGCGCGCGGCGACTTCGTCGCGTTCTGCGACGCGGACG

ACGTCGCCGACACCGGCTGGCTGGCCGCGATGGCCCAGGCGGCCAAGGAG

GCCGATCTGGTGGGAGGCGGACTGGAGACCTCCGTGCTCAGTCCCGGCCG

CGTCGACGAGCAGCCCCTGCCGATGGACGCCCAGACCGATTTCCTGCCGT

TCGCCCGGGGGGCGAACTGCGGTGCCTGGAAGGACGTCCTGACCGCGCTG

GGCGGCTGGGACGAGCGCTACCGGGGCGGCGGGGAGGACATGGACCTCTC

TABLE 28-continued

DNA Sequence of moeGT3

CTGGCGCGCCCAGCTCTGCGGTTACCTCGTCCGCTACGCGGACGACGCCC

GGATGCACTACCGGTTGCGGGACGGACTGCCGGCGCTGGCACGGCAGAAG

TGGAACTACGGCCGTTCCGGGGCCCAGTTGTACGCCGCGTACCGGCGCGC

CGGGTTCGAACGGCGCGACGGCCGGGTGGTCGTCAGGAACTGGTGCTGGC

TGCTGCTGCACGTTCCGAACCTGGTCCGGTCCACCGGACCCTGCGGCCAC

GCTGAGTCCGCTACGCGCCCGGCTGGCCGGTTTCCTGGTTTGTGA (SEQ
ID NO: 10)

TABLE 29

Amino Acid Sequence of moeGT3

VAVLRGDDEALPHWLWHLARAVWYGGGDGTGPVGLVQCGALRLRDDGLVD

GFALPPASPRTRPSPSDLLEGAYAVRRELLDADGGTAPWVALPMPLVRRR

SGGAGDPAAVLAPGTRVARRTRLVRHGYRPPAARPRNGSTPRLVSVVVPV

RNGARTLAAQLTALARQTGAVAYEVLVVDNGSTDTTREVAERARAELPDL

RIVDASDRAGESCARNRGIAAARGDFVAFCDADDVADTGWLAAMAQAAKE

ADLVGGGLETSVLSPGRVDEQPLPMDAQTDFLPFARGANCGAWKDVLTAL

GGWDERYRGGGEDMDLSWRAQLCGYLVRYADDARMHYRLRDGLPALARQK

WNYGRSGAQLYAAYRRAGFERRDGRVVVRNWCWLLLHVPNLVRSTGPCGH

AESATRPAGRFPGL (SEQ ID NO: 33)

TABLE 30

Sequence Homology of moeGT3 ref|ZP_00616987.1| Glycosyl transferase, family 2 [*Kineococcus
radiotolerans* SRS30216]
Length = 289
Score = 197 bits (500), Expect = 1e-48
Identities = 122/277 (44%), Positives = 156/277 (56%), Gaps = 8/277 (2%)

```
            SEQ ID NO: 138
Query  144  VSVVVPVRNGARTLAAQLTALARQTGAVAYEVLVVDNGSTDTTREVAERARAELPD-LRI  202
            ||||+|    |    |||  ||| |+    +||+| ||||||      |      +|  ||
Sbjct    5  VSVVIPCFNATRDLPAQLEALAGQSTVCTFEVVVSDNGSTDGLAEFVEEWSRRVPFMLRR   64
            SEQ ID NO: 139

SEQ ID NO: 243
Query  203  VDASDRAGESCARNRGIAAARGDFVAFCDADDVADTGWLAAMAQAAKEADLVGGGL----  258
            ||||   |  +  |||   ||     |+  ||||||    ||+  ||+  ++|||||   |
Sbjct   65  VDASARRGVAHARNAGCRAALADVILVCDADDVVGVGWVDAMARALEQADLVGGTLVHGH  124

SEQ ID NO: 140
Query  259  -ETSVLSPGRVDEQPLPMDAQTDFLPFARGANCGAWKDVLTALGGWDERYRGGGEDMDLS  317
             |+++     |     |  +   +|+| |||   ++| ||||||| +    ||+|++  |
Sbjct  125  LNTALVQQWRPTSPPGVLPTKLSHLPYAVGANVGLRREVFDALGGWDEGFVAGGDDVEFS  184

Query  318  WRAQLCGYLVRYADDARMHYRLRDGLPALARQKWNYGRSGAQLYAAYRRAGFERRDGRVV  377
            ||||   |+ +|   |  | + |   +| + |||    +| + |||      +| || ||    |+
Sbjct  185  WRAQHAGFCLRSAPDAVIAYRMRTTLSANVKQSYFYARSDALLMRTFRSAGVPRRGLRPL  244

SEQ ID NO: 141
Query  378  VRNWCWLLLHVPNLVRSTGPCGH-AESATRPAGRFPG  413
            +    ||+ +||    |   |    |     ||||||
Sbjct  245  ITESKWLVRNVPR-TREPGFRGQWLRRAAMLAGRFVG  280
            SEQ ID NO: 142
```

Based on the studies of the present invention, it is propose that the polypeptide encoded by the moeGT3 gene attaches is a glycosyltransferase that attaches a sugar moiety (e.g., glucose (Glc)) to the Moe intermediate compound 4, 12 or 13 in the course of moenomycin biosynthesis to yield a Moe intermediate compound 5, 14 or 15, respectively, as shown in FIG. 4.

Gene moeGT4 encodes putative 427 amino acid protein which N-terminal portion shows moderate homology (27% identity and 38% similarity) to putative family 2 GT from *Mycobacterium vahbaalenii* PYR-1. The nucleotide and polypeptide sequences are shown in Tables 31 and 32, respectively. A sequence alignment between moeGT4 and the closest homolog identified in the BLAST search is shown in Table 33. CDD search failed to locate conserved domain(s) within moeGT4. However, more careful inspection of moeGT4 sequence using the HHpred program (at ExPaSy proteomics server) showed that the C-terminus of moeGT4 exhibits a low degree of homology to chitin synthase and GT 2 conserved domains (accession numbers pfam03142 and COG1216, respectively).

TABLE 31

DNA Sequence of moeGT4.

GTGACTTCTGAGCCCGCCGCCCCGGCCGTCCCGCACCCGCCGGTGCGTCC

GGGGCCGCCGGTCCGTCTCAACCGGCCGCTGGCGCGGCGCAGGCGGCGGC

CGGCCGGGGAGGGGTTCGTGACGCACCACCTGCGGAGCACCATGGCCCGC

GGGTTCCGCCCCCCGGAGTCCTGGGAGGTCCCCGTCCGGCACGTCCTGCC

CGGTCTGCCGGCCGACGGGACTCCGCGCGCCGAGGAGGCCGCTCAGGCGC

TGCGCACGCCCGCCGGGCGGCCGGGCATCGCCCTCGTCGTGCCGACCTAC

GTCTCCCGGGTGAGCCTGGCGCGGCAGCGGGAGTGGTTCGACGCGCTGCT

GGACCAGGCGGCCGCGGTGACGCGGGACCACCCCCTGGTGCCCCTGGTGC

TGTTCGTCGGCATGCAGTGGTCGTCGGCCGAGGAGGAGCGGGAGGCGCTG

CGGCGCCTGCGTGTGCTGCTGGACGACGCCCGCACCCGGCTGCCCGGACT

GCGGATCTGCGGTCTCGCGCTGCCCGGGCCGGGCAAACCCCGCACCCTCA

ACGGGGCGATCGCCGTCGCCGAGCTCCTCGGCTGTGCGGGCGTCGGGTGG

ACCGACGACGACGTGACCCTGGAGGAGGACTGCCTGTCCCGGCTGGTGCG

TABLE 31-continued

DNA Sequence of moeGT4.

GGACTTCCTGGCGGCGGGCTGCCGCGGGGCGGTGGGCGCGACCAAGGTTG

CGCACACCCATGAGTACGCCACCTCCCGGCTGCTGTCCCGGGCCAAGGCG

ATCGCCGCCCCGGCCACGAACTACCCGCACGGCTGCTGCATCCTGGTGGC

CACCGACGTGGTGGCCGGTGGTCTGCCGGGACGCTACGTATCCGACGACG

GCTACGTGTGCTTCCGCCTCCTCGACCCCGCGCTGCCCGACCCGCTGGCC

CGGCTGCGGCTGGTTCCGGACGCCCGGTGCCACTACTACGTGGCGGGGCC

GGCCGGCGAGACCCGCCGCAGGATCCGCAGGCTGCTGCTCAACCACCTCG

TCGACCTCGCCGACTGGCCCCTGCCGGTGGTCCGTCACTACTTCCGCCAC

GTCCTGTTCGGCGGCATGTGGCCGCTGACCGGCTTCGACTCCTCCCGCGG

TGCCCGCCGCGGTGTGCAGAAGGCGCTCATCAAGTGGCTCTACTTCGCCT

GGTTCGCGGGCATCGGGGGCGAACTCTACGTGCGCGGGCTGTCCGGCAGG

CCACTGCGCCGCATCGAGTGGGCTCCCTACTCGGACATCCGCAGGCTCAC

TCCGTCGTCCTCACCCACGCGTCAGGAGAGCTGA (SEQ ID NO: 11)

TABLE 32

Amino Acid Sequence of moeGT4

VTSEPAAPAVPHPPVRPGPPVRLNRPLARRRRRPAGEGFVTHHLRSTMAR

GFRPPESWEVPVRHVLPGLPADGTPRAEEAAQALRTPAGRPGIALVVPTY

VSRVSLARQREWFDALLDQAAAVTRDHPLVPLVLFVGMQWSSAEEEREAL

RRLRVLLDDARTRLPGLRICGLALPGPGKPRTLNGAIAVAELLGCAGVGW

TDDDVTLEEDCLSRLVRDFLAAGCRGAVGATKVAHTHEYATSRLLSRAKA

IAAPATNYPHGCCILVATDVVAGGLPGRYVSDDGYVCFRLLDPALPDPLA

RLRLVPDARCHYYVAGPAGETRRRIRRLLLNHLVDLADWPLPVVRHYFRH

VLFGGMWPLTGFDSSRGARRGVQKALIKWLYFAWFAGIGGELYVRGLSGR

PLRRIEWAPYSDIRRLTPSSSPTRQES (SEQ ID NO: 34

TABLE 33

Sequence Homology of moeGT4 gb|EAS23724.1| Glycosyl transferase, family 2 [*Mycobacterium vanbaalenii* PYR-1]
Length = 426
Score = 35.8 bits (81), Expect = 3.9
Identities = 49/181 (27%), Positives = 69/181 (38%), Gaps = 29/181 (16%)

```
              SEQ ID NO: 143
Query   42  HHLRSTMARGFRPPESWEVPVRHVLPGLPADGTPRAEEAAQALRTPAGRPGIALVVPTYV  101
            || | +   +|    |||||  |  |||    |  +| |   |           ++|   |
Sbjct   52  HHARVLVRHQGQPVAFVEVPVRDALIRLPACPLPEDLDAGQPAR---------LMPISV  101
              SEQ ID NO: 244                                           SEQ ID NO: 144

Query  102  SRVSLARQREWFDALLDQAAAVTRDHPLVPLVLFVGMQWSSAEEEREALRRLRVLLDDAR  161
               + | +   |||   +  ++ |+|   +|+              +|   +    | |||
Sbjct  102  VLCTRDRPDQLADAL---KSILSLDYPEFEVVVV-----DNAARTDATAGVVAQLGDAR  152
              SEQ ID NO: 145            SEQ ID NO: 146
```

TABLE 33-continued

Sequence Homology of moeGT4

```
Query  162  TRLPGLRICGLALPGPGKPRTLNGAIAVAELLGCAGVGWTDDDVTLEEDCLSRLVRDFLA  221
                +|  | || |        | + |         | +||||  ++    |  | |  |
Sbjct  153  VR------RVAEPIPGLSTARNTGLRHA---AHPVVAFTDDDVVVDRQWLRGLARGFAR  202
              SEQ ID NO: 147            SEQ ID NO: 148

Query  222  A  222
            |
Sbjct  203  A  203
```

Based on the studies of the present invention, it is propose that the polypeptide encoded by the moeGT4 gene is a glycosyltransferase that attaches sugar moiety (e.g., N-acetylglucosamine (GlcNac)) to the Moe intermediate compound 2 or 3 in the course of moenomycin biosynthesis to yield a Moe intermediate compound 4 as shown in FIG. 4.

The 312 amino acid protein encoded by the moeGT5 gene is homologous to the central part of moeGT4 (45% identity and 59.1% similarity). HHpred results suggested that an incomplete COG1216 domain is also present in moeGT5. The nucleotide and polypeptide sequences of moeGT5 are shown in Tables 34 and 35, respectively.

TABLE 34

DNA Sequence of moeGT5

GTGCTGCGCCGTCTGGCCGAGGTGCGGGAAGCGCACCCGTCCCTGCCGCT

GACCGTCTGGGTGGGCATGCAGTACGGCCCCGGGGAGGACGAGGAGGCGC

TGCGCAGGCTGCGCCGGCTGTGCGCCCCGGTGCCCGGGGGCCCGGCCCTC

ACCGTGGTCGGCCTGGCCCTGCCCGGGCCGGGCAAGCTCCGCACGGTGAG

CACGGTCCTGCGGCTCTCCGAGGACCTCGGCTACGCCGGCTGGCTCTGGA

CGGACGACGACATCGAGATCGCCCCCCACTGCCTCGCCCTGCTGGTCTCC

CGTTTCCGGGAGCGGGGGGAGCGGGGCGCGGTCGGGGCGCATTCGGTCGC

GCTGGCCAGGGAGACGGTCACCTCACAGGCCATGGACCGGGTCTCCGGGG

TCACCGCCCCGCCGAAGGCCTGCCCGGCGGCGGCCTGCCTGGTCGTCGCG

ACGGACGTGCTGGGCACCGGCATTCCGGTCAGGCGCCTGACCGACGACGG

GTACGTGGTGTTCGAACTGCTCGACGCCGGGGCGCCCGATCCGCTGCACG

ACCTGGAGGTGCTGCCCGAGGCCCGGATCAGCTTCTACCGCGTCAGCCGC

ACCCACGACACGTTCCAGCGCCTGCGCCGCTCCCTCTACAGCCATGTGAC

CTGCGTCGCCGACTATCCCTGGCCCACCGCGCGGGTCTACCTCACCCGGG

TCCTCTTCCACGGTCTGTGGCCGCTCGCGGCGTGGGACGGCAGCCGGGGG

CCGGTGCACGGGCTGCAGCGCTGGCTGGTCAAGGGCCTGCACTTCACCTG

GTTCTGCGGGGTGGCCGGCTCGCTGGCGGTCCGGGGCGCGGTGGGACGGC

CCCTTCGCCGGGTGGCGTGGGGCGACGAGGGGGACTTCCGCAGCCCCACC

GTCGAGGAGCCCGCCGCGGGAGCGGCCGCCGGGCGCTGA (SEQ ID NO: 12)

TABLE 35

Amino Acid Sequence of moeGT5

VLRRLAEVREAHPSLPLTVWVGMQYGPGEDEEALRRLRRLCAPVPGGPAL

TVVGLALPGPGKLRTVSTVLRLSEDLGYAGWLWTDDDIEIAPHCLALLVS

RFRERGERGAVGAHSVALARETVTSQAMDRVSGVTAPPKACPAAACLVVA

TDVLGTGIPVRRLTDDGYVVFELLDAGAPDPLHDLEVLPEARISFYRVSR

THDTFQRLRRSLYSHVTCVADYPWPTARVYLTRVLFHGLWPLAAWDGSRG

PVHGLQRWLVKGLHFTWFCGVAGSLAVRGAVGRPLRRVAWGDEGDFRSPT

VEEPAAGAAAGR (SEQ ID NO: 35)

Based on the studies of the present invention, it is propose that the polypeptide encoded by the moeGT5 gene is a glycosyltransferase that attaches a sugar moiety (e.g., N-acetylglucosamine) (GlcNac)) or chinovosamine (Ch) moiety to the Moe intermediate compound 4 in the course of moenomycin biosynthesis to yield a Moe intermediate compound 6 or 7, respectively, as shown in FIG. 4. Further, based on the studies of the present invention, it is propose that the polypeptide encoded by the moeGT5 gene is a glycosyltransferase that attaches a sugar moiety (e.g., N-acetylglucosamine) (GlcNac)) or chinovosamine (Ch) moiety to the Moe intermediate compound 11 in the course of moenomycin biosynthesis to yield a Moe intermediate compound 14 or 15, respectively, as shown in FIG. 4.

C. Sugar Tailoring Genes

Seven genes were identified in cluster 1 that fit this activity profile: moeF5, moeH5, moeK5, moeM5, moeS5, moeR5 and moeE5.

The moeF5 and moeH5 genes share significant homology at the nucleotide sequence level, suggesting that the pair arose via a gene duplication event. The proteins encoded by these genes resemble a large family of ATP-dependent amidotransferases that form amides from carboxylic acids, but neither protein appeared fully functional based on sequence analysis. Therefore, we previously speculated that carboxamidation of unit F resulted from the activity of a MoeF5MoeH5 heterodimer, with MoeF5 generating ammonia from glutamine in an ATP-dependent manner and MoeH5 acting as an amidotransferase (Ostash 2007).

1. MoeF5

The product of moeF5 gene resembles putative and known asparagine synthase B related enzymes from various bacteria (36% identity and 46% similarity). The nucleotide and polypeptide sequences are shown in Tables 36 and 37, respectively. A sequence alignment between moeF5 and its closest homolog is shown in Table 38.

TABLE 36

DNA Sequence of moeF5.

ATGTGCGGCTTCGTCGGATTCAGTGACGCCGGCGCCGGGCAGGAGGACGC
CCGTGTCACGGCCGAGCGCATGCTCGCCGCCGTGGCGCACCGCGGCCCCG
ACGGCTCGGACTGGTGCCACCACCGGGGCGTCACCCTCGCGCACTGCGCC
CTGACCTTCACCGATCCGGACCACGGCGCGCAGCCGTTCGTCTCCGCGTC
GGGAGCCACCGCCGTGGTGTTCAACGGCGAGCTCTACAACCACGCCGTGC
TGGGCGACGGGCGTTGCCCTGCGCACCCGGAGGCGACACAGAAGTTCCT
GGTGGAACTCTACGAGTTGCTGGGCATGCGGATGCTCGACCGGCTGCGGG
GCATGTTCGCCTTCGCGCTGCAGGACGCCCGCACCGGCACCACGGTGCTG
GCCGCGACCGATGGGGAAGAGCCCCTCTACTAACACCCGCGTGCGAGACG
GACATCGCTTTCGCGTCGGAACTCACGTCTCTGCTGCGGCACCCCGCCGC
GCCGCGCACACCGGAGGTGCGGGCGCTCGCCGACTACCTGGTGCTCCAGG
CGTTCTGCGCCCCCGCCTCGGCCGTGTCGGGGGTGTGCAAGGTGCGCCCC
GGCAGCTACGTGACCCACCGGCACGGCGCGTTGGACGAGACCGAGTTCTG
GCGGCCCCGCCTGACCCCCGACCGGGGGGCGGGCCGCGGCCCCGGACGGC
GGGAGGCCGCGCGGCGGTTCGAGGAGCTCTTCCGCGCCGCGGTCGCCCGC
CGGATGACCAGCACCGACCGCCGCCTCGGCGTACTGCTCAGCGGCGGCCT
GGACTCCAGCGCGGTCGCCGCGGTGGCCCAGCAGCTCCTGCCGGGACGGC
CGGTGCCCACCTTCAGCGCGGGGTTCGCGGACCCGGACTTCGACGAGAGC
GACCACGCACGGGCGGTGGCGCGCCACCTCGGCACCGAGCACCATGTGGT
GCGGATCGGCGGGGCCGACCTCGCCGGTGTGGTGGAGTCCGAACTCGCCG
TGGCCGACGAGCCGTTGGCCGATCCCTCCCTGCTGCCCACACGTCTGGTC
TGCCGGGCGGCGCGAGCACGTCCGCGGCGTGCTCACCGGTGACGGCGC
GGACGAACTGCTCCTGGGCTACCGCTACTTCCAGGCCGAGCGGGCGATCG
AGCTGCTGCTGCGCGTGCTGCCGGCCCCCGGCTGGAGGCCCTCGTCCGG
CTGCTGGTGCGCCGGCTGCCGGCCCGTTCCGGCAACCTCCCCGTGACCCA
CGCCCTCGGTCTGCTGGCCAAGGGCCTGCGCGCGGCACCGGAGCACCGGT
TCTACCTCTCGACGGCGCCCTTCGGCCCGGGCGAGCTGCCACGGCTGCTC
ACCCCCGAGGCCGGGGCCGAACTGACCGGGCACGACCCGTTCACCGAGGT
GTCGCGCCTCCTGCGGGACAGCCGGGCCTGACCGGTGTCCAGCGCAGCC

TABLE 36-continued

DNA Sequence of moeF5.

AGCTCGCCGTGGTGACCCACTTCCTGCGGGACGTGATCCTCACCAAGACG
GACCGGGGCGGCATGCGCAGCTCCCTCGAGCTGCGTTCCCCCTTTCTCGA
CCTGGACCTGGTCGAGTACGGCAACTCCCTGCCCACCGGCCTGAAGCTGC
ACCGGTTCACCGGCAAGTACCTGCTGCGGCAGGTCGCCGCCGGCTGGCTG
CCCCCTTCCGTCGTCCAGCGGACGAAGCTGGGTTTCCGCGCGCCGGTGGC
GGCCCTGCTCCGCGGCGAGCTGCGGCCCCTGCTCCTGGACACCCTCTCCC
CGTCGTCCCTGCGCCGCGGCGGCCTGTTCGACACCGGGGCGGTGCGCCTG
CTGATCGACGACCACCTCGGCGGCCGGCGCGACACCTCCCGCAAGCTGTG
GGCGCTGCTGGTCTACCAGCTCTGGTTCGAGAGCCTGACGGCCGGACCCC
GCGCCCTCGAGTCCCCCGCGTACCCGGCCCTCTCCTAG (SEQ ID NO:
13)

TABLE 37

Amino Acid Sequence of moeF5

MCGFVGFSDAGAGQEDARVTAERMLAAVAHRGPDGSDWCHHRGVTLAHCA
LTFTDPDHGAQPFVSASGATAVVFNGELYNHAVLGDGALPCAPGGDTEVP
GGTLRVAGHADARPAAGHVRLRAAGRPHRHHGAGRDRWGRAPLLTPACET
DIAFASELTSLLRHPAAPRTPEVRALADYLVLQAFCAPASAVSGVCKVRP
GSYVTHRHGALDETEFWRPRLTPDRGAGRGPGRREAARRFEELFRAAVAR
RMTSTDRRLGVLLSGGLDSSAVAAVAQQLLPGRPVPTFSAGFADPDFDES
DHARAVARHLGTEHHVVRIGGADLAGVVESELAVADEPLADPSLLPTRLV
CRAAREHVRGVLTGDGADELLLGYRYFQAERAIELLLRVLPAPRLEALVR
LLVRRLPARSGNLPVTHALGLLAKGLRAAPEHRFYLSTAPFGPGELPRLL
TPEAGAELTGHDPFTEVSRLLRGQPGLTGVQRSQLAVVTHFLRDVILTKT
DRGGMRSSLELRSPFLDLDLVEYGNSLPTGLKLHRFTGKYLLRQVAAGWL
PPSVVQRTKLGFRAPVAALLRGELRPLLLDTLSPSSLRRGGLFDTGAVRL
LIDDHLGGRRDTSRKLWALLVYQLWFESLTAGPRALESPAYPALS (SEQ
ID NO: 36)

TABLE 38

Sequence Homology of moeF5 gi|20560076|gb|AAM27821.1|  ORF_10; similar to Asparagine synthase [*Pseudomonas aeruginosa*]
gi|6690135|gb|AAF24002.1|  WbpS [*Pseudomonas aeruginosa*]
Length = 627
Score = 198 bits (503), Expect = 1e-48
Identities = 193/645 (29%), Positives = 279/645 (43%), Gaps = 35/645 (5%)
Frame = +1

```
        SEQ ID NO: 149  SEQ ID NO: 150          SEQ ID NO: 151
Query 286 MCGFVGFSD-AGAGQEDARVTAERMLAAVAHRGPDGSDWCHH--RGVTLAHCALTFTD-P  453
          |||  || +   |     |     |+| ||+ |||||  +  |   ||  |    +
Sbjct   1 MCGIAGFWNITGTLLGDNARVARQMAAAIHHRGPDESGIWYEAPRAPILVHARLAVLELS   60
          SEQ ID NO: 152
```

TABLE 38-continued

Sequence Homology of moeF5

```
              SEQ ID NO: 245              SEQ ID NO: 153  SEQ ID NO: 154
Query  454  DHGAQPFVSASGATAVVFNGELYNH----AVLGDGALPCA--PGGDTEVPGGTLRVAG-H  612
            |+||    |    |   +++|||+|||       ||  +    +     |||          |
Sbjct   61  PAGSQPMHSDCGRYVLIYNGEIYNHLALRARLSEAGVTHSWRGGSDTETLLACFAQWGVE  120

SEQ ID NO: 155
Query  613  ADARPAAGHVRLRAAGRPHRHHGAGRDRWGRAPLLTPACETDIAFASELTSLLRHPAAPR  792
             +  +    |    |       |  +       ||| |    ||      +  |||||  +|   ||
Sbjct  121  STLKLTVGMFALALWDRQEKTITLARDRMGEKPLYWGWQNGVLFFASELKALKEHPLFRG  180

SEQ ID NO: 156
Query  793  TPEVRALADYLVLQAFCAPASAVSGVCKVRPGSYVTHRHGALDET----EFWRPRLTPDr  960
             +   |||  +|       ||   |   |+  |+|  |||+      +|+||      +|           +
Sbjct  181  DIDRDALALFLRYGYVPAPYSIYKGIGKLRAGSYLVLSERSLNETCEPAAYWSANAAIEE  240

Query  961  gagrgpgrreaarrfeelfraavarrMTSTDRRlgvllsggldssavaavaQQLLPGRPV  1140
                                +|          +       +                      |    |+          |        ||+
Sbjct  241  ALSNPFQGTDAEAVDLLESQLRTSISDQMVSDVPLGAFLSGGVDSSTVVALMQQQSSRPI  300

Query 1141  PTFSAGFADPDFDESDHARAVARHLGTEHHVVRIGGADLAGVVESELAVADEPLADPSLL  1320
            |||  || +|  +|| +  +|+||  |+||+|   +  +              |  +      +    ||    |  +
Sbjct  301  RTFSIGFDEPGYDEAVYAKAVAEHIGTDHTELYVNSKDALDVIPSLPKIYCEPFGDSSQI  360

SEQ ID NO: 157
Query 1321  PTRLVCRAAREHVRGVLTGDGADELLLGYRYFQ-AERAIELLLRVlpaprlealvrllvr  1497
            ||   +|      ||+   |     |+|||   |||    ||   +|          |     +|     +   |
Sbjct  361  PTLIVSGLARQQVTVALSGDGGDELFGGYNPYQFTPRVWRMLERFPHSMRRFASAFAQDL  420

Query 1498  rlparSGNLPVTHalgllakglraaPEHRFYLSTAPFGPGELPRLLTPEAGAELTGHDPF  1677
            ||| +  | |                                      |  ||     +  +                   ||+         | |
Sbjct  421  PLPEKLGKL--------RDVFASRTAEELFYRLNSHWRNHEYPVI-----GAQ--GHTAL  465
                             SEQ ID NOS: 158                              159

SEQ ID NO: 254
Query 1678  TEVSRLLRGQPGLTGVQRSQLAV-VTHFLRDVILTKTDRGGMRSSLELRSPFLDLDLVEY  1854
              +                 |  +     |      +|  +       ++   ||   |  ||      |+|||      |  +    +   |
Sbjct  466  LDTPERW---PRVDSFQHWMMAMDVQGYMPDDILVKVDRAAMANSLETRVPLIDHRVFEL  522
                             SEQ ID NO: 160

Query 1855  GNSLPTGLKLHRFTGKYLLRQVAAGWLPPSVVQRTKLGFRAPVAAllrgelrplllldtls  2034
              +|    +|+        ||+|||+|          +         +++|    |||         ||+      |||       |+                  |
Sbjct  523  AWRMPLHMKIRNGKGKWLLREVLYRHVSRELIERPKKGFSVPVSDWLRGPLKEWAESLLD  582

Query 2035  psslrrGGLFDTGAVRLLIDDHLGGRRDTSRKLWALLVYQLWFES  2169
              |++   |      |+    +|   + +|||  ||||    ||+||++|++|   |   ||
Sbjct  583  ERRLQQEGYLDSRLIRRIWNDHLAGRRDHSRRLWSVLMFQAWLES  627
```

These synthases belong to the huge glutamine amidotransferase family whose members catalyze ATP-dependent amide nitrogen transfer from glutamine to acceptor substrates in different biosynthetic pathways (Zalkin 1998). Particularly, moeF5 appears similar to the WbpS proteins from *Pseudomonas aeruginosa* O4 and *Shigella dysenteriae* type 7 which are encoded by genes grouped in clusters for the biosynthesis of O antigens (29% identity and 43% similarity) (Feng 2004, Belanger 1999). The WbpS proteins appear to be responsible for carboxyl-amidation of deoxysugar moieties (Knirel 1988) during antigen biosynthesis in the aforementioned strains. A moeF5 CDD search revealed the presence of a glutaminase domain (AsnB; cd00712) and an interrupted asparagine synthase domain (Asn synthase BC; cd01991) in the N- and C-termini, respectively.

Strain ΔmoeF5 accumulated compound 1 (Table 21), which has a mass 1 Da higher than that of the monosaccharide moe A precursor 2 accumulated by the ΔmoeGT4 strain, consistent with the presence of a carboxyl moiety in unit F of 1 instead of the carboxamide group in 2/3 (FIG. 4). Our data agree with the prediction that the moeF5 gene is involved in F ring carboxamidation. We could not detect the formation of methylated monosaccharide precursors or of any larger moe A intermediates, implying that the absence of the carboxamide moiety abolishes unit F methylation and subsequent glycosylations. Therefore, MoeF5-catalyzed carboxamidation occurs prior to, and is required for, other modifications of 1 (FIG. 4). That is, based on the studies of the present invention, it is propose that the polypeptide encoded by the moeF5 gene is a Unit F amidotransferase which participates in the conversion of Moe intermediate compound 1 in the course of moenomycin biosynthesis to yield a Moe intermediate compound 2 or 3, respectively, as shown in FIG. 4.

2. moeH5

The moeF5 translation product also displays local homology (27.1% identity and 34% similarity) to moeH5, another AsnB-like protein. The nucleotide and polypeptide sequences are shown in Tables 39 and 40, respectively. A sequence alignment between moeH5 and the closest homolog identified in the BLAST search is shown in Table 41. MoeH5 shows 32% identity, and 48% similarity to a putative amidotransferase of *Azoarcus* sp. EbN1. MoeH5 also possesses a truncated asparaginase domain and an entire amidotransferase domain.

TABLE 39

DNA Sequence of moeH5.

ATGACGGTCCGCCGCCCGGCCGCGTCCGCCCCCCGCGTCCTCCTGACCGC
GGGCCCCGACGGGGTGCGCGTGGAGGGCGACGGGGAGGCGCGCCTCGGGC
ACCCCCTCACCGGTGACCACCTGGACCCGGGCCCGCCGGCCGAAGGCGTC
TTCGCCGGGTGGAGGTGGGACGGCGAGCGCCTGGTGGCCCGCAACGACCG
CTACGGCGTCTGCCCCCTCTTCTACCGGGCCGGCGGCGGCTCACTCGCGC
TCTCCCCCGACCCGCTCGCCCTGCTGCCGGAGGACGGGCCCGTCGAGCTG
GACCACGACGCGCTCGCCGTCTTCCTGCGCGACGGGGTTCTTCCTCGCCGA
GGACACGGCCTTCGCACAGGTCCGCGCACTGCCCCCGGCGGCCACGCTCA
CCTGGGACACCGGCGGGCTGCGGCTGCGGTCCGACGGGCCGCCGCGCCCC
GGGGCCGCCGCGATGACCGAGGCGCAGGCGGTCGACGGCTTCGTCGACCT
GTTCCGCGCCTCGGTGGCCCGCCGGCTGCCCGGCGAACCGTACGACCTGC
CGCTCAGCGGCGGCCGGGACTCGCGGCACATCCTGCTCGAGCTGTGCCGC
CGCGGCGCACCGCCGCGGCGGTGCGTCAGCGGCGCCAAGTTCCCTCCCGA
CCCGGGGGCCGACGCGCGCGTGGCGGCCGCCCTGGCGGGCCGGCTCGGTC
TGCCGCACACGGTGGTGCCGCGCCCCCGTTCGCAGTTCCGCGCGGAGCTC
GCCGCCCTGCCGGCCCAGGGCATGACCACCCTGGACGGCGCGTGGACCCA
GCCGGTCCTGGCCCACCTGCGCCGCCACAGCCGCATCTCGTACGACGGTC
TCGGCGGCGGGGAGCTCGTCCAGAACCCGAGCGTGGAGTTCATCCGGGCC
AACCCCTACGACCCCGCGGACCTGCCCGGCCTGGCGGACCGGTTGCTGGC
CGCGAGCCGGACCGGCCCCACGTGGAGCACCTGCTGAGCCCCCGGACGA
ACGCCCTGTGGAGCAGGCAGGCGGCGGCGGCGCCTCGTCACCGAGCTG
GCCCGGCACGCCGACAGCGCCAGCCCGCTCAGTTCCTTCTTCTTCTGGAA
CCGGACCCGGCGCTCCATCTCCGCGGCTCCGTTCGCCCTGGGGGACGGAC
GGGTCCTGACGCACACCCCCTACCTCGACCACGCCCTCTTCGACCACCTC

TABLE 39-continued

DNA Sequence of moeH5.

GCCTCGGTGCCGCACCGCTTCCTGGTCGACGGGACGTTCCACGACCGGGC
GCTGCACCGGGCCTTCCCCGAGCACGCGGACCTGGGGTTCGCCTCGTCGG
TGCCCCAGCGGCACGGACCCGTGCTGGTCGCGCACCGACTGGCGTACCTG
CTCCGGTTCCTCGCCCACGCGACGGTCGTGGAACCGGGCTGGTGGCGCGG
CCCCGACCGCTTCCTGCAACGGCTGCTGGCCGCCGGCCGGGGCCCGGGG
CCCCGCAGCGCGTCAGCAGGCTGCAGCCCCTGGCGCTCTACCTGCTGCAG
TTGGAGGACCTCGCCGTCCGAAGGGCCCGCCGCCGGCCGTAG (SEQ ID NO: 14)

TABLE 40

Amino Acid Sequence of moeH5

MTVRRPAASAPRVLLTAGPDGVRVEGDGEARLGHPLTGDHLDPGPPAEGV
FAGWRWDGERLVARNDRYGVCPLFYRAGGGSLALSPDPLALLPEDGPVEL
DHDALAVFLRTGFFLAEDTAFAQVRALPPAATLTWDTGGLRLRSDGPPRP
GAAAMTEAQAVDGFVDLFRASVARRLPGEPYDLPLSGGRDSRHILLELCR
RGAPPRRCVSGAKFPPDPGADARVAAALAGRLGLPHTVVPRPRSQFRAEL
AALPAQGMTTLDGAWTQPVLAHLRRHSRISYDGLGGGELVQNPSVEFIRA
NPYDPADLPGLADRLLAASRTGPHVEHLLSPRTNALWSRQAARRRLVTEL
ARHADSASPLSSFFFWNRTRRSISAAPFALGDGRVLTHTPYLDHALFDHL
ASVPHRFLVDGTFHDRALHRAFPEHADLGFASSVPQRHGPVLVAHRLAYL
LRFLAHATVVEPGWWRGPDRFLQRLLAAGRGPGAPQRVSRLQPLALYLLQ
LEDLAVRRARRRP (SEQ ID NO: 37)

TABLE 41

Sequence Homology of moeH5 ref|YP_159440.1| amidotransferase, similar to asparagine synthase
(glutamine-hydrolyzing)
[*Azoarcus* sp. EbN1]
Length = 642
Score = 70.1 bits (170), Expect = 2e-10
Identities = 54/165 (32%), Positives = 80/165 (48%), Gaps = 5/165 (3%)

```
                SEQ ID NO: 161    SEQ ID NO: 162                    SEQ ID NO: 163
Query    48  EGVFAGWRWDG--ERLVARNDRYGVCPLFYRAGGGSLALSPDPLALLPEDGPV-ELDHDA  104
             +|+|        ||  +||+    |   |||+      || + +  |||    |||||
Sbjct   121  DGMFNPALWDARRKLLIGRDPLGVKPLYVHRSASMLAFATEAKALLELPGVTRELDHDV  180
                SEQ ID NO: 164

SEQ ID NO: 165
Query   105  LAVFLRTGFFLAEDTAFAQVRALPPAATLTWDTGGLR-LRSDGPPRPGAAAMTEAQAVDG  163
             +|  +|  |+   |    +   +| ||||  |+ +|    |     |   +|||+ +
Sbjct   181  VADYLHLGYVAAPHSMFRDIRKLPPATLLSVENGEVRQWRYWRLPSSVARYVTEAEWIGR  240

SEQ ID NO: 165
Query   164  FVDLFRASVARRLPGE-PYDLPLSGGRDSRHILLELCRRGAPPRR  207
             |    +|  |++ +    ||||   ||    ++ + +   |  |
Sbjct   241  IRDGMERAVHRQMVSDVPIGAFLSGGVDSSAVAFMAKHSAHPIR  285
```

Gene moeH5 controls the carboxamidation of unit B (see compound 19), since strain ΔmoeH5 accumulated the moe A precursor 17 (Table 21, FIG. 4). Expression of moeR5 in the ΔmoeH5 strain leads to the accumulation of the previously described compound 16 (Zehl 2006), supporting the structure assignment for 17 (FIG. 4). Apparently, underexpression of moeH5 in producing strains leads to the accumulation of moenomycins having the acid form of unit B (compounds 16, 17, 22). Thus, despite having high sequence homology, moeF5 and moeH5 have been shown via gene disruption to play quite different roles in moe A biosynthesis, and they cannot substitute for one another functionally in cross-complementation experiments.

The results described above have showed that MoeH5 amidates the B ring carboxyl group, but they do not explain why this modification occurs. That is, based on the studies of the present invention, it is propose that the polypeptide encoded by the moeH5 gene is a Unit B amidotransferase which participates in the conversion of Moe intermediate compound 16 or 17 in the course of moenomycin biosynthesis to yield a Moe intermediate compound 18 or 19, respectively, as shown in FIG. 4. The moeH5-controlled reaction could either be either a branch of moe A metabolism or an essential biosynthetic step prior to "decoration" of the moe A precursor with the unit A chromophore moiety. Unit A biogenesis was proposed to proceed via a MoeB4-catalyzed reaction between an amino cyclopentadione moiety and compound 16/17 (Ostash 2007). However, the presence of a gene dedicated to the conversion of the acid moe A precursor 16/17 into the amide precursor 18/19 (FIG. 4) raised questions about the proposed scheme. We coexpressed the genes for unit A biosynthesis (pOOB64b) in the 38-1+ recombinant strain, which directs the production of 19, and in its ΔmoeH5 derivative, which produces 17. Expression of pOOB64b in ΔmoeH5 yielded no new products (Table 21), while the pOOB64b+38-1+ strain produced the known compound pholipomycin 21 (Table 21, FIG. 4), which contains the Unit A chromophore (Wetzel 2005). The inability of pOOB64b+ΔmoeH5 strain to produce pholipomycin 21 implies that either 17 is not a precursor to 21 or the moeH5 is essential for moe A chromophore attachment for other reasons. (Schuricht 2000, Petricek 2006, Ostash 2007). At the moment, we propose that carboxamide 19 serves as a necessary intermediate to moe A (FIG. 4).

3. moeK5

The putative protein encoded by moeK5 is homologous to radical SAM superfamily enzymes, particularly to a presumed methyltransferase from *Pyrococcus horikoshii* OT3 (34% identity and 52% similarity). The nucleotide and polypeptide sequences are shown in Tables 42 and 43, respectively. A sequence alignment between moeK5 and the closest homolog identified in the BLAST search is shown in Table 44. The MoeK5 putative translation product showed no apparent similarity to other known sugar C-methyltransferases, such as those exemplified by NovU and TylC3, which require keto group in a position adjacent to methylation site (Thuy 2005, Takahashi 2006). A CDD search revealed radical SAM vitamin B12 binding domain (cd02068) and radical SAM domain (pfam04055) in the N- and C-halves, respectively, of moeK5. Accordingly, moeK5 could function via a SAM radical mechanism, and may not require the transformation of a sugar into an anionic form before methylation.

TABLE 42

DNA Sequence of moeK5.

CTGGGTTACATCCACACCGCGCTCAAGTCGGCCGGGTTCCACCACGTCAT
CCAGGTCGACACCCCCGCCCTGGGCCTCGACAGCGAGGGGCTGCGCAAGC
TGCTCGCGGACTTCGAGCCGGACCTGGTCGGGGTGAGCACCACGACACCC
GGTCTGCCCGGCGCCATCGAGGCGTGCGAGGCGGCCAAGAGCACCGGGGC
GAAGGTGATCCTGGGCGGGCCGCACACGGAGGTGTACGCGCACGAGAACC
TGGTCCACGAGTCCATCGACTACGTGGGCGTCGGCGAAGGCGTCACGATC
ATGCCGGAACTGGCGGAGGCGATGGAGCGGGGCGAGGAGCCGGAGGGCAT
CCGCGGCCTGGTGACCCGCAAGCACGACGGCGGTGCCGCGCCGATGGTGA
ACCTGGAGGAGGTCGGCTGGCCCGAACGCGCCGGGCTCCCGATGGACCGC
TACTACTCGATCATGGCTCCGCGGCCGTTCGCGACGATGATCTCCAGCCG
CGGCTGCCCCTTCAAGTGCAGCTTCTGCTTCAAGCAGGCCGTGGACAAGA
AGTCCATGTACCGCAGTCCCGAGGACGTCGTCGGTGAGATGACGGAGCTC
AAGGAGCGGTGGGGGGTGAAGGAGATCATGTTCTACGACGACGTGTTCAC
CCTGCACCGCGGCCGGGTGCGGGAGATCTGCGGGCTCATCGGGGAGACCG
GCCTCAAGGTCCGCTGGGAGGCGCCCACCCGCGTCGACCTGGTGCCCGAG
CCGCTGCTGGAGGCGATGGCCGGGGCCGGGTGCGTGCGCCTGCGGTTCGG
CATCGAGCACGGTGACAGCGAGATCCTCGAGCGGATGCGCAAGGAGAGCG
ACATCCAGAAGATCGAGAAGGCCGTCACCTCCGCCCACGAGGCCGGGATC
AAGGGCTTCGGGTACTTCATCGTCGGCTGGCTCGGGGAGACCCGGGAGCA
GTTCCGCAGGACCGTCGACCTCGCCTGCCGCCTCCCGCTGGACTACGCCA
GCTTCTACACCGCGACGCCCTGCCGGGCACCCCCCTGCACACGGAGTCC
GTGGCCGCCGGCCAGATCCCGCCCGACTACTGGGACCGCTTTTCGTGCGG
GGCGAGTTCGACGCGCGGATCGGGTACCTGGTGCCGGACGCGCAGGAGCG
CGCCCAGTGGGCGTACCGCTCCTTCTTCATGCGCCGCTCCATGGTCAAGC
CGCTGCTGTCGCACATGGCGGTGA (SEQ ID NO: 15)

TABLE 43

Amino Acid Sequence of moeK5

LGYIHTALKSAGFHHVIQVDTPALGLDSEGLRKLLADFEPDLVGVSTTTP
GLPGAIEACEAAKSTGAKVILGGPHTEVYAHENLVHESIDYVGVGEGVTI
MPELAEAMERGEEPEGIRGLVTRKHDGGAAPMVNLEEVGWPERAGLPMDR
YYSIMAPRPFATMISSRGCPFKCSFCFKQAVDKKSMYRSPEDVVGEMTEL
KERWGVKEIMFYDDVFTLHRGRVREICGLIGETGLKVRWEAPTRVDLVPE
PLLEAMAGAGCVRLRFGIEHGDSEILERMRKESDIQKIEKAVTSAHEAGI
KGFGYFIVGWLGETREQFRRTVDLACRLPLDYASFYTATPLPGTPLHTES
VAAGQIPPDYWDRFSCGASSTRGSGTWCRTRRSAPSGRTAPSSCAAPWSS
RCCRTWR (SEQ ID NO: 38)

TABLE 44

Sequence Homology of moeK5 ref|NP_142754.1| methyltransferase [*Pyrococcus horikoshii* OT3]
Length = 459
Score = 192 bits (489), Expect = 2e-47
Identities = 128/375 (34%), Positives = 195/375 (52%), Gaps = 13/375 (3%)

```
                SEQ ID NO: 166
Query     1 LGYIHTALKSAGFHHVIQVDTPALGLDSEGLRKLLADFEPDLVGVSTTTPGLPGAIEACE    60
            || + |      |  | +|  |  |    + |++  |+||+||++ ||  +  |    +
Sbjct    28 LGLAYLASMVREEHDVKIIDGLAEDLTFSDIAKIIKKFDPDIVGITATTSAMYDAYTVAK    87
                SEQ ID NO: 247

SEQ ID NO: 167        SEQ ID NO: 168
Query    61 AAKSTGAKV--ILGGPHTEVYAHENLVHES--IDYVGVGEGVTIMPELAEAMERGEEPEG   116
            ||+       | ++||||   +  | +|   || ||  ||  || +|+ +|  | +|
Sbjct    88 IAKNINENVFVVMGGPHV-TFTPELTMRECPCIDAVVRGEGELTFKELVDALSKGRELKG   146
                              SEQ ID NO: 248

SEQ ID NO: 169
Query   117 IRGLVTRKH----DGGAAPMV-NLEEVGWPERAGLPMDRYYSIMAPRPFATMISSRGCPF   171
            | ||   +++    +    |++ |++|+  |    ||||+| +    |  +++|||||
Sbjct   147 ILGLSYKENGKVRNEPPRPLIQNVDEIPIPSYDLLPMDKYKADGVP--FGVVMTSRGCPF   204
                                                           SEQ ID NO: 170

SEQ ID NO: 171
Query   172 KCSFCFKQA-VDKKSMYRSPEDVVGEMTELKERWGVKEIMFYDDVFTLHRGRVREICGLI   230
            | ||      |+    | |+ |++   +|+||| |  | || |  ||++   +|   |
Sbjct   205 NCVFCSSSLQFGKRWRGHSVERVIEELSILHYEYGIKEIEFLDDTFTLNKKRAIDISLRI   264

Query   231 GETGLKVRWEAPTRVDLVPEPLLEAMAGAGCVRLRFGIEHGDSEILERMRKESDIQKIEK   290
             + || + |  +|  +||+   | + +||    + ||||   ||| +    |    |+
Sbjct   265 KQEGLDISWTASSRVNTFNEKVAKAMKEGGCHTVYFGIESASPRILEFIGKGITPQQSID   324

Query   291 AVTSAHEAGIKGFGYFIVGWLGETREQFRRTVDLACRLPLDYASFYTATPLPGTPLHTES   350
            || +| + +    | ||+|+  |||+  |+  |  +| +|+|||  |  |||  |   +
Sbjct   325 AVKTAKKFGLHALGSFIIGFPDETREEVEATIKFAKKLDIDYAQFTIATPYPGTRLWEYA   384

Query   351 VAAGQIPPDYWDRFS    365
            +|   +   |  +++
Sbjct   385 IANNLLLTMNWRKYT    399
```

Gene moeK5 encodes a protein homologous to putative SAM-radical, methyl-cobalamin-dependent methyl transferases involved in the biosynthesis of fortimycin and a handful of other secondary metabolites, and we have proposed that it controls the methylation of the first sugar (unit F) (Ostash 2007). Indeed, strain ΔmoeK5 accumulated a compound 24 having a mass 14 Da less than that of compound 19 from the parental 38-1⁺ strain (Table 21), indicative of the loss of a methyl group. Methylation of unit F most likely takes place after its attachment to farnesyl-phosphoglycerate since we detected a mixture of nonmethylated and methylated monosaccharides (compounds 2 and 3, respectively; Table 21) in the ΔmoeGT4 strain. Based on the studies of the present invention, it is propose that the polypeptide encoded by the moeK5 gene is a methyltransferase which participates in the conversion of Moe intermediate compound 1 in the course of moenomycin biosynthesis to yield a Moe intermediate compound 2 or 3, respectively, as shown in FIG. 4.

4. moeM5

The predicted moeM5 translation product of moeM5 is similar to carbamoyltransferases from NodU family (33% identity and 45% similarity to putative carbamoyltransferase from *Rubrobacter xylanophilus* DSM9941) (Jabbouri 1995) as well as to those involved in antibiotic biosynthesis in various actinomycetes (29% identity and 44% similarity to GdmN involved in geldanamycin biosynthesis) (Hong 2004). The nucleotide and polypeptide sequences are shown in Tables 45 and 46, respectively. A sequence alignment between moeM5 and the closest homolog identified in the BLAST search is shown in Table 47. MoeK5 and moeM5 may govern the transfer of methyl and carbamoyl groups, respectively, on a moenuronamide precursor.

TABLE 45

DNA Sequence of moeM5.

ATGAAGGTACTGTCGCTCCACTCCGCCGGCCACGACACCGGCGTCGCCTA

CTTCGAGGACGGGCGGCTGGTCTTCGCGGTCGAGACCGAACGGCTCACCC

GGGTCAAGCACGACCACCGCTCCGACGTCGCCCTGCGGCACGTGCTCGAG

CAGGAGTGCGTGGACACCGACGGGATCGACCTGGTGGCCGTCAGCACCCC

GGTCCGCAGCGGGCTGCTGCGCATACCCGACCTGGACCGGGCCATGGAGC

GGATCGGGGCGGGCGCCCTCCACCACCGGACCGTCTGCGAGATGCTGGGG

CGGCGGGTGGAGTGCGTCGTGGTCACCCACGAGGTCTCCCACGCGGCGCT

GGCCGCCCACTACGCGGACTGGGAGGAAGGCACCGTCGTCCTCGTCAACG

AGGGCCGCGGCCAGCTCACCCGCAGCTCCCTGTTCCGGGTGACCGGCGGG

GCCCTGGAGTGGGTCGACAAGGACCCGCTGCCCTGGTACGGCAACGGCTT

CGGGTGGACGGCGATCGGGTACCTCCTCGGCTTCGGCCCGAGCCCCAGCG

TGGCGGGCAAGGTGATGGCCATGGGCGGCTACGGGCAGCCGGACCCGCGC

ATCCGCGAACAGCTGCTGTCGGTGGATCCGGAGGTGATGAACGACCGGGA

TABLE 45-continued

DNA Sequence of moeM5.

ACTCGCCGAGCGGGTGCGCGCGGACCTGGCCGGCCGGCCCGAGTTCGCCC
CCGGGTTCGAGACGGCGTCGCAGGTGGTGGCGACGTTCCAGGAGATGTTC
ACCGAGGCCGTCCGGGCGGTGCTCGACCGGCATGTGACGCGCACGGACGC
CGGGGTGGGCCCGATCGCCCTGGGCGGCGGGTGCGCCCTGAACATCGTGG
CCAACTCGGCGCTGCGGGAGGAGTACGGGCGGGACGTCGCCATCCCGCCC
GCCTGCGGGGACGCGGGTCACCTGACGGGCGCCGGCCTCTACGCCCTCGC
GCAGGTGGCCGGGGTGAAGCCGGAGCCGTTCAGCGTGTACCGCAACGGCG
GGGGCGAGGCCCGGGCCGCCGTCCTGGAGGCGGTGGAGGGCGCGGGGTTG
CGGGCCGTTCCCTACGACCGGTCCGCGGTCGCCGGGGTGCTGGCCGGGGG
CGGGGTGGTGGCGCTGACGCAGGGAGCGGCGGAACTGGGGCCGCGGGCGC
TGGGGCACCGGTCGCTGCTGGGCAGTCCCGCGGTGCCGGGCATGCGCGAG
CGGATGAGCGAGAAGCTCAAGCGGCGCGAGTGGTTCCGGCCGCTGGGCGC
CGTGATGCGCGACGAGCGCTTCGCCGGGCTGTACCCGGGGCGGGCGCCGT
CGCCGTACATGCTCTTCGAGTACCGGCTGCCGGACGGGATCGCGCCCGAG
GCCCGGCACGTCAACGGCACCTGCCGGATCCAGACCCTGGGCCCCGAGGA
GGACCGGCTGTACGGTCTGCTCGCCGAGTTCGAGGAGCTGAGCGGTGTGC
CGGCGCTGATCAACACGTCGCTCAACGGCCCGGGCAAGCCCATCGCGCAC

TABLE 45-continued

DNA Sequence of moeM5.

ACCGCCCGGGACGTGCTCGACGACTTCGCGCGCACCGACGTCGACCTCTT
CGTGTTCCACGACCTGATGGTGCGGGGCGCCGCCGCGCGGTAG (SEQ
ID NO: 16)

TABLE 46

Amino Acid Sequence of moeM5

MKVLSLHSAGHDTGVAYFEDGRLVFAVETERLTRVKHDHRSDVALRHVLE
QECVDTDGIDLVAVSTPVRSGLLRIPDLDRAMERIGAGALHHRTVCEMLG
RRVECVVVTHEVSHAALAAHYADWEEGTVVLVNEGRGQLTRSSLFRVTGG
ALEWVDKDPLPWYGNGFGWTAIGYLLGFGPSPSVAGKVMAMGGYGQPDPR
IREQLLSVDPEVMNDRELAERVRADLAGRPEFAPGFETASQVVATFQEMF
TEAVRAVLDRHVTRTDAGVGPIALGGGCALNIVANSALREEYGRDVAIPP
ACGDAGHLTGAGLYALAQVAGVKPEPFSVYRNGGGEARAAVLEAVEGAGL
RAVPYDRSAVAGVLAGGGVVALTQGAAELGPRALGHRSLLGSPAVPGMRE
RMSEKLKRREWFRPLGAVMRDERFAGLYPGRAPSPYMLFEYRLPDGIAPE
ARHVNGTCRIQTLGPEEDRLYGLLAEFEELSGVPALINTSLNGPGKPIAH
TARDVLDDFARTDVDLFVFDDLMVRGAAAR (SEQ ID NO: 39)

TABLE 47

Sequence Homology of moeM5 gb|AAO06921.1| GdmN [*Streptomyces hygroscopicus*]
Length = 682
Score = 159 bits (401), Expect = 4e-37
Identities = 167/557 (29%), Positives = 246/557 (44%), Gaps = 49/557 (8%)

```
                SEQ ID NO: 172                       SEQ ID NO: 173
Query    11  HDTGVAYFEDGRLVFAVETERLTRVKHDHRSDV-ALRHVLEQECVDTDGIDLVAVSTP--   67
             ||+  +    ||  ||  ||+ |   + +|   |         + +|    |      |
Sbjct    27  HDSAASLIRDGELVAAVEEERLNRIKKTTKFPLNAVRECLALAGARPEDVDAVGYYFPEN   86
                SEQ ID NO: 174

SEQ ID NO: 175  SEQ ID NO: 235              SEQ ID NO: 176
Query    68  -VRSGLLRI-PDLDRAMERIGAGALHHRTVCEMLGRRV---ECVVVTHEVSHAALAAHYA  122
              + |  + +   |   +  ||    |     +   |||   + |   |   +||  +++
Sbjct    87  HIDTVLNHLYTEYPRAPLRYSRELIRQR-LKEGLGWDLPDEKLVYVPHHEAHA-YSSYLH  144
                                             SEQ ID NO: 177         SEQ ID NO: 178

SEQ ID NO: 179
Query   183  SVAGKVMAMGGYGQPDPRIREQLLSVDPEVMNDRELAERVRADLAGRPEF-APGF-----  236
             |||  + +| |+     +        +    + +|    +    |     | | ||
Sbjct   204  EY--KVMGLAPWGNPETYRDTFAKLYTLQDNGEYELHGNIMVPNLVSPLFYAEGFRPRRK  261
                SEQ ID NO: 180

SEQ ID NO: 181                       SEQ ID NO: 182
Query   237  -ETASQVVATFQEMFTEAVRAVLDRHVTR---TDAGVGPIALGGGCALNIVANSA-LREE  291
              | +|   |    |   |  ++ |   +|   +|   +   +    |||| |||  |++
Sbjct   262  GEPFTQAHRDFAAALQETVEKIV-LHILEYWAKTSGHSRLCFGGGVAHNSSLNGLILKSG  320
                                                  SEQ ID NO: 237

SEQ ID NO: 183                         SEQ ID NO: 184
Query   292  YGRDVAIPPACGDAGHLTGAGLYALAQVAGVKPEPFSVYRN-------GGGEARAAVLEA  344
             +|  + ||  ||| ||    ||  |   |   |  |||| +       || |  |
Sbjct   321  LFDEVFVHPASHDAGAGEAA-YAAAASLGTLERPGKRLLSASLGPALGGREQIRARL--  377
                SEQ ID NO: 249
```

TABLE 47-continued

Sequence Homology of moeM5

```
                    SEQ ID NO: 185
Query   345 VEGAGLRAVPYDRSAV---AGVLAGGGVVALTQGAAELGPRALGHRSLLGSPAVPGMRER  401
             +  |   | +    ||    ||+|| | |+    | +| |||||||| ++          | |
Sbjct   378 ADWAPLIDVEFPDDAVETAAGLLAEGQVLGWAYGRSEFGPRALGHRSIVADARPEENRTR  437
            SEQ ID NO: 238

SEQ ID NO: 250
Query   402 MSEKLKRREWFRPLGAVMRDERFAGLYP-GRAPSPYMLFEYRLPDGIAPEAR-------H  453
            ++  +|+|| ||| |+ |      +   |   +    +  +| +||| |
Sbjct   438 INAMVKKREGFRPFAPVVTAEAARDYFDLSGADGNHEFMSFVVP--VLPERRTELGAVTH  495
                                                               SEQ ID NO: 186

SEQ ID NO: 187 SEQ ID NO: 188
Query   454 VNGTCRIQTLGPEE-DRLYGLLAEFEELSGVPALINTSLNGPGKPIAHTARDVLDDFART  512
            |+||  |+|  +   |   +| +  |+   | ||+|   |+||| |    +||  +  ||+  |   |
Sbjct   496 VDGTARVQVVSAESGERFHRLVRRFGELTGTPVLLNTSFNNNAEPIVQSLDDVVTSFLTT  555

Query   513 DVDLFVFDDLMVRGAAA  529
            |+|+   | +|  +|||  |+
Sbjct   556 DLDVLVVEDCLVRGKAS  572
```

To evaluate whether sugar tailoring reactions (particularly, O-carbamoylation of unit F) follow the formation of the lipid-phosphoglycerate-pentasaccharide scaffold of moe A, the carbamoyltransferase gene moeM5 was disrupted (see e.g., FIG. 9). The mutant strain, termed OB20a, was then evaluated for moe A function; extracts from the moeM5⁻ mutant should contain less active moe A derivatives, lacking a carbomoyl group. Indeed, moeM5 deficient mutants have been shown to produce novel moe compounds with greatly reduced antibacterial activity. The molecular mass of such compounds (m/z 1538 Da; see e.g., FIGS. 12 and 13) coincides with that of moe A lacking the carbamoyl group. Expression of a functional moeM5 gene in the OB20a mutant restored moe A biosynthesis. The purification of the intermediate accumulated in OB20a in quantities sufficient for more detailed structural elucidation has been hampered by its instability and very low levels.

Nevertheless, several conclusions may be drawn from the data obtained. First, moeM5 appears to govern carbamoylation of a moe A intermediate, which is one of several tailoring reactions involved in moes bioactivity.

Second, blocked carbamoylation does not appear to abolish the formation of pentasaccharide moiety of moe A. The ability to remove a certain chemical moiety from a given position of moe in order to obtain a more valuable derivative or to modify this position chemically would be very beneficial. For example, manipulations of genes responsible for introduction of carbamoyl, methyl, and amido groups into moe molecules and those involved in lipid-phosphoglycerate assembly are of interest since these functionalities contribute to moe bioactivity. However, it was not previously known whether the disruptions of a gene governing a certain catalytic step would lead to the production of desired intermediate. For instance, the absence of a specific chemical group on a first sugar might block the attachment of the second sugar, and thus the assembly of entire lipid-pentasaccharide scaffold would be interrupted.

Based on the studies of the present invention, it is propose that the polypeptide encoded by the moeM5 gene is a carbamoyltransferase which participates in the conversion of Moe intermediate compound 5, 6 or 7 in the course of moenomycin biosynthesis to yield a Moe intermediate compound 8, 9 or 10, respectively, as shown in FIG. 4.

Here, however, it was demonstrated that the generation of biologically active moe derivatives through genetic engineering is possible. In this instance, either carbamoyltransfer takes place after the glycoside scaffold of moe A is formed, or moe GTs possess a certain level of substrate flexibility allowing them to recognize sugars that have no specific functional groups. The result demonstrates that it is possible to switch off late steps of moe biosynthesis without disturbing the assembly of the complex pharmacophore scaffold.

5. moeR5

The putative translation product of the moeR5 gene resembles the C-terminal portion of the CapD-like NAD-dependent epimerases/dehydratases involved in capsular polysaccharide biosynthesis in various bacteria. (53% identity and 68% similarity to putative CapD protein from *Nocardioides* sp. JS614) (Lin 1994, Smith 1999). The nucleotide and polypeptide sequences are shown in Tables 48 and 49, respectively. A sequence alignment between moeR5 and the closest homolog identified in the BLAST search is shown in Table 50.

Figure 1:
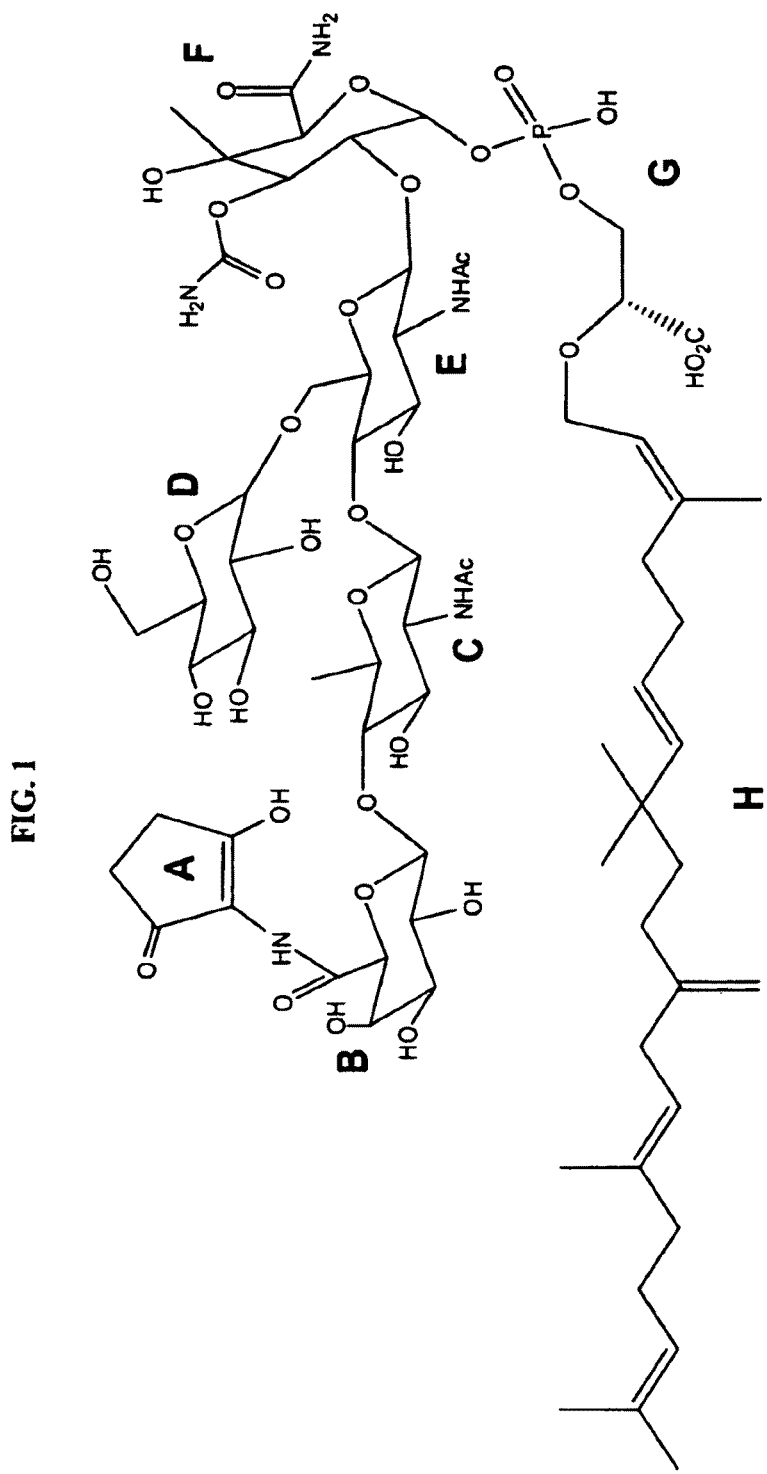
FIG. 1 shows the structure of moe A with the domains A-H involved in bioactivity and target interactions indicated in capital letters.

We have previously proposed that moeR5moeS5 encode a 4,6-dehydratase/ketoreductase pair that controls the conversion of UDP-GlcNAc into UDP-chinovosamine (Ostash 2007), the unit C sugar of moe A (FIG. 1). Consistent with this, the 38-1+ strain was shown to accumulate a moe A derivative containing GlcNAc in place of chinovosamine. A moeR5⁺moeS5⁺ 38-1⁺ strain accumulated a compound, 18, having an accurate mass and fragmentation pattern identical to a previously characterized moe A precursor (FIG. 4 and (Ostash 2007). While this result was expected, we were surprised to find that the moeR5⁺38-1⁺ strain also produces 18 (Table 21). There is a close moeS5 homolog in the *S. coelicolor* genome (Ostash 2007), and it is probable that a similar homolog exists in the *S. lividans* genome and complements the loss of moeS5 function in the moeR5⁺38-1⁺ strain. However, we cannot rule out the possibility that MoeR5 catalyzes both reactions. Co-expression of moeS5 and moeno38-1 yielded no new products (data not shown).

TABLE 48

DNA Sequence of moeR5

ATGTTTGGCGATAATTCCGTGGGGTACGACGCGAACTTTCCGGCCGGTGG

ACCTCTCACCTTGGACCTCGAGAGGATTATCGGCCGCCAACGAATAAGGA

CCGGTCTCGAGAGCAGCGCCGGATTACTGCGCGGCCGACGGATCCTGGTC

TABLE 48-continued

DNA Sequence of moeR5

ACCGGAGCCGGCGGCTACATCGGATCGGAACTGTGCCGGCAGCTCAGCCG

GTGGGAACCCGAGAGCCTCATGATGCTCGACCGGAACGAGACGGCCCTCC

ACCTGGCGGCCACCAGCATCGGGAACGTCTCCCCGTCGGTGCGGACCTCC

ATCCTCCTCGCGGACATCAGGGACTCCAGAGGGCTCGCCCGGCTGTTCCA

GCAGTGCCGGCCGGACACCGTCTTCCACGCGGCGGCCCTCAAATGGGTGC

CCATCCTGGAGAAGTTCCCCGGGGAAGCCGTCAAGACGAATGTCTTCGGC

ACCCGAGCGGTGCTCGAGGCGGCCCTGGCCGCGGACGTCGCGTTCCTGGT

GAACATCTCGACCGACAAGGCGGTCGATCCGGTCGGGGTGCTCGGATACT

CGAAACGCATAGCCGAAGGACTCACCGCGGCGGCCGCGATCCAGGCGGGC

AGACCGTACGTGAGCGTGCGCTTCGGCAACGTGCTCGGTTGCCAGGGGTC

CTTCCTCGACGTCTTCGCCCGGCAGATCGCGGCCGGCAGACCGGTGACGG

TCACCCACCCCGAGGTGACGCGCTATCTGATGACCGTCCAGGAGGCCGTG

GAACTGGTCATCCAGTCGGTCGCGCTGGGCAGCGTCGGCCACGCCCTGGT

CCTGGACATGGGGGAACAGGTCCGGATCCTCGACATCGCCAGAAGGCTCA

TCGCGCACGCCGGTGCGGAGCTCCCGGTCCGCTACGTCGGGCTGCGGCCG

GGGGAGAAGCTCACCGAGGCGCTGGTGGCCCCTTCCGAGTCCCGGTCCG

GCACGGGCATCCGAAGATCATGGAAGTGCCGGTGCCGGCCCTGAAGGCGG

GGGACGGCCCGGAACTCGACGCCTGGGGCGAGGACCAGGCCGTCGTCGCC

GCCCTGCGCGCCACCTGCCTCGCCATGGCGGGCGACGACCCGGTGGCGCA

GGACCCCGGCCACCGGCTGGTCTGA (SEQ ID NO: 17)

TABLE 49

Amino Acid Sequence of moeR5

MFGDNSVGYDANFPAGGPLTLDLERIIGRQRIRTGLESSAGLLRGRRILV

TGAGGYIGSELCRQLSRWEPESLMMLDRNETALHLAATSIGNVSPSVRTS

ILLADIRDSRGLARLFQQCRPDTVFHAAALKWVPILEKFPGEAVKTNVFG

TRAVLEAALAADVAFLVNISTDKAVDPVGVLGYSKRIAEGLTAAAAIQAG

RPYVSVRFGNVLGCQGSFLDVFARQIAAGRPVTVTHPEVTRYLMTVQEAV

ELVIQSVALGSVGHALVLDMGEQVRILDIARRLIAHAGAELPVRYVGLRP

GEKLTEALVAPSESPVRHGHPKIMEVPVPALKAGDGPELDAWGEDQAVVA

ALRATCLAMAGDDPVAQDPGHRLV (SEQ ID NO: 40)

TABLE 50

Sequence Homology of moeR5 gi|71367042|ref|ZP_00657575.1| Polysaccharide biosynthesis protein CapD
[*Nocardioides* sp. JS614]
gi|71157263|gb|EAO07657.1| Polysaccharide biosynthesis protein CapD
[*Nocardioides* sp. JS614]
Length = 667
Score = 322 bits (824), Expect = 2e−86, Method: Composition-based stats.
Identities = 185/346 (53%), Positives = 237/346 (68%), Gaps = 2/346 (0%)

```
                SEQ ID NO: 189
Query    21 LDLERIIGRQRIRTGLESSAGLLRGRRILVTGAGGYIGSELCRQLSRWEPESLMMLDRNE    80
            +++  ++||  ++   |   +  |   ||   ||++||||||| ||||||||+  ++|    ||||||+|
Sbjct   317 INITDVLGRNQLDTDVASIAGYLAGRKVLVTGAGGSIGSELCRQIYRYQPAELMMLDRDE   376
                SEQ ID NO: 190

Query    81 TALHLAATSIGNVSPSVRTSILLADIRDSRGLARLFQQCRPDTVFHAAALKWVPILEKFP   140
            +|||      ||  +    ++|  ||||  + +  +|   |||  |||||||||  +|+|++|
Sbjct   377 SALHSVQLSIHGRALLDSDDVILCDIRDEKAVRTIFANRRPDVVFHAAALKHLPMLEQYP   436

Query   141 GEAVKTNVFGTRavleaalaadvaflvNISTDKAVDPVGVLGYSKRIAEGLTAAAAIQAG   200
            ||||||| |||| ||||+|     |     ||+  |||||||||||||+| +|||  +|
Sbjct   437 AEAVKTNVIGTRTVLDAADLVGVDRFVNISTDKAANPSSVLGYSKRVAERITAAQREAS   496

Query   201 RPYVSVRFGNVLGCQGSFLDVFARQIAAGRPVTVTHPEVTRYLMTVQEAVELVIQSVALG   260
            |+|||||||||+|| | ||||||||||+||||+|+|+ ||++|| +|||+ +|
Sbjct   497 GTYLSVRFGNVLGSRGSVLAAFARQIAAGGPITVTHPDVSRFFMTIEEACQLVIQAAIG   556

SEQ ID NO: 191
Query   261 SVGHALVLDMGEQVRILDIARRLIAHAGAELPVRYVGLRPGEKLTEALVAPSES-PVRHG   319
            | |||||||||+|+|+| +|| ||  +|+ ||| |||| |   |   || ||
Sbjct   557 GPGEALVLDMGEPVKIVDVAEQLIEQAGTPVPIEYTGLREGEKLHEELFGEGEPCDVRPR   616

SEQ ID NO: 192
Query   320 HPKIMEVPVPALKAGDGPELDAWGEDQAVVAALRATCL-AMAGDDP   364
            ||  +  |||| +   |+  |   ||  ||  ||++ |||
Sbjct   617 HPLVSHVPVPPITDGEVLGLTLVGEPDDVRQALHDACLVSIEADDP   662
```

Based on the studies of the present invention, it is propose that the polypeptide encoded by the moeR5 gene is a hexose-4,6-dehydratase which participates in the conversion of Moe intermediate compound 4 in the course of moenomycin biosynthesis to yield a Moe intermediate compound 6 or 7, wherein chinovosamine is utilized as a donor, respectively, as shown in FIG. 4. Furthermoren, based on the studies of the present invention, it is propose that the polypeptide encoded by the moeR5 gene is a hexose-4,6-dehydratase which participates in the conversion of Moe intermediate compound 11 in the course of moenomycin biosynthesis to yield a Moe intermediate compound 14 or 15, wherein chinovosamine is utilized as a donor, respectively, as shown in FIG. 4.

6. moeS5

Gene moeS5, located upstream of moeR5, encodes a putative protein homologous to putative polysaccharide biosynthesis protein SC07194 from *S. coelicolor* A3(2) (63% identity and 76% similarity). The nucleotide and polypeptide sequences are shown in Tables 51 and 52, respectively. A sequence alignment between moeS5 and the closest homolog identified in the BLAST search is shown in Table 53. A CDD search revealed an RfbD domain (COG1091) in moeS5. This domain is present in many known NDP-4-dehydrohexose reductases. It is possible that the moeR5 and moeS5 genes may govern two consecutive steps of NDP-Glc-Nac transformation into NDP-chinovosamine (unit C of moe A; FIG. 1). Particularly, the NDP-Glc-NAc-4,6-dehydratase activity of moeR5 may convert NDP-Glc-NAc into NDP-4-keto-6-deoxy-Glc-Nac, and the hexose-4-ketoreductase activity of moeS5 may reduce this intermediate to yield NDP-chinovosamine.

TABLE 51

DNA Sequence of moeS5

GTGAGAGTTCTTGTCGTCGGCGGGAGCGGCTTCCTCGGGTACGAGGTGCT
CCGCCGGGCCGTGGCCGCCGGGTGGGACGTGGCCGCGACCTACCGGACCC
GCCCCGAGGAACTGCCGCCGGTCACCTGGTACCGGGCCGACCTCCGTGAC
CCGGGGCGGATGGGAGAGGTGCTGGCCCGGACCCGGCCGGCCGCGGTGAT

TABLE 51-continued

DNA Sequence of moeS5

CAACGCGTCGAGCGGACACGCCGACTGGGCGGTCACGGCCGACGGCGCGG
CCCGCCTCGCCCTGGAGGCGGCGCGCGCCGGCTGCCGACTAGTCCACGTC
TCCTCCGACGCCGTGTTCTCCGGAGCCGACGTCCACTACCCGGAGGAGGC
CCTCCCCGACCCCGTCTCCCCGTACGGCGCGGCCAAGGCCGCGGCGGAGA
CGGCCGTCAGGGTGGCCGTGCCCGAGGCCGCCGTGGTGCGCACCTCGCTC
ATCGTGGGGCACAACCGGTCCGCCCACGAGGAGGCGGTGCACGCCCTGGC
GGCCGGCCGGCGCGCCGGCGTCCTGTTCACGGACGACGTCCGCTGTCCGG
TCCACGTCGACGATCTGGCCTCCGCGCTTTTGGAGATCGCGGCGTCGGAC
GGGTCCGGGGTGTTCCACGTGGCGGGACCGGACGCGATGAACCGTCACGA
CCTGGGTGTCCTCATAGCCCGGCGGGACGGACTGGACCCGGCCCGGCTGC
CGGCCGGTCTGCGGAGCGAGGTGGCCCCGCCGGGGAACCTCGACATCCGT
CTCGTCACCGATGCCACGCGGGCCCGGCTCCGGACCCGGTTGCGGGGCGC
GCGCGAATTCCTCGGCCCCGGCGTTCCGGTGACGCGGGGCGTCCGTTGA (SEQ ID NO: 18)

TABLE 52

Amino Acid Sequence of moeS5

VRVLVVGGSGFLGYEVLRRAVAAGWDVAATYRTRPEELPPVTWYRADLRD
PGRMGEVLARTRPAAVINASSGHADWAVTADGAARLALEAARAGCRLVHV
SSDAVFSGADVHYPEEALPDPVSPYGAAKAAAETAVRVAVPEAAVVRTSL
IVGHNRSAHEEAVHALAAGRRAGVLFTDDVRCPVHVDDLASALLEIAASD
GSGVFHVAGPDAMNRHDLGVLIARRDGLDPARLPAGLRSEVAPPGNLDIR
LVTDATRARLRTRLRGAREFLGPGVPVTRGVR (SEQ ID NO: 41)

TABLE 53

Sequence Homology of moeS5 emb|CAC01594.1| putative polysaccharide biosynthesis protein [*Streptomyces coelicolor* A3(2)] SCO7194

Length = 271

Score = 335 bits (860), Expect = 1e-90
Identities = 171/269 (63%), Positives = 205/269 (76%), Gaps = 0/269 (0%)

```
        SEQ ID NO: 193
Query   3  VLVVGGSGFLGYEVLRRAVAAGWDVAATYRTRPEELPPVTWYRADLRDPGRMXEVLARTR  62
           ||||||||||| |++|+| ||| ||||+ ||| +  ||+ |||| |+ ||+|
Sbjct   3  VLVVGGSGFLGTELVRQASAAGHRVAATFATRPCDGPEATWHEVDLRDGARVEEVVASLA  62
        SEQ ID NO: 194

Query   63 PAAVINASSGHADWAVTADGAARLALEAAREGCRLVHVSSDAVFSGADVHYPEEALPDPV  122
           |  |||||| |||||||+|+ |||+ | +  ||||||||||||+ ||| |||||
Sbjct   63 PCVVINASSGSADWAVTAEGSVRLAMTAVKYDCRLVHVSSDAVFSGSRVHYDESCLPDPV  122

Query   123 SPYGAAKAAAETAVRVAVPEAAVVRTSLIVGHNRSAHEEAVHALAAGRRAGVLFTDDVRC  182
            +|||||||||| +|+  | + ||||+| +| || || | | ||||||||
Sbjct   123 TPYGAAKAAAETGIRLLAPAAVIARTSLIIGGIQSEHVRLVHDLATGSRTGALFTDDVRC  182
```

TABLE 53-continued

Sequence Homology of moeS5

```
Query  183 PVHVDDLASALLEIAASDGSGVFHVAGPDAMNRHDLGVLIARRDGLDPARLPAGLRSEVA  242
           ||||+|||+||||+| +    || |+|| |++|| |||||+||||  +||  |||+  +
Sbjct  183 PVHVEDLAAALLELAFTGACGVHHLAGKDAVSRHGLGVLIAQRDGLDASRLPEGLRAGTS  242

Query  243 PPGNLDIRLVTDATRARLRTRLRGAREFL  271
           | ||+|| + ||||+||||+||   |||
Sbjct  243 LSGALDVRLDSRATRAKLRTRVRGVHEFL  271
```

Based on the studies of the present invention, it is propose that the polypeptide encoded by the moeS5 gene is a hexose-4-ketoreductase which participates in the conversion of Moe intermediate compound 4 in the course of moenomycin biosynthesis to yield a Moe intermediate compound 6 or 7, wherein chinovosamine is utilized as a donor, respectively, as shown in FIG. 4. Further, based on the studies of the present invention, it is propose that the polypeptide encoded by the moeS5 gene is a hexose-4-ketoreductase which participates in the conversion of Moe intermediate compound 11 in the course of moenomycin biosynthesis to yield a Moe intermediate compound 14 or 15, wherein chinovosamine is utilized as a donor, respectively, as shown in FIG. 4.

7. moeE5

The putative protein encoded by the moeE5 gene appears the most similar to the putative NDP-hexose 4-epimerase from *Symbiobacterium thermophilum* IAM14863 (46% identity and 58% similarity) and other known epimerases. The nucleotide and polypeptide sequences are shown in Tables 54 and 55, respectively. A sequence alignment between moeE5 and the closest homolog identified in the BLAST search is shown in Table 56. *S. ghanaensis* produces moes $A_{12}$ and $C_1$ as minor components of moe complex in which unit F (moenuronamide) has D-galacto configuration (and not D-gluco as in Moe A) (Welzel 2005). Such a rearrangement requires epimerization of hydroxyl group in $4^{th}$ position of hexose ring and moeE5 protein appears to fit this role.

TABLE 54

DNA Sequence of moeE5.

GTGTCGAGCGATACACACGGAACGGACTTAGCGGACGGCGACGTTTTGGT

CACCGGTGCGGCCGGCTTCATCGGGTCGCACCTGGTGACGGAACTGAGGA

ATTCCGGCAGAAACGTTGTGGCGGTGGACCGGAGACCCCTTCCGGACGAC

TTGGAGAGTACGTCCCCGCCCTTTACCGGTTCGCTCCGGGAGATACGCGG

TGACCTCAACTCATTGAATCTGGTGGACTGCCTGAAAAACATCTCGACGG

TCTTCCACTTGGCCGCGTTACCCGGAGTCCGCCCGTCCTGGACCCAATTC

CCCGAGTACCTCCGGTGCAATGTACTGGCGACCCAGCGCCTGATGGAGGC

CTGTGTGCAGGCCGGCGTGGAACGCGTGGTGGTCGCCTCGTCCTCCAGCG

TABLE 54-continued

DNA Sequence of moeE5.

TCTACGGCGGCGCGGACGGCGTGATGAGCGAGGACGACCTGCCCCGTCCG

CTCTCCCCCTACGGGGTCACCAAACTCGCCGCGGAGCGGCTGGCCCTGGC

CTTCGCGGCCCGCGGCGACGCCGAGCTCTCGGTCGGCGCCCTGAGGTTCT

TCACCGTCTACGGCCCCGGCCAGCGCCCGGACATGTTCATCTCCCGGCTG

ATCCGGGCGACGCTCCGGGGCGAACCCGTCGAGATCTACGGCGACGGGAC

CCAGCTCCGCGACTTCACCCATGTGTCCGACGTGGTGCGGGCGCTGATGC

TGACCGCGTCGGTGCGGGACCGGGGCAGCGCGGTGCTGAACATCGGCACC

GGGAGCGCCGTCTCGGTCAACGAAGTGGTCTCCATGACCGCGGAGCTGAC

CGGTCTGCGCCCGTGCACCGCGTACGGTTCCGCCCGCATCGGCGACGTCC

GCTCGACCACCGCCGACGTGCGGCAGGCCCAGAGCGTCCTGGGCTTCACG

GCCCGGACGGGTCTGCGGGAAGGTCTCGCCACCCAGATCGAGTGGACCCG

GCGGTCACTGTCCGGCGCCGAGCAGGACACCGTCCCGGTCGGCGGCTCCT

CGGTGTCCGTGCCGCGGCTGTAG (SEQ ID NO: 19)

TABLE 55

Amino Acid Sequence of moeE5

VSSDTHGTDLADGDVLVTGAAGFIGSHLVTELRNSGRNVVAVDRRPLPDD

LESTSPPFTGSLREIRGDLNSLNLVDCLKNISTVFHLAALPGVRPSWTQF

PEYLRCNVLATQRLMEACVQAGVERVVVASSSSVYGGADGVMSEDDLPRP

LSPYGVTKLAAERLALAFAARGDAELSVGALRFFTVYGPGQRPDMFISRL

IRATLRGEPVEIYGDGTQLRDFTHVSDVVRALMLTASVRDRGSAVLNIGT

GSAVSVNEVVSMTAELTGLRPCTAYGSARIGDVRSTTADVRQAQSVLGFT

ARTGLREGLATQIEWTRRSLSGAEQDTVPVGGSSVSVPRL (SEQ ID NO: 42)

TABLE 56

Sequence Homology of moeS5 ref|YP_074610.1| UDP-glucose 4-epimerase [*Symbiobacterium thermophilum* IAM 14863]
Length = 292
Score = 230 bits (587), Expect = 6e-59
Identities = 138/300 (46%), Positives = 175/300 (58%), Gaps = 18/300 (6%)

TABLE 56-continued

Sequence Homology of moeS5

```
            SEQ ID NO: 195
Query    16 LVTGAAGFIGSHLVTELRNSGRNVVAVDRRPLPDDLESTSPPFTGSLREIRGDLNSLNLV   75
            ||||||||||||  || +| +||  |||||  |           +  ||| +|+|
Sbjct     5 LVTGAAGFIGSHLVEALRAAGHDVVGVDRRPGAD---------------VVGDLLTLDLA   49
            SEQ ID NO: 196                                SEQ ID NO: 197

Query    76 DCLKNISTVFHLAALPGVRPSWTQFPEYLRCNVLATQRLMEACVQAGVERVVVASSSSVY  135
            |  +  |  |||   ||||  ||+|||  ||  |+   ||||+|+      +++ |+||+|||
Sbjct    50 PLLDGVEYVVHLAGQPGVRESWSQFPAYLAGNLQTTQRLLESLRDRPLKKFVLASTSSVY  109

Query   136 GGADGVMSEDDLPRPLSPYGVTKLAAERLALAFAARGDAELSVGALRFFTVYGPGQRPDM  195
            |   ||   |+||||+|||||||+|   +   |  +    |||+||||||| |||||
Sbjct   110 GEVPMPAREDGPAMPVSPYGLTKLAAEKLCDLYGR--TAGIPWVALRYFTVYGPRQRPDM  167
                                                          SEQ ID NO: 198

Query   196 FISRLIRATLRGEPVEIYGDGTQLRDFTHVSDVVRALMLTASVRDRGSAVLNIGTGSAVS  255
            ||    |  |  |||++||||+|||||+|+|  |   |++         +|+  ||||+
Sbjct   168 AFSRWFNAALDGEPIQIYGDGSQLRDFTYVADAVTATQ-RAALNPVVGVPINVGGGSAVT  226
                                                 SEQ ID NO: 199

Query   256 VNEVVSMTAELTGLRPCTAYGSARIGDVRSTTADVRQAQSVLGFTARTGLREGLATQIEW  315
            ||  + +  |+||           ||+| |||   +     +||    | |  |||    |    |
Sbjct   227 VREAIRLIAAITGRPIRIRQLPPAPGDMRETRADTERLWREVGFRPSTPLEEGLWQQYRW  286
```

Based on the studies of the present invention, it is propose that the polypeptide encoded by the moeE5 gene is a NDP-hexose 4-epimerase which participates in the conversion of Moe intermediate compound 1 in the course of moenomycin biosynthesis to yield a Moe intermediate compound 2 or 3, as shown in FIG. 4.

D. Genes for Phosphoglycerate-Lipid Moiety Biosynthesis

Two genes in cluster 1 were identified that fit this functional profile: moeN5 and moeO5. The phosphoglycerate-moenocinol chain of moenomycin is unusual in containing a cis-allylic ether linkage and an irregular isoprenoid chain of uncertain biosynthetic provenance. Two putative prenyltransferases, moeO5 and moeN5, were identified via in silico analysis of the moe genes and proposed to participate in the production of the phosphoglycerate-lipid moiety (Ostash 2007).

1. moeN5

The product of moeN5 gene translation shows local homology to putative geranylgeranyl pyrophosphate synthase from *Chlamidia trachomatis* (30% identity and 58% similarity over 56 amino acid fragment). The nucleotide and polypeptide sequences are shown in Tables 57 and 58, respectively. A sequence alignment between moeN5 and the closest homolog identified in the BLAST search is shown in Table 59.

TABLE 57

DNA Sequence of moeN5.

ATGCTCGCCGCCGAGGCCGCCAACCGCGACCATGTCACGCGGTGCGTCGC

GCAGACCGGTGGGTCGCCGGACCTGGTGGCGCACACCGCCGCCCTGCGCC

TGTACCTGAGGGTGCCCCACTTCCTCACCGAGTGGACGACCGACCCGGAC

CGGCGGGCCGCGGTGTCCCGCGCGCTGGCCCTCGACATCGTCTCCATGAA

GCTCCTCGACGACCTGATGGACGACGACACCGGACTCGACCGGGTCGAAC

TCGCCTGTGTCTGCCTCCGCCTCCACCTGCGGGCGCTGCACGAACTGGAA

TCCCTCGCCCGGGACCCCAAGGCGGTGACGGACATCCTGGAGCAGGACGC

TABLE 57-continued

DNA Sequence of moeN5.

CGTCCACCTCTGCGGCGGCCAGATACGCACCAAACGCTCTCGGGCGACGA

ACCTCCGGGAGTGGCGCGCCCATGCGAGCACCTACGGCTCCACCTTCCTG

GGCCGCTACGGGGCACTCGCGGCCGCCTGCGGGGGGAAGGCCAACCGGC

GGACTCCGTAAGGGAGTTCGCAGAGGCTTTCGCCATGACCATCACCATGG

CGGACGACCTGACCGACTACGACCGCAACGGCGAGCGGGACGGCAACCTC

GCCCATCTGATGCGGACCGGGGCCGTGGCCGGCCAGGACGTCGTGGACCT

GCTGGAGGAGCTGCGCGGGCGGGCCCTCGCCGCGGTGGCGGCACCGCCCG

GCGCGCCCGGTCTGGTGCCGGTCGTCCACCTCTACACGGACGACGTGCTG

GTACGGCTGCTTCCCCGGCACCTGGGGGAGTGA (SEQ ID NO: 20)

TABLE 58

Amino Acid Sequence of moeN5

MLAAEAANRDHVTRCVAQTGGSPDLVAHTAALRLYLRVPHFLTEWTTDPD

RRAAVSRALALDIVSMKLLDDLMDDDTGLDRVELACVCLRLHLRALHELE

SLARDPKAVTDILEQDAVHLCGGQIRTKRSRATNLREWRAHASTYGSTFL

GRYGALAAACGGEGQPADSVREFAEAFAMTITMADDLTDYDRNGERDGNL

AHLMRTGAVAGQDVVDLLEELRGRALAAVAAPPGAPGLVPVVHLYTDDVL

VRLLPRHLGE (SEQ ID NO: 43)

TABLE 59

Sequence Homology of moeN5 gb|EAQ07619.1| Geranylgeranyl pyrophosphate synthetase [*Loktanella vestfoldensis* SKA53]
Length = 293
Score = 40.0 bits (92), Expect = 0.097
Identities = 35/119 (29%), Positives = 52/119 (43%), Gaps = 8/119 (6%)

```
              SEQ ID NO: 200            SEQ ID NO: 201
Query  141  HASTYGSTFLGRYGALAAACGGEGQP-ADSVREFAEAFAMTITMADDLTDYDRNGERDGN  199
            | + |+ |+          | | | +| |+      ||| +   + | |     |+ |
Sbjct  167  HQAKTGALFIAATQMGAVAAGQEAEPWAELGARIGEAFQVADDLRDALCDDATLGKPAGQ  226
              SEQ ID NO: 202

SEQ ID NO: 203
Query  200  LAHLMRTGAVAG---QDVVDLLEELRGRALAAVAAPPGAPGLVPVVHLYTDDVLVRLLP  255
            |  |||        |  |   +++ | |++++ | ||    | +| |    ||+|
Sbjct  227  DDLHGRPNAVAAYGVQGAVKRFDDILGGAISSIPACPGEAALAQMVRAYAD----RLVP  281
                                                        SEQ ID NO: 204
```

The low similarity of moeN5 to other known prenyltransferases can be explained by the intrinsically low sequence homology among different prenyltransferases and the uniqueness of the reactions catalyzed by moeN5 (e.g. the linkage of geranyl and farnesyl pyrophosphates to give $C_{25}$ isoprene chain). No other genes were identified within the moe clusters which would govern the unusual rearrangement of the central part of moenocinol (Schuricht 2001, Neundorf 2003). Therefore, moeN5 is likely to control both prenyltrasfer and $C_{25}$ chain rearrangement, or the latter step may be controlled by a gene outside the moe cluster. Additionally or alternatively, the rearrangement may occur spontaneously after the formation of the $C_{23}$ chain.

We disrupted moeN5 in a heterologous *S. lividans* TK24 host that was previously shown to produce moe A derivatives following integration of the appropriate genes in the chromosome. HPLC-MS analysis showed that the ΔmoeN5 strain accumulated two compounds, 22/23, having similar mass-spectral characteristics (Table 21). As is evident from LC-MS and $MS^2$ analyses of ΔmoeN5 extracts (SD), compounds 22/23 differ from compound 19, which is produced by the parental 38-1⁺ strain (FIG. 4), primarily in the structure of the polyprenol chain. Whereas moe A and all reported derivatives, including 19, contain an irregular C25 isoprenoid chain, compounds 22/23 have a C15 cis-farnesyl chain. 22 and 23 differ from one another in the structure of unit B (moe A numbering; see FIG. 1), which contains either a carboxyl group (22) or a carboxamide moeity (23). Heterogeneity at this position with regard to the unit B structure has already been reported for other moenomycins (Zehl 2006). The aforementioned results show that moeN5 encodes a prenyltransferase involved in the coupling of a C10 isoprene unit to either the C15 chain of 22/23 or its precursor(s). Based on results presented below, we suggest that the farnesylated trisaccharide precursors 8 and 9/10 are the first possible substrates for the MoeN5-catalyzed reaction (FIG. 4). That is, based on the studies of the present invention, it is propose that the polypeptide encoded by the moeN5 gene is a prenyltransferase which participates in the conversion of Moe intermediate compound 8, 9, or 10 in the course of moenomycin biosynthesis to yield a Moe intermediate compound 11, 12 or 13, respectively, as shown in FIG. 4. The farnesylated trisaccharides precursors described above antibiotic biological activity.

2. moeO5

The presence of a phosphoglycerate moiety in moe-like antibiotics is without precedent in secondary metabolism, and mechanisms of phosphorus incorporation into moe A have puzzled researchers for years. Gene moeO5, located upstream of the prenyltransferase gene moeN5, was identified as having a translation product with homology to geranylgeranylglyceryl diphosphate synthases (GGGPSs) from various Archaea (27% identity and 43% similarity to GGGPS from *Thermoplasma acidophylum*) (Nemoto 2003). The nucleotide and polypeptide sequences are shown in Tables 60 and 61, respectively. A sequence alignment between moeO5 and the closest homolog identified in the BLAST search is shown in Table 62.

TABLE 60

DNA Sequence of moeO5.

```
GTGAACGCCTCACCGCAACTGGACCACCACACGGAACTCCACGCCGCACC
ACCGCTCTGGCGGCCGGGACGCGTGCTCGCCCGGCTGCGCGAGCACCAAC
CGGGCCCCGTCCACATCATCGACCCCTTCAAGGTCCCGGTGACGGAAGCG
GTCGAGAAGGCGGCGGAGCTCACGCGGCTGGGCTTCGCCGCCGTCCTTCT
GGCCAGCACCGACTACGAGTCGTTCGAGTCGCACATGGAGCCGTACGTGG
CGGCGGTGAAGGCGGCCACCCCGTTACCGGTCGTCCTGCACTTCCCGCCC
CGCCCGGGGGCCGGCTTCCCGGTGGTCCGCGGCGCGGACGCGCTCCTGCT
GCCCGCGCTGCTGGGCTCGGGCGACGACTACTTCGTCTGGAAGAGCTTCC
TCGAGACGCTGGCCGCCTTCCCCGGCCGAATACCCCGCGAGGAGTGGCCC
GAGCTGCTCCTCACCGTCGCCCTCACCTTCGGCGAGGACCCCCGCACCGG
GGACCTGCTCGGCACCGTGCCGGTGAGCACGGCCTCCACCGAGGAGATCG
ACCGGTACCTCCACGTCGCCCGTGCCTTCGGTTTCCACATGGTGTACCTG
TACTCGCGCAACGAGCACGTGCCGCCCGAGGTCGTACGCCACTTCCGCAA
GGGGCTCGGCCCCGACCAGGTGCTCTTCGTGAGCGGCAACGTCCGCTCCG
GGCGGCAGGTCACCGAGTACCTCGACAGCGGGGCGGACTACGTGGGGTTC
GCCGGAGCCCTGGAACAGCCGGACTGGCGGTCCGCCCTCGCCGAGATCGC
CGGGAGGCGGCCCGCCGCCCCGGCCCGTCCGGGGAGCGGCGGTGA
```

(SEQ ID NO: 21)

TABLE 61

Amino Acid Sequence of moeO5

VNASPQLDHHTELHAAPPLWRPGRVLARLREHQPGPVHIIDPFKVPVTEA

VEKAAELTRLGFAAVLLASTDYESFESHMEPYVAAVKAATPLPVVLHFPP

RPGAGFPVVRGADALLLPALLGSGDDYFVWKSFLETLAAFPGRIPREEWP

ELLLTVALTFGEDPRTGDLLGTVPVSTASTEEIDRYLHVARAFGFHMVYL

YSRNEHVPPEVVRHFRKGLGPDQVLFVSGNVRSGRQVTEYLDSGADYVGF

AGALEQPDWRSALAEIAGRRPAAPARPGSGR (SEQ ID NO: 44)

TABLE 62

Sequence Homology of moeO5 gi|110553682|gb|EAT66825.1| geranylgeranylglyceryl phosphate synthase [*Thermofilum pendens* Hrk 5]
Length = 255
Score = 50.8 bits (120), Expect = 6e-05, Method: Composition-based stats.
Identities = 68/236 (28%), Positives = 110/236 (46%), Gaps = 14/236 (5%)

```
            SEQ ID NO: 205
Query    25 VLARLREHQPGPVHIIDPFKVPVTEAVEKAAELTRLGFAAVLLASTDYESFESHMEPYVA    84
            +| ++|||   + +|||  |     | |+   | +|+++  +   |  |+  +  |
Sbjct     9 ILEKIREHGAIHMTLIDPEKTTPEVAARIAREVAEAGTSAIMVGGSIGVS-EAMTDEVVL    67
            SEQ ID NO: 206                                 SEQ ID NO: 207

Query    85 AVKAATPLPVVLHFPPRPGAGFPVVRgadalllpallgsgddYFVWKSFLETLAAFPGRI   144
            |+|  +| +|+|  ||    |   +  |||+   ++|  + ||+  + ++             |
Sbjct    68 AIKRSTEVPVIL-FPGSPTA---LSRHADAVWFLSVLNSQNPYFITGAQMQG-----API   118
                           SEQ ID NO: 208 SEQ ID NO: 209

Query   145 PREEWPELLLTVALTFGEDPRTGDLLGTVPVSTASTEEIDRYLHVARAFGFHMVYLY--S   202
               +    |+|   + ||     + | +|   | +  |   |   ||  |||   |
Sbjct   119 VKRYGLEVLPLGYIIVGEGGAVSIVSYTRPLPFAKPEVVAAYALAAEYMGFQFVYLEGGS   178
            SEQ ID NO: 210

SEQ ID NO: 211
Query   203 RNEHVPPEVVRHFRKGLGPDQVLFVSGNVRSGRQVTEYLDSGADYVGFAGALEQPD       258
            | |||++|+   ||+      |  |  +|| |     +|||  +   +|+ +
Sbjct   179 GGEPVPPKIVKMV-KGV-TTLPLIVGGGIRSPEVAKELAKAGADIIVTGTIVEESE       232
                          SEQ ID NO: 212
```

These enzymes couple either $C_{20}$ or $C_{25}$ isoprene chains to sn-glycerol-1-phosphate via an ether link, thus yielding the first intermediate to archaeal membrane lipids (Nemoto 2003, Soderberg 2001, Tachibana 2000). As well as GGGPSs, moeO5 also contains a so called phosphate-binding enzymes domain (COG1646) which is related to the PcrB-FMN domain. PcrB-like protein encoding genes are also present in bacterial genomes; however, their functions remain unknown. Sequence similarity between moeO5 and GGGPSs, and the structural resemblance between the product of GGGPS activity and moenocinol-phosphoglycerate suggests that phosphoglycerate is incorporated into moe A via a moeO5-assisted transfer of either moenocinol pyrophosphate or its precursor to phosphoglycerate. The possibility cannot be excluded, at this point, that phosphoglycerate (unit G) is attached to the sugar (unit F precursor) followed by a moeO5 transfer of the isoprene chain to the F-G intermediate. Additional biochemical characterizations of moeO5 are currently underway to determine substrate preferences. The sequence analysis of moeO5 (Ostash 2007), combined with the isolation of farnesylated monosaccharide intermediates (see below), suggests that the prenylsynthase MoeO5 couples phosphoglycerate to farnesyl pyrophosphate to yield the first dedicated moe A precursor 1P (FIG. 4). This precursor is proposed to serve as the starting point for stepwise addition of the sugars.

E. Transport Genes

Four genes which meet functional criteria as components of ATP-binding cassette (ABC) transport systems have been located in moe cluster 1: moeP5, moeX5, moeD5 and moeJ5.

1. moeP5

Gene moeP5 encodes a putative ATP-binding protein (43% identity and 60% similarity) with no transmembrane domains. MoeP5 is related to DrrA-like family of ATP-ases (Kaur 1997) involved in drug resistance and lipid transport. The nucleotide and polypeptide sequences are shown in Tables 63 and 64 respectively. A sequence alignment between moeP5 and the closest homolog identified in the BLAST search is shown in Table 65.

TABLE 63

DNA Sequence of moeP5.

ATGGGCCATTCCGTCGGTGCCCGAGAGGGGTACCACGGCATGTCCGAGCC

CGCCGACCGCAAGATTCTCCTGCAGGCGCGCGGCGTCGTGAAACGCTACA

AGCGCCGCCGCGTCCTGACCGGGGTCGATCTTGTCGTGCACGCGGGCGAG

GTCGCCGCGATCGTCGGCAGCAACGGGACGGGCAAGTCCACCCTGCTCAA

GATCTGCGCCGGTCTGCTCTCCCCCGACAAAGGACGGGTCACCGTCTCCG

GCCACCTCGGCTACTGCCCGCAGAACGCGGGGGTCATGGGCTTCCTGACC

CCCCGGGAGCACTTCACCCTCTTCGGCACCGGCCGGGGCCTGAGCCGCCG

GGAGTCCGACCGCCGCGGCCGGAGACTCGCGGGAGAGCTCGACTGGGCCC

CCGCGGAGGGCGTCCTTGCCAAGGACCTGTCGGGAGGAACCCGCCAGAAG

CTGAACGTCGTCCTGTCGGCCCTGGGAGACCCGGACCTGCTGCTGCTCGA

CGAGCCCTACCAGGGCTTCGACCACGGCTCCTACGTGGACTTCTGGCAGA

GCGTCTGGGAGTGGCGCGAGGCGGGCAAGGCCGTCGTCGTGGTGACGCAC

TABLE 63-continued

DNA Sequence of moeP5.

ATGCTCAACCAGCTCGACCGGGTGGACCAGGTGCTGGACCTCACCCCCGG

CAAAGGAAGGGGCAACCGATGA (SEQ ID NO: 22)

TABLE 64

Amino Acid Sequence of moeP5

MGHSVGAREGYHGMSEPADRKILLQARGVVKRYKRRRVLTGVDLVVHAGE

VAAIVGSNGTGKSTLLKICAGLLSPDKGRVTVSGHLGYCPQNAGVMGFLT

PREHFTLFGTGRGLSRRESDRRGRRLAGELDWAPAEGVLAKDLSGGTRQK

LNVVLSALGDPDLLLLDEPYQGFDHGSYVDFWQSVWEWREAGKAVVVVTH

MLNQLDRVDQVLDLTPGKGRGNR (SEQ ID NO: 45)

TABLE 65

Sequence Homology of moeP5 gi|89319945|gb|EAS11435.1| ABC transporter related [*Mycobacterium flavescens* PYR-GCK]
Length = 243
Score = 120 bits (301), Expect = 5e−26
Identities = 79/180 (43%), Positives = 105/180 (58%), Gaps = 0/180 (0%)
Frame = +1

```
          SEQ ID NO: 213
Query 115 LTGVDLVVHAGEVAAIVGSNGTGKSTLLKICAGLLSPDKGRVTVSGHLGYCPQNAGVMGF 294
          |  ||||  +  ||| +|  ||+||||++||   |+|  |  ||  ||||||     |
Sbjct  46 LRGVDLTLQPGEVVGLVGENGSGKSTIMKILVGELAPDAGTVVRSGVLGYCPQQPVVYER 105
          SEQ ID NO: 214
Query 295 LTPREHFTLFGTgrglsrresdrrgrrlagELDWAPAEGVLAKDLSGGTRQKLNVVlsal 474
          ||  ||  ||    ++          |  |   |  |  ||||  |||+ |+ |
Sbjct 106 LTCDEHIELFARAYRMTHEGERRARRDLYEALGFERYAGTRADRLSGGTLAKLNLTLAML 165

Query 475 gdpdlllldEPYQGFDHGSYVDFWQSVWEWREAGKAVVVVTHMLNQLDRVDQVLDLTPGK 654
          || +||||||  |||   +|+  ||   |+  ++|++++|  +     |+++ |   |+
Sbjct 166 ADPQVLLLDEPYAGFDWDTYLKFWDLVARRRDDGRSVLIISHFVADEHRFDRIVKLCDGR 225
```

Based on the studies of the present invention, it is propose that the polypeptide encoded by the moeP5 gene is a ABC transporter ATP-binding protein (Table 4).

2. moeX5

Downstream of the moeP5 gene is the moeX5 gene. The putative translation product shows homology to the N-terminal half of predicted bacterial membrane proteins (26% identity and 40% similarity). The nucleotide and polypeptide sequences are shown in Tables 66 and 67, respectively. A sequence alignment between moeX5 and the closest homolog identified in the BLAST search is shown in Table 68. Using topology prediction program TMHHM, 6 transmembrane helices were identified in the moeX5 protein. It is assumed that the moeP5 and moeX5 proteins are two elements of a transport system in which moeX5 is transporter and moeP5 energizes the transport via ATP hydrolysis.

TABLE 66

DNA Sequence of moeX5.

ATGACGGCCACCCTGCGGATGGCGGAGATGACCTTCCGCGAACTGCTGCG

CCGGCGGGGCGTGCTGGGCCTGCTGCTCCTGGTCCCGCTCGTCTTCTACC

TCGGGCGTTACGACCAGACCGGCCAGGCGGTCCGGTTCGCCAGCCTCGGG

GTGGGCTTCGCGGTCAGCGCCGCGGCCCTCTTCTCCGCGGTCGGCGGCCG

GGAGATCGAACCGCTCCTGGCCCTCTCCGGGTTCCGCCCGCTCCAGCTCT

TCCTGGGCCGCCTGCTGGCCCTCCTCACCGCCGGCATGGGCGTGTCCGCC

CTCTACGCCGTGATCATCCTGGTCGGGCAGGACGTGGCGCACCCGCGGGC

CGTCGCGGTGGAACTGGCGCTGACCACACTGGTGGCGGTGCCGCTGGGAC

TGCTGCTCGGGGCGGCCGTGCCACGGGACATGGAGGGCGCCCTGCTGCTG

ATCTCCGTCATCGGCGCCCAGATGGTGATGGATCCGGCCAAGGATTCGGC

CAAGGTGCTTCCCTTCTGGTCGACCCGGGAGATCATCACCTACGCGGTCG

ACGGCGCGGACAGCGGGTCGTTCGACTCCGGGGTGGCCCACGCCGTCGGA

GTGACGCTGCTGCTGGTCGCGGTGAGCGGTTGCGTGACGGCGGGCCGATT

GCGCCGCCGGCGCCATCTGCAATTCGCGTGA (SEQ ID NO: 23)

TABLE 67

Amino Acid Sequence of moeX5

MTATLRMAEMTFRELLRRRGVLGLLLLVPLVFYLGRYDQTGQAVRFASLG

VGFAVSAAALFSAVGGREIEPLLALSGFRPLQLFLGALLALLTAGMGVSA

LYAVIILVGQDVAHPRAVAVELALTTLVAVPLGLLLGAAVPRDMEGALLL

ISVIGAQMVMDPAKDSAKVLPFWSTREIITYAVDGADSGSFDSGVAHAVG

VTLLLVAVSGCVTAGRLRRRRHLQFA (SEQ ID NO: 46)

TABLE 68

Sequence Homology of moeX5 gb|EAS99725.1| putative ABC transporter membrane protein [*Mycobacterium* sp. KMS]
Length = 500
Score = 55.5 bits (132), Expect = 2e−06
Identities = 63/237 (26%), Positives = 96/237 (40%), Gaps = 20/237 (8%)

```
              SEQ ID NO: 215                              SEQ ID NO: 216
Query    4    TLRMAEMTFRELLRRRGVLGLLLLVPLVFYLGR-----------YDQTGQAVRFASLG--     50
              || +     + +|    | +|+|||||| |              +|| | + |+ |
Sbjct   12    TLLLTRSFITDYVRNPVNLIMLILVPLVFVLVAAGSIADAMELLQGRTGAATQTATSGWA    71
              SEQ ID NO: 217
                                                          SEQ ID NO: 218
Query   51    VGFAVSAAALFSAVGGREIEPLLALSGFRPLQLFLGRL-LALLTAGMGVSALYAVIILVG    109
              ||    | |      |  | + | |+|   +|    |   || ||+ |||+      +
Sbjct   72    AGFLSGLAMYFQIRSARRADKRLQLAGLPAARLLAARAGTGLLMAGL-VSAVALAALAAR    130
                                                               SEQ ID NO: 219

Query  110    QDVAHPRAVAVELALTTLVAVPLGLLLGAAVPRDMEGALLLISVIGAQMVMDPAKDSAK-    168
              + +|   | |    +   |+ + +| |+|| +   + ||++++ +     + + ||
Sbjct  131    TGIDNPARVIVGTLMFALIYLAIGALVGAVIADPVNGAVIILLIWMIDVFVGPAGSGGDY    190

SEQ ID NO: 220          SEQ ID NO: 221
Query  169    VLPFWSTREIITYAVDGADSGSF----DSGVAHAVGVTLLLVAVSGCVTAGRLRRRR      221
              |   |    +|  + |   |        | |||    |  | || +     |   |||
Sbjct  191    VATRWFPTHFVTLWMVGTPSHHAGRLGDLGVASVWMVGALAVAGTVVSAGSRTGRRR     247
```

Based on the studies of the present invention, it is propose that the polypeptide encoded by the moeX5 gene is a ABC transporter membrane protein (Table 4).

3. moeD5 and moeJ5

Two other genes, moeD5 and moeJ5, encode proteins that both contain a nucleotide binding domain in the C-terminal region, and transmembrane segments (TMS) in the N-terminal half (5 TMS in moeJ5 and 6 TMS in moeD5 according to TMHHM program).

MoeD5 and moeJ5 are 40.9% similar to each other at the amino acid level, and display homology to putative and known ABC transporters/ABC transporter ATP binding proteins (41% identity and 55% similarity). The nucleotide and polypeptide sequences of moeD5 are shown in Tables 69 and 70, respectively. A sequence alignment between moeD5 and the closest homolog identified in the BLAST search is shown in Table 71. The nucleotide and polypeptide sequences of moeJ5 are shown in Tables 72 and 73, respectively. A sequence alignment between moeJ5 and the closest homolog identified in the BLAST search is shown in Table 74. The conserved domain search showed that moeD5 and moeD5 are most similar to transporters from DPL and MRP families involved in drug, polypeptide, lipid and anionic substances transport (Chang 2003). In its domain architecture, the moeD5 translation product is similar to the well studied *E. coli* ABC transporter MsbA which also contains only one 6 TMS transmembrane domain and 1 nucleotide binding domain (McKeegan 2003). It is possible that a moeD5/moJ5 heterodimer functions as an ATP-dependent pump. Additionally or alternatively, two ABC transporter systems may be involved in moe A efflux and/or its intramycelial transport. Multiple transport mechanisms are common for many organisms producing different antibiotics (Wilson 1999, Mendez 2001), in particular peptidoglycan biosynthesis inhibitors (Sosio 2003).

TABLE 69

DNA Sequence of moeD5.

```
                                                              GTGCTGCGC
GGCTCGGCCCGCACCTACTGGACCCTCACCGGTCTGTGGGTCCTGCTGCG
GGCGGGAACCCTGGTGGTGGGCCTGCTGTTCCAGCGGCTGTTCGACGCGC
TGGGCGCGGGCGGGGGCGTGTGGCTGATCATCGCGTTGGTGGCCGCGATC
GAGGCGGGACGGCTGTTCCTCCAGTTCGGCGTGATGATCAACAGGCTGGA
GCCGCGGGTCCAGTACGGCACCACGGCGCGGCTGCGGCACGCCCTGCTGG
GATCGGCCCTGCGCGGGTCGGAGGTGACGGCCCGCACCAGCCCCGGCGAG
TCCCTGCGAACGGTGGGCGAGGACGTCGACGAGACGGGGTTCTTCGTCGC
CTGGGCGCCGACGAACCTCGCCCACTGGCTGTTCGTCGCCGCGTCGGTCA
CGGTGATGATGCGGATCGACGCCGTGGTCACCGGCGCCCTCCTCGCCCTC
CTCGTCCTGCTGACGCTGGTCACCGCGCTGGCCCACAGCCGGTTCCTGCG
GCACCGGCGGGCCACCCGGGCCGCGTCCGGGGAGGTGGCGGGAGCCCTGC
GGGAGATGGTGGGCGCGGTGGGCGCGGTGCAGGCCGCCGCCGCCGAGCCG
CAGGTCGCCGCGCACGTCGCCGGGCTGAACGGCGCCCGTGCCGAAGCCGC
GGTGCGGGAGGAGCTGTACGCCGTCGTCCAGCGCACGGTGATCGGCAACC
CGGCCCCGATCGGGGTCGGCGTGGTGCTGCTGCTGGTCGCGGGGCGGATG
GACGAGGGGACCTTCAGCGTCGGCGATCTCGCCCTGTTCGCCTTCTACCT
GCAGATCCTGACCGAGGCCCTGGGGTCGATCGGCATGCTGTCCGTGCGGT
TGCAGCGGGTCTCGGTGGCGCTCGGCCGGATCACCAACAACCTCGGCTGC
CGGCTGCGGCGGTCCCTGGAGCGGGCCAGTCCGCCGATCGCGTCCGACGC
GCCGGGAGGGACCGGCGAGGGGGCCGCCGCCCCGGACGCCGGGCCGGAGC
CCGCCCCGCCCCTGCGGGAACTGGCCGTGCGCGGGCTGACGGCCCGCCAC
```

TABLE 69-continued

DNA Sequence of moeD5.

CCCGGGGCGGGGCACGGCATAGAGGACGTGGACCTGGTGGTGGAGCGGCA
CACCGTCACCGTGGTCACCGGCCGGGTCGGTTCCGGCAAGAGCACCCTGG
TCCGGGCCGTCCTCGGACTGCTCCCGCACGAGCGGGGCACCGTGCTGTGG
AACGGCGAACCGATCGCCGACCCCGCGTCGTTCCTGGTGGCGCCGCGCTG
CGGGTACACCCCGCAGGTCCCGTGTCTGTTCAGCGGGACGGTGCGGGAGA
ACGTCCTGCTGGGCCGGACGGCGCGGCCTTCGACGAGGCCGTGCGCCTC
GCCGTGGCGGAGCCCGACCTGGCGGCGATGCAGGACGGCCCGGACACCGT
GGTGGGCCCGCGGGGCCTGCGCCTCTCGGGCGGGCAGATCCAGCGGGTCG
CGATCGCCCGCATGCTGGTCGGCGACCCCGAACTCGTGGTGCTGGACGAC
GTCTCCAGTGCCCTGGACCCGGAGACCGAGCACCTGCTGTGGGAGAGGCT
GCTGGACGGGACGCGGACCGTGCTCGCGGTCTCCCACCGGCCCGCTCTGC
TGCGCGCGGCCGACCGCGTGGTGGTGCTCGAGGGCGGGCGGGTGGAGGCC
TCGGGCACCTTCGAGGAGGTCATGGCGGTCTCCGCCGAGATGGGCCGGAT
CTGGACGGGTGCGGGTCCGGGGGGCGGGACGCCGGGCCCGCTCCGCAGA
GCCCTCCCGCGGGGTGA (SEQ ID NO: 24)

TABLE 70

Amino Acid Sequence of moeD5

(SEQ ID NO: 47)
VLR

GSARTYWTLTGLWVLLRAGTLVVGLLFQRLFDALGAGGGVWLIIALVAAI

EAGRLFLQFGVMINRLEPRVQYGTTARLRHALLGSALRGSEVTARTSPGE

SLRTVGEDVDETGFFVAWAPTNLAHWLFVAASVTVMMRIDAVVTGALLAL

LVLLTLVTALAHSRFLRHRRATRAASGEVAGALREMVGAVGAVQAAAAEP

QVAAHVAGLNGARAEAAVREELYAVVQRTVIGNPAPIGVGVVLLLVAGRM

DEGTFSVGDLALFAFYLQILTEALGSIGMLSVRLQRVSVALGRITNNLGC

RLRRSLERASPPIASDAPGGTGEGAAAPDAGPEPAPPLRELAVRGLTARH

PGAGHGIEDVDLVVERHTVTVVTGRVGSGKSTLVRAVLGLLPHERGTVLW

NGEPIADPASFLVAPRCGYTPQVPCLFSGTVRENVLLGRDGAAFDEAVRL

AVAEPDLAAMQDGPDTVVGPRGLRLSGGQIQRVAIARMLVGDPELVVLDD

VSSALDPETEHLLWERLLDGTRTVLAVSHRPALLRAADRVVVLEGGRVEA

SGTFEEVMAVSAEMGRIWTGAGPGGGDAGPAPQSPPAG

TABLE 71

Sequence Homology of moeD5 ref|YP_075256.1| ABC transporter ATP-binding protein [*Symbiobacterium thermophilum* IAM 14863]
Length = 590
Score = 372 bits (956), Expect = 2e-101
Identities = 233/559 (41%), Positives = 313/559 (55%), Gaps = 22/559 (3%)

```
              SEQ ID NO: 222         SEQ ID NO: 223
Query    24   LVVGLLFQRLFDALGAGGGV----WLIIALVAAIEAGRLFLQFGVMINRLEPRVQYGTTA   79
              +|  |||  |   ||      |   ||||+  |    |+       |
Sbjct    33   VVPGLLTQAFFDRLTGAAPVALDPWAIIALLMAAAVARVAALAAGFFASATGRESMANLL   92
                        SEQ ID NO: 251

SEQ ID NO: 224
Query    80   RLRHALLGSALRGSEVTARTSPGESLRTVGEDV---DETGFFVAWAPTNLAHWLFVAASV   136
              | |+ |         ||||+| + +|| +||  |+ |    +       |    |  ++
Sbjct    93   R-RNVLERILEMPGAAALPESPGEALNRLRDDVLHAEETADFMLDV---VGQTTFAAVAL   148
                        SEQ ID NO: 234                 SEQ ID NO: 225

Query   137   TVMMRIDAVVTGALLALLVLLTLVTALAHSRFLRHRRATRAASGEVAGALREMVGAVGAV   196
              ++++|||  +|   + +||            |++||  |+ |     +| +|  ||
Sbjct   149   SMLLRIDARLTVLVFLPLALVLVVTRAVGRRILQNRRWSREATARVTALIAELFASVQAV   208

Query   197   QAAAAEPQVAAHVAGLNGARAEAAVREELYAVVQRTVIGNPAPIGVGVVLLLVAGRMDEG   256
              |  ||  +| ||+ || |    |   |  +    ++    |  +|   |++|||
Sbjct   209   QVAGAESRVVAHLRRLNDERRRAMVADRLLTQVLESIALNASSVGTGLILLLGARTMATG   268

SEQ ID NO: 226
Query   257   TFSVGDLALFAFYLQILTEALGSIGMLSVRLQRVSVALGRITNNL-GCRLRRSLERASPP   315
              +|+|+  |||  +|  +  +         ++   ||   |+    |     ||||||
Sbjct   269   QFTVGEFALFVYYLGYVADFTHFAGRWLALYRQAGVAKDRLLALLQGAPPTRLLRRTEIP   328

Query   316   IASDAPGGTGEGAAAPDAGPEPAPPLRELAVRGLTARHPGAGHGIEDVDLVVERHTVTVV   375
              +         |+  | ||||||   |||+ +|   +  + +||+ | | |     +|+
Sbjct   329   LRGPVP-------VPPEPPPPPAEPLRELRTEGLTYRYPDSGRGIEGVSLTIPRGSFTVI   381
                                                    SEQ ID NO: 227

Query   376   TGRVGSGKSTLVRAVLGLLPHERGTVLWNGEPIADPASFLVAPRCGYTPQVPCLFSGTVR   435
              ||||||||||+|+ ++|||  +  |||||||| ||   |+| ||  ||||| ||||||+
Sbjct   382   AGRVGSGKTTLLRVLMGLLPAQAGTVYWNGEPVADPGSFMVPPRCAATPQVPILFSGTLA   441
```

TABLE 71-continued

Sequence Homology of moeD5

```
                    SEQ ID NO: 228
Query  436 ENVLLGRDG--AAFDEAVRLAVAEPDLAAMQDGPDTVVGPRGLRLSGGQIQRVAIARMLV  493
           ||+ +|    |    ||   || ||| |+|| +| ||  ||+|||||+|| |  ||| +
Sbjct  442 ENIRMGLDATEAEVAAAVYDAVLERDLAGMEDGLETQVGARGVRLSGGQVQRTAAARMFL  501

SEQ ID NO: 228
Query  494 GDPELVVLDDVSSALDPETEHLLWERLL-DGTRTVLAVSHRPALLRAADRVVVLEGGRVE  552
           |||+++||+|||| ||| +||||| |   |||| ||| ||+++|+ |||
Sbjct  502 RRPELLIMDDLSSALDVETEQILWERLFQRDVTCLVVSHREAALRRADQIILLKDGRVV  561

Query  553 ASGTFEEVMAVSAEMGRIW  571
           || +|++| |||| +|
Sbjct  562 DRGTLDELLARSAEMRALW  580
```

TABLE 72

DNA Sequence of moeJ5.

CTGCGCGGTGAACGGACCGCCGTGGCGCTGCTCGCCCTCCTGGTCCCCGC
GGGGATGGGGCTCCAGCTGGTGGCGCCCTACCTGCTGCGCGGATTCATCG
ACGGGGCGCTCTCCGGCGACTCCCGGAAGACGCTGCTGGACCTCGCCGCC
TGGTCCCTGGCGGCCGCCGTCGGGACGCTCGTGGTCACCGCGGGCACCGA
GGCGCTGTCCTCACGGGTCGCCTGGCGCAGCACCAACCGGTTGCGCGCGG
ACCTGGTCGAGCACTGCCTGAGCCGGCCGCCGGGCTTCTACCGCAAGCAT
CCGCCCGGCGAACTCGTCGAGCGGATGGACGGCGACGTCACCCGGCTCGC
CGCGGTGATGTCGACGCTGCTGCTGGAACTGCTGGCGCAGGCACTGCTGA
TCGTCGGCATCCTCGTCGCCCTGTTCCGGCTGGAATGGCGGCTGGCCCTG
GTGGTCGCCCCGTTCGCGGCAGGCACCCTCCTGCTGCTGCGGACCCTGGT
GGGCCGCGCCATGCCCTTCGTCACCGCGCGGCAGCGGGTCGCGGCGGACC
TGCAGGGCTTCCTCGAGGAGCGCCTCGCGGCGGCGGAGGACCTCCGCGTC
AACGGGGCCTCGCGGTACACCCTGCGGGAACTCGGCGACCGGCAGGACGA
CCTGTACCGGAAGGCCCGCGACGCGGCGCGGGCCTCGGTCCGCTGGCCCG
CCACGGTGCAGGGCCTGTCCGCCGTCAGCGTCGTCCTGGCCCTGGCGGTC
AGCGCCTGGCTGCACGCCCGCGGACAGCTCTCCACGGGGACGGCCTTCGC
CTCCCTGTCCTACGCGATGCTGCTGCGCCGCCCCCTGCTCGCGGTCACCA
CCCGCTTCCGCGAACTCGAGGACGCCGCCGCGAGCGCCCAGCGGCTGAGG
GACCTGCTGGGCCACGGGACGGCGGCGCCCCGCACGGGACGCGGGACGCT
GCCGGCCGGACTGCCCGGAGTCCGCTTCGACGGGGTCTCCTTCGGCTACG
AGCCCGACGAGCCGGTGCTGCGGGACGTCTCCTTCACCCTGCGCCCCGGC
GAACGCCTCGGCGTCGTGGGACGCACCGGCAGCGGCAAGTCCACCGTGGT
CCGGCTGCTGTTCGGGCTCCACCACCCGGGGGCGGGCTCGGTGTCGGCAG
GCGGCCTGGACCTGACGGAGATCGATCCCCGGGCGCTGCGCAGCCGGGTC
GCGCTGGTCACCCAGGAGGTGCACGTCTTCCACGCCTCGCTGCGGGACAA
CCTCACCTTCTTCGACCGCTCCGTCCCCGACGACCGGCTGCGCGCCGCTC
TCGGCGAGGCCGGGCTCGGCCCCTGGCTGCGCACCCTGCCCGACGGTCTG
GACACGCCGCTCGGCGCCGGGGCCCGCGGCATGTCCGCGGGCGAGGAGCA
GCAGCTCGCGCTGGCCAGGGTGTTCCTGCGCGATCCGGGGCTGGTCCTGA

TGGACGAGCCGACGGCCCGGCTGGATCCGTACAGCGAGCGGCTCCTGATG
CCCGCGCTGGAGCGGCTGCTCGAGGGCCGCACCGCCGTCGTGGTGGAGCA
CCGCCCGCACCTGCTCCGGAACGTCGACCGGATCCTGGTGCTGGAGGAGG
GGAAGGTCGCCGAGGAGGGGGAGCGGAGGGTCCTCGCCGCCGATCCCGGG
TCGCGCTTCCACGCACTCCTCCGCACGGCCGGAGCCACCCGGTGA (SEQ ID NO: 25)

TABLE 73

Amino Acid Sequence of moeJ5

LRGERTAVALLALLVPAGMGLQLVAPYLLRGFIDGALSGDSRKTLLDLAA
WSLAAAVGTLVVTAGTEALSSRVAWRSTNRLRADLVEHCLSRPPGFYRKH
PPGELVERMDGDVTRLAAVMSTLLLELLAQALLIVGILVALFRLEWRLAL
VVAPFAAGTLLLLRTLVGRAMPFVTARQRVAADLQGFLEERLAAAEDLRV
NGASRYTLRELGDRQDDLYRKARDAARASVRWPATVQGLSAVSVVLALAV
SAWLHARGQLSTGTAFASLSYAMLLRRPLLAVTTRFRELEDAAASQRLR
DLLGHGTAAPRTGRGTLPAGLPGVRFDGVSFGYEPDEPVLRDVSFTLRPG
ERLGVVGRTGSGKSTVVRLLFGLHHPGAGSVSAGGLDLTEIDPRALRSRV
ALVTQEVHVFHASLRDNLTFFDRSVPDDRLRAALGEAGLGPWLRTLPDGL
DTPLGAGARGMSAGEEQQLALARVFLRDPGLVLMDEPTARLDPYSERLLM
PALERLLEGRTAVVVEHRPHLLRNVDRILVLEEGKVAEEGERRVLAADPG
SRFHALLRTAGATR (SEQ ID NO: 48)

TABLE 74

Sequence Homology of moeJ5 gi|51892564|ref|YP_075255.1| ABC transporter ATP-binding protein
[*Symbiobacterium thermophilum* IAM 14863]
Length = 582
Score = 375 bits (963), Expect = 3e-102, Method: Composition-based stats.
Identities = 249/545 (45%), Positives = 335/545 (61%), Gaps = 5/545 (0%)

```
              SEQ ID NO: 230         SEQ ID NO: 231
Query    19   MGLQLVAPYLLRGFID---GALSGDSRKTlldlaawslaaavgtlvvtagtEALSSRVAW    75
              +||||+  |  +||  |+|     |  +||     +|+ ||   +  |     ||     ||  |+|
Sbjct    34   IGLQLINPQILRRFLDTAAGEVSGGP--SLVTLALAFIGVAFAVQAVTVLARYLSESVSW    91
              SEQ ID NO: 232         SEQ ID NO: 233

Query    76   RSTNRLRADLVEHCLSRPPGFYRKHPPGELVERMDGDVTRLAAVMSTlllellaqallIV   135
              |+||  |||||  ||||       ||+++   |||+|||+||||  |+     |  + +||     +|++
Sbjct    92   RATNELRADLAEHCLRLDLGFHKRRTPGEMVERIDGDVTALSQFFSQLFIGVLANLVLML   151

Query   136   GILVALFRLEWRLALVVAPFaagtllllrtlvgrAMPFVTARQRVAADLQGFLEERLAAA   195
              ||||  |||  +||   + +   ||| ||  +|   +   ++|   |  +++ +|+    |+|    | |+
Sbjct   152   GILVLLFREDWRAGVAMTLFAAFTLWVLGRIHELSVPVWTRQRQASAEFYGYLGEVLSGT   211

Query   196   EDLRVNGASRYTLRELGDRQDDLYRKARDAARASVRWPATVQGlsavsvvlalavsaWLH   255
              | +|   ||   + |            | ||+    |+           +|     ||    |+|   |||+
Sbjct   212   EAIRAGGARGWALHRFLRNVQDFYRQNLAASMMFWLTWSTSIVTFAVGAALSLGVGAWLY   271

Query   256   ARGQLSTGTAFASLSYAMLLRRPLLAVTTRFRELEDAAASAQRLRDLLGHGTAAPRTGRG   315
              ||| ++ ||  +       |   ||||+    +  |    +||+  |  |+ +|+ +|       |  |
Sbjct   272   ARGGVTVGTVYLLFHYTELLRRPIEQIRTHLQELQRAGAAVERVEELFAQRTRVPDGPGR   331

Query   316   TLPAGLPGVRFDGVSFGYEPDEPVLRDVSFTLRPGERLGVVGRTGSGKSTVVRLLFGLHH   375
              ||  |    |   |||| |||   ||||||    +  |||  +|++||||||||||+  |||   +
Sbjct   332   ALPPGPLSVELVGVSFAYEPGAPVLRDVDVRIEPGEVVGLLGRTGSGKSTLARLLLRFYD   391

Query   376   PGAGSVSAGGLDLTEIDPRALRSRVALVTQEVHVFHASLRDNLTFFDRSVPDDRLRAALG   435
              |  |||    ||+|  |       +|+||    |||+  +|  ++|||||||    |  ||   |
Sbjct   392   PDAGIVRLGGVDLREATVAGVRARVGFVTQDVQLFAGTVRDNLTFFSPEVSDGRLLAVLE   451

Query   436   EAGLGPWLRTLPDGLDTPLGAGARGMSAGEEQQLALARVFLRDPGLVLMDEPTARLDPYS   495
              | ||||||++||  ||||||  +|    |+||||  |  ||||||||||++|| ++|||  +
Sbjct   452   ELGLGPWLQSLPQGLDTPLESGGGGLSAGEAQLLALARVFLADPGLVILDEASSRLDPAT   511

Query   496   ERLLMPALERLLEGRTAVVVEHRPHLLRNVDRILVLEEGKVAEEGERRVLAADPGSRFHA   555
              |  |+  |++|||||||  +++ ||     +    |||+|+|+|  |  |      ||||| |||
Sbjct   512   ESLVERAVDRLLEGRTGIIIAHRLATVERADTILILEDGRVVEYGPRAELAADPASRFFR   571

Query   556   LLRTA   560
              +||
Sbjct   572   MLRAG   576
```

Based on the studies of the present invention, it is propose that the polypeptide encoded by the moeD5 and moeJ5 genes are ABC transporters (Table 4).

G. Regulatory Genes

Genes governing the production of early building blocks of antibiotics are usually part of gene cluster for a given secondary metabolite. For example, NDP-hexoses, the first intermediates to many glycosylated antibiotics are produced from hexose-1-phosphate and NTP by dedicated nucleotidyltransferases encoded within gene clusters for biosynthesis of secondary metabolites (Kudo 2005, Luzhetskyy 2005, Murrell 2004). The association of genes for biosynthesis of isopentenyl pyrophosphate (IPP) and those for certain isoprene-derived antibiotics has also been recently demonstrated (Durr 2006, Kawasaki 2006, Dairi 2005). Genes for activated sugar and IPP biosynthesis were not identified within the moe clusters. This, along with the absence of dedicated regulatory moe genes (as yet, no traditional regulatory sequences were identified) poses intriguing questions about temporal control of enzyme "building blocks" apparently required for Moe A biosynthesis in *S. ghanaensis*.

It was found that the moeA5, moeO5, moeR5 and moeE5 genes contain codon "TTA" (2 were identified in moeE5). In the *S. coelicolor* A3(2) genome, only 145 genes out of 7825 possess TTA codons (Chater 2006).

The regulatory role of the TTA codons in genes for transcriptional activators of antibiotic production has been established (Rebets, 2006, Bibb 2005). For example, the gene for leucil tRNAUUA is expressed efficiently in late stationary phase of growth in *S. coelicolor*, thus exerting temporal control over the expression of antibiotic biosynthesis genes (Leskiw 1993). The moe clusters appears to lack a regulatory genes containing TTA codon(s), while the TAA condon is present in structural moe genes. It is likely that the different efficiency of codon TTA translation in different growth phases is an important mechanism of the temporal regulation of moe A production. However, mistranslation of TTA codons (Trepanier 2002) can negate the importance of such a suggested regulatory mechanism.

One of the unusual features of the moe clusters is the absence of pathway-specific regulatory genes. Rare TTA codons present in several moe genes were speculated to control the onset of moe A production (Ostash 2007). Mutations in the gene bldA, which encodes LeutRNAUUA, are known to affect many processes in streptomycetes, and antibiotic production is one of them (Chater 2006). It is logical to suppose that the regulatory effect of LeutRNAUUA is exerted at the translation level—i.e., that a scarcity of this tRNA until late in the cell cycle might limit the expression of TTA-containing genes. However, the pleiotropic nature of bldA mutants (Hodgson 2000), the presence of TTA codons mainly in regulatory genes and, finally, the mistranslation of TTA codons (Trepanier 2002) may lead to overinterpretation of the role of bldA gene. In this respect, moe cluster 1 is a rare case in which several TTA codons are located within structural genes, making it easier to link the bldA gene to antibiotic production.

To examine whether bldA is important for moe A biosynthesis, S. lividans J1725 carrying a mutated bldA gene (Leskiw 1991) was used. A bioassay of methanol extracts from the strains shows that J1725 coexpressing moeno38-1 and plasmid pIJ584, which carries the intact bldA gene, produced compound 19 (FIG. 14, spot 3) whereas a moeno38-1+ control strain carrying the empty vector pIJ303 did not (FIG. 14, spot 2). Evidently, the 1 gene regulates moe A production. Expression of pIJ584 in the βmoeN5 strain did not, however, enhance the production of moe A intermediate 23, as judged by LC-MS and bioassays. This experiment suggests that increasing bldA expression above wild type levels does not produce a concomitant increase in antibiotic expression, implying that other factors limit the production of moenomycins. The identity of 19 produced in 38-1$^+$pIJ584$^+$ JI725 strain was also confirmed by MS analysis (data not shown).

The wild-type S. ghanaensis strain produces moe A at a very low level, which complicates the analysis of metabolites produced by wild-type and recombinant S. ghanaensis strains. Thus, a means to increase moe expression is useful. The moe biosythesis-related genes of the invention are useful for the enrichment (i.e., overpression of moe and moe precursor molecules. In one embodiment, the invention provides a cell (prokaryotic or eukaryotic) which is genetically engineered to express one or more moe biosynthesis-related polypeptides encoded by the moe biosynthesis related genes of the invention as a means of expressing moe, a moe precursor molecule or chemical derivative thereof. In one embodiment the cell comprises a vector encoding one or more one or more moe biosynthesis-related genes of the invention. Methods useful for cloning and expression of bacterial genes in both prokaryotes and eukaryotes are well recognized in the art.

Regulatory genes (e.g., repressors, activators) may be identified by methods described above and by methods known in the art. As many bacterial genes involved in antibiotic production are expressed as operons (a cluster of structural genes with shared promoter or operator and terminator sequences), it is possible that a single protein or set of proteins may be responsible for the coordinated expression or repression of the entire moe cluster 1 and/or moe cluster 2 genes. Numerous such regulatory genes have already been identified in various antibiotic producing actinomycetes (e.g., redD involved in undecylprodigiosin biosynthesis regulation; actII-orf4 involved in actinorhodin biosynthesis regulation; dnrI involved in daunorubicin biosynthesis regulation; srmR involved in spiramycin biosynthesis regulation; strR involved in streptomycin biosynthesis regulation; ccaR involved in cepamycin and clavulanic acid biosynthesis regulation; mtmR, involved in mithramycin biosynthesis regulation). See Lombo, et al., 1999.

For example, an in silico search for homologues of such known bacterial repressors and activators, or functional regions of such known repressors and activators (e.g., DNA binding motifs) may be performed. The putative regulators may then be disrupted and moe A production (e.g., the amount of moe A) may be evaluated in the mutant. An increase in moe A production in the mutant would indicate that the putative regulator was capable of acting as a repressor of moe A production, while a decrease in moe A production would indicate that the putative regulator was capable of acting as an activator of moe A production. Additionally or alternatively, the amount (e.g., the level of expression) of individual moe gene products (either RNA or protein) may be evaluated in the regulatory mutant.

To further test the function of a putative regulatory gene, the gene could be cloned by methods described above (e.g., PCR primers could be constructed which flank the gene sequence of interest; the sequence could then be amplified, isolated, and cloned into an appropriate expression or integration vector). The gene could then be introduced into a moe-producing strain and, if cloned in a high-copy number vector or cloned in front of a strong promoter (e.g., the ermE promoter), the effects of overexpression of the putative regulatory gene could be evaluated. For example, if the putative regulator was a repressor of moe A production, overexpression would lead to a decrease, or completely abolish, moe A production. If the putative regulator was an activator, then overexpression would likely lead to an increase in moe A production, and the subsequent development of moe A over-expressing strains. (See also section V.B, below). The cloned functional copy of the gene could also be introduced into the knockout mutant to verify gene function.

V. Characterization of moe A Intermediates

A. moeGT3 Disruption

The plasmid for moeGT3 disruption pMO12 was transferred into S. ghanaensis ATCC14672 via conjugation and its homologous integration into the genome was promoted according to the described procedure (Ostash 2007). The site-specific integration of the pMO12 in the S. ghanaensis MO12 strain was confirmed via Southern analysis using DIG-labeled moeGT3 internal fragment as a probe (FIG. 15A). In the wild type strain, the moeGT3 gene resides in a 4.3-kb BamHI fragment whereas in the MO12 strain the corresponding hybridizing band is absent and a new 11-kb band is present. The latter corresponds to integration of a 7-kb pMO12 plasmid into the 4.5-kb BamHI moeGT3-containing fragment of the S. ghanaensis chromosome. Similarly, hybridization pattern of XhoI-digests of wild type and the mutant strain confirms the insertional inactivation of moeGT3 (FIG. 14A, C). Introduction of plasmid pMO14 ($P_{ermE}$-moeGT3) into MO12 strain restored moe A production.

The purified cell extracts of MO12 showed strong antibacterial activity, implying that none of the steps essential for moe A pharmacophore formation is affected in the mutant (FIG. 15B). LC-MS analysis revealed that MO12 accumulated known moenomycin $C_4$. (MmC4) as a final product (FIG. 16). This conclusion was confirmed by high-resolution mass-spectral analysis (calculated mass of negative ion of MmC4: 1418.6012 Da, observed: 1418.6016 Da). Furthermore, the strain accumulated MmC4 precursor lacking chromophore unit (calculated mass for (M–H): 1322.5801 Da; observed: 1322.5796 Da). We also observed the di- and trisaccharide fragments of MmC4 (FIG. 16), which could represent its intermediates or result from MmC4 fragmentation already in $MS^1$ experiments (such a phenomenon has been reported for moenomycins (Zehl 2006).

B. Analysis of S. lividans TK24 Strains Various Subsets of moe Genes

We performed detailed LC-MS analysis of the mixtures of moenomycins produced by the recombinant S. lividans strains. This analysis allowed us to detect and isolate the final moe A-related metabolite produced by each strain for high-resolution MS analysis (see Table 21). Certain pure compounds were also studied by MS/MS and NMR. Results of these experiments as well as the pattern of intermediates/degradation products found in the extract of recombinant strains guided our predictions of the structures of novel moenomycins as it is described below. In all cases the observed masses coincide with calculated ones for compounds shown on FIG. 4.

1. S. lividans ΔmoeN5 (Prenyltransferase Gene moeN5 Deletion in moeno38-1)

This strain accumulates two new closely related compounds 22/23 (FIG. 4) not detected in the extracts of either empty heterologous host (TK24) or other recombinant S. lividans strains. The dramatically shifted Rt of 22/23 when comparing to moe A or compound 19 is an indication of shortened lipid chain. The analysis of ΔmoeN5 extract revealed the presence of intermediates to 22/23, namely the compounds 2, 3, 5, 8, 25 (FIG. 17). The exact masses of negative ions of all aforementioned compounds coincide with calculated ones (compound 5—calculated: 943.3694 Da, observed: 943.3688 Da; 8—calculated: 986.3752 Da, observed: 943.3750 Da; 25—calculated: 1189.4546 Da, observed: 1189.4512 Da) and point to the presence of common polyprenyl chain of 15 carbons. Presence of 1072/1073 Da peak in MS² spectra of 22/23 (FIG. 18) also witness that these compounds possess pentasaccharide-phosphoglyceric acid moiety found in other moenomycins (Ostash 2007, Zehl 2006). Compounds 22/23 show the biological activity (see next section). Taking these data together, we proposed the structures of 22/23 as shown below in Formula II:

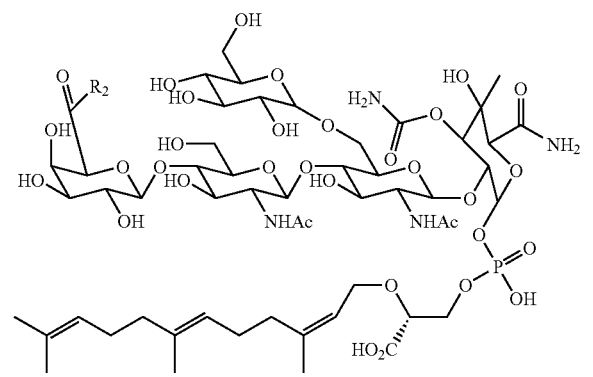

R$_2$ may be either —OH (Compound 22) or —NH$_2$ (Compound 23).

We failed to restore the production of moenomycins having C25 isoprenoid chain (e.g. 19) in ΔmoeN5 strain using several constructs where moeN5 expression was driven from constitutive P$_{ermE}$* promoter. Moreover, we revealed that moeN5 overexpression even led to decrease in 22/23 production (data not shown), pointing to the existence of as-yet-unknown regulatory mechanism governing moeN5 expression under natural conditions. Therefore we constructed plasmid pOOB63a which contains both moeO5 and moeN5 genes along with 0.6 kb moeX5-moeO5 intergenic region. We assumed that the intergenic region contains promoter responsible for expression of moeO5moeN5 operon. Indeed, introduction of pOOB63a into ΔmoeN5 strain restored the production of 19. Plasmid pMoeO5extra (contains only moeO5 under P$_{ermE}$*) did not restore the production of 19 in ΔmoeN5 strain, meaning that only gene moeN5 is responsible for the restoration of 19 production when using plasmid pOOB63a.

B. Qualitative Analysis of Antibacterial Activity of Novel Moes

We examined the bioactivity of several purified moe A intermediates described above on a B. cereus reporter strain using a disk diffusion assay. The monosaccharide intermediates had no activity, while the moenocinol-linked penta- and tetrasaccharide compounds were roughly as active as moe A itself (FIG. 19). Disaccharide 4 could not be tested due to an extremely low production level and decomposition to 2/3. Compound 22/23, which features a C15 isoprenoid chain, showed antibacterial activity at submicromolar concentrations. Neryl-moenomycin was recently shown to be biologically inactive. Other moe derivatives having a farnesyl chain may show similar activity to compound 22/23. Therefore, in one embodiment, the present invention provides moe derivatives having the following general structure.

In one embodiment, the present invention provides a moenomycin derivative having the structure:

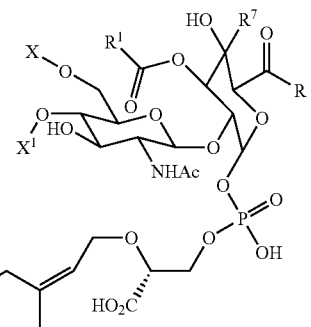

wherein

R and R$^1$ independently are selected from the group consisting of hydroxyl, and —NHR$^2$ where R$^2$ is hydrogen, alkyl, cycloalkyl, or substituted cycloalkyl;

X is hydrogen, or

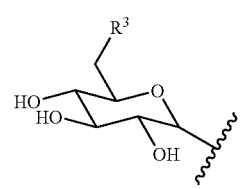

where R$^3$ is selected from the group consisting of hydrogen and hydroxyl; and

X$^1$ is hydrogen,

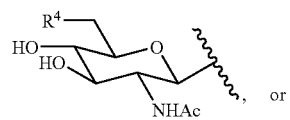

, or

-continued

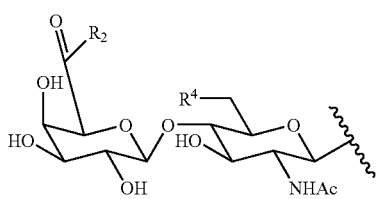

where R⁴ is selected from the group consisting of hydrogen and hydroxyl;

R⁵ is selected from the group consisting of hydroxyl, and —NHR⁶ where R⁶ is hydrogen, alkyl, cycloalkyl, or substituted cycloalkyl, and R⁷ is hydrogen or methyl, or a pharmaceutically acceptable salt, tautomer, and/or ester thereof.

In some embodiments, R and R¹ independently are —NH₂. In some embodiments, X is hydrogen. In other embodiments, X is

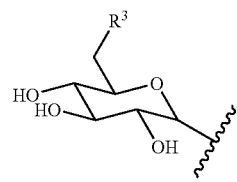

where R³ is selected from the group consisting of hydrogen and hydroxyl.

In some embodiments, X¹ is hydrogen. In other embodiments, X¹ is

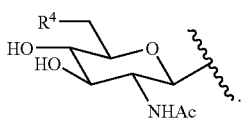

In still other embodiments, X¹ is

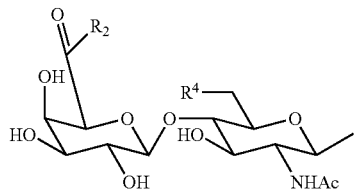

where R⁴ is selected from the group consisting of hydrogen and hydroxyl and R⁵ is selected from the group consisting of hydroxyl, and —NH₂.

In some embodiments, the structure of the moenomycin derivative is:

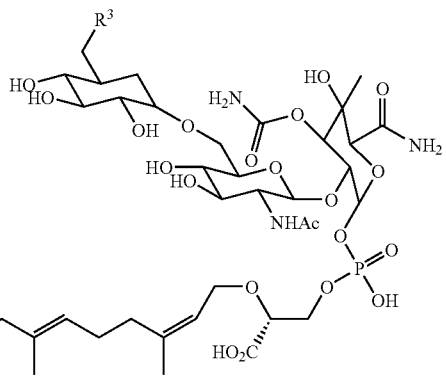

where R³ is selected from the group consisting of hydrogen and hydroxyl, or a pharmaceutically acceptable salt, tautomer, and/or ester thereof.

In some embodiments, R³ is hydrogen. In other embodiments, R³ is hydroxyl.

In some embodiments, the structure of the moenomycin derivative is:

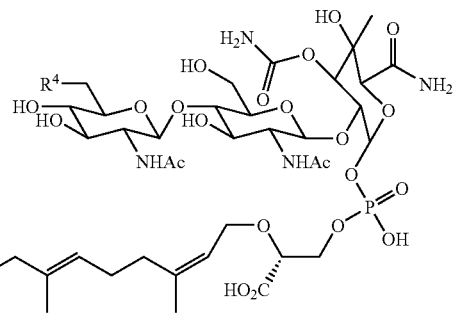

where R⁴ is selected from the group consisting of hydrogen and hydroxyl, or a pharmaceutically acceptable salt, tautomer, and/or ester thereof.

In some embodiments, R⁴ is hydrogen. In other embodiments, R⁴ is hydroxyl.

In some embodiments, the structure of the moenomycin derivative is:

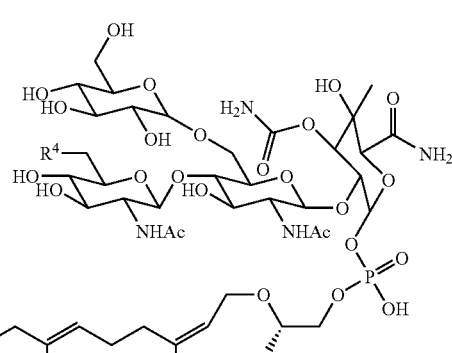

where R⁴ is selected from the group consisting of hydrogen and hydroxyl, or a pharmaceutically acceptable salt, tautomer, and/or ester thereof.

In some embodiments, $R^4$ is hydrogen. In other embodiments, $R^4$ is hydroxyl.

In some embodiments, the structure of the moenomycin derivative is:

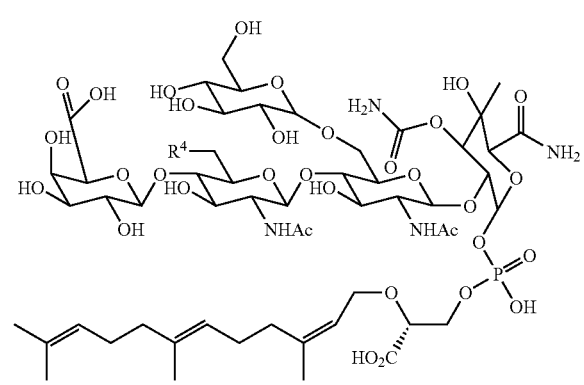

where $R^4$ is selected from the group consisting of hydrogen and hydroxyl, or a pharmaceutically acceptable salt, tautomer, and/or ester thereof.

In some embodiments, $R^4$ is hydrogen. In other embodiments, $R^4$ is hydroxyl.

In some embodiments, the structure of the moenomycin derivative is:

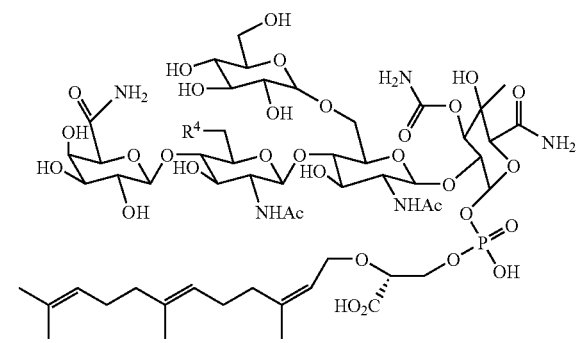

where $R^4$ is selected from the group consisting of hydrogen and hydroxyl, or a pharmaceutically acceptable salt, tautomer, and/or ester thereof.

In some embodiments $R^4$ is hydrogen. In other embodiments, $R^4$ is hydroxyl.

In some embodiments, the structure of the moenomycin derivative is:

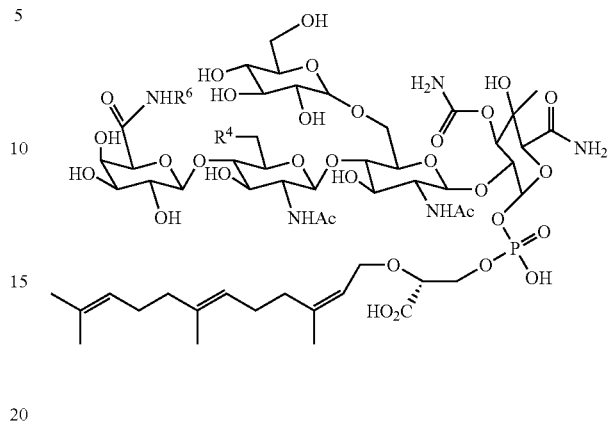

wherein $R^4$ is hydrogen or hydroxyl and $R^6$ is hydrogen, alkyl, cycloalkyl, or substituted cycloalkyl, or a pharmaceutically acceptable salt, tautomer, and/or ester thereof.

In some embodiments, $R^4$ is hydrogen. In other embodiments, $R^4$ is hydroxyl.

In some embodiments, $R^6$ is hydrogen or substituted cycloalkyl. In some preferred embodiments, substituted cycloalkyl is

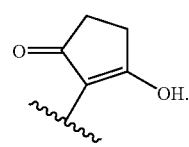

In some embodiments, $R^4$ is hydroxyl and $R^6$ is

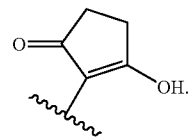

In some embodiments, pharmaceutical composition comprising the moenomycin derivative as defined above and a pharmaceutically acceptable carrier.

In another embodiment, the present invention provides a moenomycin derivative having the structure:

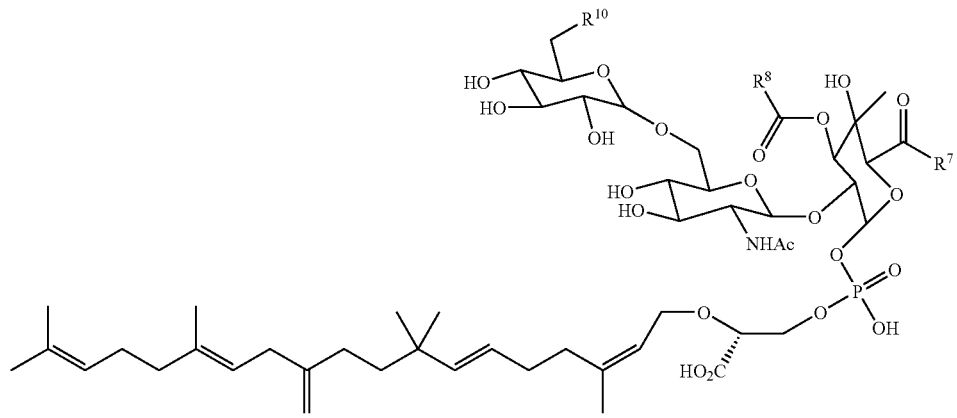

wherein $R^7$ and $R^8$ independently are selected from the group consisting of hydroxyl, and —$NHR^9$ where $R^9$ is hydrogen, alkyl, cycloalkyl, or substituted cycloalkyl; and $R^{10}$ is hydrogen or hydroxyl;

or a pharmaceutically acceptable salt, tautomer, and/or ester thereof.

In some embodiments, $R^7$ and $R^8$ independently are —$NH_2$. In some embodiments, $R^{10}$ is hydroxyl.

In some embodiments, the structure of the moenomycin derivative is:

or a pharmaceutically acceptable salt, tautomer, and/or ester thereof.

In some embodiments, pharmaceutical composition comprising the moenomycin derivative as defined above and a pharmaceutically acceptable carrier.

The moenomycin derivatives disclosed herein can be synthesized by genetic synthesis or by a conventional synthetic chemical synthesis by a person skilled in the art. The synthetic chemical synthesis can use known starting materials such as phosphoglycerate-farnesyl.

Perhaps the most surprising outcome of these studies, however, is that product 11 has biological activity (Welzel 2005) (FIG. 19). Compound 11 is shown below as Formula III:

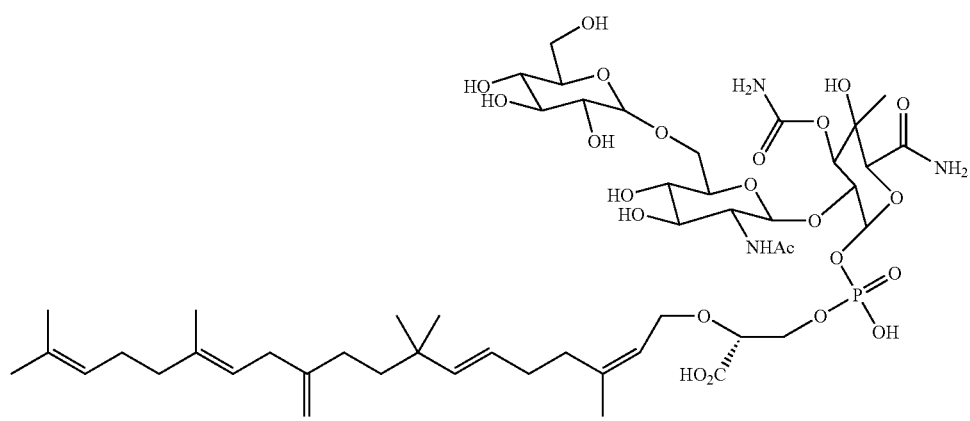 [SMILES: C=C(C/C=C(\C)CCC=C(C)C)CCC(C)(C)/C=C/CC/C(C)=C\CO[C@H](COP(=O)(O)OC1OC(C(N)=O)C(C)(O)C(OC(N)=O)C1OC1OC(COC2OC(CO)C(O)C(O)C2O)C(O)C(O)C1NC(C)=O)C(=O)O]

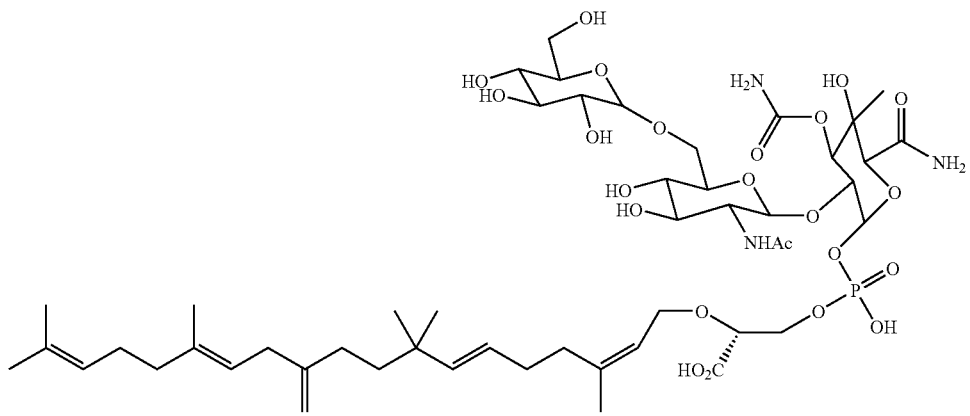 [SMILES: C=C(C/C=C(\C)CCC=C(C)C)CCC(C)(C)/C=C/CC/C(C)=C\CO[C@H](COP(=O)(O)OC1OC(C(N)=O)C(C)(O)C(OC(N)=O)C1OC1OC(COC2OC(CO)C(O)C(O)C2O)C(O)C(O)C1NC(C)=O)C(=O)O]

Compound 11 does not contain the C ring, proposed to be part of the moe A pharmacophore, but instead contains a branching glucose unit. Evidently, either the C or the D ring can confer biological activity on the EF disaccharide, although the molecular basis for their effects is unclear. A crystal structure of moe A bound to a peptidoglycan glycosyltransferase domain has been reported and shows that the C ring binds in the active site cleft while the D ring protrudes from the cleft (Lowering 2007). The resolution of the complex is not sufficient to determine if there are specific contacts from conserved amino acids to the C ring, but it is almost certain that there are none to the D ring.

IV. Moe Assembly Scheme

The bioinformatic and genetic analysis of the identified moe genes suggests a scheme of moe A biosynthesis, depicted in FIG. 4. Not wishing to be bound or limited by any theory, structures 23 and 3 witness that moe A biosynthesis starts with a unique reaction of farnesylation of phosphoglyceric acid. Sugars are transferred to the putative molecule IP one by one. The carboxamide on unit F is required to proceed through the pathway; methylation, in contrast, can occur prior to the second glycosylation, but is not required to make the moe A pentasaccharide. Carbamoylation of the first sugar (unit F, FIG. 1) appears to happen only after attachment of three sugars since we could not detect any mass-peaks corresponding to carbamoylated disaccharide precursors (FIG. 4). Prenylation to form the "mature" C25 isoprenoid chain also appears to occur only after the attachment of three sugars. The sequence of carbamoyltransferase and prenyltransferase reactions shown in FIG. 4 is proposed, however, the reverse order cannot be excluded. However, it is evident from the production of des-carbamoylated MmA pentasaccharides in a ΔmoeM5 strain and C15 MmA pentasaccharides in a ΔmoeN5 strain that carbamoylation is not required prenylation and prenylation is not required for carbamoylation. The attachment of the two remaining sugars and the chromophore completes moe A biosynthesis. Thus, the overall pathway has been delineated, although there remain questions about particular transformations, including the unusual MoeN5-catalyzed prenyl transfer reaction to generate the irregular C25 isoprenoid chain of MmA and the biochemistry of A ring biogenesis.

In one aspect of the present invention, the biosynthetic pathway for moe A may be altered for the production of phosphoglycolipid analogs. The biosynthetic pathway involves approximately ten essential (for biological activity) structural genes. The present inventors have discovered that a complex mixture of related compounds arises because the moenomycin biosynthetic machinery is flexible. Except for unit F carboxyamidation, all examined sugar tailoring reactions can be "switched off" without adverse effects on the assembly of the prenyl-phosphoglycerate-glycoside scaffold. Prenyl transfer to form the C25 lipid from the C15 precursor can also be switched off. Moreover, both MoeGT4 and MoeGT5 can accept either UDP-GlcNAc or UDP-chinovosamine as donor substrates, as evident from production of pholipomycin and moenomycin $C_3$. This, in combination with unbalanced expression of certain moe genes, leads to an interesting phenomenon where relatively simple pathway yields not one compound but a mixture of related ones. Thus, the spectrum of moenomycin metabolites and deriviates may be altered by selective deletion/overexpression of certain genes.

In some embodiments, the present invention provides for genetic manipulations of the moe A pathway for the discovery and production of clinically valuable molecules. Consistent with this expectation, we have already yielded several unexpected bioactive compounds. For example, we have found that the farnesylated moe A analog 23 has biological activity at submicromolar concentrations in a disk diffusion assay. This or other C15 derivatives may have better pharmacokinetic properties than the parent compounds, which would compensate for the evident decrease in potency. We have also shown that trisaccharide 11 is biologically active, providing an alternative scaffold for combinatorial or chemoenzymatic explorations to generate analogs.

VI. Further Examples of the Present Invention

A. Inactivation of Either Individual Moe Genes or Sets of Moe Genes to Generate Moe Derivatives, Analogs, Fragments and Novel Compounds The above description of the insertional inactivation is one possible model for how disruptions of separate moe genes leads to the generation of bacterial strain with altered profile of moes production. The generated recombinant strains may be the source of novel moes which possess better antibacterial and pharmacological properties. These novel moes may further be chemically or chemoenzymaticaly modified to produce novel compounds. For example, the 406 bp internal fragment of gene moeC4 (corresponding to amino acids 146-281 of moeC4) for 5-aminolevulinate synthase may be amplified with primers alsupHindIII and alsrp1EcoRI and cloned into pKC1139. Following the procedure utilized for moeM5 gene disruption, a S. ghanaensis strain with a deficient aminolevulinate synthase gene may be generated. The strain would then accumulate a late moe intermediate lacking the chromophore unit. This simplified moe derivative would likely have slightly reduced antibacterial activity. Additionally, its acid or amide functionality at unit B could be further modified using standard chemical techniques or chemoenzymatic approaches (which will be described in following examples) to give a compound with improved properties.

For example, a more chemically reactive unit can be attached to the aforementioned simplified moe instead of the natural C5N chromophore. By strengthening the interactions between the chromophore-saccharide portion of moe and its target (transglycosylase involved in bacterial peptidoglycan biosynthesis) it might be possible to then remove/shorten the lipid chain from moe without the loss of its biological activity.

A combination of certain mutations in individual moe genes also presents options for the production of moe analogs. For example, combining the mutations in the methyltransferase gene moeK5, the sugar tailoring gene moeR5 and the moeC4 gene, a novel moe could be produced lacking unitA (chromophore), methyl group in ring F, and bearing a hydroxyl in the C6 position of unit C. *S. ghanaensis* produces mixture of moes, and some of them are products of branches of the main moe pathway. Thus, the disruptions of certain moe genes can be used to block the shunt moe pathways.

B. Overexpression of Moe Genes in *Streptomyces ghanaensis* to Generate Moe Overproducing Strains The amplification of gene clusters for antibiotic biosynthesis in genomes of producing strains is known to lead to overproduction of the antibiotics. The availability of moe genes paves a similar path for the rational generation of moe overproducing strains. For example, protoplasts of wild-type *S. ghanaensis* strain (obtained according to the described procedure) may be transformed with alkali denaturated cosmid moeno38 (as described in Oh 1997) carrying most of the moe genes. The protoplasts may be regenerated on R2YE medium and selected for kanamycin resistance in order to isolate *S. ghanaensis* clones in which cosmid moeno38 has integrated into the host chromosome by homologous recombination. The production of moes may then be studied as described above to verify the overproducing phenotype. In this way the duplication of moe genes can be achieved.

In order to obtain *S. ghanaensis* strains with multiple copies of moe gene cluster per genome, cosmid moeno38-1 from cosmid moeno38, in which the neo gene marker has been replaced with 5.3 kb hyg-ori$T^{RK2}$-int$^{\Phi C31}$ PCR fragment of vector POOB40 by suing the h-Red recombination system (Gust 2003). The construct could be transferred into *S. ghanaensis* and recombinant colonies could be selected for hygromycin resistance. The production of moes could then be studied as described above. Sometimes the expression of only certain genes may be a limiting factor in biosynthesis of a given secondary metabolite. Therefore, the expression of individual moe genes could be useful to increase the production of moes or moe-related compound.

C. Heterologous Expression of Moe Genes

The heterologous expression of moe genes may be used to for a number of reasons such as 1) to generate recombinant strains which produce more moes than, for example, *S. ghanaensis,* 2) to produce moe derivatives, 3) to generate novel compounds resulting from the modification of metabolites other than moes with Moe proteins. The moe genes of the present invention may be expressed in a variety of cell expression systems known in the art. By way of example, but not by way of limitation, bacterial (e.g., *Streptomyces* sp., *E. coli*), mammalian (e.g., mouse, human, rat, hamster, etc., such as NIH-3T3, HeLa, HEK 293, etc.), yeast (e.g., *Saccharomyces cerevisiae, Pichia pastoris*) and insect cells (e.g., *Drosophila melanogaster* Schneider cells) may be used. Numerous expression systems, including appropriate expression vectors, cell growth media and conditions, and cell lines, are known in the art and many are commercially available.

As one example, the moeno38-1 construction (which was transferred to *S. lividans* TK24, described above) may be transferred to other organisms, e.g. *S. coelicolor* M145, by applying the conjugation protocol, also described above. The transconjugants may be selected for hygromycin. The production of moes may be checked by biochromatography and LC-MS analysis. The recombinant strains may be better producers of moes than the wild type *S. ghanaensis* strain. Further, by using ϕ-Red recombination system, for example, modified moeno38 cosmids with deletions of one or more moe genes may be obtained. Their expression in a heterologous host (as described above) would lead to production of moes analogs.

The expression of sugar tailoring moe genes in the producers of other glycoside antibiotics may lead to production of novel hybrid compounds. For example, a given sugar tailoring gene may be cloned into a *Streptomyces* expression vector (such as pMKI9 or analogs). The resulting construct may then be transferred into a strain of interest via intergeneric conjugation, protoplast transformation or electroporation (Kieser 2000). The recombinant strain could then be subject to detailed analysis in order to detect the changes in antibiotic production.

D. Overexpression of Moe Proteins in *E. coli* or *Streptomyces* and Their Use as Catalysts for Generation of Novel Molecules Purified enzymes encoded by moe genes can be used to produce novel molecules. This approach is based on certain degree of substrate promiscuity of the enzymes involved in antibiotic production. For example, the gene for moenocinol 3-phosphoglycerate synthase may be amplified from cosmid moeno38 with primers moeO5HindIIIrp (AAAAAGCTTC-CGCCCGCTCCCCGGAC; SEQ ID NO. 105) and moeO5NdeIup (AAACATATGCTCGCCCGGCTGCGC; SEQ ID NO. 106), resulting in an approximately 774 bp fragment. The amplification product may then be digested with HindIII and NdeI restriction endonucleases and cloned into respective sites of *E. coli* protein expression vector, such as pET24b (or any analogous vector that allows for affinity column protein purification). The resulting plasmid may then be introduced in an *E. coli* strain such as BL21(DE3) (or its derivatives that utilize similar strategy for induction of protein expression) using standard methods.

Alternatively, the moeO5 gene may be amplified along with its native ribosome binding site and a hexahistidine tag; desired restrictions sites may be engineered at the ends of the gene via PCR. This recombinant moeO5 gene can then be cloned into corresponding restrictions sites of a vector such as pMKI9. The resulting plasmid can be introduced into *S. ghanaensis* using the above-described procedures. His-tagged moeO5 protein may then be purified from *S. ghanaensis* using standard IMAC chromatography.

The optimal conditions for moeO5 protein expression and purification from *E. coli* or *Streptomyces* can be developed experimentally; such methods and optimizations are well known to those skilled in the art. The pure moeO5 protein may then be used in vitro to, for example, reconstitute the reaction of prenyl transfer onto 3-phosphoglycerate. The ability of moeO5 to transfer unnatural prenyl chains onto 3-phosphoglycerate may also be exploited. The products of the reaction may be monitored by HPLC-MS. Since one of the disadvantage of moe A as a clinically valuable antibiotic is its poor pharmacokinetics, due in part to the long prenyl chain, the ability to produce the moes with altered prenyl chain length/stereochemistry would be a valuable step towards improved moes.

The above-described example provides an exemplary experimental framework for development of such technology for the production of improved moes. Additionally, if the moeO5 protein appears unable to transfer prenyl chains of shorter length/different stereochemistry, then it can be subjected to directed mutagenesis to relax/change its substrate specificity (see following example). The same approach as described above for moeO5 protein may be applied to the expression of any of moe proteins; that is, their ability to catalyze novel chemical reactions can be studied using a variety of different substrates and mutagenesis may be employed to change substrate specificity.

E. Site Specific Mutagenesis of Moe Genes in Order to Generate the Mutated Moe Proteins with Novel Enzymatic Activities.

Although the enzymes involved in antibiotic production are usually able to accept unnatural substrates resembling the natural one, their inherent level of substrate promiscuity might not be sufficient to produce a different compound. Accordingly, changes to specific amino acids which are identified as important for substrate recognition/reaction catalysis can be mutated within the given protein to generate highly efficient catalyst of novel reaction. Extracts from cells expressing the mutant moe biosynthesis-related gene (i.e. a "test strain"), may be assessed for anti-microbial activity using for example, a zone inhibition assay, such as depicted in FIG. 19. Comparison may be made between extracts from the test strain and extracts from a control strain (e.g. a strain expressing the natural moe biosynthesis-related genes). Test strains that have a larger zone of inhibition compared to the control strain may possess novel moes or moe derivatives. Test strains that have a smaller zone of inhibition compared to the control strain may lack novel moes or moe deriviatives. This approach depends on detailed structural information about the protein or, at least, its functional homologues. For example, the crystal structure of moeO5 homologue, GGGPS from *Archaeoglobus fulgidus* exists, as does information about kinetics of the reactions catalyzed by this class of enzymes. Using protein fold prediction programs, the structure of moeO5 may be modeled using *A. fulgidus* GGGPS as a template. In this way, amino acids critical for substrate recognition and binding may be identified within moeO5 and mutated to alter enzyme activity, for example, to help a catalytic pocket accommodate an altered or unnatural substrate. Alternatively, the entire polypeptide or portions of the polypeptide may be mutated at random sites to create mutant libraries (Lehtovaara et al., Protein Eng. 2: 63-8 (1988)). The mutants created in this way may also be tested, using, for example, the zone of inhibition assay described above.

F. Use of DNA Fragments of Moe Genes as a Hybridization Probes for Discovery of Genes Governing the Biosynthesis of Related Phosphoglycolipid Antibiotics The moe genes of the present invention may be used to identify genes involved in the biosynthesis of other antibiotics in bacteria or other organisms. For example, the entire moeO5 gene (described above) may be labeled using non-radioactive digoxigenin or a radioactive approach (according to standard procedures) (Sambrook 1989). Genomic DNA of producers of other phosphoglycolipid antibiotics (e.g., AC326alpha, teichomycin, prasinomycin etc) may be isolated, digested with certain restriction endonucleases and separated on an agarose gel according to standard procedures. Southern analysis may then be used to identify any moeO5 homologues (i.e., the presence of positive hybridization signals using the labeled moeO5 gene with the genomic digests would demonstrate the presence of genes similar to moeO5). Therefore, the moe genes, such as moeO5, can be used to probe the genomic library of a given strain to identify, clone and characterize homologues and surrounding genes. Any other moe gene can be used in the same way as a probe for discovery of related genes in other producers.

G. Use of an Internal Fragment of Moe Genes and Homologous Recombination for Discovery of Genes Governing the Biosynthesis of Related Phosphoglycolipid Antibiotics The carbamoyltransferase moeM5 disruption plasmid pOOB20a (described above) may be transferred into *Actinoplanes teichomyceticus*, the producer of teichomycins, via standard intergeneric conjugation protocol. The integration of pOOB20a into the *A. teichomyceticus* genome may be promoted as described for the moeM5 disruption in *S. ghanaensis* ATCC 14672 strain. If there is a gene in the *A. teichomyceticus* genome which shows even moderate homology to moeM5 (50-70% at nucleotide level), then homologous recombination could occur between the moeM5 fragment on plasmid pOOB20a and the similar gene present in the host's genome. The integration of pOOB20a into *A. teichomyceticus* genome could be verified through Southern analysis, and the production of teichomycins may be monitored using bioassays and HPLC-MS analysis. Homologues of moeM5 and surrounding sequences could be rescued from pOOB20a+ *A. teichomyceticus* integrant by digesting total DNA with restriction endonucleases which do not cut the pOOB20a plasmid (HindIII, XbaI, EcoRV). In this way pOOB20a can be excised from the *A. teichomyceticus* genome along with some genomic flanking sequence (the amount of flanking sequence obtained would depend on how far the restriction sites were from the pOOB20a insertion). These digests may be set-up to be self-ligating and then used to transform competent cells such as *E. coli*. The apramycin-resistant clones resulting from this transformation can then be used for the isolation of plasmid DNA and further restriction mapping. The fragments of *A. teichomyceticus* genome can also be subcloned into suitable vectors (e.g., pUC19, pBluescript etc.) for sequencing. The described procedure would be useful to identify homologues or genes that have sequence similarity to any of the moe biosynthesis-related genes of the invention.

H. Design of Degenerate Primers on the Basis of Moe Genes for Discovery of Novel Genes One method to identify novel genes (having homology to the moe genes described above) may include designing degenerate primers capable of amplifying sequences similar to those of the identified moe genes. For example, to design such primers, the sequence of a moe gene, such as the moeO5 gene, may be aligned with sequences of known prenyl-glycerol synthases from other bacterial species, such as Archaea. The conserved amino acid residues may be identified and their significance assessed through comparison with the crystal structure of prenyl-glycerol synthases from other bacteria, such as *A. fulgidus*. Two stretches of amino acids within a conserved C-terminus of the compared proteins (e.g., 88-AD-ALLL-93 (SEQ ID NO: 252) and 190-GADYYG-195 (SEQ ID NO: 253)) can be back-translated into DNA sequence taking into account the codon usage of *Streptomyces* (if other organisms are targeted in this kind of experiment, then the choice of codons is planned according to codon usage table of that organism) and allowing for ambiguity in a third codon position. The program CODEHOP (Rose et al., *Nucl Acids Res,* 1998 26:1628-1635) can be used to design degenerate primers. PCR conditions using such degenerate primers may be developed in the course of additional experimentation using positive controls (e.g., the template DNA of the moe producer). Such PCR optimizations are well known in the art. The PCR products from unknown strains may then be cloned using, for example, PCR LIC cloning vectors (Novagen, San Diego, Calif.) according to the manufacturer's instructions. The insert can be sequenced compared with and moeO5 and other known homologues.

Examples F, G and H all describe methods in which novel moe gene homologues can be identified and isolated. Because the methods are based on sequence similarity, they allow for the discovery of genes which may have different biochemical or functional characteristics than the moe genes used to find them. Such characteristics may include but are not limited to different substrate specificity (e.g., more or less specific for a particular substrate; specificity for a different, but similar substrate); a different reaction rate (e.g., much faster or much slower, thereby allowing other reactions or modifications to occur or not); the ability to function under different reaction conditions (e.g., modified salt, temperature or pH); improved or increased stability. Any of the discovered homologues with different characteristics could prove useful in an in vitro or in vivo moe A synthesis and/or modification system, in conjunction with, or in place of, one of the identified moe genes. Additionally, identification of such moe homologues may lead to the identification of different moe-like or other antibiotic biosynthetic pathway.

I. Generating and Testing Novel Moes

The present invention provides for the generating of novel moe or moe derivatives which are capable of inhibiting the activity of bacterial transglycoslase enzymes. The novel moes may be generated according to the methods described herein, including the expression of moe biosynthesis-related genes, or fragments or variants thereof, in S. ghanaensis or a heterologous host, e.g. S. lividans. Extracts from cells expressing the moe biosynthesis-related genes, fragments, or variants thereof (i.e. a "test strain"), may be assessed for anti-microbial activity using for example, a zone inhibition assay, such as depicted in FIG. 19. Comparison may be made between extracts from the test strain and extracts from a control strain (e.g. a strain expressing the natural moe biosynthesis-related genes). Test strains that have a larger zone of inhibition compared to the control strain may possess novel biologically-active moes or moe derivatives. Test strains that have a smaller zone of inhibition compared to the control strain may lack novel moes or moe deriviatives.

Novel moes or moe derivatives might also be identified using LC-MS analysis of extracts from cells expressing the moe biosynthesis-related genes, fragments, or derivatives thereof. Comparison may be made between the LC-MS spectra of the test strain and a control strain. The appearance of new peaks may indicate the presence of novel moes or moe derivatives in that test strain. Those compounds may be purified using methods known to those of skill in the art (e.g. chromatography). The anti-microbial activity of those compounds can then be assayed using, for example, a zone of inhibition assay.

J. Improved Moe A Characteristics

In some embodiments, the modified and improved moe A formulations of the present invention ("improved moe A") are contemplated to exhibit increased bioavailability as compared to the currently available, or conventional moe A formulations such as Flavomycin®. The increased bioavailability is also likely to result in a dosage form that exhibits greater drug absorption than conventional formulations of moe A; as such, a pharmaceutically acceptable formulation for use in humans is contemplated.

Increased bioavailability can be ascertained by methods known in the art. For example, the drug absorption, distribution, and/or elimination rates may be evaluated and compared to conventional moe A, as may the different pharmacokinetic profiles. Exemplary, desirable pharmacokinetic profiles preferably include, but are not limited to: (I) a $C_{max}$ for an improved moe, such as an improved moe A, or a derivative or salt thereof, when assayed in the plasma of a mammalian subject following administration, that is preferably greater than the $C_{max}$ for the conventional aloe A administered at the same dosage; and/or (2) an AUC for an improved moe, such as an improved moe A, or a derivative or a salt thereof, when assayed in the plasma of a mammalian subject following administration, that is preferably greater than the AUC for conventional moe A, administered at the same dosage; and/or (3) a $T_{max}$ for an improved moe, such as moe A, or a derivative or a salt thereof, when assayed in the plasma of a mammalian subject following administration, that is preferably less than the $T_{max}$ for a conventional formulation moe A, administered at the same dosage. The desirable pharmacokinetic profile, as used herein, is the pharmacokinetic profile measured after the initial dose of the moe A or derivative or a salt thereof.

For example, in one embodiment, a composition comprising at least one improved formulation of moe A exhibits in comparative pharmacokinetic testing with a non-improved formulation of the same moe A (e.g. Flavomycin), administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the conventional moe A formulation.

In another embodiment, the composition comprising at least one improved moe A formulation or derivative or salt thereof, exhibits in comparative pharmacokinetic testing with a conventional moe A formulation (e.g., Flavomycin), administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the conventional moe A formulation.

In yet another embodiment, the composition comprising at least one improved moe A or a derivative or salt thereof, exhibits in comparative pharmacokinetic testing with a conventional formulation of moe A (e.g., Flavomycin), administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the conventional moe A formulation.

The moe A formulations contemplated also include a variety of pharmaceutical acceptable dosage forms. By way of example, but not by way of limitation, pharmaceutically acceptable formulations may include: formulation for oral, pulmonary, intravenous, rectal, ophthalmic, colonic, parenteral, intracisternal, intravaginal, intraperitoneal, local, buccal, nasal, and topical administration; dosage forms such as liquid dispersions, gels, aerosols, ointments, creams, tablets, sachets and capsules; dosage forms such as lyophilized formulations, fast melt formulations, controlled release formulations, delayed release formulations, extended release formulations, pulsatile release formulations, and mixed immediate release and controlled release formulations, or any combination of the above. In some embodiments, preferred formulations for administration may include oral tablets or capsules. In other embodiments, parenteral formulations may be preferred.

K. Prophylactic and Therapeutic Use of Moe A Derivatives

General.

The moe A derivatives and intermediates of the present invention can be used in treatment of bacterial infections. Specifically, the invention provides for both prophylactic and therapeutic methods of treating a subject at risk of (or susceptible to) a disorder or having a disorder associated with an bacterial infections. While not wishing to be limited by theory, administration of moe A results in inhibition of bacterial transglycosylase enzymes and killing or slowing the growth of the bacteria.

In one aspect, the invention provides a method for preventing, in a subject, a disease or condition associated with a bacterial infection, by administering to the subject a moe A derivative. Administration of a prophylactic moe A derivative can occur prior to the manifestation of symptoms characteristic of the infection, such that a disease or condition is prevented or, alternatively, delayed in its progression. In therapeutic applications, moe A derivatives are administered to a subject suspected of, or already suffering from, a bacterial infection. An amount adequate to accomplish therapeutic or prophylactic treatment is defined as a therapeutically- or prophylactically-effective dose.

Determination of the Biological Effect of a moe A Derivative Therapeutic.

In various embodiments of the invention, suitable in vitro or in vivo assays are performed to determine the effect of moe A derivatives and whether the administration is indicated for treatment of the affected tissue in a subject.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every week, every two weeks or every three weeks or within the range of 1-10 mg/kg every week, every two weeks or every three weeks. In one embodiment, a single dosage of antibody range from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Alternatively, moe A derivatives can be administered as a sustained release formulation, in which case less frequent administration is required. Dosage and frequency vary depending on the half-life of the moe A derivative in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity.

Preferably, an effective amount (e.g., dose) of a moe A derivative described herein will provide therapeutic benefit without causing substantial toxicity to the subject. Toxicity of the moe A derivative described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage can vary within this range depending upon the dosage form employed and the route of administration utilized. The exact formulation, route of administration and dosage can be chosen by the individual physician in view of the subject's condition. See, e.g., Fingi et al., In: *The Pharmacological Basis of Therapeutics*, Ch. 1 (1975).

Formulations of Pharmaceutical Compositions.

According to the methods of the present invention, the moe A derivative can be incorporated into pharmaceutical compositions suitable for administration. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18th ed., 1990). The pharmaceutical compositions are generally formulated as sterile, substantially isotonic and in full compliance with all Good Manufacturing Practice (OMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the moe A derivative are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the moe A derivative, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The moe A derivative named in this invention can be present in unsalified or unesterified form, or in salified and/or esterified form, and the naming of such moe A derivative is intended to include both the original (unsalified and unesterified) compound and its pharmaceutically-acceptable salts and esters. Also, certain moe A derivatives named in this invention can be present in more than one stereoisomeric form, and the naming of such moe A derivatives is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the moe A derivative, use thereof in the compositions is contemplated. Supplementary active compounds can also be incorporated into the compositions.

A pharmaceutical composition of the invention is formulated to be compatible with its intended route of administration. The moe A derivative compositions of the present invention can be administered by parenteral, topical, intravenous, oral, subcutaneous, intraarterial, intradermal, transdermal, rectal, intracranial, intraperitoneal, intranasal; intramuscular route or as inhalants. The moe A derivative can optionally be administered in combination with other agents that are at least partly effective in treating conditions associated with bacterial infection.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the moe A derivative in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the moe A derivative are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the moe A derivative is formulated into ointments, salves, gels, or creams as generally known in the art.

The moe A derivative can also be prepared as pharmaceutical compositions in the form of suppositories (e.g., with conventional suppository bases such as cocoa butter and other glycerides) or retention enemas for rectal delivery.

In one embodiment, the moe A is prepared with carriers that will protect the moe A derivative against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the invention are dictated by and directly dependent on the unique characteristics of the compound and the particular therapeutic effect to be achieved, and the limitations inherent in the art of compounding such moe A derivatives for the treatment of a subject.

REFERENCES

Adachi, M., Zhang, Y., Leimkuhler, C., Sun, B., LaTour, J. V., and Kahne, D. E. (2006), Degradation and reconstruction of moenomycin A and derivatives: dissecting the function of the isoprenoid chain. J Am Chem Soc. 128, 14012-14013.

Arai M, Torikata A, Enokita R, Fukatsu H, Nakayama R and Yoshida K. Pholipomycin, a new member of phosphoglycolipid antibiotics. I. Taxonomy of producing organism and fermentation and isolation of pholipomycin. J Antibiot. 1977. V. 30(12):1049-1054.

Baizman E R, Branstrom A A, Longley C B, Allanson N, Sofia M J, Gange D, Goldman R C: Antibacterial activity of synthetic analogues based on disaccharide structure of moe, an inhibitor of bacterial transglycosylase. Microbiology 2000, 146: 3129-3140.

Bardone M R, Paternoster M and Coronelli C. Teichomycins, new antibiotics from Actinoplanes teichomyceticus nov sp. II. Extraction and chemical characterization. J Antibiot. 1978. V. 31(3): 170-177.

Belanger M, Burrows L L and Lam J S. Functional analysis of genes responsible for the synthesis of the B-band O antigen of Pseudomonas aeruginosa serotype O6 lipopolysaccharide. Microbiology. 1999. V. 145:3505-3521.

Bentley S D, Chater K F, Cerdeno-Tarraga A M, Challis G L, Thomson N R, James K D, Harris D E, Quail M A, Kieser H, Harper D, Bateman A, Brown S, Chandra G, Chen C W, Collins M, Cronin A, Fraser A, Goble A, Hidalgo J, Hornsby T, Howarth S, Huang C H, Kieser T, Larke L, Murphy L, Oliver K, O'Neil S, Rabbinowitsch E, Rajandream M A, Rutherford K, Rutter S, Seeger K, Saunders D, Sharp S, Squares R, Squares S, Taylor K, Warren T, Wietzorrek A, Woodward J, Barrell B G, Parkhill J, Hopwood D A. Complete genome sequence of the model actinomycete Streptomyces coelicolor A3(2). Nature. 2002. 417:141-147.

Bibb M J. Regulation of secondary metabolism in streptomycetes. Curr Opin Microbiol. 2005. V. 8:208-215.

Bierman M, Logan R, O'Brien K, Seno E T, Rao R N, Schoner B E. Plasmid cloning vectors for the conjugal transfer of DNA from Escherichia coli to Streptomyces spp. Gene. 1992. 116:43-49.

Blondelet-Rouault, M. H., Weiser, J., Lebrihi, A., Branny, P., and Pernodet, J. L. (1997). Antibiotic resistance gene cassettes derived from the omega interposon for use in E. coli and Streptomyces. Gene 190, 315-317.

Chaffin D O, McKinnon K and Rubens C E. CpsK of Streptococcus agalactiae exhibits α2,3-sialyltransferase activity in Haemophilus ducreyi. Mol Microbiol. 2002. V. 45(1): 109-122.

Chang G. Multidrug resistance ABC transporters. FEBS Lett. 2003 Nov. 27; 555(1):102-5.

Chater K F. Streptomyces inside-out: a new perspective on the bacteria that provide us with antibiotics. Phil Trans R Soc B. 2006. V. 361:761-768.

Chen L, Walker D, Sun B, Hu Y, Walker S, Kahne D: Vancomycin analogues active against vanA-resistant strains inhibit bacterial transglycosylase without binding substrate. Proc Natl Acad Sci USA 2003, 100: 5658-5663.

Dairi T. Studies on biosynthetic genes and enzymes of isoprenoids produced by actinomycetes. J Antibiot (Tokyo). 2005 April; 58(4):227-43.

Datsenko, K. A., and Wanner, B. L. (2000). One-step inactivation of chromosomal genes in Escherichia coli K-12 using PCR products. Proc. Natl. Acad. Sci. USA 97, 6640-6645.

Decker H, Gaisser S, Pelzer S, Schneider P, Westrich L, Wohlleben W, Bechthold A. A general approach for cloning and characterizing dNDP-glucose dehydratase genes from actinomycetes. FEMS Microbiol Lett. 1996. V. 141: 195-201.

Du, Y., Li, T., Wang, Y. G. and Xia, H. Identification and Functional Analysis of dTDP-Glucose-4,6-Dehydratase Gene and Its Linked Gene Cluster in an Aminoglycoside Antibiotics Producer of Streptomyces tenebrarius H Curr. Microbiol. 49 (2), 99-107 (2004).

Durr C, Schnell H-J, Luzhetskyy A, Murillo R, Weber M, Wetzel K, Vente A and Bechthold A. Biosynthesis of the terpene phenalinolactone in Streptomyces sp. Tu6071: analysis of the gene cluster and generation of derivatives. Chem Biol. 2006. V. 13:365-377.

Eichhorn P and Aga D. Characterization of moe antibiotics from medicated chicken feed by ion-trap mass spectrometry with electrospray ionization. Rapid Commun Mass Spectrom. 2005. V. 19:2179-2186.

Feng L, Tao J, Guo H, Xu J, Li Y, Rezwan F, Reeves P, Wang L. Structure of the Shigella dysenteriae 7 O antigen gene cluster and identification of its antigen specific genes. Microb Pathog. 2004 February; 36(2):109-15.

Flett F, Mersinias V, Smith C P. High efficiency intergeneric conjugal transfer of plasmid DNA from Escherichia coli to methyl DNA-restricting streptomycetes. FEMS Microbiol Lett. 1997. 155:223-229.

Garneau S, Qiao L, Chen L, Walker S, Vederas J C: Synthesis of mono- and disaccharide analogs of moe and lipid II for inhibition of transglycosylase activity of penicillin-binding protein 1b. Bioorg Med Chem 2004, 12: 6473-6494.

Genetika. 2001 October; 37(10):1340-7. Russian.

Goldman R C, Baizman E R, Branstrom A A, Longley C B: Differential antibacterial activity of moe analogues on gram-positive bacteria. Bioorg Med Chem Lett 2000, 10: 2251-2254.

Goldman, R. C., and Gange, D. (2000). Inhibition of transglycosylation involved in bacterial peptidoglycan synthesis. Curr. Med. Chem. 7, 801-820.

Gromyko O M, Rebels Yu V, Ostash B, Luzhetskyy A, Fukuhara M, Bechthold A, Nakamura T and Fedorenko V. Generation of *Streptomyces globisporus* SMY622 strain with increased landomycin E production and it's initial characterization. J Antibiot. 2004. V. 57:383-389.

Gust B, Challis G L, Fowler K, Kieser T, Chater K F. PCR-targeted *Streptomyces* gene replacement identifies a protein domain needed for biosynthesis of the sesquiterpene soil odor geosmin. Proc Natl Acad Sci USA. 2003. 100: 1541-1546.

Halliday J, McKeveney D, Muldoon C, Rajaratnam P, Meutermans W. Targeting the forgotten transglycosylases. Biochem Pharmacol. 2006 Mar. 30; 71(7):957-67.

He H, Shen B, Korshalla J, Siegel M M and Carter G T. Isolation and structural elucidation of AC326-α, a new member of the moe group. J Antibiot. 2000. V. 53(2): 191-195.

Heijenoort van J: Formation of glycan chains in the synthesis of bacterial peptidoglycan. Glycobiol 2001, 11: 25R-36R.

Hodgson, D. A. Primary metabolism and its control in streptomycetes: a most unusual group of bacteria. (2000). Adv. Microb. Physiol. 42, 47-238.

Hong H J, Paget M S, Buttner M J. A signal transduction system in *Streptomyces coelicolor* that activates the expression of a putative cell wall glycan operon in response to vancomycin and other cell wall-specific antibiotics. Mol Microbiol. 2002 June; 44(5):1199-1211.

Hong Y S, Lee D, Kim W, Jeong J K, Kim C G, Sohng J K, Lee J H, Paik S G, Lee J J. Inactivation of the carbamoyltransferase gene refines post-polyketide synthase modification steps in the biosynthesis of the antitumor agent geldanamycin. J Am Chem Soc. 2004 Sep. 15; 126(36):11142-3.

Hopwood D. Soil to genomics: the *Streptomyces* chromosome. Ann Rev Microbiol. 2006. V. 40:1-23 (epub ahead of print)

Ishikawa J, Hotta K. FramePlot: a new implementation of the Frame analysis for the predicting protein-coding regions in the bacterial DNA with a high G+C content. FEMS Microbiol Lett. 1999. V. 174:251-253.

Iyobe S, Mitsuhashi S and Saito T. Sex pili mutants isolated by macarbomycin treatment. Antimicrob Agents Chemother. 1973. 3(5):614-620.

Jabbouri S, Fellay R, Talmont F, Kamalaprija P, Burger U, Relic B, Prome J C, Broughton W J. Involvement of nodS in N-methylation and nodU in 6-O-carbamoylation of *Rhizobium* sp. NGR234 nod factors. J Biol Chem. 1995 Sep. 29; 270(39):22968-73.

Kaplan J, Velliyagounder K, Ragunath C, Rohde H, Mack D, Knobloch J K-M and Ramamsubbu N. Genes involved in the synthesis and degradation of matrix polysaccharide in *Actinobacillus actinomycetemcomitans* and *Actinobacillus pleuropneumoniae* biofilms. J Bacteriol. 2004. V. 186: 8213-8220.

Kaur P. Expression and characterization of DrrA and DrrB proteins of *Streptomyces peucetius* in *Escherichia coli*: DrrA is an ATP binding protein. J Bacteriol. 1997 February; 179(3):569-75.

Kawasaki T, Hamano Y, Kuzuyama T, Itoh N, Seto H and Dairi T. Interconversion of the product specificity of type I eubacterial farnesyl diphosphate synthase and geranylgeranyl diphosphate synthase through one amino acid substitution. J Biochem. 2003. V. 133:83-91.

Kawasaki T, Hayashi Y, Kuzuyama T, Furihata K, Itoh N, Seto H, Dairi T. Biosynthesis of a natural polyketide-isoprenoid hybrid compound, furaquinocin A: identification and heterologous expression of the gene cluster. J Bacteriol. 2006. 188(4):1236-44.

Kieser T, Bibb M J, Buttner M J, Chater K F and Hopwood D A. Practical *Streptomyces* genetics. 2000. Norwich, England: The John Innes Foundation.

Knirel Y A, Dashunin V V, Shashkov A S, Kochetkov N K, Dmitriev B A, Hofman I L. Somatic antigens of *Shigella*: structure of the O-specific polysaccharide chain of the *Shigella dysenteriae* type 7 lipopolysaccharide. Carbohydrate Res. 1988. V. 179:51-60.

Kudo F, Kawabe K, Kuriki H, Eguchi T, Kakinuma K. A new family of glucose-1-phosphate/glucosamine-1-phosphate nucleotidylyltransferase in the biosynthetic pathways for antibiotics. J Am Chem Soc. 2005 Feb. 16; 127(6):1711-8.

Leskiw B K, Mah R, Lawlor E J and Chater K F. Accumulation of bldA-specified tRNA is temporally regulated in *Streptomyces coelicolor* A3(2). J Bacteriol. 1993. V. 175: 1995-2005.

Leskiw, B. K., Lawlor, E. J., Fernandez-Abalos, J. M., and Chater, K. F. (1991). TTA codons in some genes prevent their expression in a class of developmental, antibiotic-negative, *Streptomyces* mutants. Proc. Natl. Acad. Sci. USA. 88, 2461-2465.

Lin W S, Cunneen T, Lee C Y. Sequence analysis and molecular characterization of genes required for the biosynthesis of type 1 capsular polysaccharide in *Staphylococcus aureus*. J Bacteriol. 1994 November; 176(22):7005-16.

Lindner 1961

Liu H, Ritter T K, Sadamoto R, Sears P S, Wu M, Wong C H. Acceptor specificity and inhibition of the bacterial cell-wall glycosyltransferase MurG. Chembiochem. 2003. 4:603-609.

Lombo, Felipe, Brana A. F., Mendez, C and Salas J. A. The mirithramycin gene cluster of *Streptomyces argillaceus* contains a positive regulatory gene and two repeated DNA sequences that are located at both ends of the cluster. J. Bacteriol. 1999 January; 181(2):642-647.

Lovering, A. L., de Castro, L. H., Lim, D., and Strynadka, N. C. (2007). Structural insight into the transglycosylation step of bacterial cell-wall biosynthesis. Science. 315, 1402-1405.

Luzhetskyy A, Fedoryshyn M, Durr C, Taguchi T, Novikov V and Bechthold A. Iteratively acting glycosyltransferases involved in the hexasaccharide biosynthesis of landomycin A. Chem Biol. 2005. V. 12:725-729.

Luzhetskii A N, Ostash B E, Fedorenko V A. Interspecies conjugation of *Escherichia coli-Streptomyces globisporus* 1912 using integrative plasmid pSET152 and its derivatives]

McAlpine J B, Bachmann B O, Piraee M, Tremblay S, Alarco A M, Zazopoulos E, Farnet C M. Microbial genomics as a guide to drug discovery and structural elucidation: ECO-02301, a novel antifungal agent, as an example. J Nat Prod. 2005. 68(4):493-6.

McKeegan K S, Borges-Walmsley M I and Walmsley A R. The structure and function of drug pumps: an update. Trends Microbiol. 2003. V. 11(1):21-28.

Men H, Park P, Ge M and Walker S. Substrate synthesis and activity assay for MurG. J Am Chem Soc. 1998. V. 120: 2484-2485.

Mendez C, Salas J A. The role of ABC transporters in antibiotic-producing organisms: drug secretion and resistance mechanisms. Res Microbiol. 2001. 152(3-4):341-50.

Meyers E, Smith D, Slusarchyk W A, Bouchard I L and Weisenborn F L. The diumycins. New members of an antibiotic family having prolonged in vivo activity. J Antibiot. 1969. V. 22:490-493.

Murrell J M, Liu W, Shen B. Biochemical characterization of the SgcA1 alpha-D-glucopyranosyl-1-phosphate thymidylyltransferase from the enediyne antitumor antibiotic C-1027 biosynthetic pathway and overexpression of sgcA1 in Streptomyces globisporus to improve C-1027 production. J Nat Prod. 2004 February; 67(2):206-13.

Muth G, Nussbaumer B, Wohlleben W and Puhler A. A vector system with temperature-sensitive replication for gene disruption and mutational cloning in streptomycetes. Mol Gen Genet. 1989. V. 219: 341-348.

Nakagawa A, Wu T-S, Keller P J, Lee J P, Omura S, Floss H G. Biosynthesis of asukamycin. Formation of the 2-amino-3-hydroxycyclopent-2-enone moiety. J Chem Soc Chem Commun. 1985. P. 519-521.

Nemoto N, Oshima T, Yamagishi A. Purification and characterization of geranylgeranylglyceryl phosphate synthase from a thermoacidophilic archaeon, *Thermoplasma acidophilum*. J Biochem (Tokyo). 2003. 133(5):651-657.

Neundorf I, Kohler C, Hennig L, Findeisen M, Arigoni D and Welzel P. Evidence for the combined participation of a $C_{10}$ and a $C_{15}$ precursor in the biosynthesis of moenocinol, the lipid part of the moc antibiotics. ChemBioChem. 2003. V. 4:1201-1205.

Oh S H, Chater K F. Denaturation of circular or linear DNA facilitates targeted integrative transformation of *Streptomyces coelicolor* A3(2): possible relevance to other organisms. J Bacteriol. 1997. 179(1):122-127.

Ostash, B., Saghatelian, A., and Walker, S. (2007). A streamlined metabolic pathway for the biosynthesis of moenomycin a. Chem Biol. 14, 257-267.

Ostash B, Walker S. Bacterial transglycosylase inhibitors. Current Opin Chem Biol. 2005. 9:459-466.

Pacholec M, Freel Meyers C L, Oberthur M, Kahne D, Walsh C T. Characterization of the aminocoumarin ligase SimL from the simocyclinone pathway and tandem incubation with NovM,P,N from the novobiocin pathway. Biochemistry. 2005 Mar. 29; 44(12):4949-56.

Paton A W and Paton J C. Molecular characterization of the locus encoding biosynthesis of the lipopolysaccharide O antigen of *Escherichia coli* serotype O113. Infection Immun. 1999. V. 67(11):5930-5937.

Petricek M, Petrickova K, Havlicek L and Felsberg J. Occurrence of two 5-aminolevulinate biosynthetic pathways in *Streptomyces nodosus* subsp. *asukaensis* is linked with the production of asukamycin. J. Bacteriol. 2006. V. 188(14): 5113-5123.

Pfaller M A. Flavophospholipol use in animals: Positive implications for antimicrobial resistance based on its microbiologic properties. Diagn Microbiol Infect Dis. 2006 May 12; [Epub ahead of print].

Rascher A, Hu Z, Viswanathan N, Schirmer A, Reid R, Nierman W C, Lewis M, Hutchinson C R. Cloning and characterization of a gene cluster for geldanamycin production in *Streptomyces hygroscopicus* NRRL3602. FEMS Microbiol Lett. 2003. V. 218:223-230.

Rebets Yu V, Ostash B O, Fukuhara M, Nakamura M and Fedorenko V O. Expression of the regulatory protein LndI for landomycin E production in *Streptomyces globisporus* 1912 is controlled by the availability of tRNA for the rare UUA codon. FEMS Microbiol Lett. 2006. V. 256:30-37.

Redenbach M, Flett F, Piendl W, Glocker I, Rauland U, Wafzig O, Kliem R, Leblond P, Cullum J. The *Streptomyces lividans* 66 chromosome contains a 1 MB deletogenic region flanked by two amplifiable regions. Mol Gen Genet. 1993. 241:255-262.

Riedl S, Ohlsen K, Werner G, Witte W, Hacker J. Impact of flavophospholipol and vancomycin on conjugational transfer of vancomycin resistance plasmids. Antimicrob Agents Chemother. 2000. 44(11):3189-92.

Sambrook J, Fritsch E F and Maniatis T. Molecular cloning, a laboratory manual. 1989. Cold Spring Harbor Laboratory, Cold Spring Harbor, N.Y.

Sambrook, J., and Russel, D. W. (2001.) *Molecular Cloning: A Laboratory Manual* (Cold Spring Harbor Lab. Press, Cold Spring Harbor, N.Y.), $3^{rd}$ Ed.

Schuricht U, Endler K, Hennig L, Findeisen M and Welzel P. Studies on the biosynthesis of the antibiotic moe A. J Prakt Chem. 2000. V. 342(8). P. 761-772.

Schuricht U, Hennig L, Findeisen M, Endler K, Welzel P and Arigoni D. The biosynthesis of moenocinol, the lipid part of the moe antibiotics. Tetrahedron Lett. 2001. V. 42:3835-3837.

Sekurova, O. N., Brautaset, T., Sletta, H., Borgos, S. E., Jakobsen, M. O. M., Ellingsen, T. E., Strom, A. R., Valla, S., and Zotchev, S. B. (2004). In vivo analysis of the regulatory genes in the nystatin biosynthetic gene cluster of *Streptomyces noursei* ATCC 11455 reveals their differential control over antibiotic biosynthesis. J. Bacteriol. 186, 1345-1354.

Slusarchyk W A, Weisenborn F L. The structure of the lipid portion of the antibiotic prasinomycin. Tetrahedron Lett. 1969.8: 659-662.

Smith H E, Veenbergen V, Velde J, Damman M, Wisselink and Smits M A. The cps genes of *Streptococcus suis* serotypes 1, 2 and 9: development of rapid serotype-specific PCR assays. J Clin Microbiol. 1999. V. 37:3146-3152.

Soderberg T, Chen A and Poulter C D. Geranylgeranylglycerylphosphate synthase. Characterization of the recombinant enzyme from *Methanobacterium thermoautotrophicum*. Biochemistry. 2001. V. 40:14847-14854.

Sosio M, Stinchi S, Beltrametti F, Lazzarini A and Donadio S. The gene cluster for the biosynthesis of the glycopeptide antibiotic A40926 by *Nomomuraea* species. Chem Biol. 2003. V. 10:541-549.

Subramaniam-Niehaus, B., Schneider, T., Metzger, J. W. & Wohlleben, W. (1997). Isolation and analysis of moenomycin and its biosynthetic intermediates from *Streptomyces ghanaensis* (ATCC 14672) wildtype and selected mutants. Z. Naturforsch. 52, 217-226.

Tachibana A, Yano Y, Otani S, Nomura N, Sako Y, Taniguchi M. Novel prenyltransferase gene encoding farnesylgeranyl diphosphate synthase from a hyperthermophilic archaeon, *Aeropyrum pernix*. Molecular evolution with alteration in product specificity. Eur J Biochem. 2000 January; 267(2): 321-8.

Tahlan K, Park H U, Jensen S E. Three unlinked gene clusters are involved in clavam metabolite biosynthesis in *Streptomyces clavuligerus*. Can J Microbial. 2004. 50(10):803-10.

Takahashi H, Liu Y N, Liu H W. A two-stage one-pot enzymatic synthesis of TDP-L-mycarose from thymidine and glucose-1-phosphate. J Am Chem Soc. 2006. 128(5):1432-1433.

Takahashi S, Okanishi A, Utahara R, Nitta K, Maeda K, Umezawa H. Macarbomycin, a new antibiotic containing phosphorus. J Antibiot. 1970. V. 23(1). P: 48-50.

Taylor, J. G., Li, X., Oberthur, M., Zhu, W., and Kahne, D. E. (2006). The total synthesis of moenomycin A. J. Am. Chem. Soc. 128, 15084-15085.

Thuy T T, Lee H C, Kim C G, Heide L, Sohng J K. Functional characterizations of novWUS involved in novobiocin biosynthesis from Streptomyces spheroides. Arch Biochem Biophys. 2005. 436(1):161-7.

Trepanier N K, Jensen S E, Alexander D C and Leskiw B K. The positive activator of cephamycin C and clavulanic acid production in Streptomyces clavuligerus is mistranslated in a bldA mutant. Microbiology. 2002. V. 148: 643-656.

Wallhausser K H, Nesermann G, Prave P and Steigler A. Moe, a new antibiotic. I. Fermentation and isolation. Antimicrob Agents Chemother. 1965. P. 734-736.

Wang X, Preston III J F and Romeo T. The pgaABCD locus of Escherichia coli promotes the synthesis of a polysaccharide adhesin required for biofilm formation. J Bacteriol. 2004. V. 186:2724-2734.

Weber T, Welzel K, Pelzer S, Verne A, Wohlleben W. Exploiting the genetic potential of polyketide producing streptomycetes. J Biotechnol. 2003. V. 106: 221-232.

Weisenborn F L, Bouchard J L, Smith D, Pansy F, Maestrone G, Miraglia G, Meyers E. The prasinomycins: antibiotics containing phosphorus. Nature. 1967. V. 213: P. 1092-1094.

Welzel P, Kunisch F, Kruggel F, Stein H, Scherkenbeck J, Hiltmann A, Duddeck H, Muller D, Maggio J E, Fehlhaber H-W, Seibert O, van Heijenoort Y and van Heijenoort J. Moe A: minimum structural requirements for biological activity. Tetrahedron 1987. V. 43(3):585-598.

Welzel P: Transglycosylase inhibition. In Antibiotics and antiviral compounds—chemical synthesis and modification. Edited by Krohn K, Kirst H and Maag H. VCH Weinheim, Germany, 1993: 373-378. Welzel, P. (2005).

Welzel P. Syntheses around the transglycosylation step in peptidoglycan biosynthesis. Chem Rev. 2005. V. 105: 4610-4660.

Westrich L, Domann S, Faust B, Bedford D, Hopwood D A, Bechthold A. Cloning and characterization of a gene cluster from Streptomyces cyanogenus S136 probably involved in landomycin biosynthesis. FEMS Microbiol Lett. 1999. 170:381-387.

Wilson V T and Cundliffe E. Molecular analysis of tlrB, an antibiotic-resistance gene from tylosin-producing Streptomyces fradiae, and discovery of a novel resistance mechanism. J Antibiot. 1999. V. 52 P: 288-296.

Yuan, Y., Barrett, D., Zhang, Y., Kahne, D., Sliz, P., and Walker, S. (2007). Crystal structure of a peptidoglycan glycosyltransferase suggests a model for processive glycan chain synthesis. Proc. Natl. Acad. Sci. USA. 104, 5348-5353.

Yu T-W, Bai L, Clade D, Hoffman D, Toelzer S, Trihn K Q, Xu J, Moss S J, Leistner E and Floss H G. The biosynthetic gene cluster of the maytansinoid antitumor agent ansamitocin from Actinosynnema pretiosum. Proc Natl Acad Sci. 2002. V. 99(12):7968-7973.

Zalkin H, Smith J L. Enzymes utilizing glutamine as an amide donor. Adv Enzymol Relat Areas Mol Bid. 1998. V. 72:87-144.

Zehl M, Pitternauer E, Rizzi A, Allmaier G. Characterization of moe antibiotic complex by multistage MALDI-IT/RTOF-MS and ESI-IT-MS. J Am Soc Mass Spectrom. 2006. V. 17:1081-1090.

Zhang L, Radziejewska-Lebrecht J, Krajewska-Pietrasik D, Toivanen P and Skurnik M. Molecular and chemical characterization of the lipopolysaccharide O-antigen and its role in the virulence of Yersinia enterocolitica serotype O:8. Mol Microbiol. 1997. V. 27(1):63-76.

Zhu L, Ostash B, Rix U, Nur-E-Alam M, Mayers A, Luzhetskyy A, Mendez C, Salas J A, Bechthold A, Fedorenko V, Rohr J. Identification of the function of gene lndM2 encoding a bifunctional oxygenase-reductase involved in the biosynthesis of the antitumor antibiotic landomycin E by Streptomyces globisporus 1912 supports the originally assigned structure for landomycinone. J Org Chem. 2005. 70:631-638.

The contents of the aforementioned references are incorporated herein by reference in their entireties.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled.

What is claimed is:

1. An isolated recombinant cell expressing one or more polypeptides that comprise a moenomycin biosynthesis-related polypeptide selected from the group consisting of: MoeA4 (SEQ ID NO: 29), MoeB4 (SEQ ID NO: 30), MoeC4 (SEQ ID NO: 28), MoeB5 (SEQ ID NO: 27), Moe A5 (SEQ ID NO: 26), MoeD5 (SEQ ID NO: 47), MoeJ5 (SEQ ID NO: 48), MoeE5 (SEQ ID NO: 42), MoeF5 (SEQ ID NO: 36), MoeH5 (SEQ ID NO: 37), MoeK5 (SEQ ID NO: 38), MoeM5 (SEQ ID NO: 39), MoeN5 (SEQ ID NO: 43), MoeO5 (SEQ ID NO: 44), MoeX5 (SEQ ID NO: 46), MoeP5 (SEQ ID NO: 45), MoeR5 (SEQ ID NO: 40), MoeS5 (SEQ ID NO: 41), MoeGT1 (SEQ ID NO: 31), MoeGT2 (SEQ ID NO: 32), MoeGT3 (SEQ ID NO: 33), MoeGT4 (SEQ ID NO: 34), MoeGT5 (SEQ ID NO: 35), and variants thereof having at least about 95% sequence identity to the corresponding natural moenomycin biosynthesis-related polypeptide, wherein the cell is selected from the group consisting of: *Streptomyces lividans* TK24, *E. coli*, a mammalian cell, a yeast cell, and an insect cell.

2. The isolated recombinant cell of claim 1, wherein the cell is *Streptomyces lividans* TK24.

3. The isolated recombinant cell of claim 1, wherein the cell is *E. coli*.

4. The isolated recombinant cell of claim 1, wherein the cell is a mammalian cell.

5. The isolated recombinant cell of claim 1, wherein the cell is a yeast cell.

6. The isolated recombinant cell of claim 1, wherein the cell is an insect cell.

7. The isolated recombinant cell of claim 1, wherein the cell expresses two or more polypeptides that comprise the moenomycin biosynthesis-related polypeptide and variants thereof.

8. The isolated recombinant cell of claim 1, wherein the cell expresses three or more polypeptides that comprise the moenomycin biosynthesis-related polypeptide and variants thereof.

9. The isolated recombinant cell of claim 1, wherein the cell expresses four or more polypeptides that comprise the moenomycin biosynthesis-related polypeptide and variants thereof.

10. The isolated recombinant cell of claim 1, wherein the cell expresses five or more polypeptides that comprise the moenomycin biosynthesis-related polypeptide and variants thereof.

11. The isolated recombinant cell of claim 1, wherein the moenomycin biosynthesis-related polypeptide variants have at least about 98% sequence identity to the corresponding natural moenomycin biosynthesis-related polypeptide.

12. The isolated recombinant cell of claim 1, wherein the moenomycin biosynthesis-related polypeptide variants have at least about 99% sequence identity to the corresponding natural moenomycin biosynthesis-related polypeptide.

* * * * *